(12) United States Patent
Noji et al.

(10) Patent No.: US 7,138,629 B2
(45) Date of Patent: Nov. 21, 2006

(54) TESTING APPARATUS USING CHARGED PARTICLES AND DEVICE MANUFACTURING METHOD USING THE TESTING APPARATUS

(75) Inventors: Nobuharu Noji, Kanagawa-ken (JP); Tohru Satake, Kanagawa-ken (JP); Hirosi Sobukawa, Kanagawa-ken (JP); Toshifumi Kimba, Kanagawa-ken (JP); Masahiro Hatakeyama, Kanagawa-ken (JP); Shoji Yoshikawa, Tokyo (JP); Takeshi Murakami, Tokyo (JP); Kenji Watanabe, Kanagawa-ken (JP); Tsutomu Karimata, Kanagawa-ken (JP); Kenichi Suematsu, Kanagawa-ken (JP); Yutaka Tabe, Kanagawa-ken (JP); Ryo Tajima, Kanagawa-ken (JP); Keiichi Tohyama, Kanagawa-ken (JP)

(73) Assignee: Ebara Corporation, Tokyo (JP)

( * ) Notice: Subject to any disclaimer, the term of this patent is extended or adjusted under 35 U.S.C. 154(b) by 296 days.

(21) Appl. No.: 10/754,623

(22) Filed: Jan. 12, 2004

(65) Prior Publication Data

US 2005/0045821 A1    Mar. 3, 2005

(30) Foreign Application Priority Data

Apr. 22, 2003 (JP) .............................. 2003/117014
May 9, 2003 (JP) .............................. 2003/132304

(51) Int. Cl.
*G21K 7/00* (2006.01)
*G21N 23/99* (2006.01)
*H01J 37/28* (2006.01)
*G01N 23/225* (2006.01)

(52) U.S. Cl. .................. 250/311; 250/310; 250/492.1; 250/492.2; 250/492.3; 382/103; 382/145; 382/153; 324/751

(58) Field of Classification Search .................. None
See application file for complete search history.

(56) References Cited

U.S. PATENT DOCUMENTS

| 5,173,719 | A |   | 12/1992 | Taniguchi et al. |
| 5,373,158 | A |   | 12/1994 | Murakoshi et al. |
| 5,578,821 | A |   | 11/1996 | Meisberger et al. |
| 5,909,030 | A | * | 6/1999 | Yoshitake et al. ........ 250/492.2 |
| 6,246,775 | B1 | * | 6/2001 | Nakamura et al. .......... 382/100 |
| 6,365,897 | B1 |   | 4/2002 | Hamashima et al. |
| 6,389,152 | B1 | * | 5/2002 | Nakamura et al. .......... 382/100 |

(Continued)

FOREIGN PATENT DOCUMENTS

JP         7-297266          11/1995

(Continued)

*Primary Examiner*—John R. Lee
*Assistant Examiner*—Bernard E. Souw
(74) *Attorney, Agent, or Firm*—Westerman, Hattori, Daniels & Adrian, LLP.

(57) ABSTRACT

A system for further enhancing speed, i.e. improving throughput in a SEM-type inspection apparatus is provided. An inspection apparatus for inspecting a surface of a substrate produces a crossover from electrons emitted from an electron beam source 25•1, then forms an image under a desired magnification in the direction of a sample W to produce a crossover. When the crossover is passed, electrons as noises are removed from the crossover with an aperture, an adjustment is made so that the crossover becomes a parallel electron beam to irradiate the substrate in a desired sectional form. The electron beam is produced such that the unevenness of illuminance is 10% or less. Electrons emitted from the sample W are detected by a detector 25•11.

22 Claims, 150 Drawing Sheets

U.S. PATENT DOCUMENTS

| | | |
|---|---|---|
| 6,479,819 B1 | 11/2002 | Hamashima et al. |
| 6,532,795 B1 | 3/2003 | Brammer et al. |
| 6,583,634 B1 | 6/2003 | Nozoe et al. |
| 6,593,152 B1 | 7/2003 | Nakasuji et al. |
| 6,703,850 B1 | 3/2004 | Nozoe et al. |
| 6,797,954 B1 | 9/2004 | Shinada et al. |
| 6,865,288 B1 | 3/2005 | Shishido et al. |
| 2002/0028399 A1 | 3/2002 | Nakasuji et al. |
| 2002/0033449 A1 | 3/2002 | Nakasuji et al. |
| 2002/0036264 A1 | 3/2002 | Nakasuji et al. |
| 2002/0088940 A1 | 7/2002 | Watanabe et al. |
| 2002/0109090 A1 | 8/2002 | Nakasuji et al. |
| 2002/0117635 A1 | 8/2002 | Shinada et al. |
| 2002/0130262 A1 | 9/2002 | Nakasuji et al. |
| 2002/0142496 A1 | 10/2002 | Nakasuji et al. |
| 2002/0148961 A1 | 10/2002 | Nakasuji et al. |
| 2002/0148975 A1 | 10/2002 | Kimba et al. |
| 2002/0158198 A1 | 10/2002 | Kohama et al. |
| 2003/0020016 A1 | 1/2003 | Frosien |
| 2003/0164460 A1 | 9/2003 | Shinada et al. |
| 2003/0206027 A1 | 11/2003 | Nozoe et al. |
| 2003/0207475 A1 | 11/2003 | Nakasuji et al. |
| 2004/0183013 A1 | 9/2004 | Nakasuji et al. |
| 2004/0222377 A1 | 11/2004 | Shinada et al. |
| 2005/0045821 A1* | 3/2005 | Noji et al. .................. 250/311 |
| 2005/0253066 A1* | 11/2005 | Watanabe et al. ............ 250/310 |

FOREIGN PATENT DOCUMENTS

| | | |
|---|---|---|
| JP | 11-242943 | 9/1999 |
| JP | 2001-22935 | 1/2001 |
| JP | 2001-256915 | 9/2001 |
| JP | 2002-139465 A | 5/2002 |
| JP | 2002-184674 A | 6/2002 |
| JP | 2002-208370 A | 7/2002 |
| JP | 2002-289130 A | 10/2002 |
| JP | 2003-115274 A | 4/2003 |
| WO | WO 02/056332 A1 | 7/2002 |

* cited by examiner

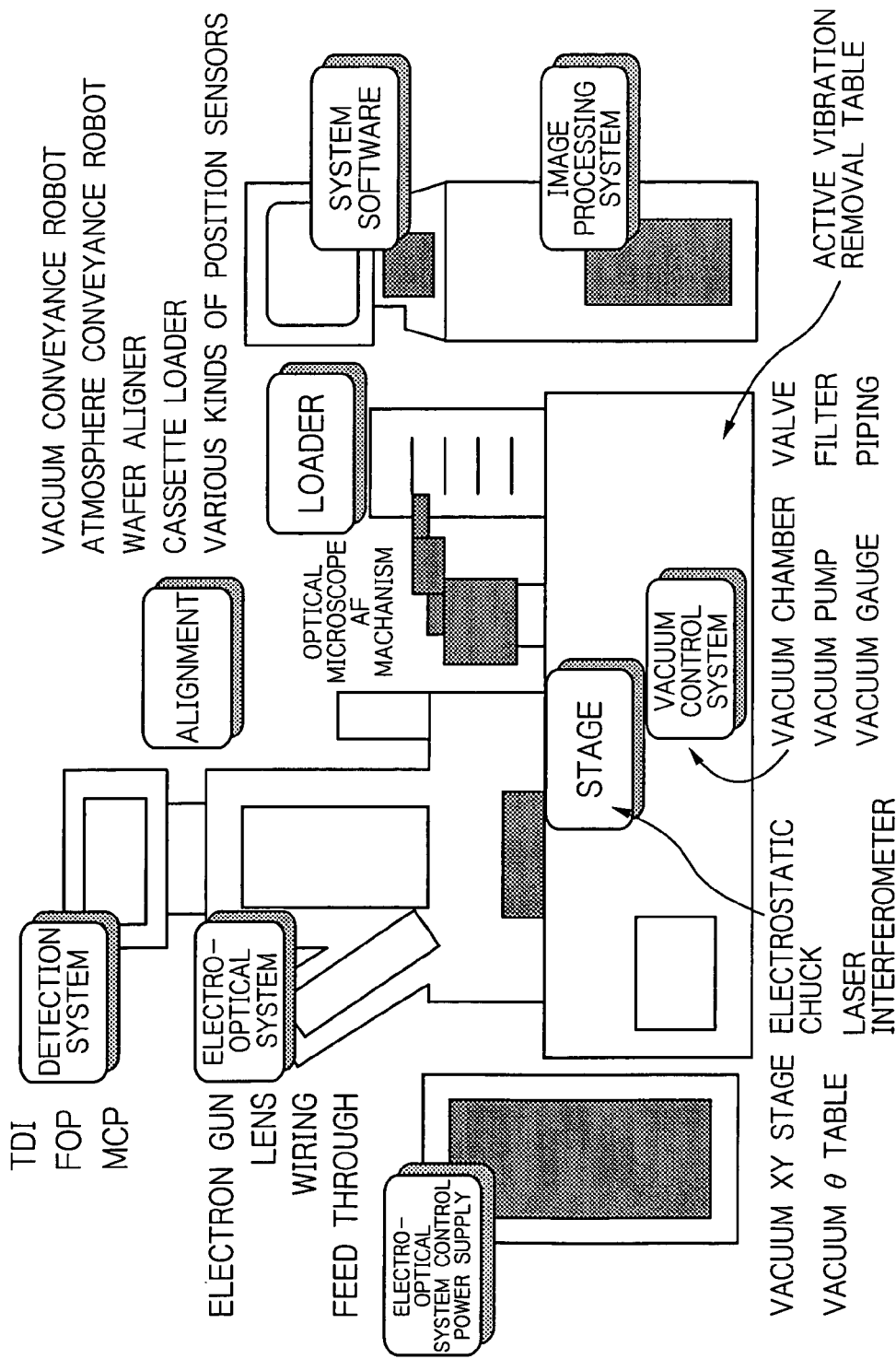

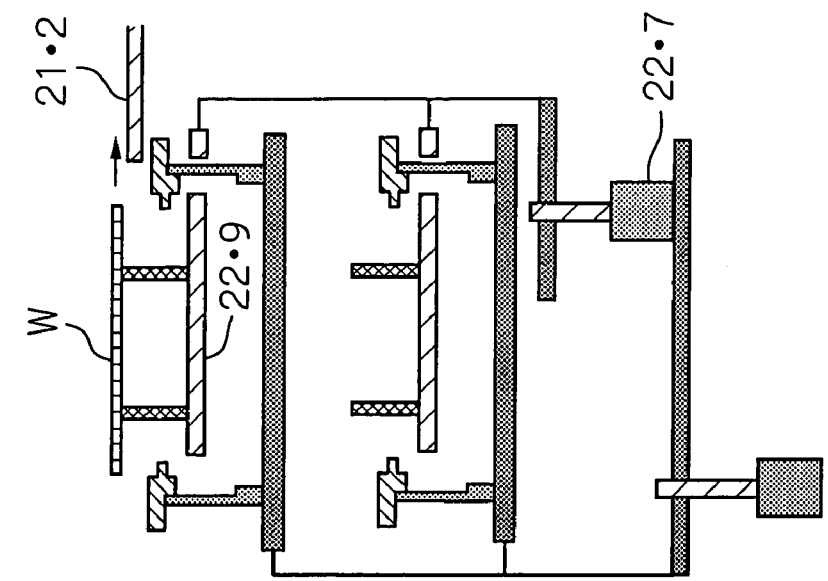
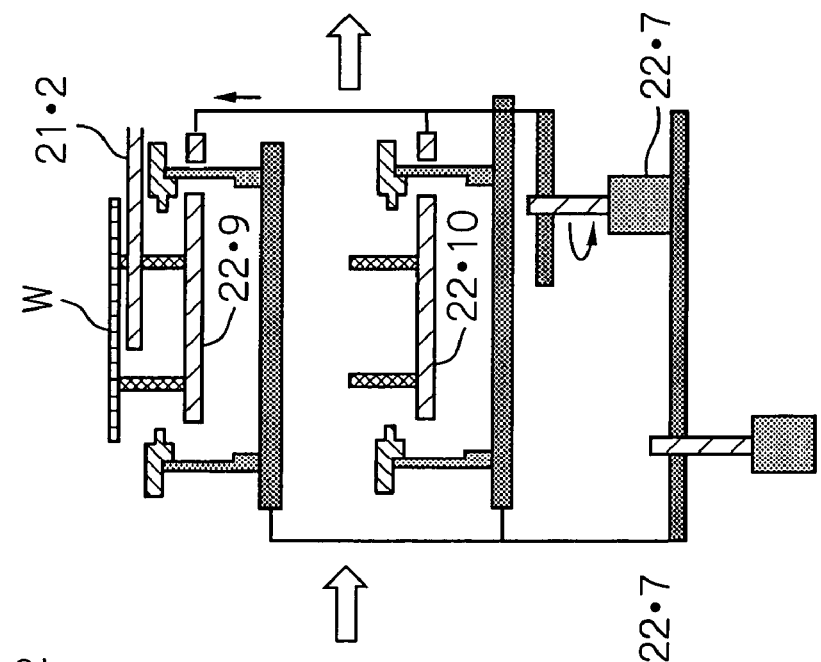
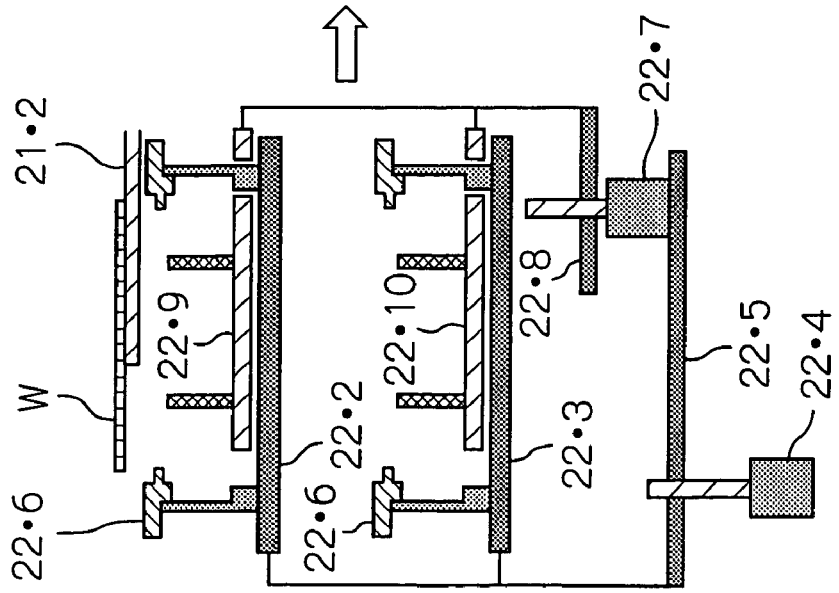

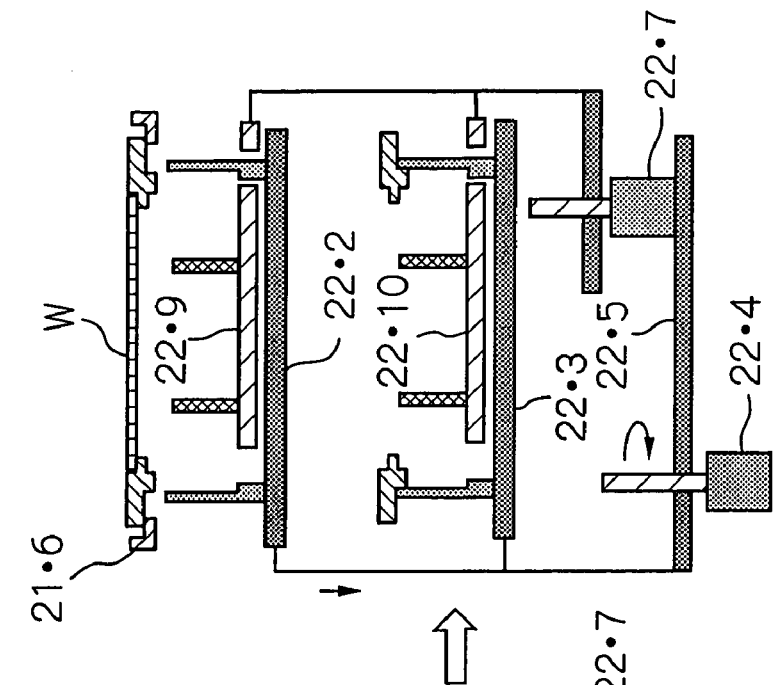
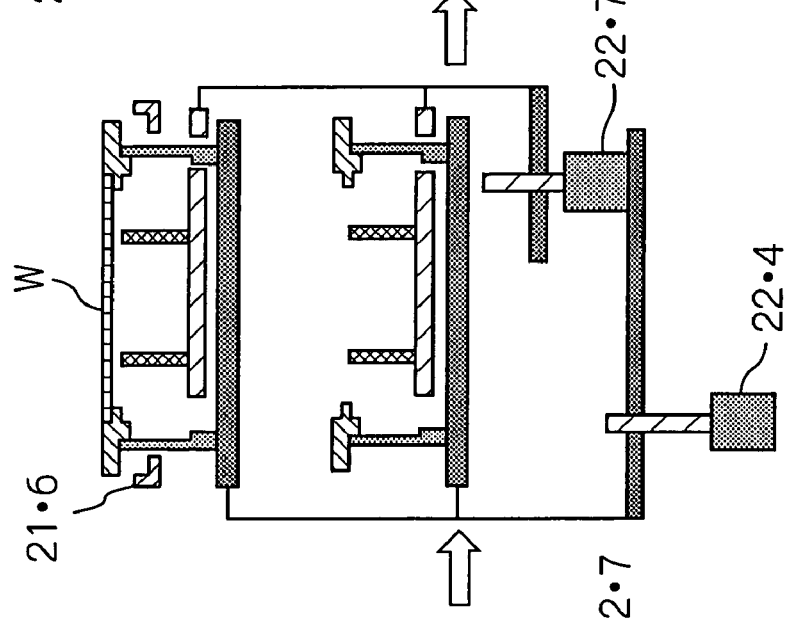
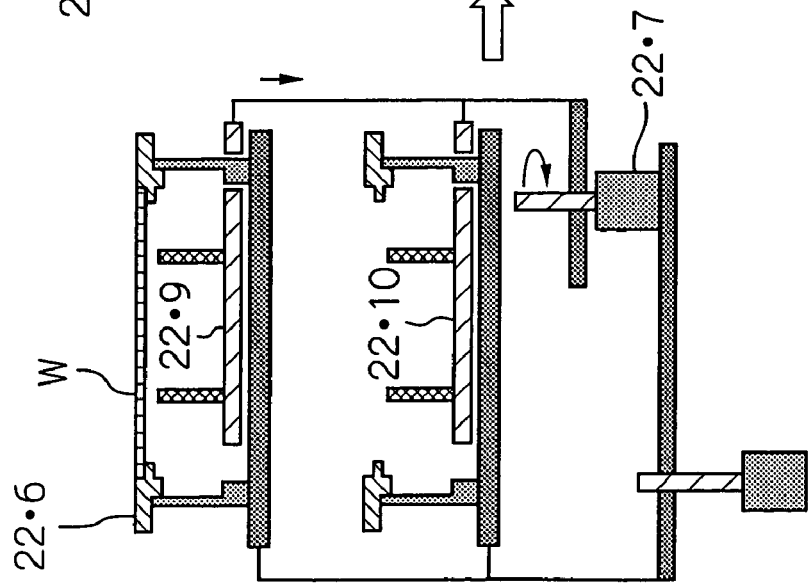

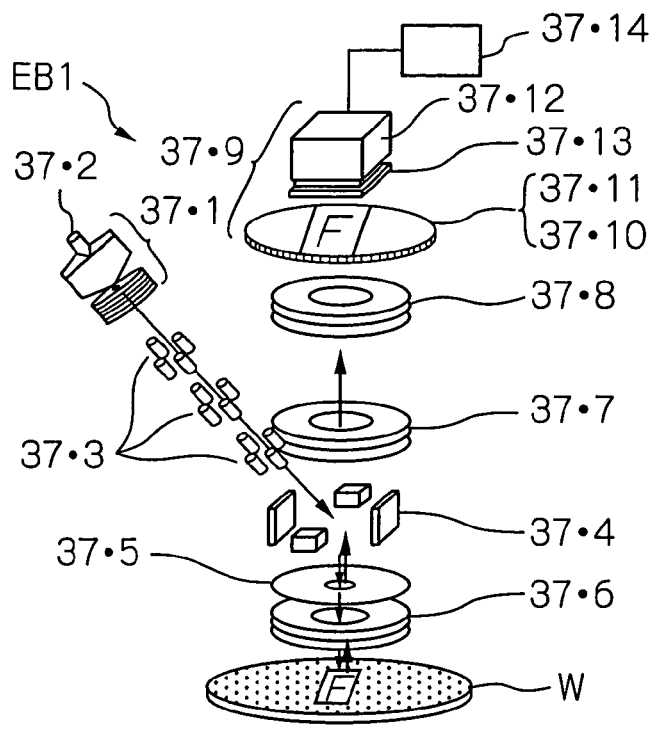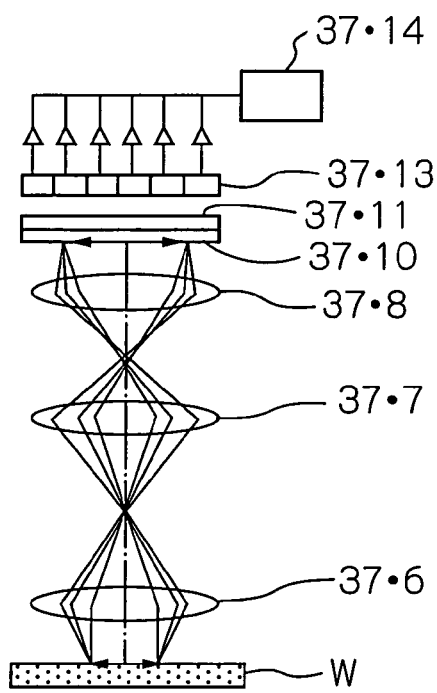
Fig. 37(A)  Fig. 37(B)
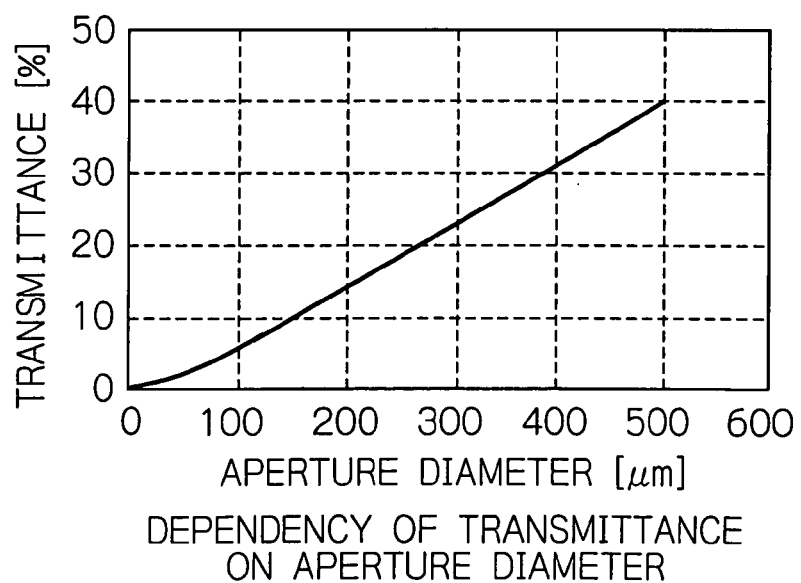
Fig. 38
DEPENDENCY OF TRANSMITTANCE ON APERTURE DIAMETER

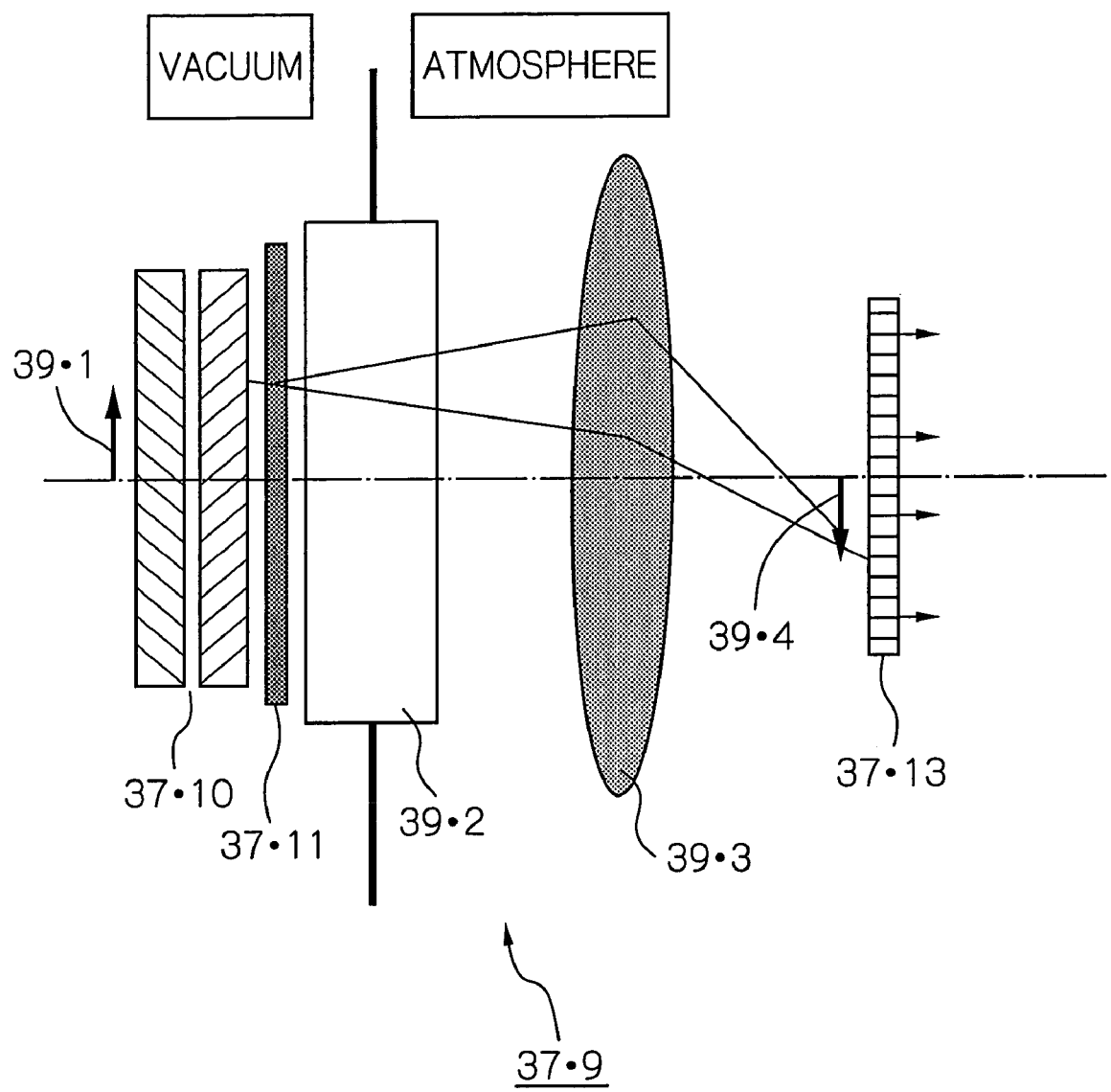

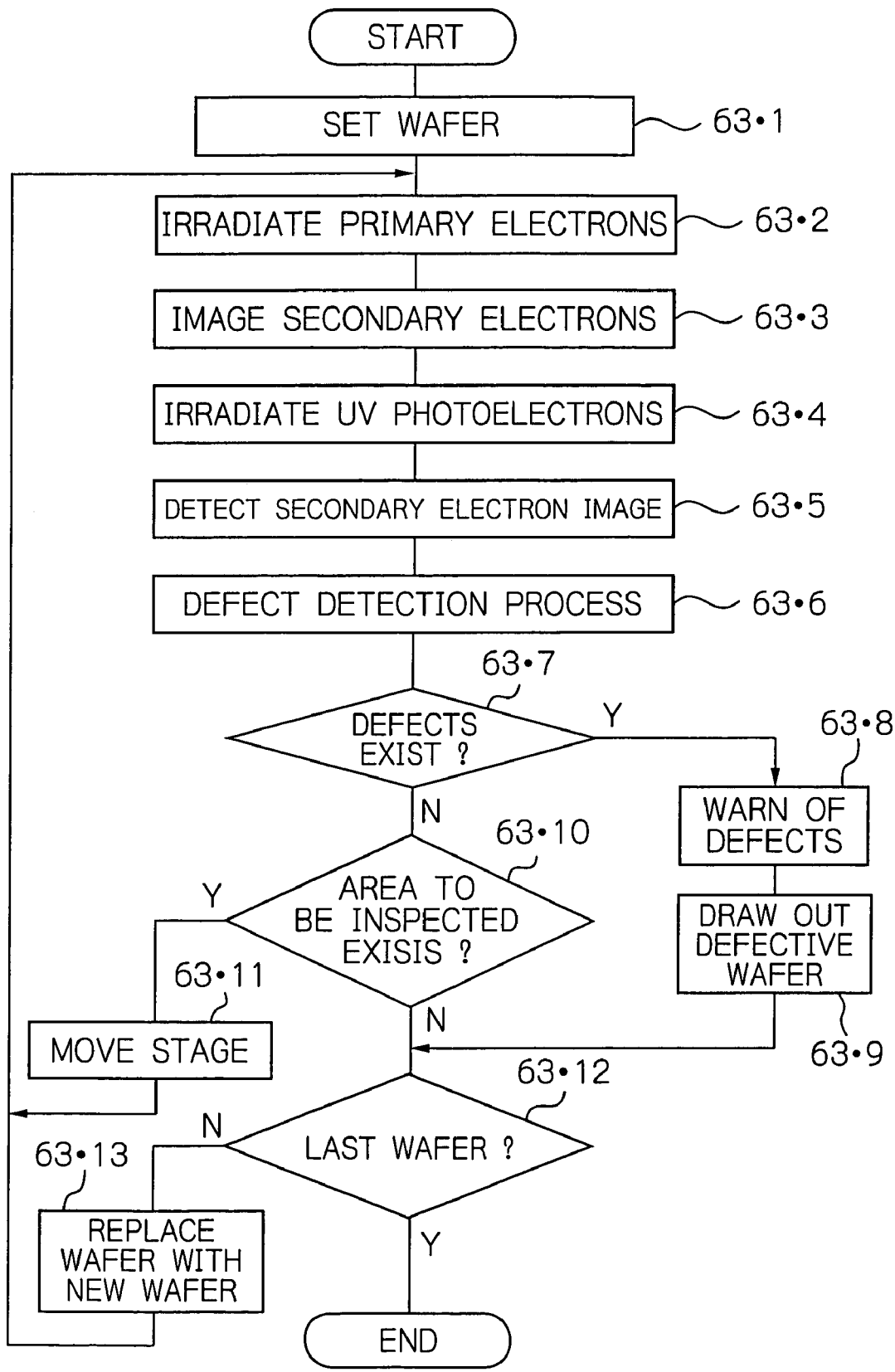

| | | (-1,2) | (0,2) | (1,2) | |
|---|---|---|---|---|---|
| | (-2,1) | (-1,1) | (0,1) | (1,1) | (2,1) |
| | (-2,0) | (-1,0) | (0,0) | (1,0) | (2,0) |
| | (-2,-1) | (-1,-1) | (0,-1) | (1,-1) | (2,-1) |
| | | (-1,-2) | (0,-2) | (1,-2) | |

▦ ORIGIN DIE
※ DIE POSITION =(0, 0)

Y DIRECTION PATTERN MATCHING
(TRANSITION OF POSITION
OF PATTERN SEARCH FOR
CALCULATION OF AMOUNT OF
θ ROTATION CORRECTION)

THIRD SEARCH DIE IMAGING AREA
SECOND SEARCH DIE IMAGING AREA
FIRST SEARCH DIE IMAGING AREA

DIE MAP PICTUE

OPERATION A   OPERATION B

Fig. 135
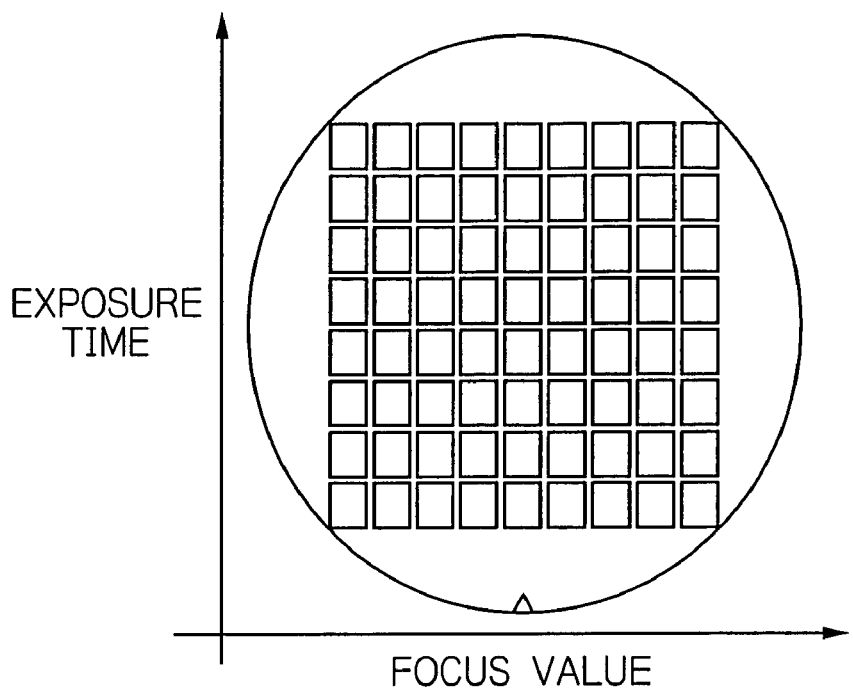
Fig. 136
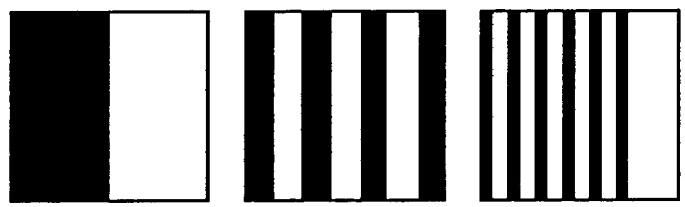
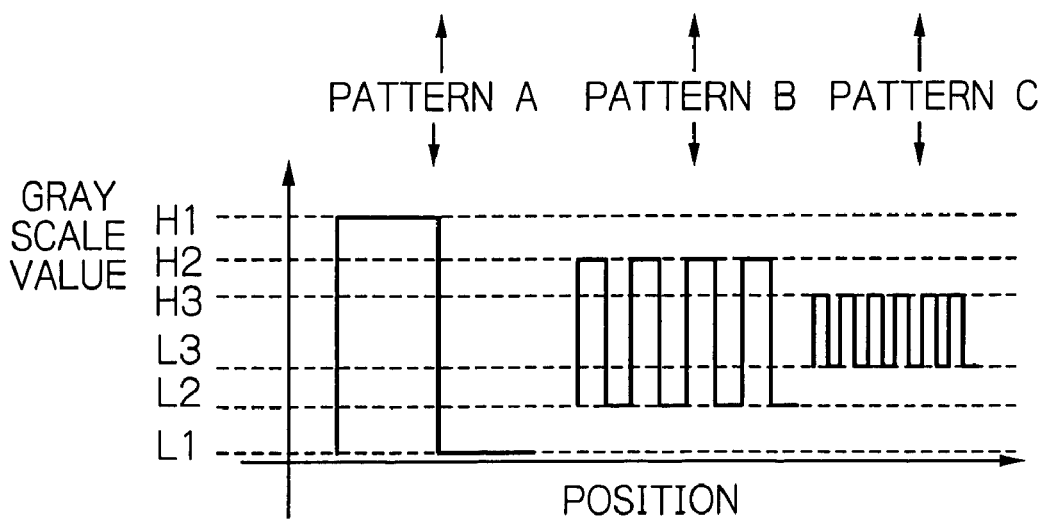

Fig. 154
PROBABILITY OF DIELECTRIC BREAKDOWN FOR EACH MATAL
| METAL | WORK FUNKTION [eV] | PROBABILITY OF DIELECTRIC BREAKDOWN |
|---|---|---|
| ALUMINUM | 4.2 | LARGE |
| GOLD | 4.9 | MIDDLE |
| PLATINUM | 5.3 | SMALL |
Fig. 155
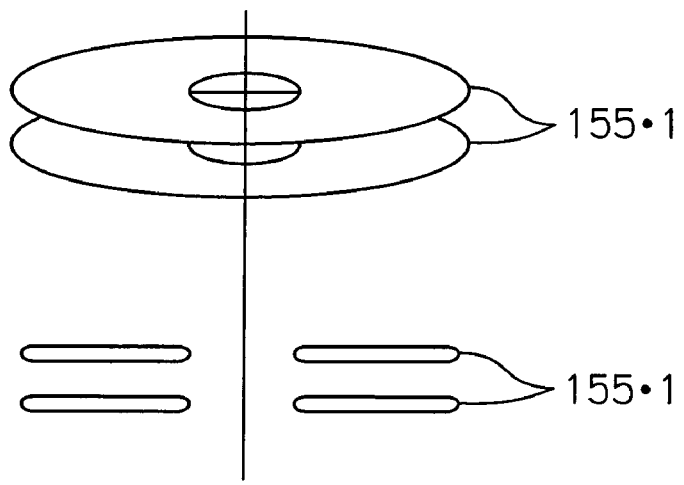
Fig. 156
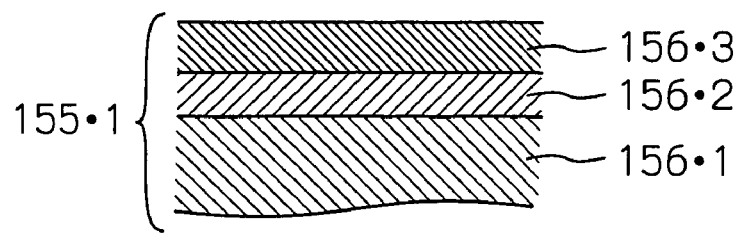

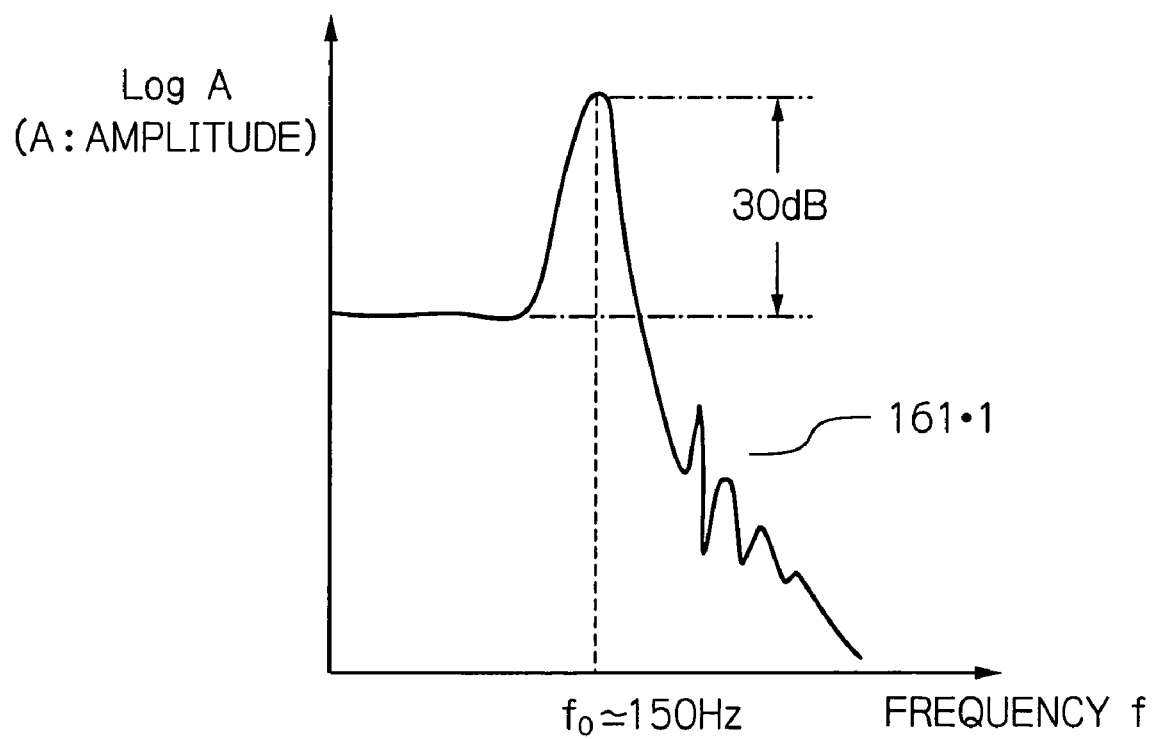

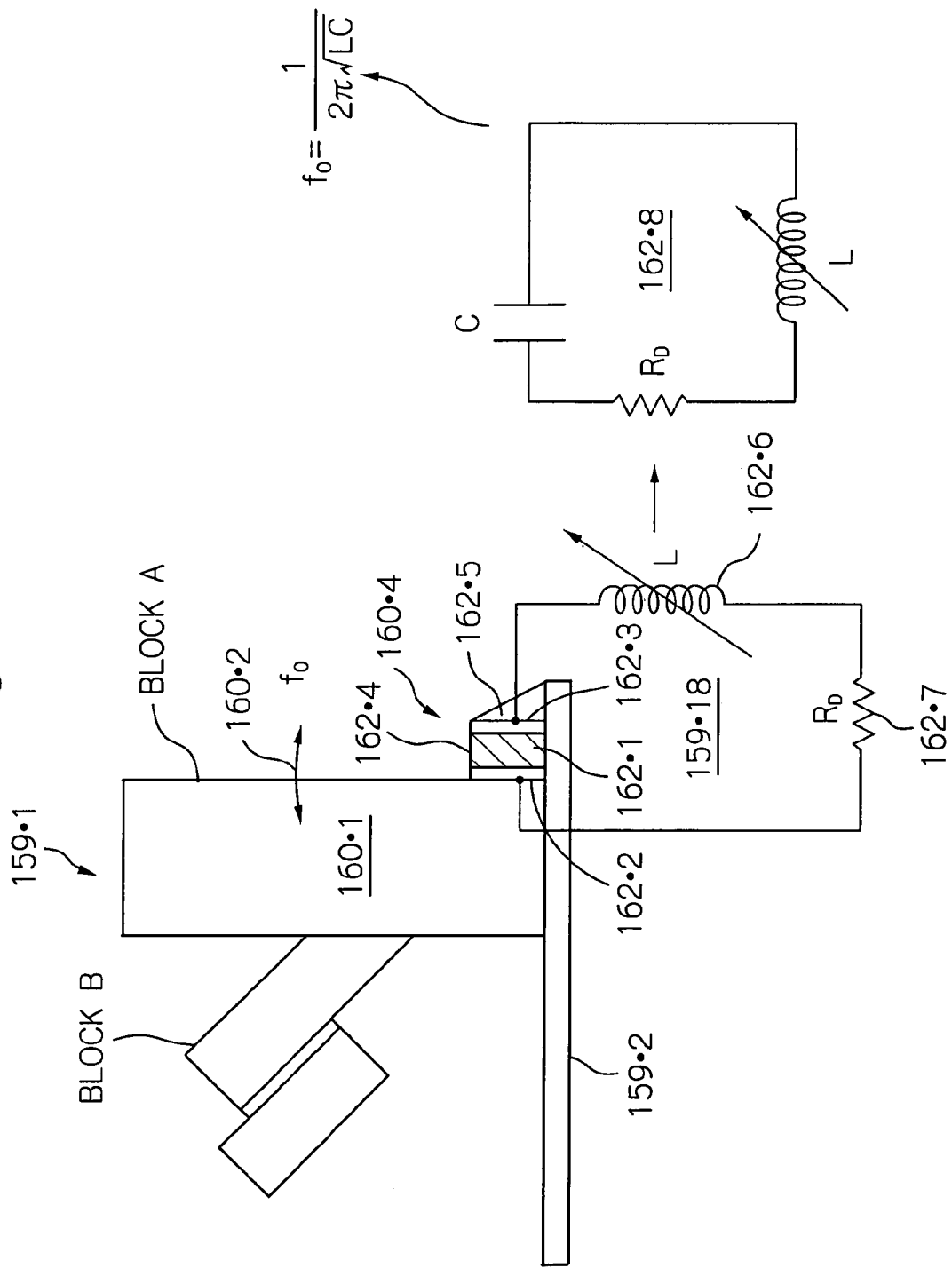

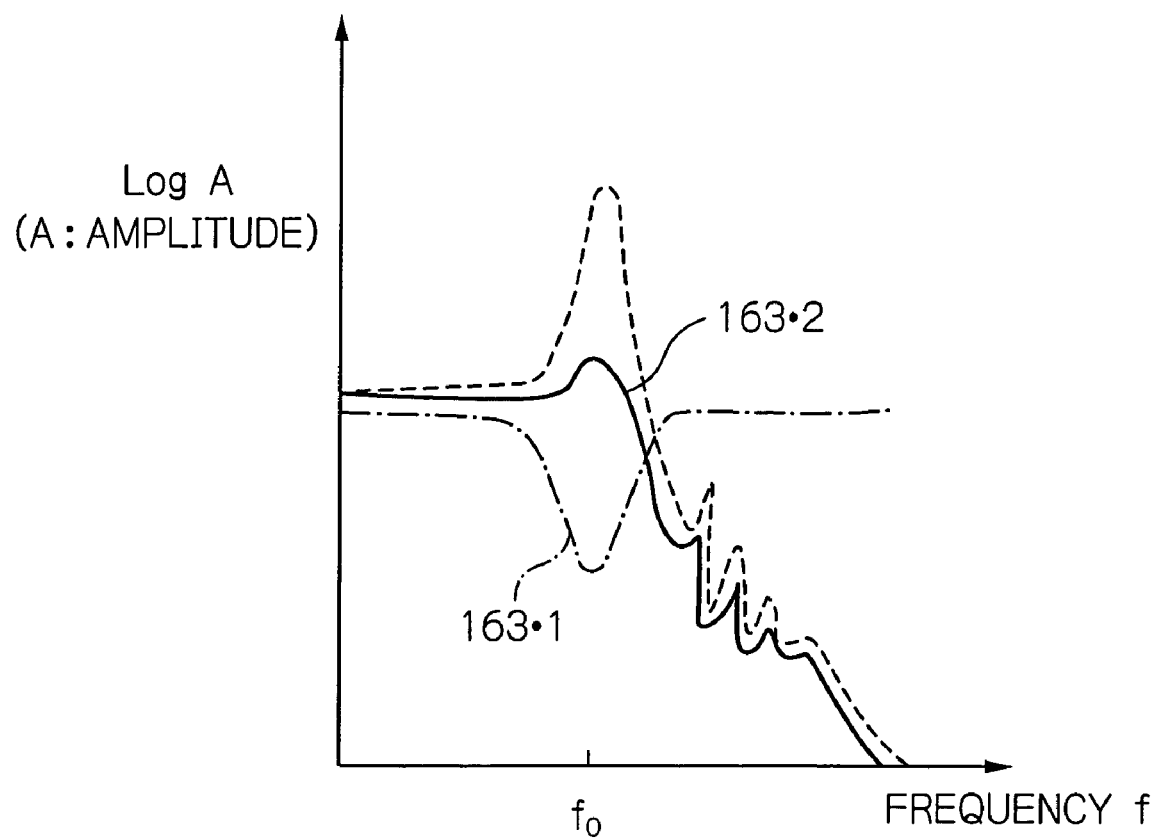

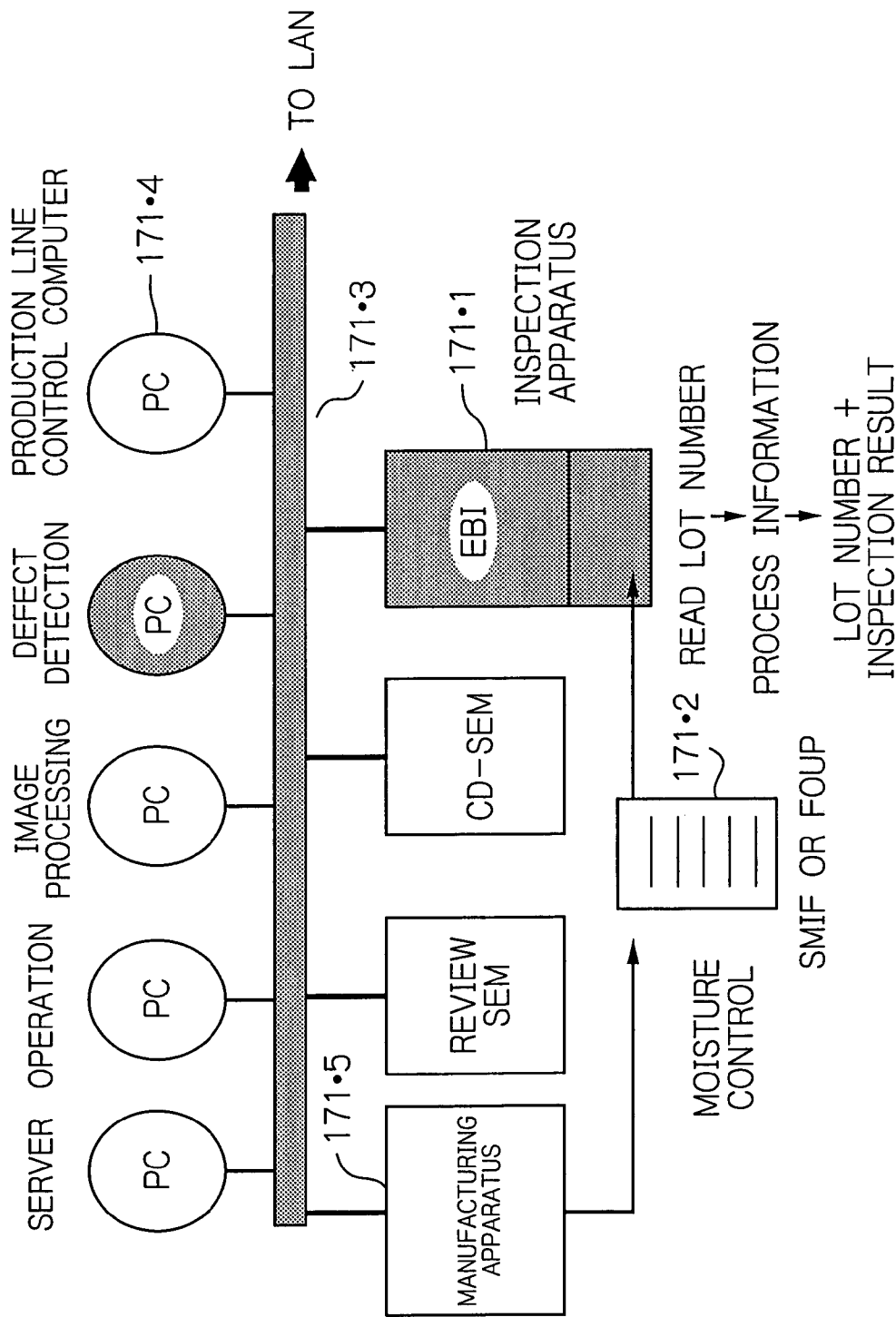

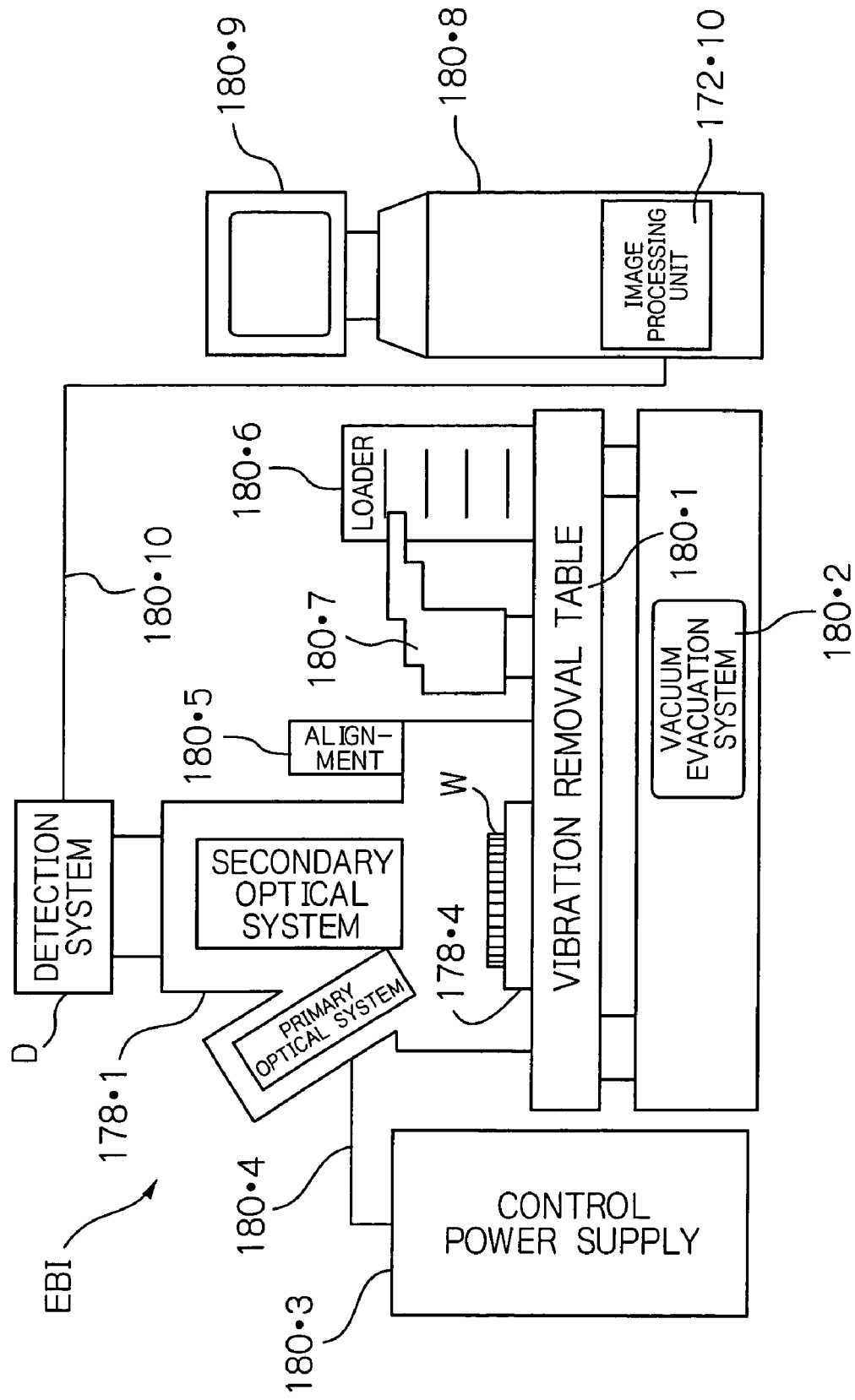

TESTING APPARATUS USING CHARGED PARTICLES AND DEVICE MANUFACTURING METHOD USING THE TESTING APPARATUS

BACKGROUND OF THE INVENTION

1. Field of the Invention

The present invention relates to an inspection apparatus inspecting defects or the like of a pattern formed on the surface of an inspection object using an electron beam, and particularly relates to an inspection apparatus irradiating an electron beam to the inspection object and capturing secondary electrons modified according to properties of the surface thereof to form image data, and inspecting in high throughput a pattern or the like formed on the surface of the inspection object based on the image data, and a device production process of producing a device in a high yield using the inspection apparatus as used for detection of wafer defects in semiconductor manufacturing. More specifically, the present invention relates to a detection apparatus with a projection electron microscope system using broad beams, and a device production process using the apparatus.

In a semiconductor process, the design rule is about to move into an era of 100 nm, and the type of production is now making a transition from low variety and large production represented by DRAM to high variety and small production found in SOC (Silicon on chip). Accordingly, the number of production steps increases, improvement in yield for each step becomes essential, and inspection of defects coming from the process becomes important. The present invention relates to an apparatus for use in inspection of a wafer or the like after each step in the semiconductor process, and relates to an inspection process and apparatus using an electron beam or a device production process using the same.

2. Description of the Related Art

As semiconductor devices is highly integrated, and patterns becomes finer, a high resolution and high throughput inspection apparatus is required. For inspecting defects of a wafer substrate having a 100 nm design rule, pattern defects or defects of particle vias in wiring having a line width of 100 nm or smaller and electric defects thereof should be observed, and hence a resolution of 100 nm or lower is required, and the inspection quantity increases due to an increase in the number of production steps resulting from high integration of the device, and therefore high throughput is required. Furthermore, as the device is increasingly multilayered, the inspection apparatus is required to have a function of detecting a contact failure (electric defects) of vias for connection of wiring between layers. Currently, optical defect inspection apparatuses are mainly used, but defect inspection apparatuses using electron beams are expected to go mainstream in stead of the optical defect inspection apparatus in terms of resolution and inspection of contact failure. However, the electron beam-type defect inspection apparatus has a disadvantage, i.e. it is inferior in throughput to the optical type.

Thus, development of an inspection apparatus having a high resolution and high throughput and being capable of detecting electric detects is required. It is said that the resolution of the optical type is maximum ½ of the wavelength of light used, which is equivalent to about 0.2 μm for commercially practical visible light, for example.

On the other hand, for the type using an electron beam, a scanning electron beam type (SEM type) is usually commercially available, the resolution is 0.1 μm and the inspection time is 8 hours/wafer (200 mm wafer). The electron beam type has a remarkable characteristic such that electric defects (breakage of wiring, poor conduction, poor conduction of vias and the like) can be inspected, but the inspection speed is very low, and development of a defect inspection apparatus performing inspection at a high speed is expected.

Generally, the inspection apparatus is expensive, inferior in throughput to other process apparatuses, and is therefore used after an important step, for example, etching, film formation, or CMP (chemical mechanical polishing) planarization processing under present circumstances.

The inspection apparatus of the scanning type using an electron beam (SEM) will be described. The SEM type inspection apparatus reduces the size of an electron beam (the beam diameter corresponds to the resolution), and scans the beam to irradiate a sample in a line form. On the other hand, a stage is moved in a direction perpendicular to the scanning direction of the electron beam to irradiate an observation area with the electron beam in a plain form. The scan width of the electron beam is generally several hundreds μm. Secondary electrons generated from the sample by irradiation with the size-reduced electron beam (refereed to as primary electron beam) are detected with a detector (scintillator+photomultiplier (photomultiplier tube) or a semiconductor-type detector (PIN diode type) or the like). Coordinates of the irradiation position and the amount of secondary electrons (signal intensity) are synthesized into an image, and the image is stored in a storage device, or outputted onto a CRT (cathode ray tube). The principle of the SEM (scanning electron microscope) has been described above, and defects of a semiconductor (usually Si) wafer in a step on progress are detected from the image obtained by this process. The inspection speed (corresponding to throughput) depends on the amount of primary electron beams (current value), the beam diameter and the response speed of the detector. 0.1 μm of beam diameter (that can be considered as resolution), 100 nA of current value and 100 MHz of detector response speed are maximum values at present and in this case, it is said that the inspection speed is about 8 hours per wafer having a diameter of 20 cm. The serious problem is that this inspection speed is very low compared to the optical type (½₀ or less of that of the optical type). Particularly, pattern defects and electric defects of a device pattern of a design rule of 100 nm or smaller formed on the wafer, i.e. of a line width of 100 nm, a via with the diameter of 100 nm or smaller and the like, and a contaminant of 100 nm or smaller can be detected at a high speed.

For the SEM-type inspection apparatus described above, the above inspection speed is considered as a limit, and a new type of inspection apparatus is required for further enhancing the speed, i.e. increasing the throughput.

SUMMARY OF THE INVENTION

For meeting the needs, the present invention provides an electron beam apparatus comprising means for irradiating an electron beam to a sample, means for guiding to a detector electrons obtaining information about the surface of the above described sample by the irradiation of the electron beam to the above described sample, and means for synthesizing as an image the electrons being guided to the detector and obtaining information about the surface of the above described sample, wherein the illuminance of the above described electron beam in an area of the above described sample illuminated with the above described electron beam is uniform.

The electrons obtaining information about the surface of the above described sample are desirably at least one of secondary electrons, reflection electrons and back-scatter electrons, or mirror electrons reflected from the vicinity of the surface of the above described sample.

By the inspection process or inspection apparatus of the present invention, defects of a substrate of a wafer or the like having wiring with the line width of 100 nm or smaller can be inspected.

BRIEF DESCRIPTION OF THE DRAWINGS

FIG. 3 shows the overall configuration of the apparatus of FIG. 1 in terms of functions;

FIGS. 20-1(A) and 21-1(B) illustrate another example of the electrostatic chuck for use in the semiconductor inspection apparatus according to the present invention;

FIG. 21 illustrates a bridge tool for use in the semiconductor inspection apparatus according to the present invention;

FIG. 22-1 illustrates the configuration and operation procedures (A) to (C) of an elevator mechanism in a load lock chamber of FIG. 22;

FIG. 22-2 illustrates the configuration and operation procedures (D) to (F) of the elevator mechanism in a load lock chamber of FIG. 22;

FIG. 25-1 shows the configuration of an electro-optic system of a projection electron microscope type beam inspection apparatus of the semiconductor inspection apparatus according to the present invention;

FIG. 25-2 shows the configuration of the electro-optic system of the scanning electron beam inspection apparatus of the semiconductor inspection apparatus according to the present invention;

FIG. 25-3 schematically shows one example of the configuration of a detector rotation mechanism of the semiconductor inspection apparatus according to the present invention;

FIG. 25-4 schematically shows one example of the configuration of the detector rotation mechanism of the semiconductor inspection apparatus according to the present invention;

FIG. 25-5 schematically shows one example of the configuration of the detector rotation mechanism of the semiconductor inspection apparatus according to the present invention;

Figure 1:
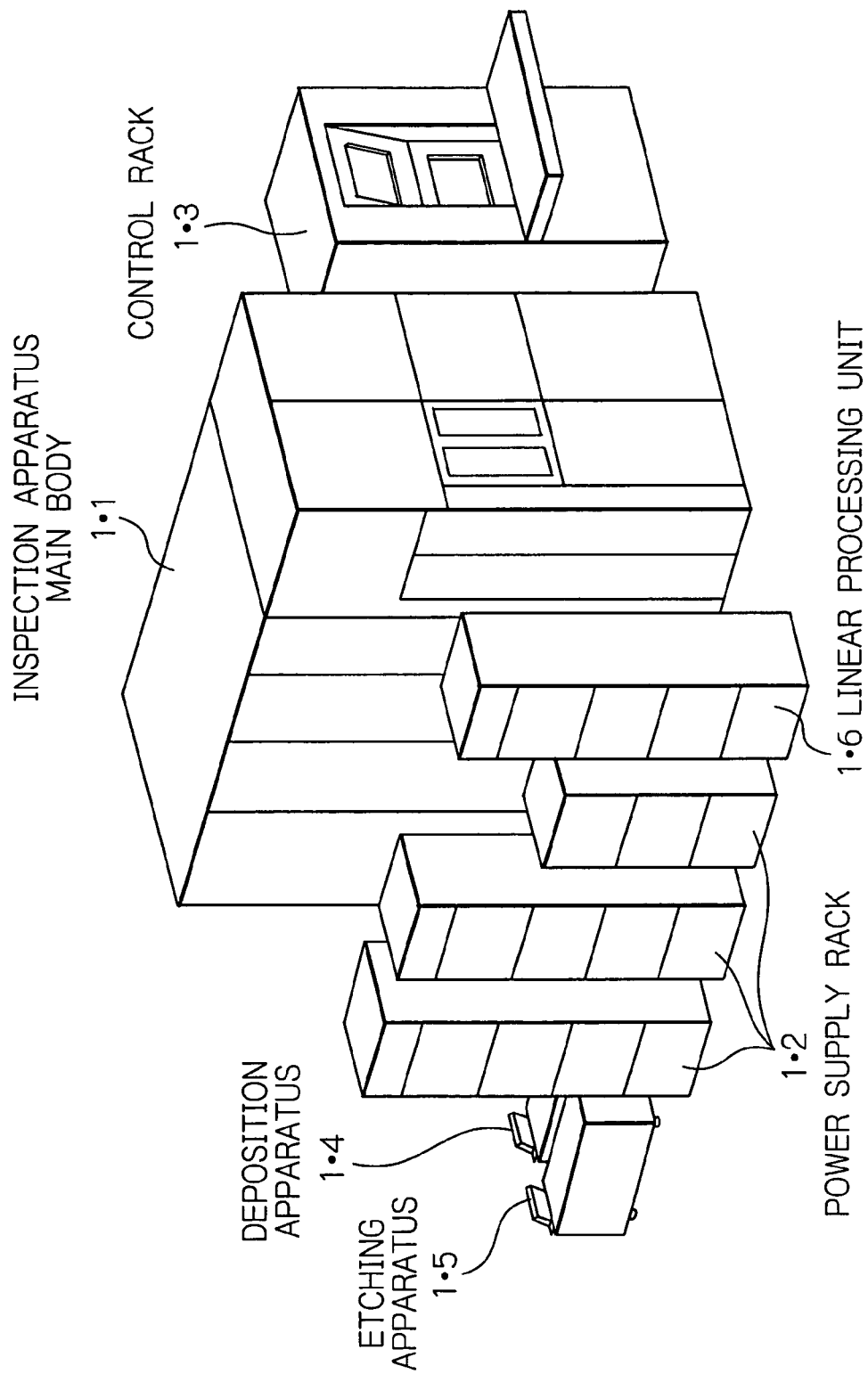
FIG. 1 shows the overall configuration of a semiconductor inspection apparatus.
Figure 13:
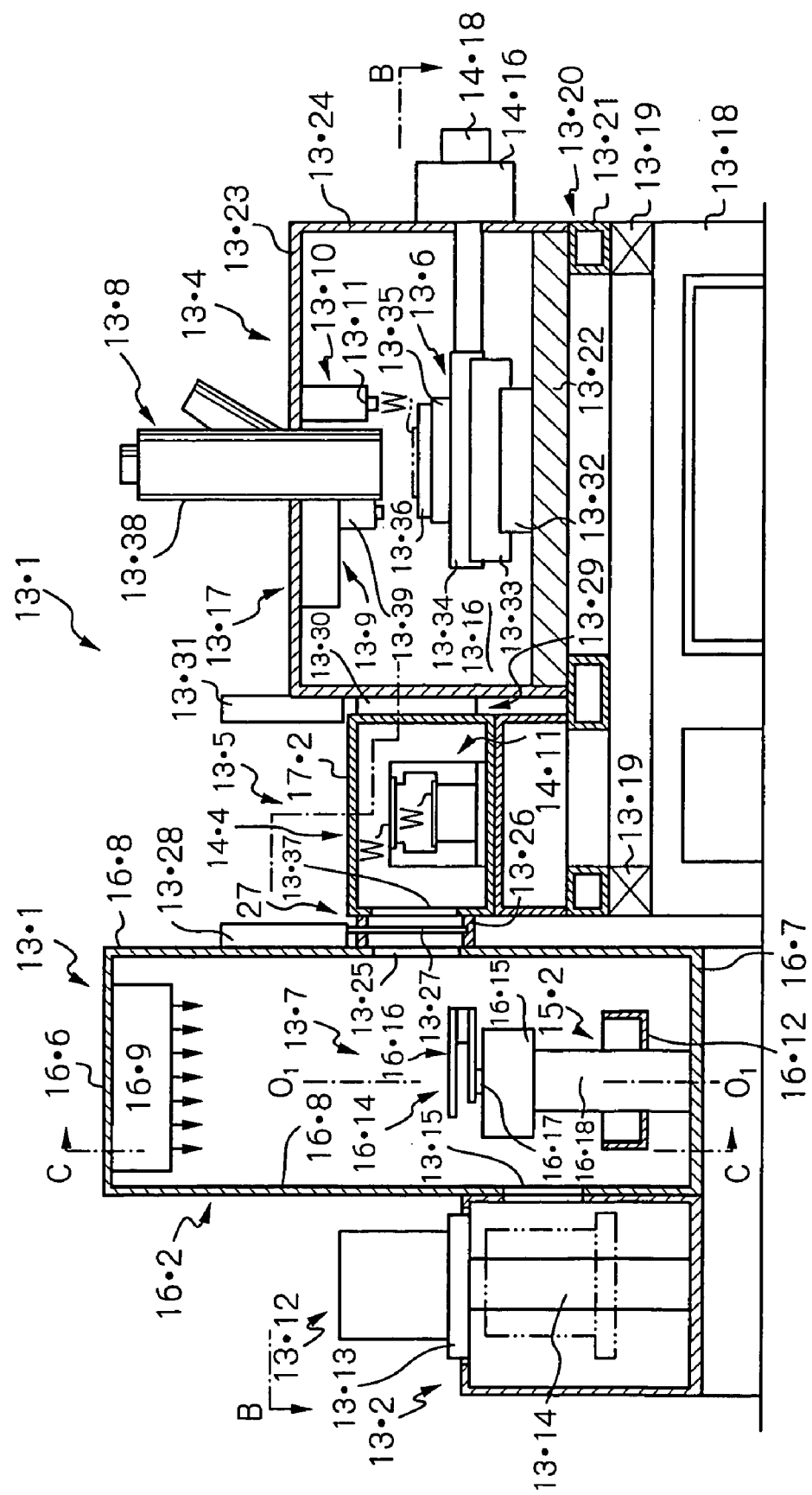
FIG. 13 is an elevational view showing main components of the semiconductor inspection apparatus according to the present invention.
Figures 1, 25:
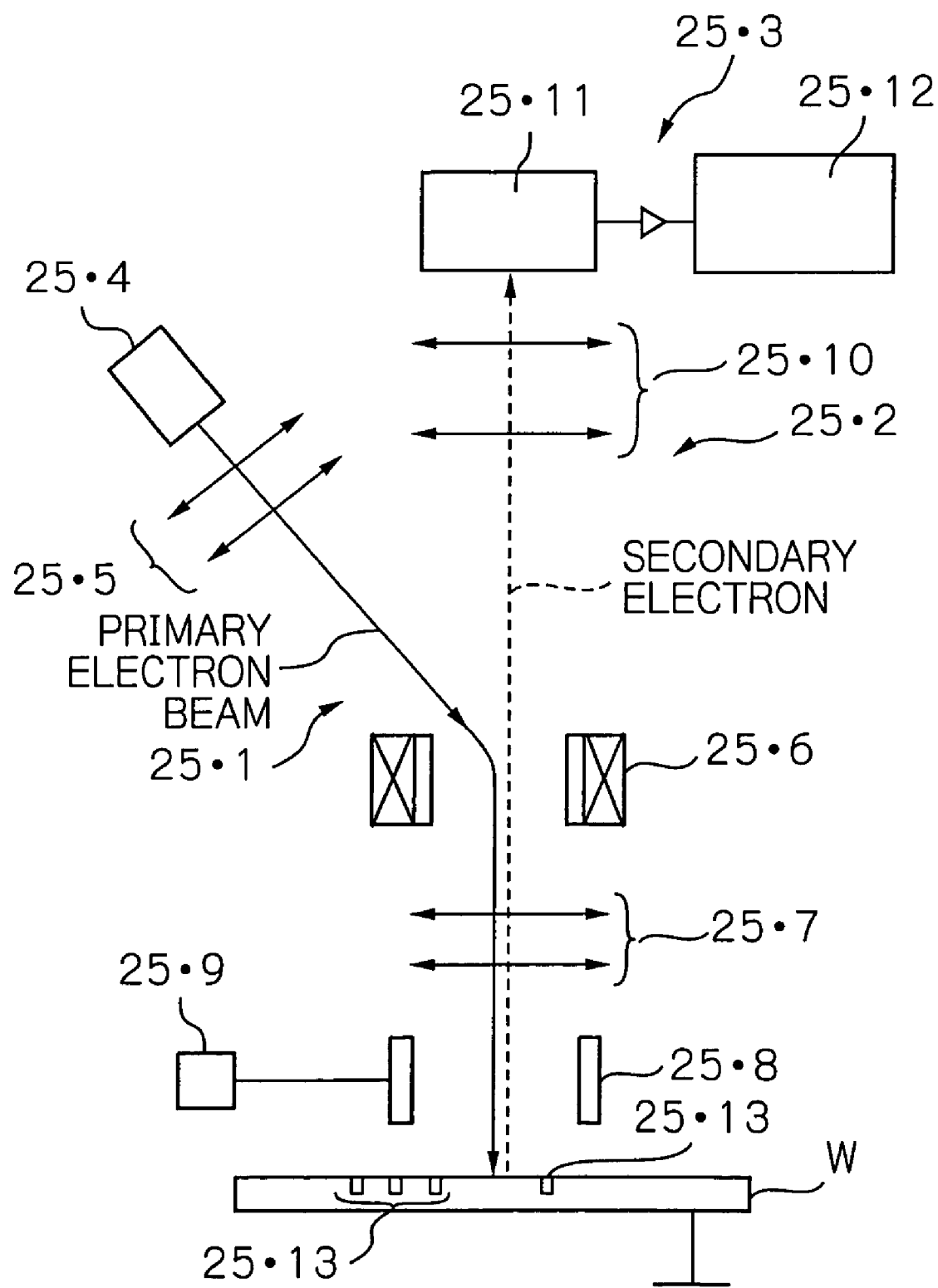
Figures 2, 25:
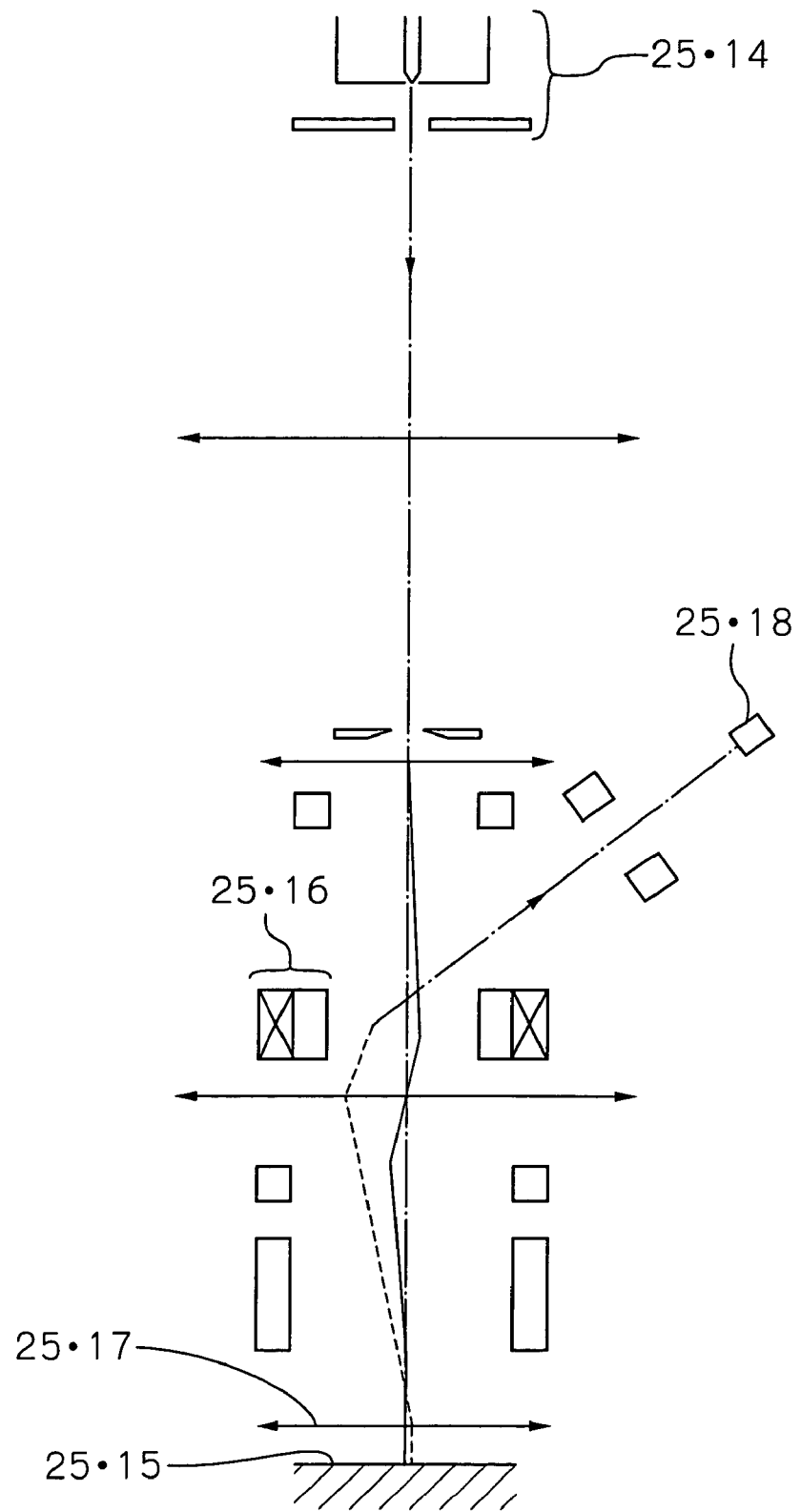
Figures 1, 27:
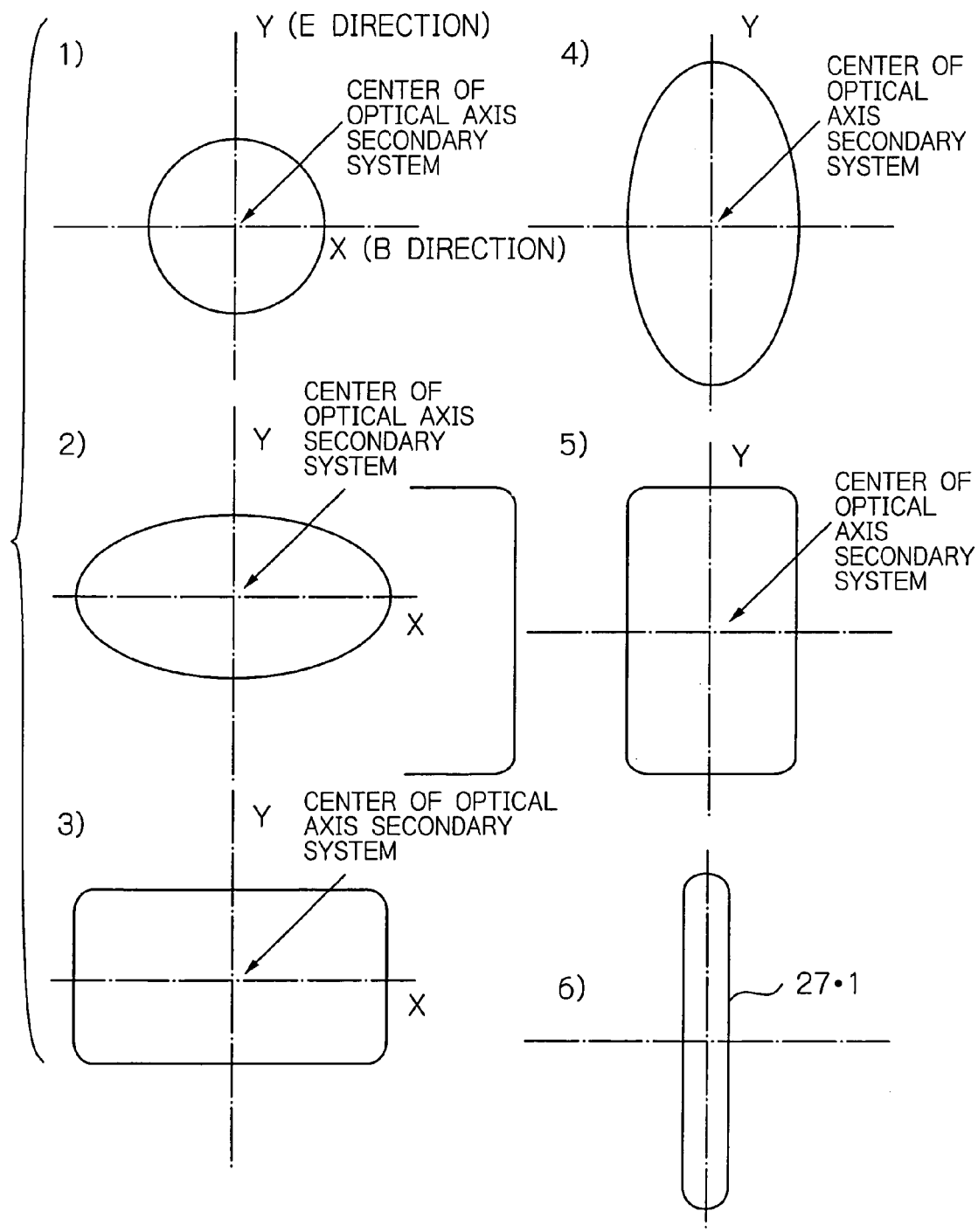
Figures 2, 27:
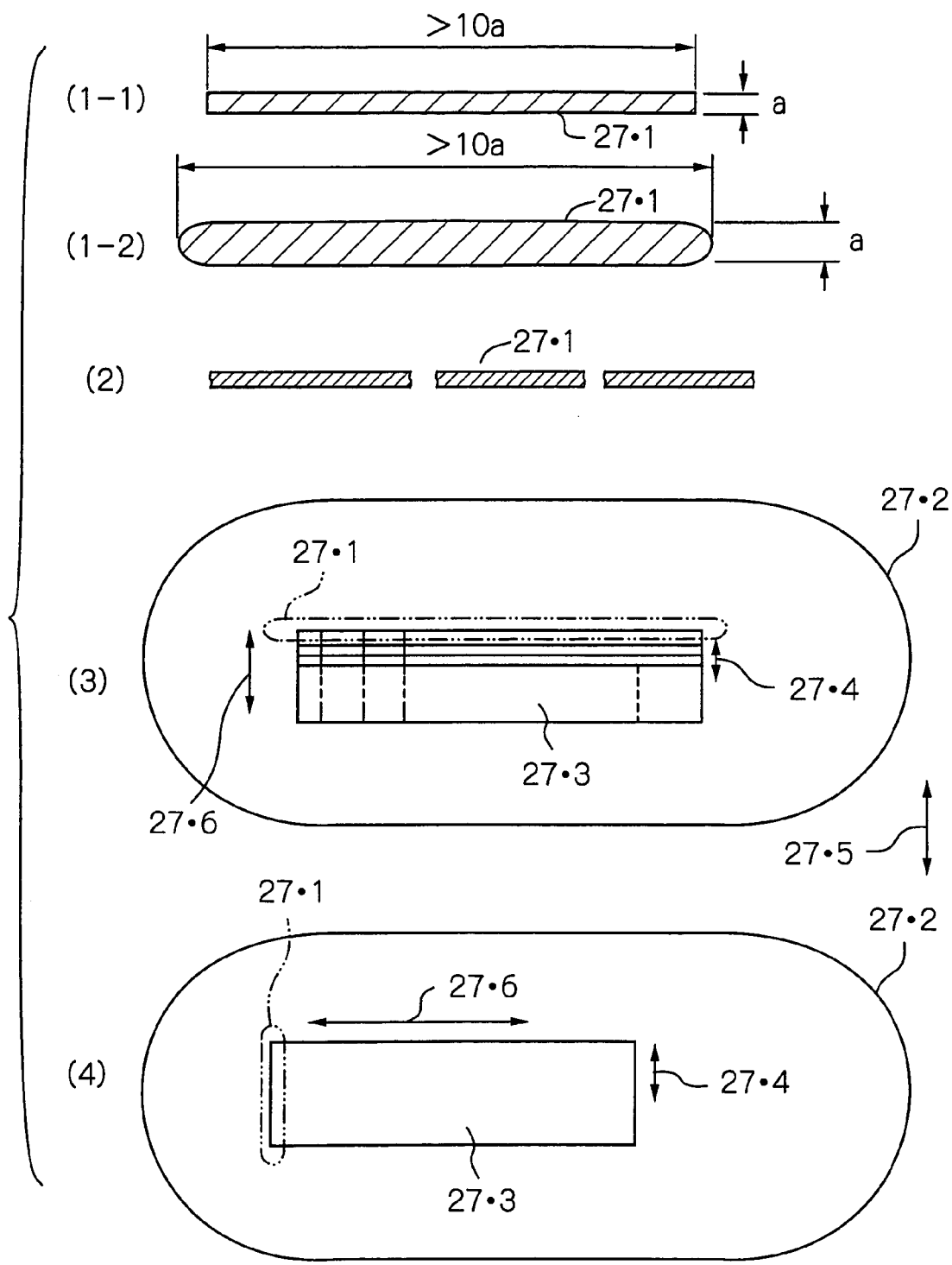
Figure 28:
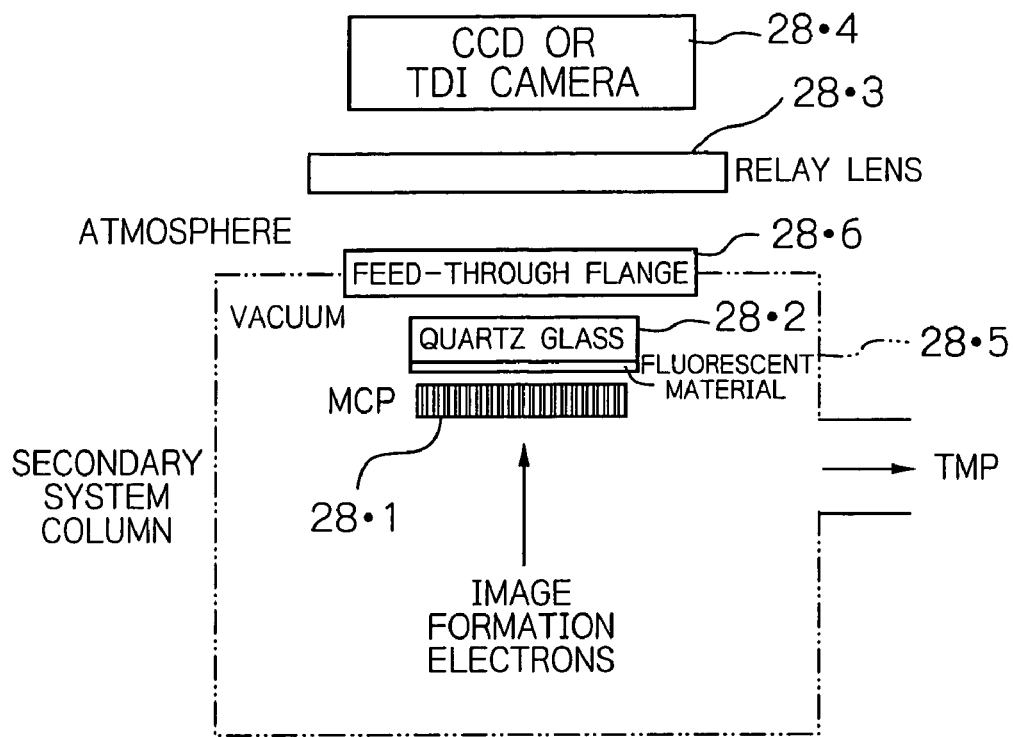
Figure 29:
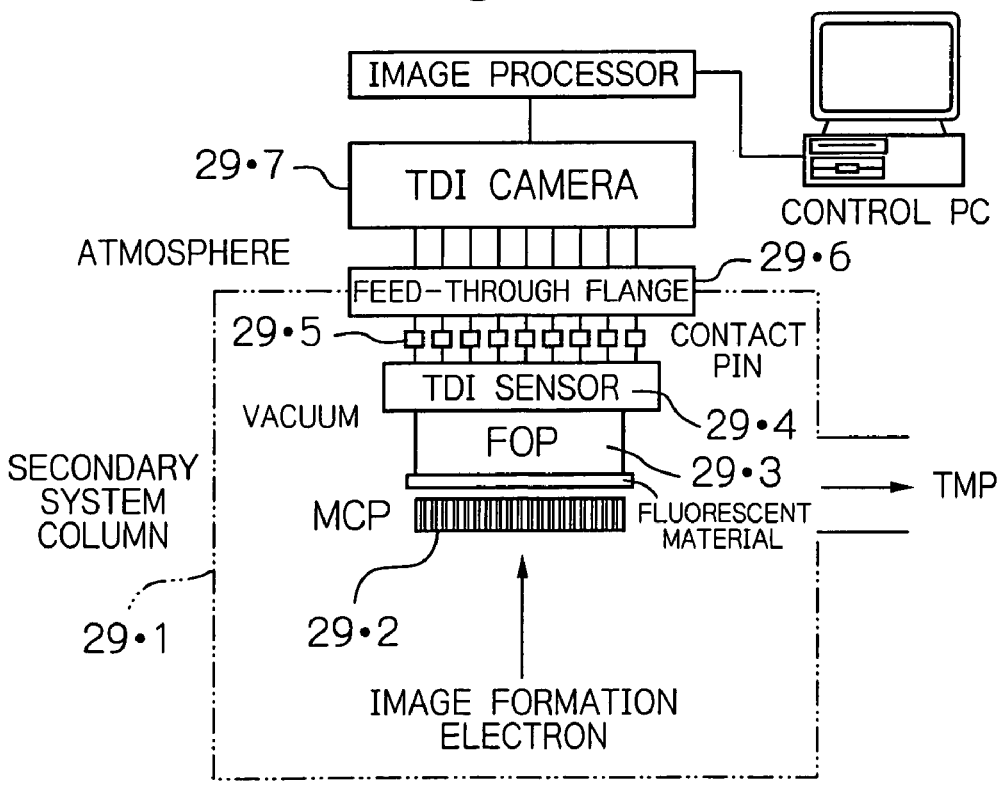
Figure 30:
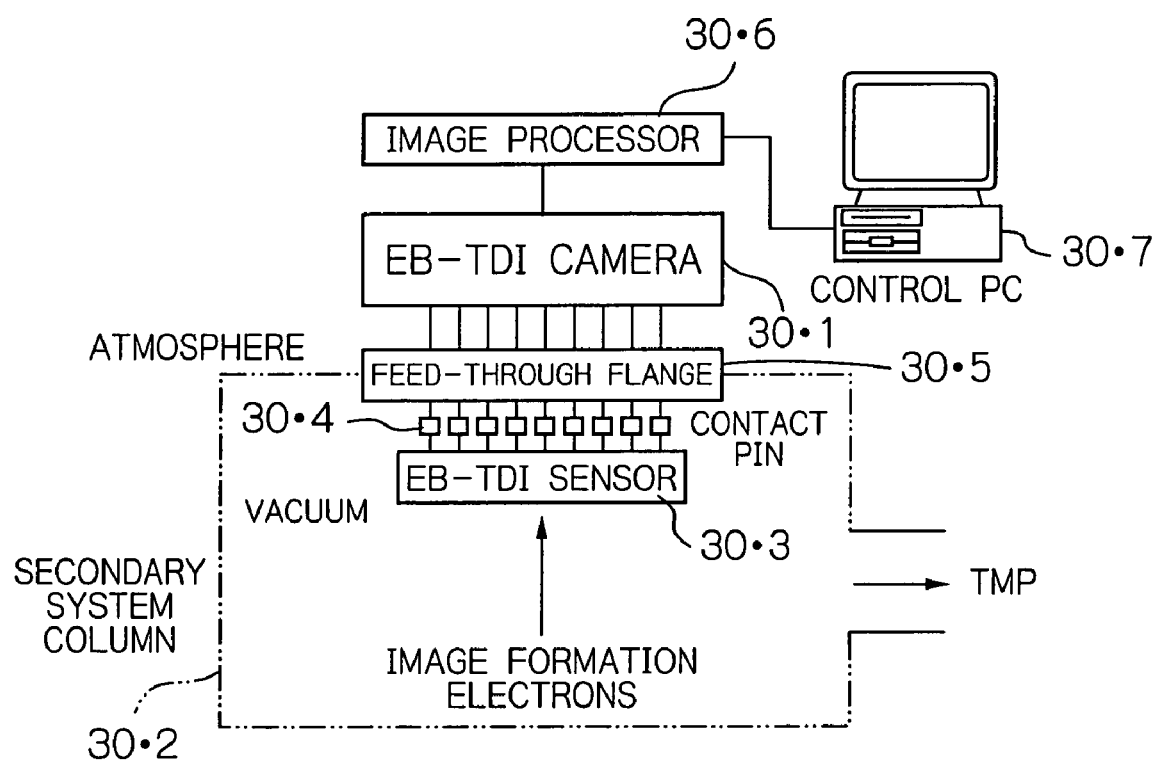
Figure 31:
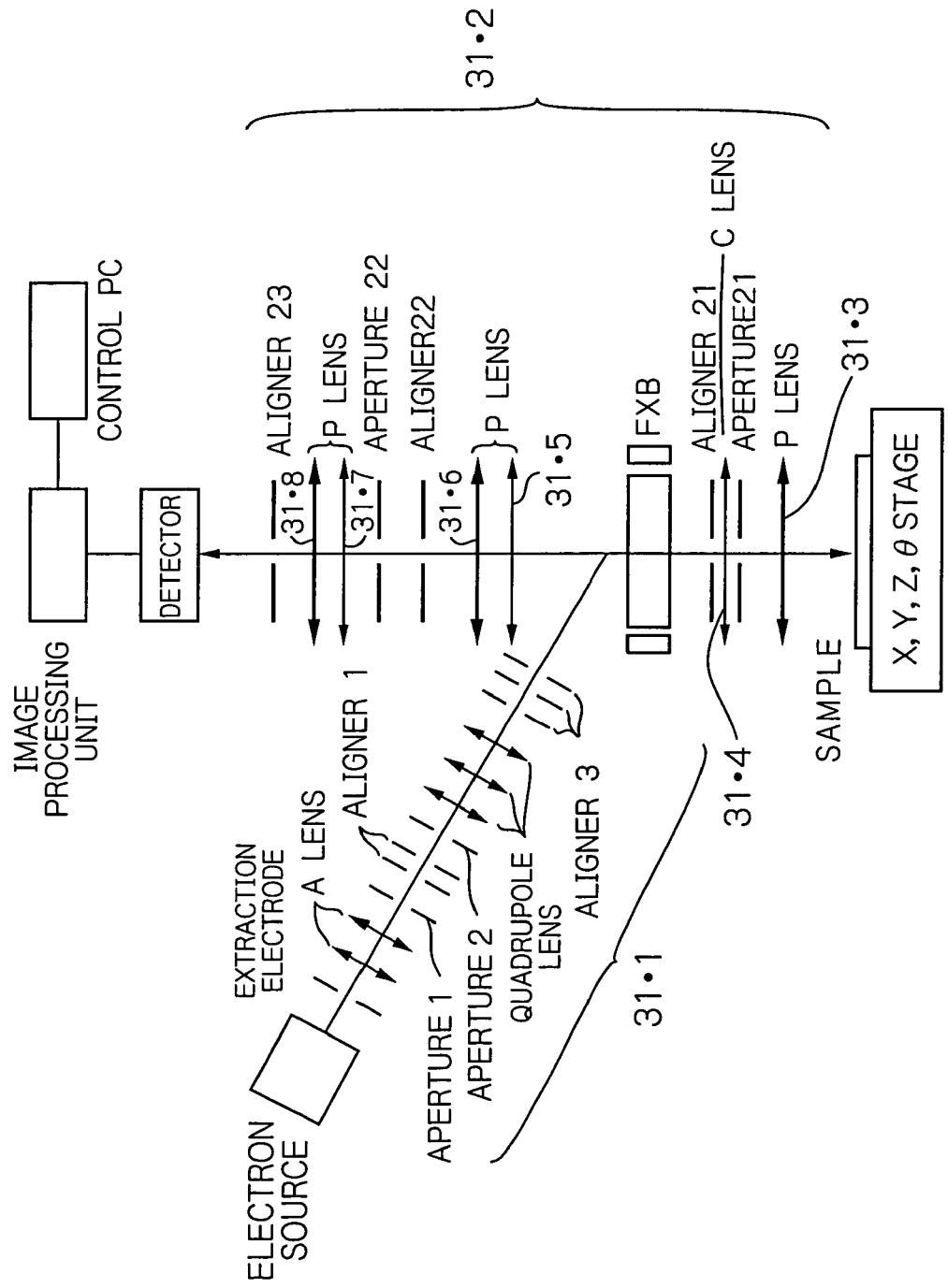
Figure 32:
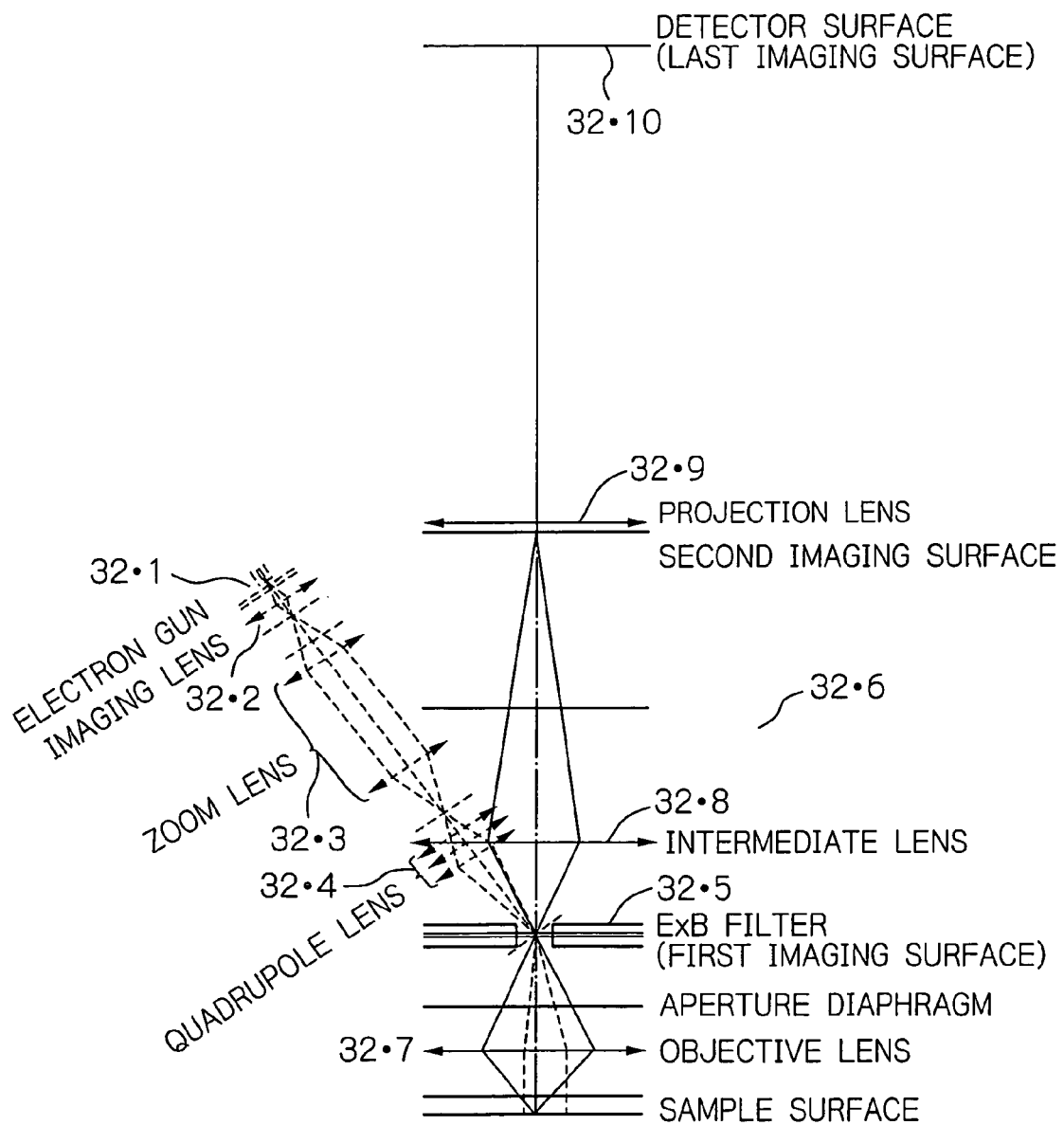
Figure 33:
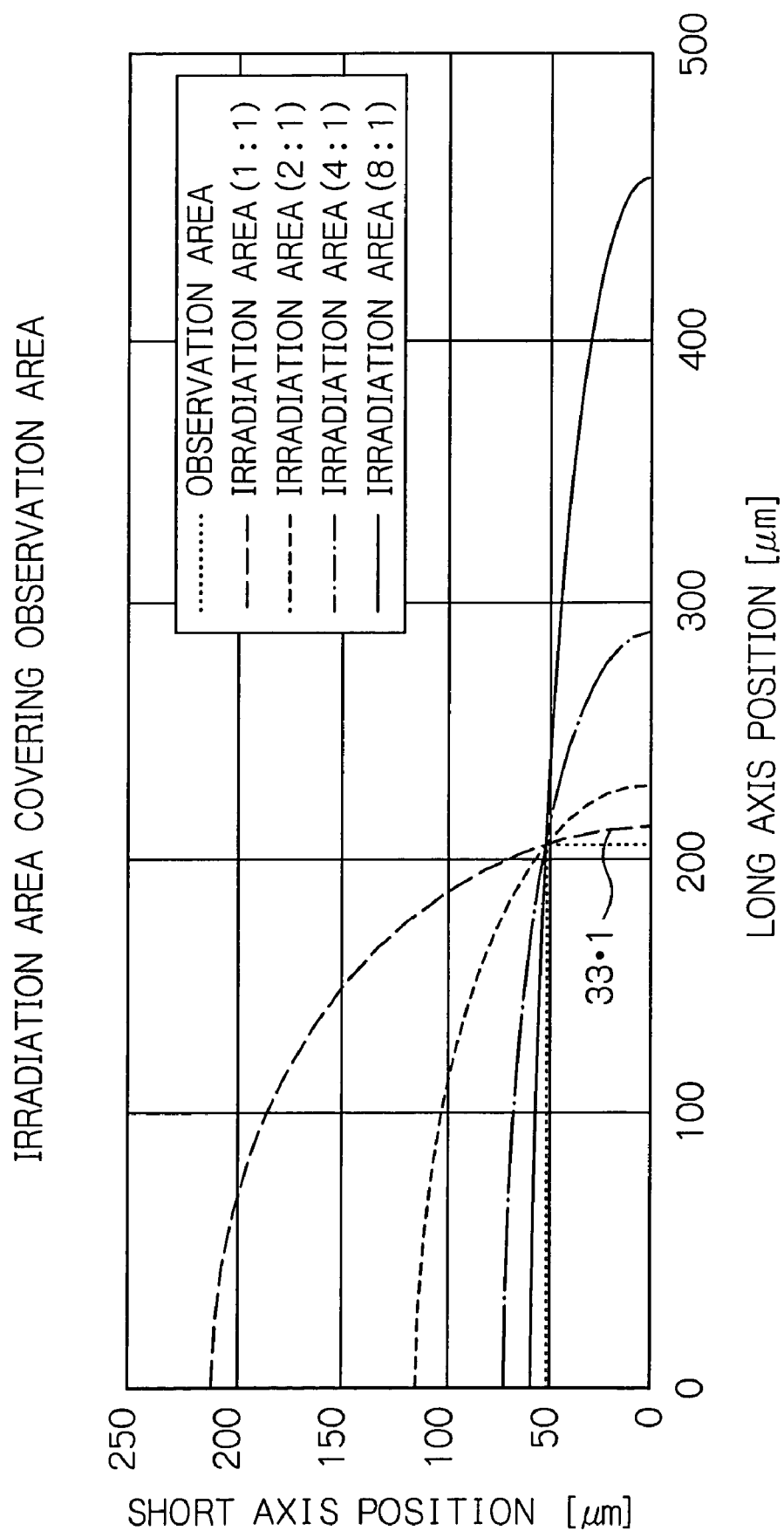
Figure 34:
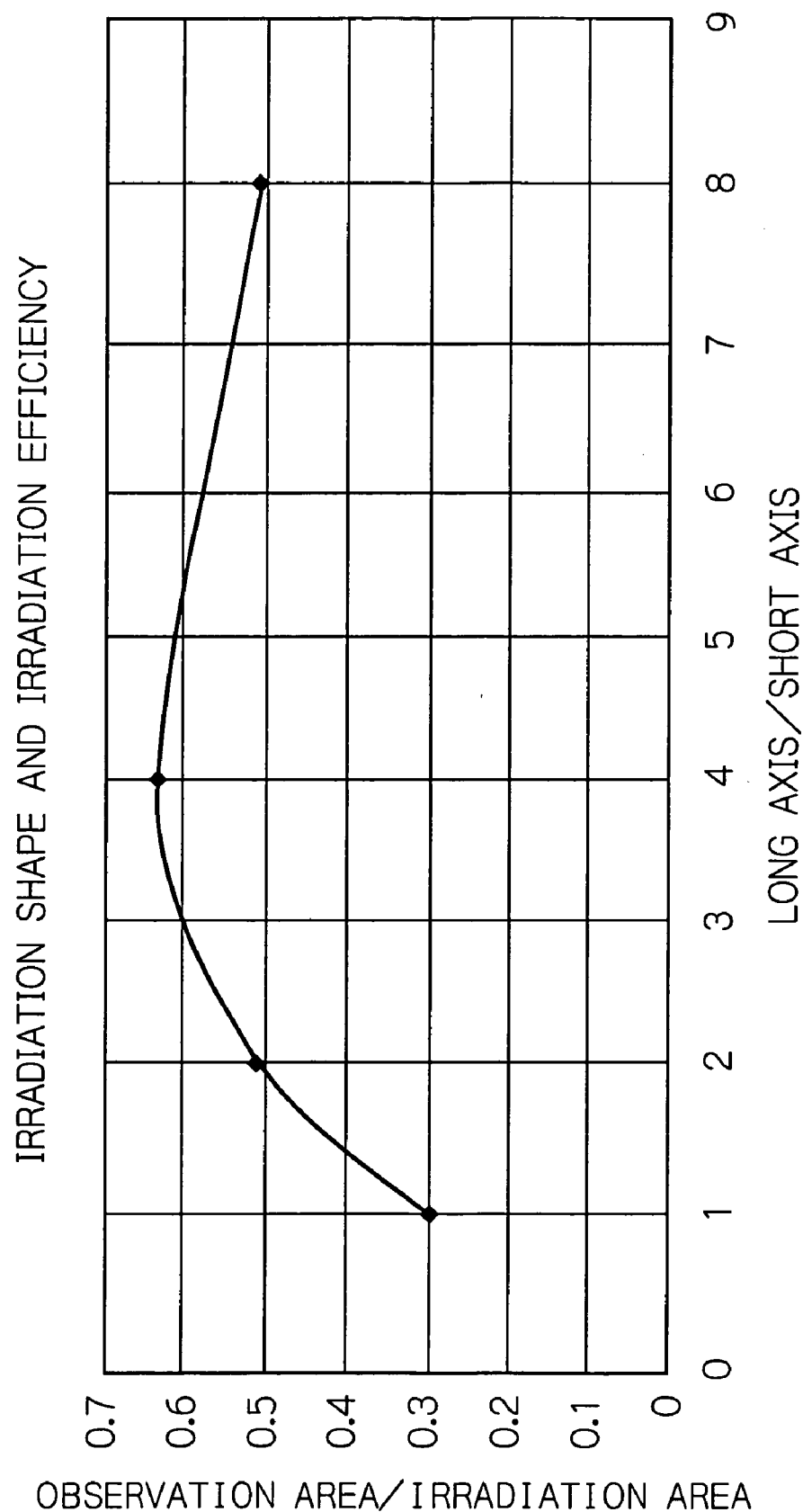
Figure 35:
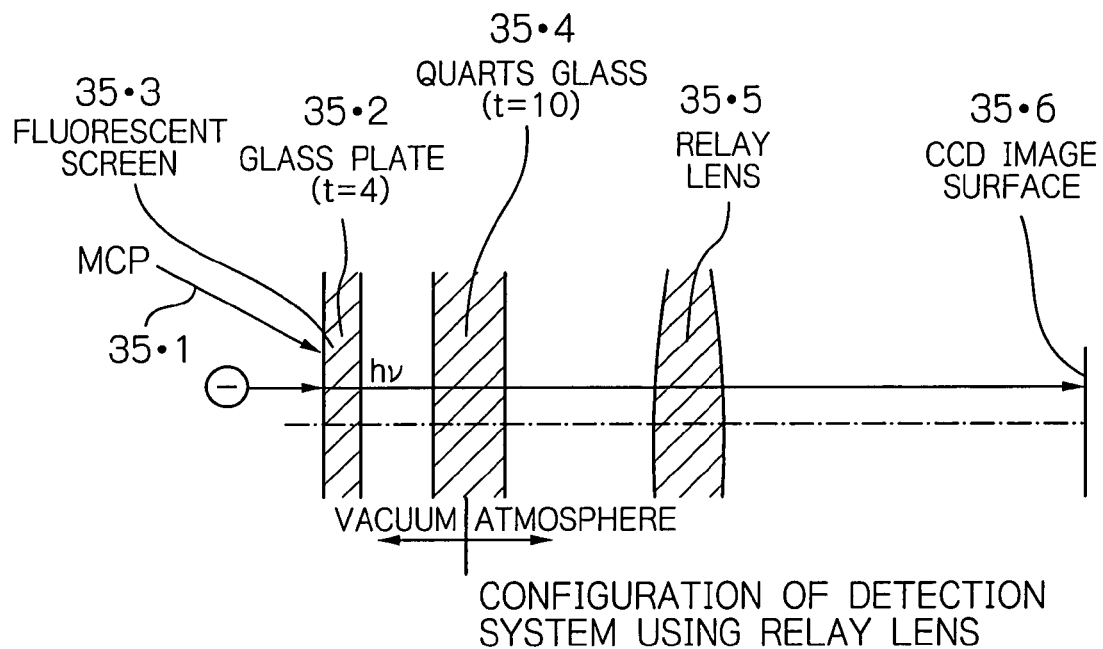
Figure 36:
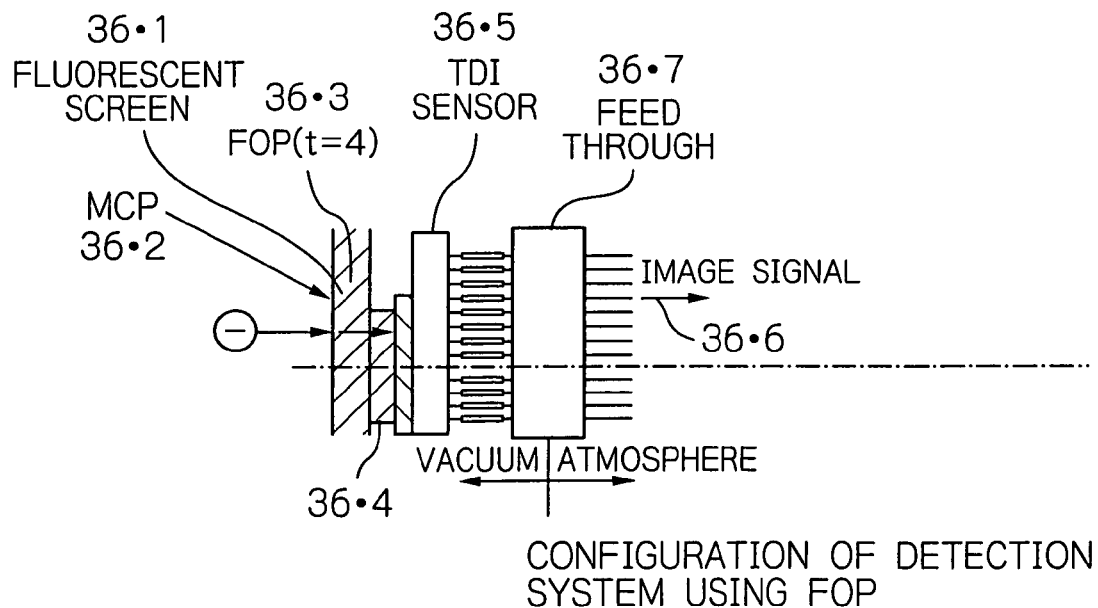
Figure 40A:
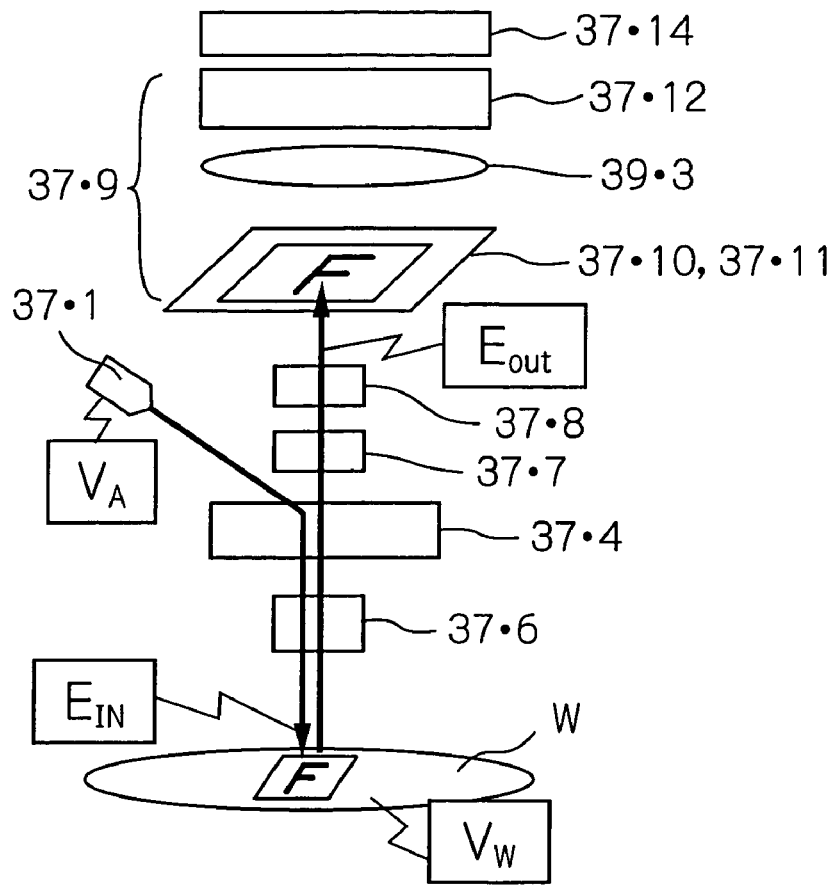
Figure 41:
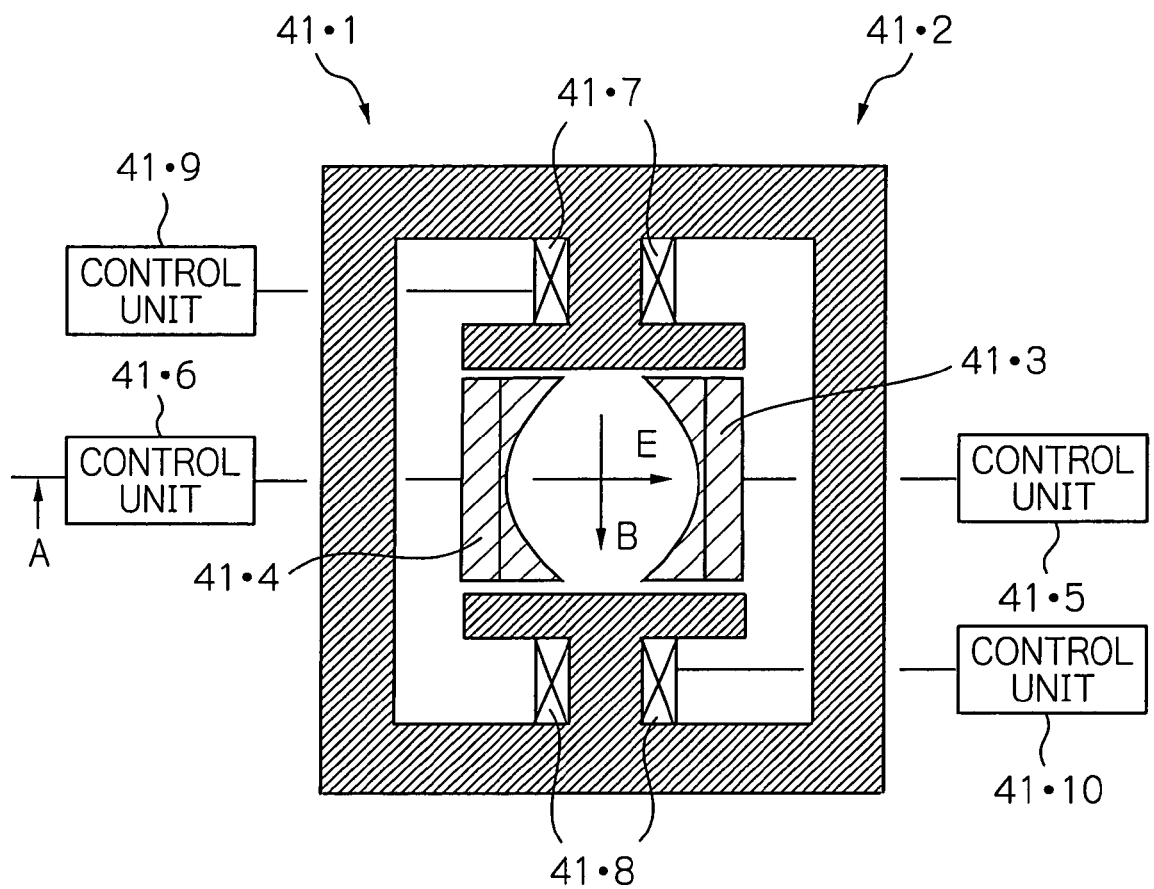
Figure 42:
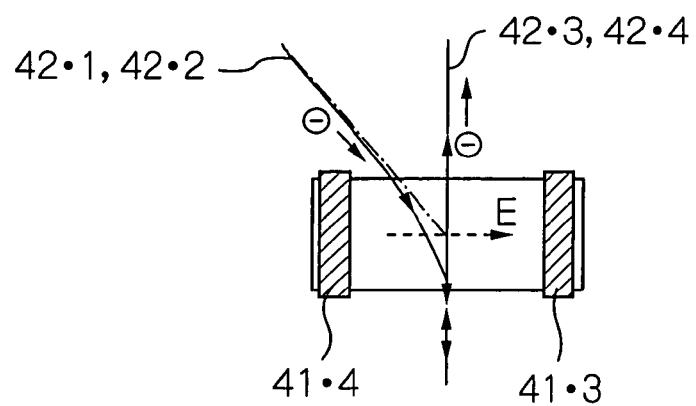
Figure 43:
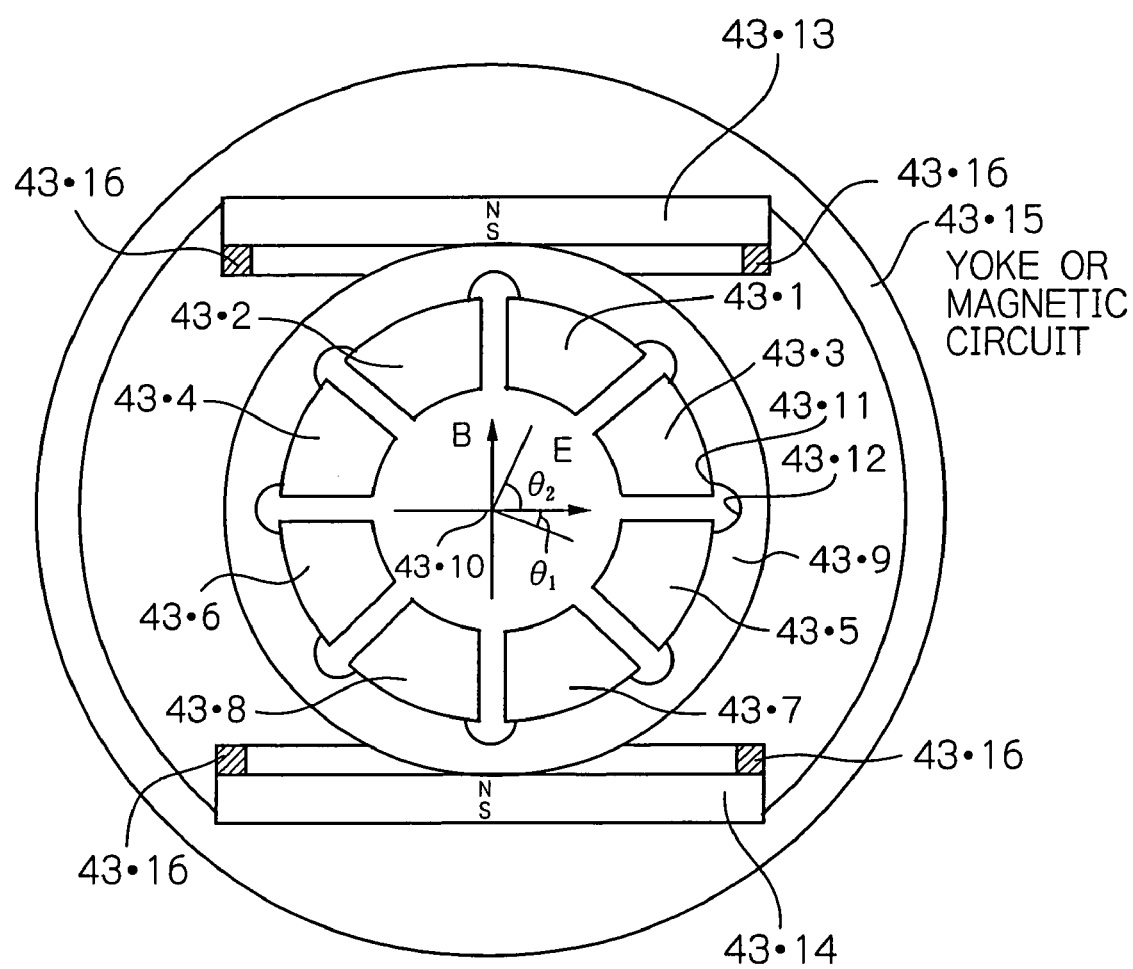
Figure 44:
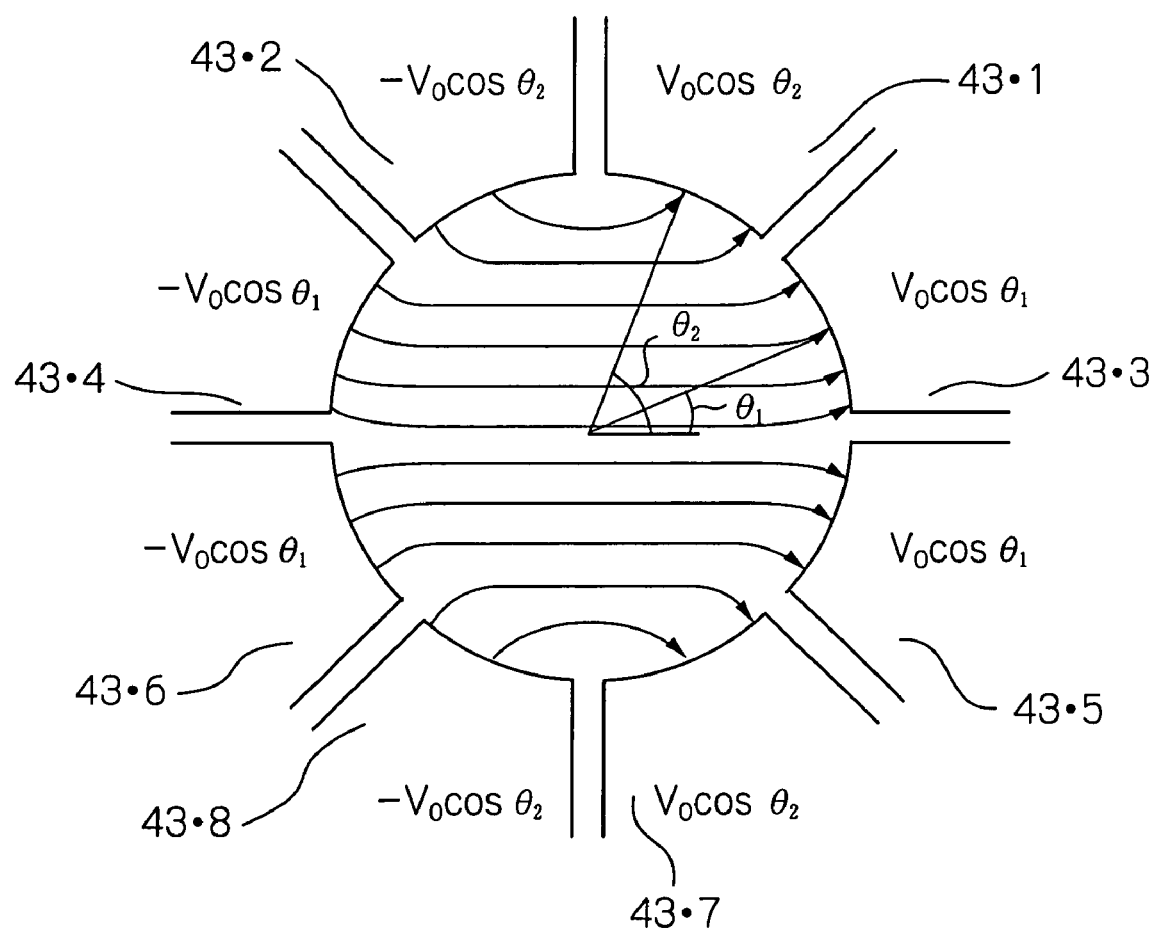
Figure 45:
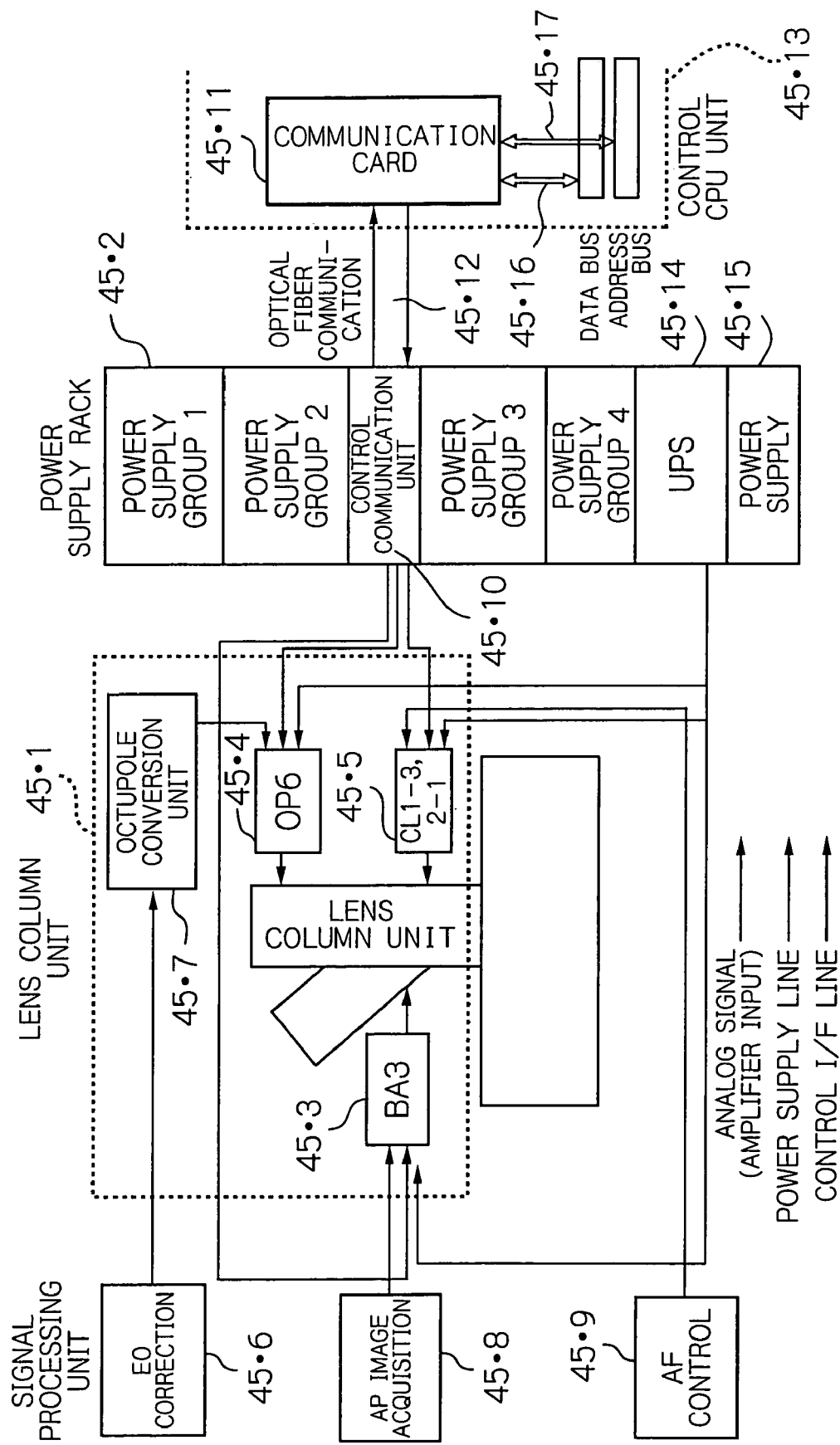
Figure 46:
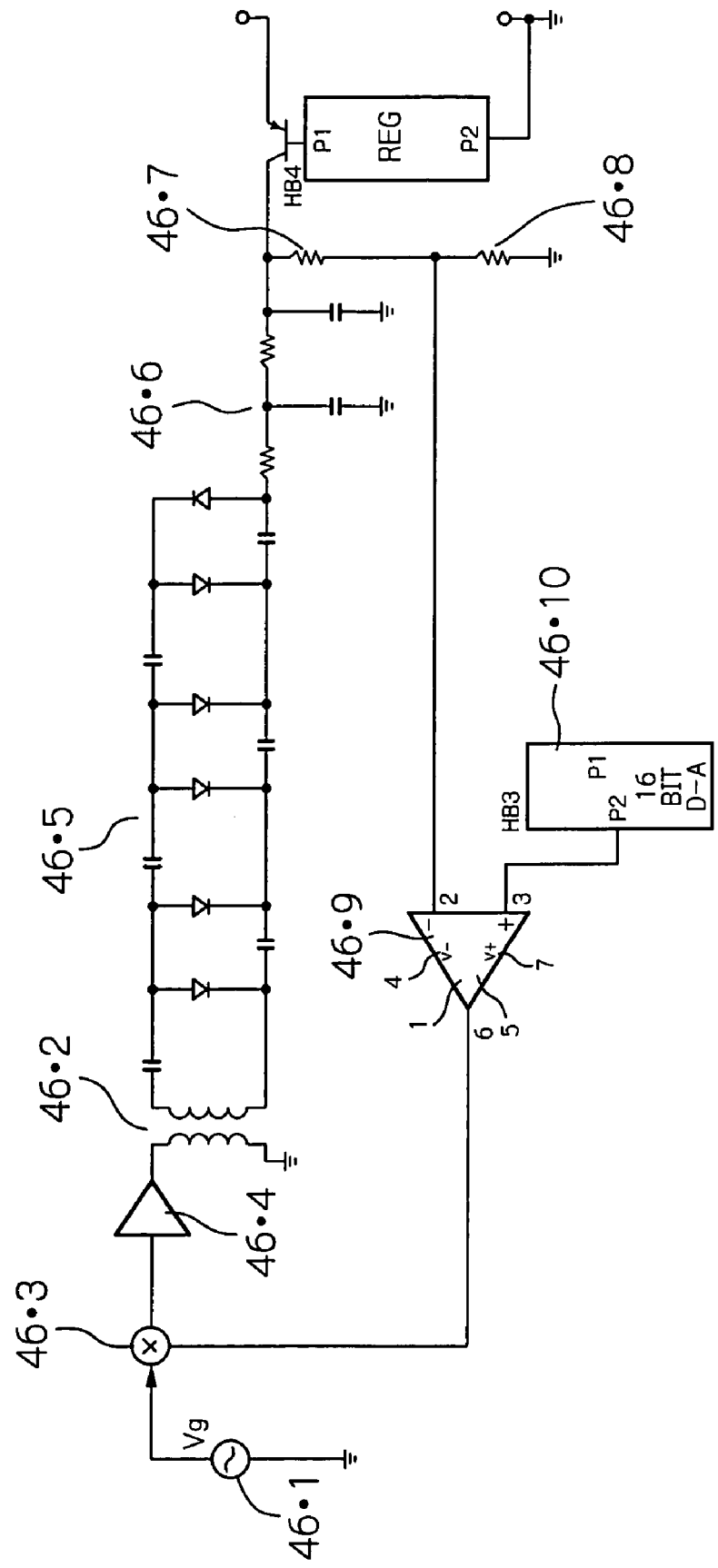
Figure 47:
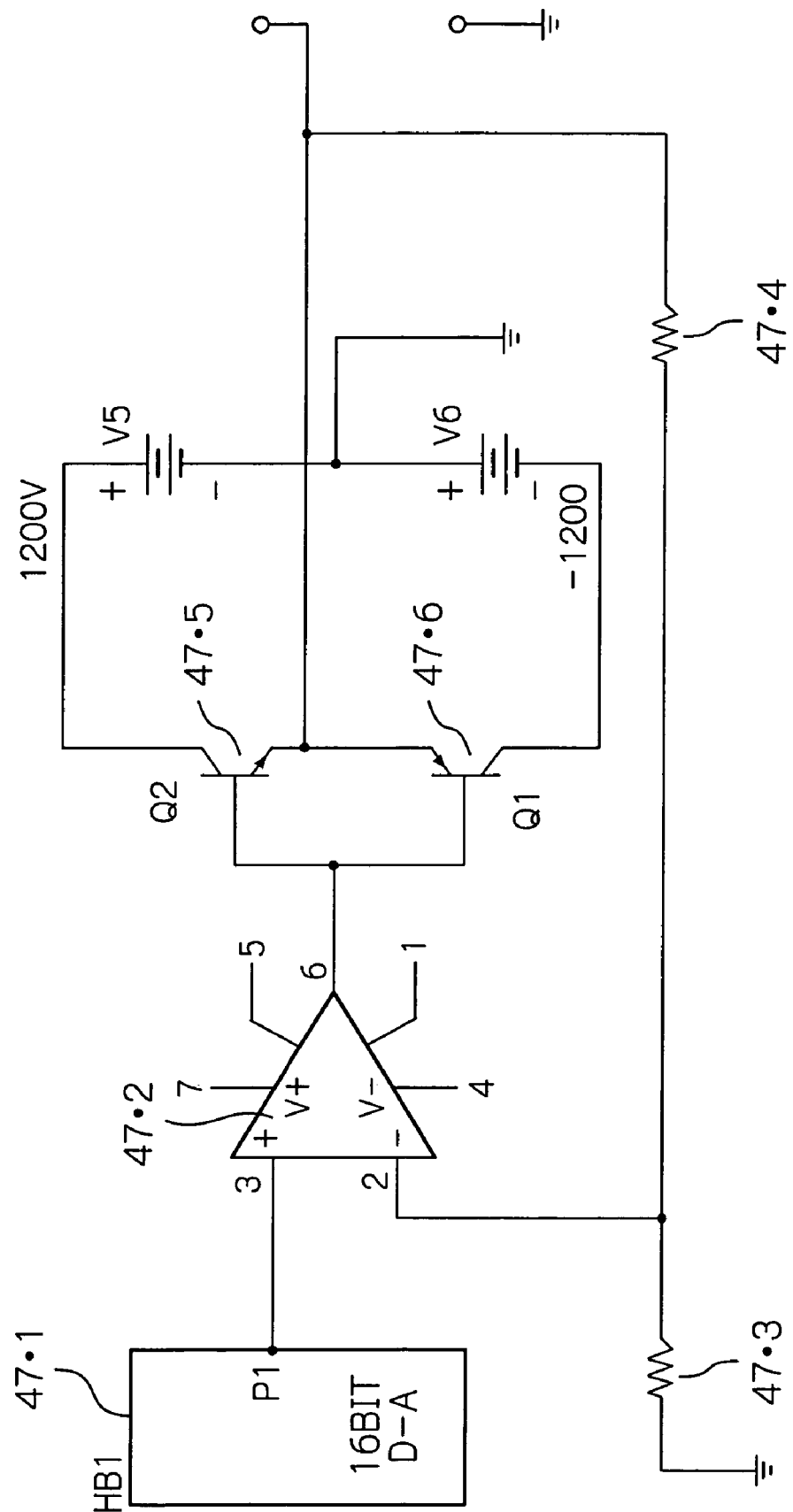
Figure 48:
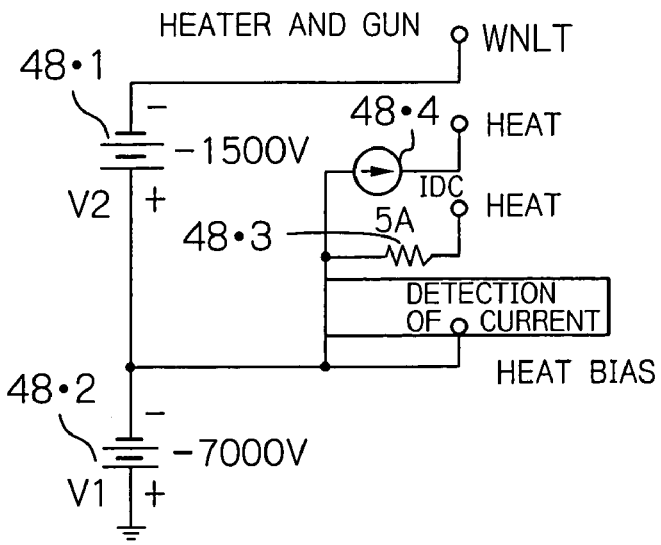
Figure 49:
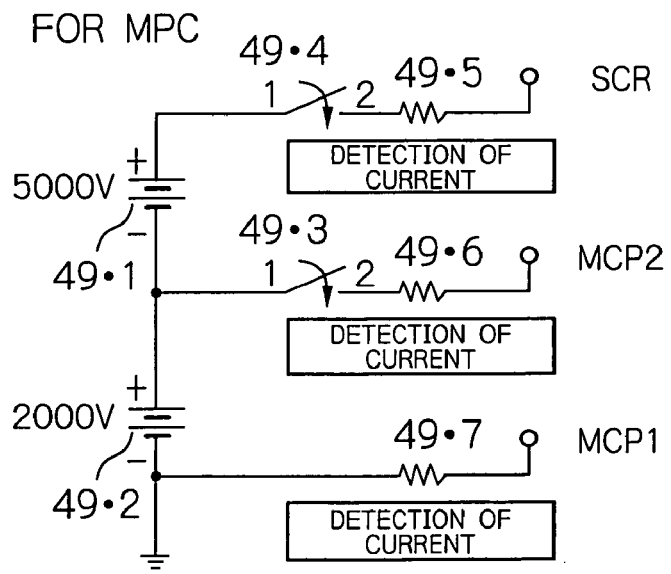
Figure 50:
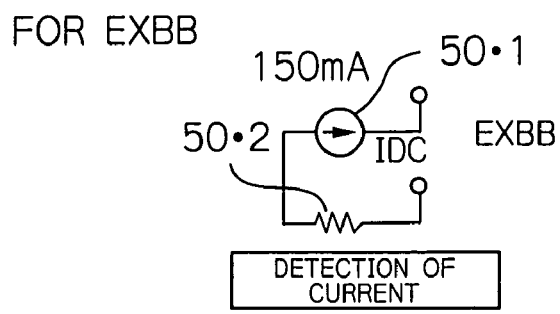
Figure 51:
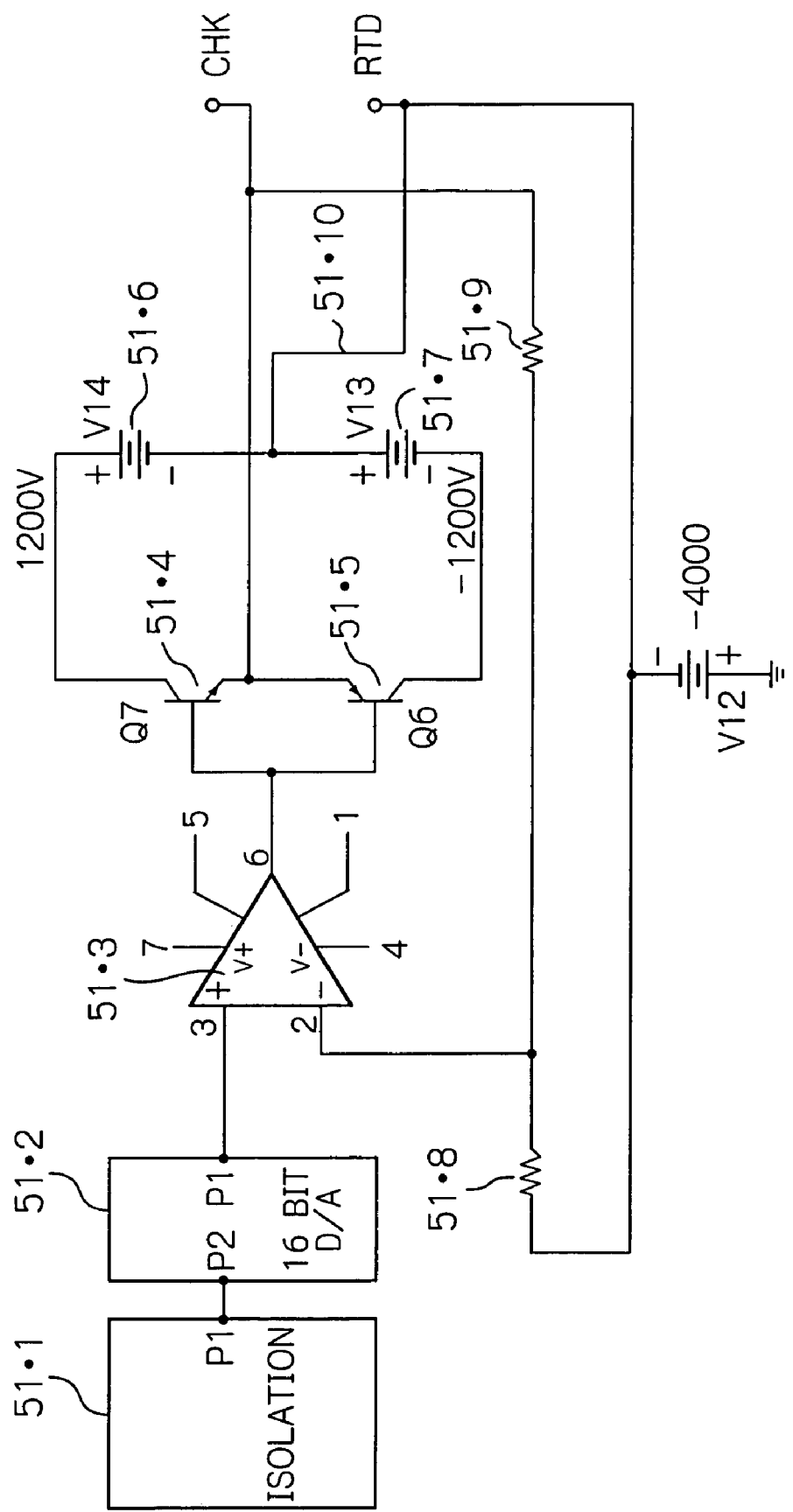
Figure 52:
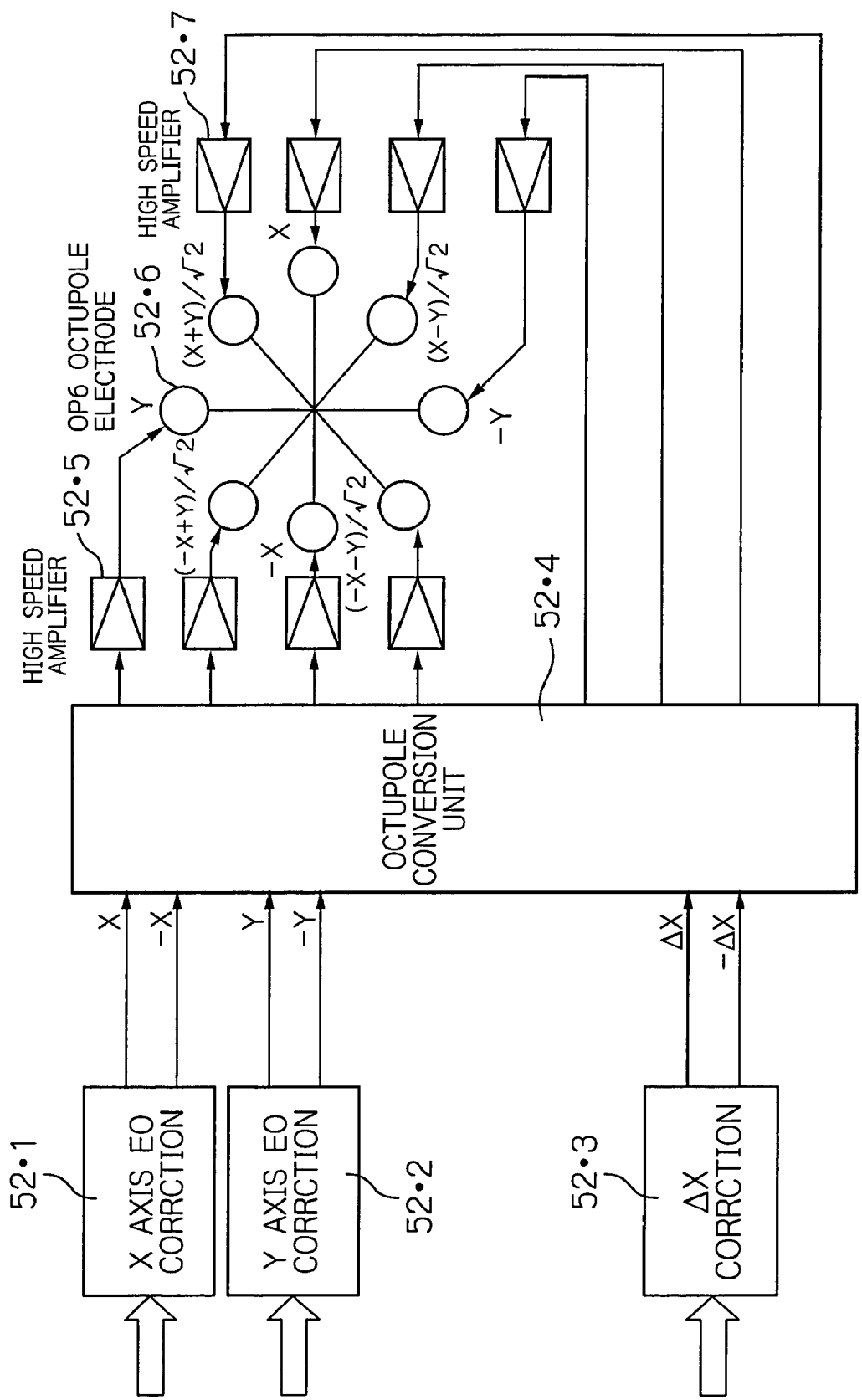
Figure 53:
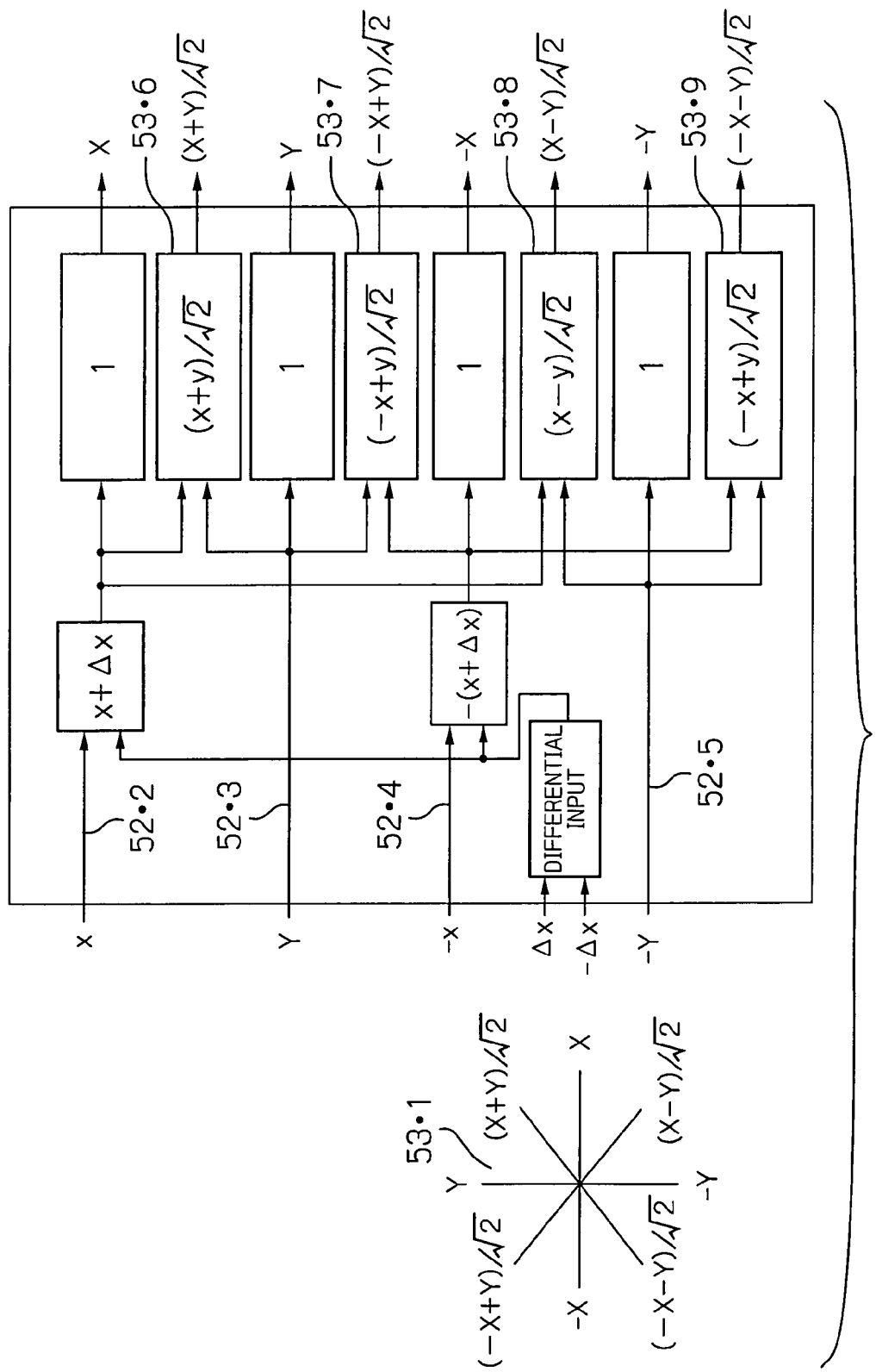
Figure 54A:
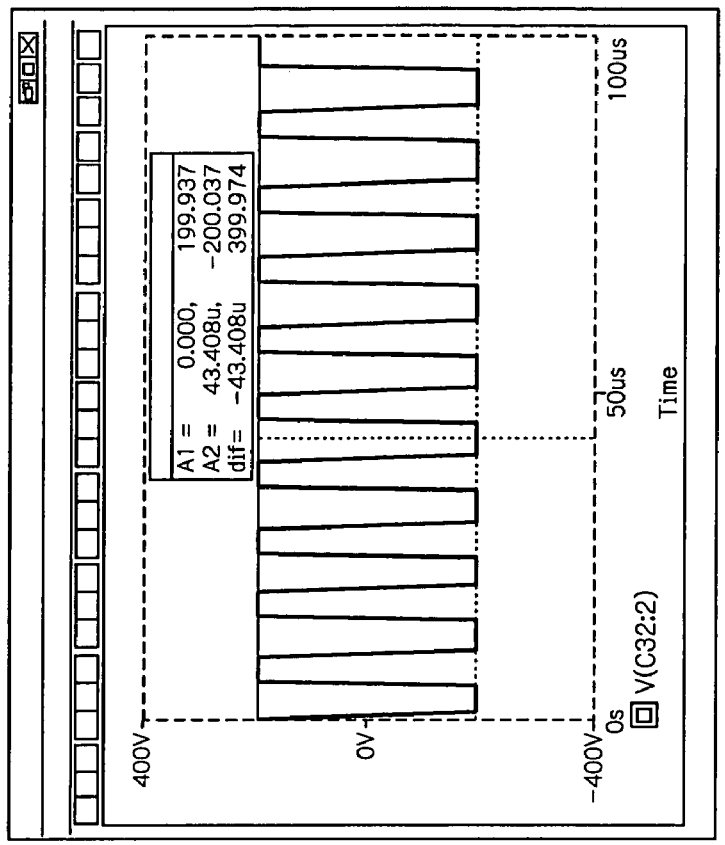
Figure 54B:
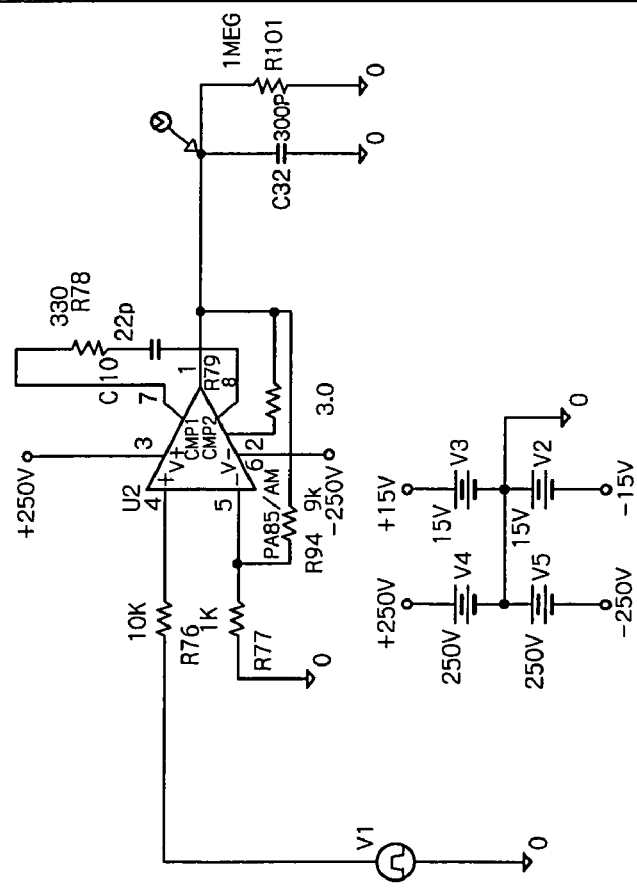
Figure 55:
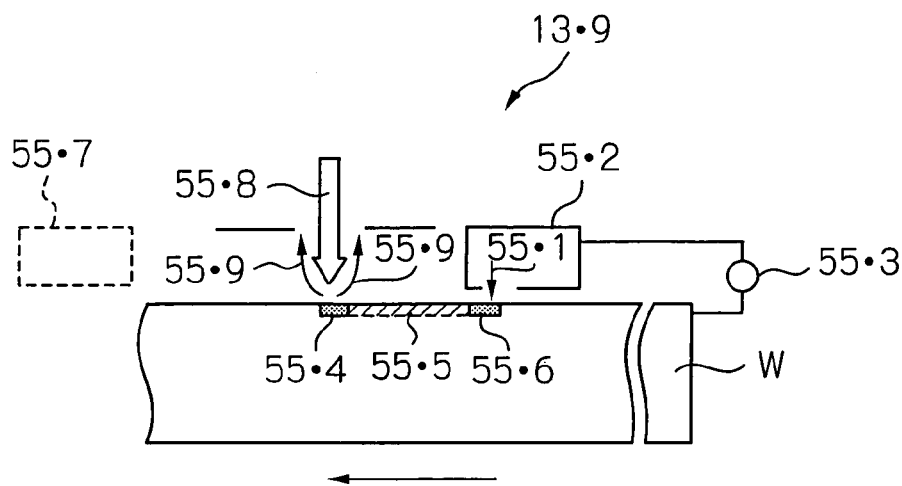
Figure 56:
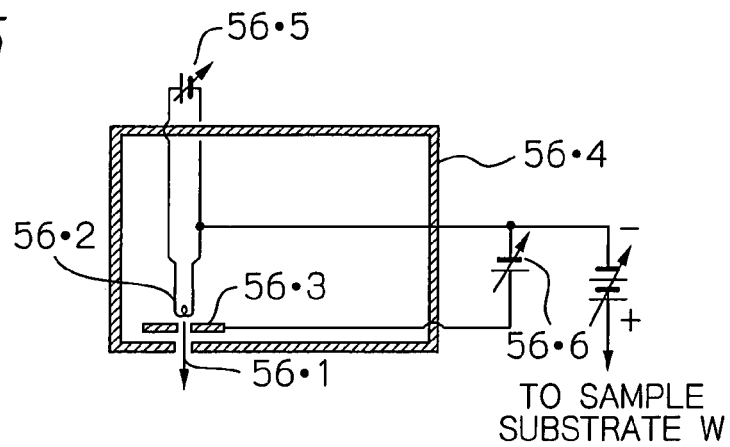
Figure 57:
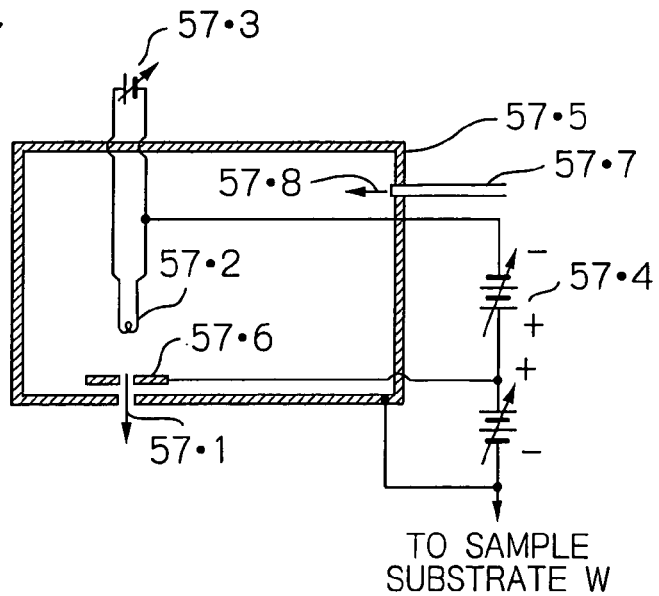
Figure 58:
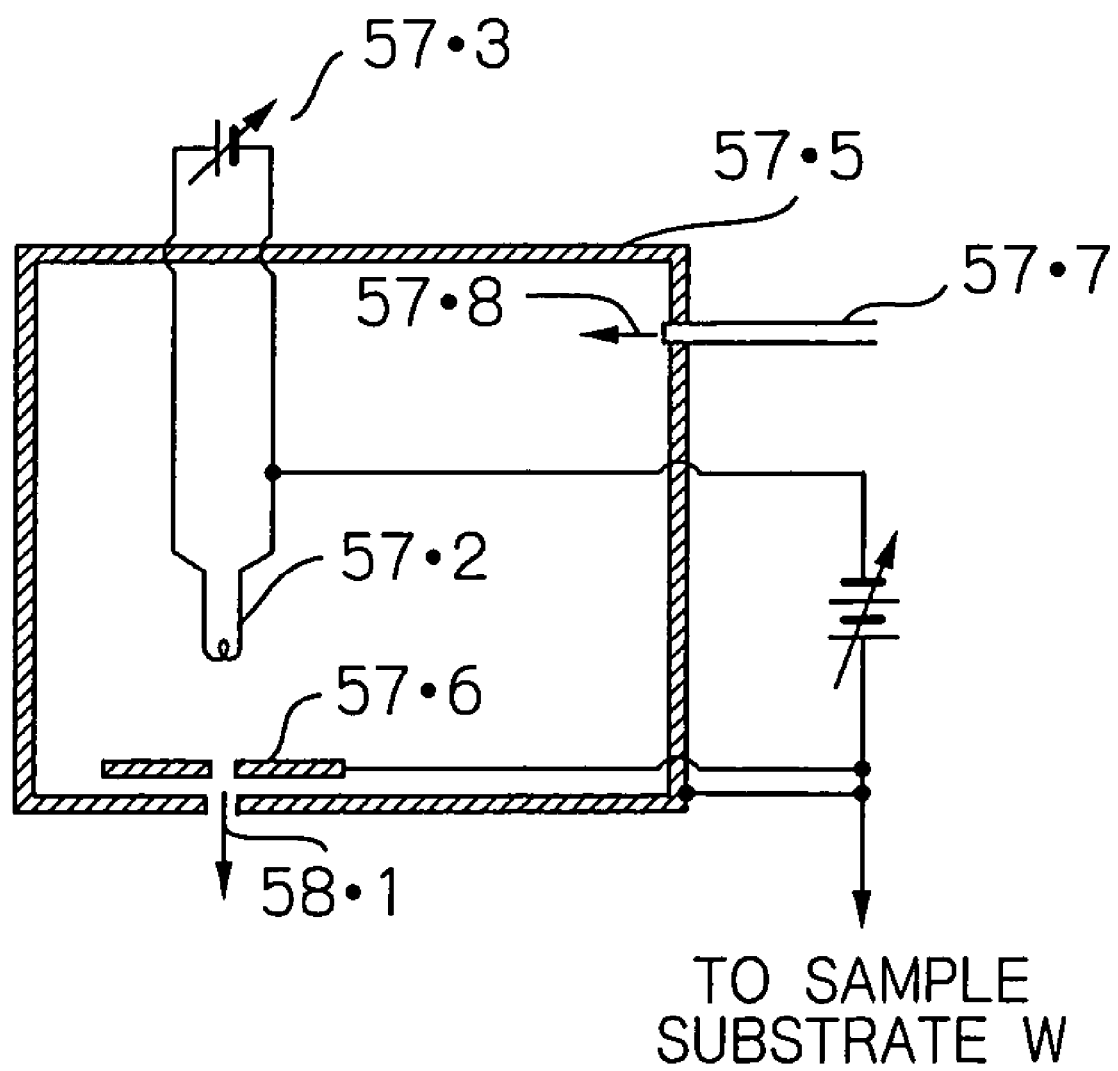
Figure 59:
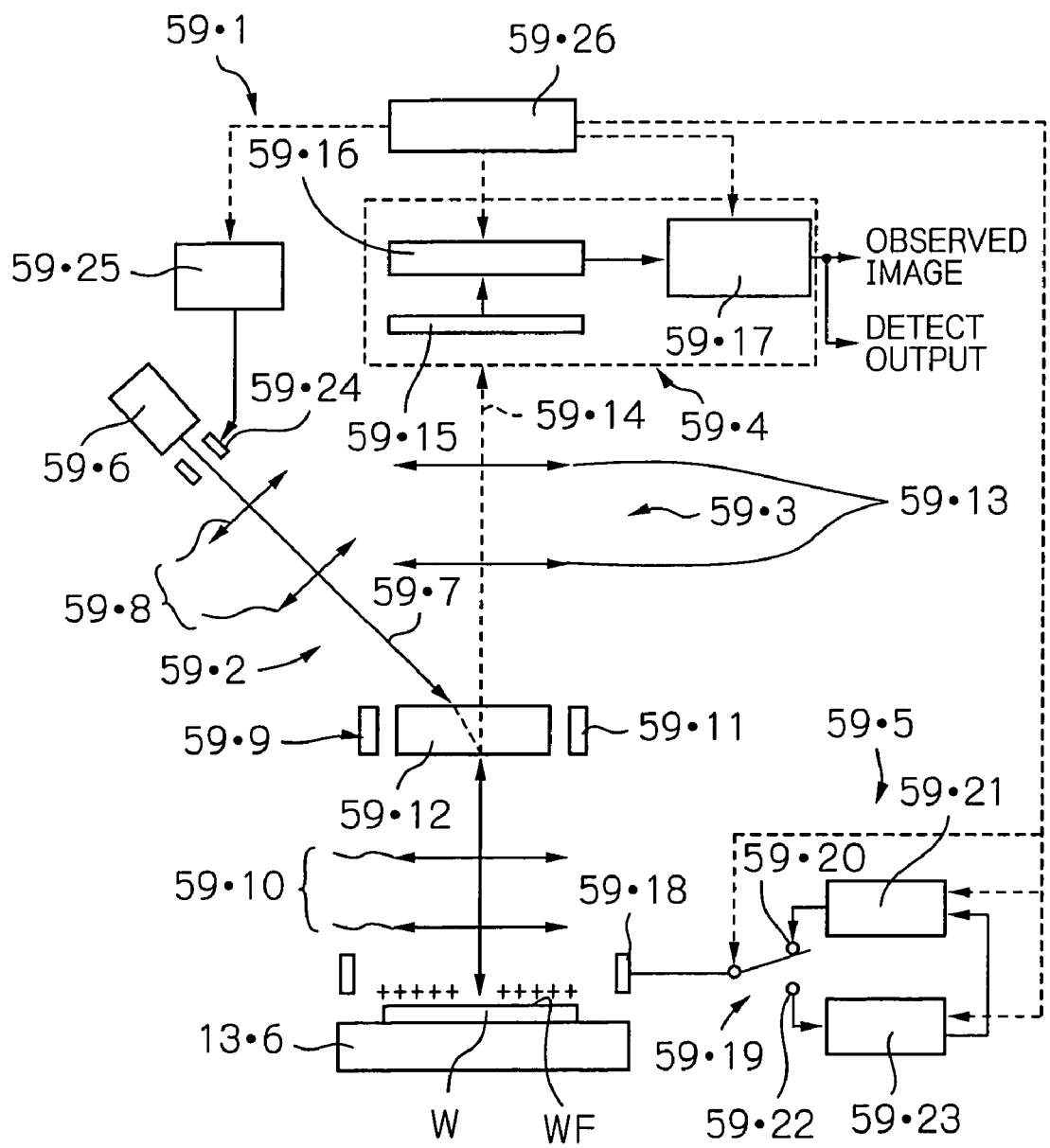
Figure 60:
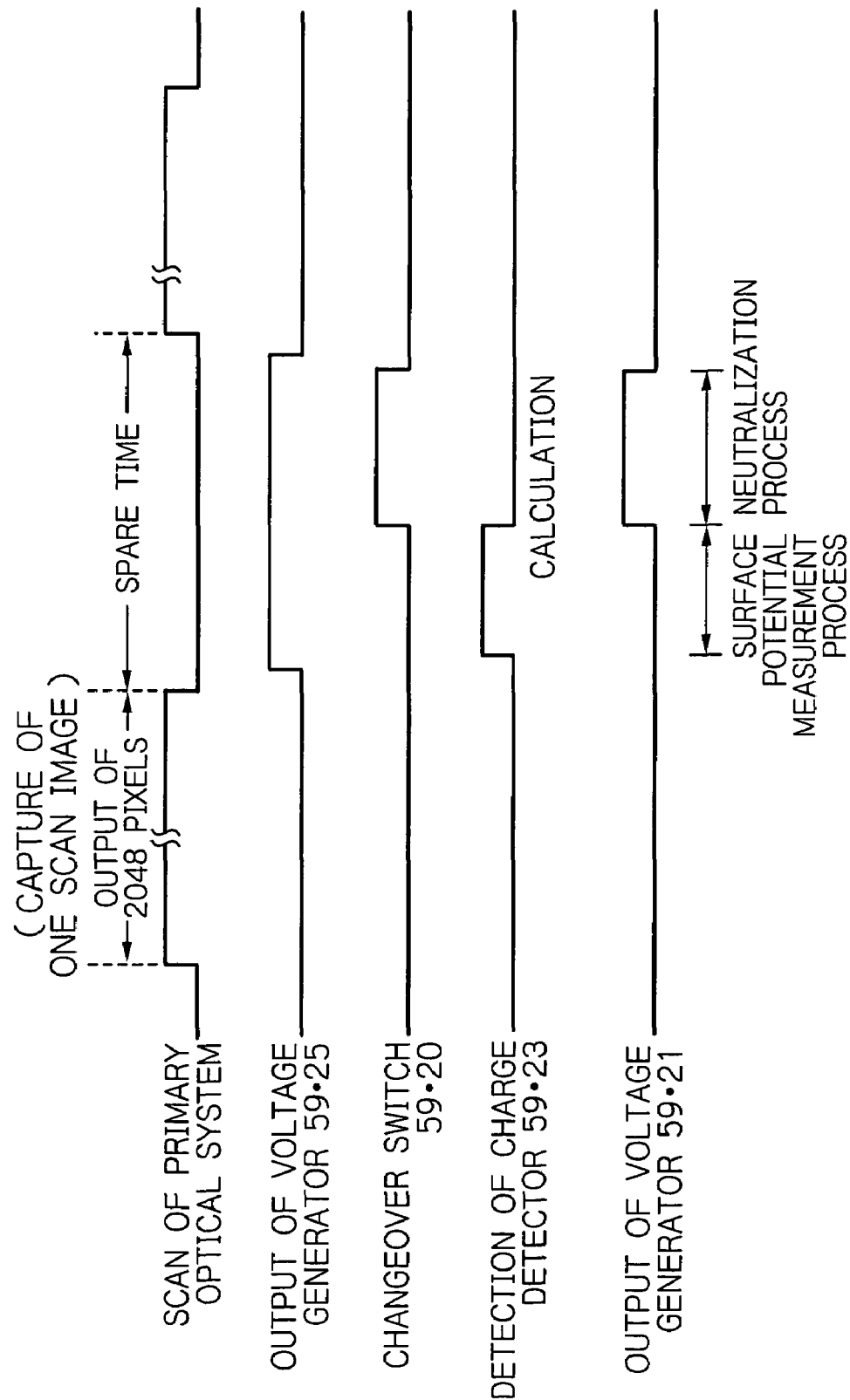
Figure 61:
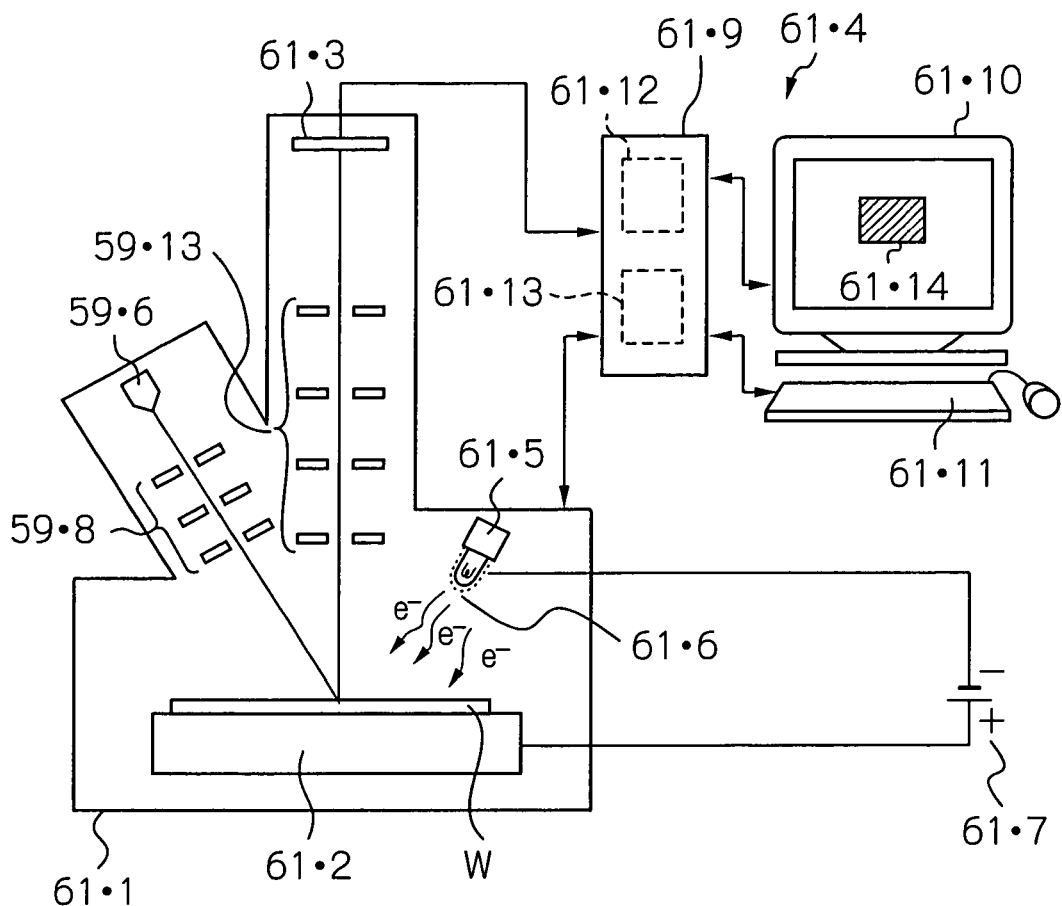
Figure 62:
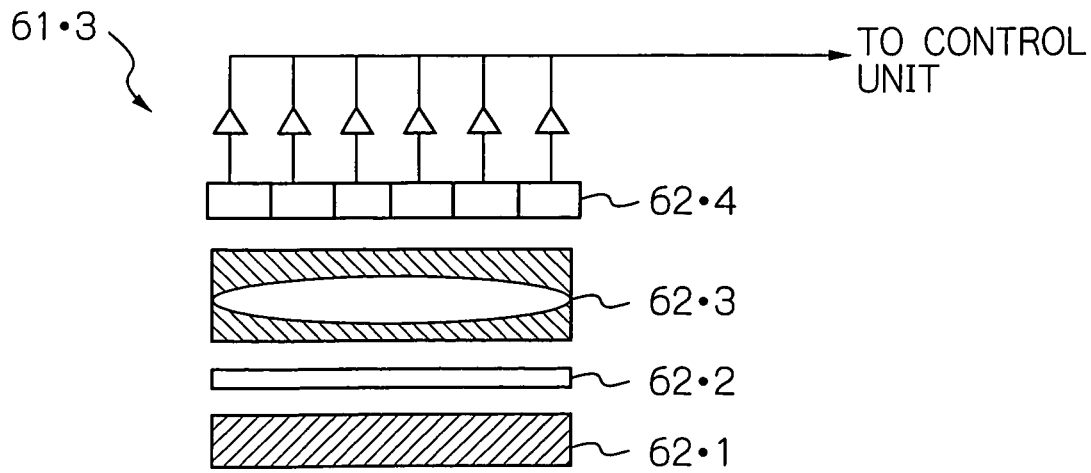
Figure 64A:
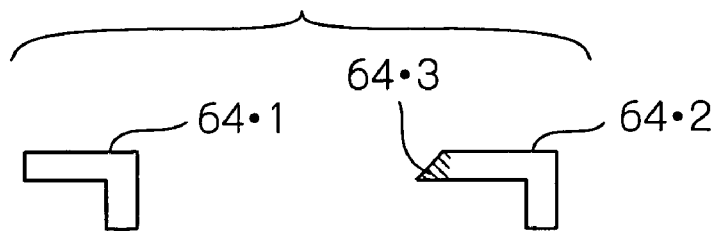
Figure 64B:
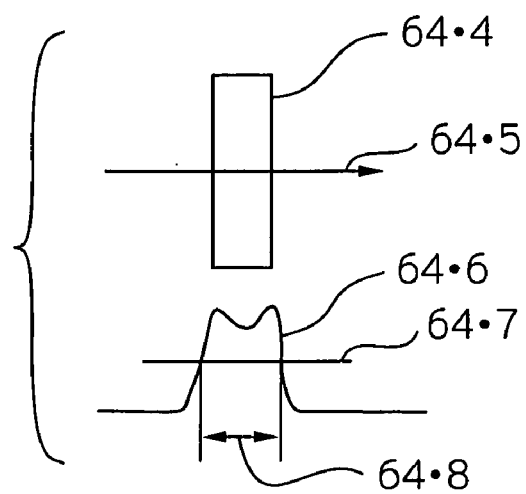
Figure 64C:
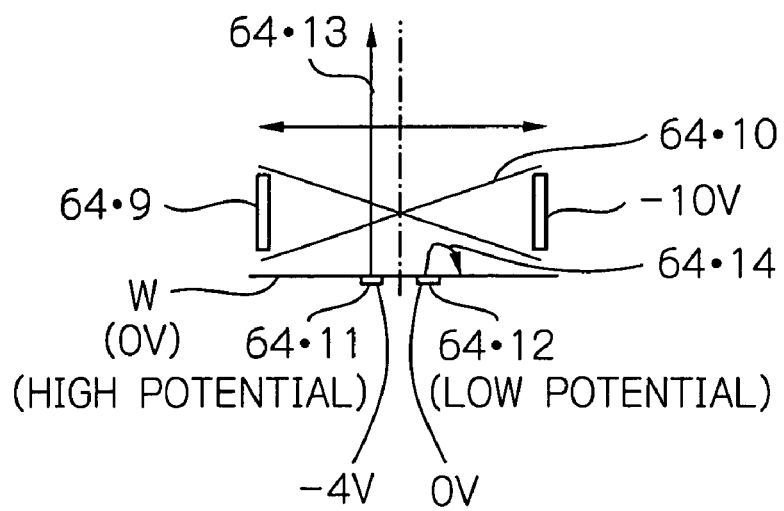
Figure 65:
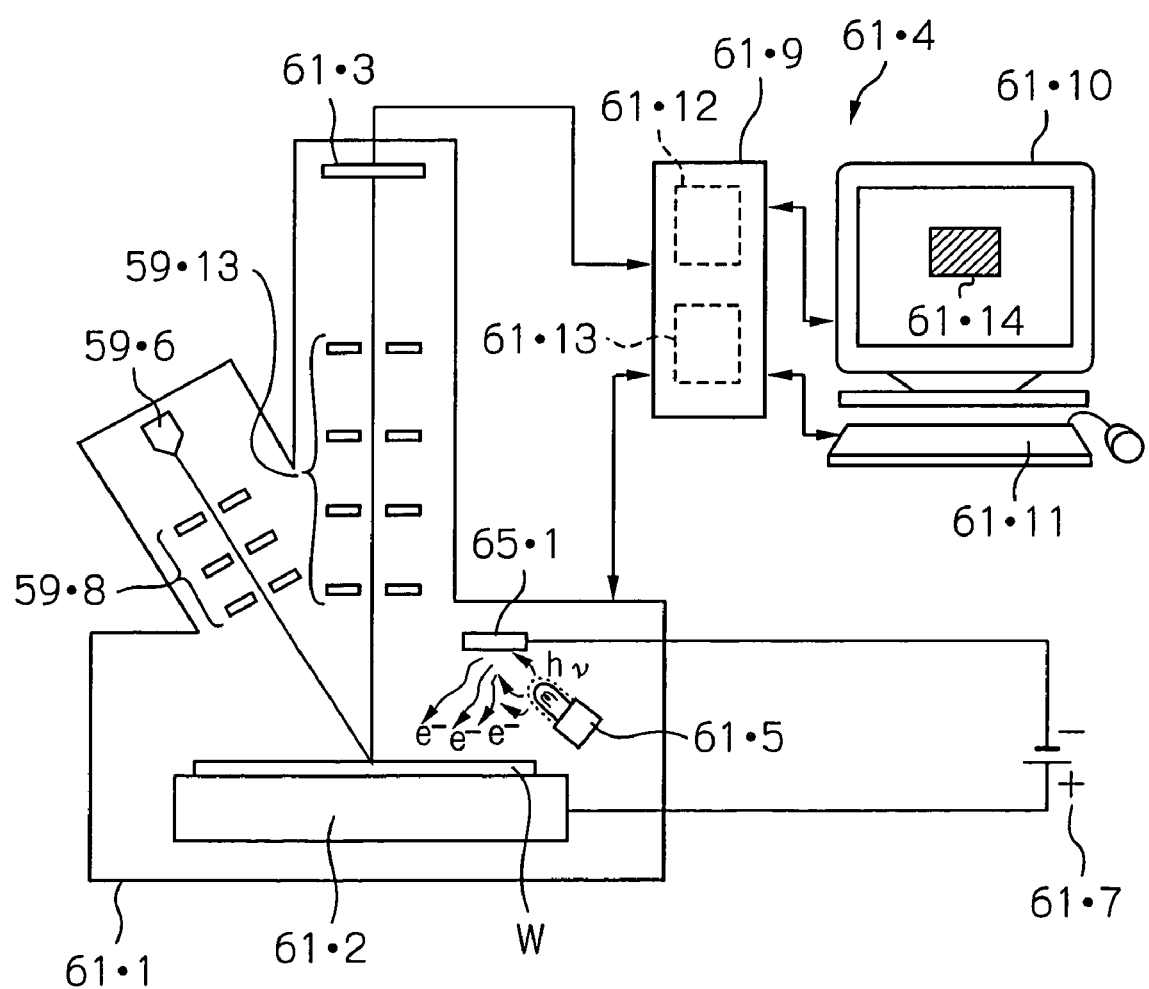
Figure 66:
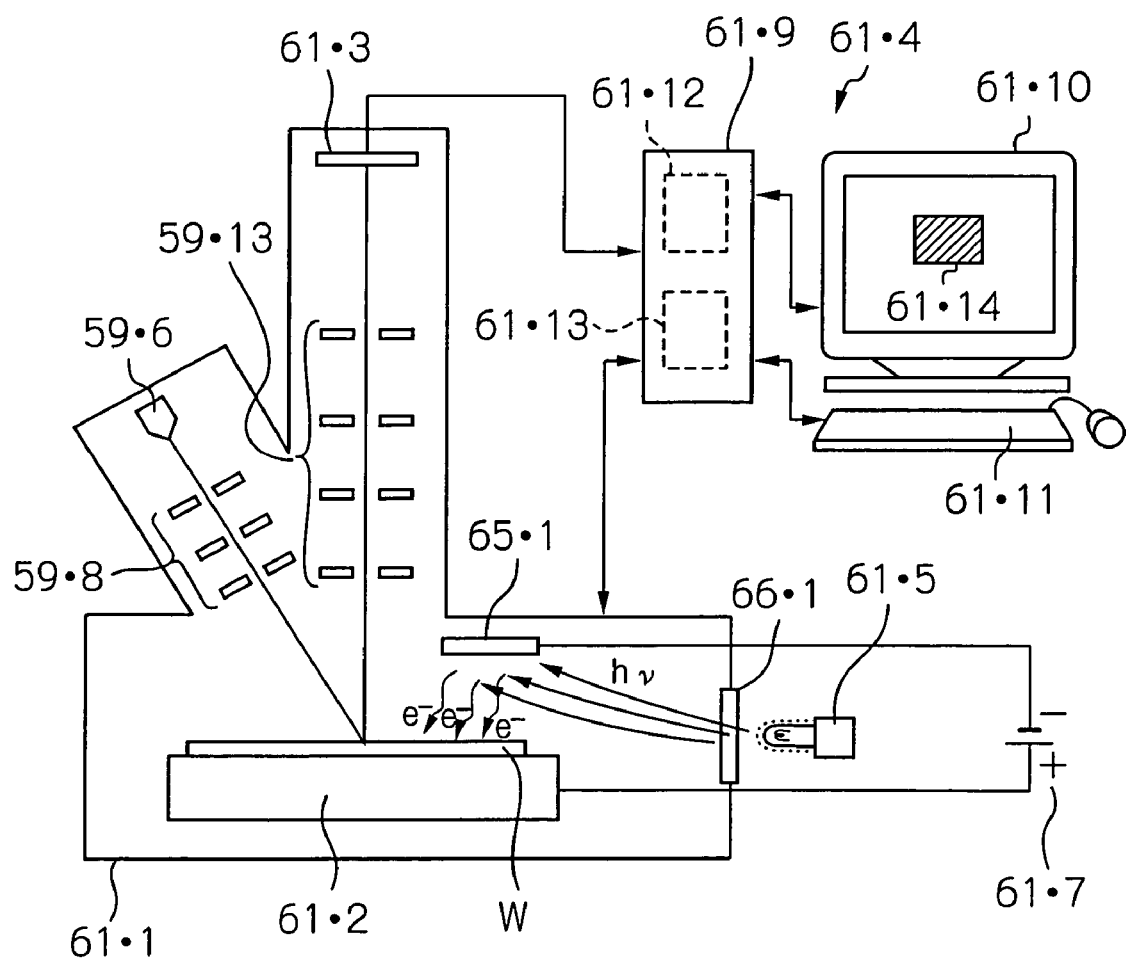
Figure 67:
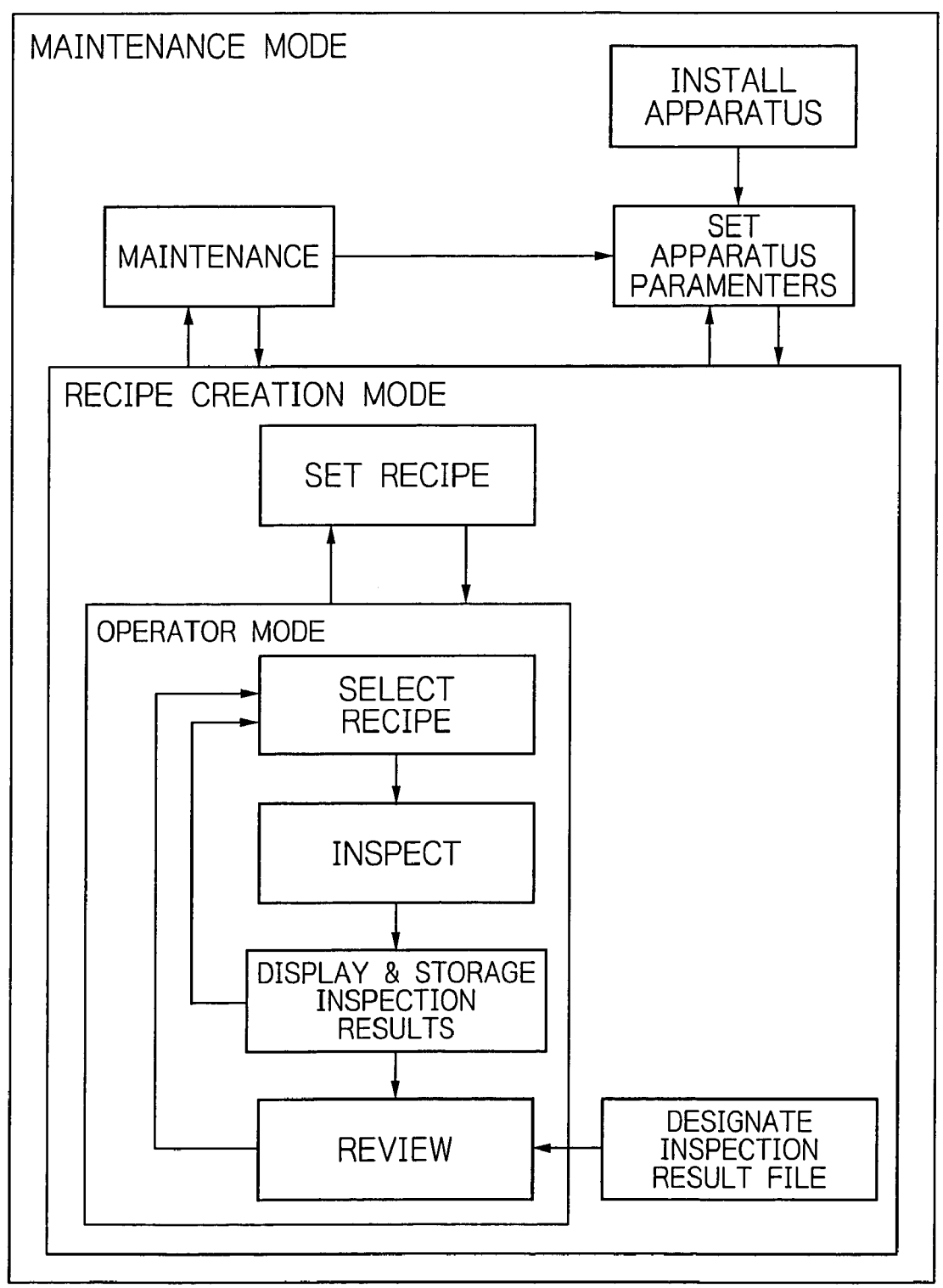
Figure 68:
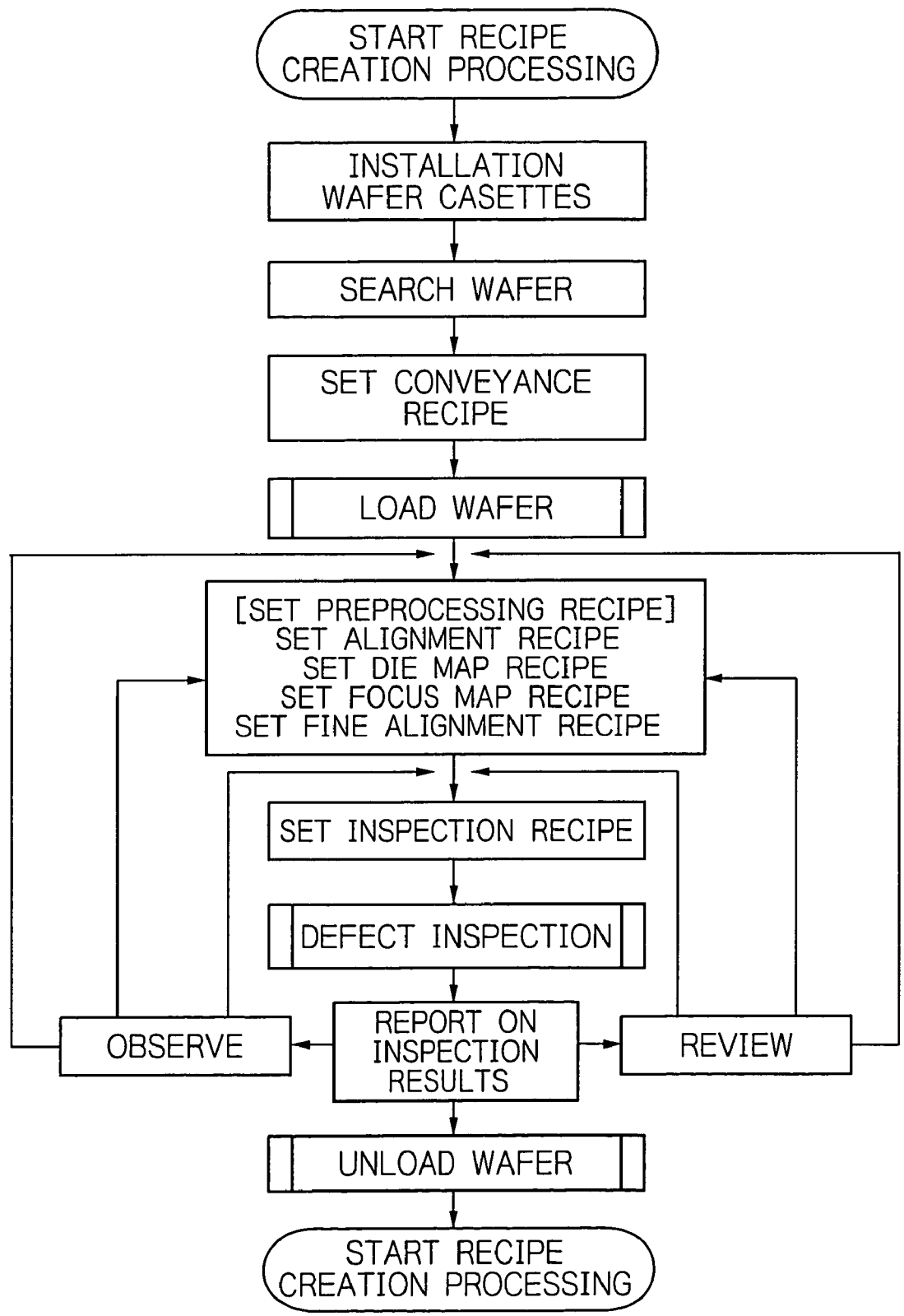
Figure 69:
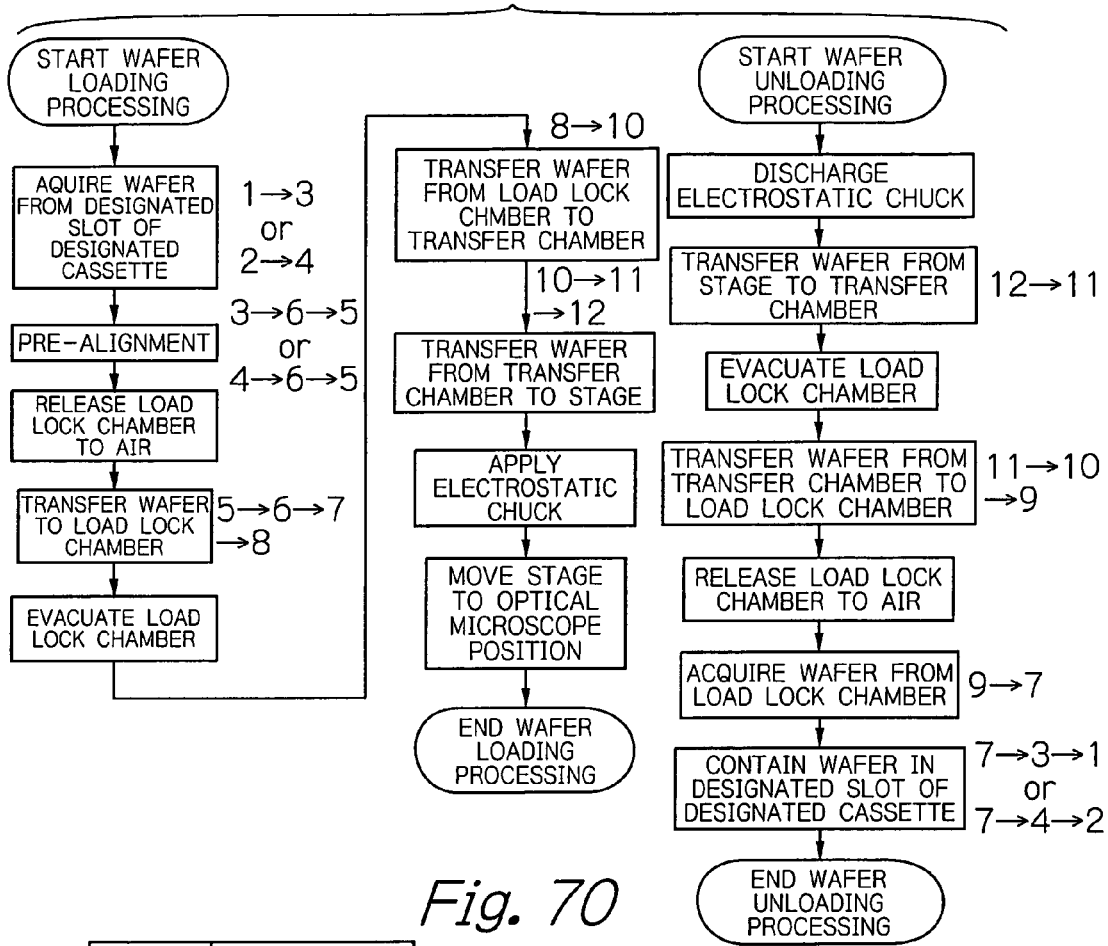
Figure 70:
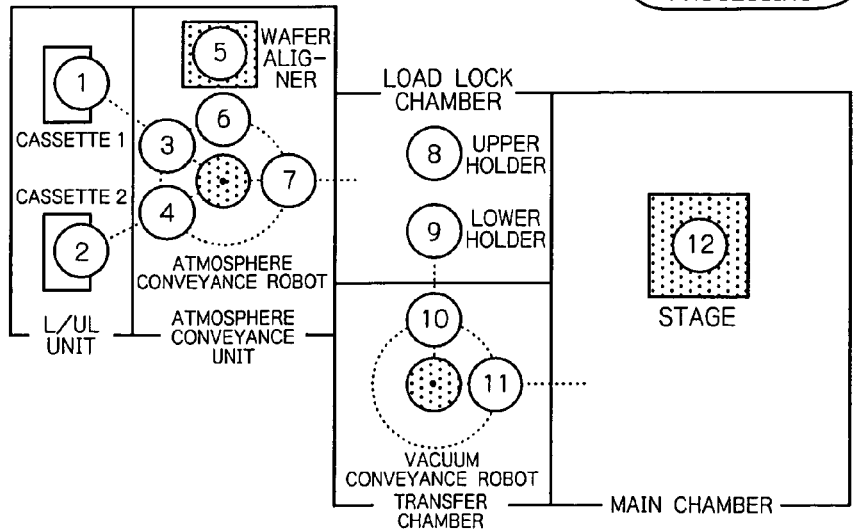
Figure 71:
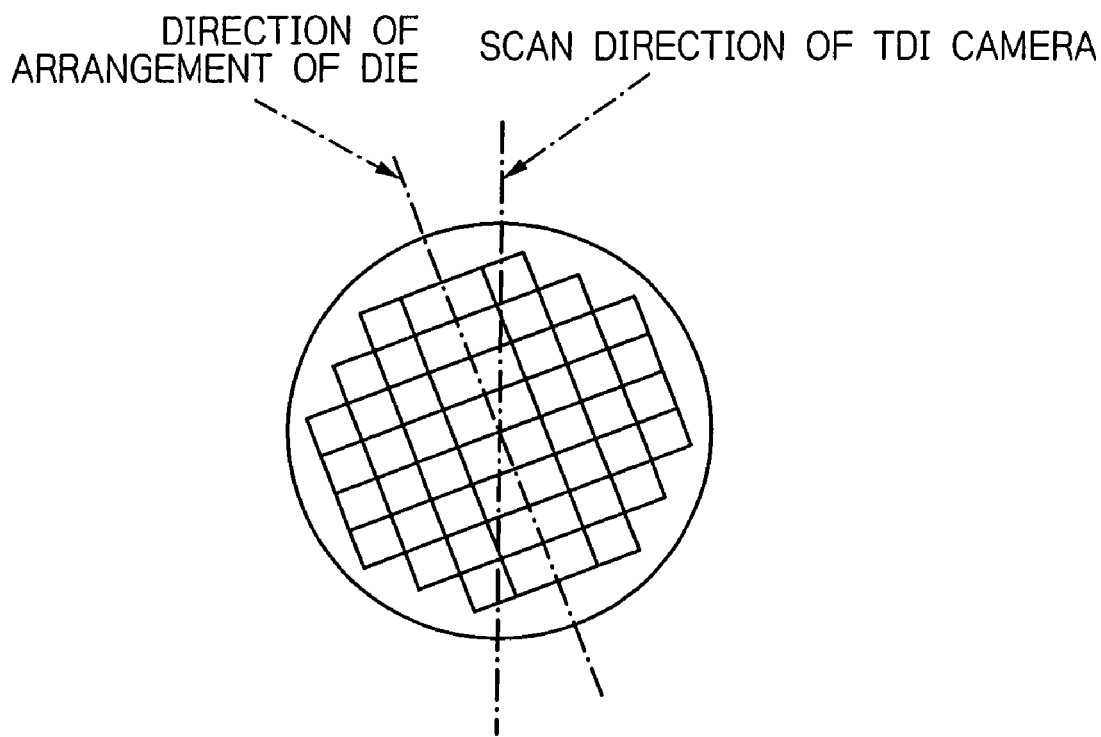
Figure 72:
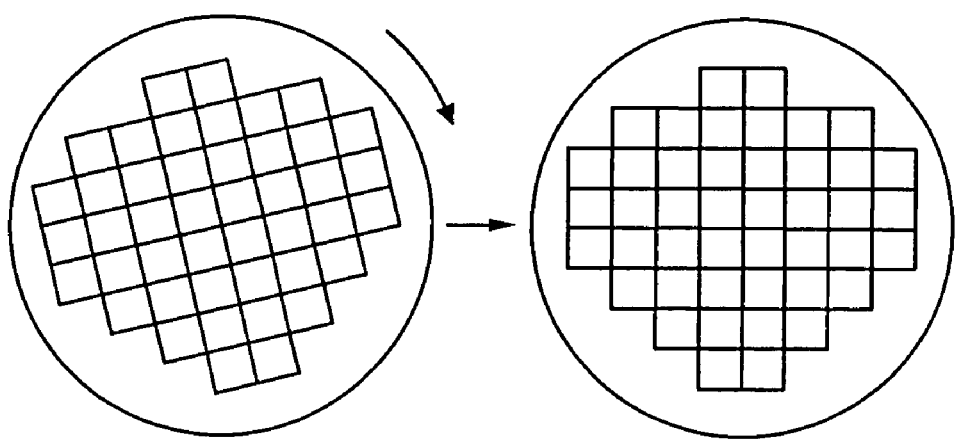
Figures 73, 74:
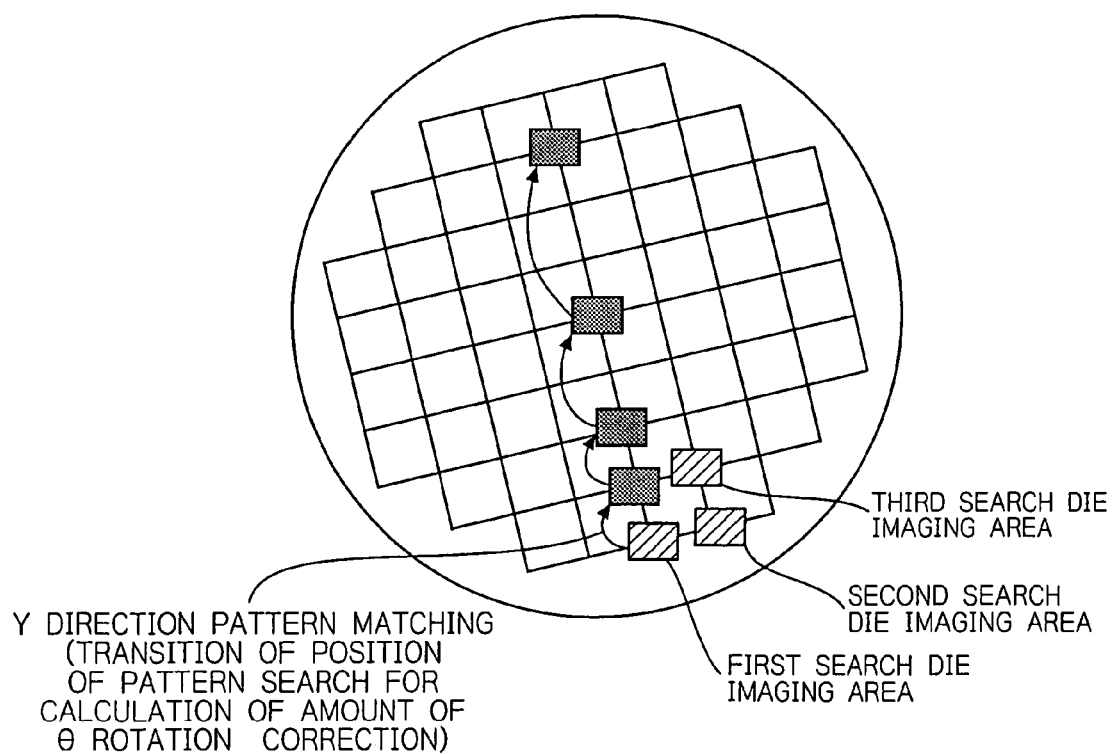
Figure 75:
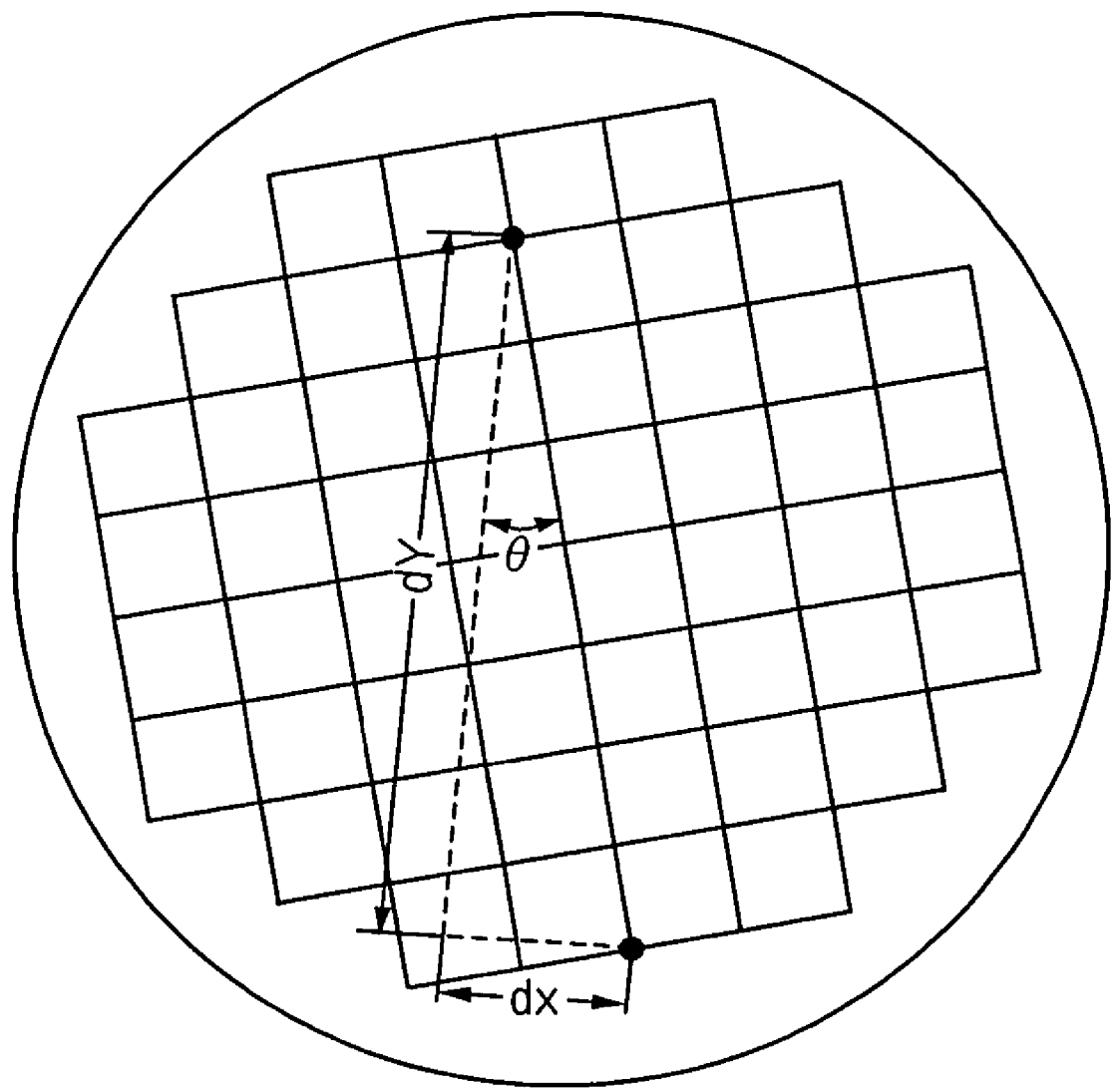
Figure 76:
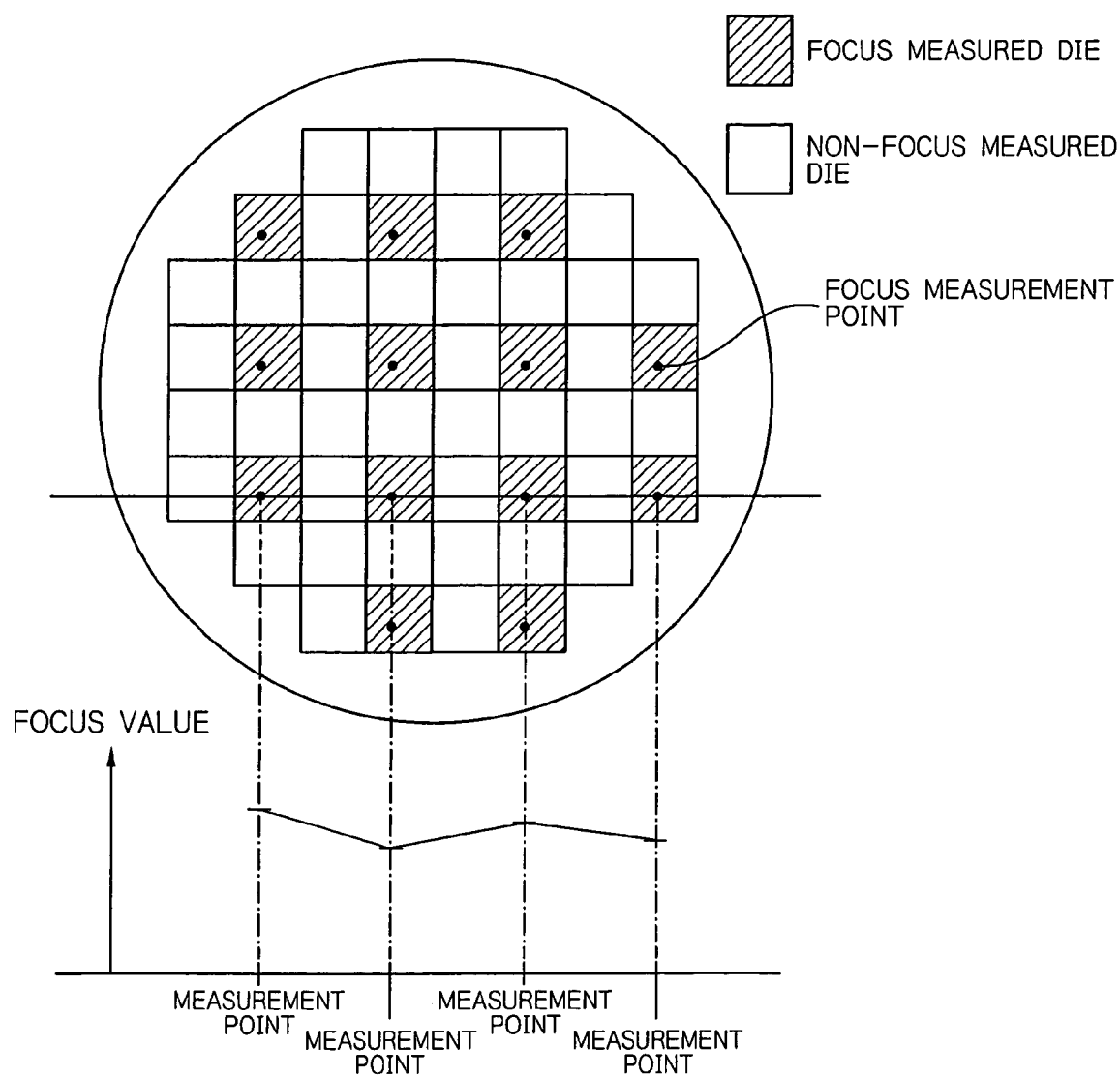
Figure 77:
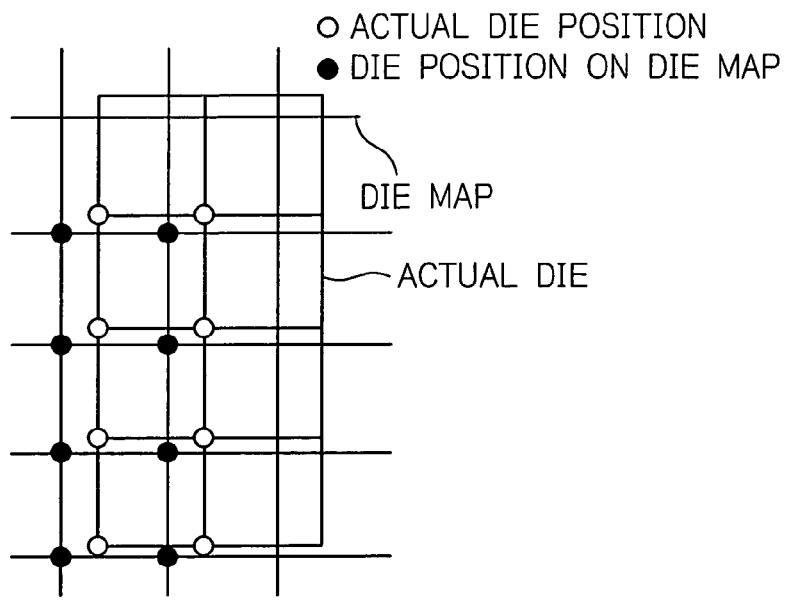
Figure 78:
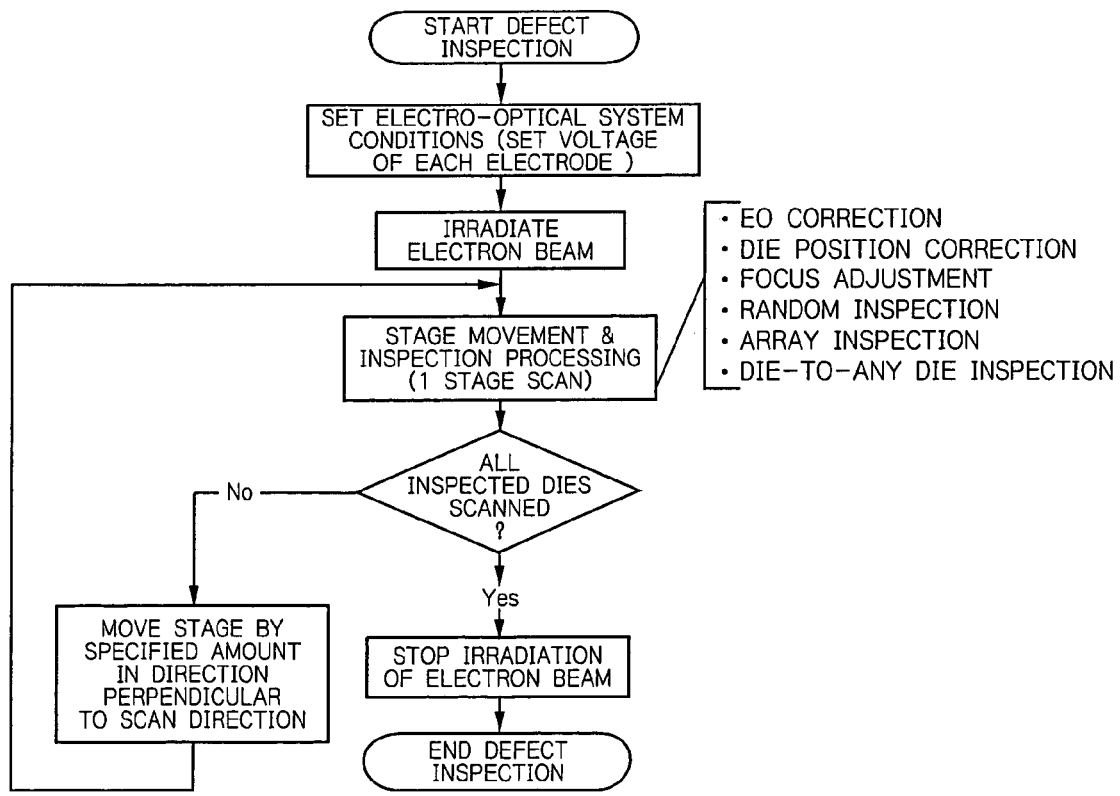
Figure 79:
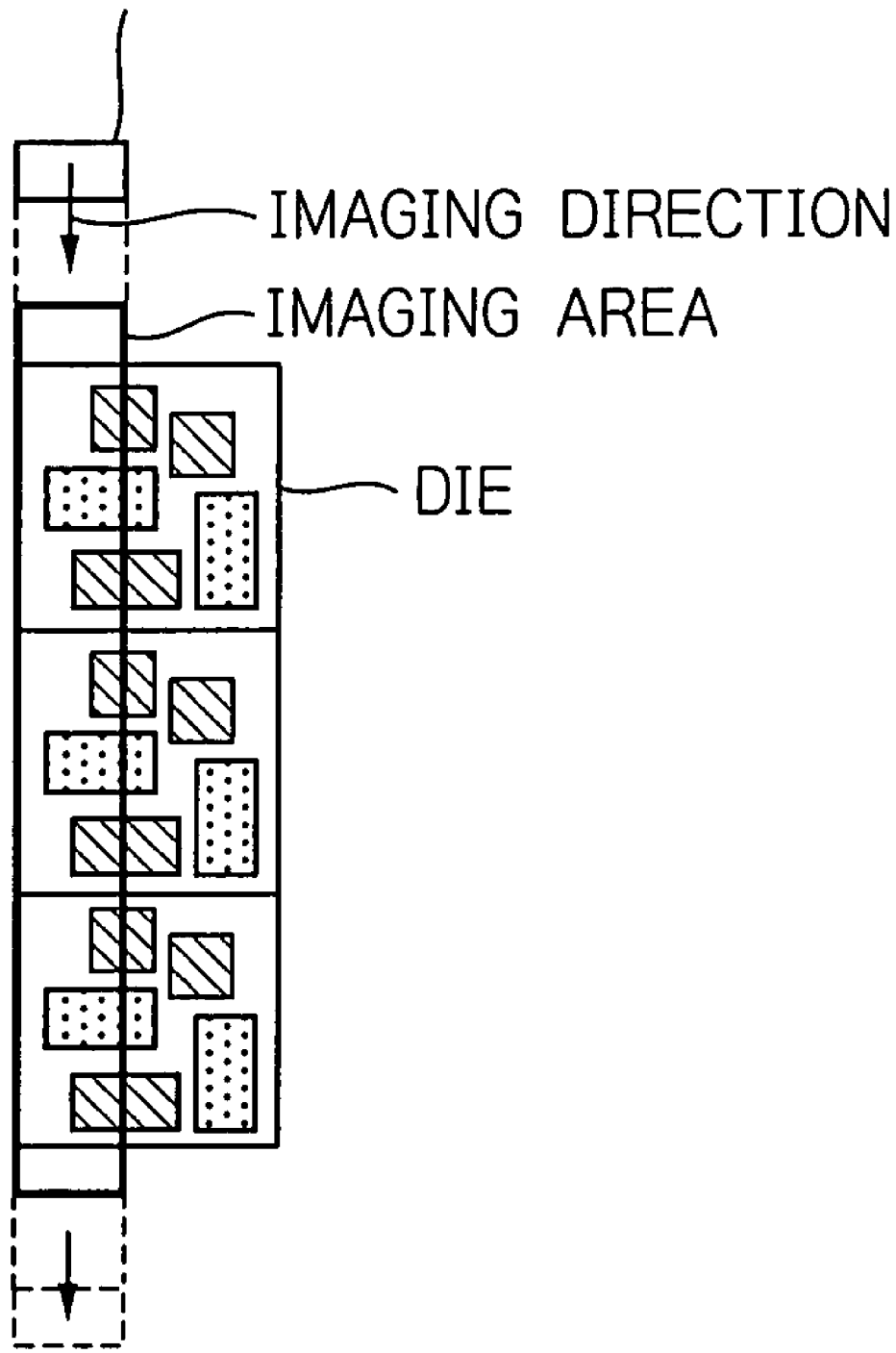
Figure 80A:
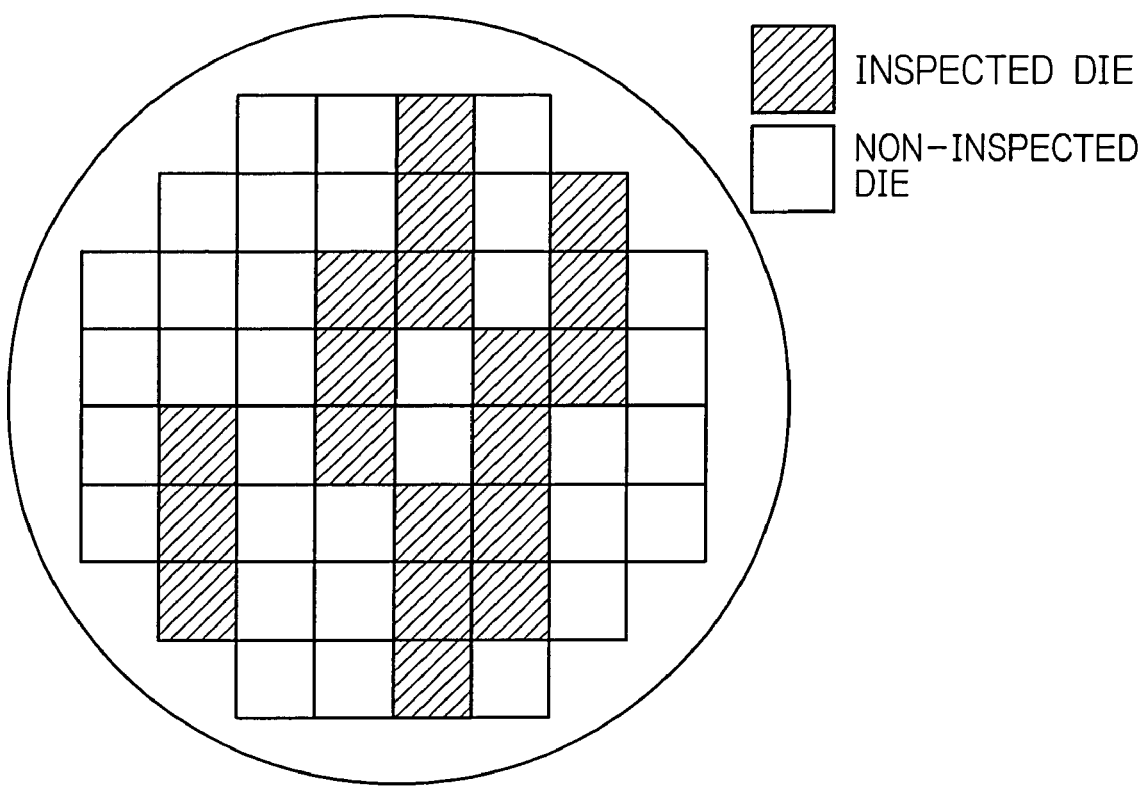
Figure 80B:
Figure 81:
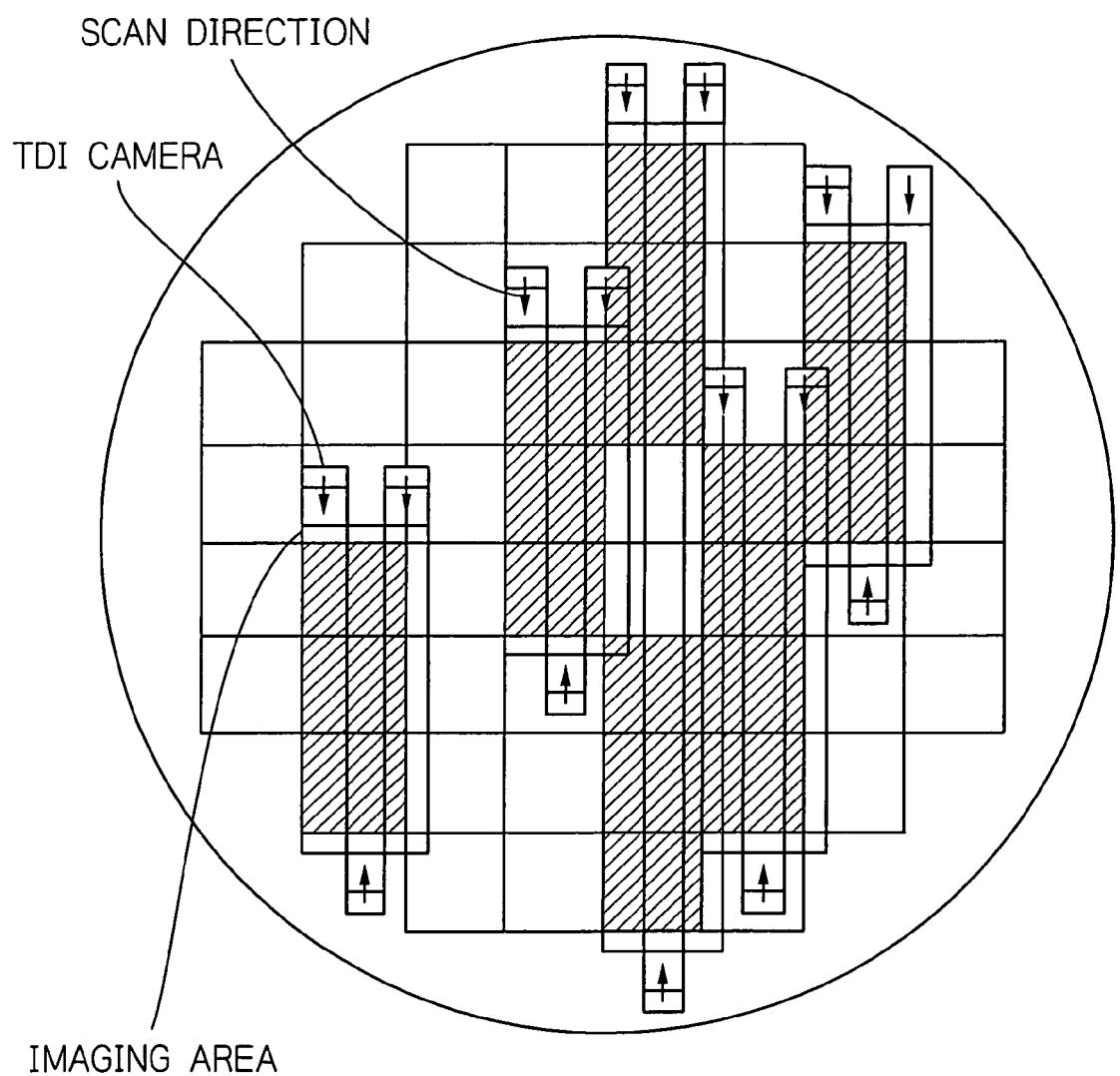
Figure 82:
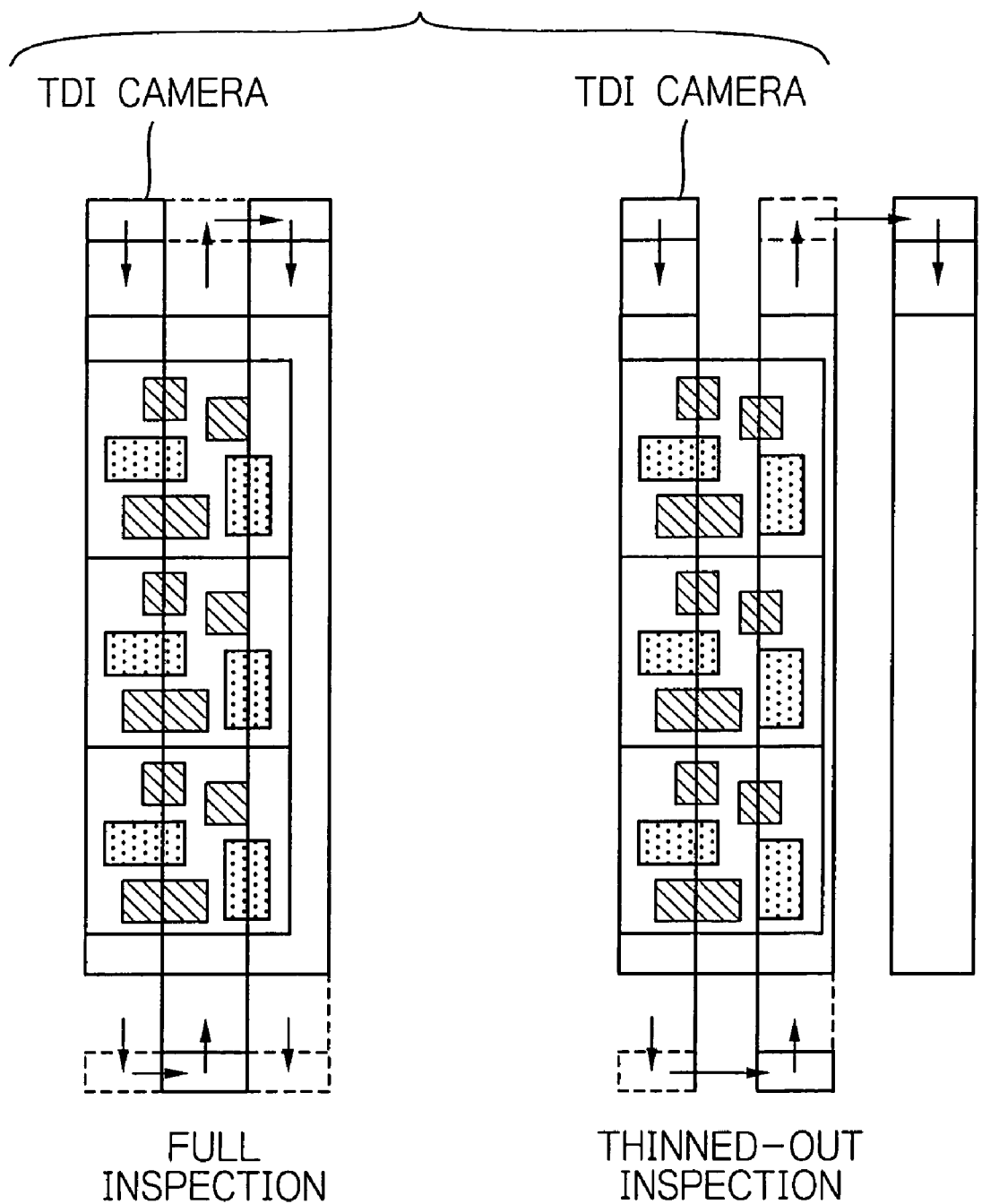
Figure 83A:
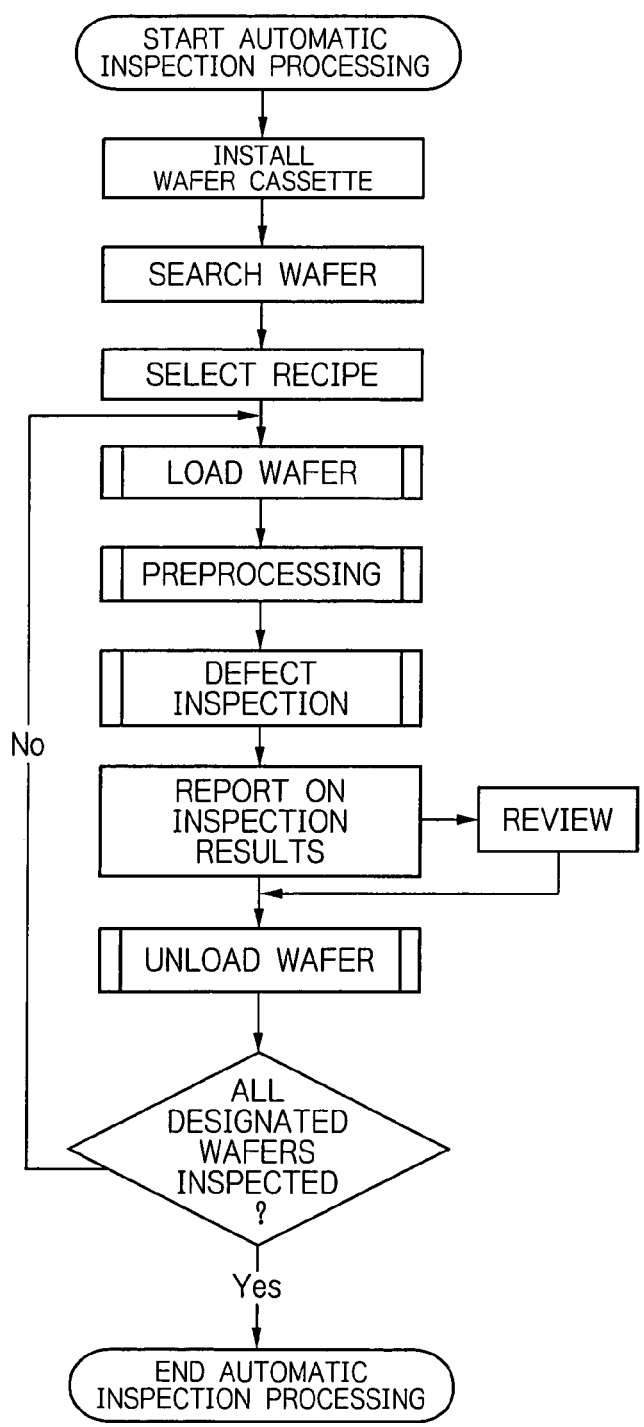
Figure 83B:
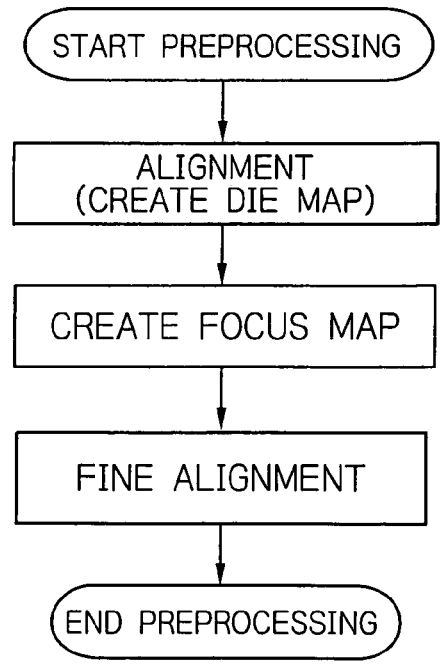
Figure 84:
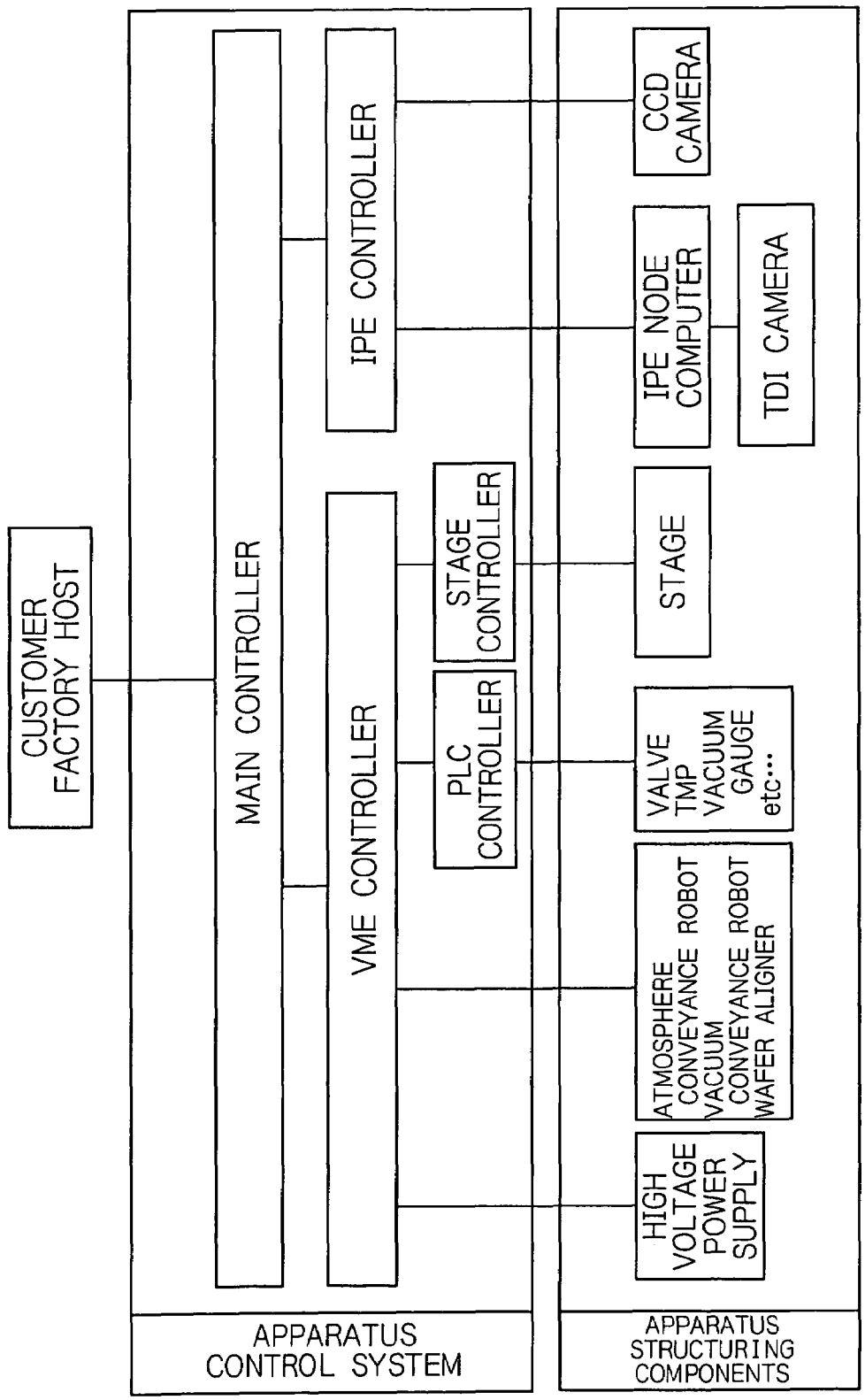
Figure 85:
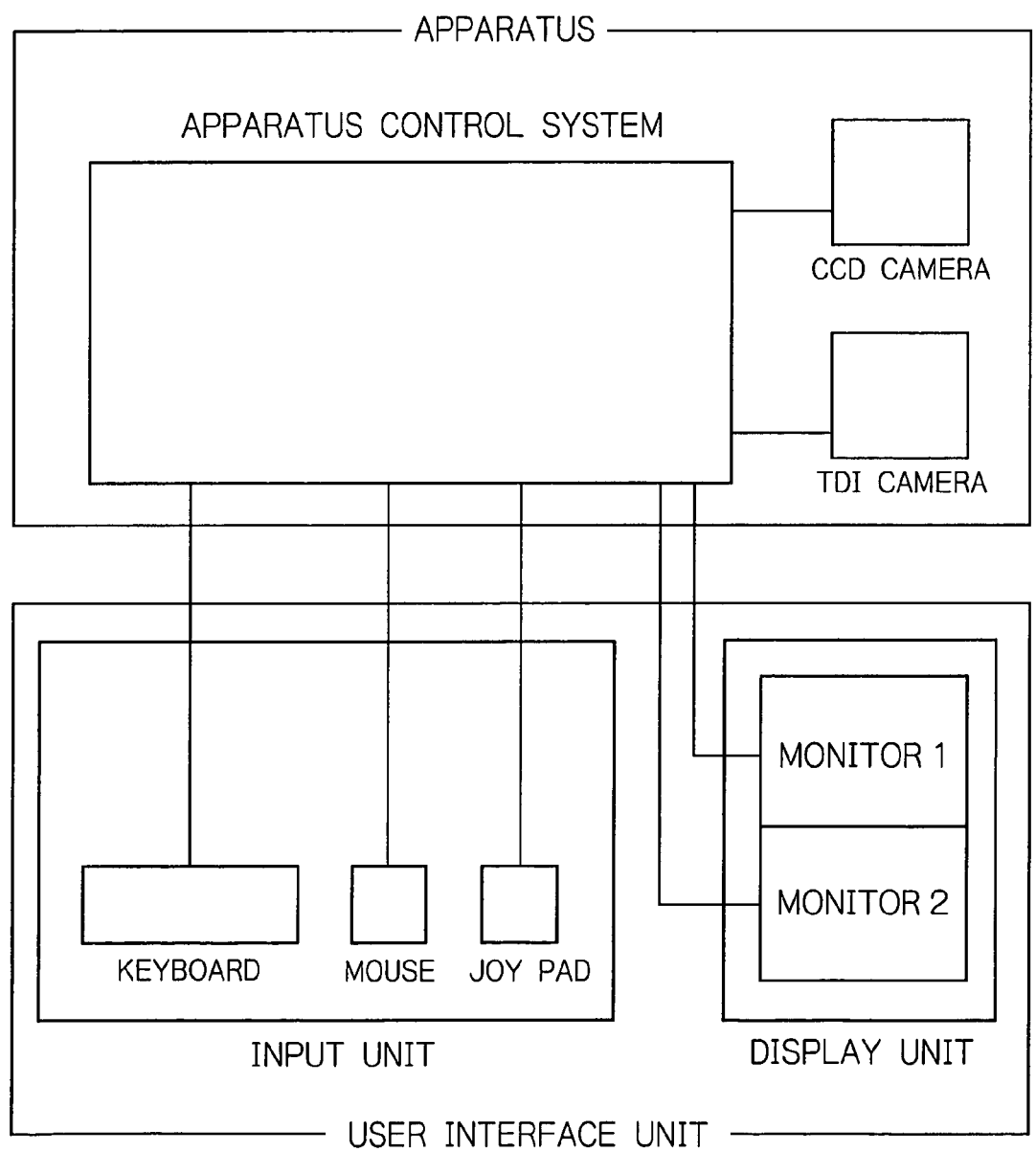
Figure 86:
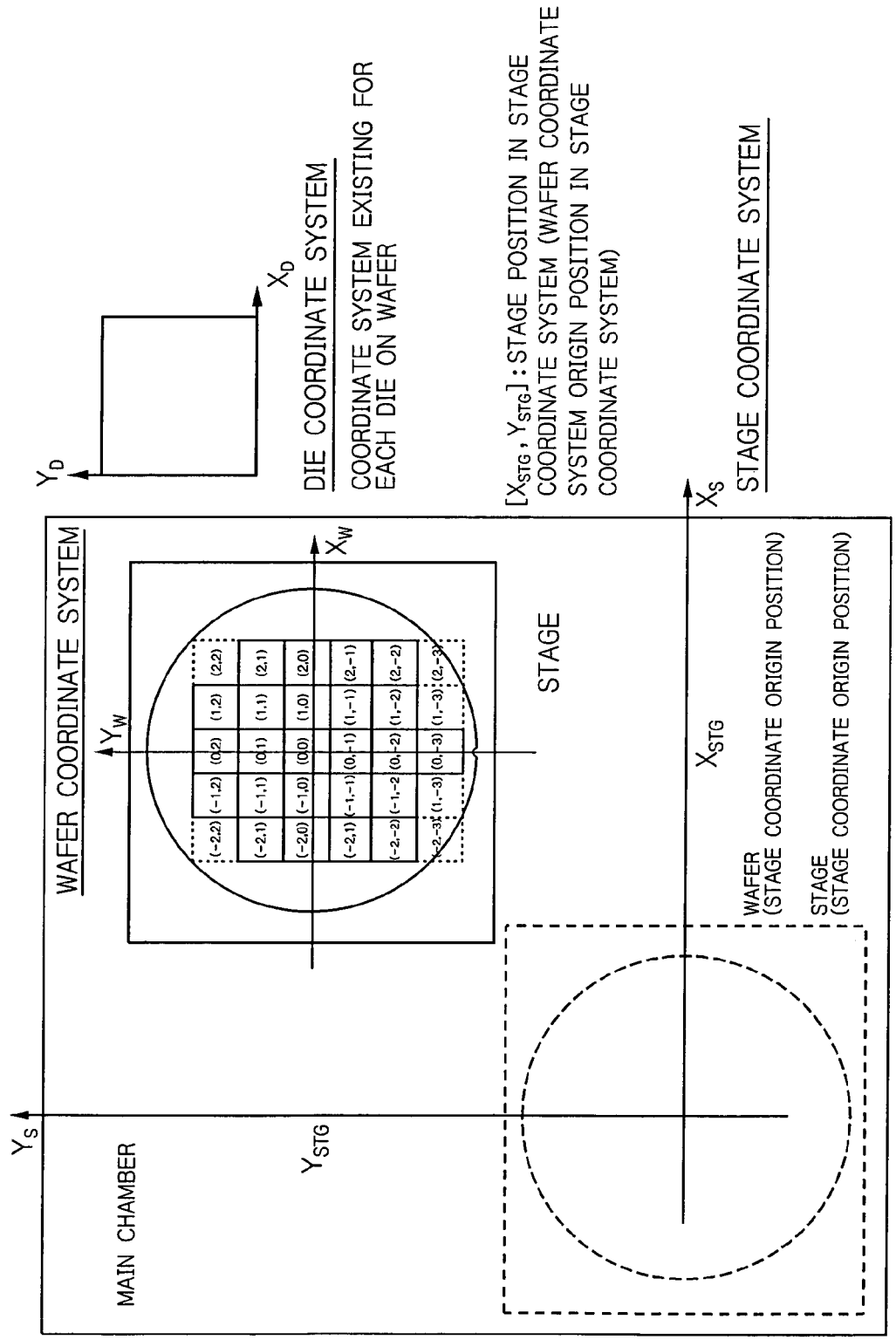
Figure 87:
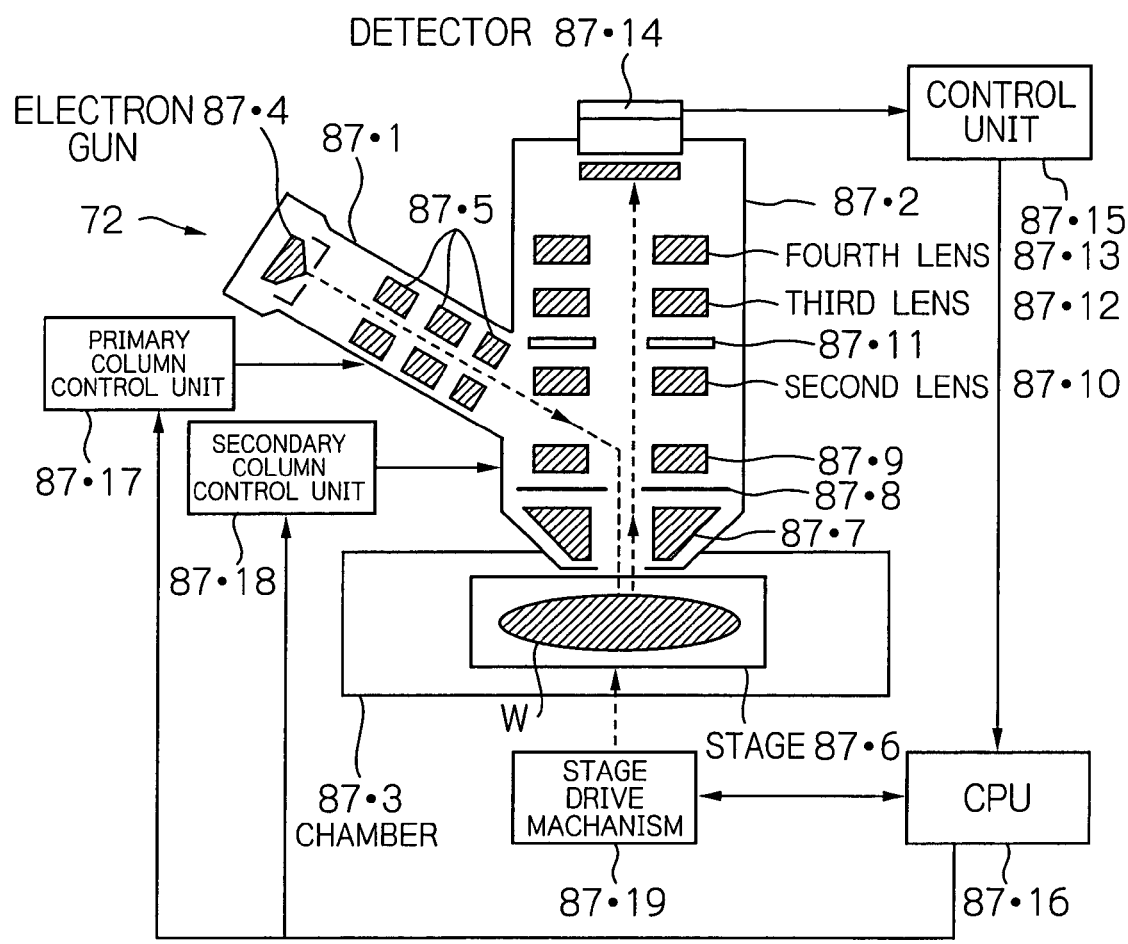
Figure 88:
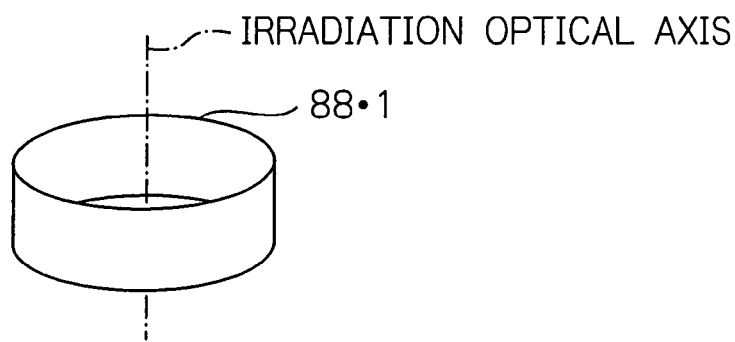
Figure 89:
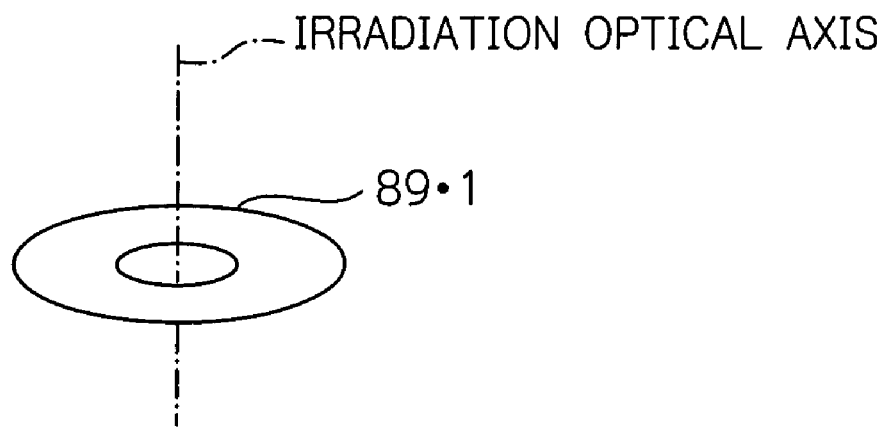
Figure 90:
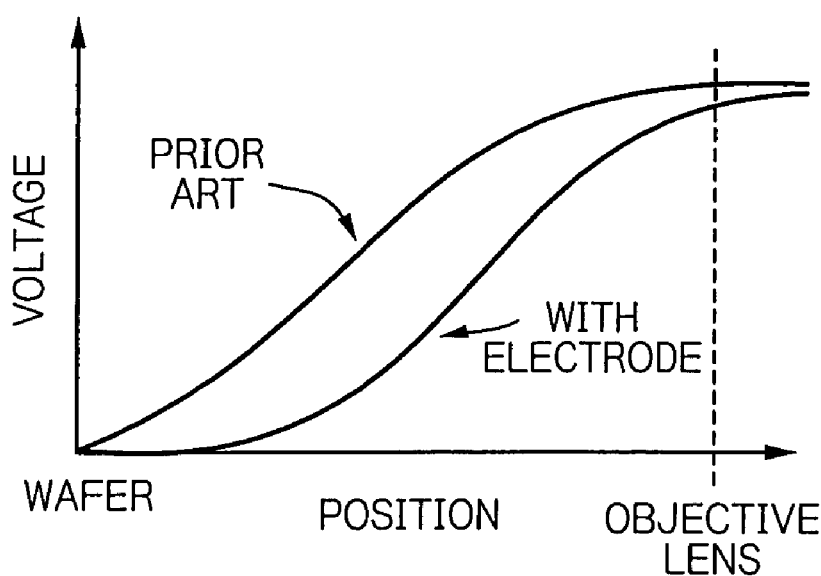
Figure 91:
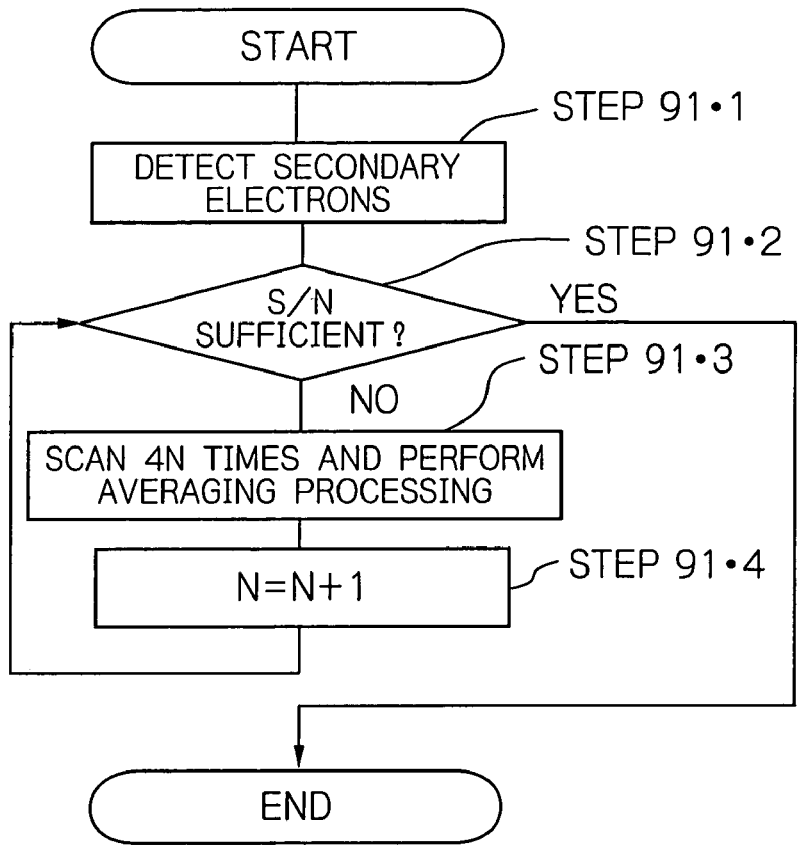
Figure 92:
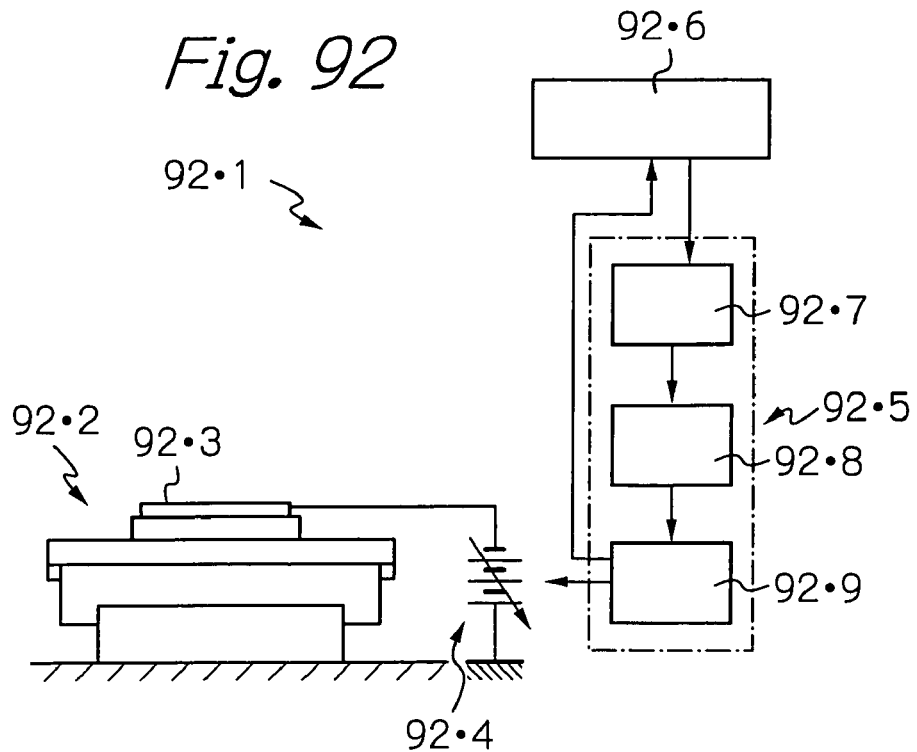
Figure 93A:
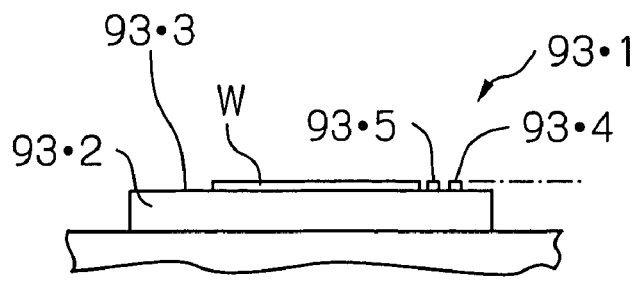
Figure 93B:
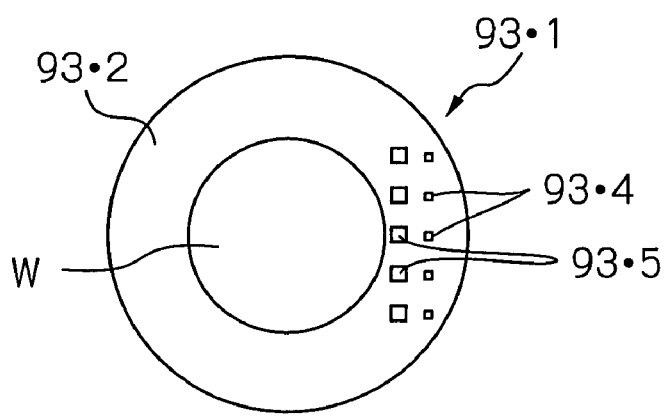
Figure 94:
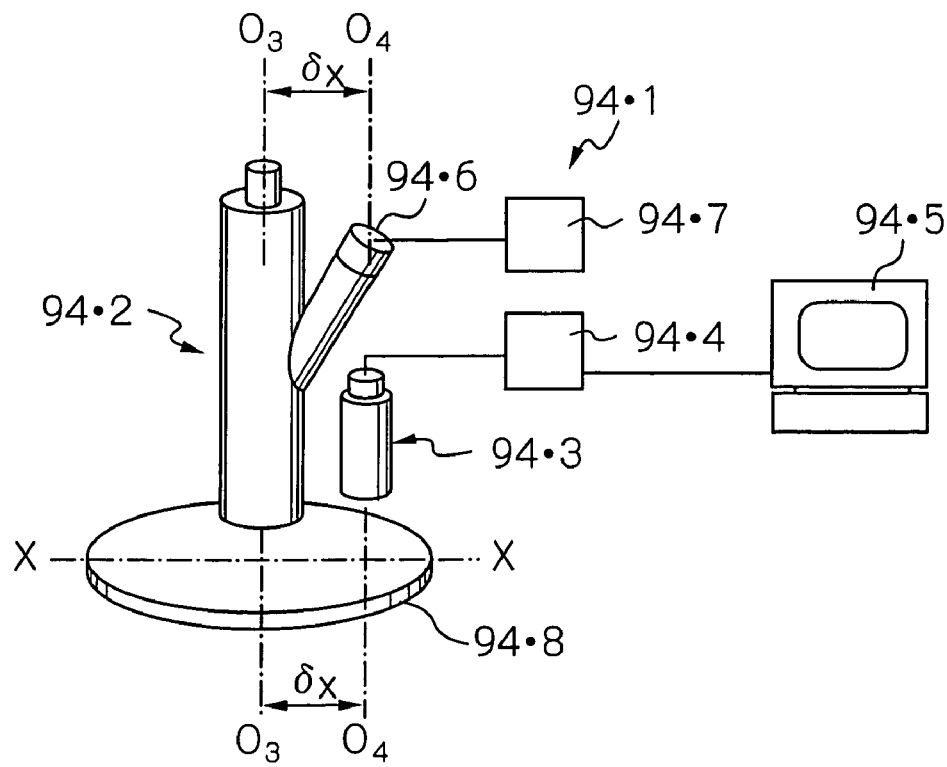
Figure 95B:
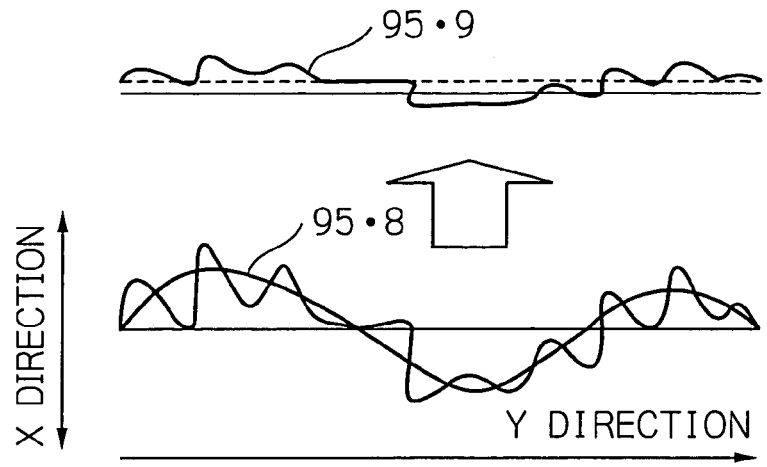
Figure 95A:
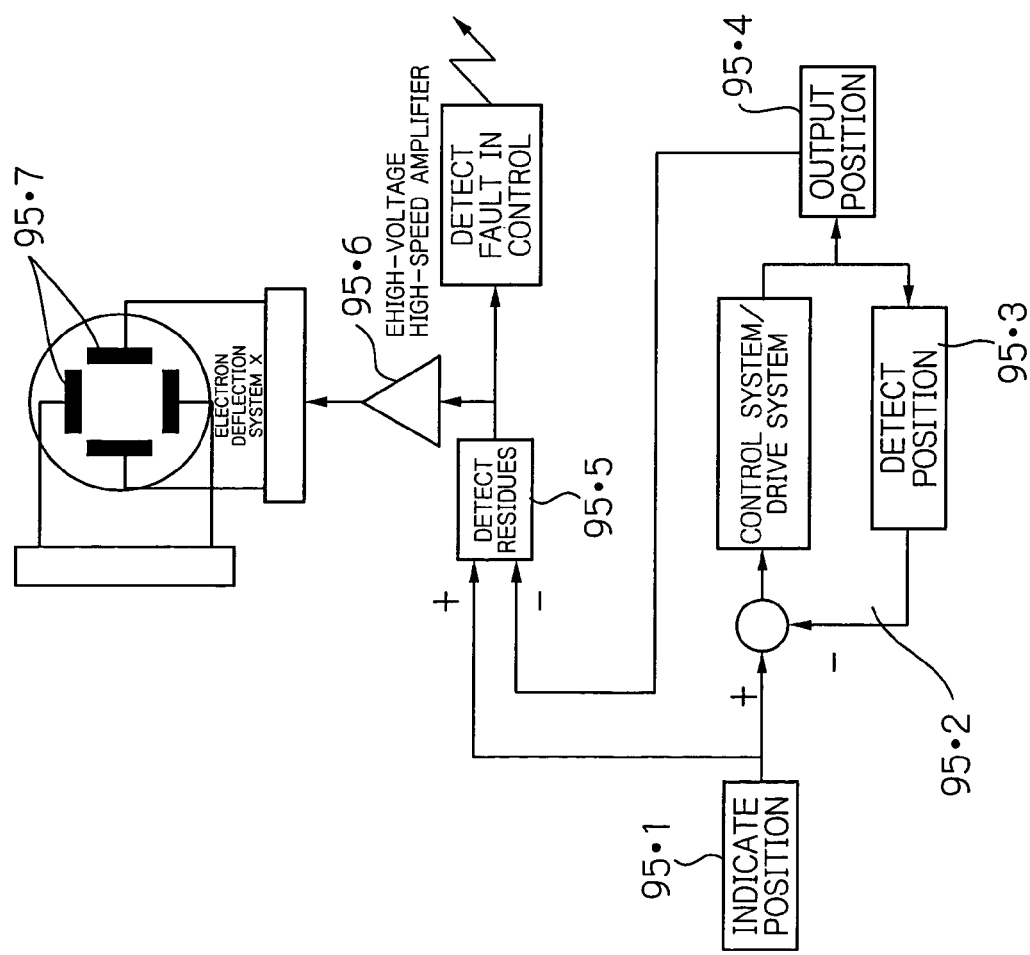
Figure 96:
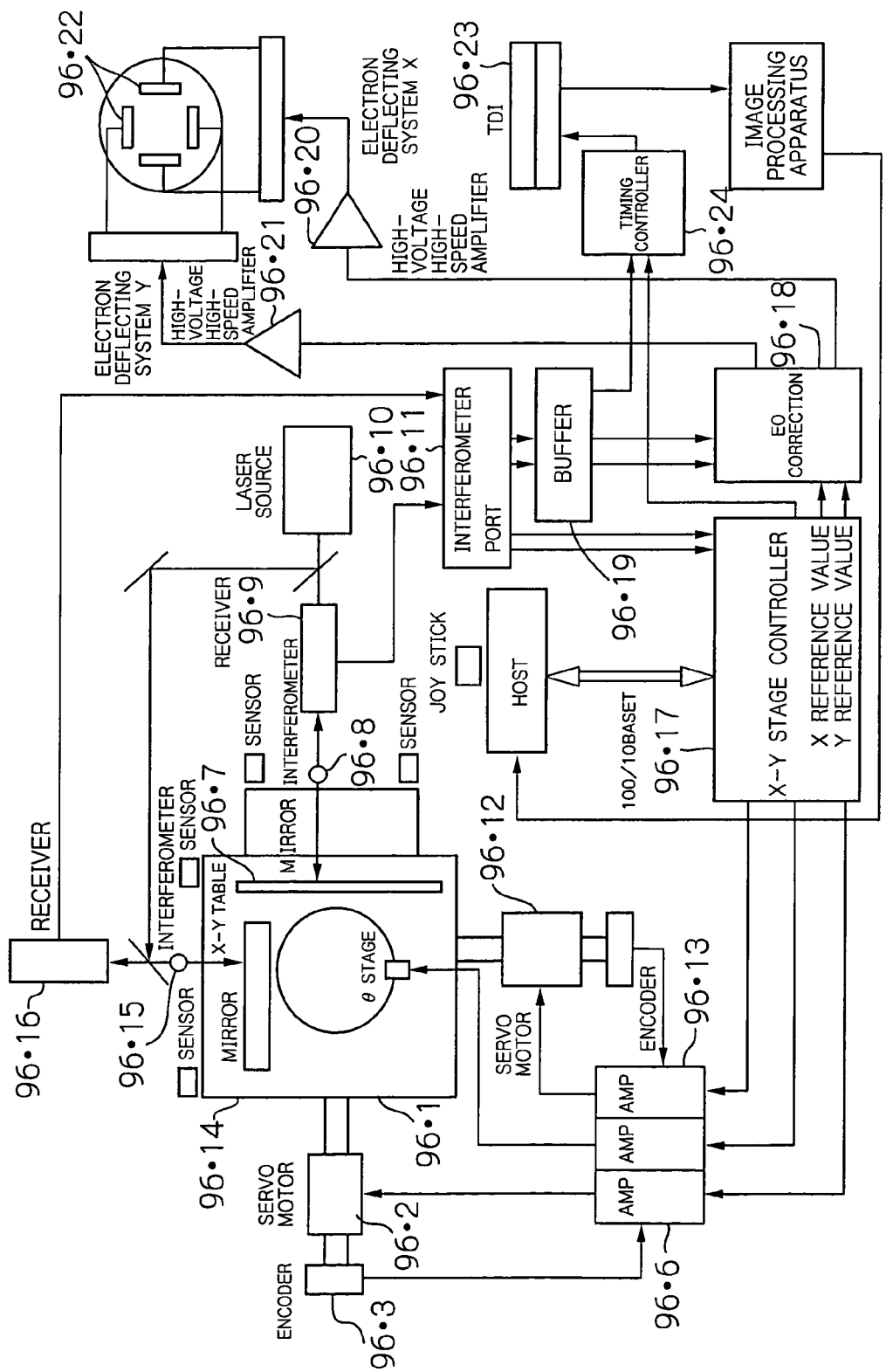
Figure 97A:
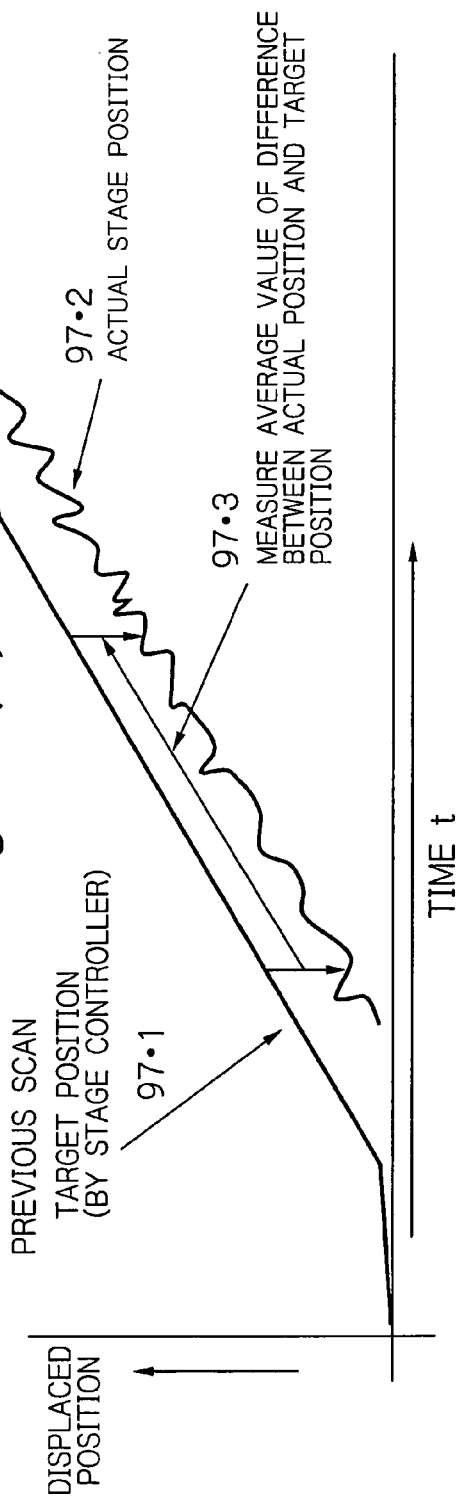
Figure 97B:
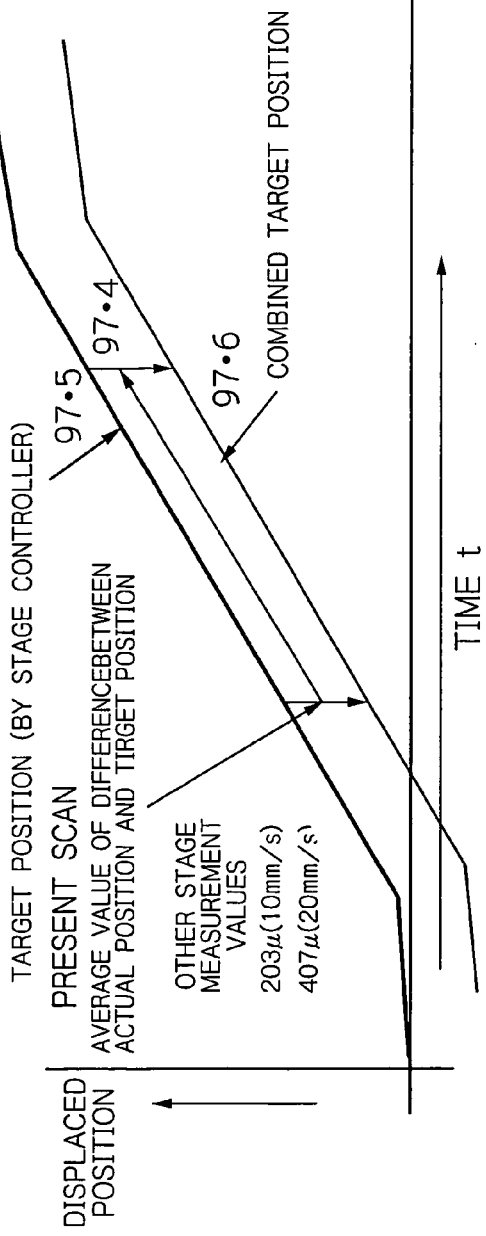
Figure 98:
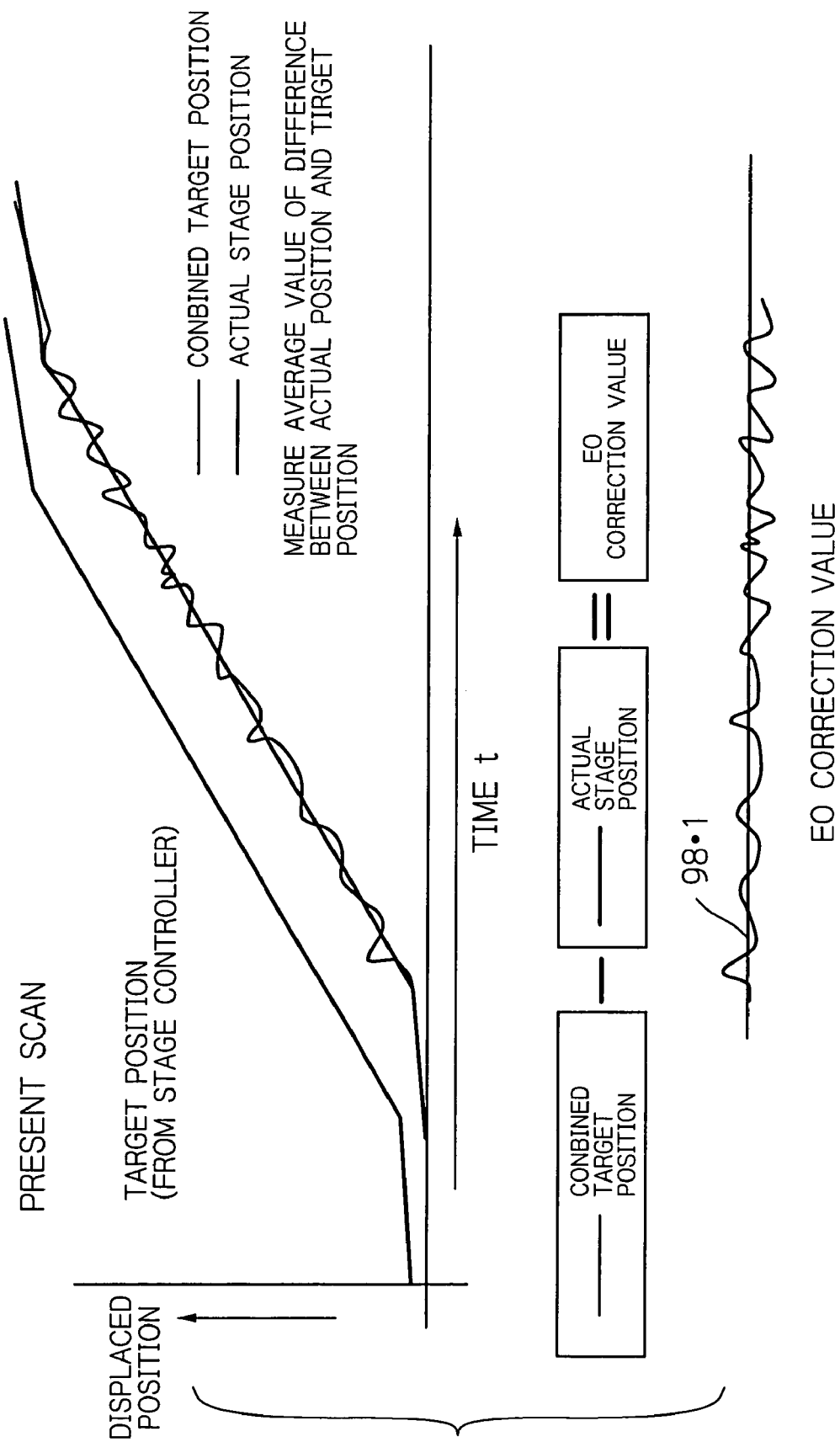
Figure 99:
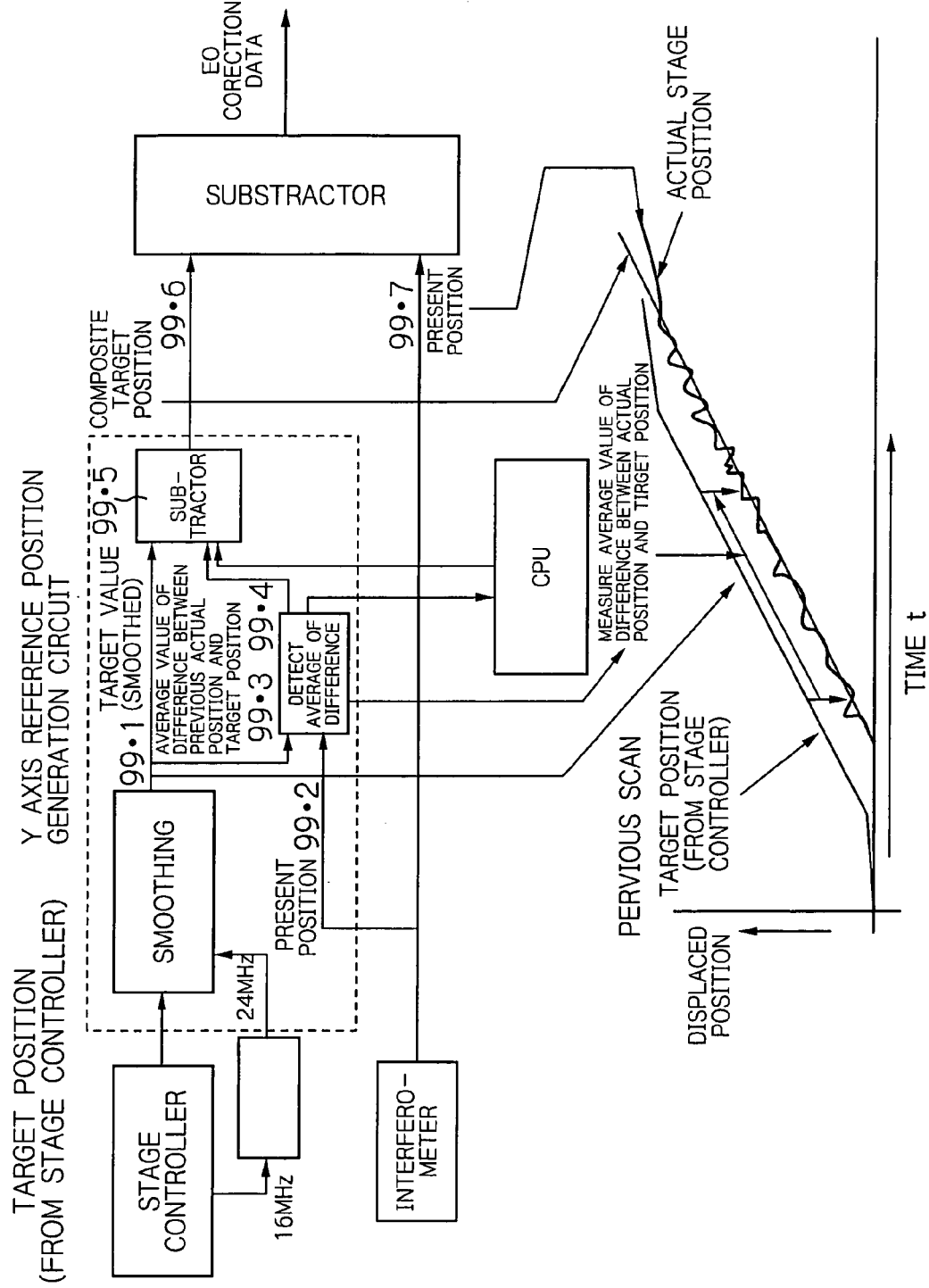
Figure 100:
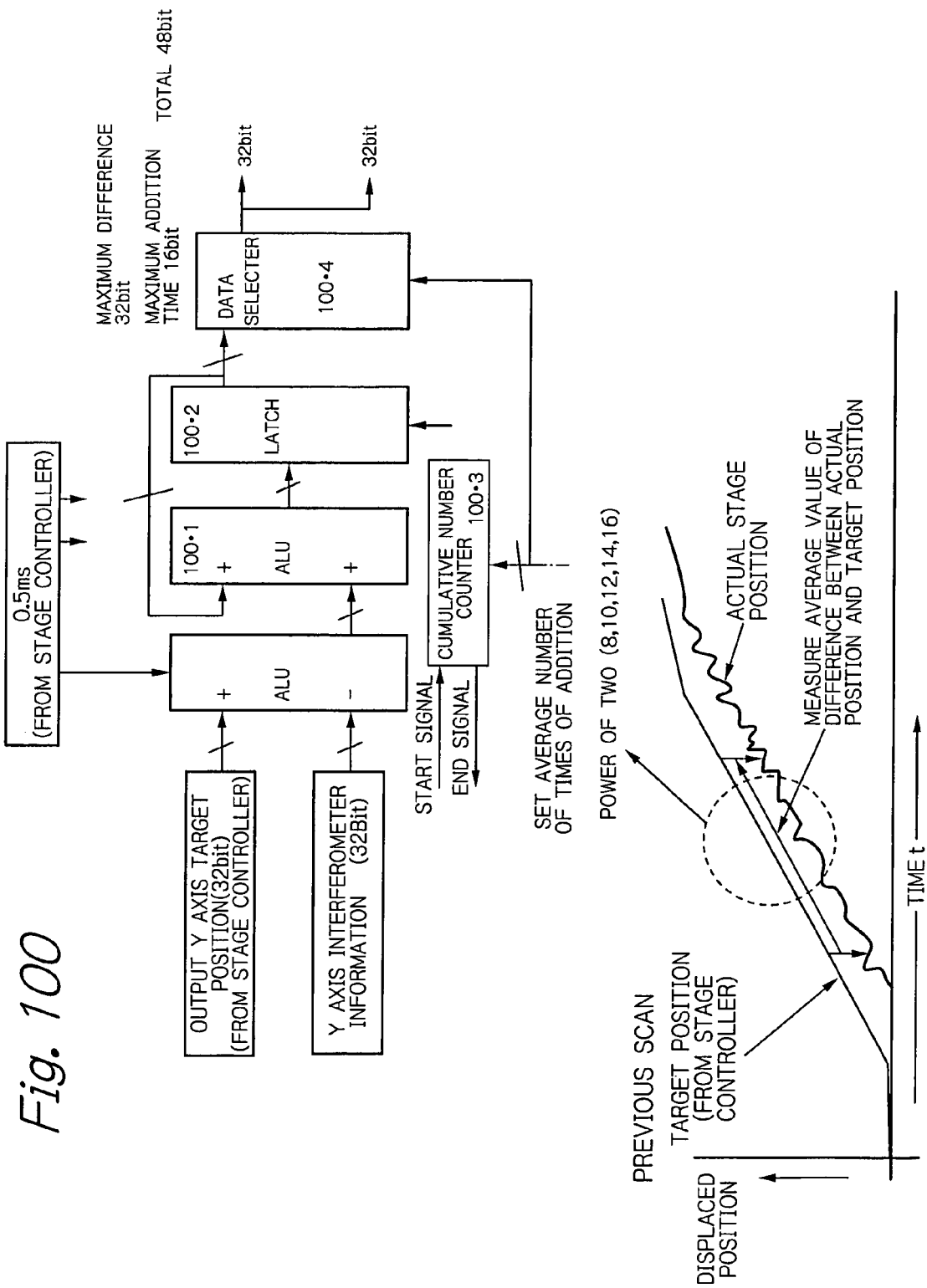
Figure 101:
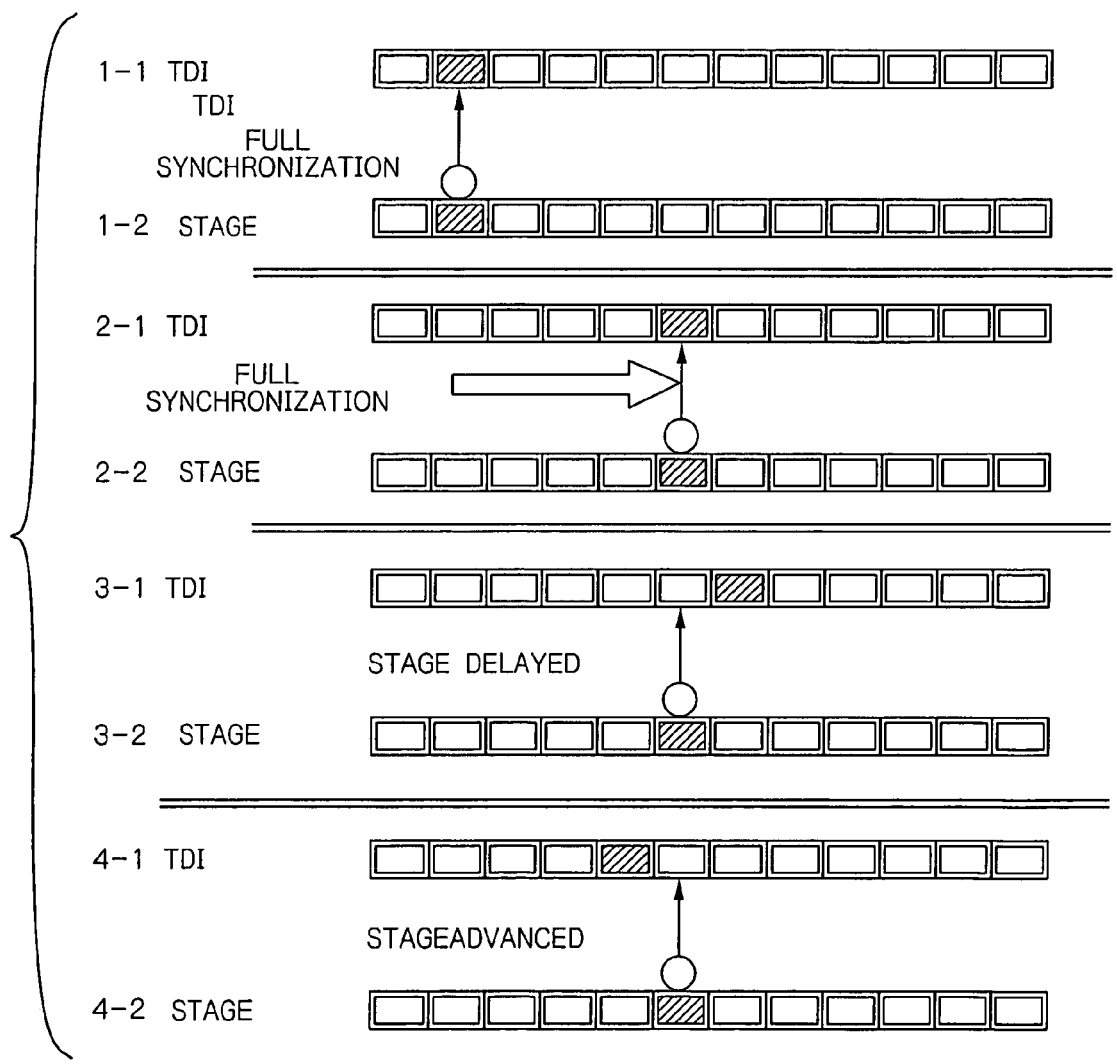
Figure 102:
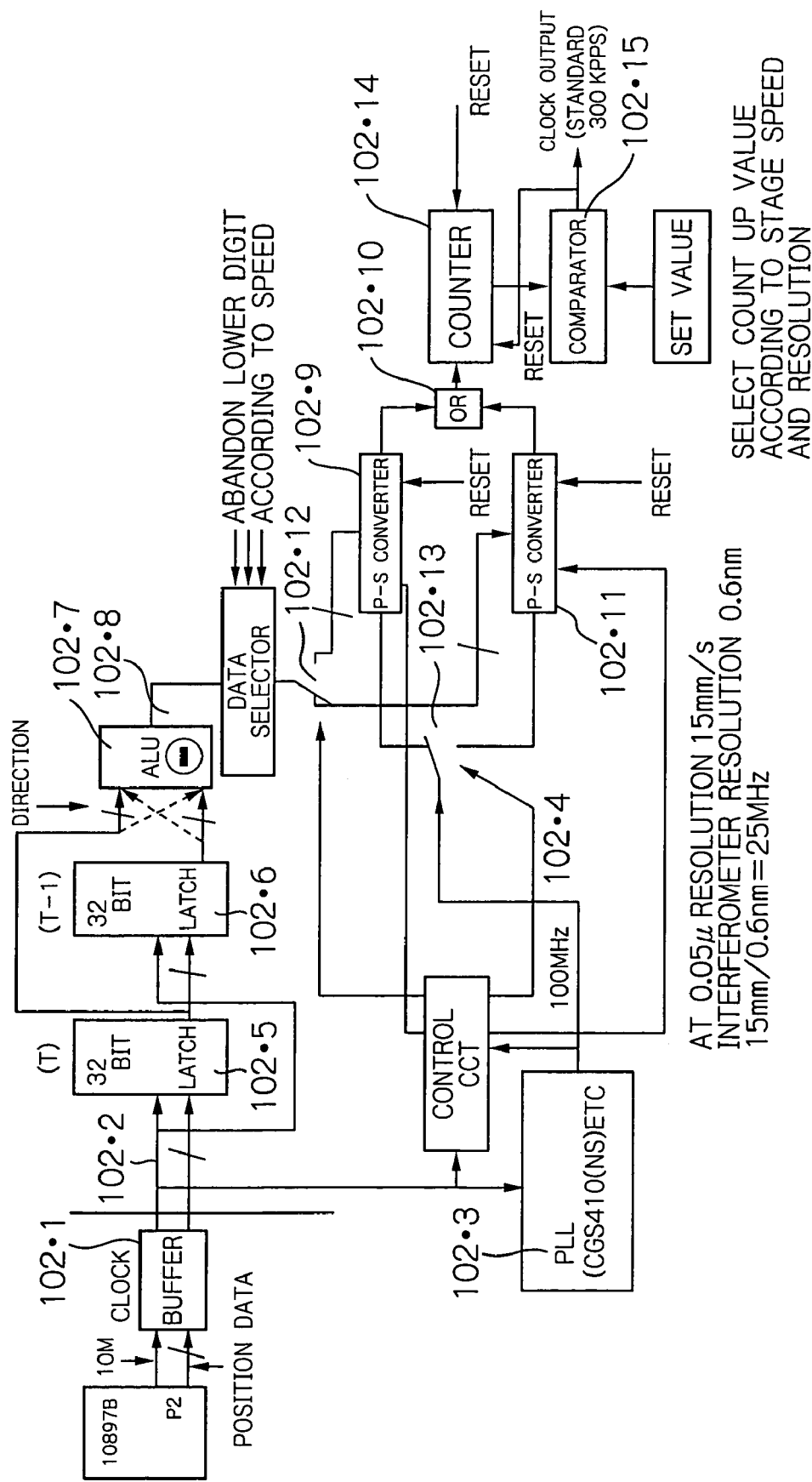
Figure 103:
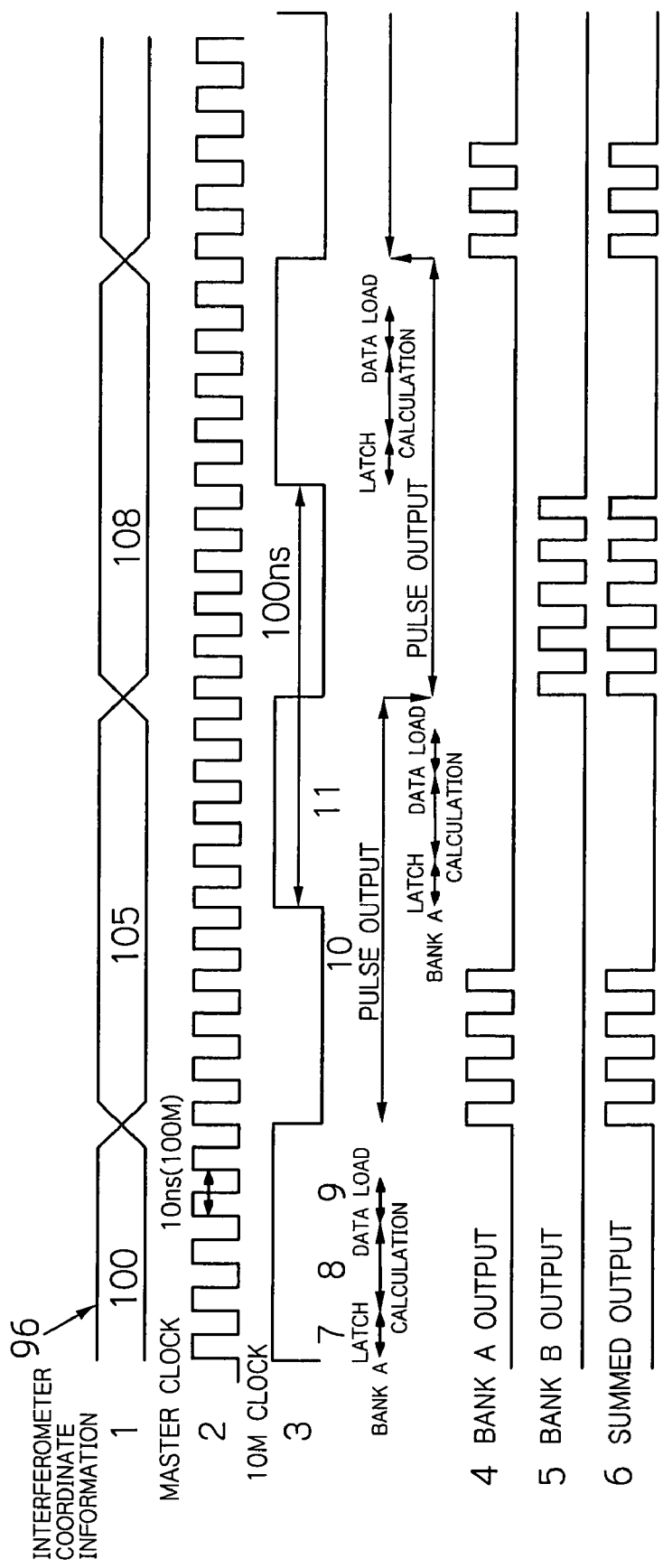
Figure 104:
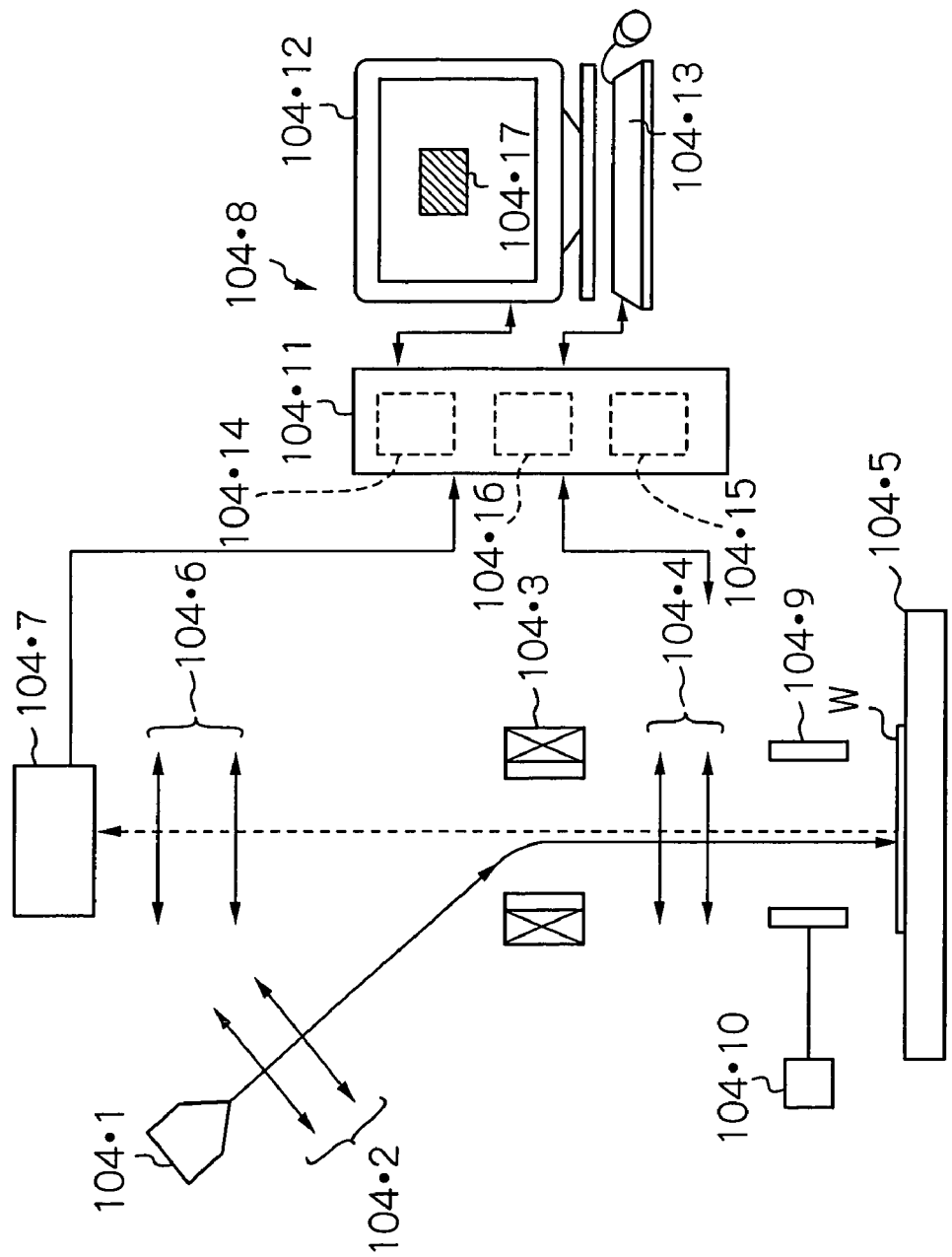
Figure 105:
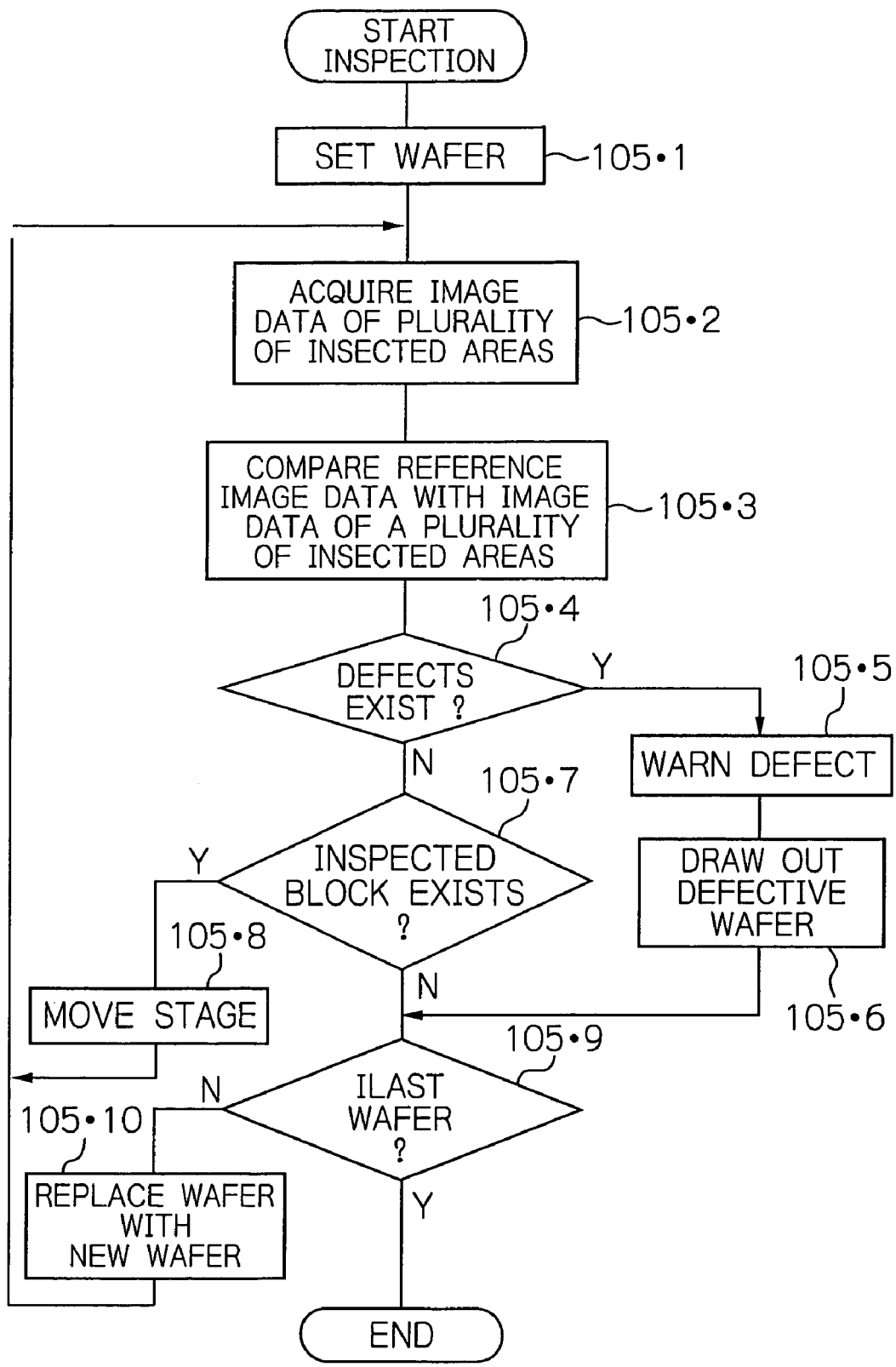
Figure 106:
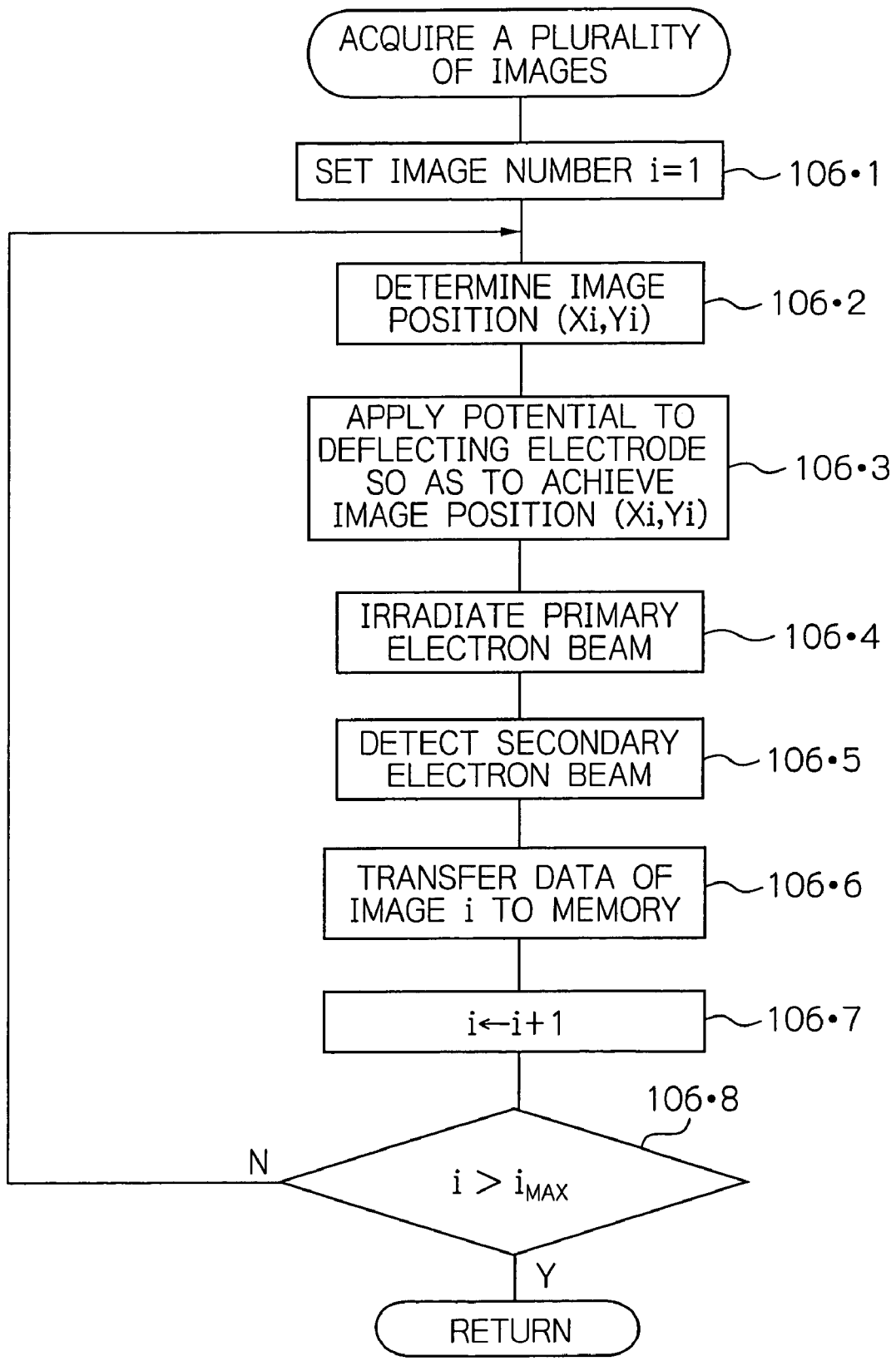
Figure 107:
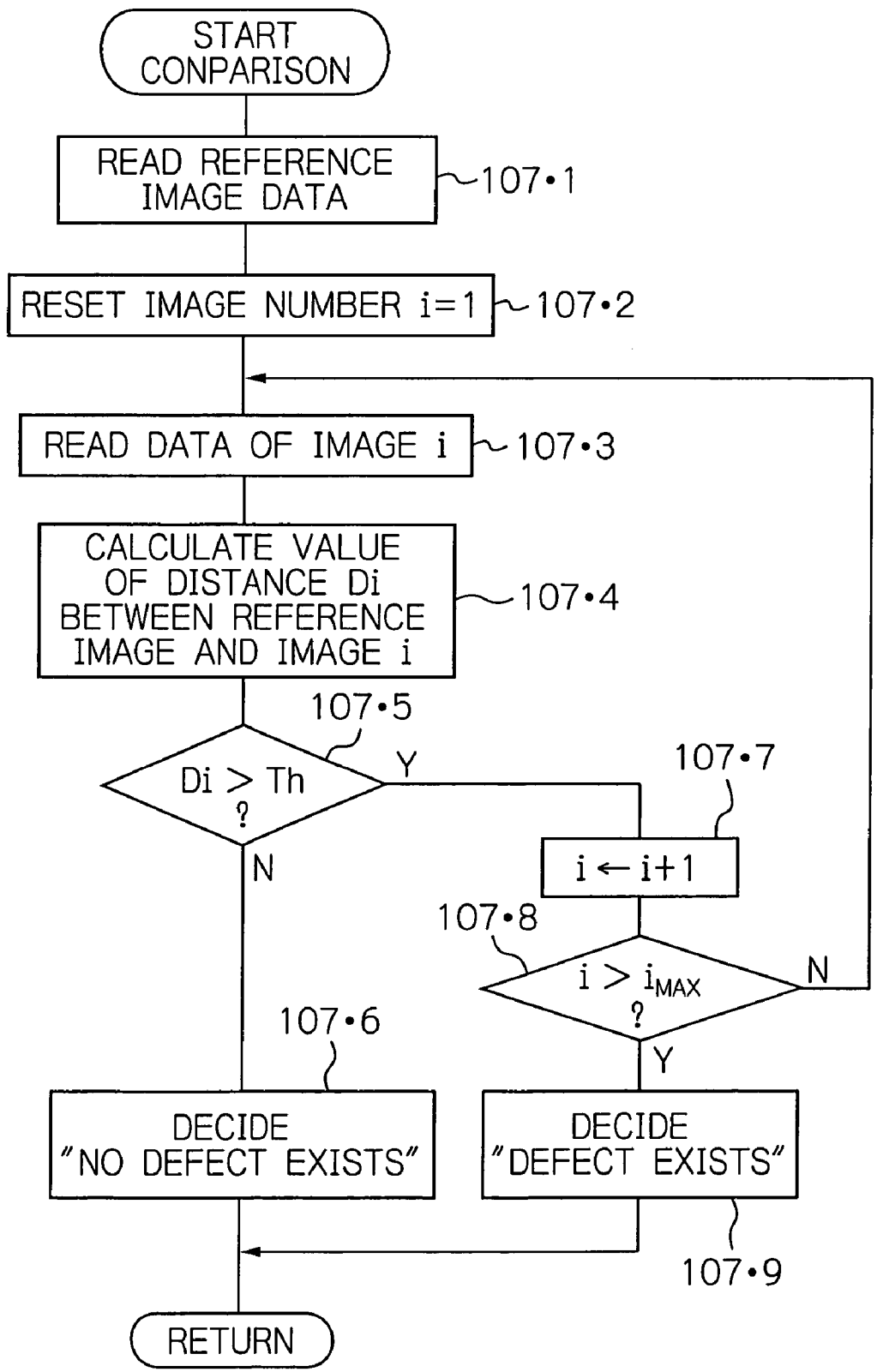
Figure 108:
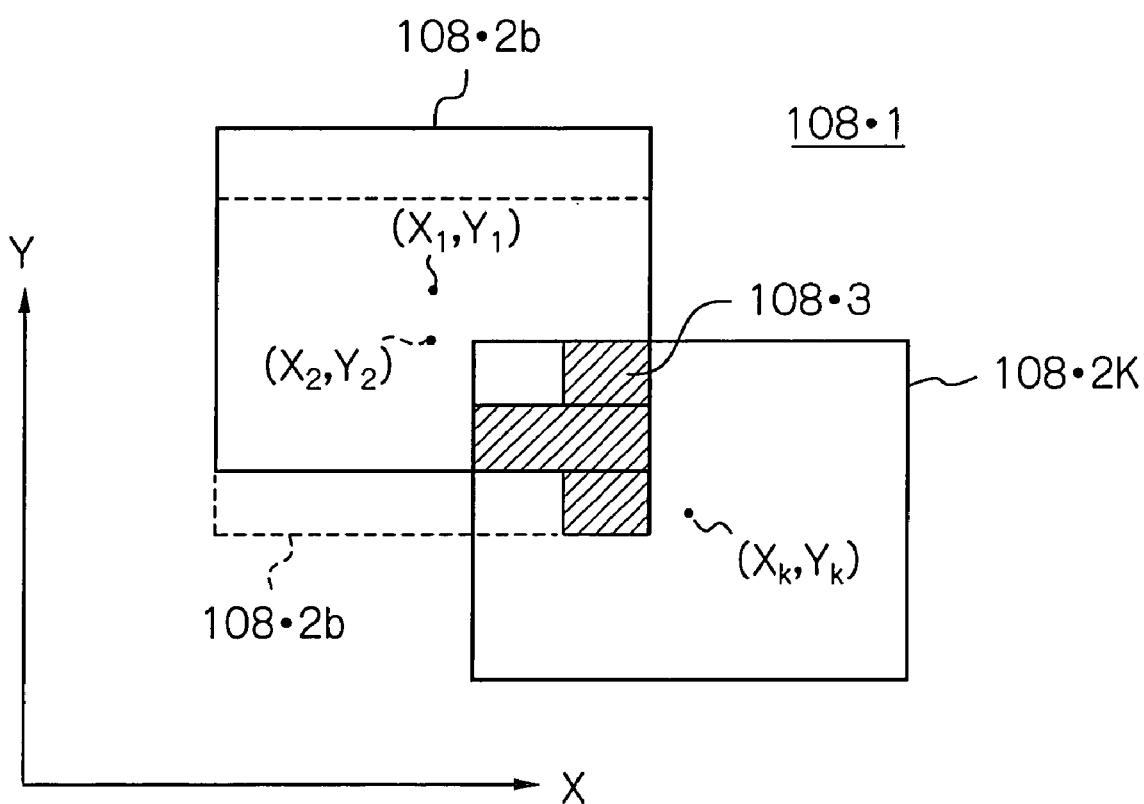
Figure 109:
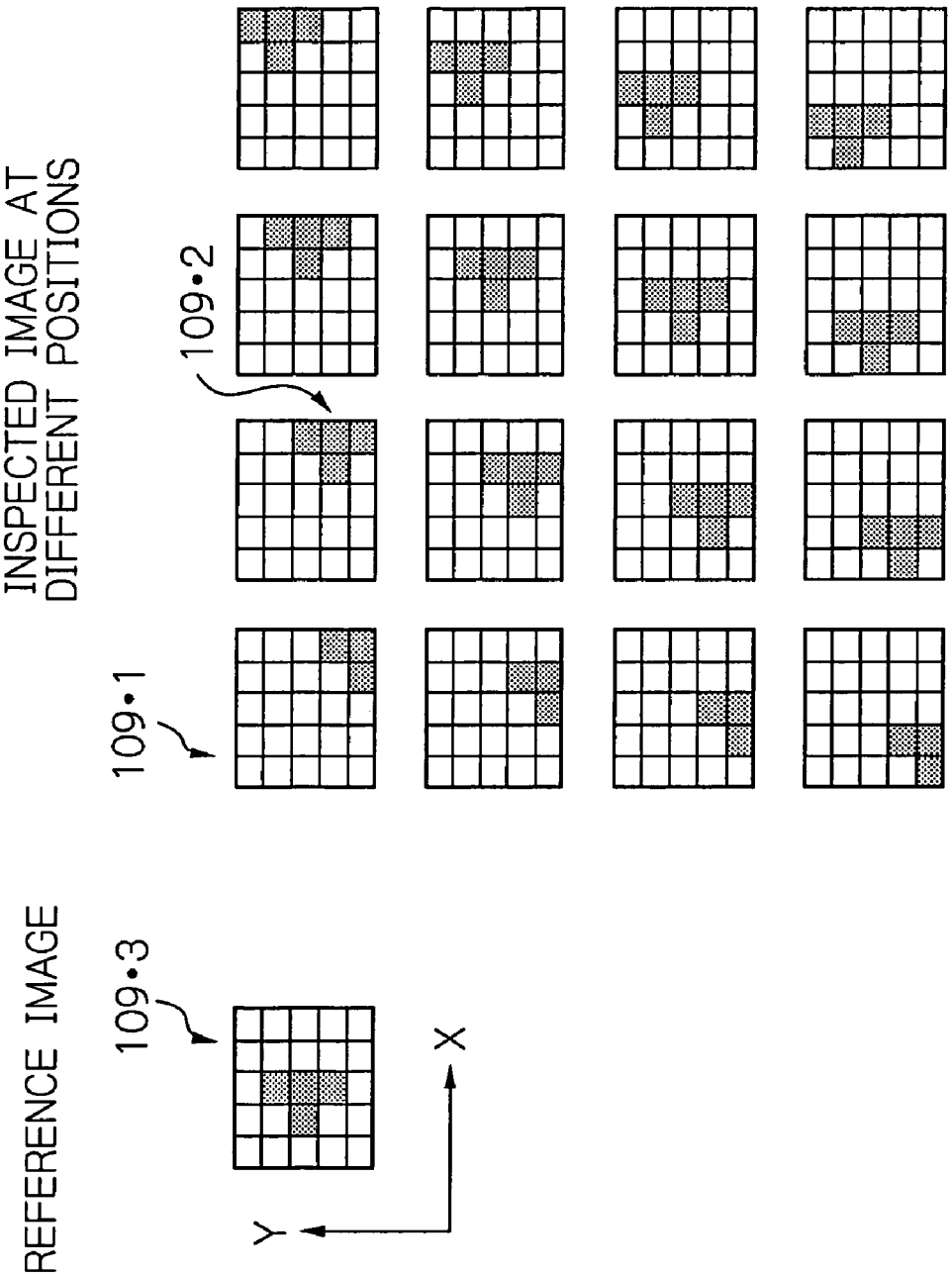
Figure 110:
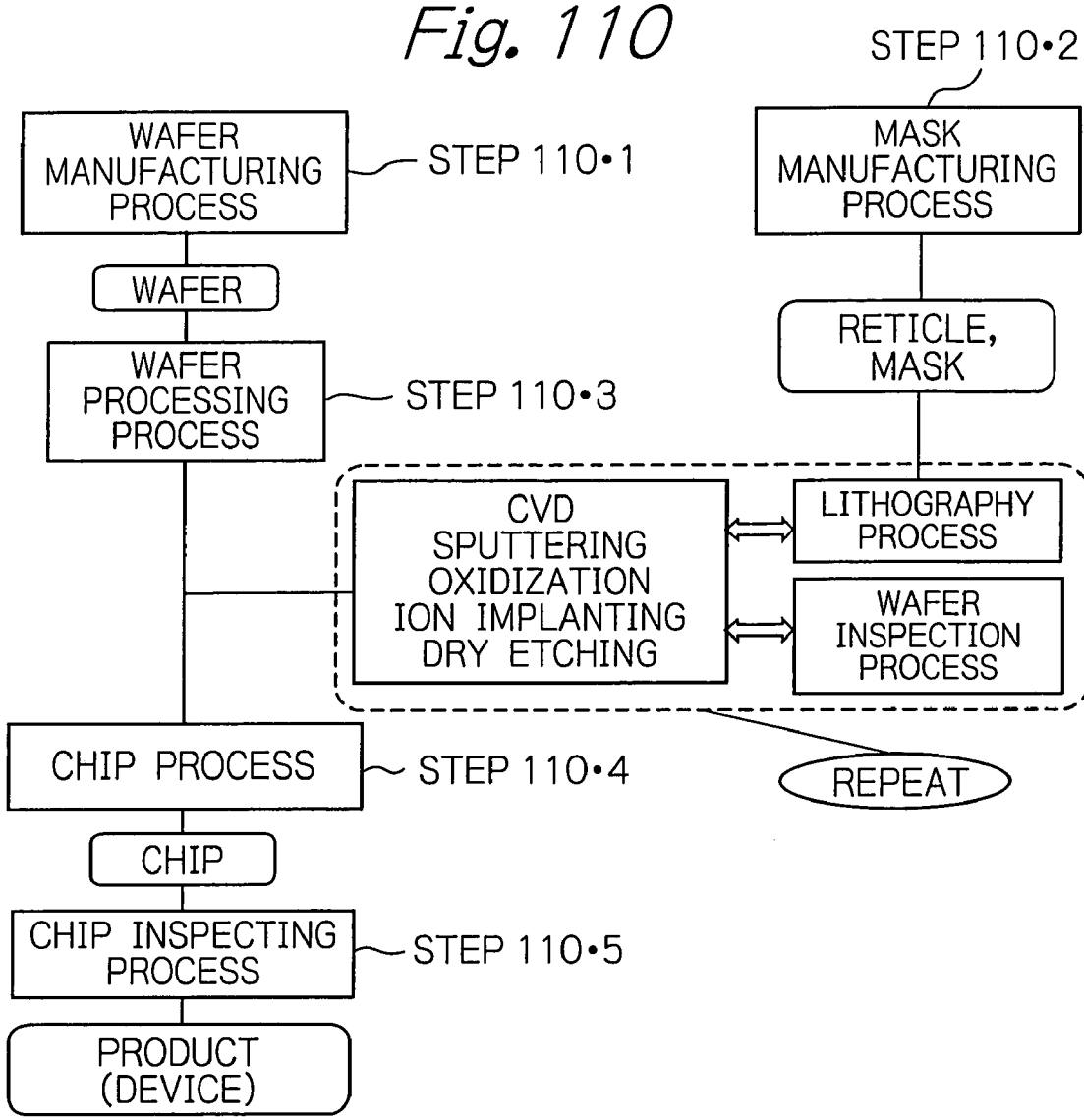
Figure 111:
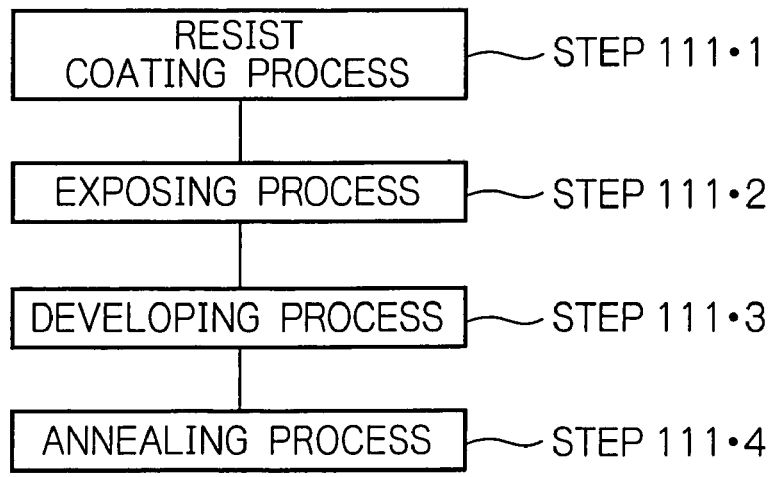
Figure 112:
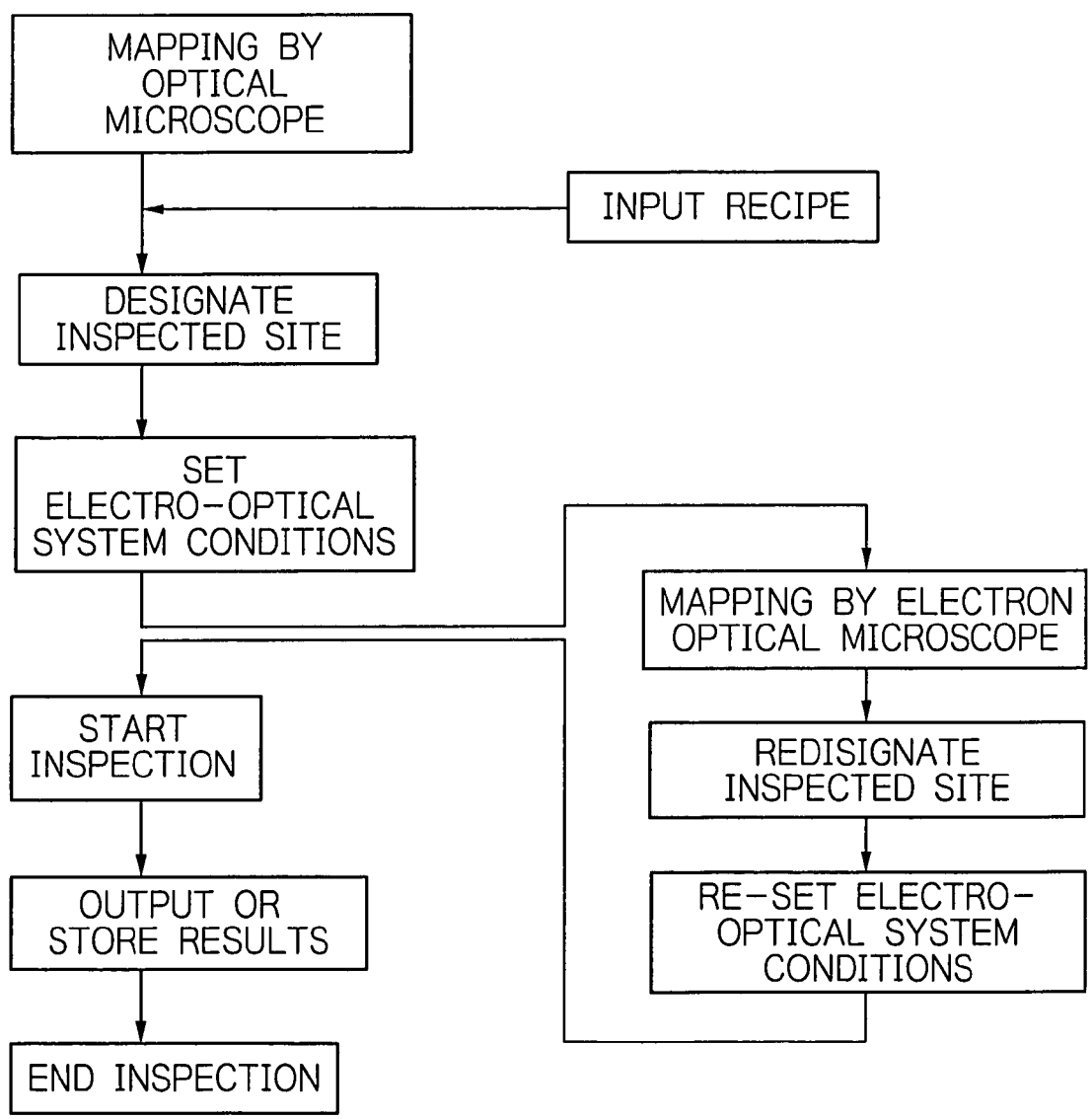
Figure 113:
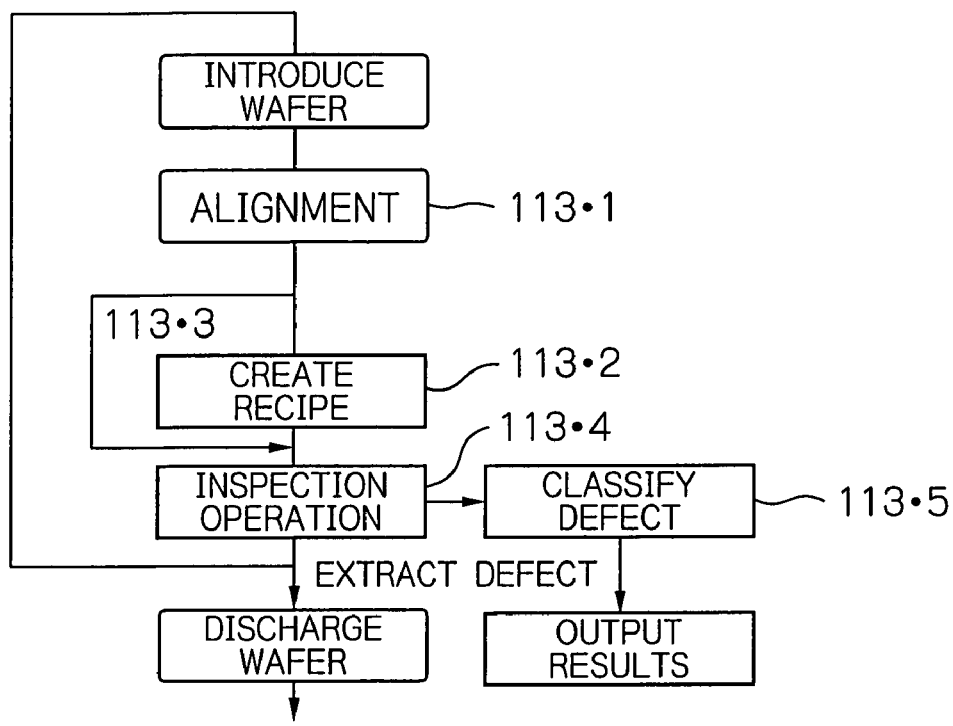
Figure 114:
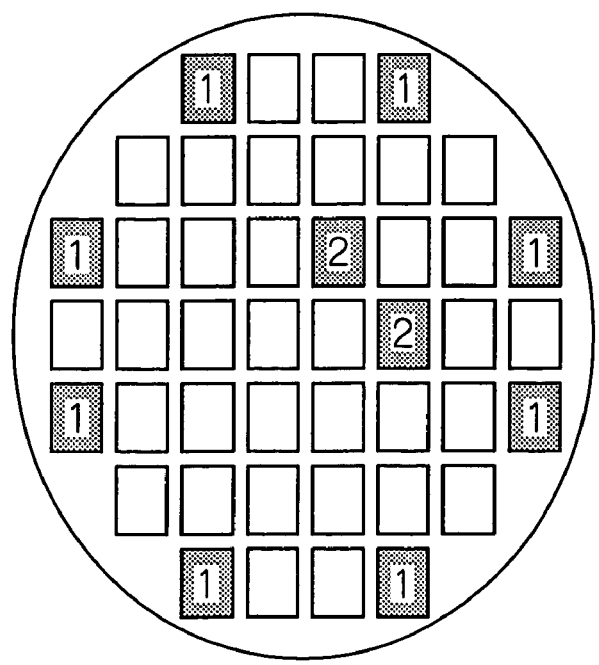
Figure 115:
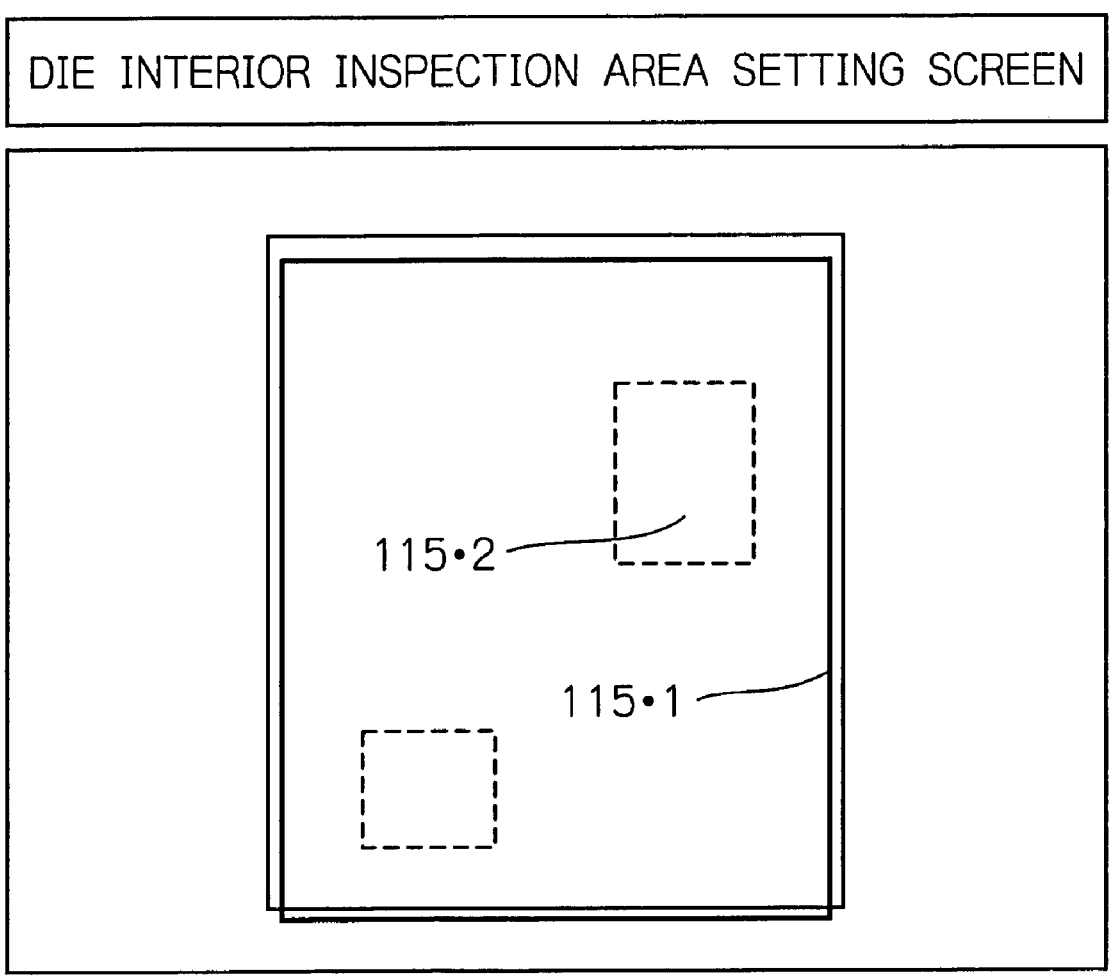
Figure 116:
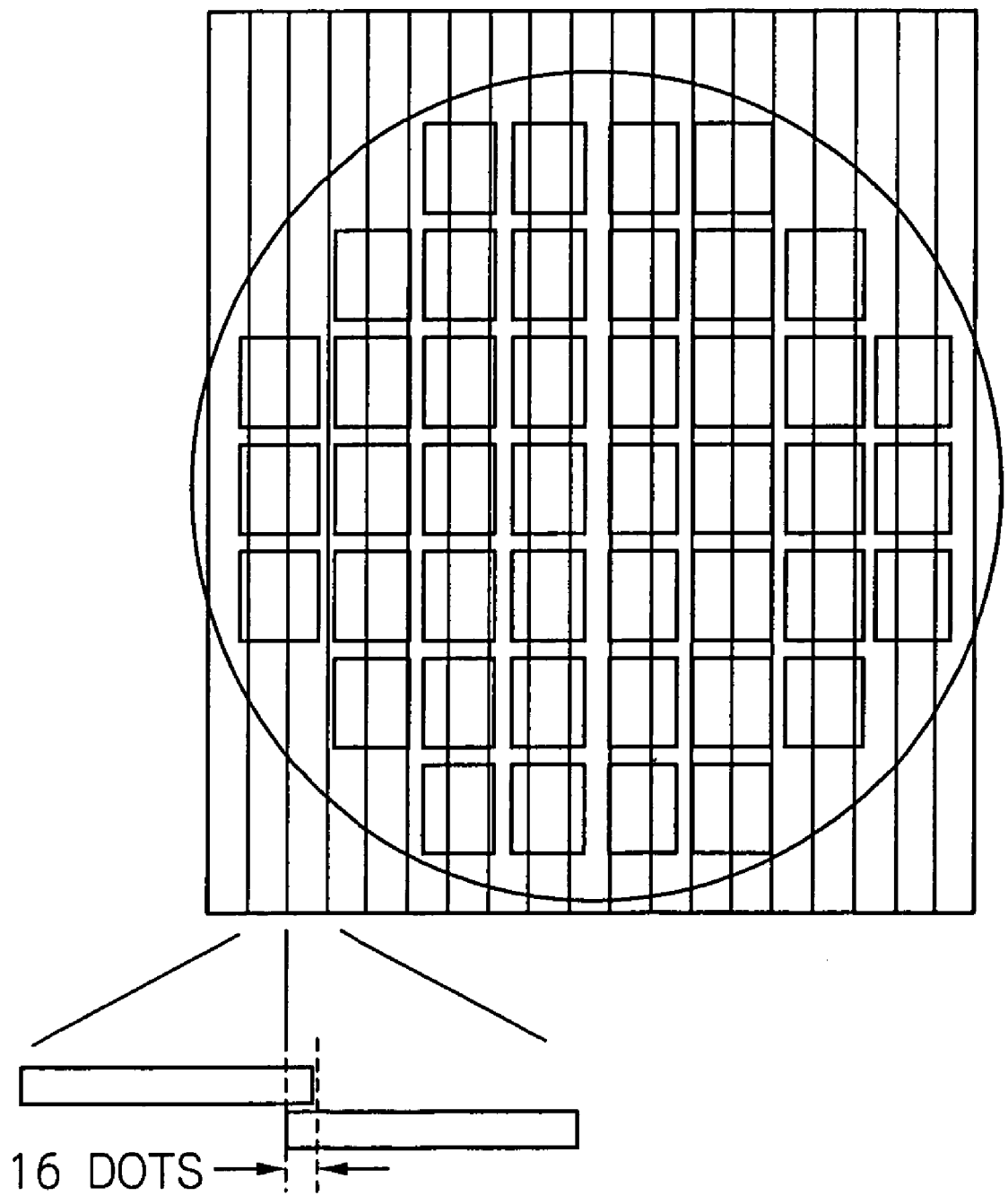
Figure 117A:
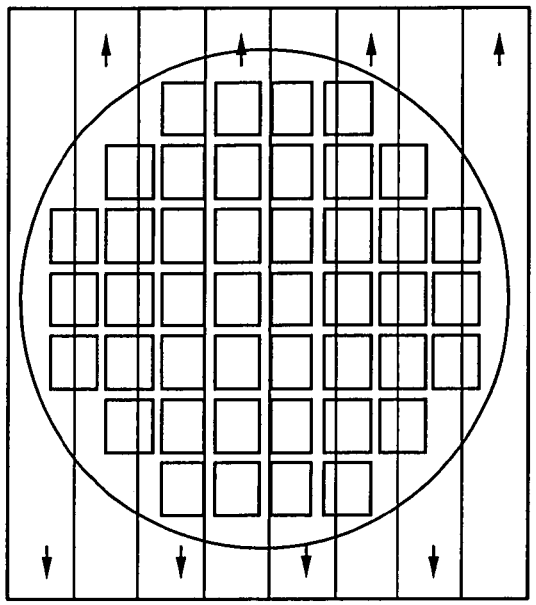
Figure 117B:
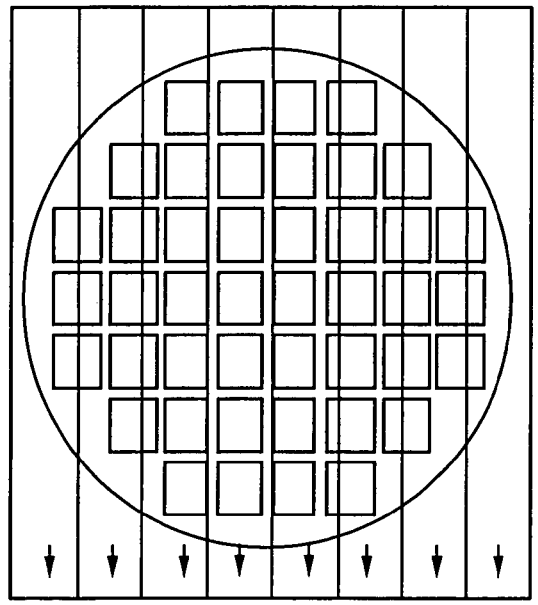
Figures 1, 118:
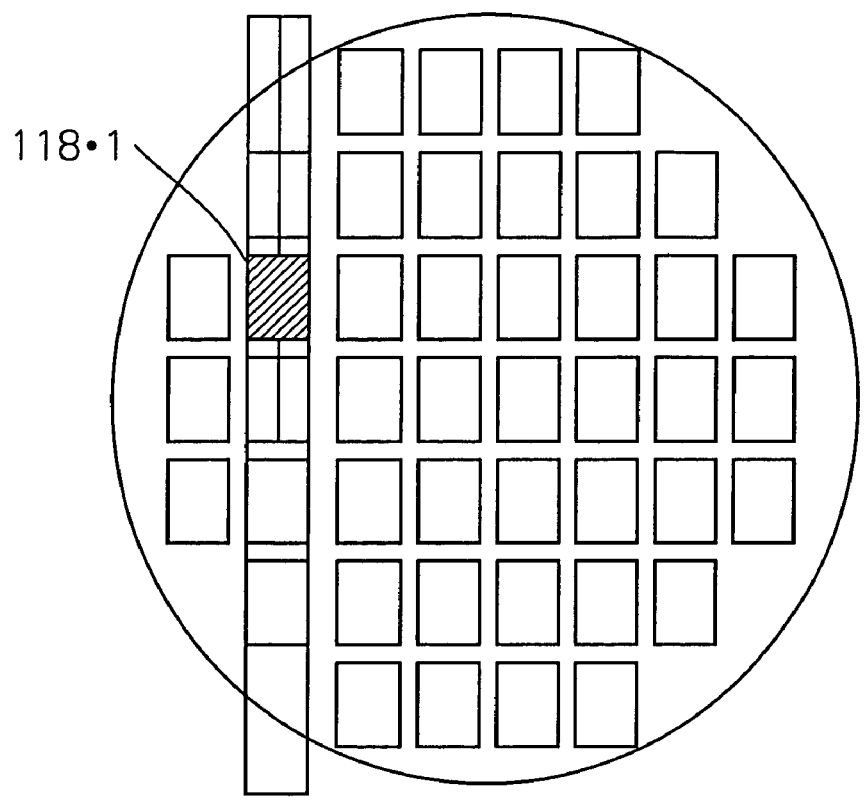
Figures 2, 118:
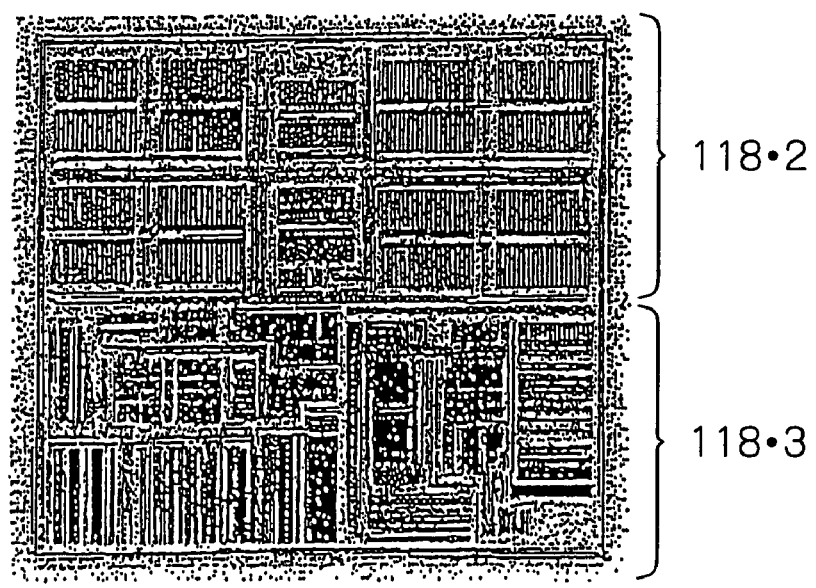
Figure 119:
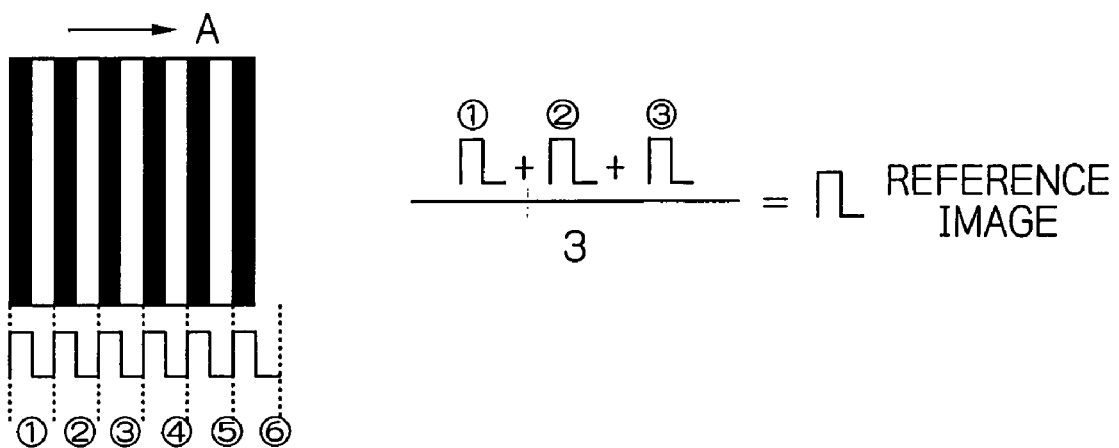
Figure 120:
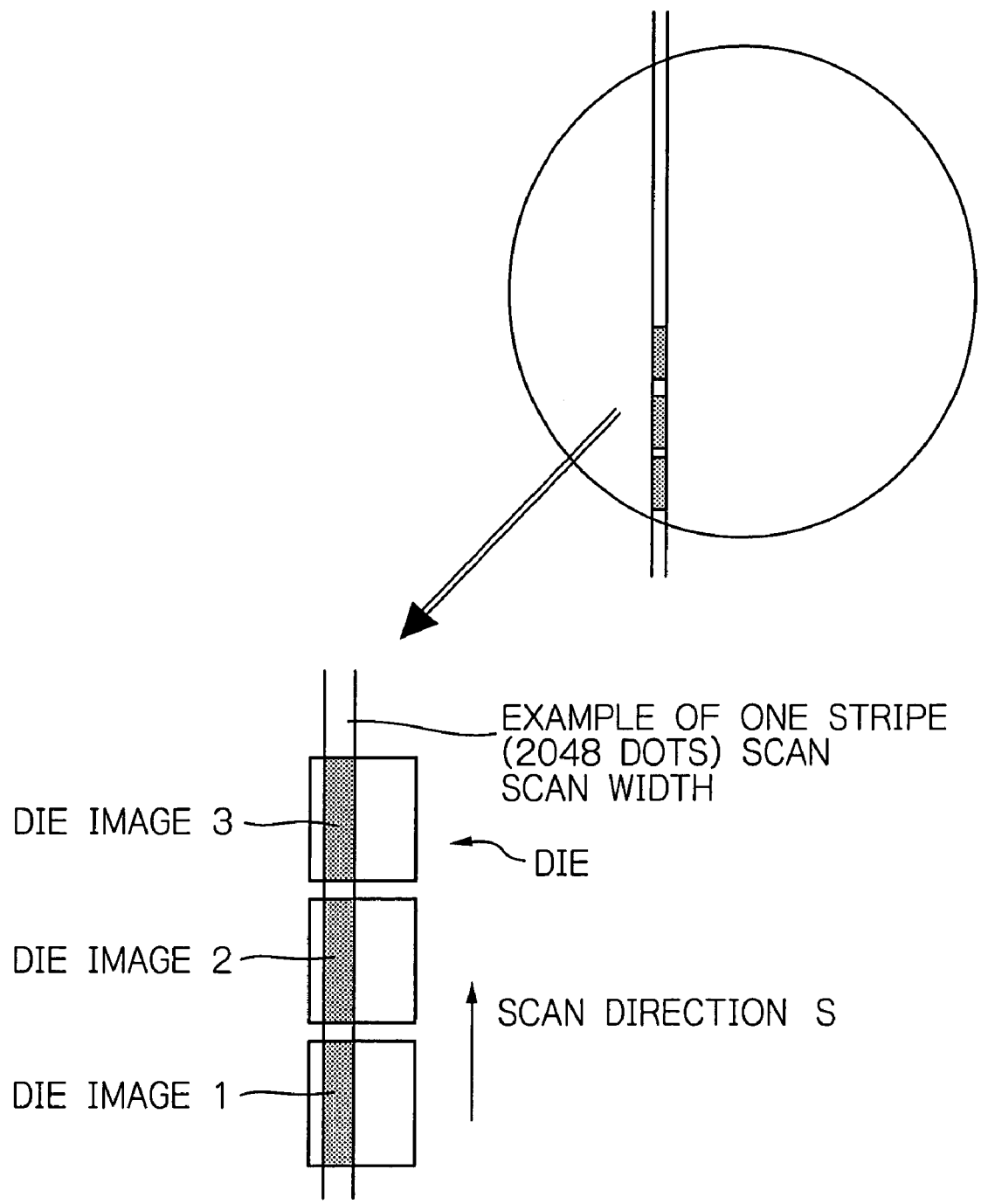
Figure 121:
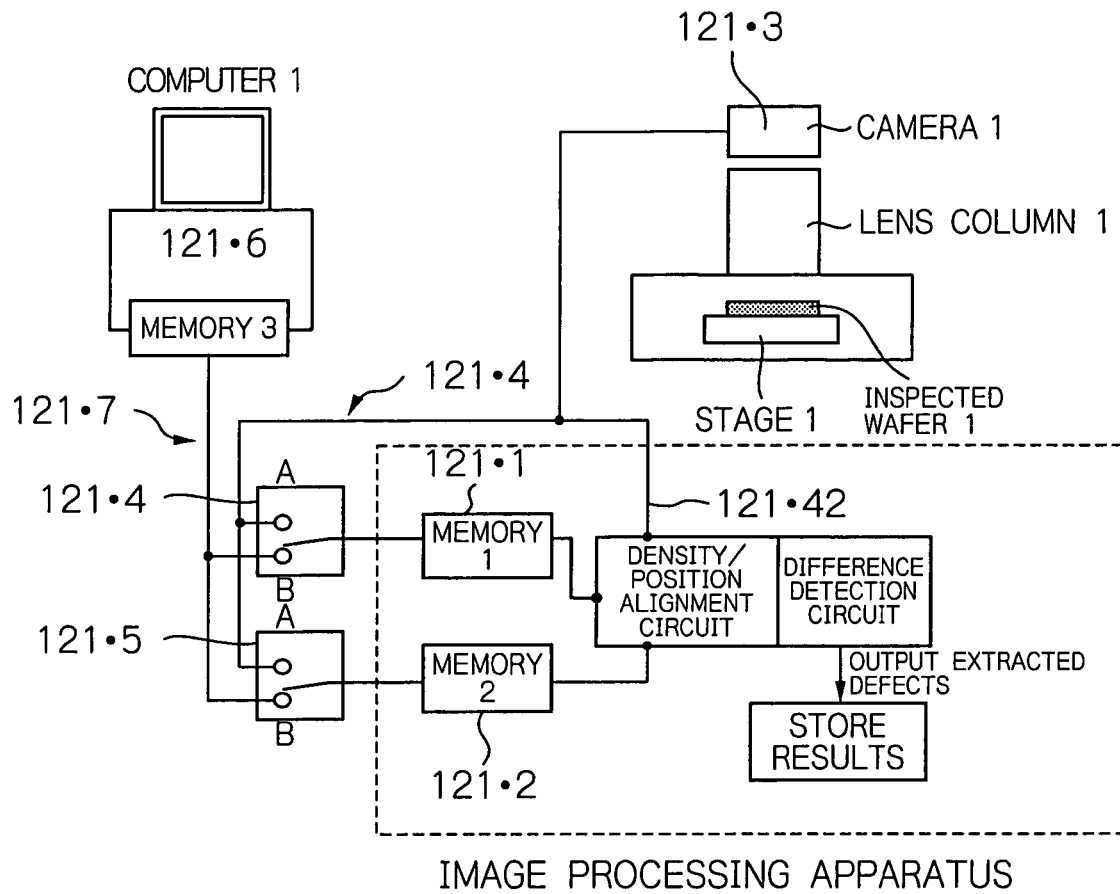
Figure 122:
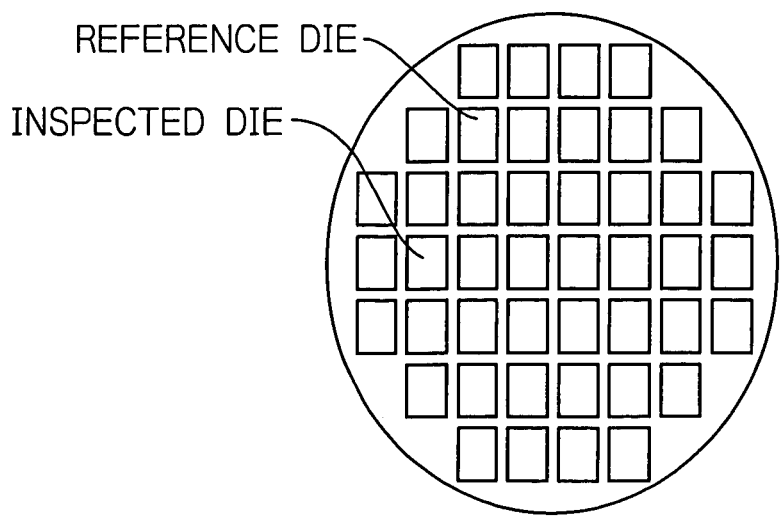
Figure 123:
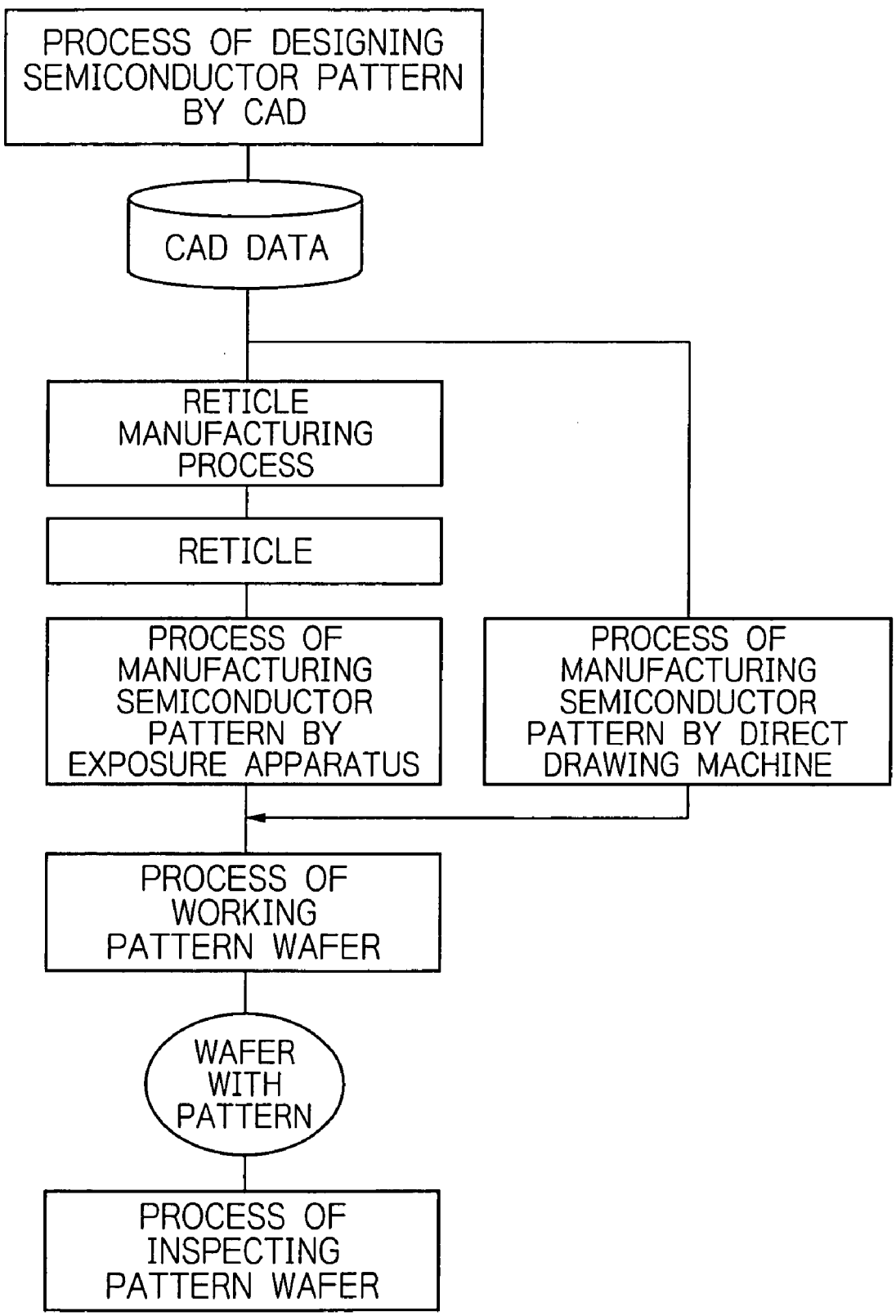
Figure 124:
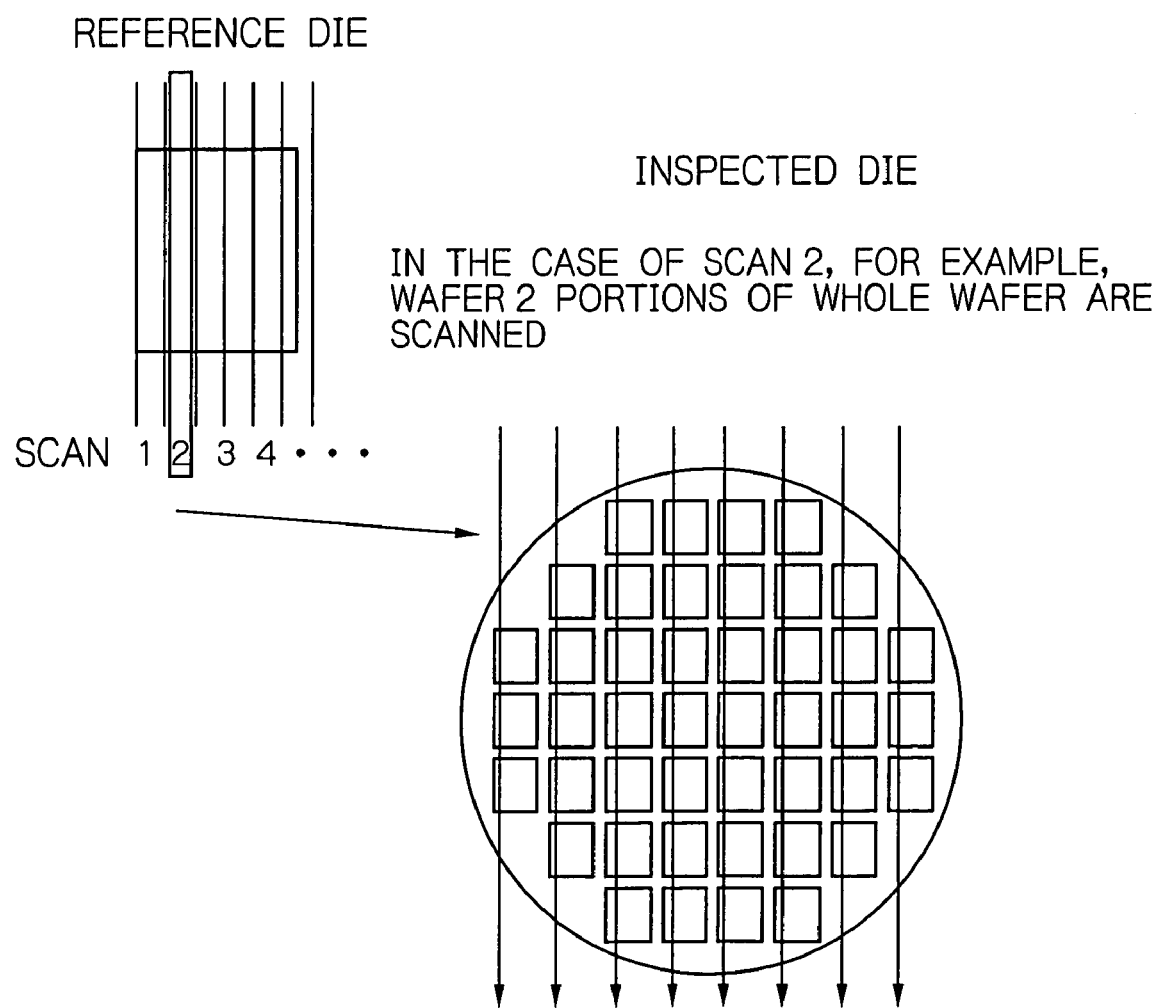
Figure 125:
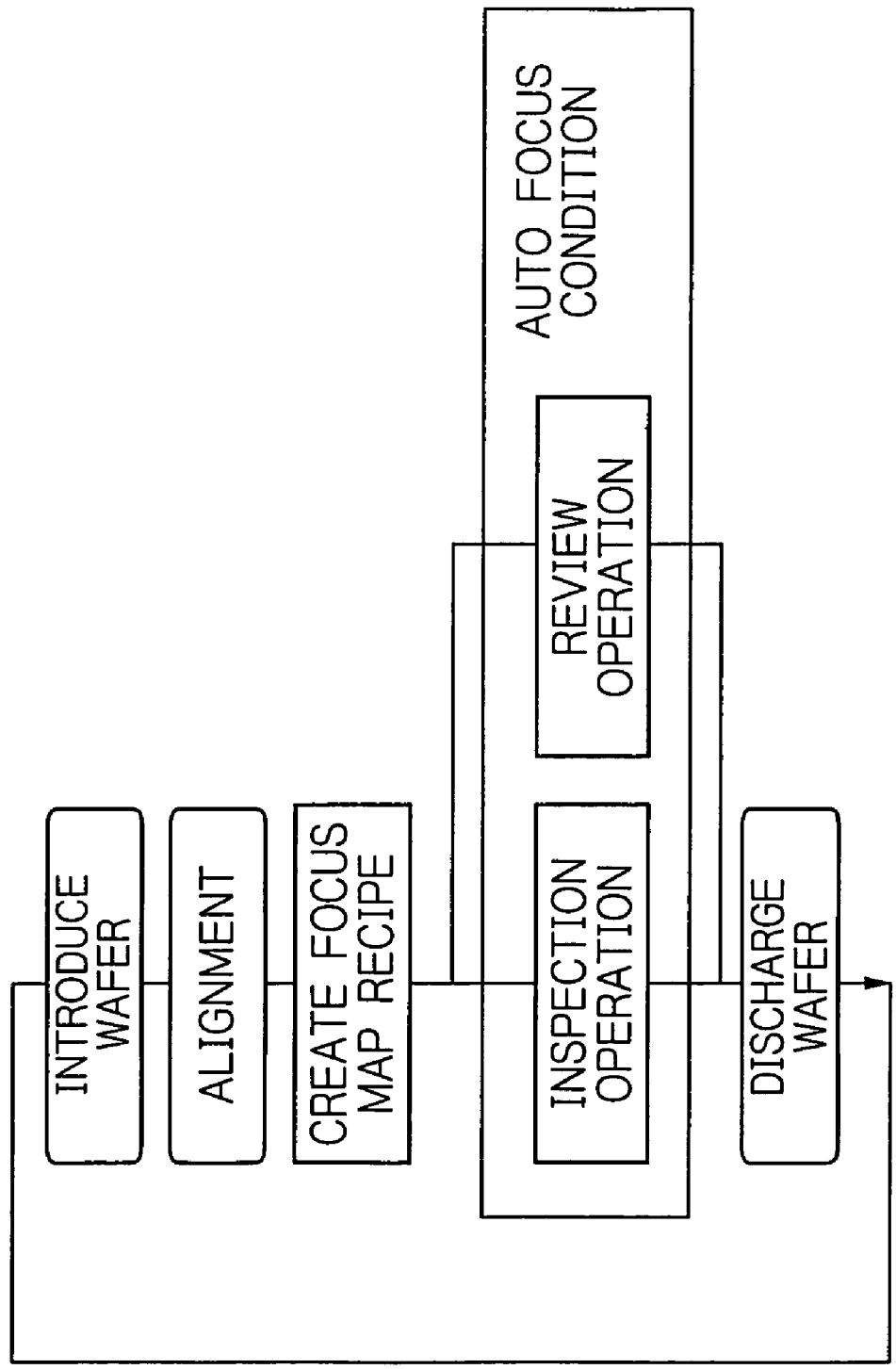
Figure 126:
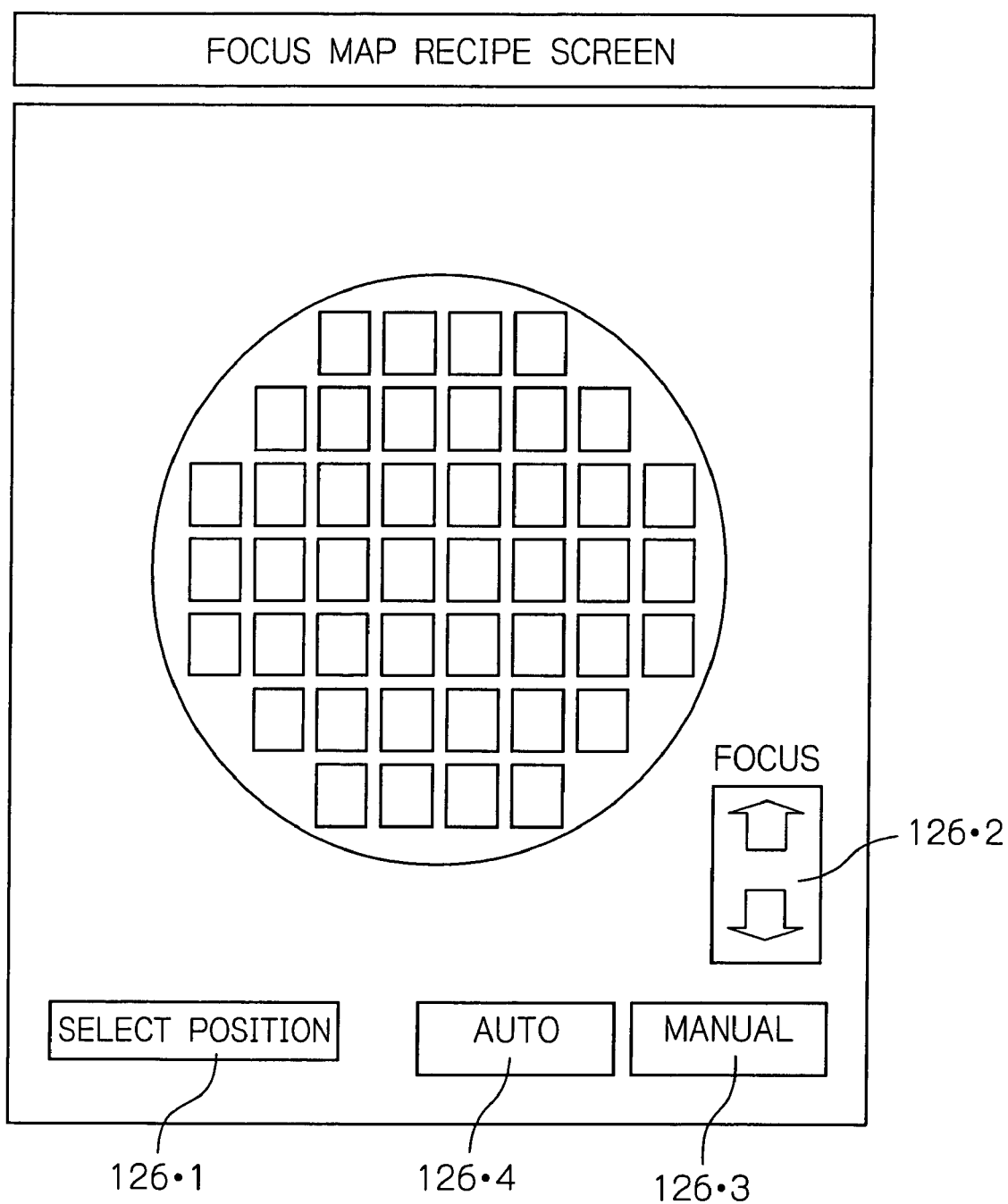
Figure 127:
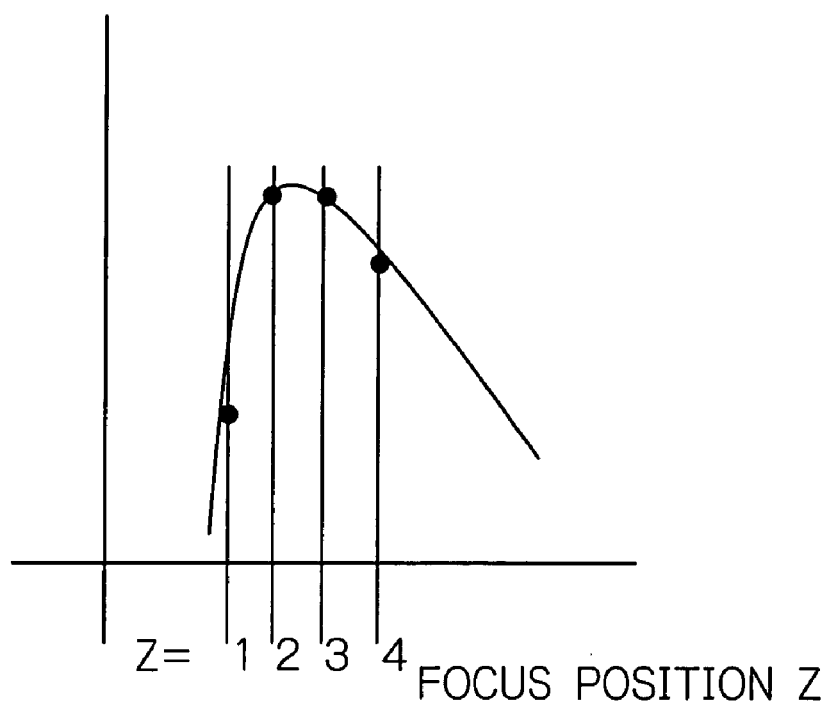
Figure 128:
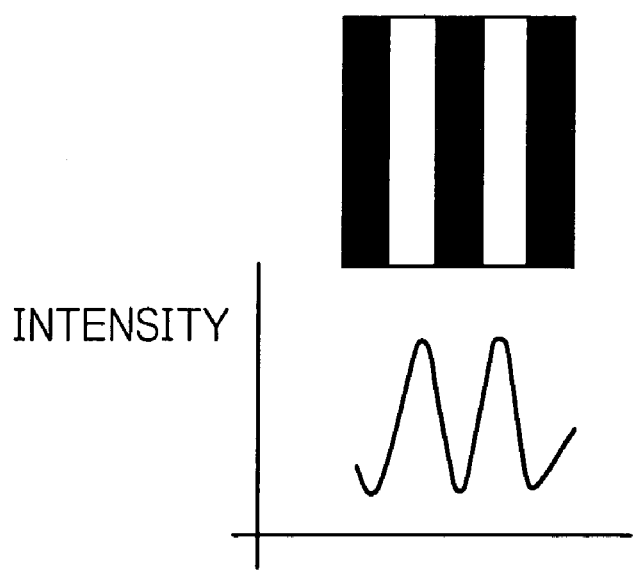
Figure 129:
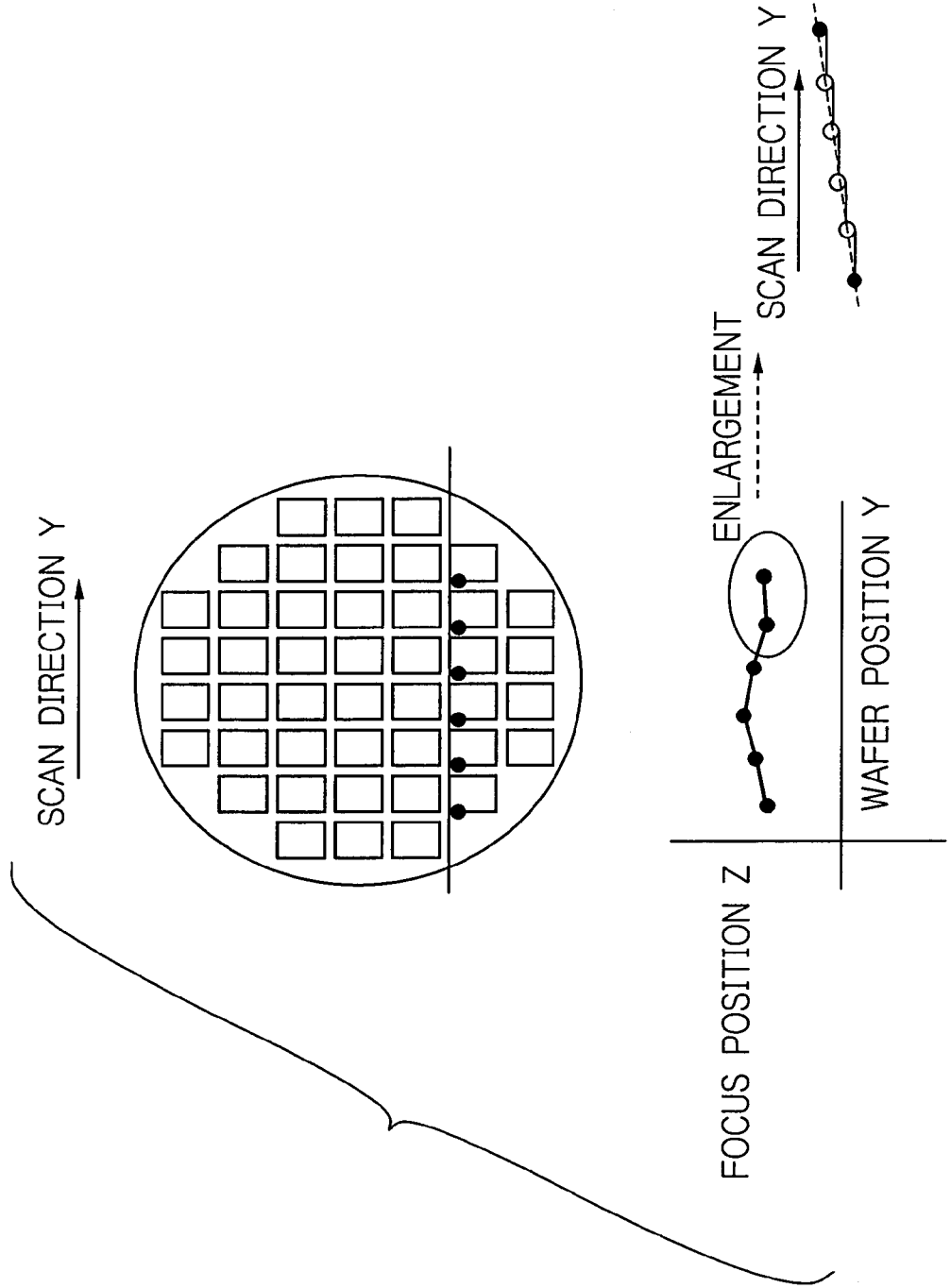
Figure 130:
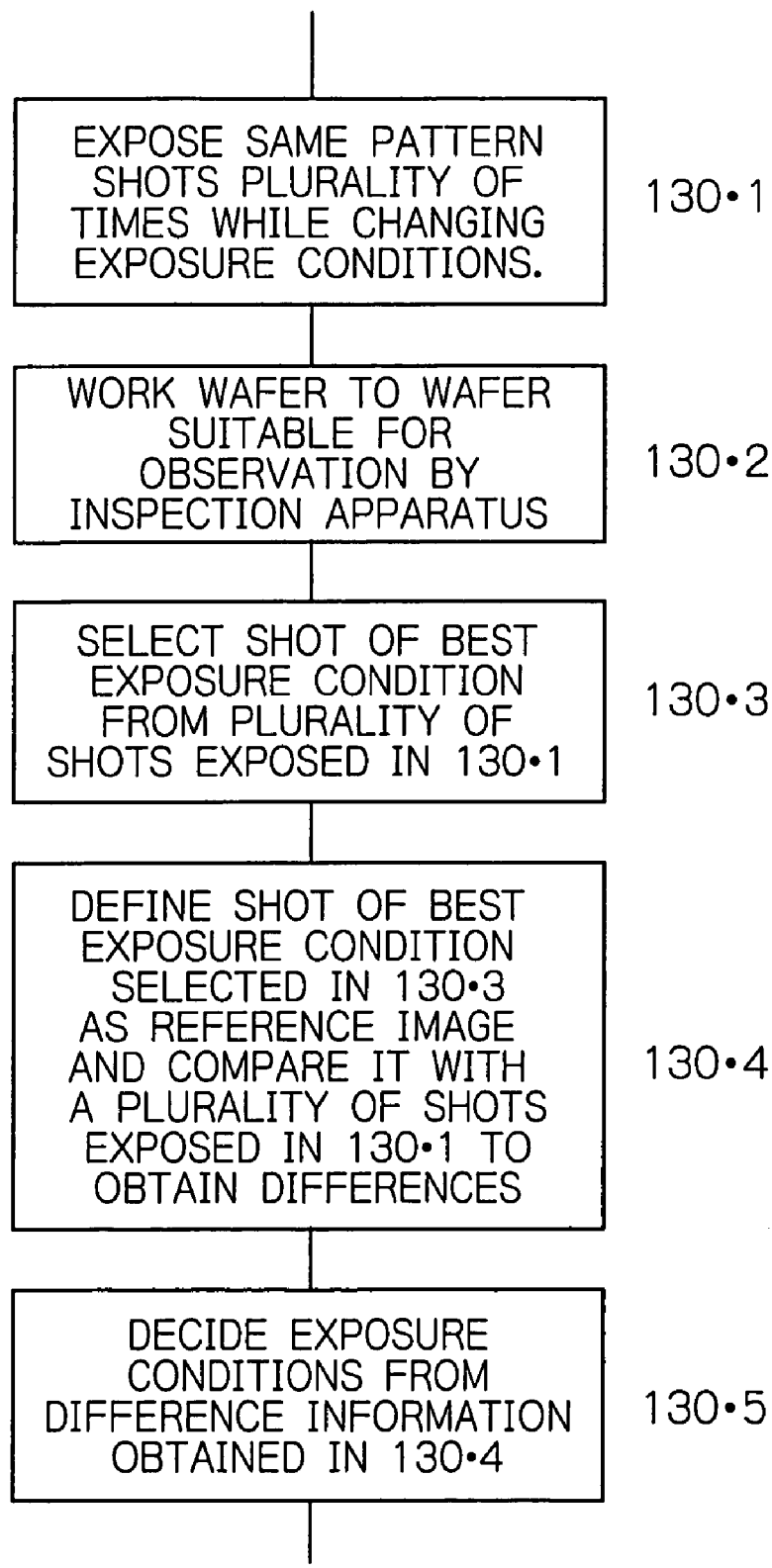
Figure 131:
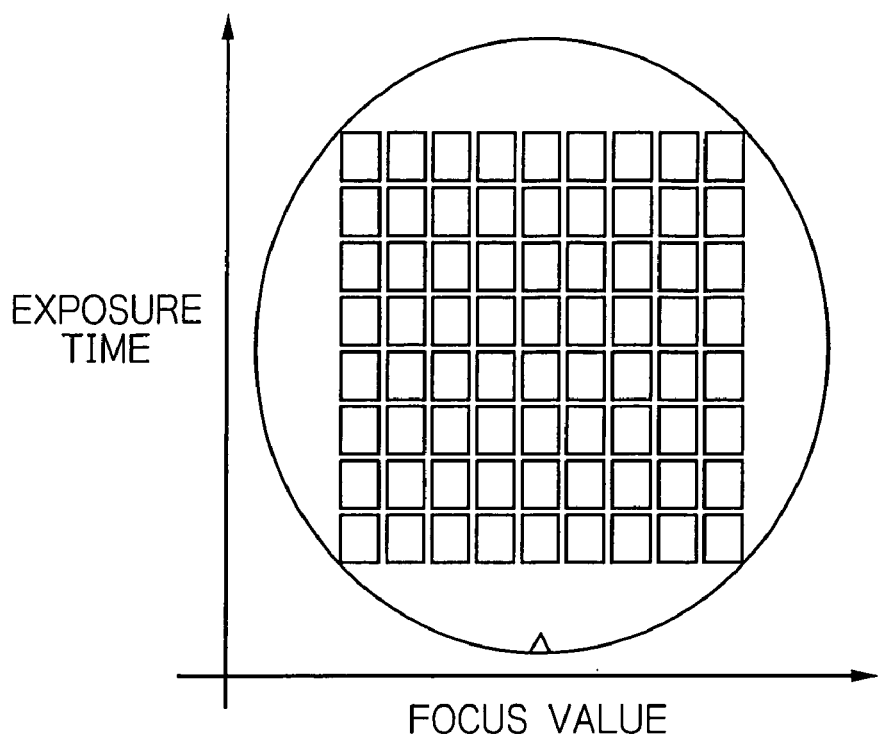
Figure 132:
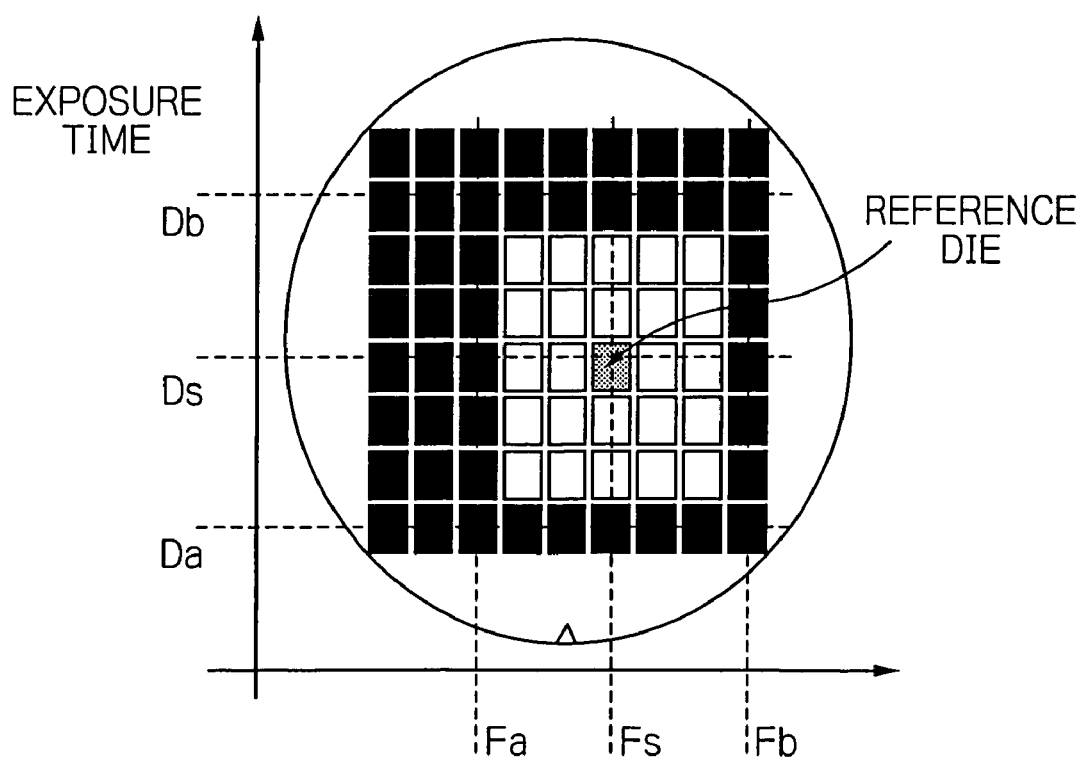
Figure 133:
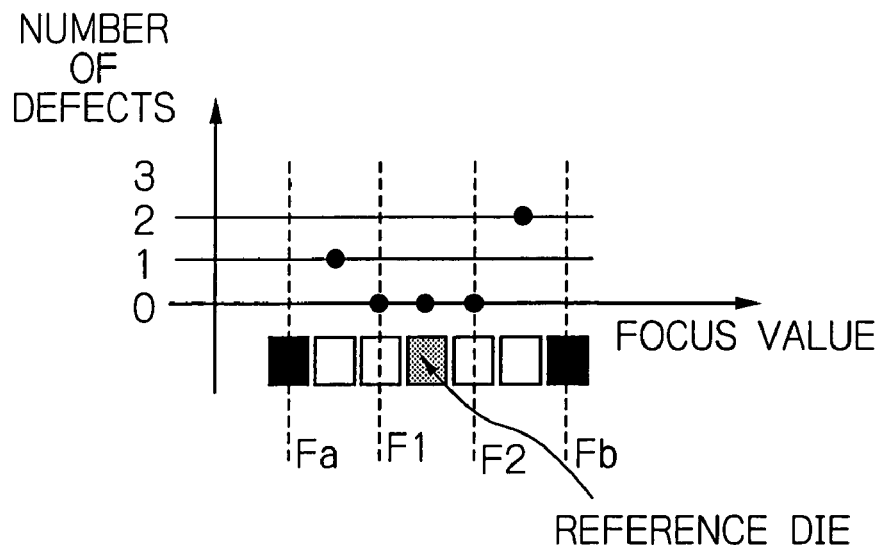
Figure 134:
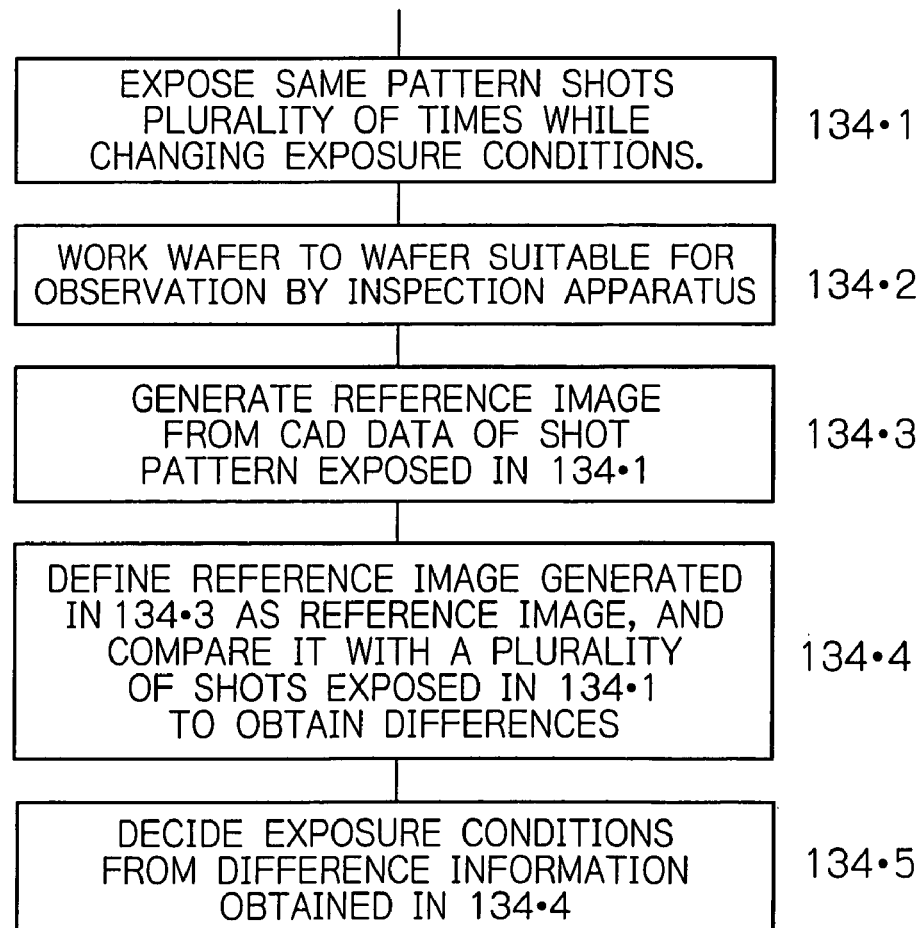
Figure 137:
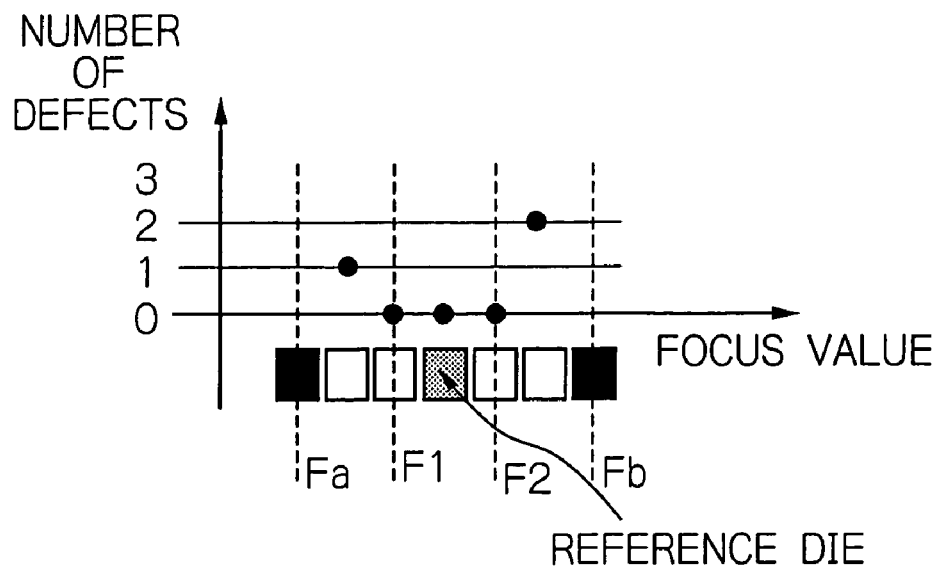
Figure 138:
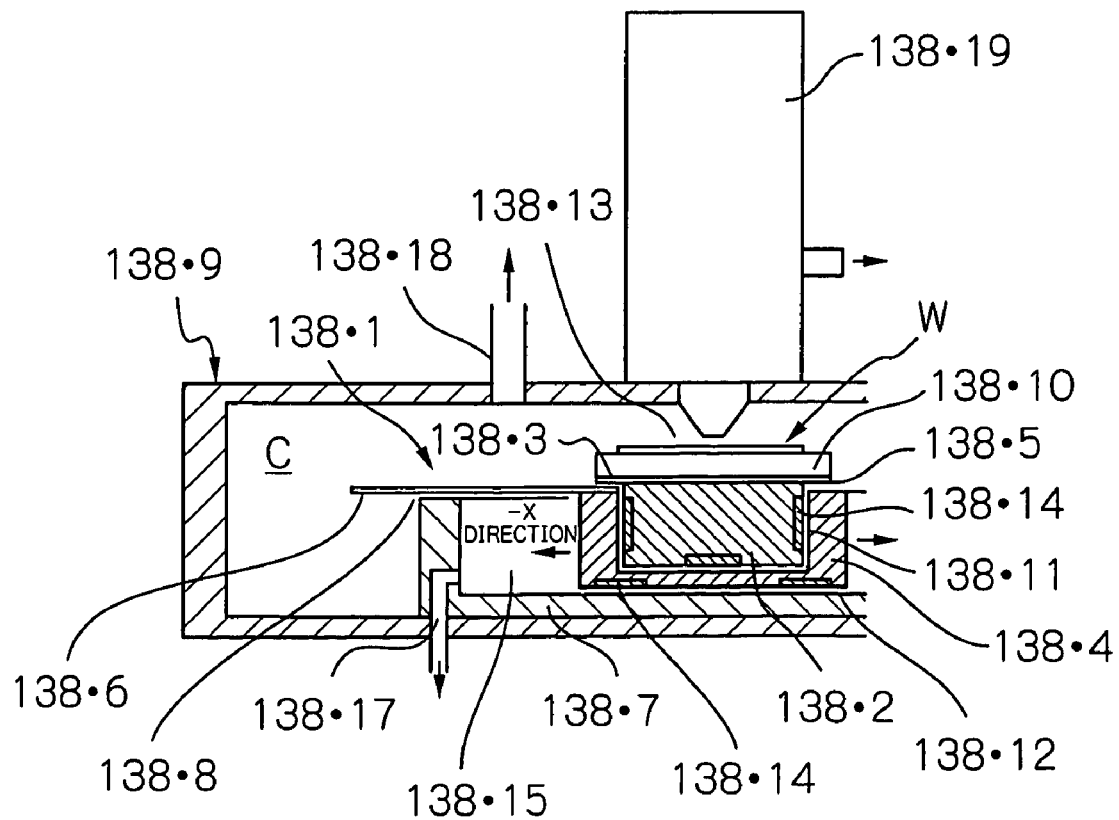
Figure 139:
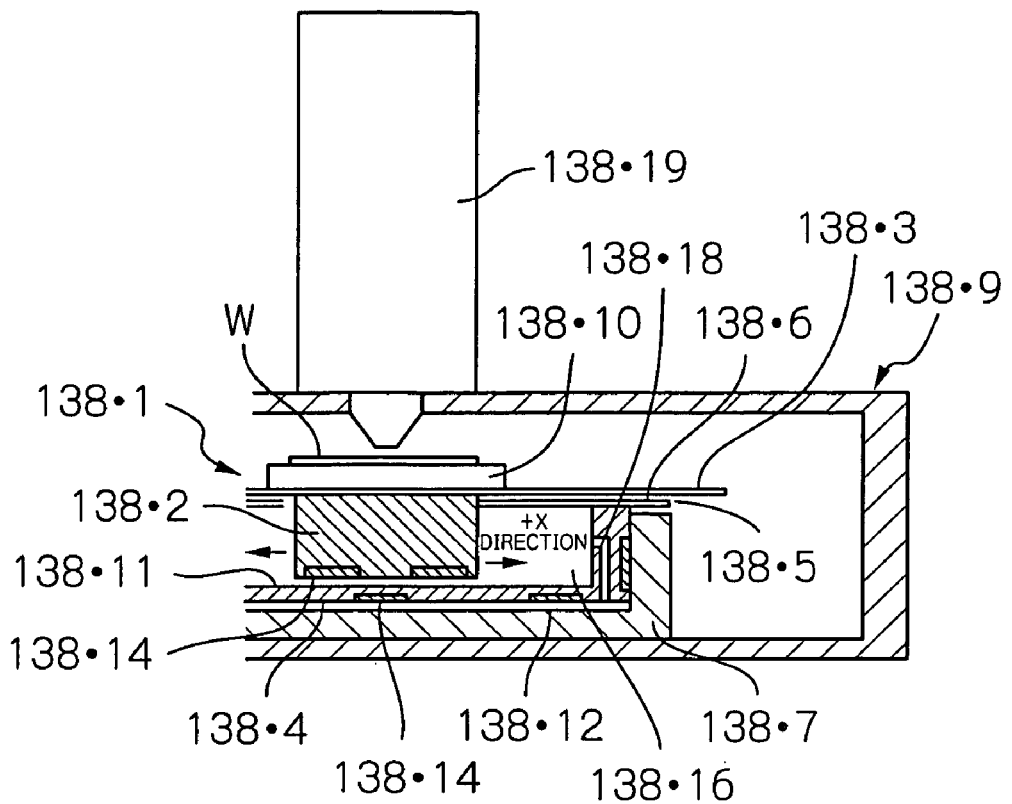
Figure 140:
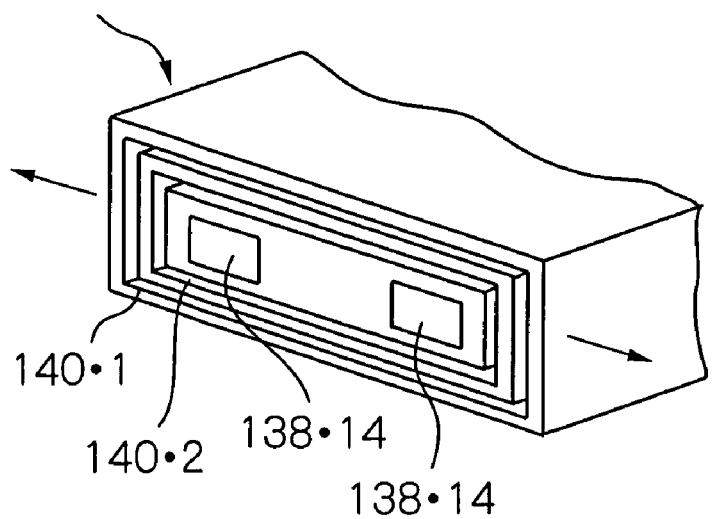
Figure 141:
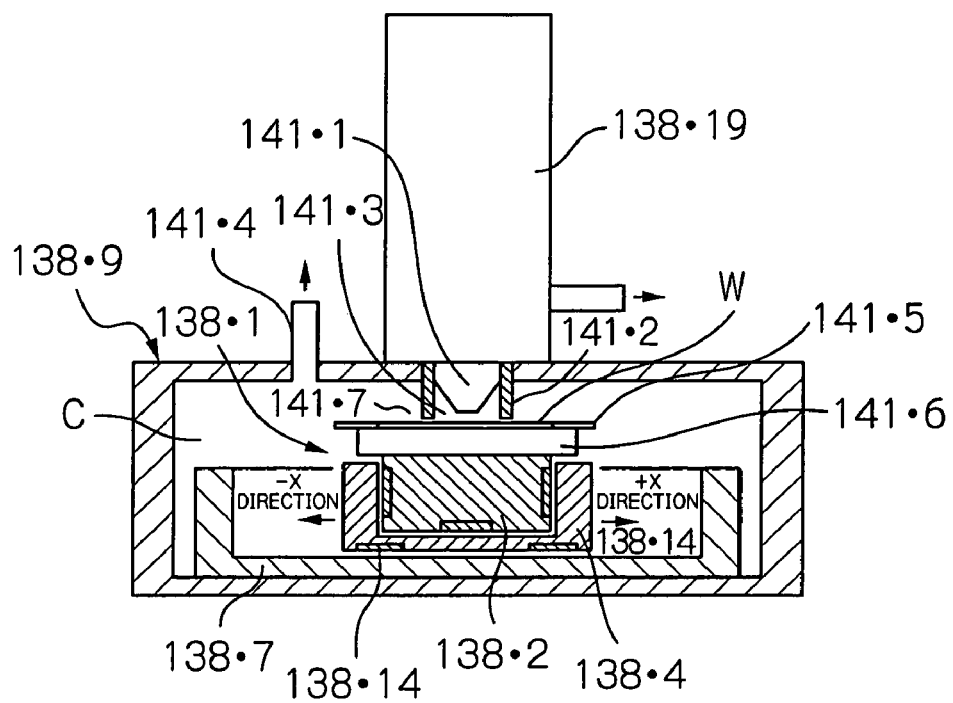
Figure 142:
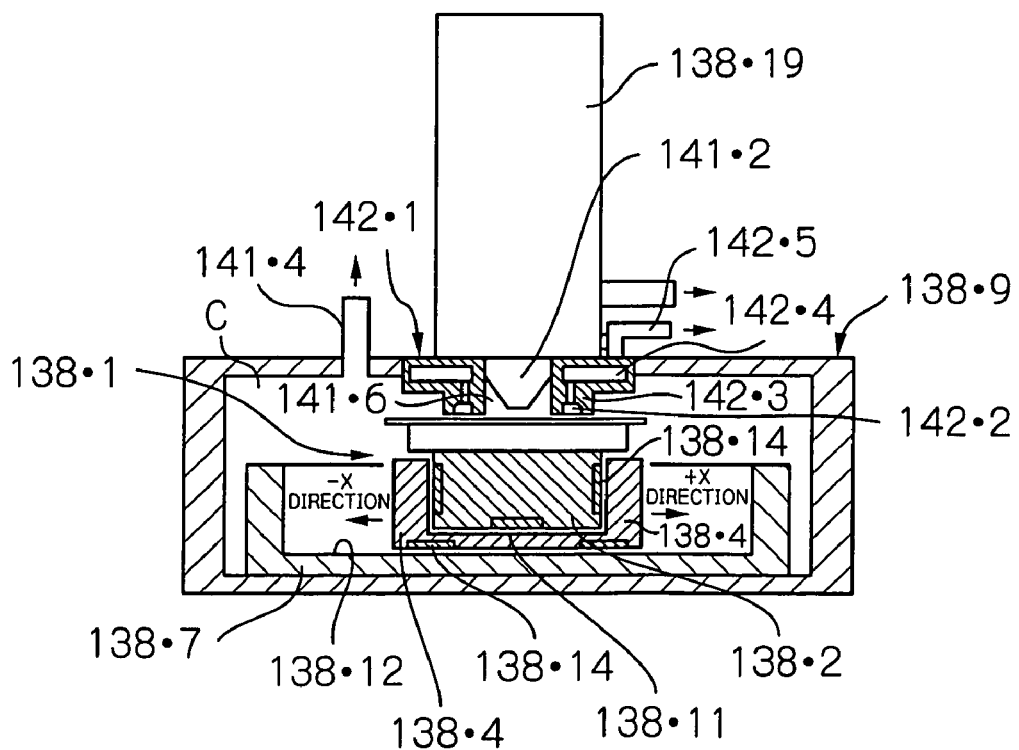
Figure 143:
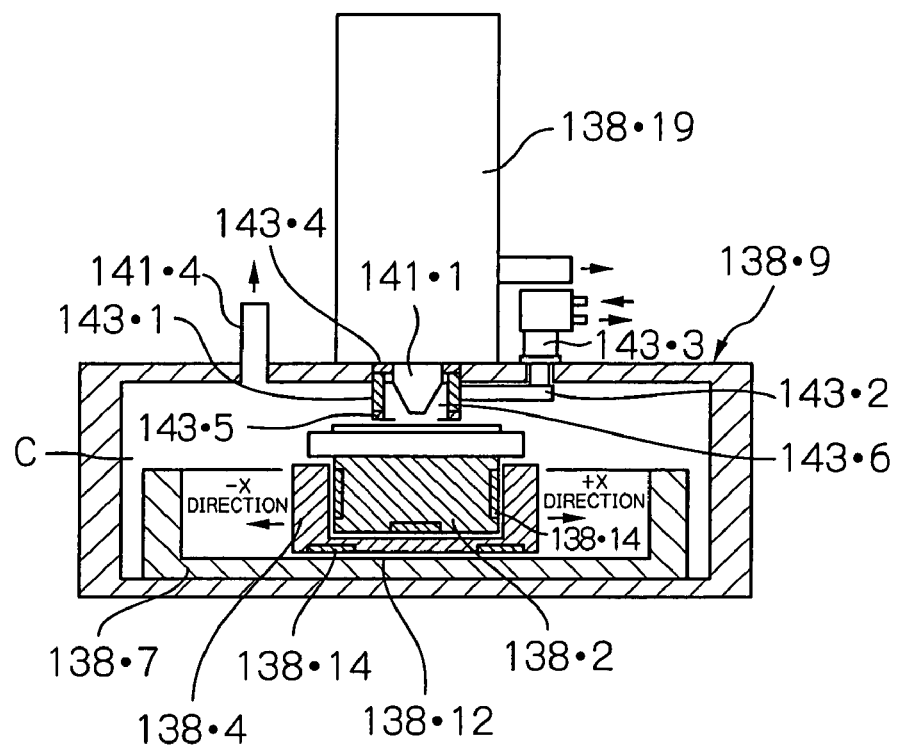
Figure 144:
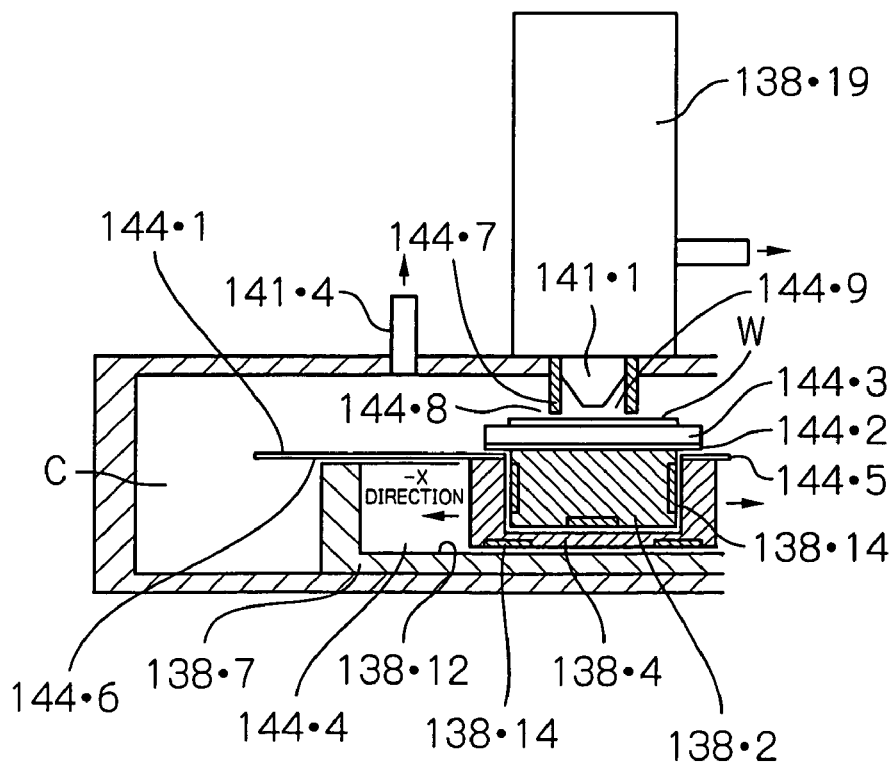
Figure 145:
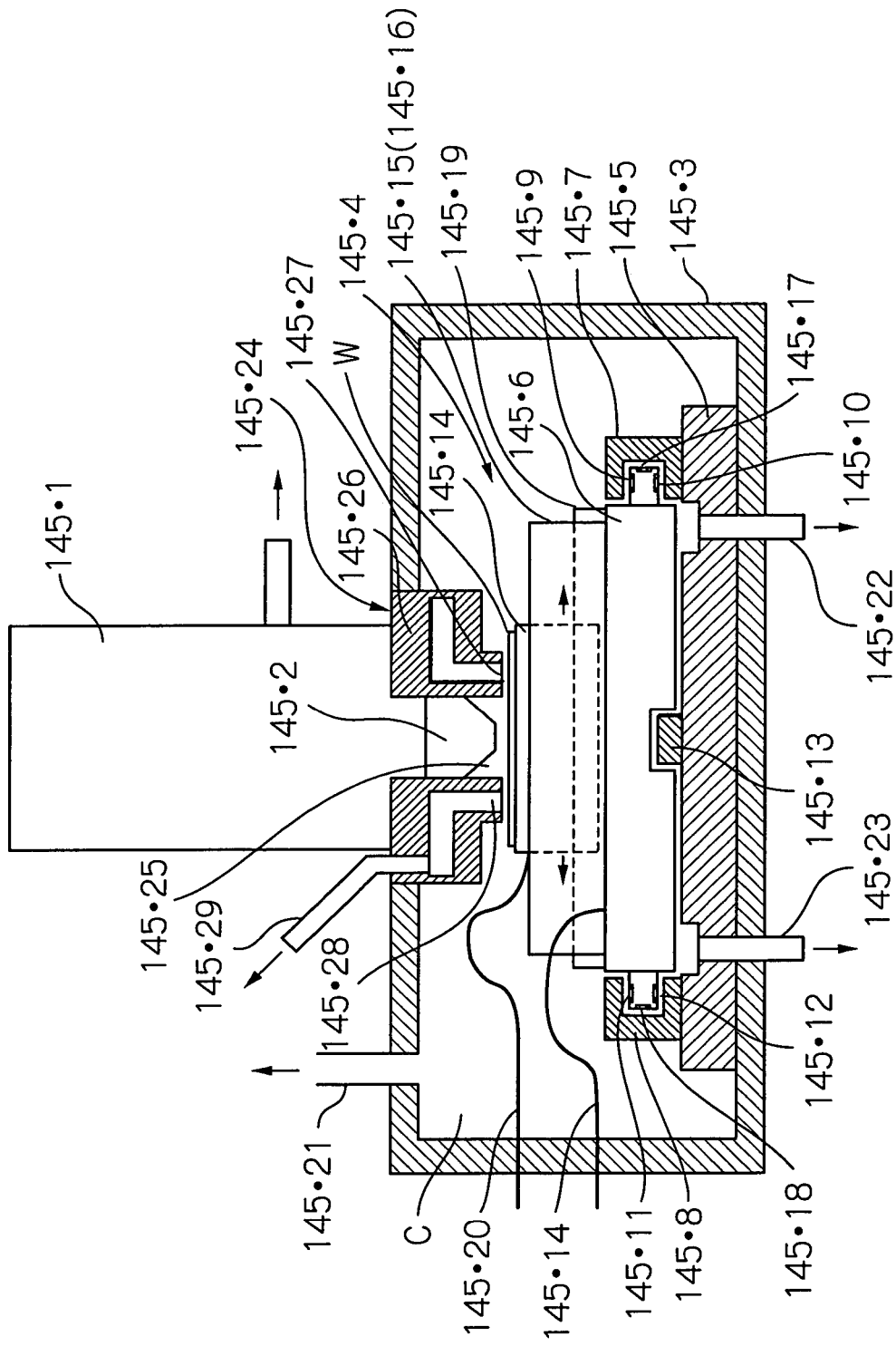
Figure 146:
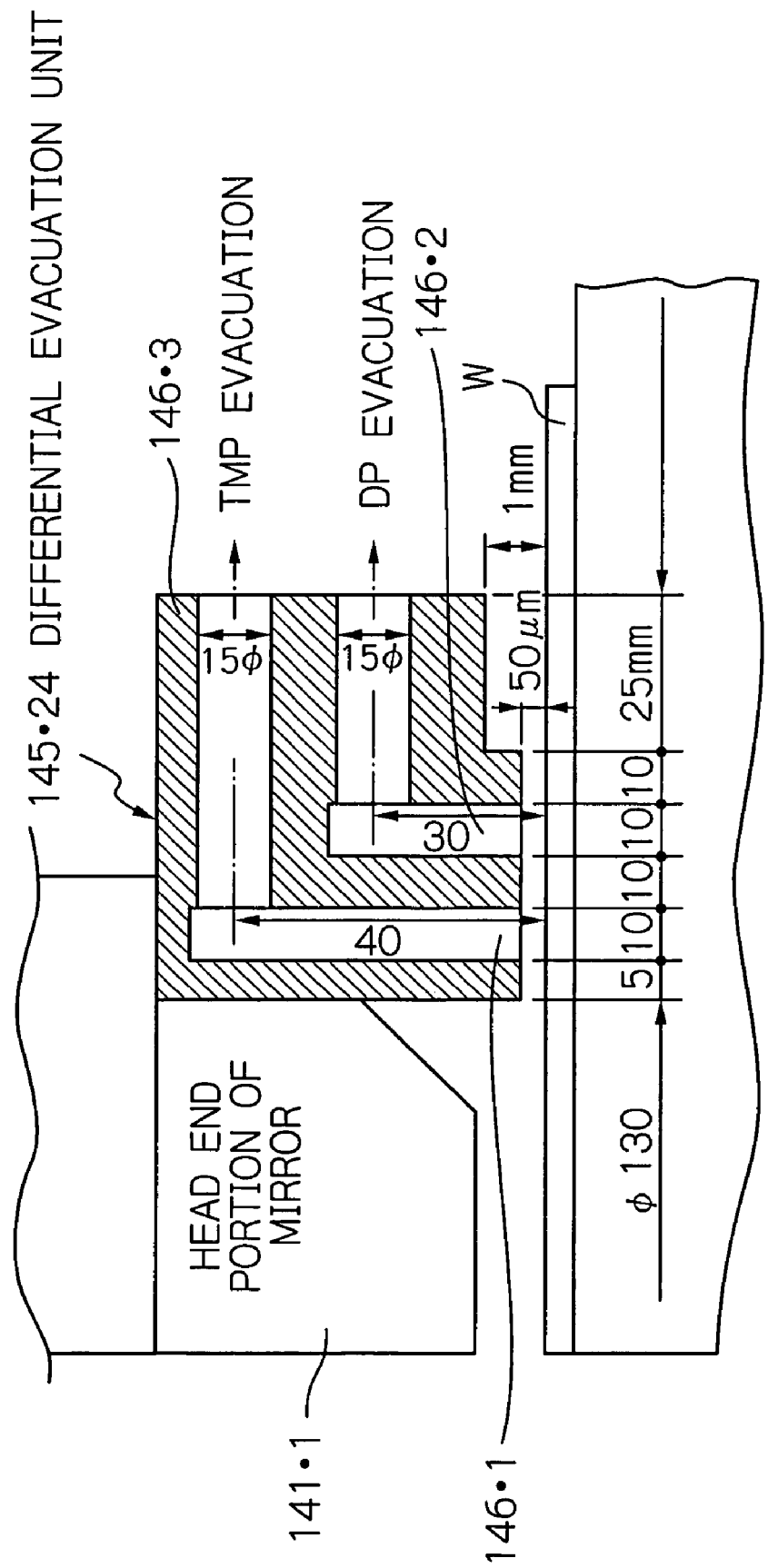
Figure 147:
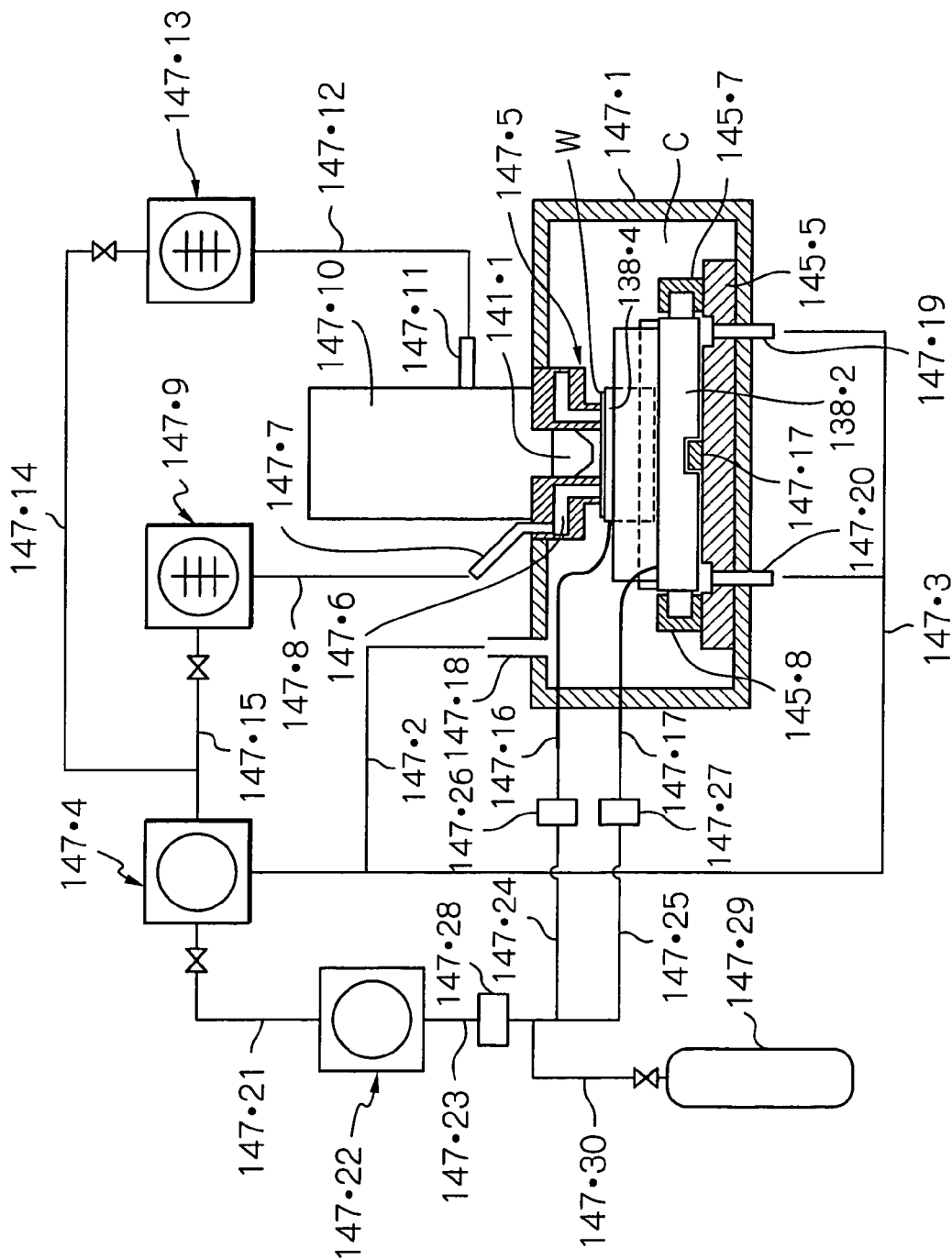
Figure 148A:
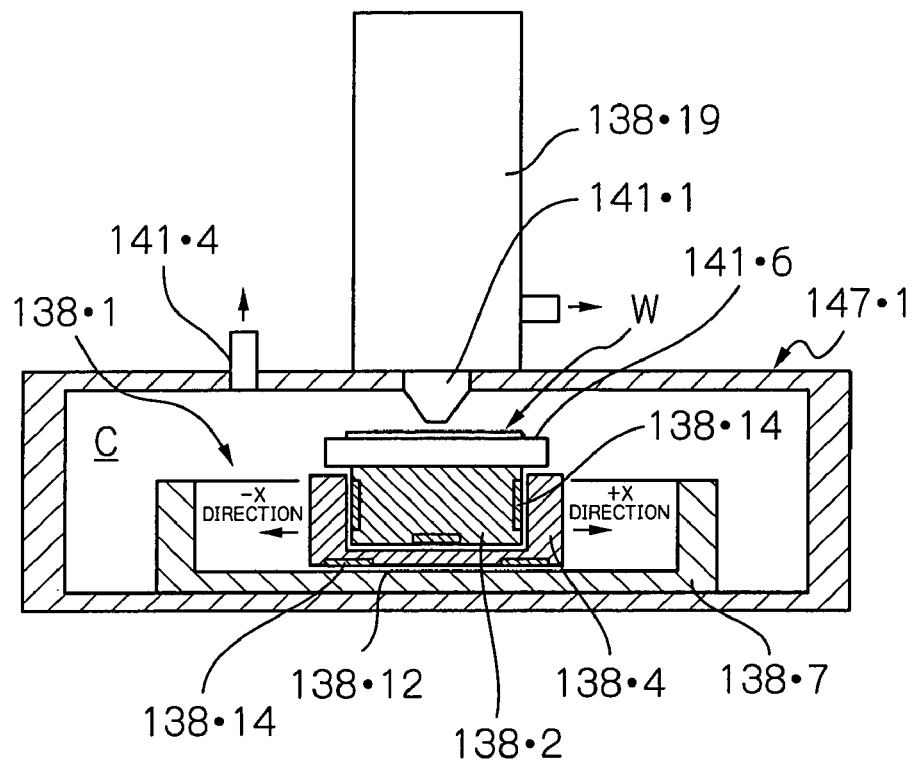
Figure 148B:
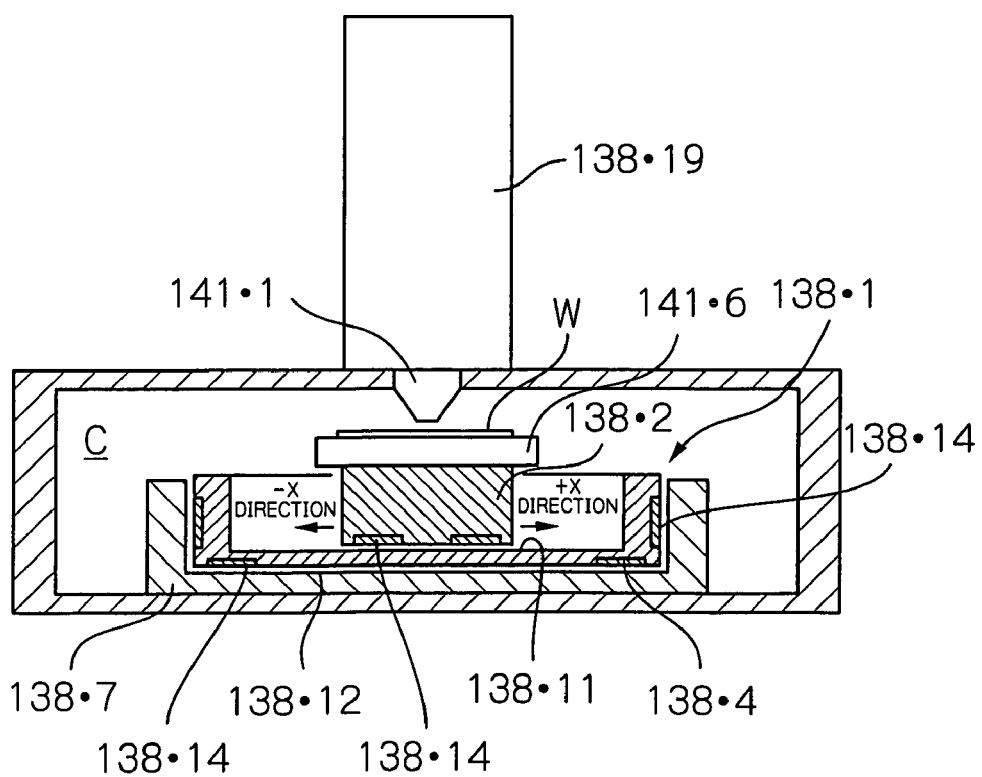
Figure 149:
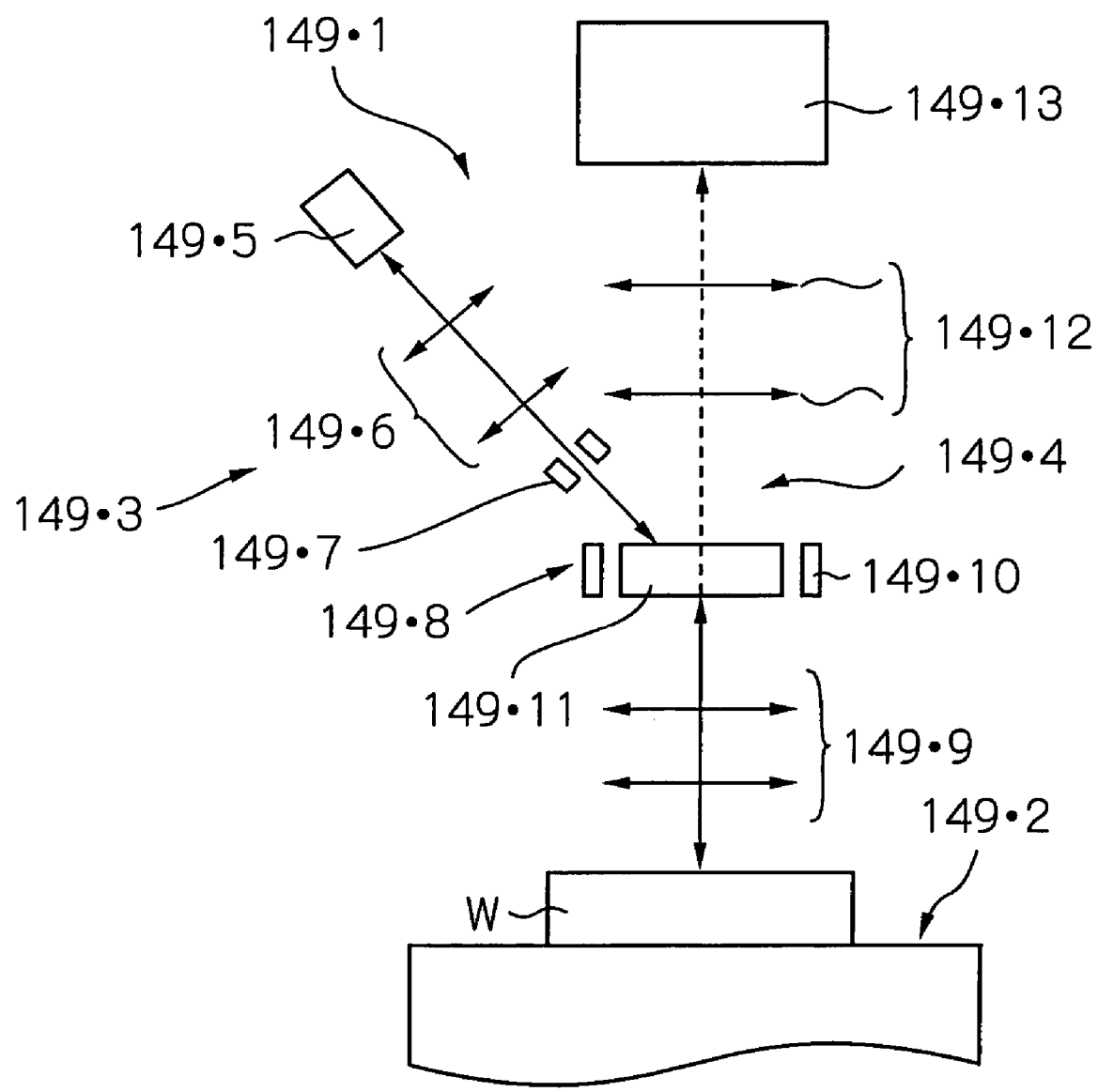
Figure 150A:
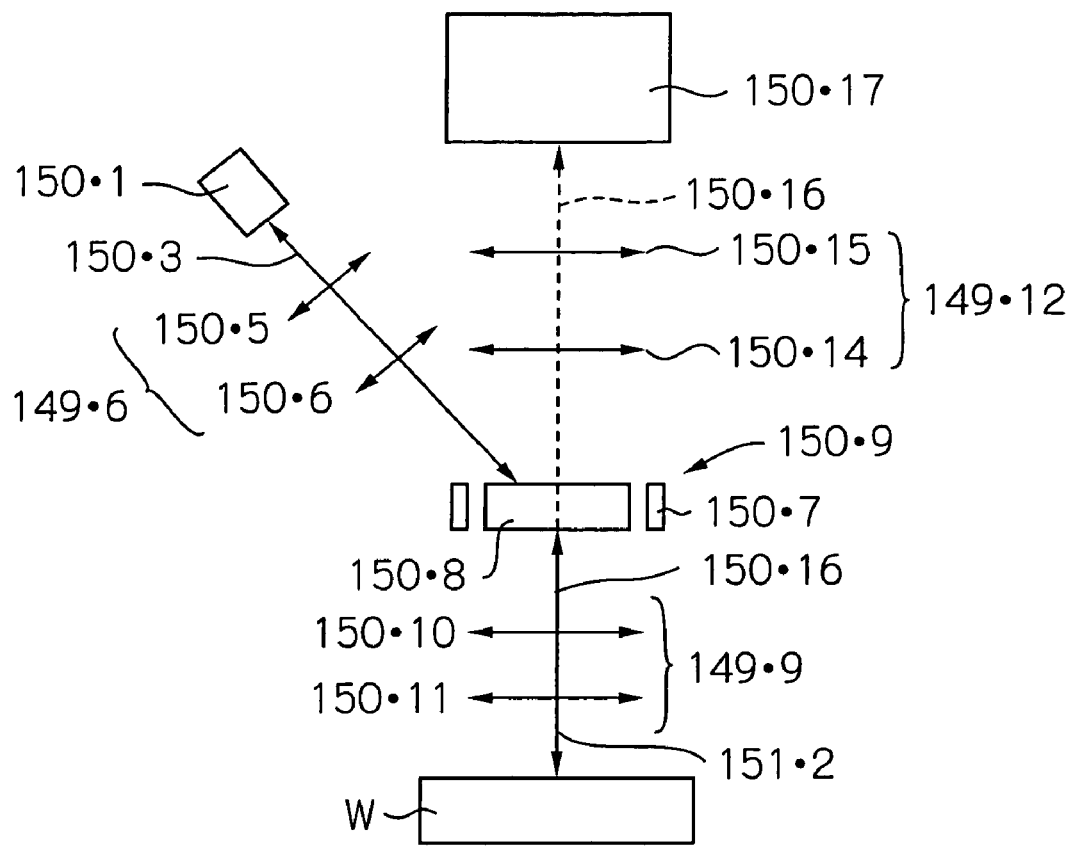
Figure 150B:
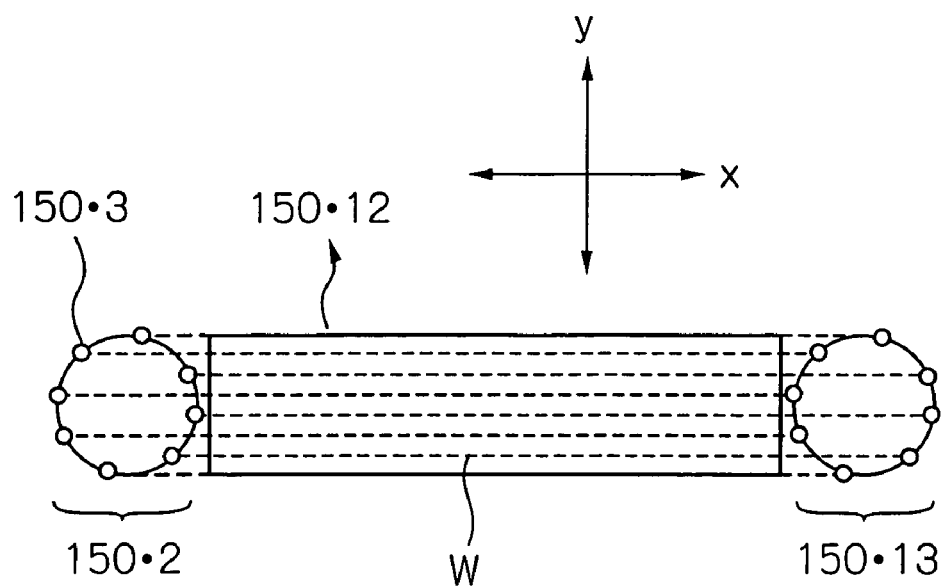
Figure 151:
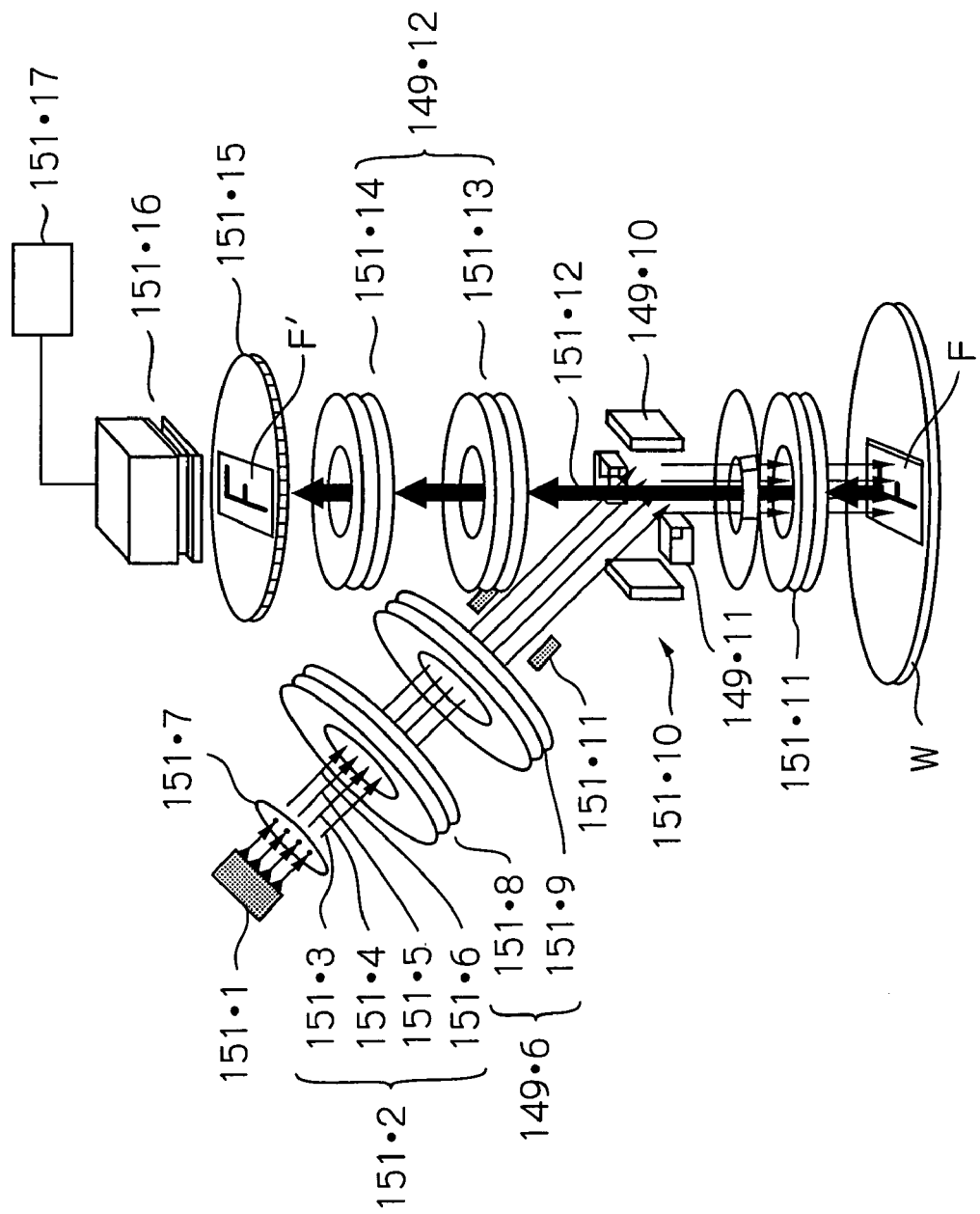
Figure 152:
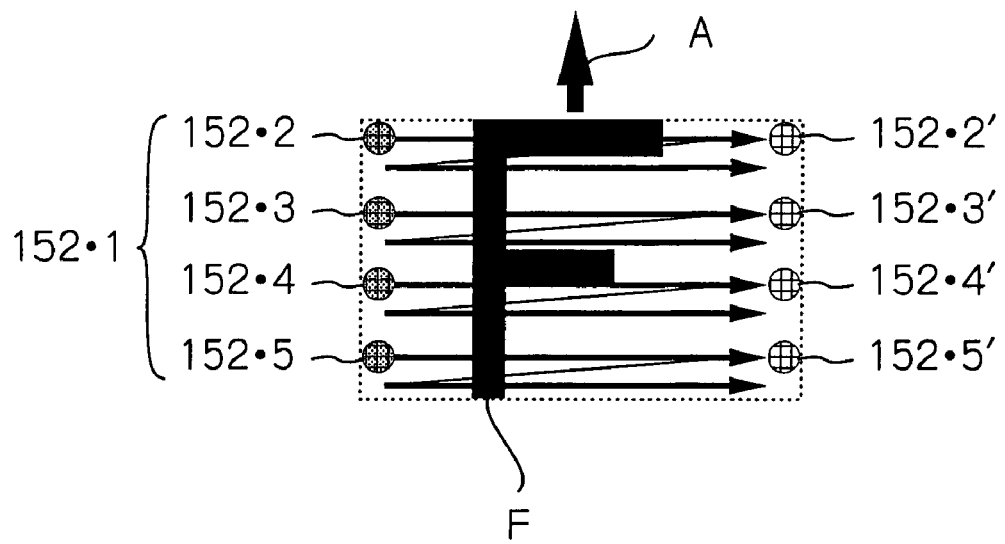
Figure 153:
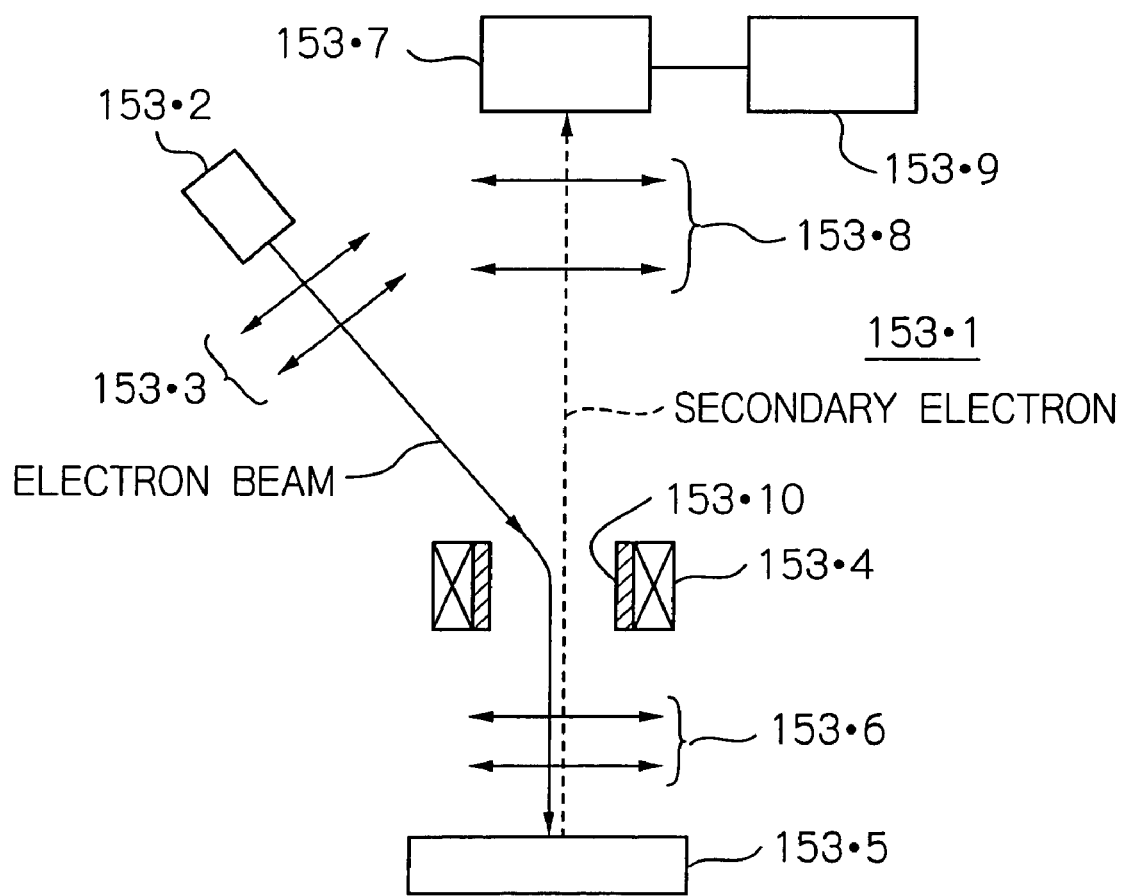
Figure 157:
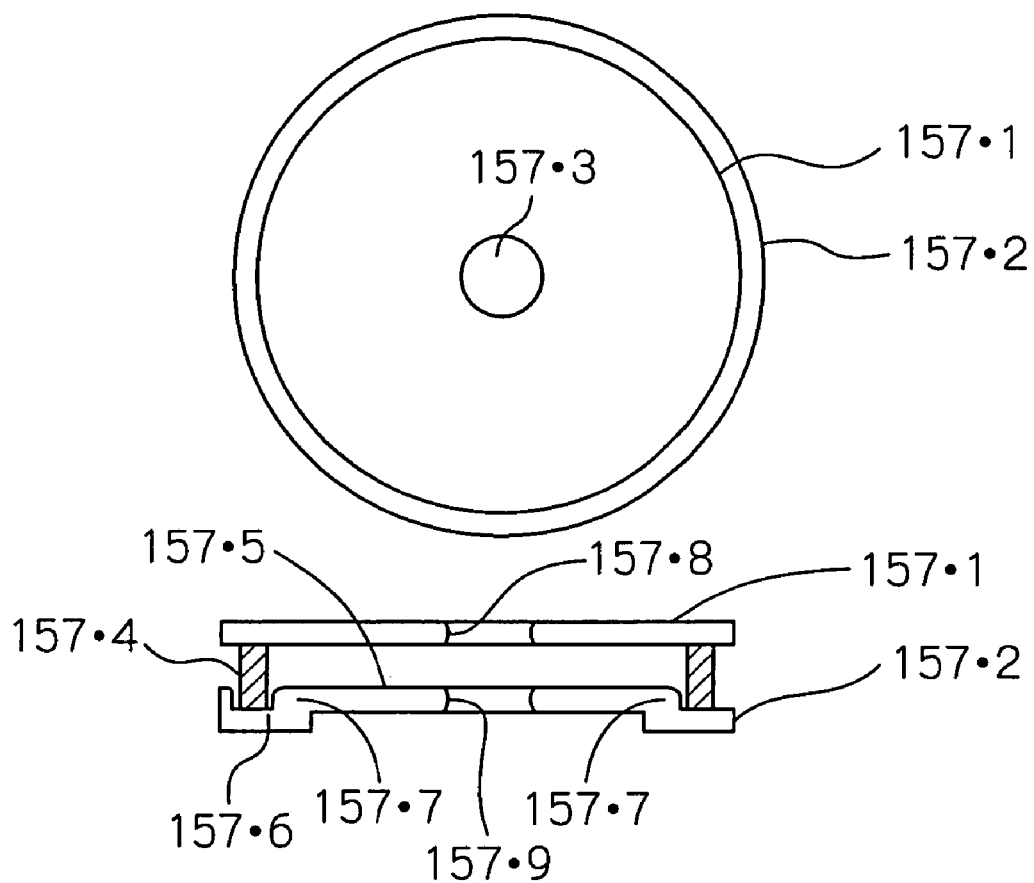
Figure 158:
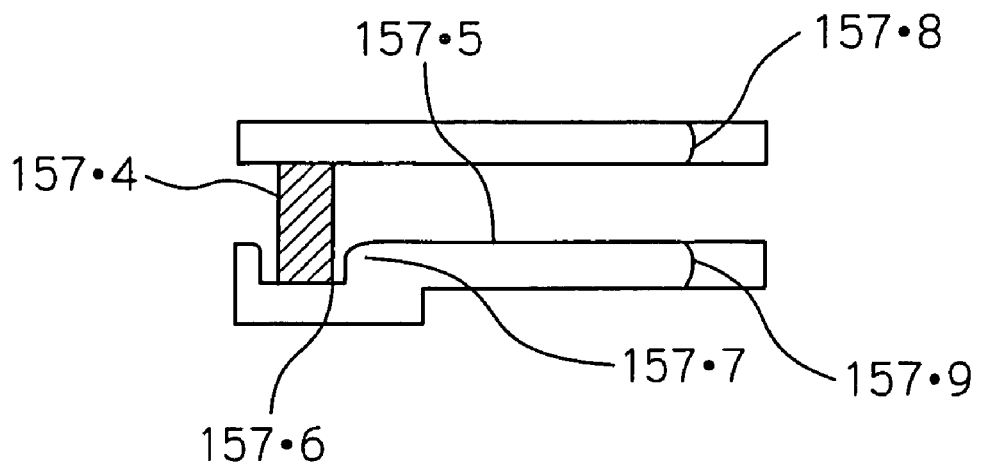
Figure 159:
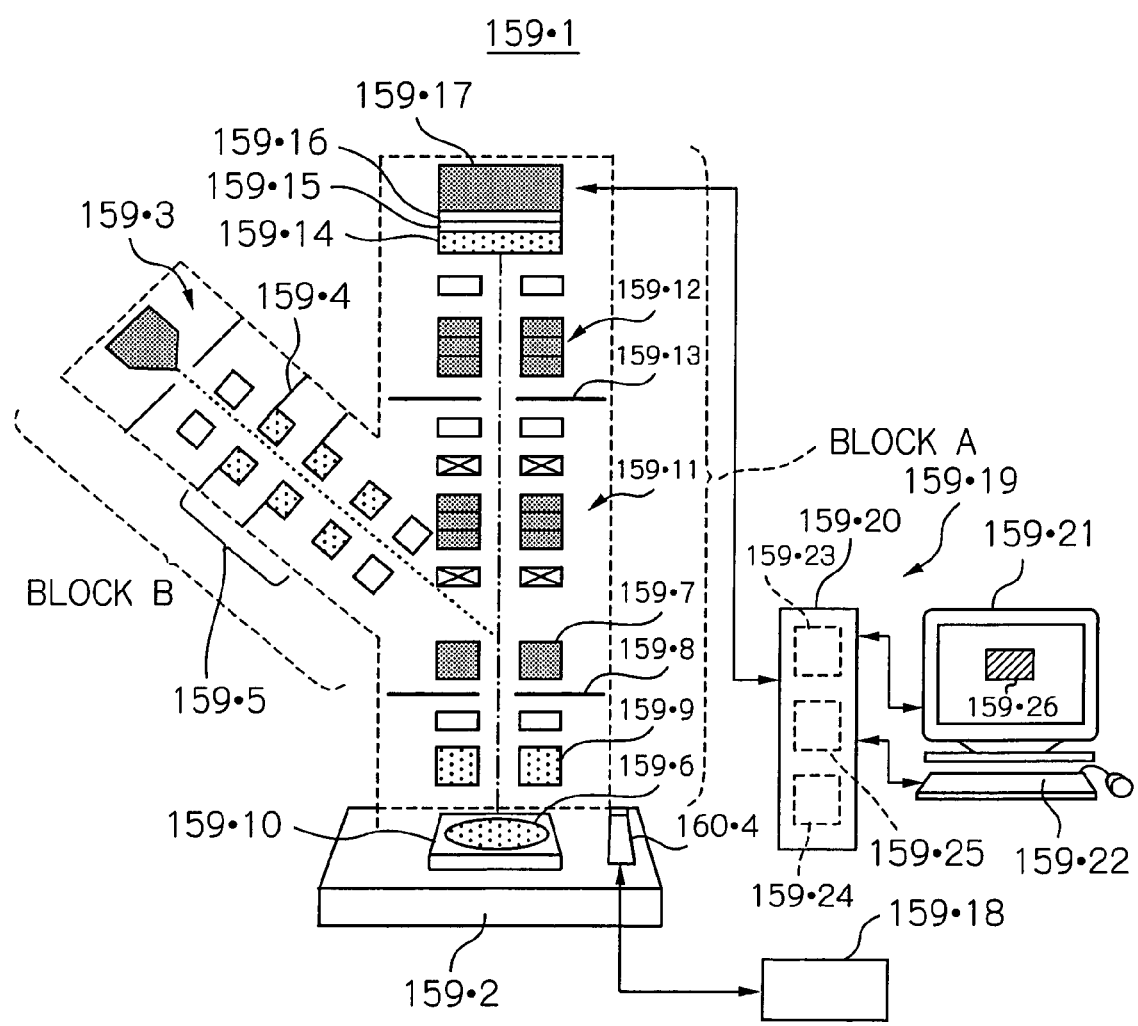
Figure 160A:
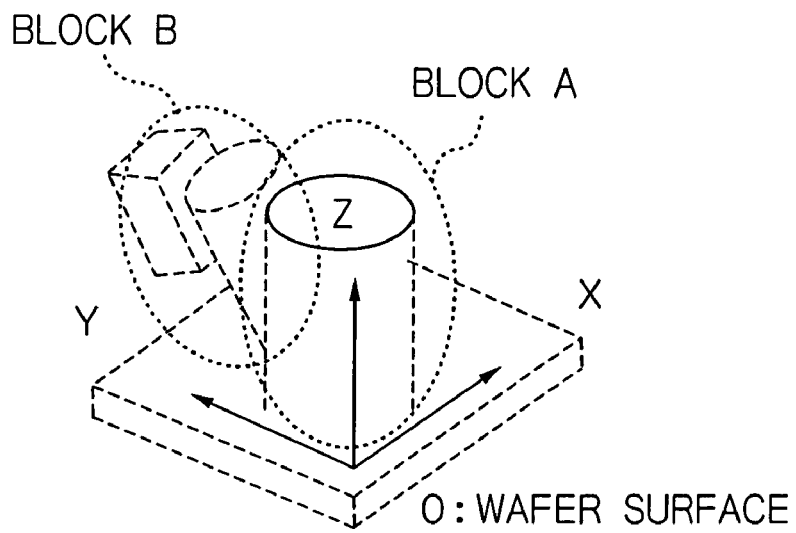
Figure 160B:
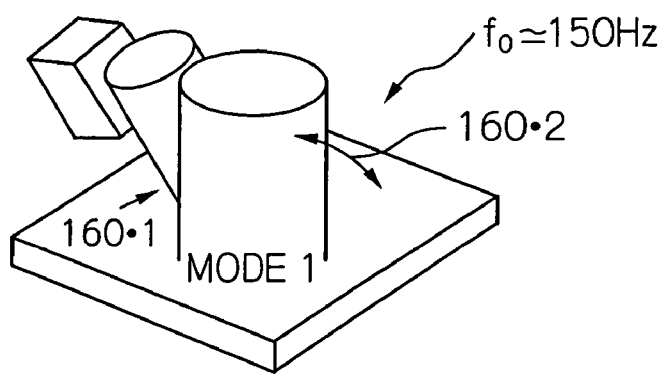
Figure 160C:
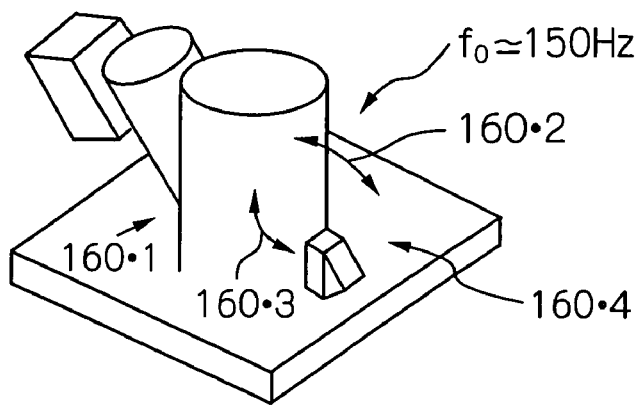
Figure 164A:
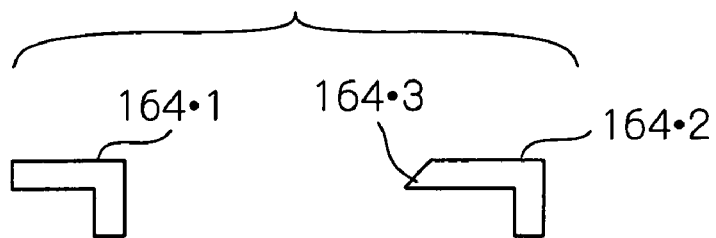
Figure 164B:
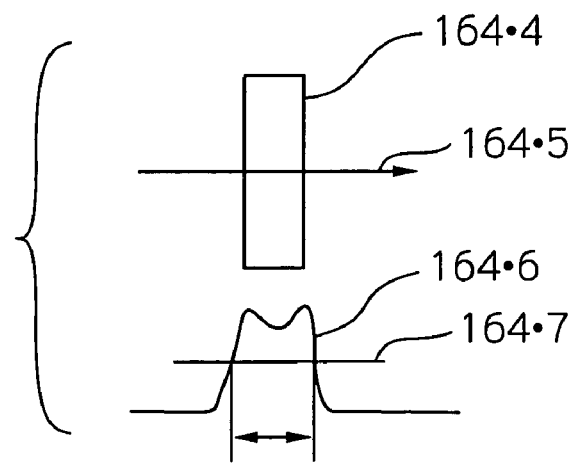
Figure 164C:
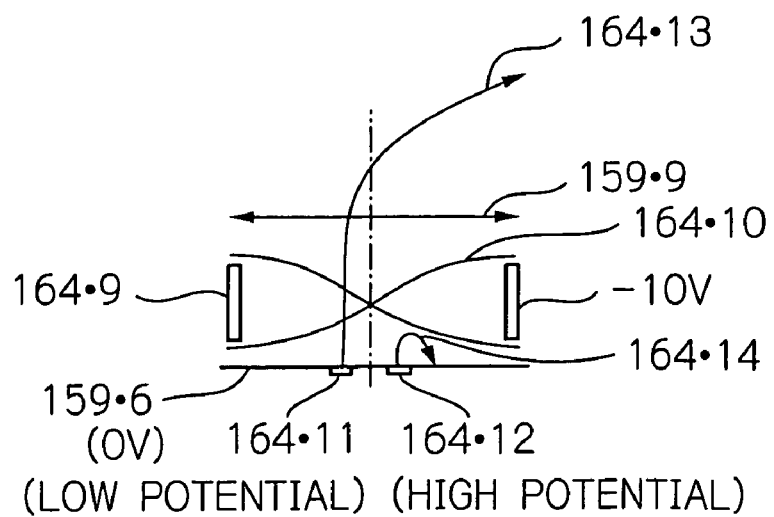
Figure 165:
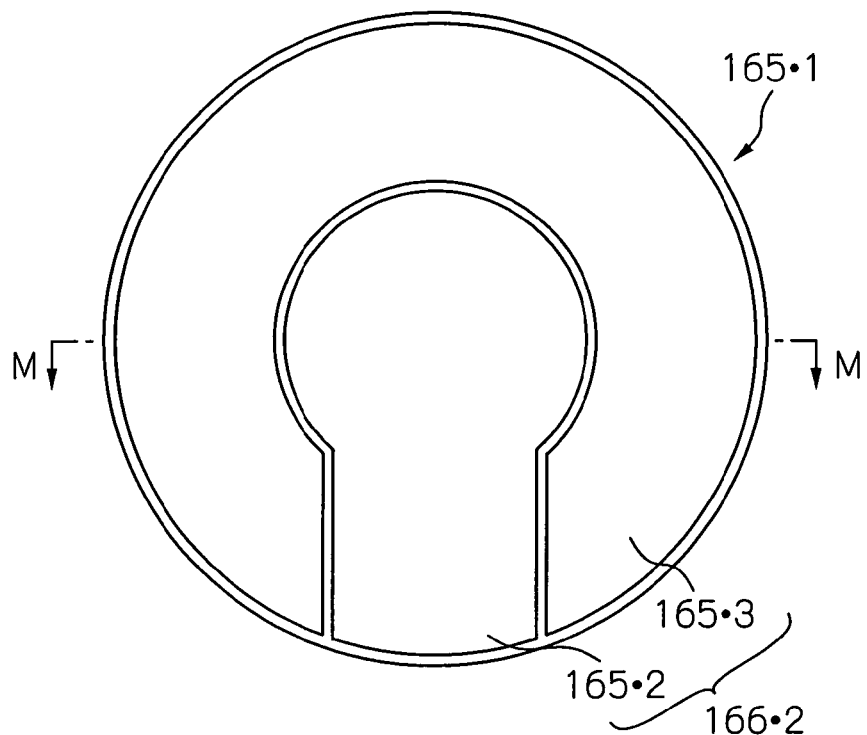
Figure 166:
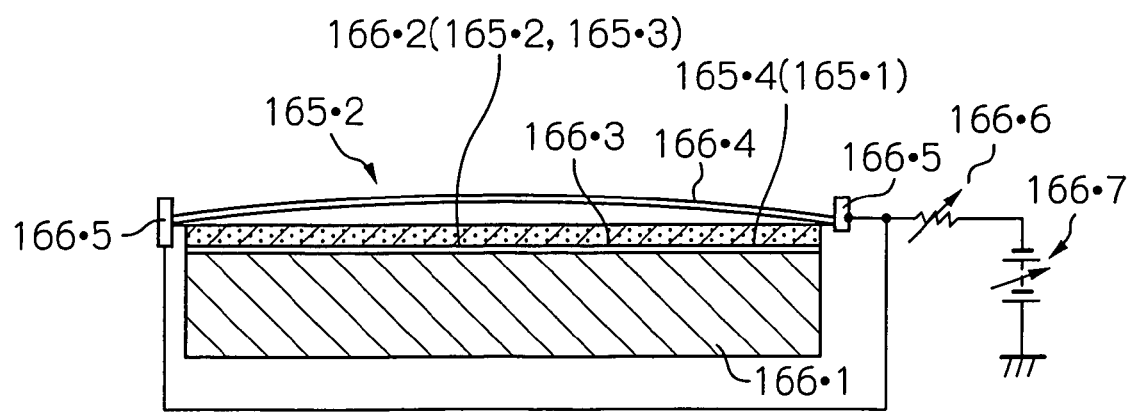
Figure 167A:
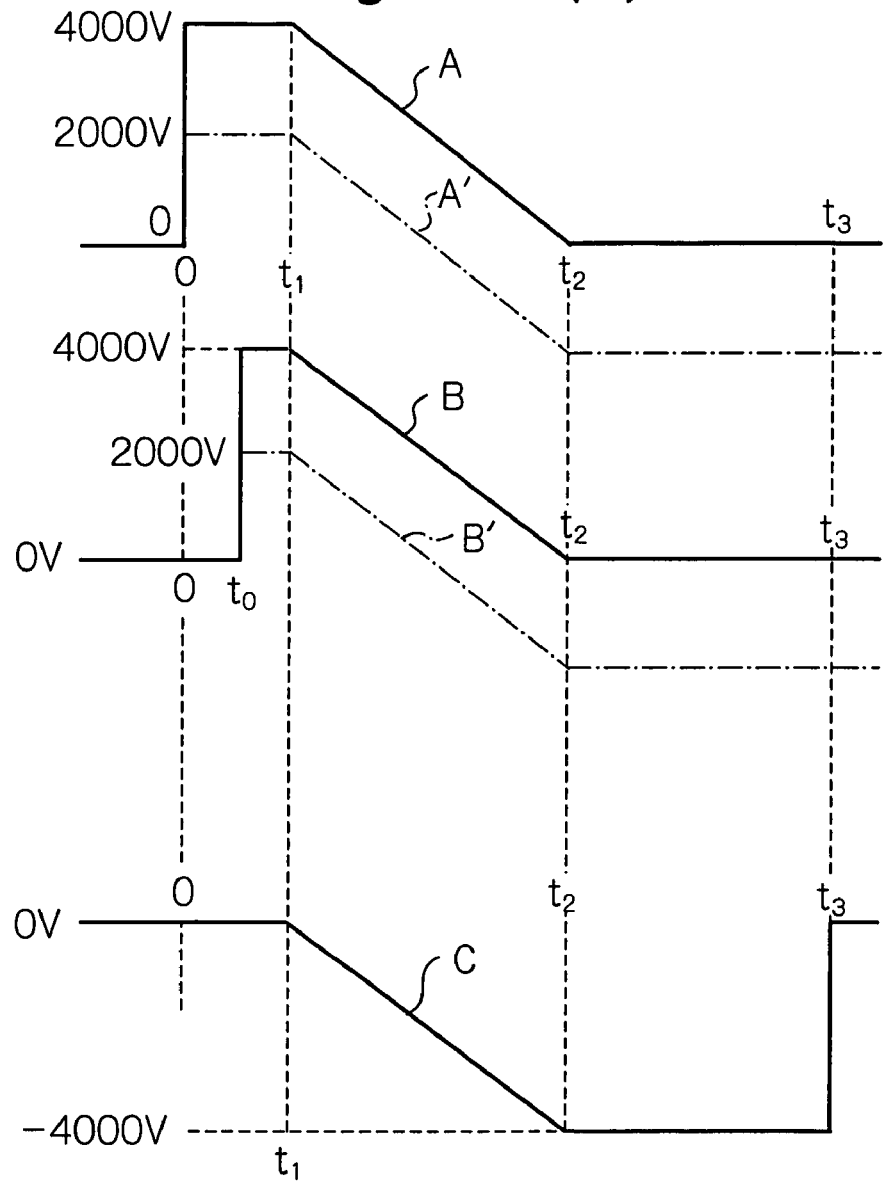
Figure 167B:
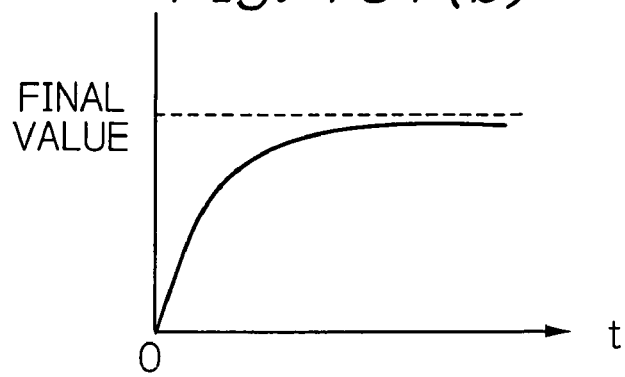
Figure 168:
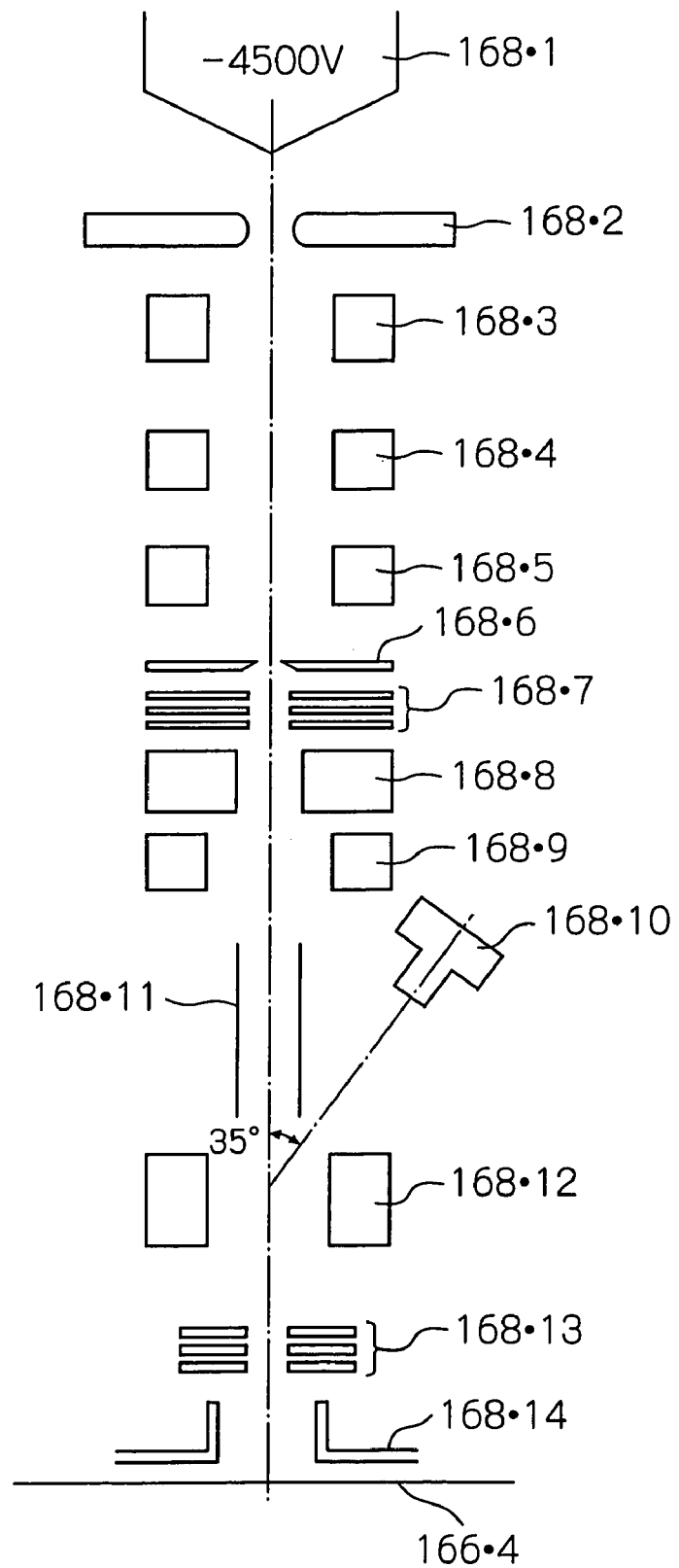
Figure 169:
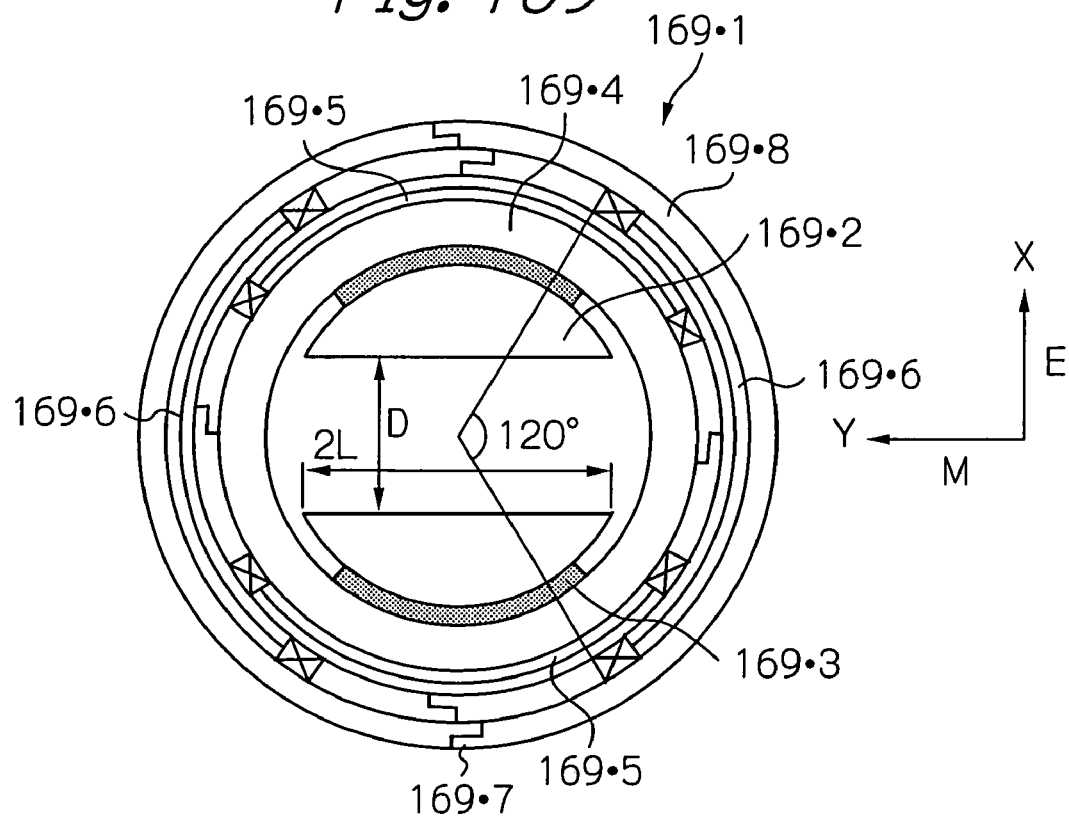
Figure 170:
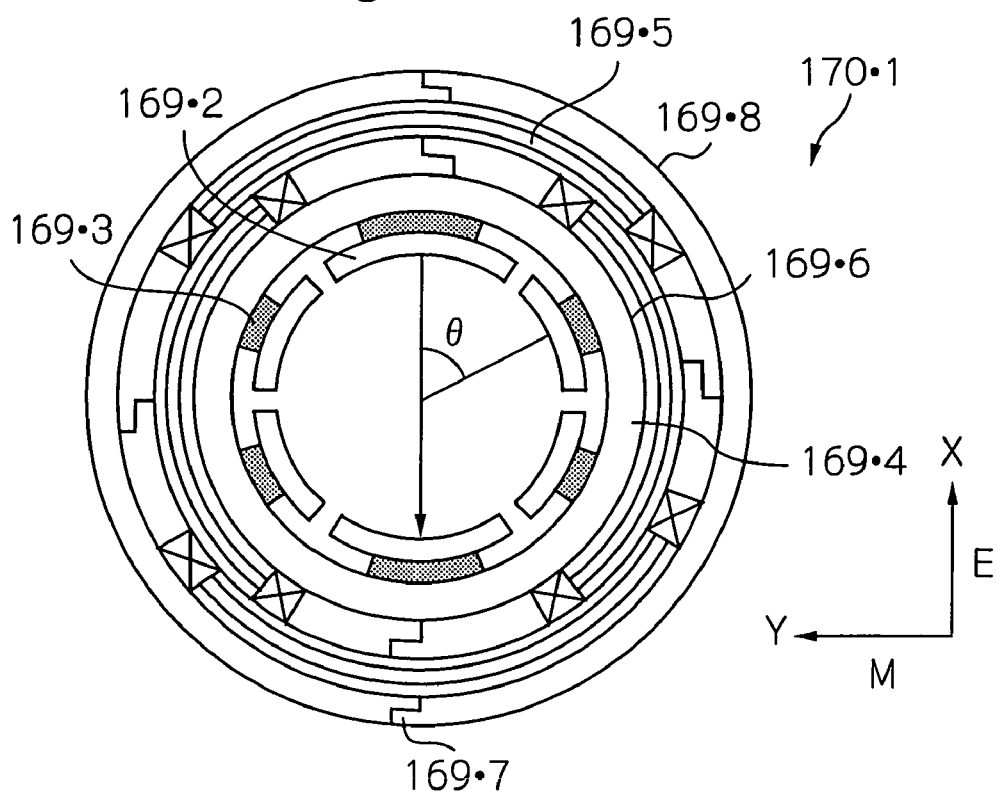
Figures 172A, 172B:
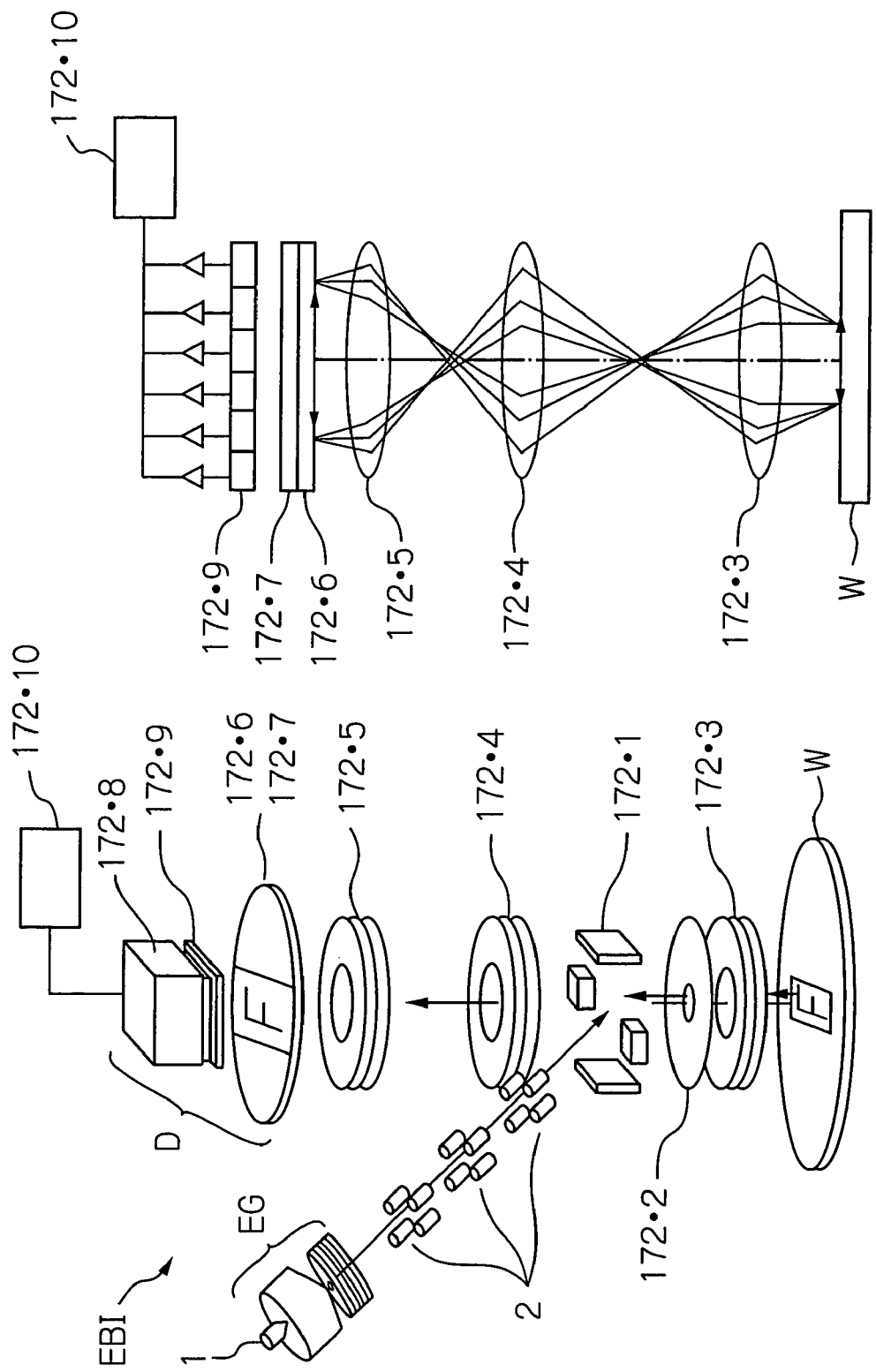
Figure 173:
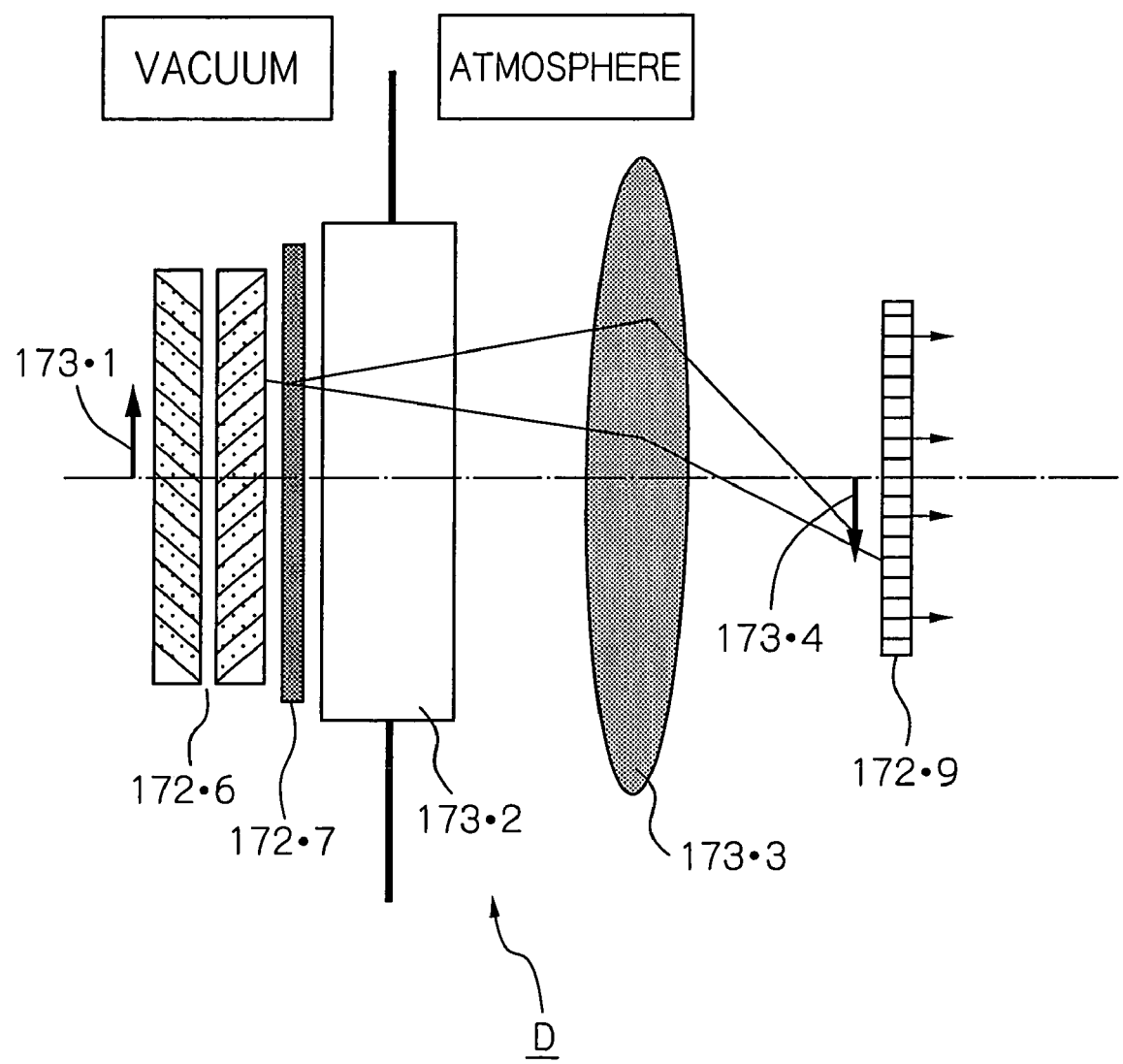
Figure 174A:
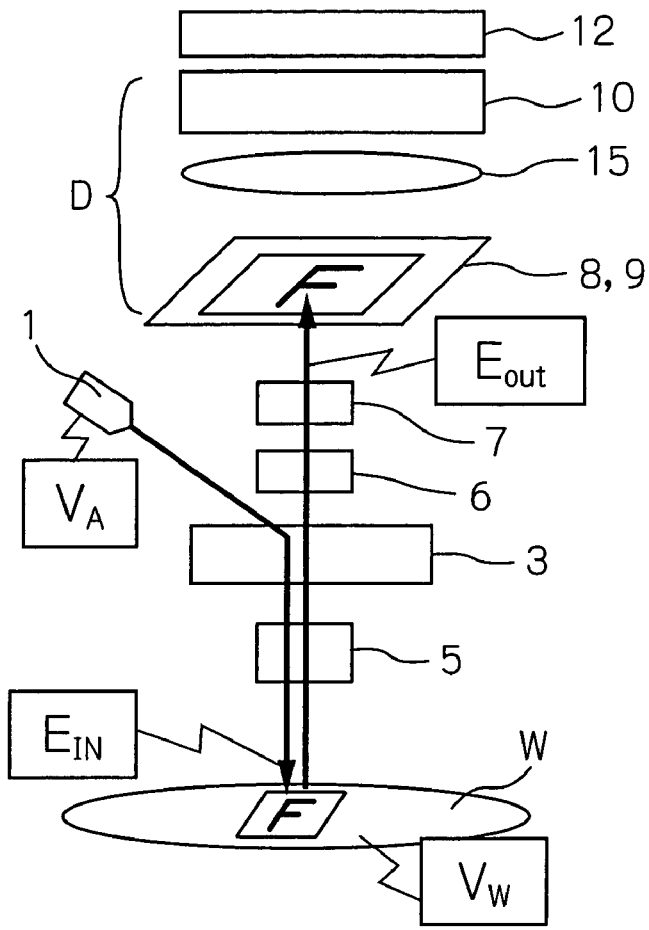
Figure 174B:
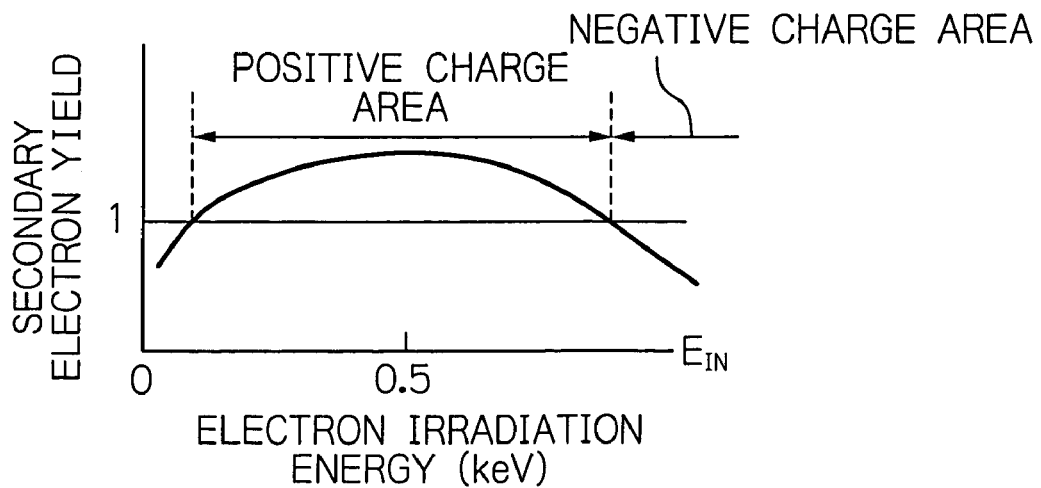
Figure 175:
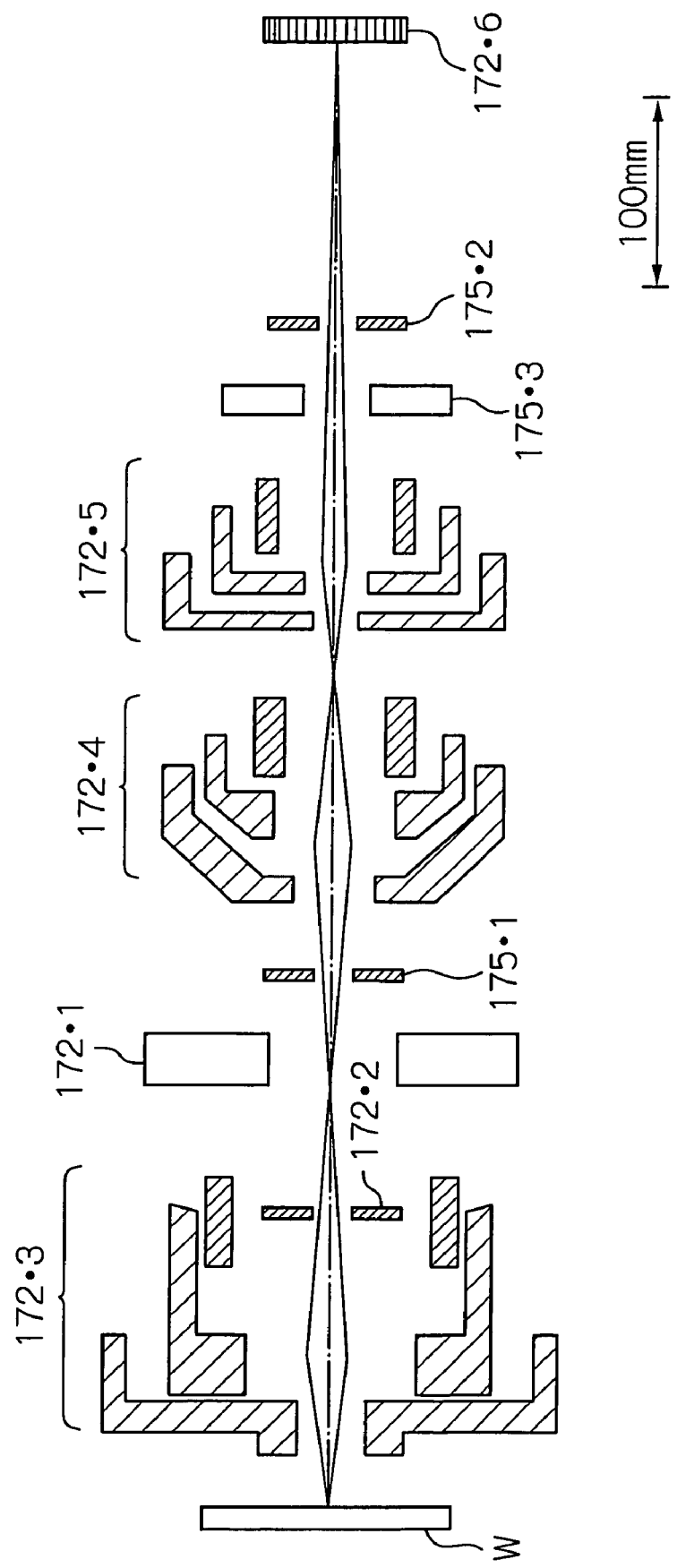
Figure 176A:
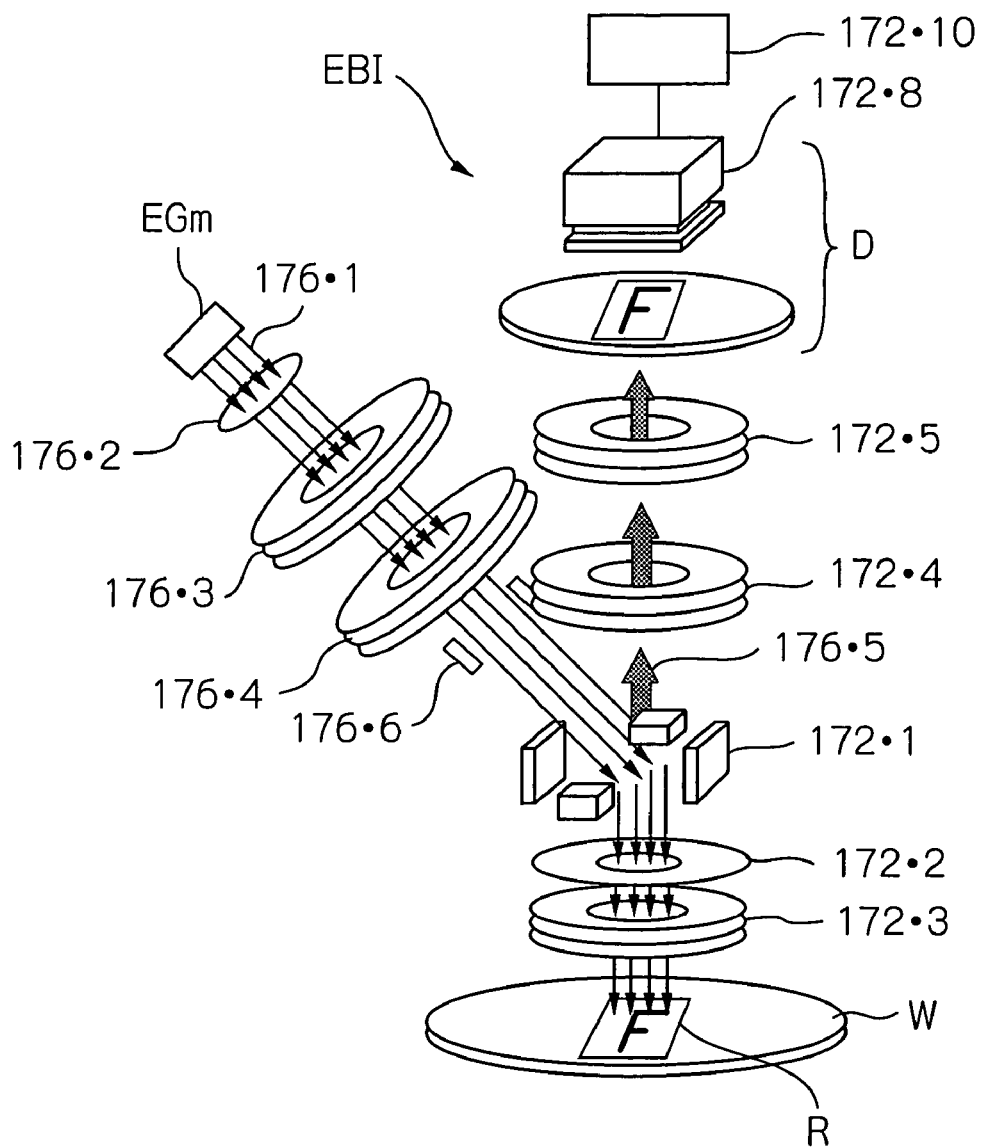
Figure 176B:
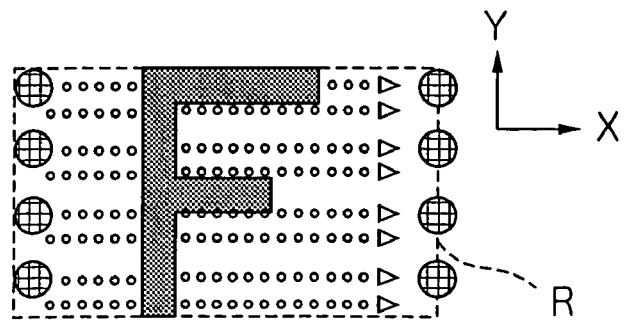
Figure 177A:
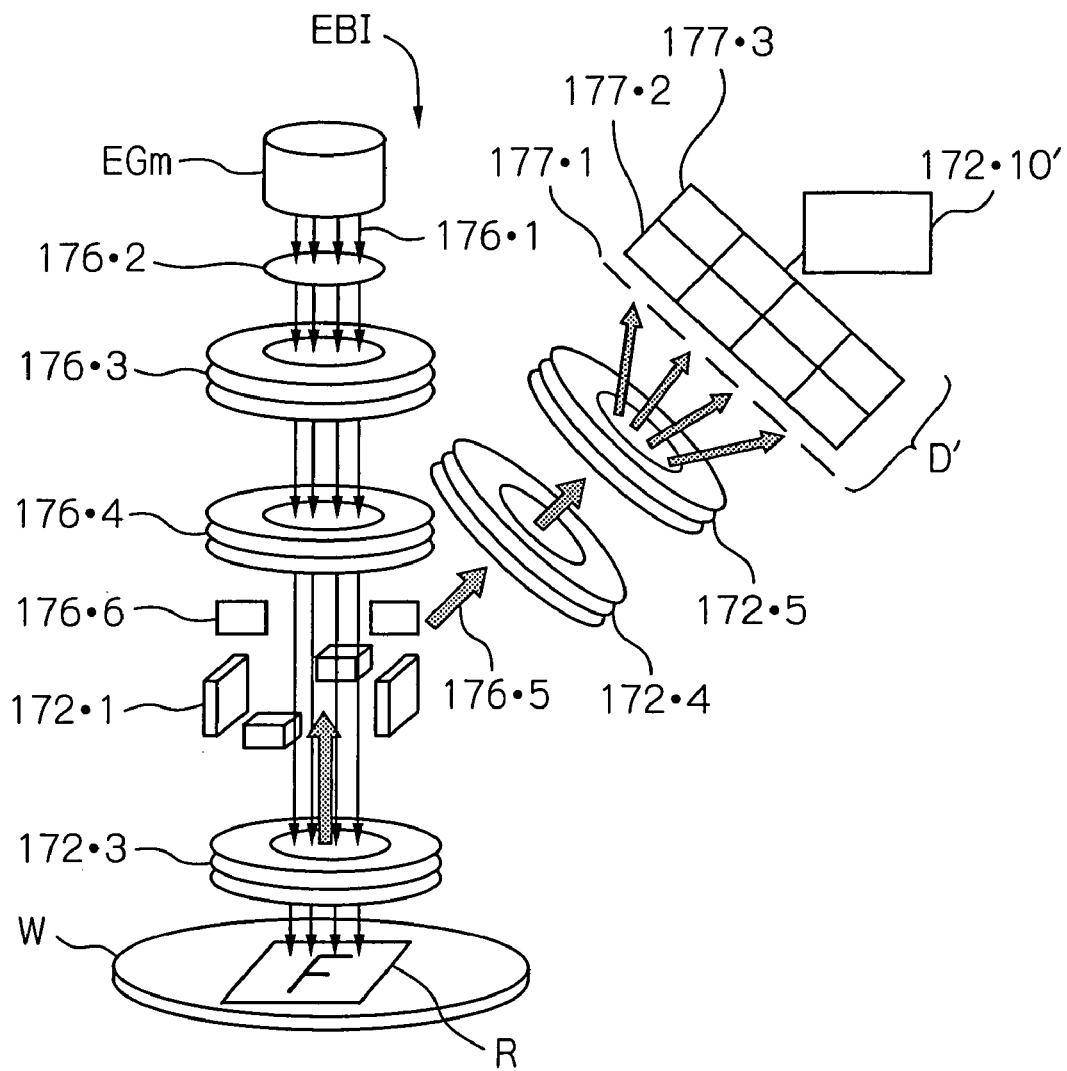
Figure 177B:
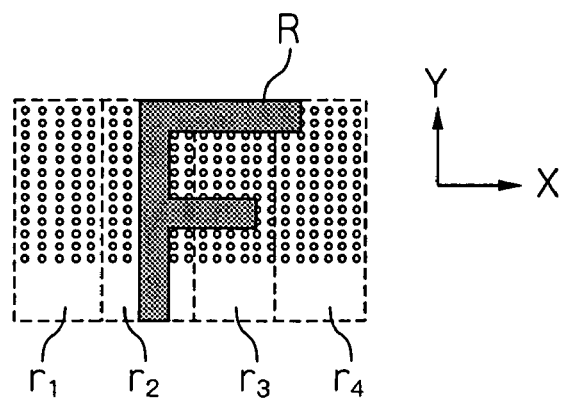
Figure 178:
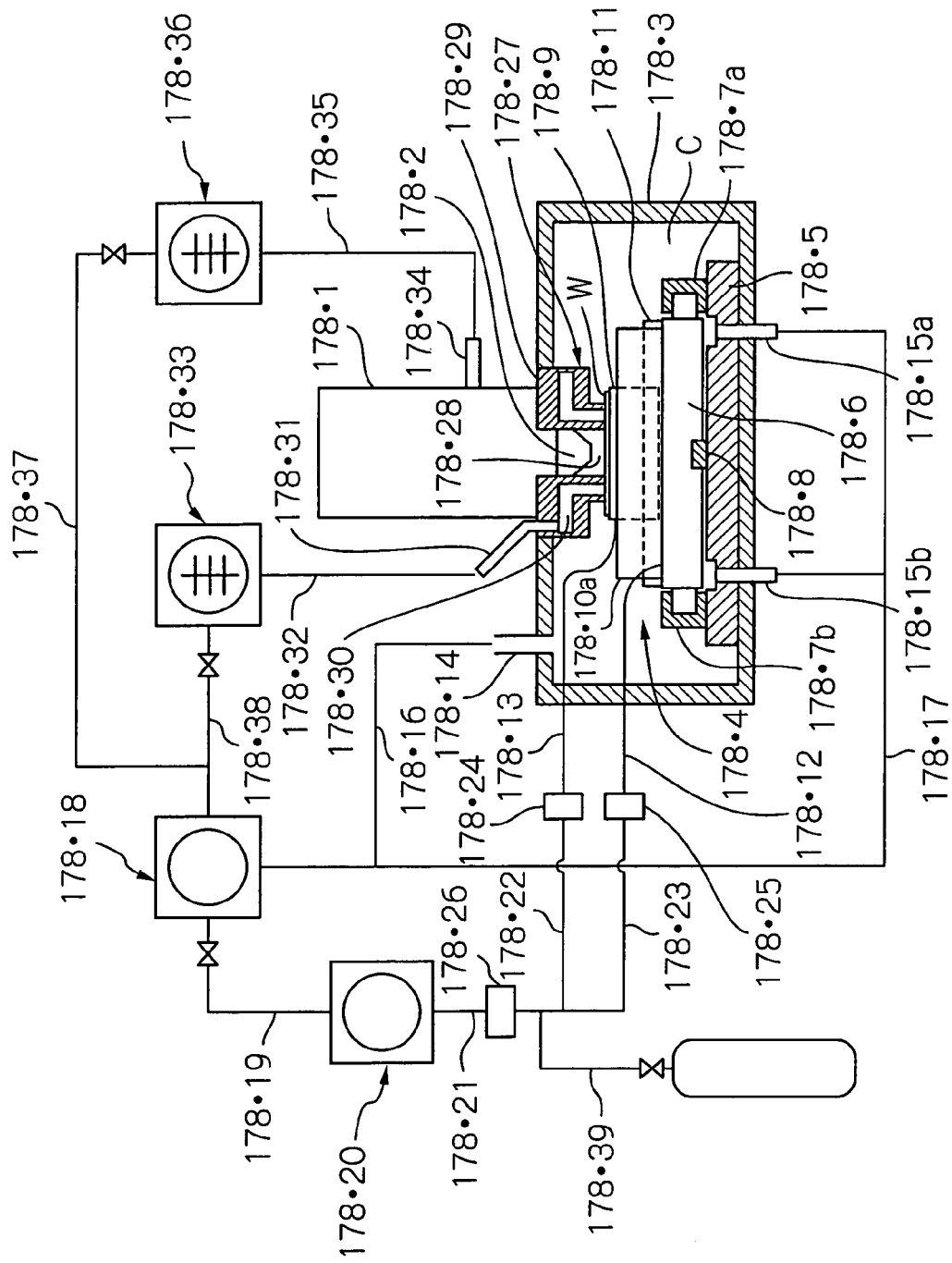
Figure 179:
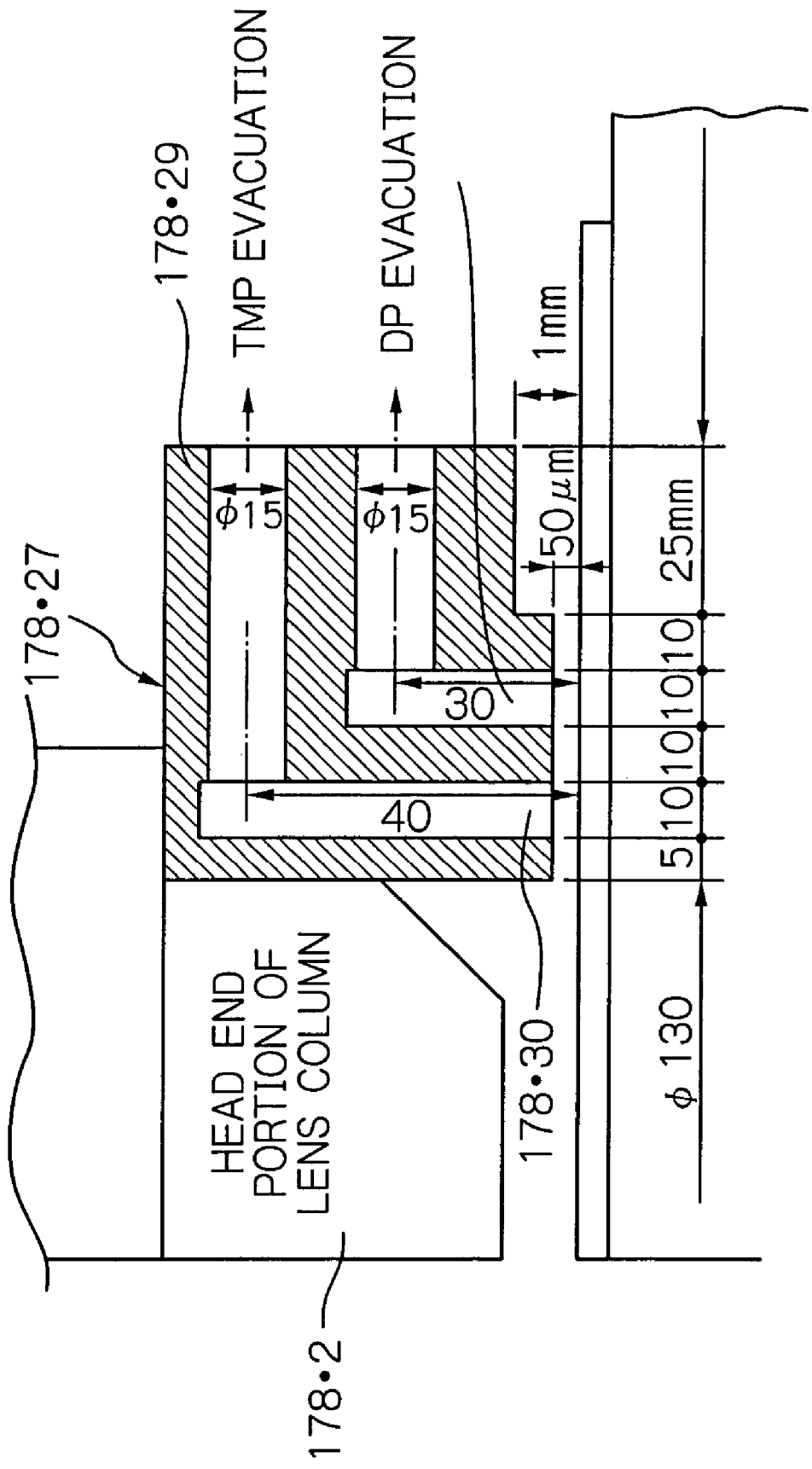

Diagrams (1) to (5) of FIG. 27-1 each illustrate a shape of a sample irradiating beam;

Diagrams (1-1) to (4) of FIG. 27-2 each illustrate an irradiation form of a linear beam;

FIG. 28 illustrates secondary electrons being taking out from a column in the semiconductor inspection apparatus according to the present invention;

FIG. 29 shows the second embodiment of the semiconductor inspection apparatus according to the present invention;

FIG. 30 shows the third embodiment of the semiconductor inspection apparatus according to the present invention;

FIG. 31 shows the fourth embodiment of the semiconductor inspection apparatus according to the present invention;

FIG. 32 shows the fifth embodiment of the semiconductor inspection apparatus according to the present invention;

FIG. 33 illustrates an irradiation area covering an observation area;

FIG. 34 illustrates the irradiation form and irradiation efficiency;

FIG. 35 shows the sixth embodiment of the semiconductor inspection apparatus according to the present invention, and shows the configuration of a detection system using a relay lens;

FIG. 36 shows the sixth embodiment of the semiconductor inspection apparatus according to the present invention, and shows the configuration of a detection system using an FOP;

FIGS. 37(A) and 37(B) show the eighth embodiment of the semiconductor inspection apparatus according to the present invention;

FIG. 38 is a graph showing dependency of the transmittance on the diameter of an opening;

FIG. 39 shows a specific example of an electron detection system in the apparatus of FIG. 37;

FIGS. 40(A) and (B) illustrate requirements for operating the electron detection system in the apparatus of FIG. 37 in three modes;

FIG. 41 shows the configuration of an E×B unit of the semiconductor inspection apparatus according to the present invention;

FIG. 42 is a sectional view along the line A of FIG. 41;

FIG. 43 shows the ninth embodiment of the semiconductor inspection apparatus according to the present invention;

FIG. 44 shows simulation of an electric field distribution;

FIG. 45 shows the configuration of a power supply unit of the semiconductor inspection apparatus according to the present invention;

FIG. 46 shows a circuit system generating a direct-current voltage in the power supply unit shown in FIG. 45;

FIG. 47 shows one example of the circuit configuration of a static bipolar power supply of the power supply unit shown in FIG. 45;

FIG. 48 shows a special power supply in the power supply unit shown in FIG. 45;

FIG. 49 shows a special power supply in the power supply unit shown in FIG. 45;

FIG. 50 shows a special power supply in the power supply unit shown in FIG. 45;

FIG. 51 shows one example of a power supply circuit for a retarding chuck in the power supply unit shown in FIG. 45;

FIG. 52 shows one example of the hardware configuration of an EO correcting deflection voltage in the power supply unit shown in FIG. 45;

FIG. 53 shows one example of the circuit configuration of an octupole conversion unit in the power supply unit shown in FIG. 45;

FIG. 54(A) shows one example of the circuit configuration of a high-speed and high-voltage amplifier in the power supply unit shown in FIG. 45, and FIG. 54(B) shows an output waveform;

FIG. 55 shows the first embodiment of a precharge unit of the semiconductor inspection apparatus shown in FIG. 13;

FIG. 56 shows the second embodiment of a precharge unit of the semiconductor inspection apparatus shown in FIG. 13;

FIG. 57 shows the third embodiment of a precharge unit of the semiconductor inspection apparatus shown in FIG. 13;

FIG. 58 shows the fourth embodiment of a precharge unit of the semiconductor inspection apparatus shown in FIG. 13;

FIG. 59 shows an imaging apparatus comprising the precharge unit shown in FIGS. 55 to 58;

FIG. 60 illustrates the operation of the apparatus of FIG. 59;

FIG. 61 shows another example of configuration of a defect inspection apparatus comprising the precharge unit;

FIG. 62 shows an apparatus for converting a secondary electron image signal into an electric signal in the apparatus shown in FIG. 61;

FIG. 63 is a flow chart illustrating the operation of the apparatus shown in FIG. 61;

FIGS. 64(a), 64(b) and 64(c) show a method for detecting defects in the flow chart of FIG. 63;

FIG. 65 shows another example of configuration of the defect inspection apparatus comprising the precharge unit;

FIG. 66 shows still another example of configuration of the defect inspection apparatus comprising the precharge unit;

FIG. 67 illustrates the operation of a control system of the semiconductor inspection apparatus according to the present invention;

FIG. 68 illustrates the operation of the control system of the semiconductor inspection apparatus according to the present invention;

FIG. 69 illustrates the operation of the control system of the semiconductor inspection apparatus according to the present invention;

FIG. 70 illustrates the operation of the control system of the semiconductor inspection apparatus according to the present invention;

FIG. 71 illustrates the operation of the control system of the semiconductor inspection apparatus according to the present invention;

FIG. 72 illustrates the operation of the control system of the semiconductor inspection apparatus according to the present invention;

FIG. 73 illustrates the operation of the control system of the semiconductor inspection apparatus according to the present invention;

FIG. 74 illustrates an alignment procedure in the semiconductor inspection apparatus according to the present invention;

FIG. 75 illustrates the alignment procedure in the semiconductor inspection apparatus according to the present invention;

FIG. 76 illustrates the alignment procedure in the semiconductor inspection apparatus according to the present invention;

FIG. 77 illustrates a defect inspection procedure in the semiconductor inspection apparatus according to the present invention;

FIG. 78 illustrates the defect inspection procedure in the semiconductor inspection apparatus according to the present invention;

FIG. 79 illustrates the defect inspection procedure in the semiconductor inspection apparatus according to the present invention;

FIGS. 80(A) and 80(B) illustrate the defect inspection procedure in the semiconductor inspection apparatus according to the present invention;

FIG. 81 illustrates the defect inspection procedure in the semiconductor inspection apparatus according to the present invention;

FIG. 82 illustrates the defect inspection procedure in the semiconductor inspection apparatus according to the present invention;

FIG. 83 illustrates the defect inspection procedure in the semiconductor inspection apparatus according to the present invention;

FIG. 84 illustrates the configuration of the control system in the semiconductor inspection apparatus according to the present invention;

FIG. 85 illustrates the configuration of a user interface in the semiconductor inspection apparatus according to the present invention;

FIG. 86 illustrates the configuration of a user interface in the semiconductor inspection apparatus according to the present invention;

FIG. 87 illustrates another function and configuration of the semiconductor inspection apparatus according to the present invention;

FIG. 88 shows an electrode in another function and configuration of the semiconductor inspection apparatus according to the present invention;

FIG. 89 shows the electrode in another function and configuration of the semiconductor inspection apparatus according to the present invention;

FIG. 90 is a graph showing a voltage distribution between the wafer and an objective lens;

FIG. 91 is a flow chart illustrating the secondary electron detection operation in another function and configuration of the semiconductor inspection apparatus according to the present invention;

FIG. 92 shows a potential application mechanism in the apparatus shown in FIG. 91;

FIGS. 93(A) and 93(B) illustrate an electron beam calibration method in the apparatus shown in FIG. 91;

FIG. 94 illustrates an alignment control method in the apparatus shown in FIG. 91;

FIGS. 95(A) and 95(B) illustrate a concept of EO correction in the apparatus shown in FIG. 92;

FIG. 96 illustrates the specific apparatus configuration for EO correction in the apparatus shown in FIG. 92;

FIGS. 97(A) and 97(B) illustrate EO correction in the apparatus shown in FIG. 92;

FIG. 98 illustrates EO correction in the apparatus shown in FIG. 92;

FIG. 99 illustrates EO correction in the apparatus shown in FIG. 92;

FIG. 100 illustrates EO correction in the apparatus shown in FIG. 92;

FIG. 101 illustrates the idea of a TDI transfer clock;

FIG. 102 illustrates the idea of the TDI transfer clock;

FIG. 103 is a timing chart illustrating the operation of the circuit of FIG. 102;

FIG. 104 shows an alteration example of the defect inspection apparatus according to the present invention;

FIG. 105 is a flow chart illustrating the operation of the apparatus shown in FIG. 104;

FIG. 106 is a flow chart illustrating the operation of the apparatus shown in FIG. 104;

FIG. 107 is a flow chart illustrating the operation of the apparatus shown in FIG. 104;

FIG. 108 illustrates the operation of the apparatus shown in FIG. 104;

FIG. 109 illustrates the operation of the apparatus shown in FIG. 104;

FIG. 110 illustrates a semiconductor device production process according to the present invention;

FIG. 111 illustrates the semiconductor device production process according to the present invention;

FIG. 112 illustrates an inspection procedure of the semiconductor device production process according to the present invention;

FIG. 113 illustrates a basic flow of the inspection procedure of the semiconductor device production process according to the present invention;

FIG. 114 shows a setting of an inspection object die;

FIG. 115 illustrates a setting of an inspection area in the die;

FIG. 116 illustrates the inspection procedure of the semiconductor device production process according to the present invention;

FIGS. 117(A) and 117(B) illustrate the inspection procedure of the semiconductor device production process according to the present invention;

FIG. 118-1 shows an example of scanning where there is one inspection die in the inspection procedure in the semiconductor device production process according to the present invention;

FIG. 118-2 shows one example of the inspection die;

FIG. 119 illustrates a method for generating a reference image in the inspection procedure of the semiconductor device production process according to the present invention;

FIG. 120 illustrates an adjacent die comparison method in the inspection procedure of the semiconductor device production process according to the present invention;

FIG. 121 illustrates the adjacent die comparison method in the inspection procedure of the semiconductor device production process according to the present invention;

FIG. 122 illustrates a reference die comparison method in the inspection procedure of the semiconductor device production process according to the present invention;

FIG. 123 illustrates the reference die comparison method in the inspection procedure of the semiconductor device production process according to the present invention;

FIG. 124 illustrates the reference die comparison method in the inspection procedure of the semiconductor device production process according to the present invention;

FIG. 125 illustrates focus mapping in the inspection procedure of the semiconductor device production process according to the present invention;

FIG. 126 illustrates focus mapping in the inspection procedure of the semiconductor device production process according to the present invention;

FIG. 127 illustrates focus mapping in the inspection procedure of the semiconductor device production process according to the present invention;

FIG. 128 illustrates focus mapping in the inspection procedure of the semiconductor device production process according to the present invention;

FIG. 129 illustrates focus mapping in the inspection procedure of the semiconductor device production process according to the present invention;

FIG. 130 illustrates focus mapping in the inspection procedure of the semiconductor device production process according to the present invention;

FIG. 131 illustrates litho-margin measurement in the inspection procedure of the semiconductor device production process according to the present invention;

FIG. 132 illustrates litho-margin measurement in the inspection procedure of the semiconductor device production process according to the present invention;

FIG. 133 illustrates litho-margin measurement in the inspection procedure of the semiconductor device production process according to the present invention;

FIG. 134 illustrates litho-margin measurement in the inspection procedure of the semiconductor device production process according to the present invention;

FIG. 135 illustrates litho-margin measurement in the inspection procedure of the semiconductor device production process according to the present invention;

FIG. 136 illustrates litho-margin measurement in the inspection procedure of the semiconductor device production process according to the present invention;

FIG. 137 illustrates litho-margin measurement in the inspection procedure of the semiconductor device production process according to the present invention;

FIG. 138 shows one example of a stage apparatus in the semiconductor inspection apparatus according to the present invention;

FIG. 139 shows one example of the stage apparatus in the semiconductor inspection apparatus according to the present invention;

FIG. 140 shows one example of the stage apparatus in the semiconductor inspection apparatus according to the present invention;

FIG. 141 shows another example of the stage apparatus in the semiconductor inspection apparatus according to the present invention;

FIG. 142 shows another example of the stage apparatus in the semiconductor inspection apparatus according to the present invention;

FIG. 143 shows still another example of the stage apparatus in the semiconductor inspection apparatus according to the present invention;

FIG. 144 shows still another example of the stage apparatus in the semiconductor inspection apparatus according to the present invention;

FIG. 145 shows another example of the stage apparatus in the semiconductor inspection apparatus according to the present invention;

FIG. 146 shows another example of the stage apparatus in the semiconductor inspection apparatus according to the present invention;

FIG. 147 shows another example of the stage apparatus in the semiconductor inspection apparatus according to the present invention;

FIGS. 148(A) and 148(B) show a conventional stage apparatus;

FIG. 149 shows an optical system and a detector in the semiconductor inspection apparatus according to the present invention;

FIGS. 150(a) and 150(b) show another embodiment of the semiconductor inspection apparatus according to the present invention;

FIG. 151 shows the electron beam apparatus of FIG. 150 in detail;

FIG. 152 shows a primary electron irradiation method in the semiconductor inspection apparatus according to the present invention;

FIG. 153 shows an embodiment of the semiconductor inspection apparatus according to the present invention, with a structure of an electrode for preventing insulation breakdown;

FIG. 154 is a table illustrating the operation of the apparatus of FIG. 153;

FIG. 155 shows the structure of the electrode in the apparatus of FIG. 153;

FIG. 156 shows the structure of the electrode in the apparatus of FIG. 153;

FIG. 157 shows the structure of the electrode in the apparatus of FIG. 153;

FIG. 158 shows the structure of the electrode in the apparatus of FIG. 153;

FIG. 159 shows the embodiment of the semiconductor inspection apparatus according to the present invention, which comprises an anti-vibration apparatus;

FIGS. 160(a) to 160(c) illustrate the apparatus of FIG. 159;

FIG. 161 illustrates the apparatus of FIG. 159;

FIG. 162 illustrates the apparatus of FIG. 159;

FIG. 163 illustrates the apparatus of FIG. 159;

FIGS. 164(a) to 164(c) illustrate a pattern matching process in the apparatus of FIG. 159;

FIG. 165 illustrates the holding of the wafer in the semiconductor inspection apparatus according to the present invention;

FIG. 166 illustrates the holding of the wafer in the semiconductor inspection apparatus according to the present invention;

FIGS. 167(a) and 167(b) illustrate the holding of the wafer in the semiconductor inspection apparatus according to the present invention;

FIG. 168 shows the electron beam apparatus comprising a chuck illustrated in FIG. 166;

FIG. 169 shows an E×B separator in the apparatus shown in FIG. 168;

FIG. 170 shows the E×B separator in the apparatus shown in FIG. 168;

FIG. 171 shows the embodiment in which the inspection apparatus according to the present invention is connected to a production line;

FIG. 172(A) schematically shows the embodiment of a projection electron microscope type apparatus capable of using secondary electrons and reflection electrons selectively;

FIG. 172(B) schematically shows the configuration of a secondary optical system of the apparatus;

FIG. 173 shows the specific configuration of a secondary electron detection system in FIG. 172(A);

FIGS. 174(A) and 174(B) illustrate different operation modes of the defect inspection apparatus shown in FIG. 172(A);

FIG. 175 shows the specific configuration of a lens of the secondary optical system of the defect inspection apparatus shown in FIG. 172(A);

FIG. 176(A) schematically shows the configuration of an alteration example of the projection electron microscope type apparatus shown in FIG. 172(A);

FIG. 176(B) illustrates a scan method of the apparatus shown in FIG. 176(A);

FIG. 177(A) schematically shows the configuration of another example of the projection electron microscope type apparatus shown in FIG. 172(A);

FIG. 177(B) illustrates the scan method of the apparatus shown in FIG. 177(A);

FIG. 178 shows the structure of a vacuum chamber and XY stage of the projection electron microscope type apparatus shown in FIG. 172(A), and an inert gas circulation pipe system therefor;

FIG. 179 shows one example of a differential pumping mechanism in FIG. 178; and

FIG. 180 schematically shows the configuration of an entire inspection system;

DETAILED DESCRIPTION OF THE PREFERRED EMBODIMENTS

Embodiments of semiconductor inspection apparatus according to the present invention will be described in detail below with reference to the drawings in the following order.

Description

1. Overall Configuration
    1-1) Main Chamber, Stage, Jacket of Vacuum Transportation System
        1-1-1) Active Vibration Removal Table
        1-1-2) Main Chamber
        1-1-3) XY Stage
    1-2) Laser Interference Measurement System
    1-3) Inspection Unit Jacket
2. Embodiments
    2-1) Transportation System 2-1-1) Cassette Holder
2-1-2) Mini-environment Apparatus
2-1-3) Main Housing
2-1-4) Loader Housing
2-1-5) Loader
2-1-6) Stage Apparatus
2-1-7) Wafer Chucking Mechanism
  2-1-7-1) Basic Structure of Electrostatic Chuck
  2-1-7-2) Chucking Mechanism for 200/300 Bridge Tool
  2-1-7-3) Wafer Chucking Procedure
2-1-8) Apparatus Configuration for 200/300 Bridge Tool
2-2) Method for Transportation of Wafer
2-3) Electro-optical System
  2-3-1) Overview
  2-3-2) Details of Configuration
    2-3-2-1) Electron Gun (electron beam source)
    2-3-2-2) Primary Optical System
    2-3-2-3) Secondary Optical System
  2-3-3) E×B Unit (Wien filter)
  2-3-4) Detector
  2-3-5) Power Supply
2-4) Precharge Unit
2-5) Vacuum Pumping System
2-6) Control System
  2-6-1) Configuration and Function
  2-6-2) Alignment Procedure
  2-6-3) Defect Inspection
  2-6-4) Control System Configuration
  2-6-5) User Interface Configuration
2-7) Descriptions of Other Functions and Configurations
  2-7-1) Control Electrode
  2-7-2) Potential Application Method
  2-7-3) Electron Beam Calibration Method
  2-7-4) Cleaning of Electrode
  2-7-5) Alignment Control Method
  2-7-6) EO Correction
  2-7-7) Image Comparison Method
  2-7-8) Device Production Process
  2-7-9) Inspection
2-8) Inspection Process
  2-8-1) Overview
  2-8-2) Inspection Algorithm
    2-8-2-1) Array Inspection
    2-8-2-2) Random Inspection
    2-8-2-3) Focus Mapping
    2-8-2-4) Litho-margin Measurement
3. Other Embodiments
  3-1) Alteration Example of Stage Apparatus
  3-2) Other Embodiments of Electron Beam Apparatus
    3-2-1) Electron Gun (lectron beam source)
    3-2-2) Structure of Electrode
  3-3) Embodiment for Anti-vibration Apparatus
  3-4) Embodiment for Wafer Holding
  3-5) Embodiment of E×B Separator
  3-6) Embodiment of Production Line
  3-7) Embodiment Using Other Electrons
  3-8) Embodiment Using Secondary Electrons and Reflection Electrons 1. Overall Configuration First, the overall configuration of the semiconductor inspection apparatus will be described.

The overall configuration of the apparatus will be described using FIG. 1. The apparatus is comprised of an inspection apparatus main body, a power supply rack, a control rack, an image processing unit, a film formation apparatus, an etching apparatus and the like. A roughing vacuum pump such as a dry pump is placed outside a clean room. The main part of the interior of the inspection apparatus main body is comprised of an electron beam optical column, a vacuum transportation system, a main housing containing a stage, a vibration removal table, a turbo-molecular pump and the like as shown in FIG. 2.

Figures 3, 25:
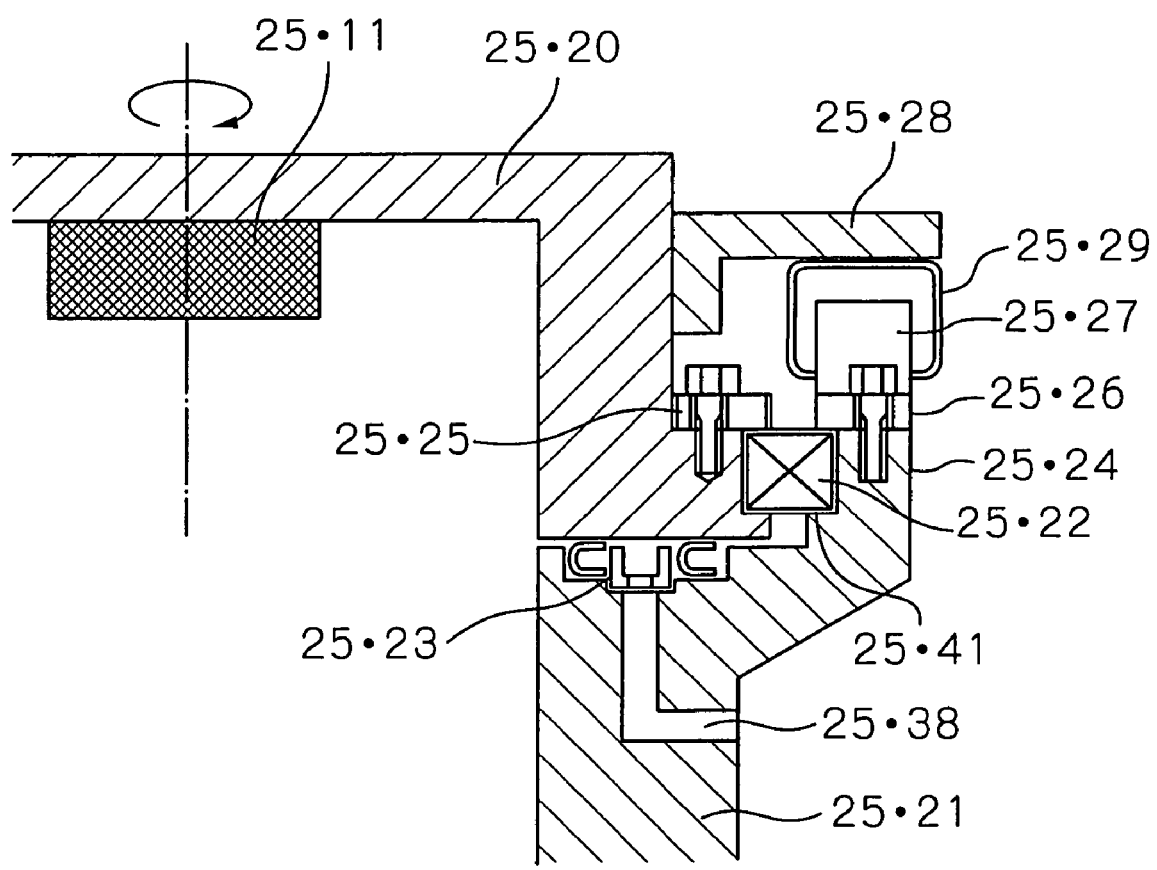
Figures 4, 25:
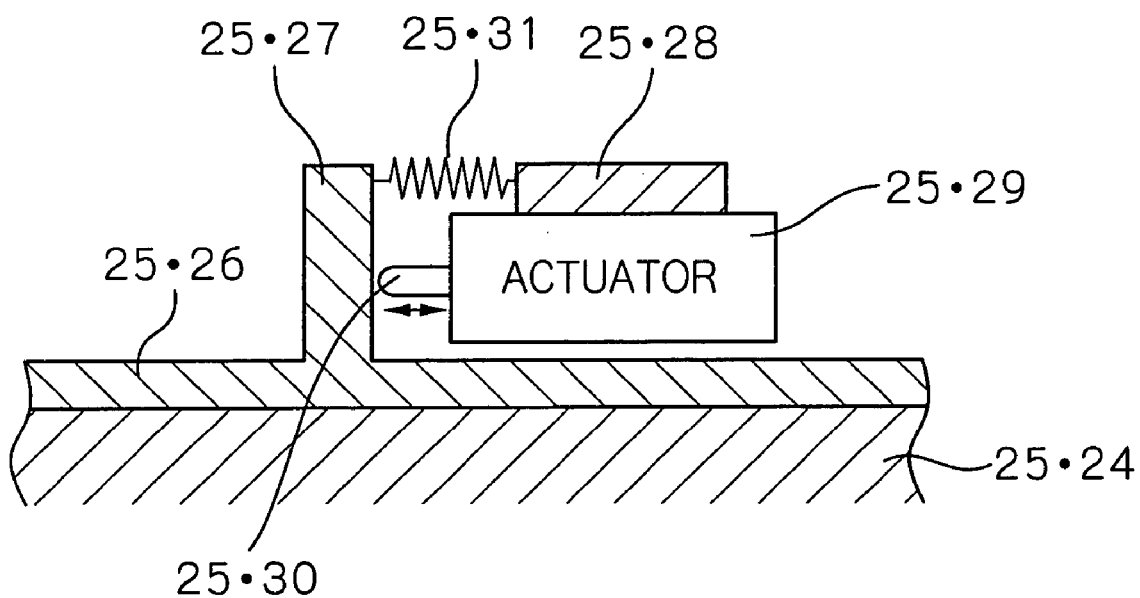
Figures 5, 25:
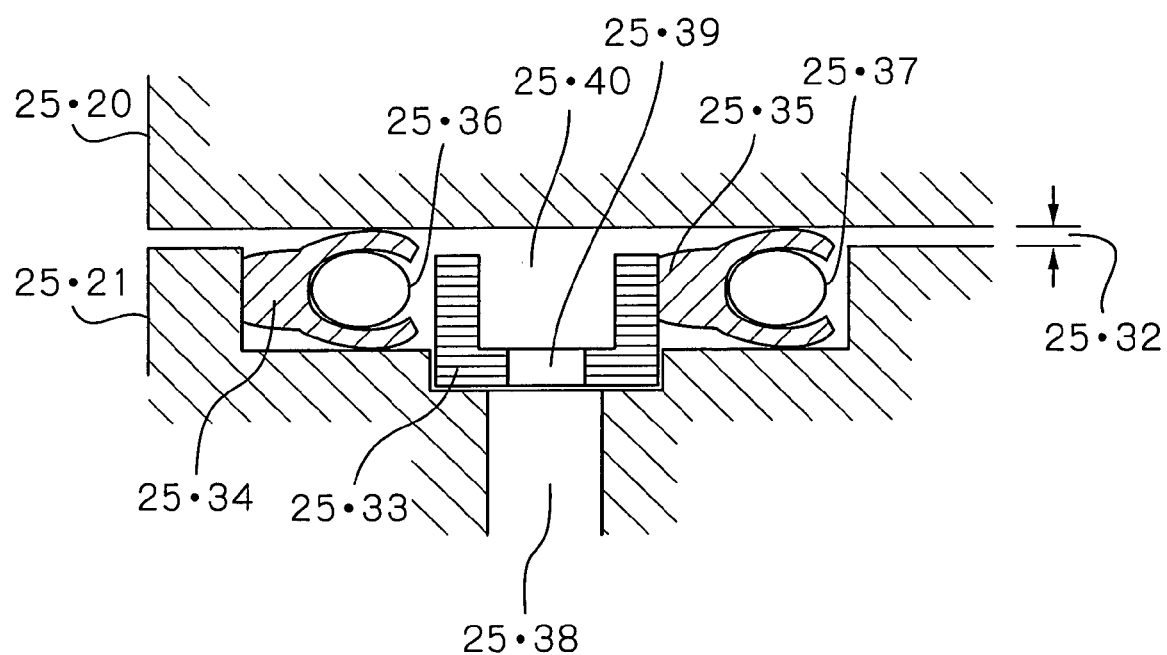

A control system comprises two CRTs and an instruction input feature (keyboard or the like). FIG. 3 shows a configuration from a viewpoint of a function. The electron beam column is mainly comprised of an electro-optical system, detection system, an optical microscope and the like. The electro-optical system is comprised of a lens and the like, and a transportation system is comprised of a vacuum transportation robot, an atmospheric transportation robot, a cassette loader, various kinds of position sensors and the like.

Here, the film formation apparatus and etching apparatus, and a cleaning apparatus (not shown) are placed side by side near the inspection apparatus main body, but they may be incorporated in the inspection apparatus main body. They are used, for example, for inhibiting the charge of a sample or cleaning the surface of the sample. If a sputtering system is used, one apparatus may have functions of both film formation and etching apparatuses.

Although not shown in the figures, associated apparatuses may be placed side by side near the inspection apparatus main body, or may be incorporated in the inspection apparatus main body depending on the purpose of use. Alternatively, the inspection apparatus may be incorporated in the associated apparatus. For example, a chemical-mechanical polishing apparatus (CMP) and the cleaning apparatus may be incorporated in the inspection apparatus main body, or a CVD (chemical vapor deposition) apparatus may be incorporated in the inspection apparatus and in this case, there are advantages that the installation area and the number of units for transportation of samples can be reduced, and transportation time can be shortened, and so on.

Similarly, the film formation apparatus such as a plating apparatus may be incorporated in the inspection apparatus main body. Similarly, the inspection apparatus may be used in conjunction with a lithography apparatus.

1-1) Main Chamber, Stage, Jacket of Vacuum Transportation System

Figure 4:
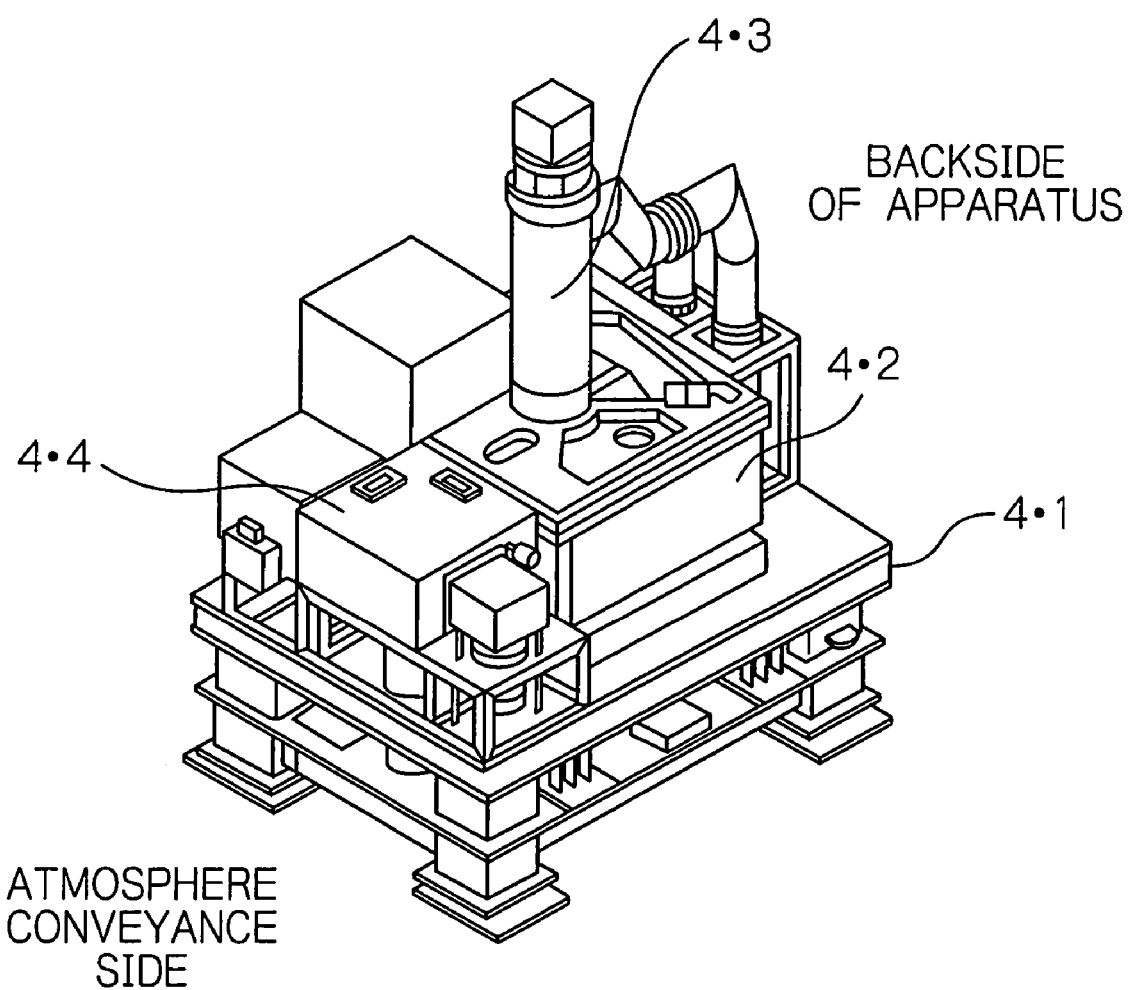
FIG. 4 shows main components of an inspection unit of the apparatus of FIG. 1.
Figure 5:
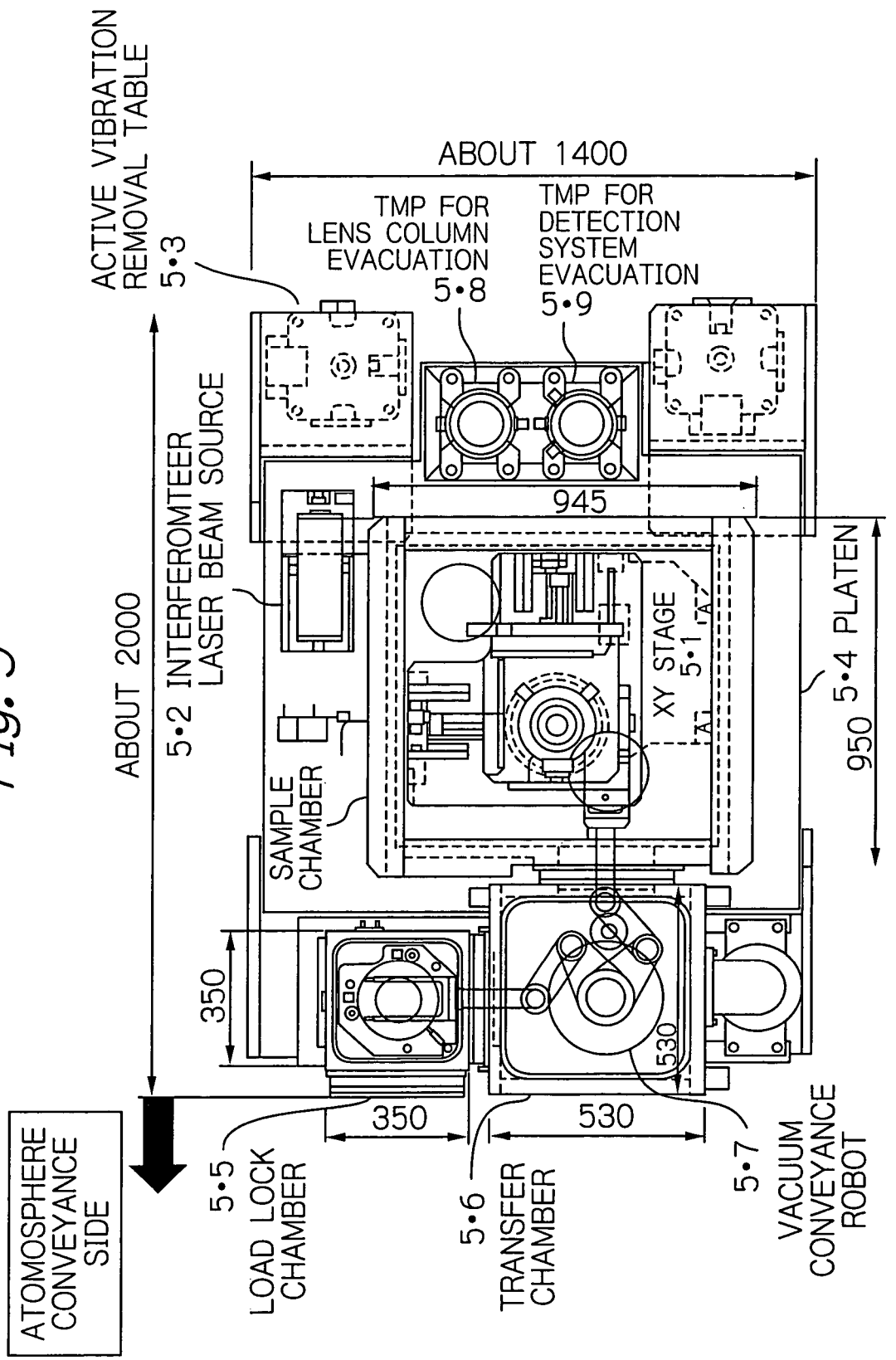
FIG. 5 shows main components of the inspection unit of the apparatus of FIG. 1.
Figure 6:
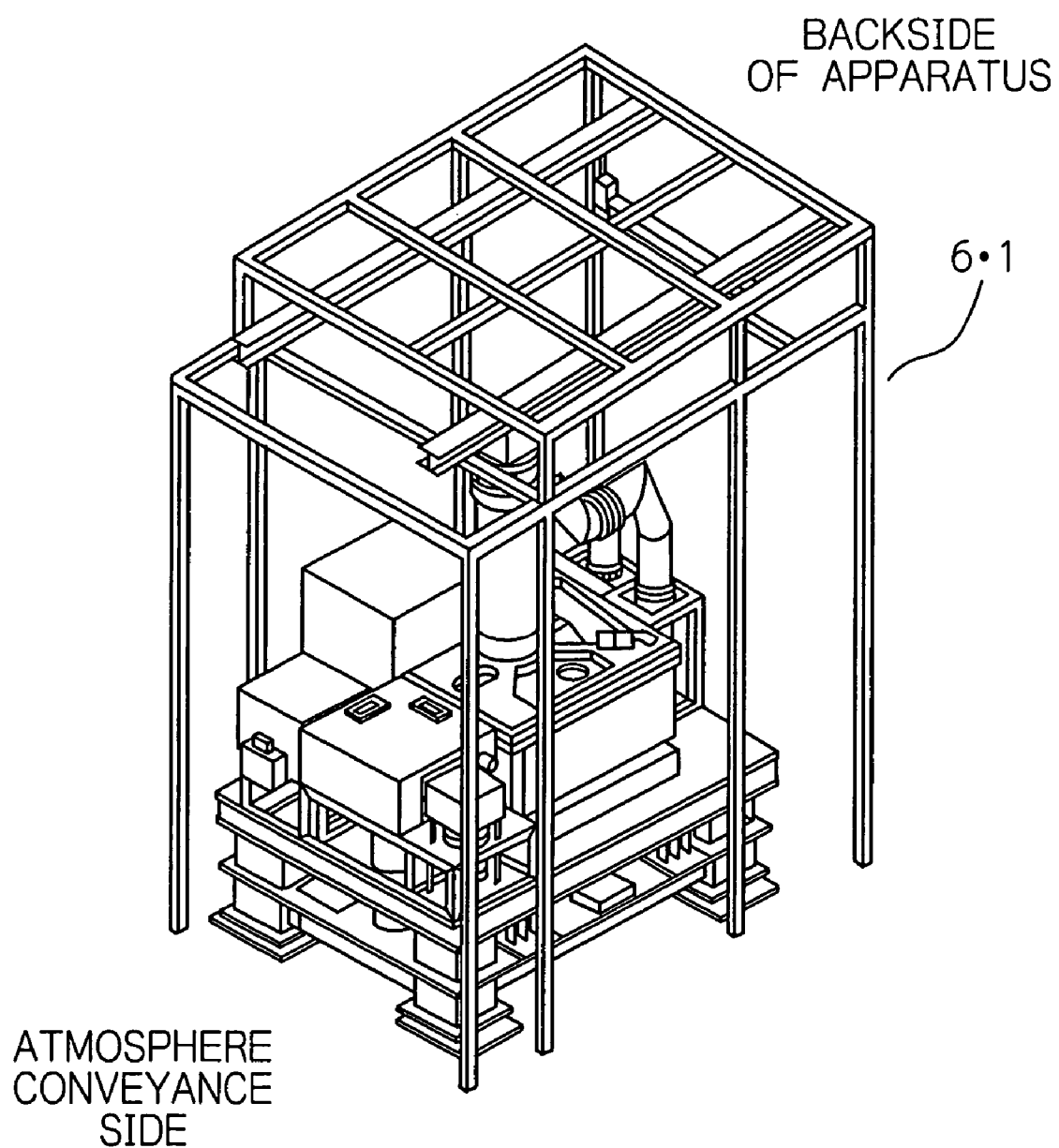
FIG. 6 shows main components of the inspection unit of the apparatus of FIG. 1.
Figure 7:
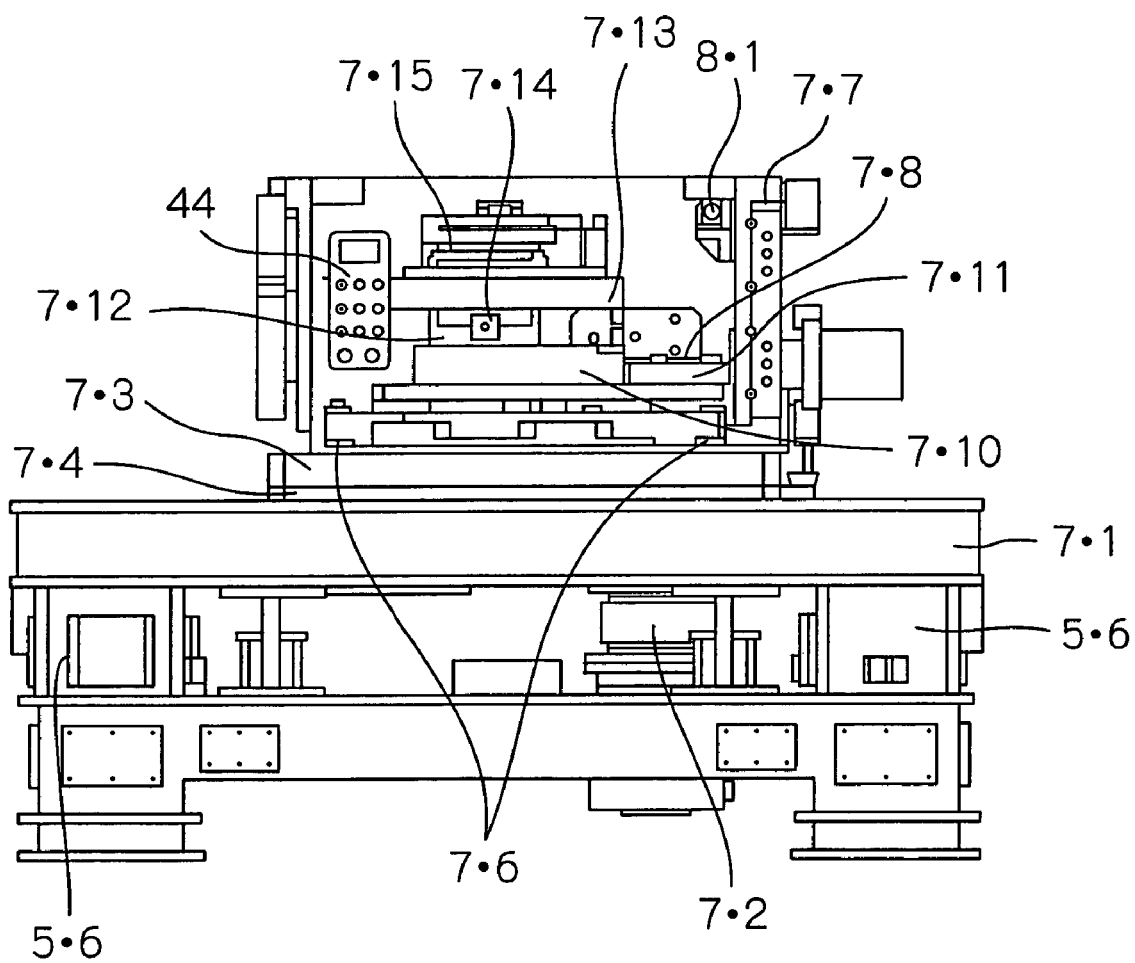
FIG. 7 shows main components of the inspection unit of the apparatus of FIG. 1.
Figure 8:
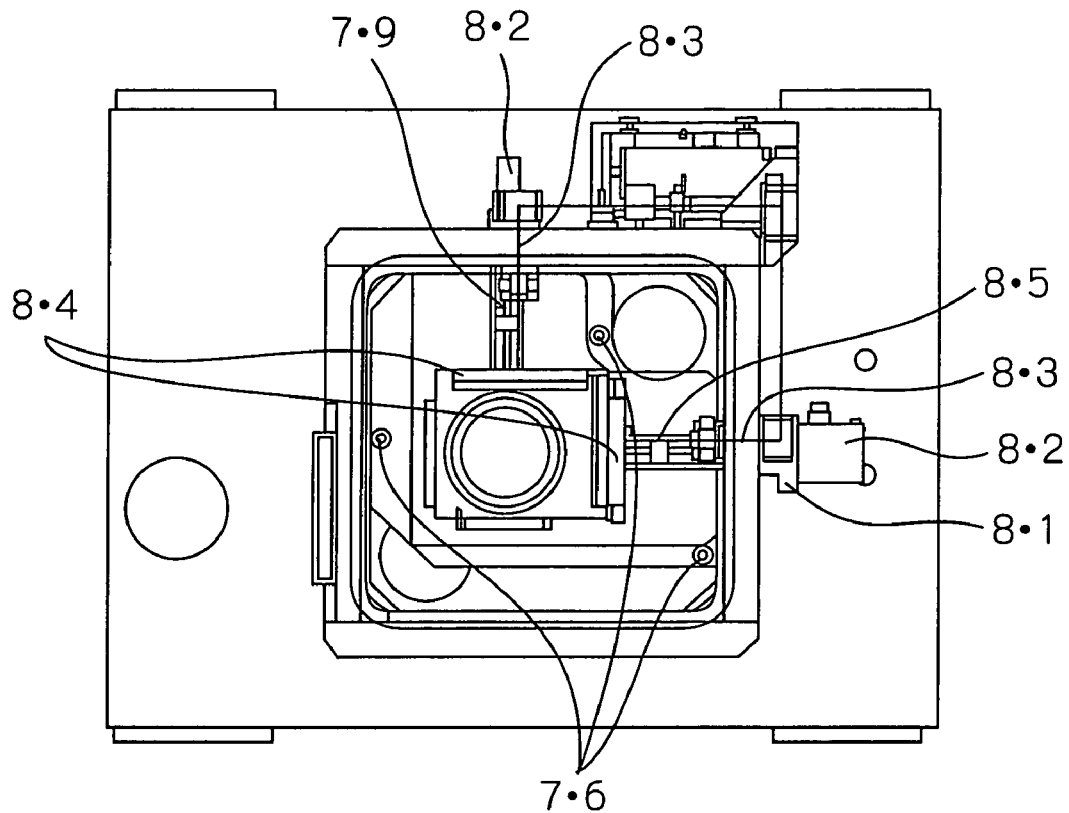
FIG. 8 shows main components of the inspection unit of the apparatus of FIG. 1.

In FIGS. 4, 5 and 6, main components of an inspection unit of the semiconductor inspection apparatus are shown. The inspection unit of the semiconductor inspection apparatus comprises an active vibration removal table 4•1 for shutting off vibration from the outside environment, a main chamber 4•2 as an inspection chamber, an electro-optical apparatus 4•3 placed on the main chamber, an XY stage 5•1 for scanning the wafer placed in the main chamber, a laser interference measurement system 5•2 for control of the motions of the XY stage, and a vacuum transportation system 4•4 accompanying the main chamber, and they are placed in positional relations shown in FIGS. 4 and 5. The inspection unit of the semiconductor inspection apparatus further comprises a jacket 6•1 for allowing environmental control and maintenance of the inspection unit, and is placed in positional relations shown in FIG. 6.

1-1-1) Active Vibration Removal Table

The active vibration removal table 4•1 has a weld platen 5•4 mounted on an active vibration removal unit 5•3, and the main chamber 4•2 as an inspection chamber, the electro-optical apparatus 4•3 placed on the main chamber, the vacuum transportation system 4•4 accompanying the main chamber and the like are held on the weld platen. In this way, vibrations in the inspection unit from the external environment can be inhibited. In this embodiment, the natural frequency is within ±25% of 5 Hz in the X direction, 5 Hz in the Y direction and 7.6 Hz in the Z direction, and the control performance is such that the transmission level of each axis is 0 dB or smaller at 1 Hz, −6.4 dB or smaller at 7.6 Hz, −8.6 dB or smaller at 10 Hz and −17.9 dB or smaller at 20 Hz (all under no load on the platen). In another structure of the active vibration removal table, the main chamber, the electro-optical apparatus and the like are suspended to be held. In still another structure, stone platen is mounted to hold the main chamber and the like.

1-1-2) Main Chamber

The main chamber 4•2 directly holds a turbo-molecular pump 7•2 in the lower part to achieve a certain degree of vacuum ($10^{-4}$ Pa or lower) in the inspection environment, and comprises therein a high accuracy XY stage 5•1 for scanning the wafer, so that a magnetic force from outside can be blocked. In this embodiment, the following structure is provided to improve the flatness of the holding surface of the high accuracy XY stage wherever possible. A lower plate 7•3 of the main chamber is placed and fixed on an especially high flatness area 7•4 (flatness of 5 µm or less in this embodiment) prepared on the weld platen. Further, a middle plate is provided as a stage holding surface in the main chamber. The middle plate is supported at three points against the lower plate of the main chamber, so that it is not directly affected by the flatness of the lower plate. In this embodiment, a support part consists of a spherical seat 7•6. The middle plate is capable of achieving a flatness of the stage holding surface at 5 µm or less when loaded with the self-weight and the weight of the stage. Furthermore, to alleviate the effect of deformation of the main chamber by a change in internal pressure (from atmospheric pressure to reduced pressure of $10^{-4}$ Pa or lower) on the stage holding surface, the middle plate is fixed directly on the weld platen at near the three points at which the middle plate is supported on the lower plate.

To accurately control the XY stage, a measurement system with a laser interferometer at a stage position is installed. An interferometer 8•1 is placed under vacuum to inhibit a measurement error, and is fixed directly on a high-rigidity chamber wall 7•7 in this embodiment to reduce vibrations of the interferometer causing directly a measurement error as small as 0. Furthermore, to eliminate errors of the measurement position and the inspection position, the extended line of the measurement area by the interferometer matches the inspection area as accurately as possible. Furthermore, a motor 8•2 for XY motions of the stage is held by the chamber wall 7•7 in this embodiment, but if it is necessary that the effect of motor vibrations on the main chamber is further inhibited, the motor 8•2 is held by the weld platen 7•1 directly, and mounted on the main chamber in a structure not transferring vibrations of a bellow and the like.

The main chamber 4•2 is composed of a material having a high magnetic permeability to block the effect of an external magnetic field on the inspection area. In this embodiment, the main chamber 4•2 has permalloy and iron such as SS 400 plated with Ni as an anticorrosive coating. In another embodiment, permendur, super permalloy, electromagnetic soft iron, pure iron or the like is used. Further, it is effective to cover the periphery of the inspection area in the chamber directly with a material having a high magnetic permeability as a magnetic shielding effect.

1-1-3) XY Stage

The XY stage 5•1 can scan the wafer with high accuracy under vacuum. Strokes of X and Y are each 200 to 300 mm for the 200 mm wafer, and 300 to 600 mm for the 300 mm wafer. In this embodiment, the XY stage is driven by the motor 8•2 for driving X and Y axes fixed on the main chamber wall, and a ball screw 8•5 attached thereto via a magnetic fluid seal 8•3. In this embodiment, since the XY motions can be performed in a state in which the ball screw for driving X and Y is fixed to the chamber wall, the stage structure is as follows.

First, in the lower stage, an Y stage 7•10 is placed, and a ball screw 7•8 for driving and a cross roller guide 7•11 are installed. On the Y stage, a middle stage 7•12 having thereon a ball screw 7•14 for driving the X axis is placed, and an X stage 7•13 is mounted thereon. The middle stage and the Y stage and x stage are connected together along the Y axis by the cross roller guide. In this way, when the Y axis is shifted, the X stage is moved by the Y stage and the connection area 7•14, and the middle stage remains fixed. Another embodiment has a two-stage structure in which the middle stage is aligned with the upper stage axis. Furthermore, in the XY stage of another embodiment, the XY stage itself is driven by a linear motor. Further, a high-accuracy mirror 8•4 (the flatness is λ/20 or less, and the material is aluminum-deposited synthetic quartz) is installed so that measurements can be made over the entire stroke by the interferometer.

Furthermore, a θ stage 7•15 is placed on the XY stage for performing wafer alignment under vacuum. In the θ stage in this embodiment, two ultrasonic motors are placed for driving, and a linear scale is placed for position control. Various cables connected to movable parts performing X, Y and θ motions are clamped by cable bears each held on the X stage and the Y stage, and connected to the outside of the main chamber via a field-through provided on the chamber wall.

Specifications of this embodiment with the above structures are shown in Tables 1 and 2.

TABLE 1

Table specifications and characteristics

| No. | Items | Criteria | Inspection process |
|-----|-------|----------|--------------------|
| 1 | X axis positioning repeatability | ±3 [µm] or less (graphical representation) | Measurement by laser length measuring machine for delivery inspection with Y axis at center |
| 2 | Y axis positioning repeatability | ±3 [µm] or less (graphical representation) | Measurement by laser length measuring machine for delivery inspection with X axis at center |

TABLE 1-continued

Table specifications and characteristics

| No. | Items | Criteria | Inspection process |
|---|---|---|---|
| 3 | θ positioning repeatability | ±0.4 [sec] (±2 pulses) or less (target) (numerical indication) | Measurement by deviation pulses at the time of stopping of rotation sensor. Measurements are made at three points of 0°, 1° and +1° |
| 4 | X axis positioning accuracy | ±20 [μm] or less (graphical representation) | Measurement by laser length measuring machine for delivery inspection with Y axis at center |
| 5 | Y axis positioning accuracy | ±20 [μm] or less (graphical representation) | Measurement by laser length measuring machine for delivery inspection with X axis at center |
| 6 | X axis backlash | ±1 [μm] or less (numerical indication) | Measurement by laser length measuring machine for delivery inspection with Y axis at center |
| 7 | X axis backlash | ±1 [μm] or less (numerical indication) | Measurement by laser length measuring machine for delivery inspection with X axis at center |
| 8 | X axis pitching | 5 [sec] or less (target) (graphical representation) | Measurement by laser length measuring machine for delivery inspection with Y axis at center and both ends |
| 9 | Y axis pitching | 5 [sec] or less (target) (graphical representation) | Measurement by laser length measuring machine for delivery inspection with X axis at center and both ends |
| 10 | X axis yawing | 5 [sec] or less (target) (graphical representation) | Measurement by laser length measuring machine for delivery inspection with Y axis at center and both ends |
| 11 | Y axis pitching | 5 [sec] or less (target) (graphical representation) | Measurement by laser length measuring machine for delivery inspection with X axis at center and both ends |
| 12 | X axis rolling | Reference value (graphical representation) | Measurement of Y axis length measuring mirror by automatic collimater with Y axis at center |
| 13 | Y axis rolling | Reference value (graphical representation) | Measurement of X axis length measuring mirror by automatic collimater with X axis at center |
| 14 | Vertical straightness | ±2 [μm] or less (graphical representation) | Measurement by straight master and ADE displacement meter. Measurements are on the cross at the center and reference values are at both ends |
| 15 | Orthogonality of X and Y axes | 10 [μm] or less (numerical indication) | Measurement by orthogonality master and dial gage |
| 16 | Distance between ORG switch and motor starting point | 1 ± 0.5 [mm] (numerical indication) | Measurement by positioning laser length measuring machine |

TABLE 2

System specifications and characteristics

| No. | Items | Criteria | Inspection process |
|---|---|---|---|
| 1. | X axis lateral displacement | ±0.5 μm or less @10 mm/sec, @15 mm/sec ±1.0 μm or less @30 mm/sec ±2.0 μm or less @60 mm/sec (excluding chamber vibration components during acceleration and deceleration) (graphical representation) | Y axis-X axis deviation during movement from 0 to 20 mm at 20 mm/sec, with Y axis at center |
| 2. | X axis positioning accuracy | ±0.5 μm or less (graphical representation) | Stop accuracy after movement from 0 to 20 mm at 20 mm/sec, with Y axis at center |
| 3. | Y axis positioning accuracy | ±0.5 μm or less (graphical representation) | Stop accuracy after movement from 0 to 20 mm at 20 mm/sec, with X axis at center |
| 4. | Y axis positioning accuracy | ±3.0 μm or less @10 mm/sec, @15 mm/sec ±5.0 μm or less @30 mm/sec. @60 mm/sec (graphical representation) | deviational variation after movement at constant speed, with x axis at center |

1-2) Laser Interference Measurement System

Figure 9:
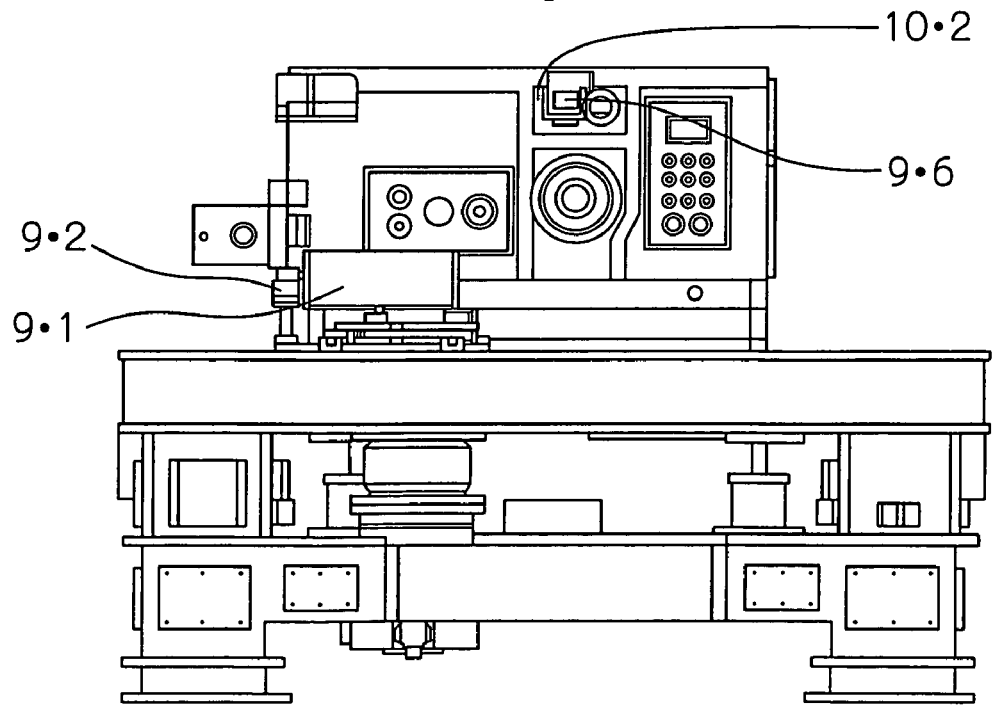
FIG. 9 shows main components of the inspection unit of the apparatus of FIG. 1.
Figure 10:
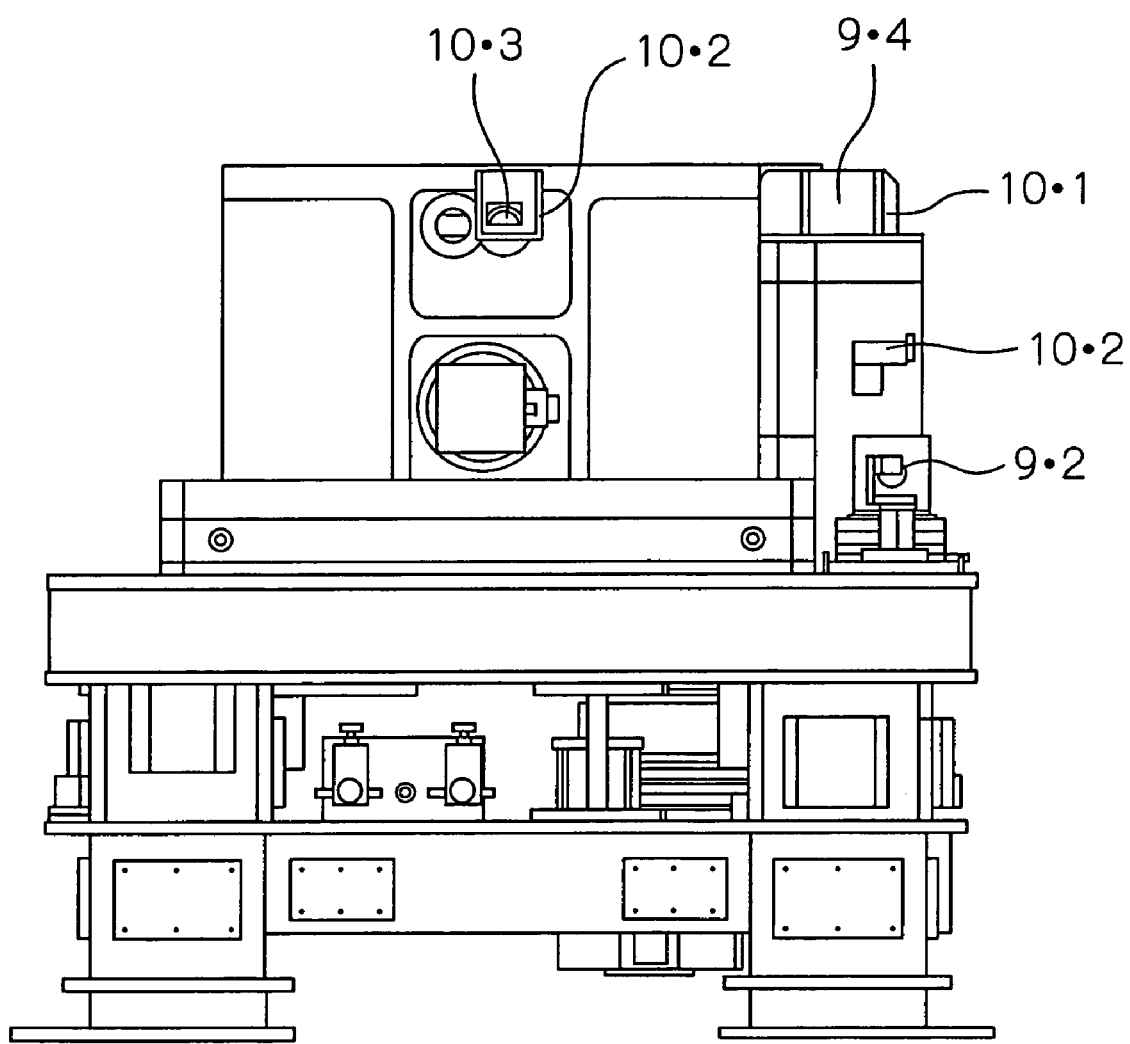
FIG. 10 shows main components of the inspection unit of the apparatus of FIG. 1.

The laser interference measurement system is comprised of a laser optical system having an optical axis which is parallel to X and Y axes and has an inspection position on its extended line, and an interferometer 8•1 placed therebetween. The optical system in this embodiment is placed in positional relations shown in FIGS. 9 and 10. Laser light emitted from a laser 9•1 placed on the weld platen is erected upright by a bender 9•2, and then bent to be parallel with a measurement plane by a bender 10•1. Further, the laser light is split into light for X axis measurement and light for Y axis measurement by a splitter 9•4, then bent to be parallel with the Y axis and the X axis by a bender 10•3 and a bender 9•6, respectively, and guided into the main chamber.

An adjustment method in starting the optical system will be described below. First, an adjustment is made so that laser light emitted from the laser is bent perpendicularly by the bender 9•2, and bent horizontally by the bender 10•1. Then, the bender 10•3 is adjusted so that an optical axis of light bent by the bender 10•3 and reflected by a mirror 8•4 placed accurately perpendicularly to the Y axis and returned perfectly matches an optical axis of incident light. By making an observation of the optical axis just behind the laser with the interferometer removed so as not to interrupt reflected light, an accurate adjustment can be made. Furthermore, the optical axis adjustment of the X axis can be performed independently with the splitter 9•4 and the bender 9•6 after performing the optical axis adjustment of the Y axis. The adjustment can be performed as that of the Y axis. Further, after the axes of incident light and reflected light of the X axis and the Y axis are adjusted, the intersection point of the optical axes (assuming that no mirror exists) should be made to match the wafer inspection position. As a result, a bracket fixing the bender 10•3 can move perpendicularly to the Y axis, and a bracket fixing the bender 9•6 can move perpendicularly to the X axis with incident light and reflected light perfectly matching each other. Further, the bender 10•1, the splitter 9•4, the bender 10•3 and the bender 9•6 can desirably move vertically while retaining their respective positional relations.

Furthermore, a method for adjustment of optical axes associated with replacement of the laser in the apparatus in operation after initiation will be described below. In the apparatus in operation in which the inside of the main chamber is kept under vacuum, the optical axis or the like having an interferometer removed has a difficulty. Thus, a tool for placing targets 10•2 at several points on an optical path outside the main chamber so that the optical path in the start can be assessed only outside the main chamber is prepared. After replacement of the laser, the adjustment made in the start can be reproduced by adjusting the optical axis with respect to the target 10•2 only with an adjustment feature provided on a laser mounting seat.

1-3) Inspection Unit Jacket

Figure 11:
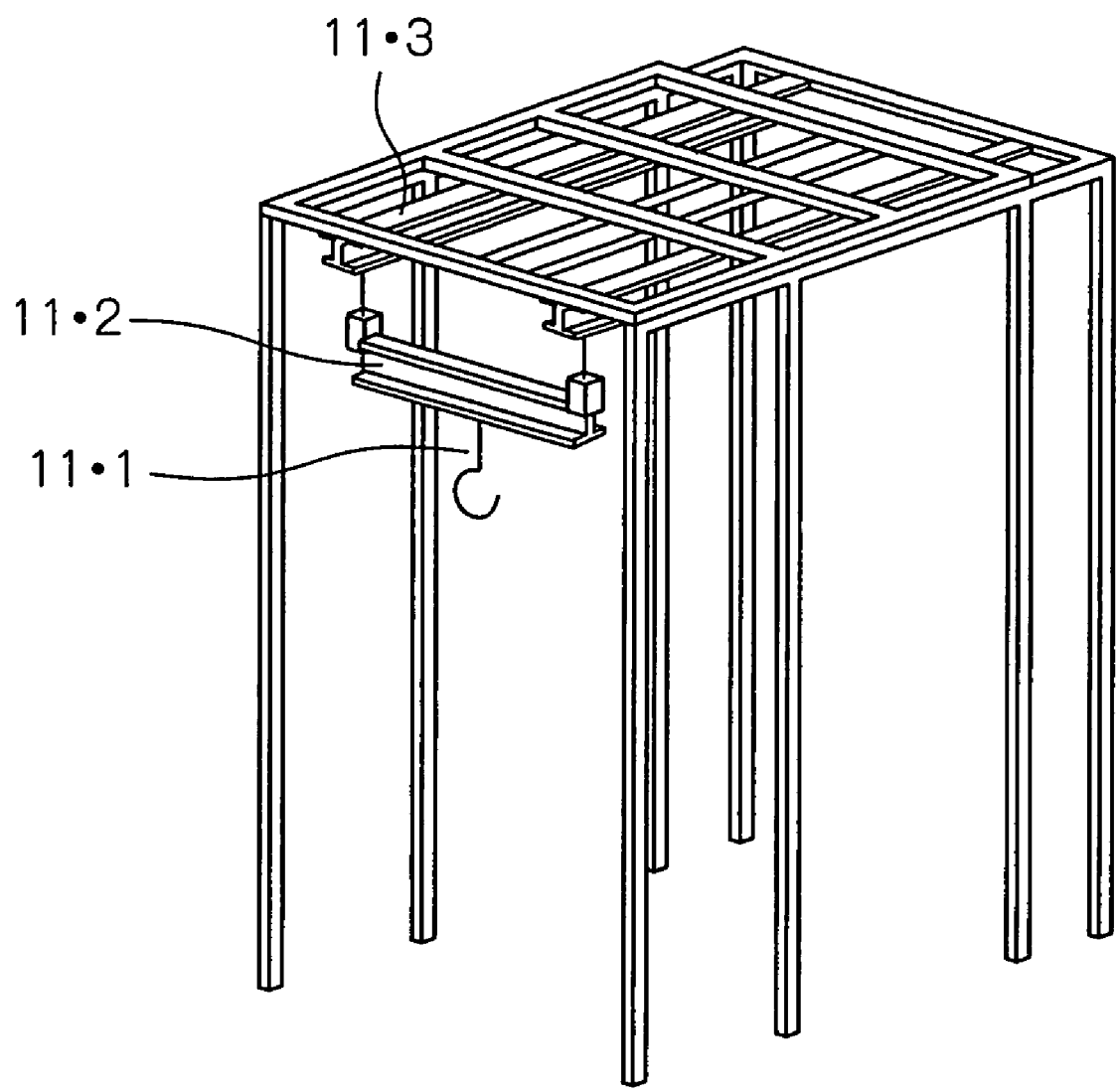
FIG. 11 shows a jacket of the apparatus of FIG. 1.
Figure 12:
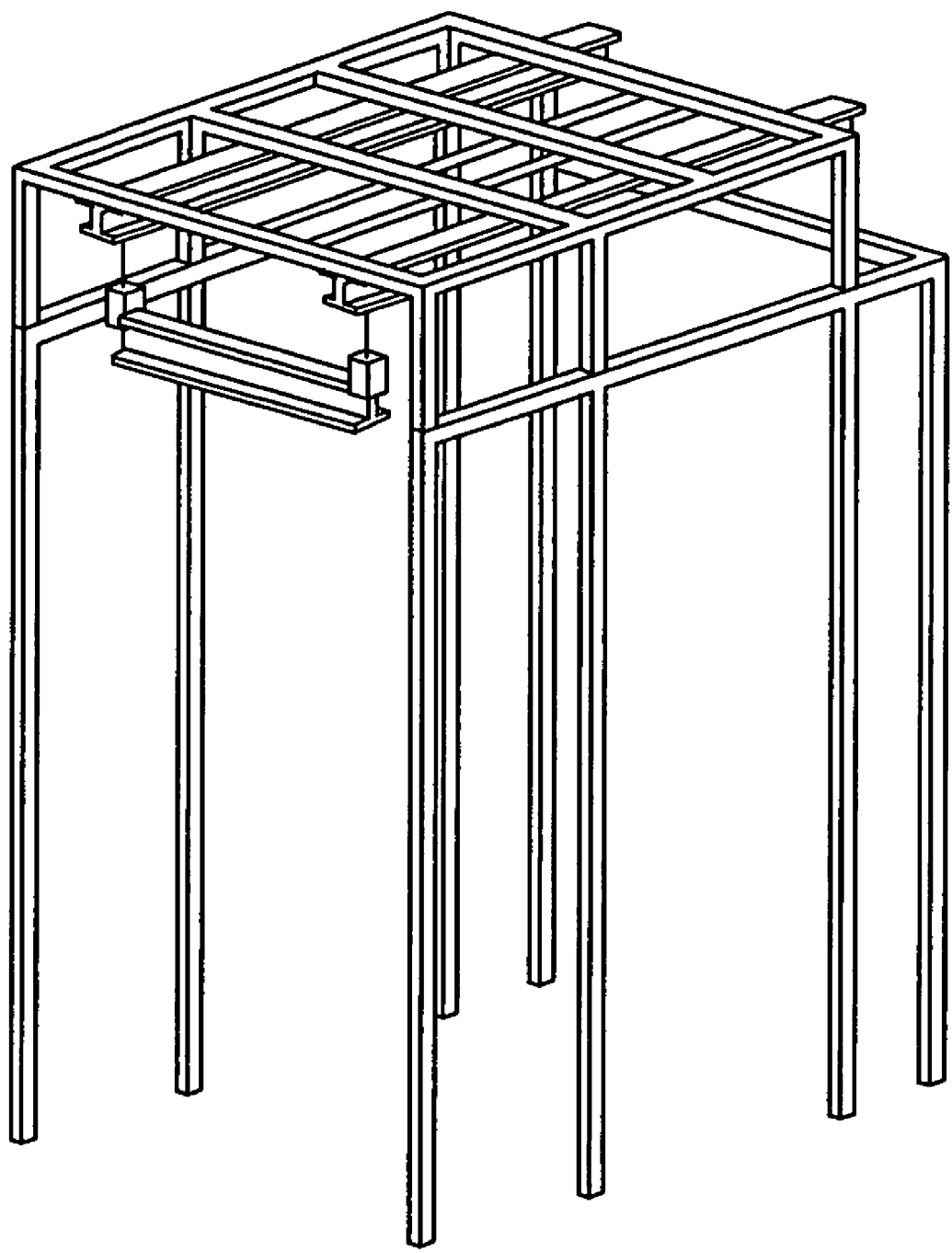
FIG. 12 shows the jacket of the apparatus of FIG. 1.

An inspection unit jacket 4•7 can be provided with a feature as a flame structure for maintenance. In this embodiment, a containable twin crane 11•1 is provided on the upper part. The crane 11•1 is mounted on a traverse rail 11•2, and the traverse rail is placed on a traveling rail (longitudinal) 11•3. The traveling rail is usually housed as shown in FIG. 11, during maintenance, the traveling rail rises as shown in FIG. 12, so that the stroke in the vertical direction of the crane can be increased. Consequently, an electro-optical apparatus 4•3, a main chamber top plate and the XY stage 5•1 can be attached to/detached from the back face of the apparatus by the crane included in the jacket during maintenance. Another embodiment of the crane included in the jacket has a crane structure having a rotatable open-sided axis.

Furthermore, the inspection unit jacket can also have a function as an environment chamber. This has an effect of magnetic shielding along with control of temperature and humidity as required.

2. Embodiments

Preferred embodiments of the present invention will be described below as a semiconductor inspection apparatus inspecting a substrate, i.e. a wafer having a pattern formed on the surface as an inspection object, with reference to the drawings.

2-1) Transportation System

Figure 14:
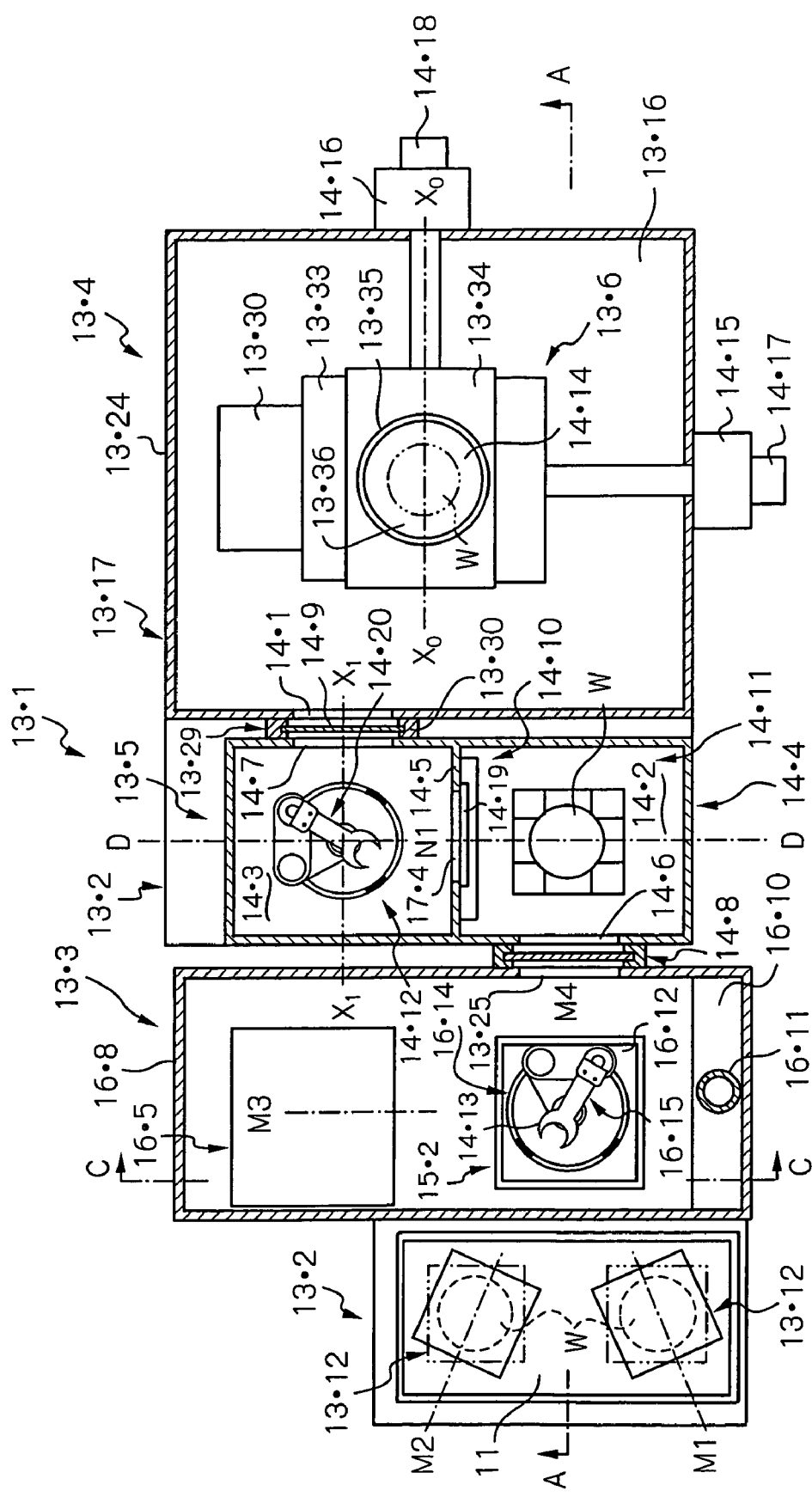
FIG. 14 is a front view showing main components of the semiconductor inspection apparatus according to the present invention.

FIGS. 13 and 14 show main components of the semiconductor inspection apparatus according to the present invention with an elevational view and a front view. This semiconductor inspection apparatus 13•1 comprises a cassette holder 13•2 holding cassettes each containing a plurality of wafers, a mini-environment apparatus 13•3, a loader housing 13•5 constituting a working chamber, a loader 13•7 loading the wafer from the cassette holder 13•2 to a stage apparatus 13•6 placed in a main housing 13•4, and an electro-optical apparatus 13•8 placed in a vacuum housing, and they are placed in positional relations shown in FIGS. 13 and 14.

The semiconductor inspection apparatus 13•1 further comprises a precharge unit 13•9 placed in the vacuum main housing 13•4, a potential application mechanism applying a potential to the wafer, an electron beam calibration mechanism, and an optical microscope 13•11 constituting an alignment control apparatus 13•10 for positioning the wafer on the stage apparatus.

2-1-1) Cassette Holder

The cassette holder 13•2 holds a plurality of cassettes 13•12 (two cassettes in this embodiment) (e.g. closed cassettes such as SMIF and FOUP manufactured by Assist Co. Ltd.) each containing a plurality of wafers (e.g. 25 wafers) housed with arranged vertically in parallel. The cassette holder 13•2 may be freely selected and placed such that if cassettes are conveyed by a robot or the like and automatically loaded into the cassette holder 13•2, the cassette holder 13•2 having a structure suitable for this arrangement is selected, and if cassettes are manually loaded, the cassette holder having an open cassette structure suitable for this arrangement is selected. In this embodiment, the cassette holder 13•2 has a form in which the cassettes 13•12 are automatically loaded, and for example, a lift table 13•13, and a lift mechanism 13•14 vertically moving the lift table 13•13, wherein the cassette 13•12 can be automatically set on the lift table 13•13 in a state shown by a chain line in FIG. 14, and after the cassette 13•12 is set, it is automatically rotated to a state shown by a solid line in FIG. 14, and directed to a rotation axis line of a first transportation unit in the mini-environment apparatus.

Furthermore, the lift table 13•13 is descended to a state shown by a chain line in FIG. 13. In this way, a cassette holder having a well known structure may be used as appropriate for any of the cassette holder to be used when the cassette is automatically loaded and the cassette holder when the cassette is manually loaded, and detailed descriptions of their structures and functions are not presented.

Figure 15:
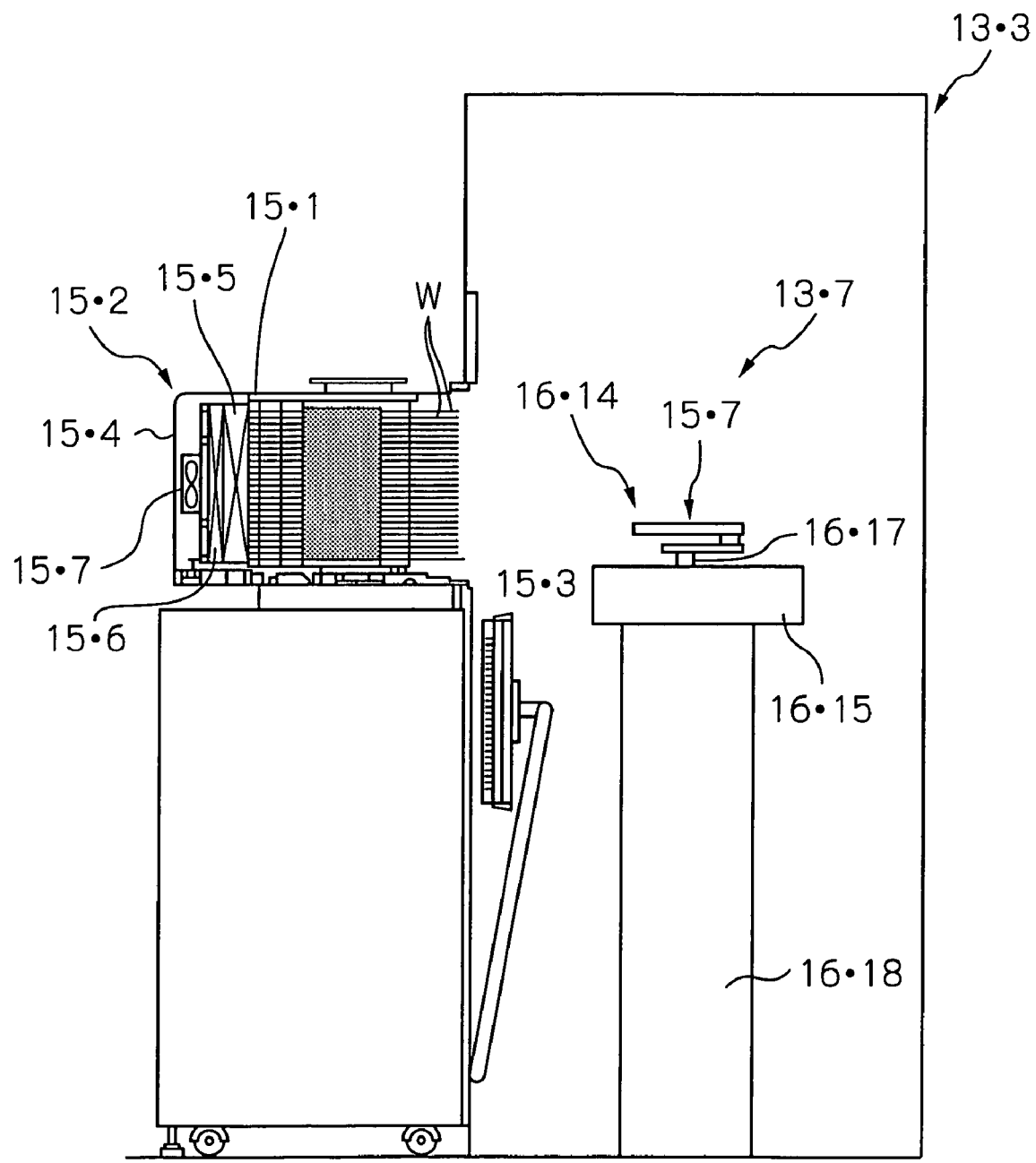
FIG. 15 shows one example of the configuration of a cassette holder of the semiconductor inspection apparatus according to the present invention.

In another embodiment, as shown in FIG. 15, a plurality of 300 mm substrates are housed in a trench pocket (not described) fixed in a box main body 15•1, and are conveyed, stored and so on. A substrate transportation box 15•2 is comprised of the prismatic box main body 15•1, a substrate loading/unloading door 15•3 communicating with a substrate loading/unloading door automatic opening/closing apparatus so that an opening on the side face of the box main body 15•1 can be mechanically opened and closed, a lid 15•4 located opposite to the opening and covering openings for attachment and detachment of filters and a fan motor, the trench pocket (not shown) for holding a substrate W (FIG. 13), an ULPA filter 15•5, a chemical filter 15•6 and a fan motor 15•7. In this embodiment, substrates are loaded/unloaded by a robot-type first transportation unit 15•7 of the loader 13•7.

Furthermore, the substrate or wafer housed in the cassette 13•12 is to be inspected, and such inspection is performed after or during a process of processing the wafer during the semiconductor production step. Specifically, the substrate or wafer undergoing a film formation step, CMP, ion implantation and the like, the wafer having a wiring pattern formed on the surface, or the wafer having no wiring pattern yet formed on the surface is housed in the cassette. For the wafer housed in the cassette 12•12, a large number of wafers are spaced vertically and arranged in parallel, and therefore an arm of the first transportation unit can be moved vertically so that they can be held by the wafer at any position and the first transportation unit described later. Furthermore, the cassette is provided with a feature for controlling a moisture content in the cassette to prevent oxidization and the like of the wafer surface after the process. For example, a dehumidifying agent such as silica gel is placed in the cassette. In this case, any dehumidifying agent having an effect of dehumidification may be used.

2-1-2) Mini-Environment Apparatus

In FIGS. 13 to 16, the mini-environment apparatus 13•3 comprises a housing 16•2 constituting a mini-environment space 16•1 arranged for undergoing control of the atmosphere, a gas circulating apparatus 16•3 for circulating a gas such as cleaning air in the mini-environment space 16•1 to control the atmosphere, a discharge apparatus 16•4 collecting and discharging part of air supplied into the mini-environment space 16•1, and a pre-aligner 16•5 placed in the mini-environment space 16•1 to roughly position the substrate or wafer as an inspection object.

Figure 16:
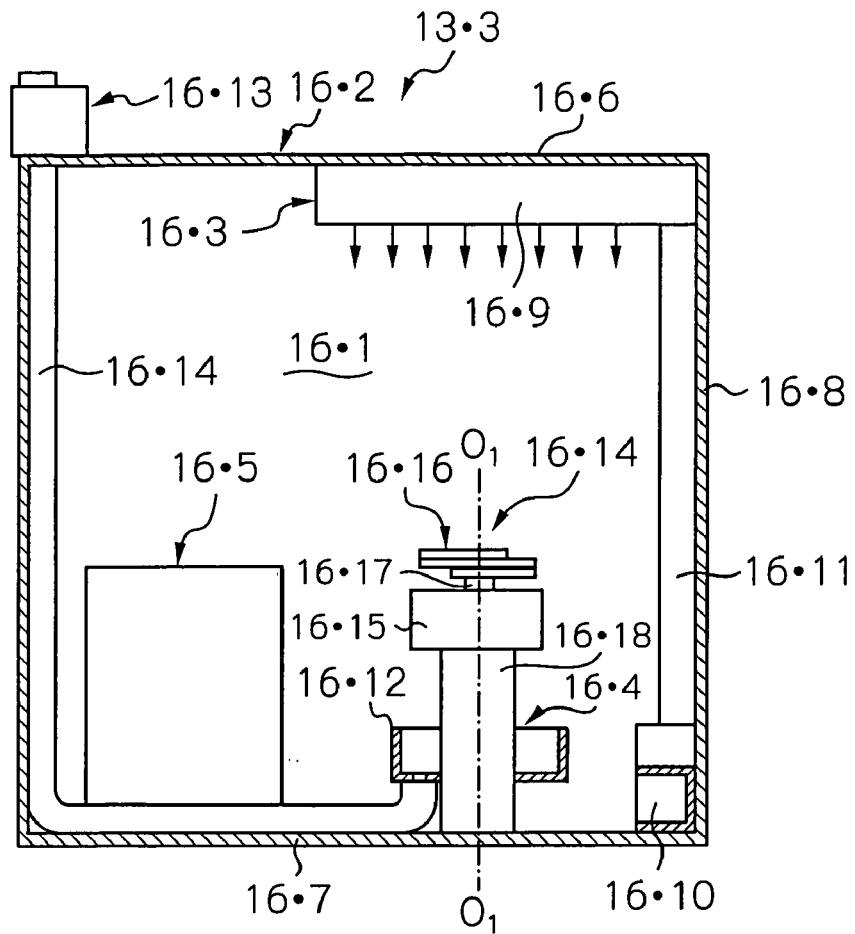
FIG. 16 shows the configuration of a mini-environment apparatus of the semiconductor inspection apparatus according to the present invention.
Figure 17:
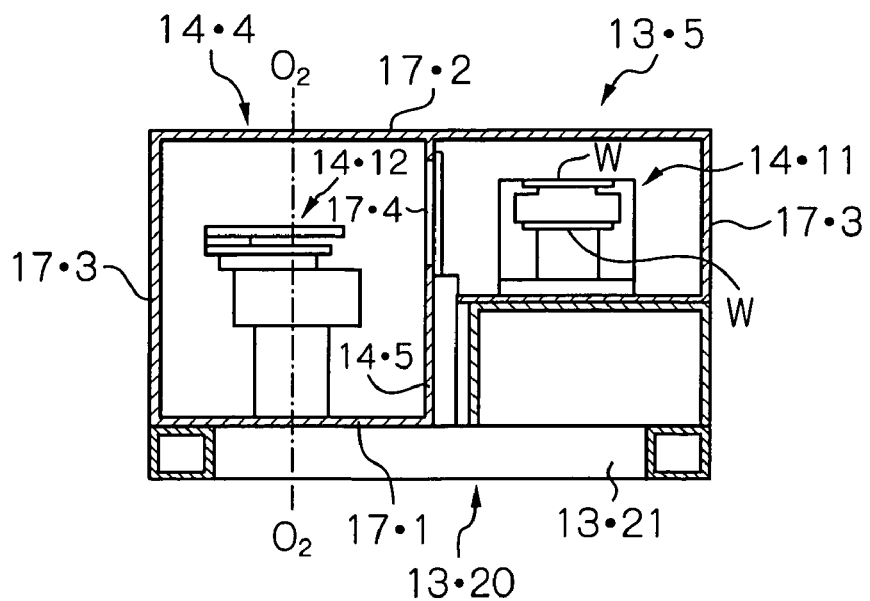
FIG. 17 shows the configuration of a loader housing of the semiconductor inspection apparatus according to the present invention.

The housing 16•2 has a top wall 16•6, a bottom wall 16•7 and a circumference wall 16•8 surrounding the circumference, and isolates the mini-environment space 16•1 from outside. To atmosphere-control the mini-environment space 16•1, the gas circulating apparatus 16•3 comprises a gas supply unit 16•9 mounted on the top wall 16•6 to clean a gas (air in this embodiment) and flow the clean air just downward in a laminar form through one or more gas blowout holes (not shown) in the mini-environment space 16•1, a collection duct 16•10 placed on the bottom wall 16•7 to collect air flowed away toward the bottom in the mini-environment space 16•1, a conduit 16•11 connecting the collection duct 16•10 and the gas supply unit 16•9 to return the collected air back to the gas supply unit 16•9, as shown in FIG. 16.

In this embodiment, the gas supply unit 16•9 introduces about 20% of air to be supplied from outside the housing 16•2 and cleaning the air, but the ratio of the gas introduced from outside can be arbitrarily selected. The gas supply unit 16•9 comprises an HEPA or ULPA filter having a well known structure for producing clean air. The downward laminar flow, namely down flow, is principally supplied in such a manner as to flow through the transportation plane by the first transportation unit placed in the mini-environment space 16•1, described later, to prevent deposition of pasty dust occurring from the transportation unit on the wafer. Thus, a blast nozzle of the down flow is not necessarily located near the top wall as shown in the figure, but may be at any location on the upper side of the transportation plane by the transportation unit. Furthermore, it is not required to flow the gas throughout the mini-environment space 16•1.

Furthermore, in some cases, ion air can be used as clean air to ensure cleanness. Furthermore, a sensor for observing the cleanness may be provided in the mini-environment space 16•1, and the apparatus may be shut down when the cleanness drops.

An entrance 13•15 is formed in an area adjacent to the cassette holder 13•2 in the circumference wall 16•8 of the housing 16•2. A shutter apparatus having a well known structure may be provided near the entrance 13•15 to close the entrance 13•15 from the mini-environment apparatus side. The laminar down flow produced near the wafer may flow at a flow rate of 0.3 to 0.4 m/sec. The gas supply unit 16•9 may be provided outside the mini-environment space 16•1, instead of being provided inside the mini-environment space 16•1.

The discharge apparatus 16•4 comprises a suction duct 16•12 placed in the lower part of the transportation unit at a location on the lower side of the wafer transportation plane of the transportation unit, a blower 16•13 placed outside the housing 16•2 and a conduit 16•14 connecting the suction duct 16•12 and the blower 16•13. This discharge apparatus 16•4 suctions a gas flowing downward along the circumference of the transportation unit and containing dust that may occur from the transportation unit with the suction duct 16•12, and discharges the gas to outside the housing 16•2 through the conduit 16•14 and the blower 16•13. In this case, the gas may be discharged into a discharge pipe (not shown) placed near the housing 16•2.

The pre-aligner 16•5 placed in the mini-environment space 16•1 optically or mechanically detects an orientation flat (flat portion formed on the outer edge of a circular wafer, which is hereinafter referred to as ori-fla) formed on the wafer, and one or more V-type cutouts or notches formed on the outer edge of the wafer to predefine the position of the wafer in the direction of rotation about the axial line O—O with accuracy within about ±1°. The pre-aligner 16•5 constitutes part of a mechanism determining the coordinates of an inspection object, and plays a role to roughly position the inspection object. The pre-aligner 16•5 itself may have a well known structure, and thus the structure and operation thereof are not presented.

Furthermore, although not shown in the figure, a collection duct for discharge apparatus may be provided also in the lower part of the pre-aligner 16•5 to discharge air containing dust discharged from the pre-aligner 16•5 to outside.

2-1-3) Main Housing

In FIGS. 13 to 15, the main housing 13•4 constituting the working chamber 13•16 comprises a housing main body 13•17, and the housing main body 13•17 is supported by a housing supporting apparatus 13•20 placed on a vibration blocking apparatus or anti-vibration apparatus 13•19 placed on a base frame 13•18. The housing supporting apparatus 13•20 comprises a frame structure 13•21 assembled in a rectangular form. The housing main body 13•17 is fixedly placed on the frame structure 13•21, comprises a bottom wall 13•22 placed on the frame structure, a top wall 13•23, and a circumference wall 13•24 connected to the bottom wall 13•22 and the top wall 13•23 to surround the circumference, and isolates the working chamber 13•16 from outside. In this embodiment, the bottom wall 13•22 is made of relatively thick steel plate so that the bottom wall 13•22 is not deformed by the weight of equipment such as the stage apparatus and the like placed above, but other structure may be adopted.

In this embodiment, the housing main body and the housing supporting apparatus 13•20 are made to have a rigid structure, and the anti-vibration apparatus 13•19 prevents transfer of vibrations to this rigid structure from a floor on which the base frame 13•18 is placed. An entrance 14•1 for loading/unloading the wafer is formed on an area of the circumference wall 13•24 of the housing main body 13•17 adjacent to a loader housing described later.

Furthermore, the anti-vibration apparatus 13•19 may be an active type having a pneumatic spring, magnetic bearing or the like, or may be a passive type having the same. In any case, the apparatus may have a well known structure, and therefore the structure and function of the apparatus itself are not described here. The working chamber 13•16 is kept in a vacuum atmosphere by a vacuum apparatus (not shown) having a well known structure. A control apparatus 2 for controlling the operation of the overall apparatus is placed below the base frame 13•18. The pressure of the main housing is usually at $10^{-4}$ to $10^{-6}$ Pa.

2-1-4) Loader Housing

In FIGS. 13 to 15 and FIG. 17, the loader housing 13•5 comprises a housing main body 14•4 constituting a first loading chamber 14•2 and a second loading chamber 14•3. The housing main body 14•4 has a bottom wall 17•1, a top wall 17•2, a circumference wall 17•3 surrounding the circumference, and a partition wall 14•5 partitioning the first loading chamber 14•2 and the second loading chamber 14•3, and can isolate both the loading chambers from outside. The partition wall 14•5 is provided with an opening or entrance 17•4 to give and take the wafer between the loading chambers. Furthermore, entrances 14•6 and 14•7 are formed in areas of the circumference wall 17•3 adjacent to the mini-environment apparatus and the main housing.

The housing main body 14•4 of the loader housing 13•5 is placed and supported on a frame structure 13•21 of the housing supporting apparatus 13•20. Thus, transfer of vibrations of the floor to the loader housing 13•5 is also prevented. The entrance 14•6 of the loader housing 13•5 is matched with an entrance 13•25 of the housing 16•2 of the mini-environment apparatus 13•3, and there a shutter apparatus 14•8 selectively inhibiting communication between the mini-environment space 16•1 and the first loading chamber 14•2 is provided.

The shutter apparatus 14•8 has a seal material 13•26 surrounding the periphery of entrances 13•25 and 14•6 and fixed in close contact with a side wall 17•3, a door 13•27 inhibiting passage of air through the entrance in cooperation with the seal material 13•26, and a drive apparatus 13•28 driving the door. Furthermore, the entrance 14•7 of the loader housing 13•5 is matched with the entrance 14•1 of the housing main body 13•17, and there a shutter apparatus 13•29 selectively seal-inhibiting communication between the second loading chamber 14•3 and the working chamber 13•16 is provided. The shutter apparatus 13•29 has a seal material 13•30 surrounding the periphery of entrances 14•7 and 14•1 and fixed in close contact with side walls 17•3 and 13•24, a door 14•9 inhibiting passage of air through the entrance in cooperation with the seal material 13•30, and a drive apparatus 13•31 driving the door.

Further, an opening formed in the partition wall 14•5 is provided with a shutter apparatus 14•10 selectively seal-inhibiting communication between first and second loading chambers by closing the opening with the door. The shutter apparatuses 14•8, 13•29 and 414•10 can air-tightly seal the chambers when they are in a closed state. These shutter apparatuses may be well known shutter apparatuses, and therefore detailed descriptions of the structures and functions thereof are not presented.

Furthermore, a method of supporting the housing 16•2 of the mini-environment apparatus 13•3 is different from a method of supporting the loader housing, and to prevent vibrations from the floor from being transferred through the mini-environment apparatus 13•3 to the loader housing 13•5 and the main housing 13•4, a cushion material for prevention of vibrations may be so situated as to air-tightly surround the periphery of the entrance between the housing 16•2 and the loader housing 13•5.

Figure 18A:
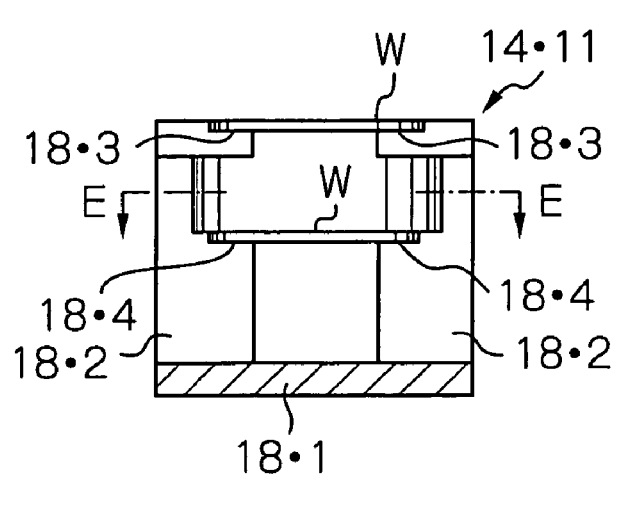
FIG. 18 shows the configuration of the loader housing of the semiconductor inspection apparatus according to the present invention.
Figure 18B:
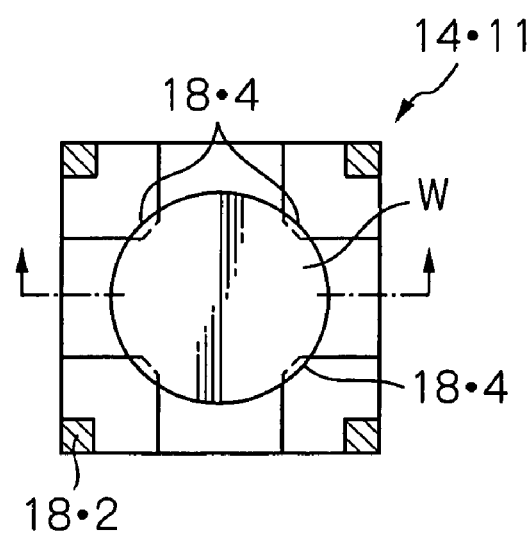

In the first loading chamber 14•2 is provided a wafer rack 14•11 supporting a plurality of wafers (two wafers in this embodiment) in a horizontal state with the plurality of wafers spaced vertically. As shown in FIG. 18, the wafer rack 14•11 has poles 18•2 mutually spaced and fixed upright at four corners of the rectangular substrate 18•1, two-stage support portions 18•3 and 18•4 are formed on each pole 18•2, and the periphery of the wafer W is borne on the support portion to hold the wafer. The leading ends of the arms of first and second transportation units described later are brought close to the wafer from between adjacent poles to hold the wafer by the arms.

Loading chambers 14•2 and 14•3 can be atmosphere-controlled to be in a high vacuum state (degree of vacuum is $10^{-4}$ to $10^{-6}$ Pa) by a vacuum pumping apparatus (not shown) having a well known structure including a vacuum pump (not shown). In this case, the first loading chamber 14•2 is kept in low vacuum atmosphere as a low vacuum chamber, and the second loading chamber 14•3 is kept in a high vacuum atmosphere as a high vacuum chamber, thus making it possible to effectively prevent contamination of the wafer. By employing this structure, the wafer which is housed in the loading chamber and is to be inspected for defects next can be conveyed into the working chamber without delay. By employing this loading chamber, together with the principle of a multi-beam electron apparatus described later, the throughput of defect inspection can be improved, and the degree of vacuum of the periphery of an electron source required to be stored under high vacuum conditions can be kept at as high as possible.

First and second loading chambers 14•2 and 14•3 are each connected to an evacuation pipe and a vent pipe for inert gas (e.g. dry pure nitrogen) (not shown). Consequently, the atmospheric pressure state in each loading chamber is achieved with inert gas ventilation (introducing an inert gas to prevent deposition on the surface of gases such as oxygen gas other than the inert gas). The apparatus itself for inert gas ventilation may have a well known structure, and therefore detailed descriptions thereof are not presented.

Furthermore, in the inspection apparatus of the present invention using an electron beam, it is important that such a material as, typically, lantern hexaboride ($L_aB_6$) used for an electron source of an electro-optical system described later is prevented as much as possible from contacting oxygen and the like in order to prolong the life of the electron source, when the material is heated to such a high temperature that thermal electrons are emitted. This can be more reliably accomplished by performing the atmosphere control described above in the pre-stage where the wafer is loaded into the working chamber in which the electro-optical system is placed.

2-1-5) Loader

The loader 13•7 comprises a robot-type first transportation unit 16•14 placed in the housing 16•2 of the mini-environment apparatus 13•3, and a robot-type second transportation unit 14•12 placed in the second loading chamber 14•3.

The first transportation unit 16•14 has a multi-nodular arm 16•16 capable of rotating about an axial line $O_1$—$O_1$ with respect to a drive unit 16•15. The multi-nodular arm may have any structure, but in this embodiment, it has mutually rotatably attached three parts.

One part of the arm 16•16 of the first transportation unit 16•14, namely a first part closest to the drive unit 16•15 is attached to a shaft 16•17 capable of rotating by a drive mechanism (not shown) having a well known structure, provided in the drive unit 16•15. The arm 16•16 can rotate about an axial line $O_1$—$O_1$ by the shaft 16•17, and can expand and contract in the radial direction with respect to the axial line $O_1$—$O_1$ as a whole by relative rotation among parts. A holding apparatus 14•13 holding the wafer such as a mechanical chuck or electrostatic chuck having a well known structure is provided at the leading end of a third part remotest from the shaft 16•17 of the arm 16•16. The drive unit 16•15 can be moved vertically by a lift mechanism 16•18 having a well known structure.

In this first transportation unit 16•14, the arm 16•16 extends in a direction M1 or M2 of one of two cassettes held in the cassette holder, and a wafer housed in the cassette is placed on the arm or held by a chuck (not shown) mounted on the arm at the end to take out the wafer. Thereafter, the arm contracts (into a state shown in FIG. 14), rotates to a position in which the arm can extend in a direction M3 of the pre-aligner 16•5, and stops at the position. Then, the arm extends again and places the wafer held by the arm on the pre-aligner 16•5. The arm receives the wafer from the pre-aligner 16•5 in the opposite manner, then further rotates and stops at a position in which the arm can extend toward the second loading chamber 14•2 (in direction M4), and places the wafer on a wafer seat in the second loading chamber 14•2. Furthermore, if the wafer is mechanically held, the wafer is held at its periphery (range of about 5 mm from the edge). This is because a device (circuit wiring) is formed on the entire wafer except for the periphery, and holding this area may cause destruction and failure of the device.

The second transportation unit 14•12 has a structure essentially identical to that of the first transportation unit, and the only different point is that transportation of the wafer is carried out between the wafer rack and the holding surface of the stage apparatus, and detailed descriptions thereof are not presented.

In the loader 13•7 described above, first and second transportation units 16•14 and 14•12 convey the wafer from the cassette held in the cassette holder onto the stage apparatus 13•6 placed in the working chamber 13•16 and transport the wafer in the opposite manner in almost a horizontal state, and the arm of the transportation unit moves vertically only when the wafer is taken from and inserted into the cassette, the wafer is placed onto and taken from the wafer rack, and the wafer is placed onto and taken from the stage apparatus. Thus, large wafer, for example, wafer having a diameter of 300 mm can be moved smoothly.

Since the stage has a mechanism applying a backward bias to the wafer, the arm is made to have a potential identical or close to that of the stage or a floating potential when the arm is placing the wafer onto the stage or taking the wafer from the stage, whereby a trouble such as a discharge due to potential short is avoided.

2-1-6) Stage Apparatus

The stage apparatus 13•16 comprises a fixed table 13•32 placed on the bottom wall 13•22 of the main housing 13•4, a Y table 13•33 moving in the Y direction (direction perpendicular to the sheet plane in FIG. 1) on the fixed table, an X table 13•34 moving in the X direction (lateral direction in FIG. 1) on the Y table, a rotation table 13•35 capable of rotating on the X table, and a holder 13•36 placed on the rotation table 13•35. The wafer is held on a wafer holding surface 14•14 of the holder 13•36 in a releasable manner. The holder 13•36 may have a well known structure capable of holding in a releasable manner the wafer mechanically or in an electrostatic chuck mode. The stage apparatus 13•6 uses a servo motor, and encoder and various kinds of sensors (not shown) to operate the plurality of tables described above, whereby the wafer held by the holder on the holding surface 14•14 can be positioned in the X direction, Y direction and Z direction (vertical direction in FIG. 13) with respect to an electron beam emitted from the electro-optical apparatus, and in the direction of rotation about an axial line vertical to the wafer supporting surface (θ direction) with high accuracy.

Furthermore, for positioning in the Z direction, for example, the position of the holding surface on the holder may be fine-adjusted in the Z direction. In this case, a reference position of the holding surface is detected by a position measurement apparatus (laser interference distance measuring apparatus using the principle of the interferometer) using a laser having a very small diameter, and the position is controlled by a feedback circuit (not shown), and/or the notch of the wafer or the position of the oriental-flat is measured to detect a plane position or rotation position of the wafer with respect to the electron beam, and a rotation table is rotated by a stepping motor or the like capable of performing control at a very small angle to control the position.

For preventing occurrence of dust in the working chamber wherever possible, servo motors 14•15 and 14•16 and encoders 14•17 and 14•18 for stage apparatus are placed outside the main housing 13•4. Furthermore, the stage apparatus 13•6 may have a well known structure, which is used in, for example, a stepper, and therefore detailed descriptions of the structure and operation are not presented. Furthermore, the laser interference distance measuring apparatus described above may have a well known structure, and therefore detailed descriptions of the structure and operation are not presented.

An obtained signal can be normalized by previously inputting the rotational position and X and Y positions of the wafer with respect to the electron beam to a signal detection system or image processing system described later. Further, a wafer chuck mechanism provided in the holder gives a voltage for chucking the wafer to an electrode of an electrostatic chuck, and holds three points (preferably equally spaced along the circumference) on the outer edge of the wafer to perform positioning. The wafer chuck mechanism comprises two fixed positioning pins, and one pressing clamp pin. The clamp pin can realize automatic chucking and automatic releasing, and comprises a conduction area for application of a voltage.

Furthermore, in this embodiment, the table moving in the lateral direction is the X table, and the table moving in the vertical direction is the Y table in FIG. 14, but the table moving in the lateral direction may be the Y table, and the table moving in the vertical direction may be the X table in this figure.

2-1-7) Wafer Chucking Mechanism 2-1-7-1) Basic Structure of Electrostatic Chuck

For matching the focus of the electro-optical system with the sample surface correctly and quickly, irregularities on the sample surface or wafer surface are preferably as small as possible. Thus, the wafer is adsorbed to the surface of an electrostatic chuck fabricated with high flatness (preferably flatness of 5 μm or less).

Electrode structures of the electrostatic chuck include a unipole type and a dipole type. The unipole type is a process in which conduction is previously established on the wafer, and a high voltage (generally about several tens to hundreds V) is applied to between the wafer and one electrostatic chuck electrode to adsorb the wafer, while in the dipole type, it is not necessary to force the wafer into conduction, and the wafer can be adsorbed simply by applying positive and negative voltages to two electrostatic chucks, respectively. Generally, however, to obtain stable adsorption conditions, two electrodes should be formed into an intricate shape like comb teeth, and thus the shape of the electrode becomes complicated.

On the other hand, for inspection of the sample, a predetermined voltage (retarding voltage) should be applied to the wafer in order to obtain conditions for image forming for the electro-optical system or ensure the state of the sample surface that can be easily observed with electrons. It is necessary that this retarding voltage should be applied to the wafer, and that the electrostatic chuck should be the unipole type described above to stabilize the potential of the wafer surface. (However, as described later, the electrostatic chuck should be made to function as a dipole type until conduction with the wafer is established with a conduction needle. Thus, the electrostatic chuck has a structure capable of switching between the unipole type and the dipole type).

Thus, it is required to mechanically contact the wafer to force the wafer into conduction. However, the need for prevention of contamination of the wafer has intensified, and it is required to avoid mechanical contact with the wafer, and there are cases where contact with the edge of the wafer is not acceptable. In this case, conduction must be established on the back face of the wafer.

On the back face of the wafer, a silicon oxide film is usually formed, and it is impossible to establish conduction in this state. Thus, needles are made to contact the back face of the wafer at two or more locations, and a voltage is applied to between the needles, whereby the oxide film can be locally destructed to establish conduction with silicon as a wafer base material. The voltage applied to the needles is a DC voltage or AC voltage of several hundreds V. Furthermore, the material of the needle should be nonmagnetic, and have abrasion-resistance and a high melting point, and tungsten or the like can be considered as such a material. Furthermore, to impart durability or prevent contamination of the wafer, it is effective to coat the surface with TiN or diamond. Furthermore, to ensure that conduction with the wafer has been established, it is effective to apply a voltage to between the needles to measure a current.

It is the chucking mechanism shown in FIG. 19 that has been fabricated in view of the background described above. The electrostatic chuck is provided with electrodes 19•1 and 19•2 that desirably have an intricate shape like comb teeth to adsorb the wafer W with stability, three pusher pins 19•3 for giving and taking the wafer, and two or more conduction needles 19•4 for applying a voltage to the wafer. Furthermore, a correction ring 19•5 and a wafer dropping mechanism 19•6 are placed around the electrostatic chuck.

The pusher pin 19•3 already protrudes from the electrostatic chuck surface when the wafer W is conveyed by a robot hand, and when the wafer W is placed on the pusher pin 19•3 by the operation of the robot hand, the pusher pin 19•3 slowly descends and places the wafer W onto the electrostatic chuck. When the wafer is taken from the electrostatic chuck, the opposite operation is made to pass the wafer W to the robot hand. The surface material of the pusher pin 19•3 should be selected so as to eliminate the possibility that the wafer position is shifted, and that the wafer is contaminated, silicon rubber, fluorine rubber, ceramics such as SiC or alumina, a resin such as Teflon or polyamide, or the like is desirably used.

There are several methods for the drive mechanism of the pusher pin 19•3. One is a method of placing a nonmagnetic actuator in the lower part of the electrostatic chuck. This may include a method of directly linear-driving the pusher pin by an ultrasonic linear motor, and a method of linear-driving the pusher pin by a combination of a rotational ultrasonic motor and a ball screw or rack & pinion gear. In this method, the pusher mechanism can be compactly arranged on a table of an XY stage on which the electrostatic chuck is mounted, the number of wirings of the actuator, limit sensor and the like considerably increases. The wiring extends from the table making XY motions to a sample chamber (main chamber or main housing), but is bent with the motion of the stage, and therefore it should be placed with a large flexure R, and thus takes up a large space. Furthermore, the wiring may become a particle source, and should be replaced periodically, and therefore a necessary minimum number of wirings should be used.

Thus, as a different method, an external drive force is supplied. When the stage moves to a position at which the wafer W is attached/detached, a shaft protruding into a vacuum atmosphere through a bellow is driven by an air cylinder provided outside a chamber to press a shaft of a pusher drive mechanism provided in the lower part of the electrostatic chuck. The shaft is connected to a rack pinion or link mechanism in the pusher drive mechanism, and the reciprocating motion of the shaft is associated with the vertical motion of the pusher pin. When the wafer W is given and taken with the robot hand, the shaft is pushed into the vacuum atmosphere with the air cylinder with the speed adjusted at an appropriate level by a controller, whereby the pusher pin 19•3 is caused to rise.

Furthermore, the external source for driving the shaft is not limited to the air cylinder, but may be a combination of the servo motor and the rack pinion or ball screw. Furthermore, a rotating shaft can be used as the external drive source. In this case, the rotating shaft operates via a vacuum seal mechanism such as a magnetic fluid seal, and the pusher drive mechanism includes a mechanism converting rotation into a linear motion.

The correction ring 19•5 has an action of keeping uniform an electric field distribution at end portion of the wafer, and a potential essentially the same as that of the wafer is applied to the correction ring 19•5. However, to eliminate influences of a very small gap between the wafer and the correction ring and a very small difference in surface height between the wafer and the correction ring, a potential slightly different from that of the end portion of the wafer may be applied. The correction ring has a width of about 10 to 30 mm in the radial direction of the wafer, and a nonmagnetic and conductive material, for example titanium, phosphor bronze, aluminum coated with TiN or TiC may be used for the correction ring.

The conduction needles 19•4 is supported on a spring 19•7, and is lightly pressed against the back face of the wafer with a spring force when the wafer is placed on the electrostatic chuck. In this state, electric conduction with the wafer W is established by applying a voltage as described above.

An electrostatic chuck main body is comprised of nonmagnetic plane electrodes 19•1 and 19•2 made of tungsten or the like, and a dielectric body formed thereon. For the material of the dielectric body, alumina, aluminum nitride, polyimide or the like may be used. Generally, ceramics such as alumina is a complete isolator having a specific volume resistance of about $10^{14}$ Ωcm, and therefore causes no charge transfer within the material, and a coulonbic force acts as absorption force. On the other hand, by slightly adjusting a ceramic composition, the specific volume resistance can be reduced to about $10^{10}$ Ωcm, whereby charge transfer occurs within the material, and thus so called a Johnson-Rahbek force acts stronger than the coulonbic force acts as a wafer absorption force. As the absorption force increases, the applied voltage can be reduced accordingly, a larger margin for insulation destruction can be provided, and a stable absorption force can easily be obtained. Furthermore, by processing the surface of the electrostatic chuck into, for example, a dimple shape, particles may fall to a valley area of the dimple even if particles and the like are deposited on the surface of electrostatic chuck surface, thus making it possible to expect an effect of reducing the possibility that the flatness of the wafer is affected.

From the above, a practical electrostatic chuck is such that aluminum nitride or alumina ceramics adjusted to have a specific volume resistance of about $10^{10}$ Ωcm is used as a material, irregularities of dimple shape or the like are formed on the surface, and the flatness of the surface formed by a set of the convexes is about 5 μm.

2-1-7-2) Chucking Mechanism for 200/300 Bridge Tool

Figure 19A:
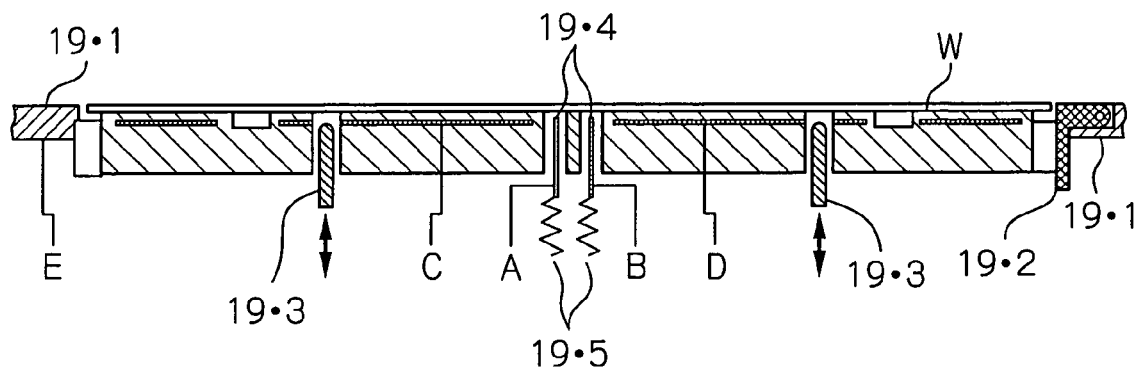
FIGS. 19(A) and 19(B) illustrate an electrostatic chuck for use in the semiconductor inspection apparatus according to the present invention.
Figure 19B:
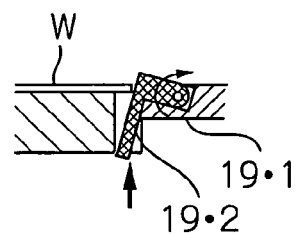
Figure 20:
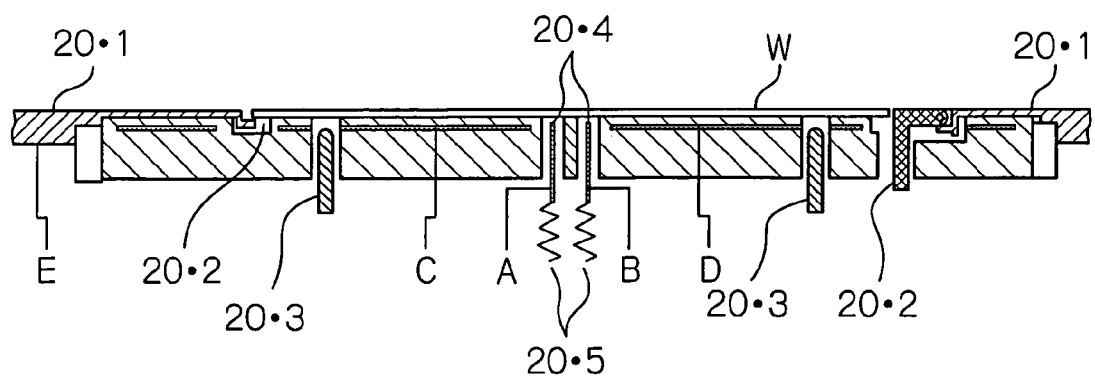
FIG. 20 illustrates the electrostatic chuck for use in the semiconductor inspection apparatus according to the present invention.

The apparatus is required to inspect two types of 200 mm wafer and 300 mm wafer without mechanical modification. In this case, the electrostatic chuck should chuck two types of wafer having different sizes, and a correction ring matching the size of the wafer should be placed on the periphery of the wafer. FIGS. 19(A), 19(B) and 20 show a structure therefor.

FIG. 19 shows the wafer W of 300 mm placed on the electrostatic chuck. The correction ring 19•1 having an inner diameter (gap of about 0.5 mm) slightly larger than the size of the wafer W is positioned in such a manner as to be interlocked with a metallic ring part on the outer edge of the electrostatic chuck. The correction ring 19•1 are provided with wafer dropping mechanisms 19•2 at three locations. The wafer dropping mechanism 19•2 is driven by a vertical drive mechanism associated with the drive mechanism of the pusher pin 19•3, and is supported rotatably about a rotating shaft provided in the correction ring 19•1.

When the wafer W is received from the robot hand, the pusher pin drive mechanism operates to push the pusher pin 19•3 upward. In appropriate timing therewith, the wafer dropping mechanism 19•2 provided in the correction ring 19•1 rotates under a drive force as shown in FIG. 19(B). Then, the wafer dropping mechanism 19•2 forms a taper plane guiding the wafer W to the center of the electrostatic chuck. Then, the wafer W is placed on the pusher pin 19•3 pushed upward, and thereafter the pusher pin 19•3 was made to descend. By appropriately adjusting action timing of the drive force for the wafer dropping mechanism 19•2 together with the descending of the pusher pin 19•3, the wafer W has its position corrected by the taper plane of the dropping mechanism 19•2 and placed on the electrostatic chuck so that the center of the wafer W almost matches the center of the electrostatic chuck.

It is desired that a low frictional material such as Teflon, preferably a conductive low frictional material (e.g. conductive Teflon, conductive diamond like carbon, TIB coating) is formed on the taper plane of the dropping mechanism 19•2. Furthermore, symbols A, B, C, D and E in the figure denote terminals (described later) for applying a voltage, and reference numeral 19•4 denotes a wafer conducting needle for detecting that the wafer W is placed on the electrostatic chuck, which is pushed upward by a spring 19•5.

FIG. 20 shows the wafer W of 200 mm placed on the same electrostatic chuck. The surface of the electrostatic chuck is exposed because the diameter of the wafer is smaller than that of the electrostatic chuck, and therefore a correction ring 20•1 having a size so large that the electrostatic chuck is completely covered. The positioning of the correction ring 20•1 is performed in the same manner as in the case of the correction ring for the 300 mm wafer.

A step is provided on the inner edge of the correction ring 20•1, and the correction ring 20•1 is fitted in a ring groove 20•2 on the electrostatic chuck side. This is a structure for covering the surface of the electrostatic chuck with a conductor (correction ring 20•1) so that the surface of the electrostatic chuck is not seen through a gap between the inner edge of the correction ring 20•1 and the outer edge of the wafer W when the 200 mm wafer is placed. This is because if the surface of the electrostatic chuck is exposed, the surface of the electrostatic chuck is electrically charged to disturb the potential of the sample surface when an electron beam is applied.

Replacement of the correction ring 20•1 is performed by providing a correction ring replacement space at a predetermined position in a vacuum chamber, and conveying therefrom a correction ring having a necessary size by a robot and attaching the correction ring to the electrostatic chuck (inserting the correction ring into an interlocked part).

The correction ring for the 200 mm wafer is provided with the wafer dropping mechanism 20•2 as in the case of the correction ring for the 300 mm wafer. A recess is formed on the electrostatic chuck side so as not to interfere with the wafer dropping mechanism 20•2. The method of placing the wafer on the electrostatic chuck is identical to that for the 300 mm wafer. Furthermore, symbols A, B, C, D and E denote terminals for applying a voltage, reference numeral 20•3 denotes a push pin similar to the push pin 19•3, and reference numeral 20•4 denotes a wafer conducting needle similar to the wafer conducting needle 194.

Figure 2A:
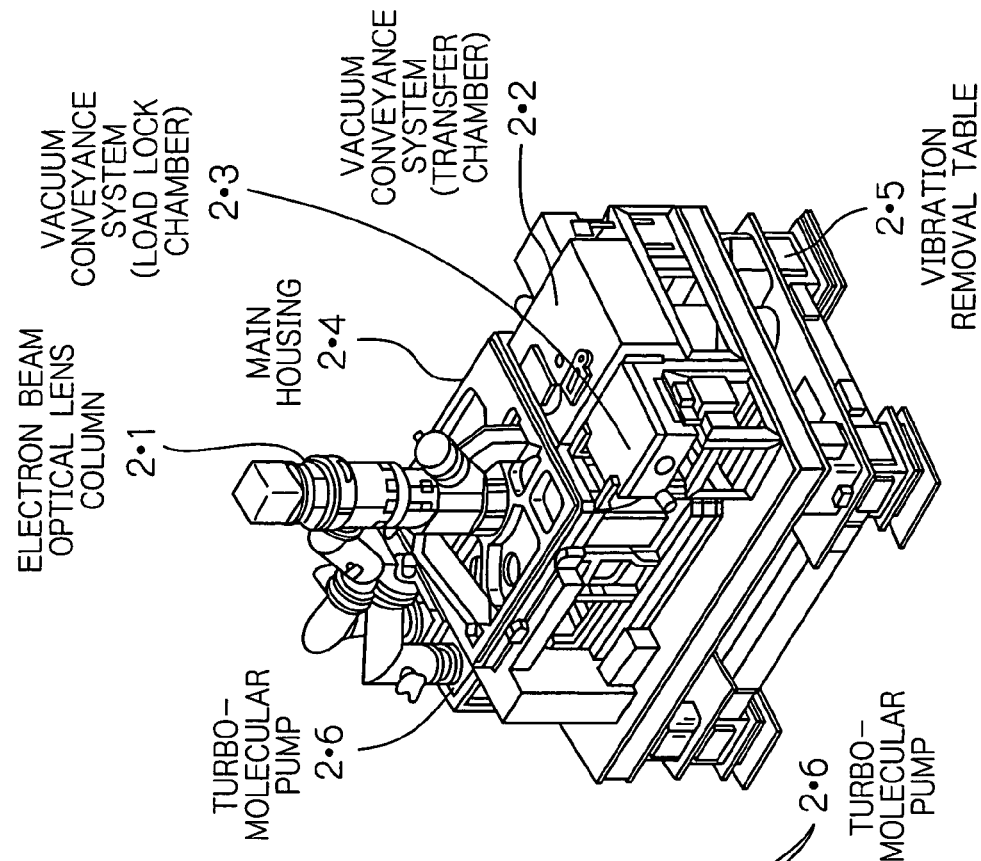
FIG. 2 shows the overall configuration of the apparatus of FIG. 1.
Figure 2B:
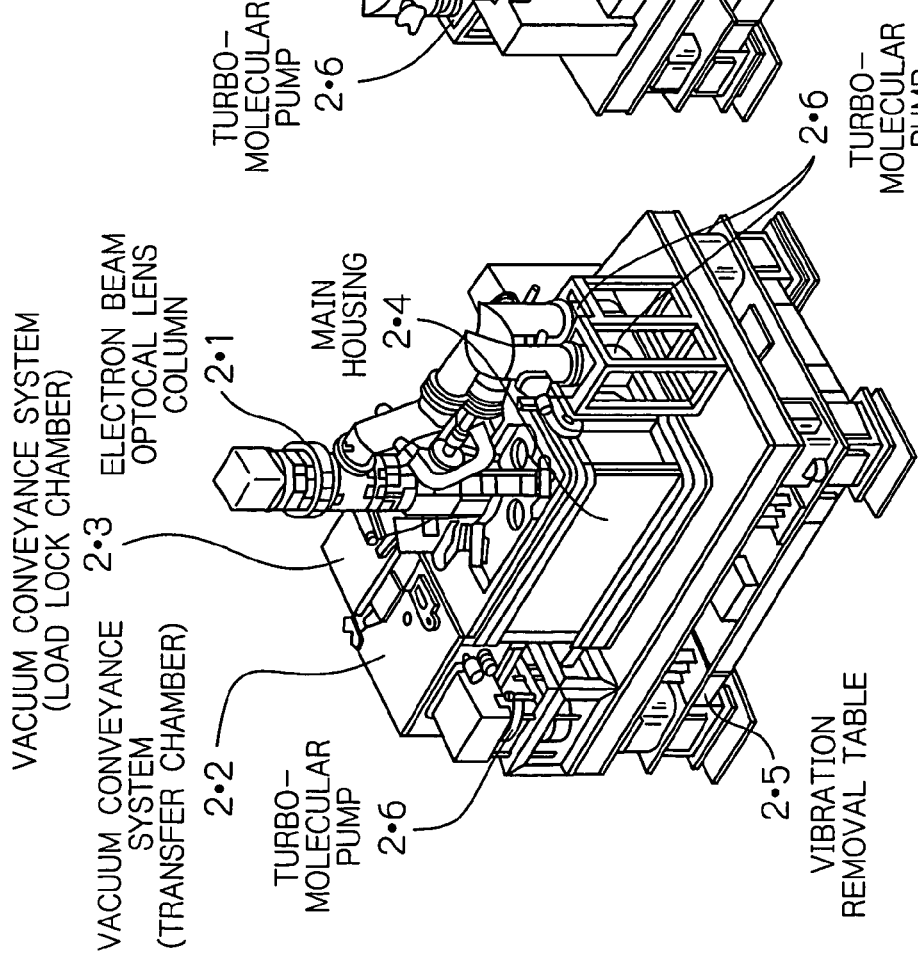
Figures 1A, 20:
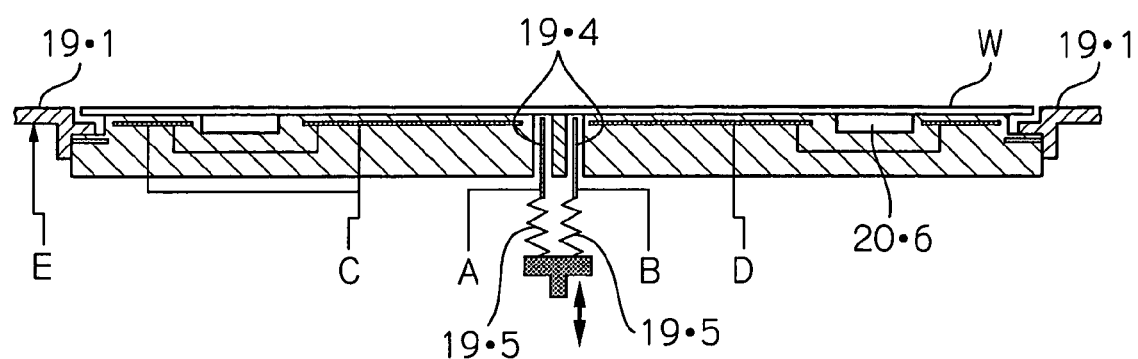
Figures 1B, 20:
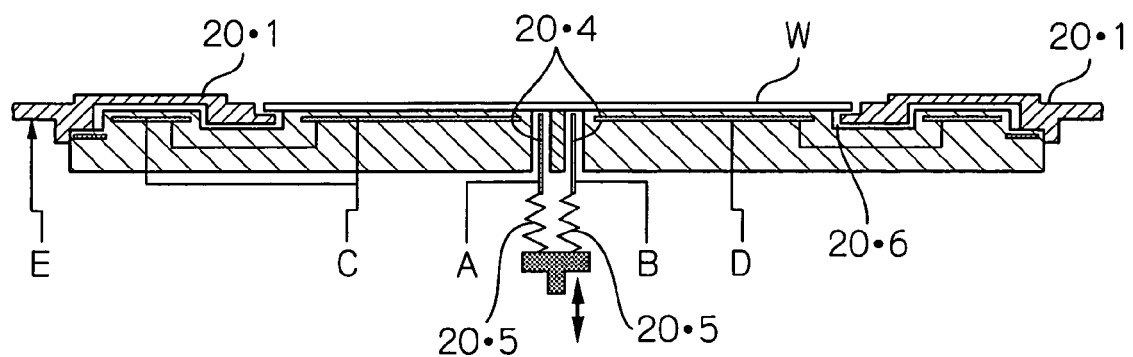
Figure 21:
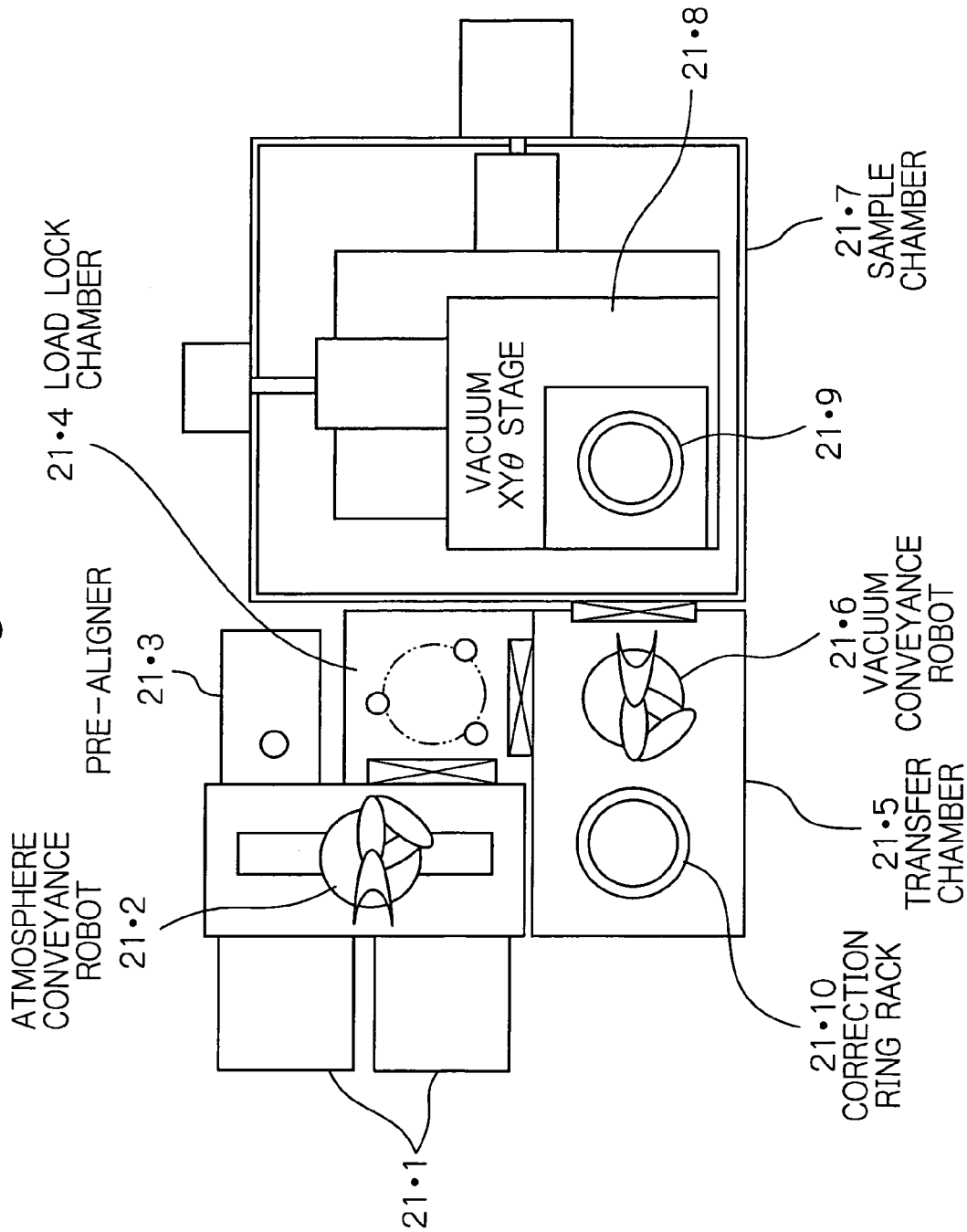

FIGS. 20-1(A) and 20-1(B) schematically show the configuration of the electrostatic chuck capable of coping with both types of 300 mm wafer and 200 mm, in which FIG. 20-1(A) shows the 300 mm wafer placed on the electrostatic chuck, and FIG. 20-1(B) shows the 200 mm wafer placed on the electrostatic chuck. As apparent from FIG. 20-1(A), the electrostatic chuck has a width large enough to place the 300 mm wafer thereon, and as shown in FIG. 21-2(B), the central area of the electrostatic chuck has a width large enough to place the 200 mm wafer thereon, and a groove 20•6 in which the inner ridge of the correction ring 20•1 is to be fitted is provided in such a manner as to surround the wafer. Furthermore, symbols A, B, C, D and E denote terminals for applying a voltage.

In the case of the electrostatic chuck shown in FIGS. 20-1(A) and 20-1(B), whether the wafer is placed on the electrostatic chuck, whether the wafer is correctly placed on the electrostatic chuck, whether the correction ring exists, and so on are optically detected. For example, by placing an optical sensor above the electrostatic chuck, and detecting an optical path length when light emitted from the optical sensor is reflected by the wafer and returned back to the optical sensor, whether the wafer is placed horizontally or slantingly can be detected. Furthermore, existence/nonexistence of the correction ring can be detected by providing a light transmitter slantingly irradiating an appropriate point in a space where the correction ring should be placed, and a light receiver receiving reflected light from the correction ring. Further, by providing a combination of the light transmitter slantingly irradiating the appropriate point in the space where the correction ring for the 200 mm wafer should be placed and the light receiver receiving reflected light from the correction ring, and a combination of the light transmitter slantingly irradiating the appropriate point in the space where the correction ring for the 300 mm wafer should be placed and the light receiver receiving reflected light from the correction ring, and detecting which light receiver receives reflected light, which of the correction ring for the 200 mm wafer and the correction ring for the 300 mm wafer is placed on the electrostatic chuck can be detected.

2-1-7-3) Wafer Chucking Procedure

The wafer chucking mechanism having the structure described above chucks the wafer according to the following procedure.

(1) A correction ring matching the size of the wafer is carried by a robot and placed on the electrostatic chuck.

(2) The wafer is placed on the electrostatic chuck by transportation of the wafer by a robot hand and vertical motions of the pusher pin.

(3) A voltage is applied to the electrostatic chuck in a dipole type (positive and negative voltages are applied to terminals C and D) to adsorb the wafer.

(4) A predetermined voltage is applied to a conducting needle to destruct an insulation film (oxide film) on the back face of the wafer.

(5) A current between terminals A and B is measured to check whether conduction with the wafer is established.

(6) A transition of the electrostatic chuck to a unipole type adsorption is made (terminals A and B are set to GRD, and the same voltage is applied to terminals C and D).

(7) The voltage of the terminal A (, B) is decreased while keeping a difference in potential between the terminal A (, B) and the terminal C (,D), and a predetermined retarding voltage is applied to the wafer.

2-1-8) Apparatus Configuration for 200/300 Bridge Tool

Figure 22:
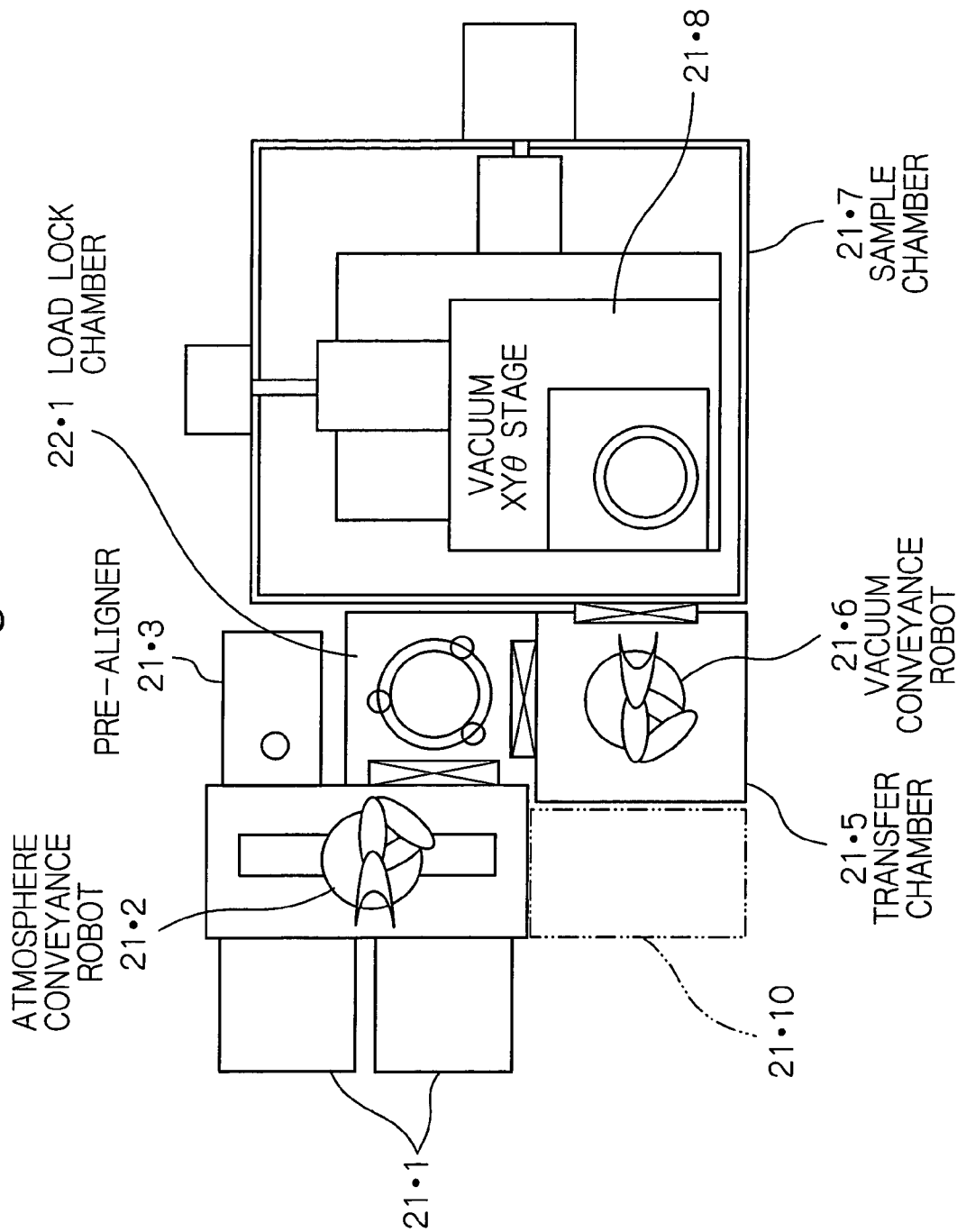
FIG. 22 illustrates another example of the bridge tool for use in the semiconductor inspection apparatus according to the present invention.

The configuration for achieving an apparatus capable of inspecting the 200 mm wafer and the 300 mm wafer without mechanical modification is shown in FIG. 21 and FIG. 22. Aspects in which the apparatus is different from the apparatus dedicated for the 200 mm wafer or the apparatus dedicated for the 300 mm wafer will be described below.

At an installation site 21•1 of the wafer cassette that is replaced for specifications of the 200/300 mm wafer, FOUP, SMIF, the open cassette and the like, the wafer cassette appropriate to the wafer size and the type of wafer cassette determined depending on user specifications can be placed. An atmosphere transportation robot 21•2 has a hand capable of coping with different wafer sizes, i.e. a plurality of wafer dropping portions are provided in conformity with the wafer sizes, and the wafer is placed on the hand at a location matching the wafer size. The atmosphere transportation robot 21•2 sends the wafer from the installation site 21•1 to a pre-aligner 21•3, regulates the orientation of the wafer, then takes the wafer from the pre-aligner 21•3, and sends the wafer into a load lock chamber 21•4.

A wafer rack in the load lock chamber 21•4 has a similar structure, a plurality of dropping portions matching wafer sizes are formed in a wafer support portion of the wafer rack, the height of the robot hand is adjusted so that the wafer placed on the hand of the atmosphere transportation robot 21•2 is placed in the dropping portion matching the size of the wafer, the wafer is inserted into the wafer rack, and then the robot hand descends to place the wafer in a predetermined dropping portion of the wafer support portion.

The wafer placed on the wafer rack in the load lock chamber 21•4 is then taken from a load lock chamber 21•3 by a vacuum transportation robot 21•6 installed in a transfer chamber 21•5, and conveyed onto a stage 21•8 in the sample chamber 21•7. The hand of the vacuum transportation robot 21•6 has a plurality of dropping portions matching wafer sizes as in the case of the atmosphere transportation robot 21•2. The wafer placed in a predetermined dropping portion of the robot hand is placed on the electrostatic chuck having previously mounted a correction ring 21•9 matching the wafer size in the stage 21•8, and fixedly adsorbed by the electrostatic chuck. The correction ring 21•9 is placed on a correction ring rack 21•10 provided in the transportation chamber 21•5. Then, the vacuum transportation robot 21•6 takes the correction ring 21•9 matching the wafer size from the correction ring rack 21•10, and conveys the correction ring 21•9 onto the electrostatic chuck, fits the correction ring 21•9 in a positioning interlocked part formed on the outer edge of the electrostatic chuck, and then places the wafer on the electrostatic chuck.

When the correction ring is replaced, the opposite operation is carried out. That is, the correction ring 21•9 is removed from the electrostatic chuck by the robot 21•6, the correction ring is returned back to the correction ring rack 21•10 in the transfer chamber 21•5, and the correction ring matching the size of the wafer to be inspected next is conveyed from the correction ring rack 21•10 to the electrostatic chuck.

In the inspection apparatus shown in FIG. 21, the pre-aligner 21•3 is located close to the load lock chamber 22•4, and therefore the wafer is easily returned back to the pre-aligner for realignment if alignment of the wafer is not adequate enough to place the correction ring in the load lock chamber, thus bringing about an advantage that time loss in the step can be reduced.

FIG. 22 shows an example of changing a site where the correction ring is placed, in which the correction ring rack 21•10 is omitted. In the load lock chamber 22•1, the wafer rack and the correction ring rack are formed in a layered form, and they can be placed in an elevator to move vertically. First, to place the correction ring matching the size of the wafer to be inspected next on the electrostatic chuck, the vacuum transportation robot 21•6 moves the elevator of the load lock chamber 22•1 to a position where the correction ring can be taken out. When, the correction ring is placed on the electrostatic chuck by the vacuum transportation robot 21•6, then the elevator is manipulated so that the wafer to be inspected can be transferred, and the wafer is taken from the wafer rack by the vacuum transportation robot 21•6, and then placed on the electrostatic chuck. This configuration requires an elevator in the load lock chamber 22•1, but can downsize the vacuum transportation chamber 21•5, and is thus effective in reducing a foot print of the apparatus.

Furthermore, a sensor detecting whether or not the wafer exists on the electrostatic chuck is desirably placed at a position such that the sensor can cope with any of different wafer sizes, but if it is impossible, a plurality of sensors working in the same manner may be placed for each wafer size.

The inspection apparatus described with respect to FIG. 21 employs a procedure in which the correction ring is placed on the electrostatic chuck, and the wafer is positioned so that the wafer fits the inner diameter of the correction ring. Then, the inspection apparatus shown in FIG. 22 employs a procedure in which the correction ring is mounted on the wafer in the load lock chamber 22•1, and the wafer with the correction ring mounted thereon is conveyed together with the correction ring into the sample chamber 21•7, and mounted on the electrostatic chuck on the stage. Mechanisms for realizing the procedure include an elevator mechanism for vertically moving an elevator to pass the wafer from the atmosphere transportation robot to the vacuum transportation robot, shown in FIGS. 22-1 and 22-2. A procedure of conveying the wafer using this mechanism will be described below.

As shown in FIG. 22-1 (A), the elevator mechanism provided in the load lock chamber has multistage (two-stage in the figure) correction ring supports base so situated as to be movable in the vertical direction. An upper-stage correction ring support base 22•2 and lower-stage correction ring support base 22•3 are fixed on a first base 22•5 rising/descending with rotation of a first motor 22•4, whereby the first base 22•5 and upper and lower correction ring support bases 22•2 and 22•3 move upward or downward with rotation of the first motor 22•4.

The correction ring 22•6 having an inner diameter matching the size of the wafer is placed on each correction ring support base. For the correction ring 22•6, two types having different inner diameters, i.e. the type for the 200 mm wafer and the type for the 300 mm wafer, are prepared, and they have the same outer diameter. In this way, by using correction rings having the same outer diameter, mutual compatibility is provided, thus making it possible to place the correction ring in the load lock chamber in an arbitrary combination of the correction ring for the 200 mm wafer and the correction ring for the 300 mm wafer. That is, for a line in which 200 mm wafers and 300 mm wafers flow in a mixed form, inspection can be performed flexibly for either type of wafer with the upper stage set for the 300 mm wafer and the lower stage set for the 200 mm wafer. Furthermore, for a line in which wafers of the same size flow, wafers in upper and lower stages can be inspected alternately with upper and lower stages set for the 200 mm or 300 mm wafer, thus making it possible to improve the throughput.

A second motor 22•7 is placed on the first base 22•5, and a second base 22•8 is vertically movably attached to the second motor 22•7. An upper wafer support base 22•9 and a lower wafer support base 22•10 are fixed on the second base 22•8. Consequently, when the second motor 22•7 rotates, the second base 22•8 and upper and lower wafer support bases 22•9 and 22•10 move upward or downward in one united body.

Then, as shown in FIG. 22-1(A), the wafer W is placed on the hand of the atmosphere transportation robot 21•2 and loaded into the load lock chamber 22•1, and then as shown in FIG. 22-1(B), the second motor 22•7 is rotated in a first direction to move the wafer support bases 22•9 and 22•10 upward to place the wafer W on the upper-stage wafer support base 22•9. In this way, the wafer W is moved from the atmosphere transportation robot 21•1 to the wafer support base 22•9. Thereafter, as shown in FIG. 22-1(C), the atmosphere transportation robot 21•2 is moved backward, and when the backward movement of the atmosphere transportation robot 21•2 is completed, the second motor 22•7 is rotated in a direction opposite to the first direction to move the wafer support bases 22•9 and 22•10 downward as shown in FIG. 22-1(D). In this way, the wafer W is placed on the correction ring 22•6 in the upper-stage.

Then, as shown in FIG. 22-1(E), the hand of the vacuum transportation robot 21•6 is introduced into the load lock chamber 22•1 and stopped at below the correction ring 22•6. In this state, the first motor 22•4 is rotated, and as shown in FIG. 22-1(F), the first base 22•5, the upper and lower correction ring support bases 22•2, 22•3, the second motor 22•7, and the upper and lower wafer support bases 22•9 and 22•10 are moved downward, whereby the correction ring 21•6 placed on the upper-stage wafer support base 22•9, and the wafer W can be placed on the hand of the vacuum transportation robot 21•6 and loaded into the sample chamber 21•7.

The operation of returning the wafer inspected in the sample chamber 21•7 back to the load lock chamber 21•4 is carried out in a procedure opposite to the procedure described above, and the wafer loaded onto the wafer support base together with the correction ring by the vacuum transportation robot is transferred to the correction ring support base, then to the wafer support base, and finally placed on the atmosphere transportation robot. Furthermore, in FIGS. 22-1 and 22-2, the operation of giving and taking the wafer in the upper stage is described, but the same operation can be carried out in the lower stage by adjusting the heights of the hands of the atmosphere transportation robot 21•2 and the vacuum transportation robot 21•6. In this way, by appropriately changing the heights of the hands of the atmosphere transportation robot 21•2 and the vacuum transportation robot 21•6, the wafer that has not been inspected yet can be loaded into the sample chamber from one stage, and then the inspected wafer can be unloaded to the other stage from the sample chamber in an alternate manner.

2-2) Method for Transportation of Wafer

Transportation of the wafer from the cassette 13•12 supported by the cassette holder 13•2 to the stage apparatus 13•6 placed in the working chamber 13•16 will now be described in order (see FIGS. 14 to 16).

If the cassette is manually set as described previously, the cassette holder 13•2 having a structure suitable for this application is used, while if the cassette is automatically set, the cassette holder 13•2 having a structure suitable for this application is used. In this embodiment, when the cassette 13•12 is set on the lift table 13•13 of the cassette holder 13•2, the lift table 13•13 is made to descend by the lift mechanism 13•14, and the cassette 13•12 is matched with the entrance 13•15. When the cassette is matched with the entrance 13•15, a cover (not shown) provided in the cassette is opened, a cylindrical cover is placed between the cassette and the entrance 13•15 of the mini-environment apparatus 13•3 to isolate the inside of the cassette and the inside of the mini-environment space from the outside. The structures thereof are well known, and therefore detailed descriptions of the structures and functions are not presented. Furthermore, if a shutter apparatus for opening and closing the entrance 13•15 is provided on the mini-environment apparatus 13•3 side, the shutter apparatus operates to open the entrance 13•15.

On the other hand, the arm 16•16 of the first transportation unit 16•14 is stopped while being oriented in any of the direction M1 and the direction M2 (oriented in the direction M1 in this description), and when the entrance 13•15 is opened, the arm extends to receive one of wafers housed in the housing at the leading end. Furthermore, adjustment of the position of the arm and the wafer to be taken from the cassette in the vertical direction is performed with the vertical movement of the drive unit 16•15 of the first transportation unit 16•14 and the arm 16•16 in this embodiment, but it may be performed with the vertical movement of the lift table of the cassette holder or with both the vertical movements.

When the reception of the wafer by the arm 16•16 is completed, the arm contracts and operates the shutter apparatus to close the entrance (if the shutter apparatus exists), and then the arm 16•16 rotates about the axial line $O_1$—$O_1$ so that it can extend in the direction M3. Then, the arm extends to place the wafer placed on the leading end or held by the chuck on the pre-aligner 16•5, and the orientation of the wafer in the rotational direction (orientation about the central axial line perpendicular to the wafer plane) is positioned within a predetermined range by the pre-aligner 16•5. When the positioning is completed, the transportation unit 16•14 receives the wafer from the pre-aligner 16•5 at the leading end of the arm, and then makes the arm contract so that the arm can be extend in the direction M4. Then, the door 13•27 of the shutter apparatus 14•8 moves to open entrances 13•25 and 13•37, and the arm 16•16 extends to place the wafer on the upper stage or lower stage side of the wafer rack 14•11 in the first loading chamber 14•2. Furthermore, before the shutter apparatus 14•8 is opened to pass the wafer to the wafer rack 14•11 as describe previously, the opening 17•4 formed in the partition wall 14•5 is air-tightly closed with the door 14•19 of the shutter apparatus 14•10.

In the process of transportation of the wafer by the first transportation unit 16•14, clean air flows (as a down flow) in laminar form from the gas supply unit 16•9 provided on the housing of the mini-environment apparatus 13•3 to prevent deposition of dust on the wafer during transportation. Part of air around the transportation unit (about 20% of air supplied from the supply unit, which is mainly contaminated air, in this embodiment) is suctioned from the suction duct 16•12 of the discharge apparatus 16•4 and discharged to the outside of the housing. Remaining air is collected via the collection duct 16•10 provided on the bottom of the housing and returned back to the gas supply unit 169.

When the wafer is placed in the wafer rack 14•11 in the first loading chamber 14•2 of the loader housing 13•5 by the first transportation unit 16•14, the shutter apparatus 14•8 is closed to seal the loading chamber 14•2. Then, an inert gas is filled in the first loading chamber 14•2 to purge air, and then the inert gas is discharged to create a vacuum atmosphere in the loading chamber 14•2. The vacuum atmosphere of the fist loading chamber 14•2 may have a low degree of vacuum. When a satisfactory degree of vacuum is achieved in the loading chamber 14•2, the shutter apparatus 14•10 operates to open the shutter 14•5 of the entrance 17•4 closed with the door 14•19, the arm 14•20 of the second transportation unit 14•12 extends to receive one wafer from the wafer seat 14•11 by a holding apparatus at the leading end (placing the wafer on the leading end, or holding the wafer by a chuck mounted at the leading end). When the reception of the wafer is completed, the arm contracts, and the shutter apparatus 14•10 operates again to close the entrance 17•4 with the door 14•19.

Furthermore, before the shutter apparatus 14•10 is opened, the arm 14•20 takes a posture in which the arm 14•20 can extend in the direction N1 of the wafer rack 14•11. Furthermore, entrances 14•7 and 14•1 are closed with the door 14•9 of the shutter apparatus 13•29 before the shutter apparatus 14•10 is opened as described previously, communication between the second loading chamber 14•3 and the working chamber 13•16 is inhibited in an air-tight state, and the second loading chamber 14•3 is evacuated.

When the shutter apparatus 14•10 closes the entrance 17•4, the second loading chamber 14•3 is evacuated again to have a degree of vacuum higher than that of the first loading chamber 14•2. In the meantime, the arm of the second transportation unit 16•14 is rotated to a position in which it can extend toward the stage apparatus 13•6 in the working chamber 13•16. On the other hand, in the stage apparatus 13•6 in the working chamber 13•16, the Y table 13•33 moves upward to a position in which the center line $X_0$—$X_0$ of the X table 13•34 almost matches the X axis line $X_1$—$X_1$ passing through the rotation axis line $O_2$—$O_2$ of the second transportation unit 14•12 in FIG. 14, and the X table 13•34 moves to a position close to the leftmost position in FIG. 14, and waits in this state. When the degree of vacuum of the second loading chamber 14•3 is approximately the same as that of the working chamber 13•16, the door 14•9 of the shutter apparatus 13•29 moves to open the entrances 14•7 and 14•1, and the arm extends so that the leading end of the arm holding the wafer approaches the stage apparatus 13•6 in the working chamber 13•16. The wafer is placed on the holding surface 14•14 of the stage apparatus 13•6. The placement of the wafer is completed, the arm contracts, and the shutter apparatus 13•29 closes the entrances 14•7 and 14•1.

Since the stage has a mechanism applying a backward bias potential (retarding potential) to the wafer, the arm is made to have a potential identical or close to that of the stage, or the arm is made to have a floating potential when the arm goes to place or take the wafer, whereby a trouble such as a discharge due to a short of the potential is avoided. Furthermore, as another embodiment, the bias potential to the wafer may be kept off when the wafer is conveyed onto the stage apparatus.

If the bias potential is controlled, the potential is kept off until the wafer is conveyed to the stage, and the bias potential may be turned on and applied after the wafer is conveyed to the stage. For timing of applying the bias potential, tact time is preset, and the bias potential may be applied based on the tact time, or placement of the wafer on the stage is detected with a sensor, and the bias potential may be applied using the detection signal as a trigger. Furthermore, the closing of the entrances 14•7 and 14•1 by the shutter apparatus 13•29 is detected, and the bias potential may be applied using the detection signal as a trigger. Further, if the electrostatic chuck is used, adsorption by the electrostatic chuck is confirmed, and this may be used as trigger to apply the bias potential.

The operation of conveying the wafer in the cassette 13•12 onto the stage apparatus has been described above, and for returning the wafer, which has been placed on the stage apparatus 13•6 and processed, from the stage apparatus 13•6 into the cassette 13•12, the operation opposite to that described above is made. Furthermore, since a plurality of wafers are placed on the wafer rack 14•11, the wafer can be conveyed between the cassette and the wafer rack 14•11 in the first transportation unit 16•14 while the wafer is conveyed between the wafer rack 14•11 and the stage apparatus 13•16 in the second transportation unit 14•12, thus making it possible to carry out inspection processing efficiently.

Specifically, if a processed wafer A and an unprocessed wafer B exist in the wafer rack 14•11, the unprocessed wafer B is first moved to the stage 13•6. In the mean time, the processed wafer A is moved from the wafer rack to the cassette 13•12 by the arm, and an unprocessed wafer C is taken from the cassette 13•12 by the arm, positioned by the pre-aligner 16•5, and then moved to the wafer rack 14•11 of the loading chamber 14•2.

In this way, in the wafer rack 14•11, the processed wafer A can be replaced with the unprocessed wafer C while the wafer B is processed. Furthermore, depending on the use of the apparatus for performing inspection and evaluation, a plurality of stage apparatuses 13•6 are placed side by side, and the wafer is moved to each apparatus from one wafer rack 14•11, whereby a plurality of wafers can be subjected to the same processing.

Figure 23:
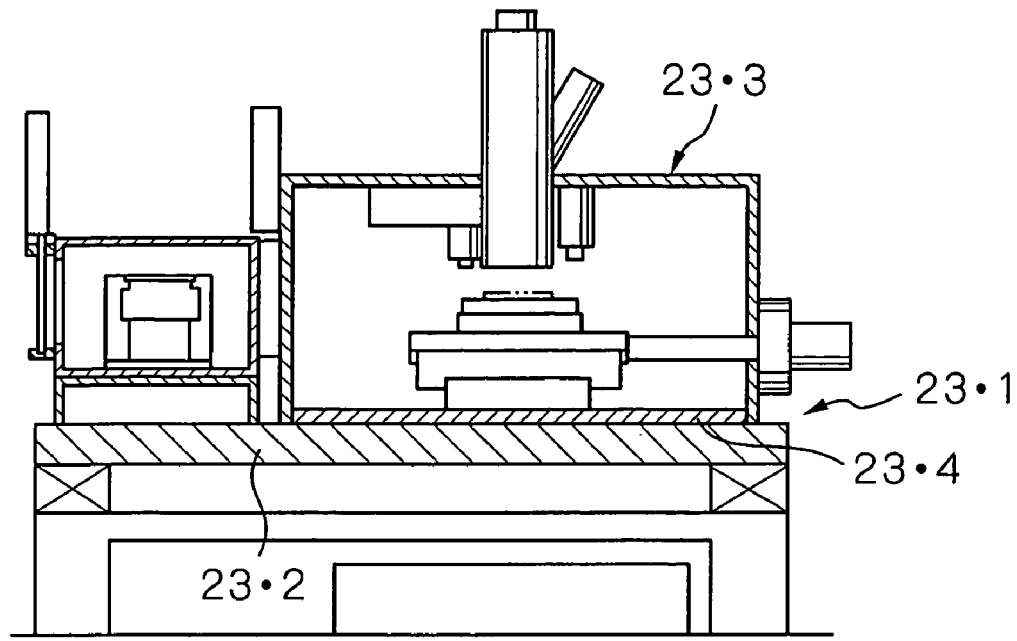
FIG. 23 shows an alteration example of a method of supporting a main housing in the semiconductor inspection apparatus according to the present invention.
Figure 24:
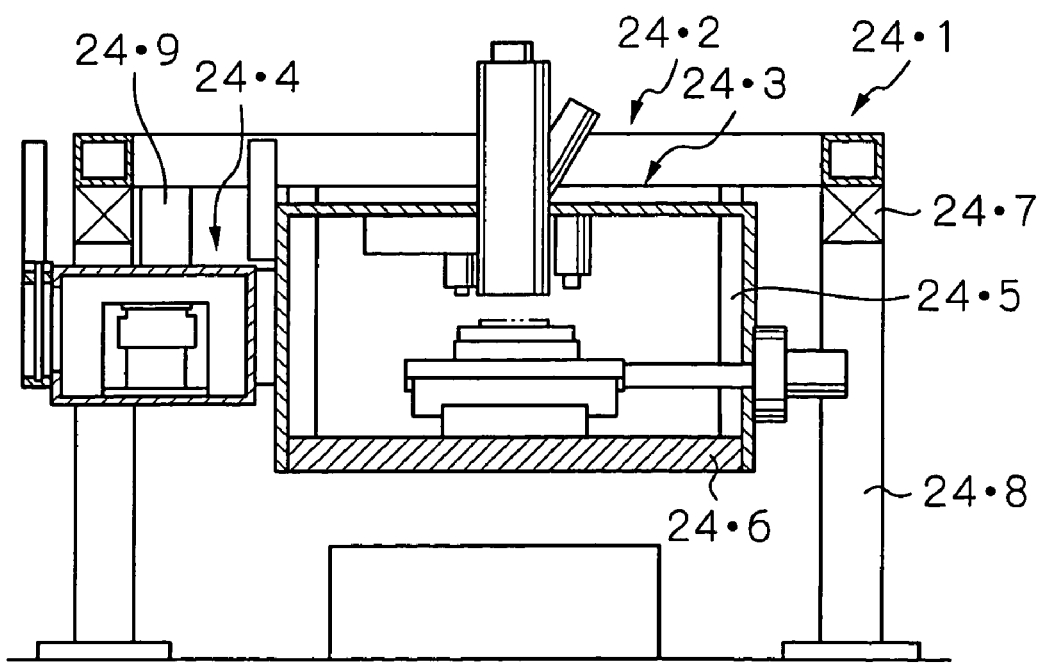
FIG. 24 shows an alteration example of the method of supporting a main housing in the semiconductor inspection apparatus according to the present invention.

FIG. 23 shows an alteration example of a method of supporting the main housing 13•4. In the alteration example shown in FIG. 23, a housing supporting apparatus 23•1 is composed of a thick and rectangular steel plate 23•2, and the housing main body 23•3 is placed on the steel plate. Thus, a bottom wall 23•4 of the housing main body 23•1 is thinner than the bottom wall of the embodiment described previously. In an alteration example shown in FIG. 24, a housing main body 24•3 and a loader housing 24•4 are supported in a suspended state by a frame structure 24•2 of a housing supporting apparatus 24•1.

The lower ends of a plurality of longitudinal frames 24•5 fixed to the frame structure 24•2 are fixed at four corners of a bottom wall 24•6 of the housing main body 24•3, and a circumference wall and a top wall are supported by the bottom wall. An anti-vibration apparatus 24•7 is placed between the frame structure 24•2 and a base frame 24•8. Furthermore, the loader housing 24•4 is suspended by a suspending member 24•9 fixed to the frame structure 24•2. In the alteration example of the housing main body 24•3 shown in this figure, the total weight at the center of gravity of the main housing and various kinds of devices provided therein can be reduced owing to the support in a suspended manner. In the method for supporting the main housing and the loader housing including the above alteration example, vibrations from the floor are not transferred to the main housing and the loader housing.

In another alteration example (not shown), only the housing main body of the main housing is supported from below by the housing supporting apparatus, and the loader housing can be placed on the floor in the same manner as the case of the adjacent mini-environment apparatus 13•3. Furthermore, in still another alteration example, only the housing main body of the main housing 13•4 is supported by the frame structure in a suspended manner, and the loader housing can be placed on the floor in the same manner as the case of the adjacent mini-environment apparatus.

According to the embodiments described above, the following effects can be exhibited.

(1) The entire configuration of a projection electron microscope type inspection apparatus using an electron beam can be obtained, and an inspection object can be processed with high throughput.
(2) Clean air is flowed through the inspection object in the mini-environment space to prevent deposition of dust, and a sensor for observing the cleanness is provided, whereby the inspection object can be inspected while monitoring dust in the space.
(3) Since the loading chamber and the working chamber are integrally supported via the vibration preventing apparatus, the inspection object can be supplied to the stage apparatus and inspected without being influenced by the external environment.

2-3) Electro-Optical System
 2-3-1) Overview

The electro-optical system 13•8 comprises an electro-optical system comprising a primary electro-optical system (hereinafter referred to simply as primary optical system) 25•1 schematically shown in FIG. 25-1, provided in a column 13•38 fixed to the housing main body 13•17, and a secondary electro-optical system (hereinafter referred to simply as secondary optical system) 25•2, and a detection system 25•3. The primary optical system 25•1 is an optical system irradiating an electron beam to the surface of the wafer W as an inspection object, and comprises an electron gun 25•4 emitting an electron beam, a lens system 25•5 comprised of an electrostatic lens converging a primary electron beam emitted from the electron gun 25•4, a Wien filter or E×B separator 25•6, and an objective (or cathode) lens system 25•7, and they are placed in order with the electron gun 25•4 situated at the uppermost position as shown in FIG. 25-1. A lens constituting the objective lens system 25•7 of this embodiment is a retarding electric field objective lens. In this embodiment, the optical axis of the primary electron beam emitted from the electron gun 25•4 is slanted with respect to the axis (perpendicular to the surface of the wafer) of irradiation beam irradiated to the wafer W as an inspection object. An electrode 25•8 is placed between the objective lens system 25•7 and the wafer W as an inspection object. The electrode 25•8 is axially symmetric with respect to the axis of irradiation beam of the primary electron beam, and voltage-controlled by a power supply 25•9.

The secondary optical system 25•2 comprises a lens system 25•10 comprised of an electrostatic lens penetrable to secondary electrons separated from the primary optical system by the E×B type deflector 25•6. This lens system 25•10 functions as a magnifying lens magnifying a secondary electron image.

The detection system 25•3 comprises a detector 25•11 and an image processing unit 25•12 placed on an imaging surface of the lens system 25•10.

The direction of incident of the primary beam is usually the E direction of the E×B filter (direction opposite to the electric field), and this direction is identical to the integration direction of an integration-type line sensor (TDI: time delay integration). The integration direction of the TDI may be different from the direction of the first beam.

The electron beam optical system column comprises the following components.

(1) Column Magnetic Shield

A nickel alloy such as permalloy or a magnetic material such as iron is suitably used for a member constituting the column, whereby an effect of inhibiting the influence of magnetic disturbance can be expected.

(2) Detector Rotation Mechanism

To match the scan axis direction of the stage with the scan direction of the detector, the column 13•38 has in its upper part a detector rotation mechanism eliminating a deviation in the scan direction caused by assembly of apparatus by allowing the detector 25•11 such as the TDI to rotate at ±several degrees about the optical axis while keeping the inside of the column 13•38 under vacuum. In this mechanism, about 5 to 40 seconds are required for rotational resolution and rotational position reproducibility. This arises from the requirement that a deviation between the scan direction of the stage and the scan direction of the detector should be about 1/10 of one pixel during the scanning of an image of one frame. According to the detector rotation mechanism, an angular error between the direction of movement of the stage and the integration direction of the TDI can be adjusted to be 10 mrad or less, preferably 1 mrad or less, more preferably 0.2 mrad or less.

One example of the configuration of the detector rotation mechanism will be described below using FIGS. 25-3 to 25-5. FIG. 25-3 shows the overall configuration of the detector rotation mechanism provided in the upper part of the column 13•38, FIG. 25-4 is a schematic diagram of a mechanism for rotating an upper column, and FIG. 25-5 shows a mechanism for sealing the upper column and a lower column.

In FIG. 25-3, the upper end of the column 13•38 is comprised of an upper column 25•20 having the detector 25•11 attached thereto, and a lower column 25•21 fixed to the main housing 13•4. The upper column 25•20 is supported on the lower column 25•21 via a bearing 25-22 and can rotate about the optical axis of the secondary optical system, and a seal portion 25•23 is provided between the upper column 25•20 and the lower column 25•21 to keep the inside of the column 13•38 under vacuum. Specifically, the seal portion 25•23 is placed between the lower end of the upper column 25•20 and the upper end of the lower column 25•21, a flange portion 25•24 is provided at the upper end of the lower column 25•21 in such a manner as to surround the upper column 25•20, and the bearing 25•22 is placed between the flange portion 25•24 and the side face of the upper column 25•20.

Bearing clamps 25•25 and 25•26 for clamping the bearing 25•22 are screwed to the upper column 25•20 and the lower column 25•21, respectively. Further, to rotate the upper column 25•20 with respect to the lower column 25•21, a drive mechanism shown in FIG. 25-4 is provided. That is, a raised portion 25•27 is provided in part of the bearing clamp 25•26 provided at the upper end of the flange portion 25•24, while an actuator 25•29 is fixed on a mounting member (bracket) 25•28 protruding from the upper column 25•20. A shaft 25•30 of the actuator 25•29 contacts the raised portion 25•27, and a precompression spring 25•31 given a force for attraction toward the raised portion 25•27 is provided between the flange portion 25•24 and the mounting member (bracket) 25•28 having the actuator 29•29 fixed thereon. Consequently, by activating the actuator 25•29 to change the length of the shaft 25•30 protruding from the actuator 25•29, the upper column 25•20 can be rotated at a desired angle in a desired direction with respect to the lower column 25•21.

For the rotation accuracy described above, the movement resolution of the actuator 25•29 is desirably 5 to 10 μm. Furthermore, the actuator 25•29 may be a piezo actuator or actuator motor-driving a micrometer. Furthermore, a sensor capable of measuring a relative distance between the bracket 25•28 for fixing the actuator 25•29 and the raised portion 25•27 is desirably mounted to measure a rotational position of the detector 25•11. For the sensor, a linear scale, potentiometer, laser displacement meter, deformation gage or the like may be used.

The seal portion 25•23 is placed so that a very small gap 25•32 (FIG. 25-5) is formed between the upper end face of the lower column 25•21 and the lower end face of the upper column 25•20 as shown in FIG. 25-5 to keep the inside of the column 13•38 under vacuum. The seal portion 25•23 comprises a partition ring 25•33 solidly fixed at the center, and two elastic seals 25•34 and 25•35, and springs 25•36 and 25•37 for ensuring the contact pressure of the seal surface to improve a sealing performance are provided between lip portions of the elastic seals 25•34 and 25•35, respectively. An air exhaust port 25•39 communicating with an air exhaust channel 25•38 formed in the lower column 25•21 is provided at the center of the partition ring 25•33. The elastic seals 25•34 and 25•35 are preferably made of a material having a very small frictional coefficient and being excellent in slidability and for example, Omni-seal manufactured by Huron Co., Ltd. (USA) may be used.

In this way, the elastic seal is doubly placed, and a space 25•40 between the elastic seals is evacuated, whereby even if the upper column 25•20 rotates to cause a very small leak to occur in the elastic seal 25•35 on the atmosphere side, the leaked air is exhausted through the air exhaust channel 25•38, and thus the pressure of the space 25•40 does not significantly increase. Therefore, no leak occurs from the elastic seal 25•34 into the column, so that the vacuum in the column is never degraded. The space 25•40 may be continuously evacuated, but it is also possible to evacuate the space 25•40 only when the detector rotation mechanism is activated. This is because the leak is more likely to occur when the detector is rotated, and sufficient sealing is ensured with the pressure of contact between the elastic seals 25•34 and 25•35 and the lower end of the upper column 25•20 when the detector is not rotated.

It is important that the pressure of contact between the elastic seals 25•34 and 25•35 and the upper and lower surfaces is appropriately set, and this can be realized by adjusting the size of the gap 25•32. The adjustment of the gap 25•32 can be performed by inserting a shim 25•41 between the bearing 25•22 and the upper end face of the lower column 25•21. By inserting the shim 25•41 in this position, the height of the bearing 25•22 with respect to the lower column 25•21 can be changed. On the other hand, for the upper column 25•20, the bearing 25•22 is held between clamps 25•25 and 25•26, and therefore the bearing 25•22 moves vertically together with the upper column 25•20, and the gap 25•32 between the upper column 25•20 and the lower column 25•21 changes by the thickness of the shim 25•41.

Furthermore, depending on specifications of the column, a sufficient performance is obtained even if only a single seal is provided instead of providing double seals and the space between seals is not evacuated as shown in FIG. 25-5. However, double seals are more reliable, and allow a high vacuum to be easily produced. Furthermore, the springs 25•36 and 25•37 are provided in the elastic seals 25•34 and 25•35 in the above description, but if the elastic seals 25•34 and 25•25 are sufficiently pressed against the upper and lower surfaces with a pressure difference between the vacuum and the atmosphere, or the elastic seals 25•34 and 25•35 themselves have sufficient repulsive forces, the springs 25•36 and 25•37 may be omitted.

To match the direction of the detector with the direction of the stage with the rotation mechanism having the configuration described above, the detector 25•11 is rotated in a very small amount, the scan imaging of the detector 25•11 is carried out on each such an occasion, and the angle of the detector 25•11 is matched with the angle when the most sharp image is obtained. A specific process thereof will be described below.

In the rotatable range of the detector rotation mechanism, the detector 25•11 is rotated at a very small angle to carry out the scan imaging of the detector 25•11, and the obtained image is subjected to image processing, whereby a numerical value allowing evaluation of image quality such as a contrast is determined. This process is repeated to determine a relation between the rotational position of the detector 25•11 and the image quality, and a rotational position for best image quality is determined. Then, the detector 25•11 is rotated to the position to complete the operation of positioning the detector 25•11.

An allowable value for a positional deviation between the stage and the detector 25•11 depends on the requirement that a deviation between the scan direction of the stage and the scan direction of the detector should be about 1/10 of one pixel during the scanning of an image of one frame in the detector 25•11. Thus, an allowable angular deviation when pixels are arranged in 500 stages along the scan direction is about 40 seconds.

To set the angular deviation between the stage and the detector to 40 seconds or less, a method in which the relation between the position of the detector and the image quality described above is expressed as a numerical value by a method such as multinominal approximation, and, a position of the detector 25•11 for best image quality is determined, or a method in which the detector 25•11 is first roughly rotated to form an image, an approximate relation between the position of the detector and the image quality is determined, a range of a position of the detector for best image quality is identified, the detector is again rotated in a very small amount in this range to carry out the same operation, and a position of the detector for best image quality is accurately determined can be used. To prevent occurrence of an angular deviation after matching the angles of the stage and the detector in this way, it is effective to provide a lock mechanism. For example, a planar part is placed between the bearing clamps 25•25 and 25•26, and this platy part and the bearing clams 25•25 and 25•26 are fixed together with a bolt.

(3) NA Movement Mechanism

The NA is held by a mechanism capable of moving several centimeters along the optical axis or in a direction orthogonal to the light axis, and allows an adjustment to be made so that the NA is situated at an optically optimum position according to a change in magnifying power. A plurality of NAs can be desirably mounted on a NA holding unit, and by adding such a mechanism, the NA can be replaced while keeping the inside of the column under vacuum when the NA is degraded or a change in transmittance is desired.

Furthermore, a heater unit is desirably installed in the NA holding unit to provide an effect of inhibiting degradation of the NA by keeping the NA at a high temperature. Furthermore, it is effective to install a piping unit for a reactive gas, so that the NA can be cleaned while keeping the inside of the column under vacuum.

(4) Isolation Valve

A valve allowing the inside of the column to be partitioned into a plurality of spaces is desirably installed in the column. Specifically, it is effective to install the valve so that the space of an MCP unit or electron gun unit can be separated from the space of the stage unit. Such a configuration enables maintenance of the periphery of the stage and the like to be carried out while keeping the MCP unit and the electron gun unit under vacuum. Furthermore, conversely, maintenance of the MCP unit and the electron gun unit can be carried out while keeping the stage unit and the like under vacuum.

(5) Shield Barrel

The optical axis is preferably surrounded by a grounded cylindrical member, and by providing such a configuration, an effect of inhibiting the influence of electric external disturbance can be expected.

(6) Orifice Before MCP

An orifice-like or slim cylindrical member is placed between a series of electro-optical system and the MCP unit reduces, and by providing a configuration such that a conductance of a path extending through a space between the electro-optical system and MCP unit, the pressure of the MCP unit can be easily kept at about 1/5, preferably about 1/10, more preferably about 1/100 of the pressure of the electro-optical system.

(7) Integration of Electrodes and Enhancement of Accuracy

Parts required to be installed on an electro-optically concentric axis with accuracy of several µm or smaller are desirably assembled by a method such as inter-member combination processing or cooling fit.

(8) Optical Microscope

An optical microscope is provided to compare a sample image under low magnifying power and an image seen under light with an electron beam image. The magnification is about 1/10 to 1/5000, preferably about 1/20 to 1/1000, more preferably about 1/20 to 1/100 of that of electron beam image. An image of light from the sample surface can be detected by a two-dimensional solid imaging device (CCD), and displayed on a CRT. Furthermore, it can be stored in a memory.

(9) Coaxial Ion Pump

By installing a non-vibration type vacuum pumping system such as an ion pump rotation-symmetrically around an optical axis near the electron gun unit and the MCP unit, an effect of keeping such a place under high vacuum while offsetting the influences of charged particles and magnetic fields by the pumping system itself can be expected. This is because a reduction in conductance of piping is alleviated when the ion pump is connected to the electron gun unit and the like to evacuate the same.

Specific embodiments will be described below.

(1) Embodiment 1

Figure 26:
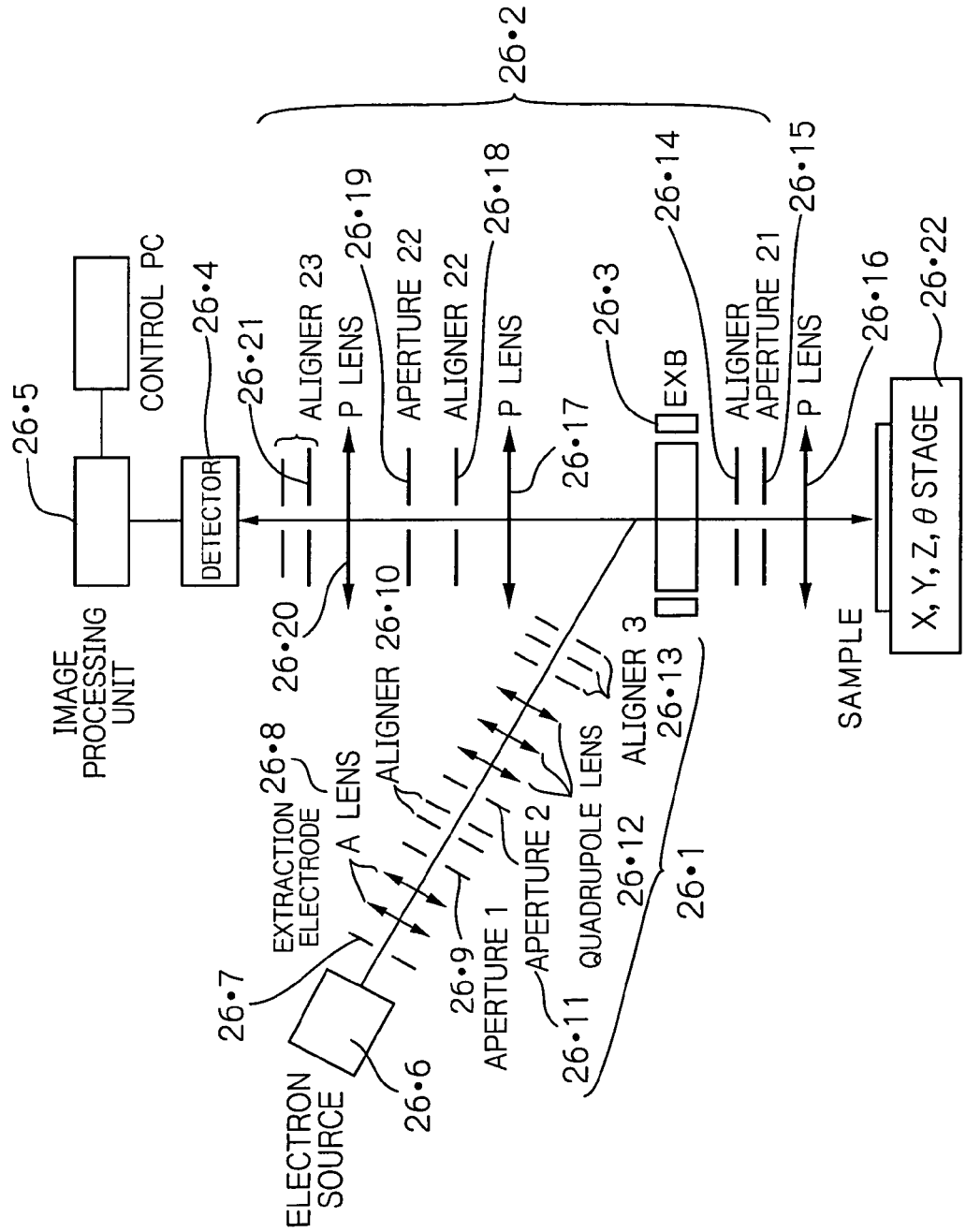
FIG. 26 is the first embodiment of the semiconductor inspection apparatus according to the present invention.

The embodiment is one example of inspection apparatus mainly comprised of a vacuum chamber, a vacuum pumping system, a primary optical system, a secondary optical system, a detector, an image processing unit and a computer for control. One example thereof is shown in FIG. 26.

A primary optical system 26•1 for illuminating an electron beam to a sample, and a secondary optical system 26•2 for guiding electrons emitted from the sample surface, for example secondary electrons, reflection electrons, backscattered electrons, to the detector are provided. The secondary optical system is a projection electron microscope type optical system. A beam separator 26•3 of E×B is used for separating the primary system and the secondary system. Furthermore, an image signal of an electron detected by a detector 26•4 is an optical signal or/and an electric signal, and processed by an image processing unit 26•5. Furthermore, at this time, if the number of electrons entering the detector is 200 or less per one pixel equivalent area, an image can be formed satisfactorily. Of course, the image can be satisfactorily formed if the number of electrons is 200 or greater per one pixel area.

An electron gun 26•6 as a component of the primary optical system uses LaB$_6$ as a heat filament (cathode), and derives electrons from a cathode with a Wenelt and draw electrode 26•7. Then, a beam is converged to an aperture 26•9 with a two-stage A lens (Einzell lens) 26•8 to form a crossover. Then, the beam passes through a two-stage aligner 26•10, an aperture 26•11, a three-stage quadrupole lens 26•12 and a three-stage aligner 26•13, enters a beam separator, is deflected in the direction of the sample surface, passes through an aperture 26•14 and a P lens (objective lens) 16•16 of the secondary system, and is applied to the sample surface almost vertically.

The aligner (deflector) 26•10 making the beam to pass through a beam area highly uniform in crossover and having a high luminance by the aperture 26•9, and specifying an angle of a beam incident to the quadrupole lens by the aperture 26•11 is used for adjustment to cause the beam enter at the center of the optical axes of the aperture 26•11 and the quadrupole lens 26•12. The quadrupole lens 26•12 is used for deformation of the beam shape by changing paths of the beam in two directions, for example X and Y directions. For example, in the shape of the sample irradiation beam, a change in ratio of shapes of circular, elliptic, rectangular and rectangular/elliptic shapes in x and y directions can be achieved (see FIG. 27). After passing through the quadrupole lens, the beam is adjusted to pass through an aperture 26•15 and the center of the P lens (objective lens) 26•16 by the aligner 26•14, and enters the sample surface. At this time, the shape of the irradiation beam can be symmetrically formed for at least one of two axes. The beam may have an asymmetric shape. Energy of the beam applied to the sample surface is finally determined by a difference in voltage between the cathode and the sample surface. For example, when the voltage of the cathode is 5.0 kV and the voltage of the sample surface is 4 kV, energy of the irradiation beam is 1 keV (see FIG. 26).

In this case, the voltage error is ±10 V, and the energy error is ±20 eV. Furthermore, if secondary electrons are used as detection electrons, the sample is negatively charged, and secondary electrons are emitted from the sample in this state, made to form an image under magnification by the secondary optical system, and guided to the detection system when the beam irradiation energy of 1.5 keV±10 eV to 5 keV±10 eV is used. If the irradiation energy is 50±10 eV to 1500 eV±10 eV, the sample surface is positively charged, and emitted secondary electrons are guided to the detection system. When the sample is positively charged, the operation can be carried out with a relatively low damage, but the sample is more easily influenced by charge-up or unevenness in surface potential due to the charge-up. In the negative charge operation, an image can be easily obtained with stability, and the influence of charge-up or distortion of the image due to unevenness in surface potential by the charge-up can be reduced compared to the case of positive charge.

Furthermore, at the location of the aperture 26•15, the operation may be carried out with positions of crossovers of the secondary system and the primary system deviated from each other. For example, the crossover of secondary electrons is formed on the center of the secondary system optical axis for the secondary system, and the crossover of the primary system is formed at a position deviated by 50 to 500 μm from the center of the optical axis of the secondary system (may be either X or Y). Consequently, two crossovers of the primary system and the secondary system never overlap each other in the aperture 26•15, and the current density can be alleviated, thus making it possible to inhibit expansion of blurs due to the space charge effect when the amount of beam current is large. This is effective when the current density of the primary system irradiation beam is greater than $1\times10^{-3}$ A/cm$^2$, for example. For any lower current density, there is no influence even if the centers of optical axes are identical.

For electrons emitted from the sample surface, at least one type of secondary electrons, reflection electrons and back scattered electrons are used. The levels of energy emitted from the sample surface are 0 to 10 eV, 1000 eV±10 eV and 10 to 1000 eV, respectively, for incident beam energy of 1000 eV±10 eV, for example. Furthermore, electrons passing through a thin film or a bored sample (e.g. slancil mask) are used. In this case, for the former thin sample, the incident energy is reduced by the amount equivalent to the thickness of the sample, and for the bored sample, the incident energy remains unchanged.

A focused ion beam (FIB) may be used instead of the electron beam. A Ga ion source of a liquid metal is generally used as the FIB source, but other liquid metal ion source using a metal that is easily liquefied, or an ion source of a different type, for example a duoplasmatron using a discharge may be used.

For the sample, various samples such as a tip of about 10×10 mm, and 2, 4, 6, 8 and 12 inch wafers are used. Particularly, it is effective in detection of defects of a wiring pattern having a line width of 100 nm or smaller and a via having a diameter of 100 nm or smaller, and contaminants, and also convenient for detection of electric defects of the pattern and the via. For the sample, Si wafers, semiconductor device wafers made by processing Si, micromachined wafers, substrates for liquid crystal displays, head-processed wafers for hard disks and the like are used.

For the secondary system 26•2, an example will be described in which a projection type optical system to make electrons emitted from the sample, for example secondary electrons, reflection electrons, back-scattered electrons and transmission electrons form an image under magnification and guide the electrons to the detection system is used. As an example of the lens configuration of a column, the lens is constituted by a P lens (objective lens) 26•16, the aperture 26•15, the aligner 26•14, the beam separator 26•3, a P lens (intermediate lens) 26•17, the aligner 26•18, the aperture 26•19, a P lens (projection lens) 26•20, an aligner 26•21, and a micro-channel plate (MCP) unit. A hermetic quartz glass is placed on an upper flange of the column. A relay lens and a two-dimensional charge coupled device (2D-CCD) are placed thereon, and an image formed on a fluorescent screen is formed on a 2D-CCD sensor.

Emitted electrons from the sample surface form a crossover in the aperture 26•15 at the P lens (objective lens) 26•16, and are made to form an image at the center of the beam separator 26•3. The operation under conditions of forming an image at the center of the beam separator is effective because the effect of an aberration of a secondary beam occurring in the beam separator 26•3 can be reduced to a low level. This is because for example, the deflection amount/aberration varies depending on the image height when the beam is made to pass at E×B, and therefore the aberration suffered by image formation components can be reduced to a minimum due to formation of the image. Since this is also true for the primary system, not only image formation conditions are formed on the sample but also an image formation point is formed near the center of the beam separator, whereby the aberration of the primary beam is reduced, and unevenness of the current density on the sample is effectively reduced.

To adjust the beam to be situated at the center of the P lens (intermediate lens) 26•17 thereon, the aligner 26•14 is used. To adjust the beam to be situated at the center of the P lens (projection lens) 26•20 in the upstream thereof, the aligner 26•18 is used. To adjust the beam to be situated at the center of the MCP thereon, the aligner 26•21 exists. The magnification of the P lens (objective lens) 26•16 is 1.5× to 3×, the magnification of the P lens (intermediate lens) 26•17 is 1.5× to 3×, and the magnification of the P lens (projection lens) 26•20 is 30× to 50×. To achieve these magnifications, a voltage appropriate to each of the magnifications is applied to each lens to make an adjustment. Furthermore, to make a fine adjustment of a focus, a dedicated focus correction lens is incorporated in the P lens (objective lens) system, and focusing is achieved by fine adjustment of the voltage applied to the electrode. At locations of the aperture 26•15 and the aperture 26•19, the aperture 26•15 can be used to cut noises, and the aperture 26•19 can be used so that it plays a role to determine an aberration/contrast if the crossover is formed in both cases.

For the size, for example, the aperture 26•15 and the aperture 26•19 can be used at $\phi$30 to $\phi$2000 μm, preferably $\phi$30 to $\phi$1000 μm, more preferably $\phi$30 to $\phi$500 μm. At this time, if the aberration, the transmittance and the contrast characteristic are mainly determined with the aperture 26•15, the aperture 26•15 is used at, for example, $\phi$30 to $\phi$500 μm, and the aperture 26•19 is used at $\phi$1000 to $\phi$2000 μm. If the aberration, the transmittance and the contrast characteristic are mainly determined with the aperture 26•19, for example, the aperture 26•19 is used at $\phi$30 to $\phi$500 μm, and the aperture 26•15 is used at $\phi$1000 to $\phi$2000 μm.

Furthermore, astigmatic electrodes may be placed above and below the P lens (intermediate lens) 27•17. The electrodes are used to correct an astigmatic aberration occurring due to the beam separator 26•3 and the like. For example, an astigmatic electrode having an electrode configuration of 4, 6 or 8 poles can be used. For example, different voltages may be applied to the eight electrodes to correct the astigmatic aberration and the spherical aberration.

Furthermore, in the lens operation when a reflection electrode image and back-scattered electrons are used, the P lens (projection lens) 26•20 in the last stage is effective in cutting noises of secondary electrons if a retarding lens (negative voltage application lens) is used for the P lens. Usually, the amount of secondary electrons is greater than the amount of reflection electrodes by a factor of 10 to 1000, and therefore the retarding lens is especially effective when image formation is performed using reflection electrons/back-scattered electrons. For example, when a cathode voltage of a primary system electron source is 4 kV, a sample potential is 3 kV, the level of reflection electron energy from the sample is 1 keV, and when a detector voltage is an installation voltage, a difference in energy level between the reflection electron and the secondary electron is about 1 keV at the site of a P electrode. At this time, in the negative voltage lens operation of the P lens (projection lens), conditions such that the central voltage allows the reflection electron to pass and cuts off the secondary electron can be used. The conditions can be determined by means of simulation.

For the beam separator 26•3, a separator operating with E×B where the electrode is orthogonal to the magnetic pole, or only with a magnetic field B is used. As an example, an E×B is comprised of an E electrode forming an electric field distribution and a magnetic pole having a pole face orthogonal to the E electrode and forming a magnetic flux density distribution in a direction orthogonal to the E electrode. For example, when the optical axis of the secondary system is perpendicular to the sample surface, the incident beam of the primary system can be set at 10 to 90 degrees with respect to the axis of the secondary system. At this time, the beam of the primary system is deflected with E×B and can perpendicularly enter the sample surface, and emitted electrons from the sample surface are guided in the direction of the optical axis, i.e. in the direction perpendicular to the sample surface with E×B. This is achieved by a voltage applied to the E electrode, and a magnetic flux density formed in the B electrode. For example, a voltage of ±2 kV±1 V is applied to a pair of E electrodes, a magnetic flux density distribution is formed in parallel from a pair of B electrodes and for example, at the center of E×B, a magnetic flux density of 1 to 60 G±1 G in the direction of the magnetic pole is produced (see FIG. 26).

Furthermore, E×B can also be applied to the inversed deflection relation of the primary system and the secondary system. That is, the incident beam source of the primary system is provided just above the sample, the detector of the secondary system is provided at an angle of 10 to 80 degrees with respect to the axis of the primary system, the beam of the primary system is made to enter the sample without applying a deflection force thereto with E×B, and the deflection force is applied to electrons emitted from the sample (beam of secondary system), whereby the electrons can be guided to the detector.

In the detector 26•4, signal electrons are introduced into an electron multiplier tube 28•1 such as an MCP, and amplified electrons are applied to a fluorescent screen to form a fluorescent image. The fluorescent screen has a glass plate 28•2 such as quartz glass coated with a fluorescent material on one side. The fluorescent image is formed by a relay lens system 28•3 on a two-dimensional CCD 28•4. This relay lens system and the CCD are placed on the column. A hermetic glass 28•6 is placed on an upper flange of the column, the vacuum environment in the column is separated from the external atmospheric environment, the fluorescent image is formed on the CCD with deformation/contrast degradation being reduced, and the fluorescent image can be efficiently formed.

An integration-type line image sensor (TDI-CCD) camera can be used instead of the CCD. In this case, TDI imaging can be performed while the sample is stage-moved, for example, in the direction of the E electrode or the direction of the B magnetic pole on the stage. For example, when the number of TDI integration stages is 256, one stage has 2048 pixels, the element size is 15×15 μm, and the magnification of the MCP image formation with respect to the sample surface is 300×, the size of the sample surface may be 30/30 μm for the MCP surface if the line/space is 0.1/0.1 μm. When the magnification of the relay lens is 1×, imaging is performed with the size of two elements being equivalent to 30 μm. At this time, electrons emitted from the sample position equivalent to one element, i.e. the sample size of 0.05×0.05 μm are integrated during movement on the stage equivalent to 256 element stages, and the total amount of acquired light increases to allow imaging to be performed. This is especially effective when the stage speed is high such as a speed corresponding to a line rate of 100 kHz to 600 kHz. This is because when the line rate is high, the number of acquired electrons per element, i.e. the intensity of acquired light per element of the TDI sensor decreases, and thus integration can be carried out to enhance the final density of acquired light and increase the contrast and S/N. The line rate is 0.5 kHz to 100 MHz, preferably 1 kHz to 50 MHz, more preferably 20 kHz to 10 MHz. In correspondence therewith, a video rate is 1 to 120 MHz/tap, preferably 10 to 50 MHz/tap, more preferably 10 to 40 MHz/tap. Furthermore, the number of taps is 1 to 520, preferably 4 to 256, more preferably 32 to 128 (see FIGS. 28 and 29).

The CCD and the TDI sensor/camera that are used have characteristics of low noises and high sensitivities. For example, they can be set at 100 to 100000 DN/(nJ/cm$^2$) but above all, if they are used at 1000 to 50000 DN/(nJ/cm$^2$), the efficiency is improved. Further, if they are used at 10000 to 50000 DN/(nJ/cm$^2$), a high quality image can be obtained with good S/N even when the line rate is high.

Furthermore, when the image is acquired using the CCD or TDI sensor, it can be used in a state in which a region of the number of pixels×the number of stages almost matches an area irradiated with the primary beam, thus improving efficiency and reducing noises. For the noise, electrons from a site of a large image height other than areas miscellaneously used may reach the detector as noises. To reduce these noises, it is effective to reduce beam irradiations at a site other than an effective field. Image information acquired by the CCD or TDI sensor is converted into an electric signal, and subjected to data processing by an image processor. Through this image processing, image comparison is carried out on a cell-to-cell, die-to-die, die-to-any die basis, and thus defects can be inspected. For example, pattern defects, particle defects, and potential contrast defects (e.g. electric connection defects of wiring and plating) are inspected.

For the stage 26•22, a stage installed with a combination of at least one of X, Y, Z and θ movement mechanisms is used. In this electron beam inspection apparatus, the following components can be used as the components described above.

Primary System

Electron source: W filament, $L_aB_6$ filament, TFE, FE Lens: made of metal or ceramic, phosphor bronze as metal, Ti, Al, Einzwell lens, quadrupole lens Aligner: lenses of 4 poles, 6 poles and 8 poles Aperture: materials, Mo, Ta, Ti, phosphor bronze Secondary System Lens: made of metal or ceramic, phosphor bronze as metal, Ti, Al, ceramic electrode subjected to treatment such as Au plating Einzell lens, quadrupole lens Aligner: lenses of 4 poles, 6 poles and 8 poles Aperture: materials, Mo (molybdenum), Ta, Ti, phosphor bronze Electron Beam Separator E electrode: made of metal or ceramic, phosphor bronze as metal, Ti, Al, ceramic electrode subjected to treatment such as Au plating B magnetic pole: permalloy B, permalloy C, etc., material having a high saturation magnetic flux density and magnetic permeability (e.g. $10^3$ to $10^7$, preferably $10^4$ to $10^7$, more preferably $10^5$ to $10^7$)

Sample

Si wafer, 3 to 5 group compound semiconductor wafer, crystal substrate, head-processed wafer of hard disk, 2, 4, 6, 8 and 12 inch wafers Detector MCP/fluorescent screen/relay lens/CCP MCP/fluorescent screen/relay lens/TDI MCP/fluorescent screen/FOP (fiber optic plate)/TDI Photomultiplier Multi-photomultiplier The detector can be used in the combinations described above. The MCP has a function to amplitude entering electrons, and the electrons exiting therefrom are converted into light by the fluorescent screen. If the amount of entering electrons is so large that they are not required to be amplified, the operation can be performed without the MCP. Furthermore, a scintillator can be used instead of the fluorescent screen. A light signal thereof (or image signal) is transmitted to the TDI or forms an image under a predetermined magnification in the case of the relay lens, and under a magnification of 1× (light signal is transmitted in a ratio of 1:1) in the case of the FOP. The photomultiplier amplifies a light signal and converts the light signal into an electric signal, and the multi-photomultiplier has a plurality of photomultipliers arranged.

Image Processor

The image processor has functions of image comparison, defect detection, defect classification, image data recording and the like.

In the electron beam inspection apparatus, an irradiation beam shape of the primary beam symmetrical with respect to at least one axis of X and Y axes can be used. Accordingly, an acquired image can formed with a low aberration and low deformation on the electron beam entrance surface of the detector by the beam having an optical axis at the center.

Furthermore, if the CCD or TDI is used as the detector, a sufficient S/N ratio can be achieved in an area corresponding to one pixel, for example in an area where the number of entering electrons is 200/pixel or smaller in formation of one pixel on the MCP, thus making it possible to use the detector for image processing and defect detection. In the projection type optical system, for example, noise cut and aberration reduction effects can be achieved by specifying the size of the aperture 26•15 or 26•19, and therefore by placing an aperture having a diameter of 30 μm to 1000 μm, for example, an improvement in S/N ratio can be achieved, thus making it possible to acquire an image of high resolution and high quality in an area of 200 electrons/pixel.

TDI performs integration equivalent to the number of stages for the direction of movement of the stage. Integration equivalent to 256 stages is performed in this embodiment, but the number of integration stages is appropriately 114 to 8192, preferably 114 to 4096, more preferably 512 to 4096. Even if there is slight unevenness in illuminance of the primary beam in the direction of integration, and there is unevenness in signal electrons from the sample, the unevenness is equalized due to the effect of integration, and detected electron information is constant and stable. Thus, in consideration of a direction where unevenness in illuminance of the primary electron beam easily occurs, the direction of movement of the stage can be determined so that the direction where the illuminance unevenness easily occurs matches the direction of integration of the TDI. The image can be continuously acquired by using the TDI, but the CCD may be used to scan the stage in the step and repeat mode to acquire the image. That is, the operation of stopping the stage at a specific location to acquire an image, then moving the stage to a next location, and stopping the stage there to acquire an image is repeated. A similar operation can be carried out using the TDI. That is, the still mode of the TDI (pause image acquirement mode, in which the stage is stopped) is used, or an image of a certain area (e.g. 2048 pixels×2048 pixels) is acquired by a usual image acquirement process of the TDI, and then the stage is moved to a next location (no image is acquired during the movement), where an image is similarly acquired. Thus, in this case, inspection is performed without stopping the movement of the stage.

When the appearance of the sample surface is magnified by electrons to form an image on the detector, an aberration, a blur and the like of the secondary optical system is desirably within one pixel if the resolution of the image is limited to about one pixel of the CCD or TDI. Since the aberration and the blur grow if electrons are deflected at E×B, signal electrons such as secondary electrons, reflection electrons and back-scattered electrons are adjusted to travel in straight lines with no deflection force given thereto in the secondary optical system in this embodiment. That is, the central axis of the secondary optical system is a straight line passing through the center of the field of view of the sample, the center of E×B and the center of the detector.

Furthermore, since cases other than the embodiment described above are acceptable as long as no blur occurs in the image of the secondary optical system, such cases are included in this invention as a matter of course.

(2) Embodiment 2

When the TDI sensor/camera is used for the detector in the inspection apparatus similar to the embodiment 1, the image can be acquired more quickly and efficiently if the number of images/stages is 2048 to 4096, the number of taps is 32 to 128, and the sensitivity is 10000 to 40000 DN/(nJ/cm$^2$). At this time, the line rate may be 100 to 400 kHz, and the video rate may be 10 MHz to 40 MHz. At this time, the operation is capable of being done when an 8 inch Si wafer, for example LSI device wafer is used, the resolution is 0.1 μm/pixel, and inspection time per one wafer is ⅛ to 2 hours.

At this time, when the resolution is 0.1 μm/pixel, a contrast of 3 to 30% is achieved, and thus image observation and defect detection can be sufficiently performed even with a pattern shape of, for example, LS:0.2/0.2 μm in sample observation and defect inspection. A defect having a shape other than L/S can be detected by comparison using a change in contrast as long as the defect has a size of one pixel or greater. A contrast of 5 to 30% is achieved, thus making it possible to perform observation and defect inspection by image processing. Furthermore, for the LSI device wafer, defects of the design rule or smaller can be detected. Defects equivalent to the half pitch of the wiring width can be detected for the memory, and defects equivalent to the gate length can be detected for the logic.

When defects are detected using the TDI sensor/camera and an image processing mechanism, the image can be continuously formed to perform inspection continuously by the TDI operation. At this time, the sample is placed on the stage, and continuous operations are similarly carried out to obtain the image. The speed of the stage is essentially determined by v=f×D, wherein v represents a stage speed, f represents a line frequency and D represents a size corresponding to sensor pixels on the sample (determined by a projection magnification). For example, when f is 300 kHz and D is 0.1 μm, v equals 30 mm/s.

FIG. 29 shows an example of a detection system having a configuration different from that of the embodiment 1 shown in FIG. 28. In this case, an MCP 29•2, an FOP 29•3, a TDI sensor/package 29•4, a contact pin 29•5 and a field-through flange 29•6 are provided in a column 29•1 under vacuum, and an output of the TDI sensor 29•4 is received by a TDI camera 29•7 through the field-through flange 29•6. Furthermore, the FOP 29•3 is coated with a fluorescent material to form a fluorescent image by electrons from the MCP 29•2. The fluorescent image is transmitted to the TDI sensor 29•4 by the FOP 29•3. An image signal of the TDI sensor 29•4 is transmitted to the TDI camera 29•7 via the contact pin 29•5 and the field-through flange 29•6. At this time, use of the FOP 29•3 can reduce an optical signal transmission loss. For example, the transmittance increases by a factor of about 5 to 20 compared the relay lens. This is especially effective when the TDI operation is carried out. This is because quicker activation is possible due to high intensity of the acquired optical signal, and signal unevenness of a fiber shape is reduced to a negligible level by integration of the TDI. Here, the contact pin 29•5 for connecting pins of the TDI sensor 29•4 and the field though flange 29•6 is required. The contact pin 29•5 is connection-fixed to one side (e.g. pin of field-through) by fit contact, and contacts the pin of the TDI sensor/package with an elastic force of a spring (not shown).

Consequently, the pin of the field-through flange 29•6 and the pin of the TDI sensor/package 29•4 can be installed with a low pressing force, in a parallel position and at a low impedance. In a high speed operation sensor, a large number of pins are used and for example, more than 100 pins are required. If the number of pins is large, the installation pressure (pressing force) increases, and thus the TDI sensor/package 29•4 may be broken. Such points have been overcome to make installation possible.

As shown in FIG. 28, the CCD or TDI is usually installed at the atmosphere side, and the MCP and the fluorescent screen are installed under vacuum, but by placing the CCD or TDI under vacuum, the relay optical system such as the FOP can be curtailed, thus making it possible to improve transmission efficiency.

(3) Embodiment 3

In this embodiment, an EB-CCD or EB-TDI is used for the detector (see FIG. 30) in the embodiments 1 and 2. The EB is an electron beam, and the EB-CCD or EB-TDI directly inputs the electron beam, and converts it into an electric signal (not detecting an optical signal).

Use of the EB-TDI sensor/camera can inject electrons directly into an image portion of the sensor, accumulate charges. This means that it is unnecessary to use the fluorescent screen, the relay lens and hermetic glass used in the usual detector. That is, since an electric signal can be obtained directly from an electron signal without temporarily converting an electron signal image into an optical signal image, and thus a loss associated with the conversion can be considerably reduced. That is, image deformation by the fluorescent screen, hermetic glass and the relay lens system, degradation in contrast, and deleterious effects such as variations in magnification can be considerably reduced. Furthermore, due to reduction in the number of components, downsizing, cost-reduction and quick operations can be achieved. Quick operations can reduce a signal transmission speed loss and an image formation speed loss.

One example of a unit of the EB-TDI is shown in FIG. 30. See the embodiment 1 for the optical system. The surface of a TDI sensor 30•3 is placed in the upper part of a secondary system column, i.e. on the image-forming point the upper part of the P lens (projection lens). The unit is comprised of a TDI sensor/package 30•3, a contact pin 30•4, a field-through 30•5, a TDI camera 30•1, and image processor 30•6 and a control PC 30•7. Emitted electrons (any of secondary electrons, reflection electrons and back-scattered electrons) from the sample surface are made to form an image by the secondary system and enter the surface of the TDI sensor 30•3. Charges are accumulated in accordance with the amount of electrons, and an electric signal for image formation is formed by the TDI camera 30•1.

A pin of the sensor package 30•3 and a pin of the field-through flange 30•5 are connected together by the contact pin 30•4. In this aspect, this embodiment is similar to the embodiment 2. In this case, since an electric image signal is converted directly into an electric signal by the TDI sensor 30•3, components and parts can be curtailed and the transmission channel can be shortened compared to the detectors of the embodiments 1 and 2. This makes it possible to achieve improvement in S/N due to reduction in noises, speed enhancement, downsizing and cost-reduction.

The EB-TDI 30•1 is used in this embodiment, but the EB-CCD may be similarly used. Particularly, this configuration is effective if the number of required pins is greater than 100 due to a large number of pixels or to perform high speed operations. A contact pin for connecting the pin of the field-through and the package is required. The contact pin is constituted by a spring material and a contact plate on one side (e.g. on the package side), and can reduce the contact width. If there are a large number of contact pins, for example 100 or more contact pins, a pressing force at the time of connection increases, and if the total force exceeds 5 kg, a problem of rupture of the package arises. Thus, a contact pin having a pressing force limited to 50 to 10 g/pin by adjustment of a spring force is used.

Furthermore, the number of incident electrons is insufficient when the EB-CCD or EB-TDI is used, an MCP being an electron multiplier tube can be used. Furthermore, for the number of images/stages, the number of stages, the number of taps, the line rate and the video rate, conditions similar to those of the embodiments 1 and 2 may be used. The sensitivity can be 0.1 to 10000 DN/electron.

(4) Embodiment 4

In the inspection apparatus similar to the embodiments 1, 2 and 3, a primary system 31•1 has the same configuration, but a secondary system 31•2 has a different configuration as shown in FIG. 31. To achieve a higher resolution, a two-stage P lens (objective lens) 31•3, a two-stage P lens (intermediate lens) 31•5, and a two-stage P lens (projection lens) 31•8 are used. Further, the P lens (intermediate lens) is notably a zoom lens. Consequently, a projection-type beam optical system having a higher resolution and a larger visual field size compared to conventional systems can be achieved, and an image of any magnification can be acquired in the zoom range.

2-3-2) Details of Configuration

An electron gun, a primary optical system, a secondary optical system, an ExB unit, a detector and a power supply of an electro-optical system shown in FIGS. 25-1 to 31 will be described in detail below.

2-3-2-1) Electron Gun (Electron Beam Source)

A thermal electron beam source is used as an electron beam source. An electron emission (emitter) material is $L_aB_6$. Any other material can be used as long as the material has a high melting point (low vapor pressure at high temperature) and a small work function. A material having the leading end formed into a conic shape, or a material having a conic shape with the leading end cut off is used. The diameter of the leading end of the truncated cone is about 100 µm. For other types, an electric field emission type electron beam source or thermal electric field emission type is used, but when a relatively wide area (e.g. 100×25 to 400×100 µm$^2$) is irradiated with a large amount of current (about 1 µA) as in the present invention, a thermal electron source using $L_aB_6$ is most suitable. Furthermore, in the SEM system, a thermal electric field electron beam source (TFE type) and a short key type are generally used. The thermal electron beam source is a system in which the electron emission material is heated to emit electrons, and the thermal electric field emission electron beam source is a system in which a high electric field is applied to the electron emission material to emit electrons, and an electron beam emission portion is heated to stabilize the emission of electrons. In this system, extraction of electron beams under efficient conditions called shot key conditions can be performed by selecting the temperature and the electric field intensity and recently, this system has been often used.

2-3-2-2) Primary Optical System

A part forming an electron beam applied from an electron gun, and irradiating an electron beam having a two-dimensional cross section such as a rectangular, circular or elliptic cross section or a linear electron beam onto the wafer surface is called a primary electro-optical system. By controlling lens conditions of the primary electro-optical system, the beam size and the current density are controlled. By an ExB filter (Wien filter) at a primary/secondary electro-optical system connection portion, a primary electron beam is made to enter the wafer at a right angle (±5°, preferably ±3°, more preferably ±1°).

Thermal electrons emitted from a $L_aB_6$ cathode are made to form an image on a gun diaphragm as a crossover image by a Wenelt, triple anode lens, double anode, or single anode. An electron beam having the angle of incidence to the lens modified by an illumination visual field diaphragm is made to form an image on an NA diaphragm in a form of rotational asymmetry by controlling a primary system electrostatic lens, and then applied to the wafer surface. The rear stage of a quadrupole lens of the primary system is comprised of a three-stage quadrupole (QL) and a one-stage aperture aberration correcting electrode. The quadrupole lens has a constraint of strict alignment accuracy, but notably has a strong convergence action compared to the rotational symmetry lens, and is capable of correcting an aperture aberration corresponding to a spherical aberration of the rotational symmetry lens by applying an appropriate voltage to the aperture aberration correcting electrode. Consequently, a uniform plane beam can be applied to a predetermined area. Furthermore, the electron beam can be scanned by a deflector.

The shape and area of the irradiation electron beam on the sample surface includes the shape and area of an imaging area of the TDI-CCD on the sample, and it is desirable that the illuminance in the electron beam irradiation area is uniform, and illuminance unevenness is 10% or less, preferably 5% or less, more preferably 3% or less.

The shape and area of the TDI-CCD in this embodiment is equivalent to a pixel number of 2048×512, with the pixel size being 16 µm×16 µm, and therefore its overall shape is a rectangle of about 32.8 mm×8.2 mm. When the magnification of the secondary optical system is 160×, the irradiation area on the sample surface is 1/160 of 32.8 mm×8.2 mm, and is therefore a rectangle of 205 µm×51.2 µm.

Thus, the electron beam irradiation area in this case is desirably a rectangle including a rectangle of 205 µm×51.2 µm, but it may be a rectangle having round corners, ellipse, circle or the like as shown in FIG. 27-1 as long as its shape and area meets the above conditions. When the magnification of the secondary optical system is 320×, the irradiation area is 1/320 of 32.8 mm×8.2 mm, which is equivalent to a rectangle of 102.4 μm×25.6 μm, thus being ¼ of the irradiation area with the magnification of 160×.

In this way, in the present invention, a beam with a relatively large area including imaging areas of the TDI-CCD as a detector is applied to the sample, the imaging areas on the sample correspond to pixels of the TDI-CCD, respectively, and electrons emitted from these imaging areas on the sample are made to form an image on the TDI-CCD at a time to perform detection.

The irradiation shape of the electron beam may be linear, and may be scanned to ensure an irradiation are the same as that of a plane beam. A linear beam 27•1 refers to a beam having a shape in which the length-to-width ratio is 10:1 or greater as shown in FIGS. 27-2(1-1) and 27(1-2), it is not limited to a rectangle but may be an ellipse. Furthermore, the linear beam 27•1 may have interrupted at some midpoint as shown in FIG. 27-2(2). The scanning of the beam reduces the time period over which the beam is continuously applied to the same location of the sample, and thus has an advantage that the influence of charge up on the sample is reduced.

FIGS. 27-2(3) and 27-2(4) show a relation between a multi-pixel imaging area 27•3 of the TDI-CCD and the linear beam 27•1 on an inspection subject 27•2. Among them, in FIG. 27-2(3), the linear beam 27•1 is placed at almost a right angle (e.g. 90°±3°, preferably 90°±1°) with respect to an integration direction 27•4 of the TDI-CCD or a direction of movement 27•5 of the XY stage, and a direction of scan 27•6 of the beam is identical to the integration direction 28•4 or the direction of movement 27•5 of the XY stage (e.g. 0°±1°, preferably 0°±1 minute, more preferably 0°±1 second).

FIG. 27-2(4) shows another example, in which the linear beam 27•1 is almost parallel to the integration direction 27•4 of the TDI-CCD or the direction of movement of the XY stage (e.g. 90°±1°, preferably 90°±1 minute, more preferably 90°±3 seconds).

2-3-2-3) Secondary Optical System

A two-dimensional secondary electron image produced by an electron beam applied to the wafer is formed at a visual field throttling position by an electrostatic lens equivalent to an objective lens, and magnified and projected by a lens (PL) in the rear stage. This image formation and projection optical system is called a secondary electro-optical system. A negative bias voltage (retarding electric field voltage) is applied to the wafer. The retarding electric field has an effect of retarding the irradiation beam to reduce damage on the sample, and accelerating secondary electrons generated from the sample surface with a difference in potential between the objective lens and the wafer to reduce a color aberration. Electrons converged by the objective lens are made to form an image on the FA by the intermediate lens, and the image is magnified and projected by the projection lens, and formed on a secondary electron detector (MCP). In this optical system, the NA is placed between the objective lens and the intermediate lens, and optimized to constitute an optical system capable of reducing an off-axis aberration.

To correct a production-related error of the electro-optical system, and an astigmatic aberration and an anisotropic magnification of an image occurring with passage through an E×B filter (Wien filter), an electrostatic octupole (STIG) is placed to make a correction, and an axial shift is corrected with a deflector (OP) placed between lenses. In this way, a projection type optical system with a uniform resolution in the visual field can be achieved.

The optical system will be further described using a few embodiments.

(1) Embodiment 5

FIG. 32 shows an electro-optical system. Primary electrons emitted from an electron gun 32•1 pass through an image formation lens 32•2, then a two-stage zoom lens 323 and then a three-stage quadrupole 32•4, and are deflected at 35° by an E×B filter 32•5, and applied to the sample surface through an objective lens 32•7 in an opposite direction in parallel to the optical axis of a secondary optical system 32•6. Furthermore, for the quadrupole lens, a multipole lens having two or more poles may be used, and not only a lens having an even number of poles but also a lens having an odd number of poles may be used. Furthermore, the quadrupole lens has 3 to 20 stages, preferably 3 to 10 stages, more preferably 3 to 5 stages.

Secondary electrons, reflection electrons and back-scattered electrons emitted from the sample surface with irradiation of primary electron beam are made to form an image at the center of the E×B filter 32•5 by the objective lens 32•7, subjected to scaling by an intermediate lens 32•8, and then made to form an image just before a projection lens 32•9. The image formed with the intermediate lens 32•8 is magnified by a factor of about 30 to 50 by the projection lens 32•9 and formed on the detector surface 32•10.

The image formation lens 32•2 enables an image to be formed just before the zoom lens 32•3 even if the accelerating voltage is changed, and is constituted by a one-stage lens in FIG. 32, but may be constituted by a multiple-stage lens.

If the accelerating voltage of primary electron beam is fixed, the irradiation area and shape of primary electron beam on the sample surface almost depends on the conditions of the zoom lens 32•3 and the conditions of the quadrupole lens 32•4. The zoom lens 32•3 changes the irradiation area during maintaining the beam shape. The quadrupole lens 32•4 can change the size of the beam, but is used mainly to change the beam shape (length-to-width ratio of ellipse). FIG. 32 shows the two-stage zoom lens 32•3 and the three-stage quadrupole lens 32•4, but the number of stages may be increased.

The case will be discussed below where the size of one pixel of the detector is 16 μm×16 μm, and the size of the detector is 2048×512 pixels. When the magnification of the secondary optical system 32•6 is 160×, the size on the sample equivalent to one pixel is 16 μm÷0.160=0.1 μm, and the observation area is 204.8×51.2 μm. The irradiation area covering the observation area has an elliptic shape, and thus changes in a variety of ways depending on the ratio between the long axis and the short axis of the ellipse. This situation is shown in FIG. 33. In FIG. 33, the horizontal axis shows the position of the long axis and the longitudinal axis shows the position of the short axis. In consideration of the optimum irradiation shape, it is not desired that the beam is applied to areas other than an observation area 33•1. To achieve the optimum irradiation shape, an irradiation shape with the largest irradiation efficiency obtained by dividing the area of the observation area by the area of the irradiation area should be found.

FIG. 34 shows a plot of the ratio of the long axis to the short axis in the shape of the irradiation area versus the irradiation efficiency. From this plot, it can be understood that a shape with the best irradiation efficiency is provided when the ratio of the long axis to the short axis in the irradiation elliptic shape equals the ratio of the long axis to the short axis in the rectangular observation area. That is, a beam shape for thoroughly irradiating the observation area of 204.8×51.2 µm is a beam shape of 290×72.5 µm. In fact, the shape of the irradiation beam slightly grows due to influences of the aberration of the irradiation optical system and illuminance unevenness of the electron gun. To achieve this irradiation beam shape, the quadrupole lens 32•4 may be adjusted so that an image just before the quadrupole lens 32•4 forms an elliptic irradiation area on the sample surface by an optical system including the quadrupole lens 32•4 and the objective lens 32•7. In this case, it is only required that a necessary irradiation area and a sufficiently uniform irradiation current density over the entire irradiation area should be obtained, and it is not necessary to make the irradiation beam form an image on the sample surface. The size of the image just before the quadrupole lens 32•4 is adjusted with the zoom lens 32•3 so that a predetermined irradiation area can be obtained on the sample surface.

Now, for example, assume that the magnification of the secondary electro-optical system 32•6 is changed from 160× to 320×. At this time, the size equivalent to one pixel on the sample surface is 0.05 µm×0.05 µm (16 µm÷320=0.05 µm), and the observation area is 102.4×25.6 µm. If the irradiation area is kept at a magnification of 160× in this state, the amount of a signal reaching one pixel of the detector is proportional to the area ratio, and therefore equals ¼ of the signal amount when the magnification is 160×. Provided that an image of a signal amount corresponding to average 400 electrons per pixel is seen when the magnification is 160×, the standard deviation of fluctuations by shot noises at this time is $\sqrt{(400)}=20$. Accordingly, the S/N ratio is 400/20=20. To obtain an image of the same S/N ratio when the magnification is 320×, the same signal amount should be within one pixel. The area per pixel on the sample is ¼ of the original area, and accordingly the secondary electron signal amount density per unit area should be quadrupled.

If landing energy represented as a difference in acceleration energy of primary electrons and the potential of the sample surface is fixed, the irradiation current density is approximately proportional to the secondary electron signal amount density. Thus, it can be understood that the irradiation current density should be quadrupled. To quadruple the irradiation current density, the irradiation current should be simply quadrupled, or the irradiation area should be reduced to ¼ of the original area. To reduce the irradiation area to ¼ of the original area, the irradiation size should be reduced to ½ of the original size for both the long and short axes. Since both the observation area and irradiation area are analogously scaled down by a factor of 2, the observation area can be sufficiently irradiated.

As means for increasing the irradiation current density, the irradiation current may be increased, or the irradiation area may be decreased. However, it is more desirable that the irradiation area is reduced, taking it consideration that areas other than the observation area are preferably prevented from being irradiated.

Table 3 shows the voltages of the primary optical system lens and the obtained irradiation sizes on the sample for secondary optical system magnifications of 320× and 160×, respectively. As a result, an irradiation area capable of sufficiently keeping up with the secondary optical system magnification can be obtained. Although not shown in Table 3, the irradiation size for the magnification of 80× may be an ellipse of 620 µm×180 µm, and the irradiation size for the magnification of 480× may be an ellipse of 100 µm×30 µm. In this way, it is desirable that the irradiation size is changed according to a change or shift in magnification.

TABLE 3

|  |  | Magnification of 160× | Magnification of 320× |
|---|---|---|---|
| Zoom Lens (V) | ZL1 | −1960 | −1390 |
|  | ZL2 | −1020 | −1300 |
| Quadrupole lens (V) | QL1x | 640 | → |
|  | OL1y | −640 | → |
|  | QL2x | −490 | → |
|  | QL2y | 490 | → |
|  | QL3x | 70 | → |
|  | QL3y | −70 | → |
| Irradiation size (µm) | x | 310 | 155 |
|  | y | 90 | 50 |

If the observation area is illuminated with an electron beam, a method in which a plurality of electron beams each having an area smaller than the observation area are scanned to illuminate the observation area can be used other than the method in which the observation area is illuminated with a rectangular or elliptic electron beam having an area covering the entire observation area. The number of beams is 1 to 1000, preferably 2 to 100, more preferably 4 to 40. A linear beam with two or more beams linked together may be scanned. In this case, by scanning the beam in a direction perpendicular to the long direction of the line, a wider area can be inspected with one scan. In this case, the CCD or TDI may be used for the detector. To form a linear beam, for example, an electron source of LaB6 is used, and the beam is made to pass through a linear slit in the optical system. Furthermore, a cathode with an electron source having a sharp and slender leading end may be used to form a linear beam. Furthermore, the stage is moved continuously or intermittently in at least one of directions of the XY plane during scan of the beam so that the entire inspection area is covered.

(2) Embodiment 6

FIG. 35 shows the configuration of a detection system using a relay lens. Secondary electrons made to form an image on the surface of an MCP (micro-channel plate) 35•1 in the secondary optical system are amplified according to a voltage applied to between the electron incidence surface and the emission surface of the MCP 35•1 while passing through a channel in the MCP 35•1. The structure and operation of the MCP 35•1 are well known, and thus are not described in detail here. In this embodiment, the pixel size on the MCP 35•1 is 26 µm, and the diameter of the channel in an effective area of 1024 pixels wide and 512 pixels long is 6 µm. Electrons amplified in the MCP 35•1 are emitted from the emission surface of the MCP 35•1, and enter a fluorescent screen 35•3 coated on an opposite glass plate 35•2 having a thickness of about 4 mm to generate fluorescence having an intensity consistent with the amount of electron signal. Since a thin transparent electrode is coated between the glass plate 35•2 and the fluorescent screen 35•3 and a voltage of about 2 to 3 kV is applied to between the electrode and the MCP emission surface, expansion of electrodes between the MCP and the fluorescent screen is restricted as much as possible to avoid the blur of the image. Further, since electrons emitted from the MCP 35•1 enter the fluorescent screen 35•3 with appropriate energy, luminous efficiency is improved. Furthermore, the materials of the transparent electrode and the glass plate 35•2 coated with the fluorescent screen 35•3 may be any materials as long as they allow light to pass efficiently.

A light intensity signal, into which an electric signal is converted on the fluorescent screen 35•3, passes through the glass plate 35•2, then through an optically transparent plate 35•4 insulating vacuum from the atmosphere, then through a relay lens 35•5 imaging light generated on the fluorescent screen 35•3, and enters a light receiving surface 35•6 of a CCD or TDI sensor placed at the imaging position. In this embodiment, the relay lens 35•5 has an imaging scale factor of 0.5, and a transmittance of 2%.

Light impinging on the light receiving surface 35•6 is converted into an electric signal by the CCD or TDI sensor, and the electric signal of the image is outputted to an uptake apparatus. The TDI sensor used in this embodiment has a pixel size of 13 μm, 2048 horizontal effective pixels, 144 integration stages, and 8 taps and a maximum line plate of 83 kHz, but a TDI sensor having a larger number of horizontal effective pixels and integration stages may be used in view of technological advance of the TDI sensor in the future. Furthermore, the structure and operation of the TDI sensor are known, and thus are not described in detail here.

In Table 4, the secondary electron emission current density, the secondary optical system imaging scale factor, the number of pixel incident electrons obtained when the TDI line rate is determined, the TDI gray scale pixel tone value and the stage speed in this embodiment are shown in the columns of the Embodiment 1.

TABLE 4

|  | Example 1 | Example 2 |
|---|---|---|
| Number of integration stages | 144 | 512 |
| Line rate (Hz) | 1.0E+04 | 3.0E+05 |
| Emission secondary electron current density (A/m$^2$) | 3.5 | 610 |
| Secondary optical system transmittance | 0.01 | 0.046 |
| Secondary optical system image scale | 260 | 320 |
| MCP aperture ratio | 0.6 | 0.6 |
| MCP gain | 1.8E+04 | 4.5E+01 |
| MCP output current (A) | 2.0E−0.6 | 2.0E−0.6 |
| Fluorescent screen light emission intensity (W) | 8.7E−06 | 8.7E−06 |
| Relay lens imaging scale factor | 0.5 | — |
| Relay lens transmittance | 0.02 | — |
| FOP magnification | — | 1 |
| FOP transmittance | — | 0.4 |
| Incident energy density (nJ/cm$^2$) | 0.079 | 0.004 |
| TDI Responsivity (DN/(nJ/cm$^2$)) | 246 | 9000 |
| Gray scale pixel tone value (DN) | 19.4 | 39.1 |
| Number of incident electrons per unit (electrons/pixel) | 18.9 | 448.3 |
| Stage speed (m/s) | 0.001 | 0.015 |

The full scale of the gray scale pixel tone value described here is 255 DN. This is due to the fact that the current MCP dynamic range is no more than 2 μA. An epoch-making improvement in MCP dynamic range cannot be currently expected, and therefore to obtain a certain pixel tone value, it is important that minimum 200 DN/(nJ cm$^2$) of TDI responsivity is ensured.

(3) Embodiment 7

FIG. 36 shows the configuration of a detection system using an FOP. The structure and operation of a fluorescent screen 36•1 and the like are the same as those of the embodiment 5. However, the effective area of an MCP 36•2 in this embodiment has a pixel size of 16 μm, which is equivalent to 2048 (wide)×512 (long) pixels. Unlike the embodiment 5, a fluorescent screen 36•1 is coated on an FOP (fiber optic plate) 36•3 having a thickness of about 4 mm, instead of the glass plate. A light intensity signal, into which an electric signal is converted at the fluorescent screen 36•1, passes through fibers of the FOP 36•3. The light emission surface of the FOP 36•3 is coated with a transparent electrode, and this provides a ground potential. Light emitted from the FOP 36•3 passes through another FOP 364 with the thickness of, for example, 3 mm contacting the FOP 36•3 with no gap therebetween, and enters the light receiving surface of a CCD or TDI sensor 36•5 placed on the light emission surface of the FOP 36•4 via an optically transparent adhesive. Since light is not scattered over fibers of the FOP, image quality is not significantly influenced if the pixel size of the CCD or TDI sensor 36•5 is sufficiently larger than the fiber diameter.

In this embodiment, the fiber diameter of the FOP is 6 μm, and the pixel size of the TDI sensor 36•5 is 16 μm. By making the incidence side and the emission side of the FOP have different fiber diameters, the magnification of the image can be changed, but this causes deformation and distortion to grow, and therefore the fiber diameters are the same in this embodiment. The transmittance is about 40% in this embodiment.

The CCD or TDI sensor 36•5 is placed under vacuum, and an electric signal 36•6 of the image, into which an optical signal is converted, is outputted to an uptake apparatus through a field through 36•7 insulating the atmosphere from vacuum.

The CCD or TDI sensor 36•5 may be placed under the atmosphere, and the atmosphere may be insulated from vacuum by the FOP, but in consideration of reduction in transmittance and growth of deformation with an increase in thickness of the FOP, such a configuration is less likely positively adopted.

The TDI sensor 36•5 used in this embodiment has a pixel size of 16 μm, 2048 horizontal effective pixels, 512 integration stages, and 32 taps and a maximum line plate of 300 kHz, but a TDI sensor having a larger number of horizontal effective pixels and integration stages may be used in view of technological advance of the TDI sensor in the future.

The secondary electron emission current density, the secondary optical system imaging scale factor, the number of pixel incident electrons obtained when the TDI line rate is determined, the TDI gray scale pixel tone value and the sage speed in this embodiment are shown in the columns of the embodiment 2 in Table 4.

(4) Embodiment 8

FIG. 37(A) schematically shows the configuration of a projection electron microscope type defect inspection apparatus EBI, and FIG. 37(B) schematically shows the configurations of a secondary optical system and a detection system of the defect inspection apparatus EBI. In FIG. 37, an electron gun 37•1 has a thermal electron emitting LaB$_6$ cathode 37•2 capable of operating under a large current, and primary electrons emitted in a first direction from the electron gun 37•1 pass through a primary optical system including a several-stage quadrupole lens 37•3 to have the beam shape adjusted, and then pass through a Wien filter 37•4. The traveling direction of primary electrons is changed to a second direction by the Wien filter 37•4 so that they are inputted to a sample W as an inspection object. Primary electrons leaving the Wien filter 37•4 and traveling in the second direction have the beam diameter reduced by an NA aperture plate 37•5, pass through an objective lens 37•6, and is applied to the sample W.

In this way, in the primary optical system, a high luminance electron gun made of $LaB_6$ is used as the electron gun 37•1, and thus making it possible to obtain a primary beam having a large current and a large area with low energy compared to the conventional scanning defect inspection apparatus. The electron gun 37•1 is made of $LaB_6$, has a truncated conic shape and a diameter of 50 μm or greater, and can extract electrons at an intensity of $1 \times 10^3$ $A/cm^2sr$ to $1 \times 10^8$ $A/cm^2sr$ at a primary electron draw voltage of 4.5 kV. The intensity is preferably $1 \times 10^5$ $A/cm^2sr$ to $1 \times 10^7$ $A/cm^2sr$ at 4.5 kV. The intensity is further preferably $1 \times 10^6$ $A/cm^2sr$ to $1 \times 10^7$ $A/cm^2sr$ at 10 kV. Furthermore, the electron gun 37•1 can also extract electrons at an intensity of $1 \times 10^6$ $A/cm^2sr$ to $2 \times 10^{10}$ $A/cm^2sr$ at a primary electron extraction voltage of 4.5 kV as a shot key type. The intensity is preferably $1 \times 10^6$ $A/cm^2sr$ to $5 \times 10^9$ $A/cm^2sr$ at 10 kV. Furthermore, a shot key type made of ZrO may be used for the electron gun 37•1.

The shape of an irradiation area in which primary electrons are applied to the sample W is approximately symmetric to two other orthogonal axes not including the optical axis of primary electrons, unevenness in illuminance of primary electrons in the area in which primary electrons are applied to the sample is 10% or less, preferably 5% or less, more preferably 3% or less, thus being very uniform. In this case, the beam shape may be used even if the shape is not approximately symmetric to two other orthogonal axes not including the optical axis of primary electrons as described above.

In this embodiment, the sample W is irradiated with a plane beam having the cross section formed into, for example, a rectangular shape of 200 μm×50 μm, thus making it possible to irradiate a small area having a predetermined area on the sample W. To scan the sample W with the plane beam, the sample W is placed on a high accuracy XY stage (not shown) accommodating, for example, 300 mm wafer, and two-dimensionally moved on the XY stage with the plane beam fixed. Furthermore, since it is not necessary to concentrate primary electrons onto a beam spot, the plane beam has a low current density, and the sample W is not significantly damaged. For example, the current density of the beam spot is 10 $A/cm^2$ to $10^4$ $A/cm^2$ in the conventional beam scanning defect inspection apparatus, while the current density of the plane beam is only 0.0001 $A/cm^2$ to 0.1 $A/cm^2$ in the defect inspection apparatus of FIG. 37. The current density is preferably 0.001 $A/cm^2$ to 1 $A/cm^2$. The current density is more preferably 0.01 $A/cm^2$ to 1 $A/cm^2$. On the other hand, the dose is $1 \times 10^{-5}$ $C/cm^2$ in the conventional beam scanning system, while it is $1 \times 10^{-6}$ $C/cm^2$ to $1 \times 10^{-1}$ $C/cm^2$ in the system of this embodiment, and the system of this embodiment has a higher sensitivity. The dose is preferably $1 \times 10^{-4}$ $C/cm^2$ to $1 \times 10^{-1}$ $C/cm^2$, further preferably $1 \times 10^{-3}$ $C/cm^2$ to $1 \times 10^{-1}$ $C/cm^2$.

The incident direction of the primary electron beam is basically the E direction of ExB 37•4, i.e. a direction of an electric field, the integration direction of the TDI and the direction of movement of the stage are made to match this direction. The incident direction of the primary electron beam may be the B direction, i.e. a direction in which a magnetic field is applied.

Secondary electrons, reflection electrons and back-scattered electrons are generated from the area of the sample W irradiated with primary electrons. First, for explanation of detection of secondary electrons, secondary electrons emitted from the sample W are magnified by the objective lens 37•6 and pass through the NA aperture plate 37•5 and the Wien filter 37•4 so as to travel in a direction opposite to the second direction, and are then magnified again by an intermediate lens 37•7, and further magnified by a projection lens 37•8 and enter a secondary electron detection system 37•9. In the secondary optical system 37•9 guiding secondary electrons, the objective lens 37•6, the intermediate lens 37•7 and the projection lens 37•8 are all high accuracy electrostatic lenses, and the magnification of the secondary optical system is variable. Primary electrons are made to impinge on the sample W at almost a right angle (±5 or less, preferably ±3 or less, more preferably ±1 or less), and secondary electrons are taken out at almost a right angle, so that shades by irregularities on the surface of the sample W never occur.

The Wien filter 37•4 is also called an ExB filter, has an electrode and a magnet, has a structure in which the electric field is orthogonal to the magnetic field, and has a function of bending primary electrons at, for example, 35° to the sample direction (direction perpendicular to the sample) while moving in a straight line at least one of the secondary electron, the reflection electron and the back-scattered electron from the sample.

The secondary electron detection system 37•9 receiving secondary electrons from the projection lens 37•8 comprises a micro-channel plate (MCP) 37•10 propagating incident secondary electrons, a fluorescent screen 37•11 converting electrons leaving the MCP 37•10 into light, and a sensor unit 37•12 converting light leaving the fluorescent screen 37•11 into an electric signal. The sensor unit 37•12 has a high sensitivity line sensor 37•13 comprised of a large number of solid imaging devices two-dimensionally arranged, fluorescence emitted from the fluorescent screen 37•11 is converted into an electric signal by the line sensor 37•13, the electric signal is sent to an image processing unit 37•14, and processed in parallel, in multistage and at a high speed.

While the sample W is moved to have individual areas on the sample W irradiated with a plane beam and scanned in order, the image processing unit 37•14 accumulate data about the XY coordinates and images of areas including defects one after another, and generate an inspection result file including the coordinates and images of all areas of the inspection object including defects for one sample. In this way, inspection results can be collectively managed. When this inspection result file is read, a defect distribution and a detailed defect list of the sample are displayed on a display of the image processing unit 12.

Actually, of various kinds of components of the defect inspection apparatus EBI, the sensor unit 37•12 is placed under an atmosphere, but other components are placed in a column kept under vacuum, and therefore in this embodiment, a light guide is provided on an appropriate wall surface of the column, and light emitted from the fluorescent screen 37•11 is taken out into the atmosphere via the light guide and passed to the line sensor 37•13.

Provided that the amount of electrons emitted from the sample W is 100%, the ratio of electrons that can reach the MCP 37•10 (hereinafter referred to as "transmittance") is expressed by the following equation:

transmittance (%)=(amount of electrons that can reach MCP 37•10)/(amount of electrons emitted from sample $W$)×100.

The transmittance depends on the aperture area of the NA aperture plate 37•5. As an example, a relation between the transmittance and the aperture diameter of the NA aperture plate is shown in FIG. 38. Actually, at least one of the secondary electron, the reflection electron and the backscattered electron generated from the sample reach the electron detection system D in the ratio of 200 to 1000 electrons per pixel.

The center of the image projected under magnification and formed on the detector, and the center of the electrostatic lens are on a common axis, the electron beam has the common axis as an optical axis between a deflector and the sample, and the optical axis of the electron beam is perpendicular to the sample.

FIG. 39 shows a specific example of the configuration of the electron detection system 37•9 in the defect inspection apparatus EBI of FIG. 37. A secondary electron image or reflection electron image 38•1 is formed on the incident surface of the MCP 37•10 by the projection lens 37•8. The MCP 37•10 has, for example, a resolution of 6 μm, a gain of $10^3$ to $10^4$, and 2100×520 active pixels, and propagates electrons according to the electron image 39•1 to irradiate the fluorescent screen 37•11. Consequently, fluorescence is emitted from areas of the fluorescent screen 37•11 irradiated with electrons, and the emitted fluorescence is discharged into the atmosphere via the light guide 39•2 of low deformation (e.g. 0.4%). The discharged fluorescence is made to enter the line sensor 37•13 via an optical relay lens 39•3. For example, the optical relay lens 39•3 has a magnification of ½, a transmittance of 2.3%, and a deformation of 0.4%, and the line sensor 37•13 has 2048×512 pixels. The optical relay sensor 39•3 forms an optical image 39•4 matching the electron image 39•1 on the incident surface of the line sensor 37•1. An FOP (fiber optic plate) may be used instead of the light guide 39•2 and the relay lens 39•3, and the magnification in this case is 1. Furthermore, if the number of electrons per pixel is 500 or greater, an MCP may be omitted.

The defect inspection apparatus EBI shown in FIG. 37 can be operated in one of a positive charge mode and a negative charge mode for secondary electrons by adjusting an acceleration voltage of the electron gun 37•1 and a sample voltage applied to the sample W and using the electron detection system 37•9. Further, by adjusting the acceleration voltage of the electron gun 37•1, the sample voltage applied to the sample W and objective lens conditions, the defect inspection apparatus EBI can be operated in a reflection electron imaging mode in which high energy reflection electrons emitted from the sample W by irradiation of primary electrons is detected. The reflection electrode has energy the same as the energy with which the primary electron enters the sample W, and has a higher level of energy than that of the secondary electron, and is therefore hard to be influenced by a potential by charge of the sample surface or the like. For the electron detection system, an electron impact detector such as an electron impact CCD or electron impact TDI outputting an electric signal matching the intensity of secondary electrons or reflection electrons may also be used. In this case, the MCP 37•10, the fluorescent screen 37•11 and the relay lens 39•3 (or FOP) are not used, but the electron impact detector is installed at the imaging position and used. This configuration enables the defect inspection apparatus EBI to operate in a mode suitable for the inspection object. For example, the negative charge mode or reflection electron imaging mode may be used to detect defects of metal wiring, defects of gate contact (GC) wiring or defects of a resist pattern, and the reflection electron imaging mode may be used to detect poor conduction of a via or residues on the bottom of the via after etching.

Figure 40B:
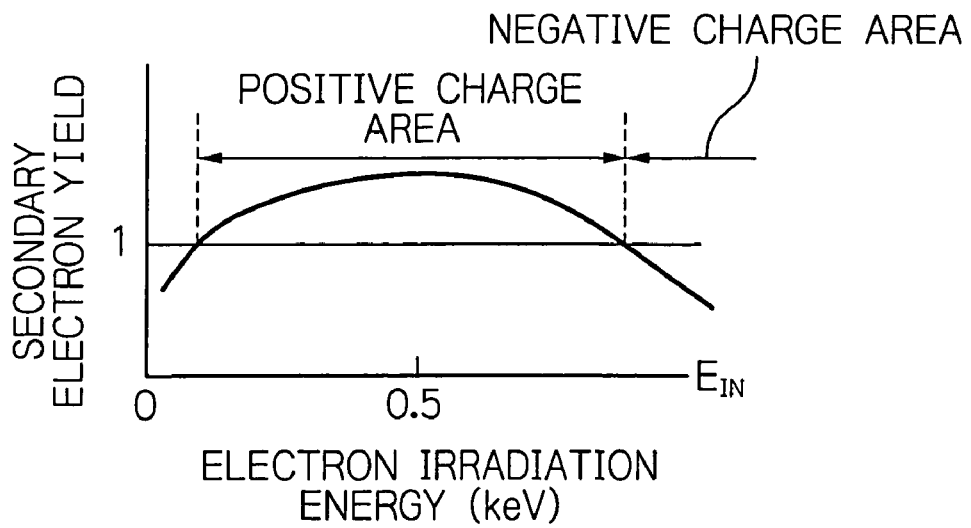

FIG. 40(A) illustrates requirements for operating the defect inspection apparatus EBI of FIG. 37 in the above three modes. The acceleration voltage of the electron gun 37•1 is $V_A$, the sample voltage applied to the sample W is $V_W$, irradiation energy of primary electrons when the sample is irradiated is $E_{IN}$, and signal energy of secondary electrons impinging upon the secondary electron detection system 37•9 is $E_{OUT}$. The electron gun 37•1 is configured so that the acceleration voltage $V_A$ can be changed, the variable sample voltage $V_W$ is applied to the sample W from an appropriate power supply (not shown). Then, if the acceleration voltage $V_A$ and the sample voltage $V_W$ are adjusted and the electron detection system 37•9 is used, the defect inspection apparatus EBI can operate in the positive charge mode in a range where a secondary electron yield is greater than 1, and operate in the negative charge mode in a range where the secondary electron yield is less than 1 as shown in FIG. 40(B). Furthermore, by setting the acceleration voltage $V_A$, the sample voltage $V_W$ and the objective lens conditions, the defect inspection apparatus EBI can use a difference in energy between the secondary electron and the reflection electron to distinguish between the two types of electrons, and thus can operate in the reflection electron imaging mode in which only reflection electrons are detected.

One example of values of $V_A$, $V_W$, $E_{IN}$ and $E_{OUT}$ for operating the defect inspection apparatus EBI in the reflection electron imaging mode, the negative charge mode and the positive charge mode will be described below.

Reflection Electron Imaging Mode $V_A$=−4.0 kV±1° V (preferably ±0.1°, more preferably ±0.01° or less).

$V_W$=−2.5 kV±1° V (preferably ±0.1°, more preferably ±0.01° or less).

$E_{IN}$=1.5 keV±1° V (preferably ±0.1°, more preferably ±0.01° or less).

$E_{out}$=4 keV or less.

Negative Charge Mode $V_A$=−7.0 kV±1V (preferably ±0.1V, more preferably ±0.01V or less).

$V_W$=−4.0 kV±1V (preferably ±0.1V, more preferably ±0.01V or less).

$E_{IN}$=3.0 keV±1V (preferably ±0.1V, more preferably ±0.01V or less).

$E_{out}$=4 keV+α (α: energy width of secondary electrons).

Positive Charge Mode $V_A$=−4.5 kV±1V (preferably ±0.1V, more preferably ±0.01V or less).

$V_W$=−4.0 kV±1V (preferably ±0.1V, more preferably ±0.01V or less).

$E_{IN}$=0.5 keV±1V (preferably ±0.1V, more preferably ±0.01V or less).

$E_{out}$=4 keV+α (α: energy width of secondary electrons).

As described above, principally, a fixed potential of 4 kV±10V (preferably 4 kV±1 V, more preferably 4 kV±0.01V or less) is applied as a potential $V_W$ for both the positive charge mode and negative charge mode in the case of the secondary electron mode. On the other hand, in the case of the reflection electron mode, the acceleration potential $V_A$ is set to 4 kV±10V (preferably 4 kV±1V, more preferably 4 kV±0.01V or less), and the sample potential $V_W$ is set to any potential lower than the acceleration potential of 4 kV or less. In this way, secondary electrons or reflection electrons as a signal impinge on the MCP as a detector with optimum energy of 4 keV±10 eV±α (preferably 4 keV±1 eV, more preferably 4 keV±0.01 eV).

The way of setting potentials described above corresponds principally to the case where energy of signal electrons made to pass through the secondary optical system is set to 4 keV, and an electron image on the sample surface is formed on the detector, and by changing this energy, the set potentials in the secondary electron mode and reflection electron mode can be changed to obtain an electron image appropriate to the type of sample. For the negative charge mode, an area of electron irradiation energy lower than that of a positive charge area of FIG. 40 (B) (e.g. 50 eV or less) can be used.

Actually, the detected amounts of secondary electrons and reflection electrodes vary with surface compositions of inspected areas on the sample W, pattern shapes and surface potentials. That is, the yield of secondary electrons and the mount of reflection electrons vary depending on the surface composition of the inspection object on the sample W, and the yield of secondary electrons and the amount of reflection electrons are greater in pointed areas or corners of the pattern than in plane areas. Furthermore, if the surface potential of the inspection object on the sample W is high, the amount of emitted secondary electrons decreases. In this way, the intensities of electron signals obtained from secondary electrons and reflection electrons detected by the detection system 37•9 vary with the material, the pattern shape and the surface potential.

2-3-3) E×B Unit (Wien Filter)

The Wien filter is a unit of an electromagnetic prism optical system having an electrode and a magnetic pole placed orthogonally to each other to orthogonalize an electric field and a magnetic field. If electric and magnetic fields are selectively provided, an electron beam impinging thereupon in one direction is deflected, and an electron beam impinging in a direction opposite thereto can create conditions in which effects of a force received from the electric field and a force received from the magnetic field are offset (Wien conditions), whereby a primary electron beam is deflected and applied onto a wafer at a right angle, and a secondary electron beam can travel in a straight line toward a detector.

The detailed structure of an electron beam deflection unit of an E×B unit will be described using FIG. 41 and FIG. 42 showing a longitudinal plane along the A—A line of FIG. 41. As shown in FIG. 41, a field of an electron beam deflection unit 41•2 of an E×B unit 41•1 has a structure in which an electric field and a magnetic field are orthogonalized in a plane perpendicular to the optical axis of a projection optical unit, i.e. E×B structure. Here, the electric field is generated by electrodes 41•3 and 41•4 each having a concave curved surface. The electric field generated by the electrodes 41•3 and 41•4 is controlled by control units 41•5 and 41•6, respectively. On the other hand, electromagnetic coils 41•7 and 41•8 are placed in such a manner that they are orthogonal to the electrodes 41•3 and 41•4 for generating electric fields, whereby magnetic fields are generated. Furthermore, the electrodes 41•3 and 41•4 for generating electric fields is point-symmetric, but they may be concentric.

In this case, to improve uniformity of the magnetic field, pole pieces having parallel and plain shapes are provided to form a magnetic path. The behavior of the electron beam in the longitudinal plane along the A—A line is as shown in FIG. 42. Applied electron beams 42•1 and 42•2 are deflected by electric fields generated by the electrodes 41•3 and 41•4 and magnetic fields generated by electromagnetic coils 41•7 and 41•8, and then enter the sample surface at a right angle.

Here, the position and angle at which the irradiation electron beams 42•1 and 42•2 enter the electron beam deflection unit 41•2 are uniquely determined when energy of electrons is determined. Further, control units 41•5, 41•6, 41•9 and 41•10 control electric fields generated by the electrodes 41•3 and 41•4 and magnetic fields generated by the electromagnetic coils 41•7 and 41•8 so that secondary electrons 42•3 and 42•4 travel in a straight line, i.e. the requirement for the electric field and magnetic filed of v×B=E is met, whereby secondary electrons travel in straight line through the electron beam deflection unit 41•2, and impinge on the projection optical system. Here, v represents the speed of the electron (m/s), B represents the magnetic field (T), e represents the amount of electric charge (C), and E represents the electric field (V/m).

Here, the E×B filter 41•1 is used for separation of primary electrons and secondary electrons, but the magnetic field can be used for the separation as a matter of course. Furthermore, only the electric field may be used to separate primary electrons and secondary electrons. Further, it may be used to separate primary electrons and reflection electrons as a matter of course.

Now, as the embodiment 9, an alteration example of the E×B filter will be described with reference to FIG. 43. FIG. 43 is a sectional view taken along a plane perpendicular to the optical axis. Four pairs of electrodes 43•1 and 43•2, 43•3 and 43•4, 43•5 and 43•6, and 43•7 and 43•8 for generating electric fields are formed by a nonmagnetic conductive material, are cylindrical as a whole, and are fixed with screws (not shown) on the inner surface of an electrode supporting barrel 43•9 made of insulating material, or the like. The axis of the electrode supporting barrel 43•9 and the axis of the cylinder formed by electrodes are made to match an optical axis 43•10. A groove 43•11 parallel to the optical axis 43•10 is provided on the inner surface of the electrode supporting barrel 43•9 between the electrodes 43•1 to 43•8. The area of the inner surface is coated with a conductive material 43•12, and set at an earth potential.

If a voltage proportional to "cos θ1" is given to the electrodes 43•3 and 43•5, a voltage proportional to "−cos θ1" is given to the electrodes 43•6 and 43•4, a voltage proportional to "cos θ2" is given to the electrodes 43•1 and 43•7, and a voltage proportional to "−cos θ2" is given to the electrodes 43•8 and 43•2 when electric fields are generated, almost uniform parallel electric fields can be obtained in an area equivalent to about 60% of the inner diameter of the electrode. The results of simulation of an electric filed distribution are shown in FIG. 44. Furthermore, four pairs of electrodes are used in this example, but uniform parallel electric fields can be obtained in an area equivalent to about 40% of the inner diameter even if a three pairs of electrodes are used.

Generation of magnetic fields is performed by placing two rectangular platinum alloy permanent magnets 43•13 and 43•14 in parallel outside the electrode supporting barrel 43•9. A raised portion 43•16 composed of a magnetic material is provided around the surfaces of the permanent magnets 43•13 and 43•14 on the optical axis 43•10 side. This raised portion 43•16 compensates for outward convex deformation of a magnetic line of flux on the optical axis side 43•10, and its size and shape can be determined by simulation analysis.

A yoke or magnetic circuit 43•15 made of ferromagnetic material is provided outside the permanent magnets 43•13 and 43•14 so that a channel situated opposite to the optical axis 43•10 of the magnetic line of flux by the permanent magnets 43•13 and 43•14 forms a barrel concentric with the electrode supporting barrel 43•9.

An E×B separator shown in FIG. 43 may be applied not only to the projection type electron beam inspection apparatus shown in FIG. 25-1 but also to a scanning electron beam inspection apparatus.

One example of the scanning electron beam inspection apparatus is shown in FIG. 25-2. An electron beam is applied from an electron gun 25•14 to a sample 25•15. A primary system electron beam passes through an E×B 25•16, but travels in a straight line with no deflection force exerted thereon at the time of incidence, is focused by an objective lens 25•17, and enters the sample 25•15 at almost a right angle. Electrons exiting from the sample 25•15 are guided to a detector 25•18 with a deflection force exerted thereon by the E×B 25•16. In this way, by adjusting an electric field and a magnetic field of the E×B 25•16, one of charged particle beams of the primary system and the secondary system can be made to travel in a straight line, with the other traveling in a straight line in any direction.

Furthermore, if the E×B 25•16 is used, the deflection force is exerted to cause an aberration in a direction of deflection, and therefore an E×B deflector may be further provided between the electron gun 25•14 of the primary system optical system and the E×B 25•16 for correcting the aberration. Furthermore, for the same purposes, the E×B detector may be further provided between the detector 25•18 of the secondary system and the E×B 25•16.

In the scanning electron beam inspection apparatus or scanning electron microscope, finely focusing with the primary system electron beam leads to an improvement in resolution and therefore generally, the primary system electron beam is made to travel in a straight line as shown in FIG. 25•2 with no excessive reflection force exerted on the primary electron beam, and the secondary beam is deflected. However, if conversely, it is more preferable that the primary beam is deflected and the secondary beam is made to travel in a straight line, such a configuration may be adopted. Similarly, in the projection type electron beam inspection apparatus, it is generally preferable that a deflection force causing no aberration is not given to the secondary beam to match imaging areas on the sample with pixels on a CCD of the detector. Thus, generally, the primary beam is deflected and the secondary beam is made to travel in a straight line as shown in FIG. 25-1, but if it is more preferable that the primary beam is made to travel in a straight line and the secondary beam is deflected, such a configuration may be adopted.

Furthermore, the intensities of the electric field and the magnetic field of E×B may be set differently for each mode of the secondary electron mode and the reflection electron mode. The intensities of the electric field and the magnetic field can be set so that an optimum image can be obtained for each mode. When it is not required that the set intensity should be changed, the intensity may be kept a constant level as a matter of course.

As apparent from the above description, according to this example, both the electric field and magnetic field can take uniform areas sufficiently around the optical axis, and the irradiation range of the primary electron beam is expanded, the aberration of the image made to pass the E×B separator can be kept at an uninfluential level. Furthermore, since the raised portion 43•16 is provided in the periphery of the magnetic pole forming the magnetic field, and the magnetic pole is provided outside an electric field generating electrode, a uniform magnetic field can be generated, and deformation of the electric field by the magnetic pole can be reduced. Furthermore, since a permanent magnet is used to generate the magnetic field, the overall E×B separator can be contained in a vacuum. Further, the electric field generating electrode and a magnetic path forming magnetic circuit have concentric cylindrical shapes having an optical axis as a central axis, whereby the overall E×B separator can be downsized.

2-3-4) Detector

A secondary electron image from a wafer, which is formed in the secondary optical system, is first amplified by a micro-channel plate (MCP), then enters a fluorescent screen, and is converted into an optical image. As principle of the MCP, several millions to several tens of millions of very slender conductive glass capillaries each having a diameter of 1 to 100 μm and a length of 0.2 to 10 mm, preferably a diameter of 2 to 50 μm and a length of 0.2 to 5 mm, more preferably a diameter of 6 to 25 μm and a length of 0.24 to 1.0 mm are bundled together to form a thin plate, and by applying a predetermined voltage thereto, each of capillaries acts as an independent secondary electron amplifier, and a secondary electron amplifier is formed as a whole. The image converted into light by this detector is projected on the TDI-CCD in a ratio of 1:1 in an FOP system placed under the atmosphere via a vacuum transparent window.

Now, the operation of the electro-optical apparatus having the configuration described above will be described. As shown in FIG. 25-1, a primary electron beam emitted from the electron gun 25•4 is converged by the lens system 25•5. The converged primary electron beam is made to enter the E×B-type deflector 25•6, deflected so as to irradiate the surface of the wafer W at a right angle, and made to form an image on the surface of the wafer W by the objective lens system 25•8.

Secondary electrons emitted from the wafer by irradiation of the primary electron beam are accelerated by the objective lens 25•8, enters the E×B-type deflector 25•6, and travels though the deflector in a straight line, and is guided through the lens system 25•10 of the secondary optical system to the detector 25•11. The secondary electrons are then detected by the detector 25•11, and a detection signal thereof is sent to the image processing unit 25•12. Furthermore, a high voltage of 10 to 20 kV is applied to the objective lens 25•7, and the wafer is placed.

Here, if the wafer W has the via 25•13, the electric field of the electron beam irradiation surface of the wafer is 0 to −0.1 V/mm (− indicates a high potential at the wafer W side) provided that the voltage given to the electrode 25•8 is −200 V. In this state, no discharge occurs between the objective lens system 25•7 and the wafer W, and the defect inspection for the wafer W can be performed, but efficiency of detection of secondary electrons is slightly reduced. Thus, a series of operations for irradiating an electron beam to detect secondary electrons are carried out, for example, four times, the obtained detection results of the four time operations are subjected to processing such as cumulative addition and averaging to obtain a predetermined detection sensitivity.

Furthermore, when the wafer has no via 25•13, no discharge occurs between the objective lens 25•7 and the wafer, and defect inspection for the wafer can be performed even if the voltage given to the electrode 25•8 is +350 V. In this case, secondary electrons are converged by the voltage given to the electrode 25•8, and are further converged by the objective lens 25•7, and thus efficiency of detection of secondary electrons in the detector 25•11 is improved. Accordingly, the speed of processing as a wafer defect apparatus is enhanced, and inspection can be carried out in high throughput.

2-3-5) Power Supply

A power supply unit of the apparatus is mainly comprised of a direct current high voltage precision power supply having about several hundreds output channels for control of electrodes, and has its supply voltage varied depending on the role of the electrode and the positional relation. In view of demands on resolution and accuracy of images, the power supply unit is required to have stability in the order of several 100 ppm or less, preferably 20 ppm or less, more preferably several ppm or less with respect to the set value. To minimize variations of the voltage with time and temperature, noise ripples and the like as factors impairing stability, and some contrivance is made for a circuit system, selection of parts and implementation.

Types of power supplies other than electrodes include a heating constant current source for a heater, a high-voltage and high-speed amplifier for two-dimensionally deflecting a beam to confirm aligning of the beam near the center of an aperture electrode when the primary beam is centered, a heating constant current source for a heater, a constant current source for an electromagnetic coil for E×B as an energy filter, a retarding power supply for applying a bias to a wafer and a power supply generating a potential for adsorbing a wafer to an electrostatic chuck, a high-voltage and high-speed amplifier for making an EO (electron optical) correction, and an MCP power supply amplifying electrons with principle of a photomultiplier.

FIG. 45 shows the overall configuration of the power supply unit. In this figure, an electric power is supplied to an electrode of a column portion 45•1 through a connection cable from a power supply rack 45•2 and high-speed and high-voltage amplifiers 45•3, 45•4 and 45•5, although not shown in the figure. The high-speed and high-voltage amplifiers 45•3 to 45•5 are broadband amplifiers, and deal with signals of high frequencies (DC-MHz), and therefore they are placed near the electrode to prevent an increase in electrostatic capacity of a cable in order to inhibit property degradation and an increase in power consumption due to the electrostatic capacity of the cable. An correction signal is outputted from an EO correction 45•6, and converted into an voltage having a phase and a magnitude matching a vector value for each electrode of an octupole at an octupole conversion unit 45•7, and the voltage is inputted to the high-speed and high-voltage amplifier 45•4, amplified, and then supplied to an electrode included in a column.

An AP image acquisition block 45•8 has a role as an auxiliary function such that a serrate wave is generated from the AP image acquirement block 45•8 to ensure centering of a beam near the center of an aperture electrode when a primary beam is centered, and applied to a deflection electrode of the column portion 45•1 by the high-speed and high-voltage amplifier. The beam is two-dimensionally deflected, whereby the magnitude of a beam current received at the aperture electrode is related to the position, and an image is displayed to set the beam position to the mechanical central position.

An AF control 46•9 achieves a function such that a voltage corresponding to the best focal condition measured in advance is stored in a memory, the value of the voltage is read according to the stage position, the voltage is converted into an analog voltage by a D/A converter, the voltage is applied a focus adjustment electrode included in the column portion 45•1 through the high-speed and high-voltage amplifier 45•5, and an observation is made while maintaining the optimum focus position.

The direct current high voltage precision power supply having about several hundreds output channels for control of voltages, comprised of power supply groups 1 to 4, is housed in the power supply rack 45•2. The power supply rack 45•2 constitutes a system capable of receiving commands from a CPU unit 45•13 by means of a communication card 45•11, an optical fiber communication 45•12 having electric insulation quality to ensure safety and prevent occurrence of a grand loop to prevent entrance of noises, and the like, by a control communication unit 45•10, and sending a status such as abnormality of power supply apparatus. A UPS 45•14 prevents destruction of apparatus, abnormal discharges, risks to human bodies and the like caused by overrunning of the system when control abnormality occurs due to service interruption and unexpected power blockage. A power supply 45•15 is a power reception unit of the main body, and is configured so that safety cooperation can be achieved as an overall inspection apparatus including interlock, current limitation and the like.

The communication card 45•11 is connected to a data bus 45•16 and an address bus 45•17 of the control CPU unit 45•13, so that real time processing can be carried out.

FIG. 46 shows one example of the circuit configuration of a static high voltage unipolar power supply (for lens) for a circuit system where a static DC of several hundreds to several tens kilovolts is produced. In FIG. 46, a signal source 46•1 is caused to generate an alternating current voltage having a frequency providing an optimum magnetic permeability of a trans 46•2, and the voltage is made to pass through a multiplier 46•3, and then guided to a drive circuit 46•4 to generate a voltage having an amplitude several tens to several hundreds times greater by the trans 46•2. A cock craft walten circuit 46•5 is a circuit increasing a voltage while performing rectification. By combination of the trans 46•2 and the cock craft walten circuit 46•5, a desired DC voltage is obtained, and by a low pass filter 56•6, further flatness is achieved to reduce ripples and noises. A high-voltage output is divided according to the resistance ratio of output voltage detection resistances 46•7 and 46•8 to obtain a voltage within a range of voltages capable of being dealt with by a usual electronic circuit. Because stability of this resistance mostly determines voltage accuracy, elements excellent in temperature stability, long term variations and the like are used, and in view of the fact that the division ratio is especially important, measures are taken such that a thin film is formed on the same insulation substrate, or resistance elements are brought into close contact with one another so that the temperature does not vary.

The result of the division is compared to the value of a reference voltage generating D/A converter 46•10 by a calculation amplifier 46•9, and if there is a difference, the output of the calculation amplifier 46•9 is increased or decreased, and an AC voltage having an amplitude matching the value thereof is outputted from the multiplier 46•3 to form a negative feedback. Although not shown in the figure, the output of the calculation amplifier 46•9 is made to be unipolar, or the quadrant of response of the multiplier 46•3 is limited to prevent saturation. The calculation amplifier 46•9 requires a very large amplification gain (120 dB or greater), and is mostly used in an open loop as an element, and therefore a low noise operation amplifier is used. The reference voltage generating D/A converter 46•10 requires stability equivalent to or higher than that of the output voltage detection resistances 46•7 and 46•8 in terms of accuracy. To generate this voltage, a reference IC having a constant voltage diode using a hand gap combined with a thermostabilization feature using a heater (not shown) is often used, but a Peltier element is used instead of the heater so that thermostability can be further improved. Furthermore, the Peltier element may be used in a single or multi-stage for thermostabilization of the output voltage detection resistances 46•7 and 46•8.

FIG. 47 shows one example of the circuit configuration of a static bipolar power supply (for aligner or the like). The basic concept is such that V5 and V6 are generated with a power supply equivalent to that of the circuit of FIG. 46, and the voltages are used to input command values from a component 47•1 to a linear amplifier constituted by components 47•1 to 47•6 to form a bipolar high-voltage power supply. Generally, the calculation amplifier 47•2 operates at around ±12 V, and therefore although not shown in the figure, amplification circuits by discrete elements are required between the component 47•2 and the components 47•5 and 47•6 to amplify the voltage from ±several volts to ±several hundreds to several thousands volts. Notices about characteristics required for the components 47•1 to 47•4 are the same as those described with the circuit of FIG. 46.

FIGS. 48 to 50 each show an example of a circuit of a special power supply, and FIG. 48 shows an example of a circuit for a heater and a gun, which is constituted by components 48•1 to 48•4. A voltage source 48•1, a resistance 48•3 and a power supply 48•4 are superimposed on a bias voltage source 48•2. The power supply 48•4 for a heater is constituted by a constant current source, the value of an actually passing current is detected by the resistance 48•3, and although not shown in the figure, the value is temporarily digitized, isolated with optical fibers or the like, and sent to the control communication unit 45•10. For the setting of the voltage value of the voltage source 48•1, the current value of the power supply 48•4 and the like, the value from the control communication unit 45•10 is inversely converted in the same principle, and the value is set for an actual power setting unit.

FIG. 49 shows an example of a power supply circuit for an MCP, which is comprised of voltage sources 49•1 and 49•2, relay circuits 49•3 and 49•4, and current detection circuits 49•5, 496 and 49•7. A terminal MCP1 makes measurements from several Pas for measurement of the value of a current passing into the MCP, and is thus required to have a strict shield structure to prevent entrance of leaked currents and noises. A terminal MCP2 includes current measurement after amplification by the MCP, and can calculate an amplification gain from the ratio of values of currents passing through the resistances 49•6 and 49•7. The resistance 49•5 measures a current on a fluorescent screen. Measurement and setting at the superimposed portion are the same as those at the heater and gun.

FIG. 50 shows an example of a circuit of a constant current source for an E×B magnetic field coil constituted by components 50•1 and 50•2, which generally outputs a current of several hundred mA. Stability of the magnetic field as an energy filter is important, and stability in the order of several ppm is required.

FIG. 51 shows one example of a power supply for a retarding and electrostatic chuck, which is constituted by components 51•1 to 51•9. A power supply similar to the static bipolar power supply (for aligner) of FIG. 46 is superimposed on a bias power supply (for retarding) 51•10. Measurement and setting at the superimposed portion are the same as those at the heater and gun (FIG. 48).

FIG. 52 shows one example of the hardware configuration of an EO correcting deflection electrode, which is constituted by components 52•1 to 52•7. An correction signal is inputted to an octupole conversion unit 52•4 from an X axis EO correction 52•1 and a Y axis EO correction 52•2, and an output after conversion is sent to a high-speed amplifier 52•5. The voltage is amplified from several tens of volts to several hundreds of volts by the high-speed amplifier 52•5, and then applied to EO correction electrodes 52•6 situated at angular intervals of 45°. A ΔX correction 52•3 is an input for fine correction such as correction of mirror bend, and is added to an X signal within the octupole conversion unit 52•4.

FIG. 53 shows one example of the circuit configuration of the octupole conversion unit, which performs vector operation from signals 53•2, 53•3, 53•4 and 53•5 for electrodes 53•1 situated at angular intervals of 45° other than X and Y axes, and generate equivalent voltages. The example of operation in this case uses values described at components 53•6, 53•7, 53•8 and 53•9. This can be achieved by an analog resistance network, or read of the table by a ROM when components 53•6 to 53•9 are digital signals.

FIG. 54 shows one example of a high-speed and high voltage amplifier, which is constituted by components 54•1 to 54•11. An example of a waveform during output of a short wave is shown in FIG. 54(B). In this example, Power Operation Amplifier PA 85A manufactured by APEX Co., Ltd. (U.S.A) is used to form an amplifier, and a bandwidth covering a mega-band, an output range of about ±200 V, and a through rate larger than about 1000 V/μs can be achieved, thus achieving dynamic characteristics required for the high-speed and high-voltage amplifier.

2-4) Precharge Unit

As shown in FIG. 13, the precharge unit 13•9 is placed in proximity to the column 13•38 of the electro-optical apparatus 13•8 in the working chamber 13•16. This inspection apparatus is a type of apparatus irradiating an electron beam to a substrate as an inspection object, i.e. a wafer to inspect a device pattern or the like formed on the wafer surface, and therefore information of secondary electrons or the like generated by irradiation of the electron beam is used as information of the wafer surface, but the wafer surface may be charged (charge-up) depending on conditions of a wafer material, energy of irradiation electrons and the like. Further, strongly charged sites and weakly charged sites may appear on the wafer surface. Unevenness in charge amount on the wafer surface causes unevenness in information of secondary electrons, thus making it impossible to obtain precise information.

Thus, in the embodiment of FIG. 13, a precharge unit 13•9 having a charged particle irradiation unit 13•39 is provided to prevent such unevenness. Before inspection electrons are directed to predetermined sites of the wafer to be inspected, charged particles are irradiated from the charged particle irradiation unit 13•39 of the precharge unit 13•9 to eliminate charge unevenness. For the charge-up on the wafer surface, an image on the wafer surface as an inspection object is formed in advance, and the image is evaluated to perform detection, and the precharge unit 13•9 is operated based on the detection. Furthermore, in this precharge unit 13•9, the focus of a primary electron beam may be shifted, i.e. the beam shape may be blurred to irradiate the wafer.

FIG. 55 shows main parts of the first embodiment of the precharge unit 13•9. Charged particles 55•1 are applied from a charged particle irradiation beam source 55•2 to the sample substrate W while being accelerated by a voltage set by a bias power supply 55•3. An inspection subject area 55•4 is an area already subjected to charged particle irradiation as preprocessing together with an area 55•5. An area 55•6 is one being irradiated with charged particles. In this figure, the sample substrate W is scanned in a direction shown by an arrow in the figure, but if the sample substrate W is scanned to and fro, another charged particle beam source 55•7 is placed on the opposite side of a primary electron beam source, and the charged particle beam sources 55•2 and 55•7 are turned on and off alternately in synchronization with the scan direction of the sample substrate W as shown by a dotted line in the figure. In this case, if energy of charged particles is too high, the yield of secondary electrons from an insulation portion of the sample substrate W exceeds 1, and thus the surface is positively charged, and even if the yield is 1 or less, the phenomenon is implicated if secondary electrons are generated to reduce irradiation efficiency, and therefore it is effective to set the voltage to a landing voltage of 100 eV or less (ideally a voltage of 0 eV to 30 eV) at which generation of secondary electrons is rapidly reduced.

FIG. 56 shows the second embodiment of the precharge unit 13•9. In this figure, a type of irradiation beam source irradiating an electron beam 56•1 as a charged particle beam is shown. The irradiation beam source is comprised of a hot filament 56•2, an anode electrode 56•3, a shield case 56•4, a filament power supply 56•5 and an anode power supply 56•6. The anode 56•3 is provided with a slit having a thickness of 0.1 mm, a width of 0.2 mm and a length of 1.0 mm, and the positional relation between the anode 56•3 and the filament (thermal electron emission source) 56•2 is a form of a three-pole electron gun. The shield case 56•4 is provided with a slit having a width of 1 mm and a length of 2 mm, and is situated at a distance of 1 mm from the anode 56•3, and is assembled so that the slit centers of the shield case 56•4 and the anode 56•3 match each other. The material of the filament is tungsten (W), which is current-heated at 2A, so that an electron current of several microamperes is obtained at an anode voltage of 20 V and a bias voltage of 30 V.

The example shown here is only one example and, for example, the material of the filament (thermal electron emission source) may be a metal having a high melting point such as Ta, Ir or Re, thoria coat W, an oxide cathode or the like, and the filament current varies depending on the material, the line diameter and the length as a matter of course. Furthermore, other types of electron guns can be used as long as appropriate values can be set for the electron beam irradiation area, the electron current and energy.

FIG. 57 shows the third embodiment of the precharge unit 13•9. A type of irradiation beam source irradiating ions 57•1 as a charged particle beam is shown. This irradiation beam source is comprised of a filament 57•2, a filament power supply 57•3, an emission power supply 57•4 and an anode shield case 57•5, and an anode 57•6 and the shield case 57•5 are provided with slits having the same size of 1 mm×2 mm, and are assembled so that the centers of both slits match each other at intervals of 1 mm. Ar gas 57•8 is introduced up to about 1 pa into the shield case 57•5 through a pipe 57•7, and the shield case 57•5 is operated in an arc discharge type by the hot filament 57•2. The bias voltage is set to a positive value.

FIG. 58 shows the case of a plasma irradiation process as the fourth embodiment of the precharge unit 13•9. Its structure is the same as that of FIG. 57. It is operated in an arc discharge type by the hot filament 57•2 in the same manner as described above, but by setting the bias voltage to 0 V, plasma 58•1 is leaked through the slit by a gas pressure and applied to the sample substrate. In the case of plasma irradiation, both positive and negative surface potentials on the surface of the sample substrate can be brought close to 0 because of the group of particles having both positive and negative charges compared to other processes.

The charged particle irradiation unit placed in proximity to the sample substrate W has a structure shown in FIGS. 55 to 58. In those figures, charged particles 55•1 are irradiated under appropriate conditions so that the surface potential is 0 for a difference in surface structure of the sample substrate, such as an oxide film and a nitride film and each of sample substrates in different fabrication steps. After the sample substrate is irradiated under optimum irradiation conditions, i.e. the potential of the surface of the sample substrate W is equalized or neutralized with charged particles, an image is formed with electron beams 55•8 and 55•9 and defects are detected.

As described above, in this embodiment, deformation of a measurement image with charge does not occur or deformation is very little if any owing to processing just before measurement by irradiation of charged particles, thus making it possible to measure defects correctly. Furthermore, since the stage can be scanned by application of a large current (e.g. 1 µA to 20 µA, preferably 1 µA to 10 µA, more preferably 1 µA to 5 µA), which has caused problems if used, a large amount of secondary electrons are emitted from the surface of the wafer, and therefore a detection signal having a good S/N ratio (e.g. 2 to 1000, preferably 5 to 1000, more preferably 10 to 100) is obtained, resulting in an improvement in reliability of defect detection. Furthermore, because of the high S/N ratio, satisfactory image data can be created even if the stage is scanned at a higher speed, thus making it possible to increase throughput of inspection.

FIG. 59 schematically shows an imaging apparatus comprising the precharge unit according to this embodiment. This imaging apparatus 59•1 comprises a primary optical system 59•2, a secondary optical system 59•3, a detection system 59•4, and charge controlling means 59•5 for equalizing or reducing charges with which an imaging object is electrified. The primary optical system 59•2 is an optical system irradiating an electron beam to an inspection object W (hereinafter referred to as object), and comprises an electron gun 59•6 emitting electron beams, an electrostatic lens 59•8 collecting a primary electron beam 59•7 emitted from the electron gun 59•6, a Wien filter or E×B deflector 59•9 deflecting the primary electron beam so that its optical axis is perpendicular to the surface of the object, and an electrostatic lens 59•10 collecting the electron beam. They are placed in descending order with the electron gun 59•6 situated at the uppermost position, and in such a manner that the optical axis of the primary electron beam 59•7 emitted from the electron gun is slanted with respect to a line vertical to the surface of the object W (sample surface), as shown in FIG. 59. The E×B deflector 59•9 is comprised of an electrode 59•11 and an electromagnet 59•12.

The secondary optical system 59•3 comprises an electrostatic lens 59•3 placed on the upper side of the E×B deflector 49•9 of the primary optical system. The detection system 59•4 comprises a combination 59•15 of a scintillator and a micro-channel plate (MCP) converting secondary electrons 59•14 into a light signal, a CCD 59•16 converting the light signal into an electric signal, and an image processing apparatus 59•17. The structure and the function of the primary optical system 59•2, the secondary optical system 59•3 and the detection system 59•4 are the same as those of the conventional technique, and therefore detailed descriptions thereof are not presented.

In this embodiment, the charge controlling means 59•5 for equalizing or reducing charges with which the object is electrified comprises an electrode 59•18 placed close to the object W between the object W and the electrostatic lens 59•10 of the primary optical system 59•2 closest to the object W, a changeover switch 59•19 electrically connected to the electrode 59•18, a voltage generator 59•21 electrically connected to one terminal 59•20 of the changeover switch 59•19, and a charge detector 59•23 electrically connected to the other terminal 59•22 of the changeover switch 59•19. The charge detector 59•23 has a high impedance. The charge reducing means 59•5 further comprises a grid 59•24 placed between the electron gun 59•6 of the primary optical system 59•2 and the electrostatic lens 59•8, and a voltage generator 59•25 electrically connected to the grid 59•24. A timing generator 59•26 indicates operation timing to the CCD 59•16 and image processing apparatus 59•17 of the detection system 59•4, the changeover switch 59•19 of the charge reducing means 59•5, the voltage generator 59•21 and the charge detectors 69•23 and 59•25.

The operation of the electron beam apparatus having the configuration described above will now be described. The primary electron beam 59•7 emitted from the electron gun 59•6 passes through the electrostatic lens 59•8 of the primary optical system 59•2 to reach the E×B deflector 59•9, and is deflected so as to be perpendicular to the surface (object surface) WF of the object W by the E×B deflector 59•9, and applied to the surface of the object W through the electrostatic lens 59•10. The secondary electrons 59•14 are emitted from the surface WF of the object W according to properties of the object. The secondary electrons 59•14 are sent through the electrostatic lens 59•13 of the secondary optical system 59•3 to the combination 59•15 of a scintillator and an MCP of the detection system 59•4, and converted into light by the scintillator, the light is subjected to photoelectric conversion by the CCD 59•16, and the converted electric signal causes the image processing apparatus 59•17 to form a two-dimensional image (having a gray scale). Furthermore, as in the case of this normal type of inspection apparatus, the primary electron beam to be irradiated to the object can be applied to entire required sited on the object surface WF to collect data of the object surface by scanning the primary electron beam with well known deflecting means (not shown), or moving a table T supporting the object in the two-dimensional direction of X and Y, or by combination thereof.

A charge is generated near the surface of the object W with the primary electron beam 59•7 applied to the object W, and the object W is positively charged. As a result, the secondary electrons 59•14 generated from the surface WF of the object W have the path changed according to the situation of the charge by the Coulomb force. As a result, the image formed in the image processing apparatus 59•17 is deformed. The charge of the object surface WF varied with the properties of the object W, and therefore if the wafer is used as an object, the charge is not the same on the same wafer, and varies with time. Thus, when patterns at two sites on the wafer are compared, defect detection may occur.

Thus, in this embodiment according to the present invention, utilizing spare time after the CCD 59•16 of the detection system 59•4 captures an image equivalent to one scan, the charge amount of the electrode 59•18 placed near the object W is measured by the charge detector 59•23 having a high impedance. A voltage for irradiating electrons appropriate to the measured charge amount is generated by the voltage generator 59•21, the changeover switch 59•19 is operated to connect the electrode 59•18 to the voltage generator 59•21 after the measurement, and the voltage generated by the voltage generator is applied to the electrode 59•18 to offset the charge. In this way, no deformation occurs in the image formed in the image processing apparatus 59•17. Specifically, when a usual voltage is given to the electrode 59•18, a converged electron beam is applied to the object W, but if a different voltage is given to the electrode 59•18, focusing conditions are significantly shifted, a large area expected to be charged is irradiated in a small current density, and the positive charge of the positively charged object is neutralized, whereby the voltage of the large area expected to be charged can be equalized to a specific positive (negative) voltage, or the charge is equalized and reduced, whereby a lower positive (negative) voltage (including zero volt) can be achieved. The operation for offsetting the charge is carried out for each scan.

The Wenelt electrode or grid 59•24 has a function to stop the electron beam applied from the electron gun 59•6 in timing of spare time so that the measurement of the charge amount and the operation for offsetting the charge are carried out with stability. Timing of the above operation, which is indicated by the timing generator 59•26, is for example timing shown in the timing chart of FIG. 60. Furthermore, if the wafer is used as an object, the charge amount varies depending on the position of the wafer, and therefore a plurality of pairs of electrodes 59•18, changeover switches 59•19, voltage generators 59•21 and charge detectors 59•23 can be provided in the scanning direction of the CCD and fractionalized to perform more accurate control.

According to this embodiment, the following effects can be exhibited.

(1) Deformation of the image occurring due to charge can be reduced irrespective of the properties of the inspection object.

(2) Because charge is equalized and offset utilizing spare time in measurement time in the conventional process, the throughput is not affected at all.

(3) Because processing can be carried out in real time, time for post-processing, a memory and the like are not required.

(4) Observation of the image and detection of defects can be performed at a high speed and with high accuracy.

FIG. 61 shows the outlined configuration of a defect inspection apparatus comprising a precharge unit according to another embodiment of the present invention. This defect inspection apparatus comprises the electron gun 59•6 emitting a primary electron beam, the electrostatic lens 59•8 deflecting and shaping the emitted primary electron beam, a sample chamber 61•1 capable of being evacuated by a pump (not shown), a stage 61•2 situated in the sample chamber and capable of moving in a horizontal plane with a sample such as a semiconductor wafer W placed thereon, the electrostatic lens 59•13 of a projection system map-projecting a secondary electron beam and/or a reflection electron beam emitted from the wafer W by irradiation of the primary electron beam under predetermined magnification to form an image, a detector 61•3 detecting the formed image as a secondary electron image of the wafer, and a control unit 61•4 controlling the entire apparatus and detecting defects of the wafer W based on the secondary electron image detected by the detector 61•3. Furthermore, not only secondary electrons but also reflection electrons contribute to the secondary electron image described above, but the image is referred to as a secondary electron image herein.

In the sample chamber 61•1, a UV lamp 61•5 emitting a light beam in a wave range including ultraviolet light is placed above the wafer W. The glass surface of this UV lamp 61•5 is coated with a photoelectron emission material 61•6 emitting photoelectrons e⁻ resulting from a photoelectronic effect by the light beam emitted from the UV lamp 61•5. The UV lamp 61•5 may be any light source emitting a light beam in a wave range having a capability of emitting photoelectrons from the photoelectron emission material 61•6. Generally, a low pressure mercury lamp emitting ultraviolet light of 254 nm is advantageous in terms of a cost. Furthermore, the photoelectron emission material 61•6 may be any material as long as it has a capability of emitting photoelectrons and for example, Au or the like is preferable.

The photoelectron described above has energy different from that of the primary electron beam, i.e. energy lower than that of the primary electron beam. Here, the low energy refers to the order of several electron volts to several tens of electron volts, preferably 0 to 10 eV. The present invention can use any means for generating electrons of such low energy. For example, a low energy electron gun (not shown) may be provided in place of the UV lamp 61•5.

Further, in the case where energy of the electron gun is controlled, the defect inspection apparatus of this embodiment comprises a power supply 61•7. The negative pole of this power supply 61•7 is connected to the photoelectron emission material 61•6, and the positive pole is connected to the stage 61•2. Thus, the photoelectron emission material 61•6 has a negative voltage applied thereto with respect to the voltage of the stage 61•2 and the wafer W. Energy of the low energy electron beam can be controlled with the predetermined voltage.

The detector 61•3 may have any configuration as long as the secondary electron image formed by the electrostatic lens 59•13 can be converted into a signal capable of being subjected to post-processing. For example, as shown in FIG. 62 in detail, the detector 61•3 may comprise a micro-channel plate (MCP) 62•1, a fluorescent screen 62•2, a relay optical system 62•3, and an imaging sensor 62•4 constituted by a large number of CCD elements. The micro-channel plate 62•1 has a large number of channels in a plate, and further generates a large number of electrons while secondary electrons or reflection electrons made to form an image by the electrostatic lens 59•13 pass through the channels. That is, it amplified secondary electrons. The fluorescent screen 62•2 converts secondary electrons into light by emitting fluorescence by amplified secondary electrons. The relay lens 62•3 guides the fluorescence to the CCD imaging sensor 62•4, and the CCD imaging sensor 62•4 converts the intensity distribution of secondary electrons on the surface of the wafer W into an electric signal or digital image data for each element and outputs the same to the control unit 61•4.

The control unit 61•4 may be constituted by a general personal computer 61•8. The computer 61•8 comprises a control unit main body 61•9 performing various kinds of control and computation processing according to a predetermined program, a CRT 61•10 displaying the result of processing by the main body, and an input unit 61•11 such as a keyboard and a mouse for an operator to input commands. Of course, the control unit 61•4 may be constituted by hardware dedicated to defect inspection apparatus, a workstation or the like.

The control unit main body 61•9 is comprised of a CPU, a RAM, a ROM, a hard disk and various kinds of control boards such as a video board (not shown). A secondary electron image storage area for storing electric signals received from the detector 61•3, i.e. digital image data of secondary electron images of the wafer W is assigned on a memory of a RAM, hard disk or the like. Furthermore, a defect detection program 61•13 for reading secondary electron image data from a storage area 61•12, and automatically detecting defects of the wafer W according to a predetermined algorithm based on the image data is stored on the hard disk in addition to a control program for controlling the entire defect inspection apparatus. For example, the defect inspection program 61•13 has a function to compare the inspection site of the wafer W to another inspection site, and report a pattern different from patterns of most other sites to the operator as defects and display the pattern, for example. Further, a secondary electron image 61•14 may be displayed on a display unit of the CRT 61•10 to detect defects of the wafer W by visual observation of the operator.

The action of the electron beam apparatus according to the embodiment shown in FIG. 61 will now be described using the flowchart of FIG. 63 as an example. First, the wafer W to be inspected is set on the stage 61•2 (step 63•1). In this case, a large number of wafers W stored in a loader (not shown) may be automatically set on the stage 61•2 on a one-by-one basis. Then, a primary electron beam is emitted from the electron gun 59•6, and applied to a predetermined inspection area on the surface of the set wafer W through the electrostatic lens 59•8 (step 63•2). Secondary electrons and/or reflection electrons (hereinafter referred to only as "secondary electrons") are emitted from the wafer W irradiated with the primary electron beam and as a result, the wafer W is charged up to a positive potential.

Then, a generated secondary electron beam is made to form an image on the detector 61•3 under a predetermined magnification by the electrostatic lens 59•13 in an enlarged projection system (step S63•3). At this time, the UV lamp 61•5 is made to emit light with a negative voltage applied to a photoelectron emission material 65•1 with respect to the stage 61•2 (step 63•4). As a result, ultraviolet light with the frequency of v emitted from the UV lamp 61•5 causes photoelectrons to be emitted from the photoelectron emission material 65•1 with its energy quantum of hv (h represents Planck constant). The photoelectrons $e^-$ are applied from the negatively charged photoelectron emission material 61•6 to the wafer W positively charged up to electrically neutralize the wafer W. In this way, the secondary electron beam is made to form an image on the detector 61•3 without being substantially influenced by the positive potential of the wafer W.

The image of the secondary electron beam (having alleviated image faults) emitted from the wafer W electrically neutralized in this way is detected by the detector 61•3, and converted into digital image data, and the image data is outputted (step 63•5). Then, the control unit 61•4 carries out processing for detection of defects of the wafer W based on the detected image data according to the defect detection program 61•13 (step 63•6). In this defect detection processing, the control unit 61•4 extracts a defective portion by comparing detection images of detected dies as described previously if the wafer has a large number of the same dies. A reference secondary electron image of the wafer having no defects, previously stored in the memory, may be compared with an actually detected secondary electron image to automatically detect a defective portion. At this time, the detection image may be displayed on the CRT 61•10, and a portion judged as a defective portion may marked, whereby the operator can finally check and determine whether the wafer W actually has defects or not. A specific example of this defect detection process will be further described later.

If it is determined that the wafer W has defects as a result of the defect detection processing of step 63•5 (positive determination in step 63•7), the operator is warned of existence of defects (step 63•8). As a method of warning, for example, a message indicating existence of defects may be displayed on the display unit of the CRT 61•10, and at the same time, an enlarged image 61•14 of a pattern having defects may be displayed. The defective wafer may be immediately taken from the sample chamber 61•1, and stored in a storage site different from a site for wafers having no defects (step 63•9).

As a result of the defect detection processing in step 63•6, whether any area to be inspected still exists or not is determined for the wafer W as a current inspection object (step 63•10) if it is determined that the wafer W has no defects (negative determination in step 63•7). If an area to be inspected still exists (positive determination in step 63•10), the stage 61•2 is driven to move the wafer W so that other area to be inspected next is within the area irradiated with the primary electron beam (step 63•11). Then, processing returns to step 63•2, where the same processing is repeated for the other inspection area.

If no area to be inspected exists (negative determination in step 63•10), or after the step of taking the wafer (step 63•9), whether the wafer W as a current inspection object is the last wafer or not, i.e. whether or not any that has not been inspected yet exists on a loader (not shown) is determined (step 63•12). If the wafer in not the last wafer (negative determination in step 63•12), the inspected wafer is stored in a predetermined place, and instead a new wafer that has not been inspected yet is set on the stage 61•2 (step 63•13). Then, processing returns to step 63•2, where the same processing is repeated for the wafer. If the wafer is the last wafer (positive determination in step 63•12), the inspected wafer is stores in a predetermined storage place to complete all steps. The identification numbers of cassettes, the identification numbers of wafers, for example, the lot numbers are stored for management.

Irradiation of UV photoelectrons (step 63•4) can be carried out in any timing and within any time period as long as the secondary electron image can be detected (step 63•5) in a state in which positive charge-up of the wafer is avoided, and image faults are reduced. The UV lamp 61•5 may be lit all the time while processing of FIG. 63 is continued, but the UV lamp 61•5 may be lit and unlit periodically with the time period defined for each wafer. In the latter case, as timing of light emission, light emission may be started before the secondary electron beam is made to form an image (step 63•3) and before the primary electron beam is applied (step 63•2), other than the timing shown in FIG. 63. Irradiation of UV photoelectrons is preferably continued at least during detection of secondary electrons, but the irradiation of UV photoelectrons may be stopped even before or during detection of the secondary electron image if the wafer is electrically neutralized sufficiently.

Specific examples of the defect detection process at step 63•6 are shown in FIGS. 64(*a*) to (*c*). First, in FIG. 64(*a*), an image 64•1 of a die detected fist and an image 64•2 of another die detected second are shown. If it is determined that an image of another die detected third is identical or similar to the first image 6•41, it is determined that an area 64•3 of the second die image 64•2 has defects, and thus the defective area can be detected.

An example of measurement of a line width of a pattern formed on the wafer is shown in FIG. 64(*b*). Reference numeral 64•6 denotes an intensity signal of actual secondary electrons when an actual pattern 64•4 on the wafer is scanned in a direction 64•5, and a width 64•8 of an area where this signal continuously exceeds a threshold level 64•7 defined by correction in advance can be measured as the line width of the pattern 64•4. If the line width measured in this way is not within a predetermined range, it can be determined that the pattern has defects.

An example of measurement of a potential contrast of a pattern formed on the wafer is shown in FIG. 64(*c*). In the configuration shown in FIG. 61, an axis-symmetric electrode 64•9 is provided above the wafer W and for example, a potential of −10 V is given with respect to the wafer potential of 0 V. A equipotential surface of −2 V at this time has a shape denoted by reference numeral 64•10. Here, patterns 64•11 and 64•12 formed on the wafer have potentials of −4 V and 0 V, respectively. In this case, secondary electrons emitted from the pattern 64•11 have a upward velocity equivalent to kinetic energy of 2 eV at the −2 V equipotential surface 64•10, and therefore the secondary electrons jump over the potential barrier 64•10, escape from the electrode 64•9 as shown in an orbit 64•13, and are detected by the detector 61•3. On the other hand, secondary electrons emitted from the pattern 64•12 cannot jump over the −2 V potential barrier, and is returned back to the wafer surface as shown in an orbit 64•14, and therefore the secondary electrons are not detected. Thus, the detection image of the pattern 64•11 is bright, while the detection image of the pattern 64•12 is dark. In this way, the potential contrast is obtained. If the brightness of the detection image and the potential are corrected in advance, the potential of the pattern can be measured from the detection image. The defective area of the pattern can be evaluated from the potential distribution.

Furthermore, if there is an area floating in the die, an electric charge can be added by the precharge unit to charge the floating area and establish electrical connection to produce a potential difference between the area and a grounded area. Potential contrast data in this state can be acquired and analyzed to identify the floating area. It can be used as a defect identification process when killer defects and the like exist. The potential contrast data may be converted into a potential contrast image to compare the potential contrast image with a potential contrast image of a pattern of another die, or compare the potential contrast image with a potential contrast image acquired from design data of the CAD or the like.

FIG. 65 shows the outlined configuration of a defect inspection apparatus comprising a precharge unit according to another embodiment of the present invention. Furthermore, components the same as those of the embodiment of FIG. 61 are given like symbols, and detailed descriptions thereof are not presented. In this embodiment, as shown in FIG. 65, the glass surface of the UV lamp 61•5 is not coated with the photoelectron emission material. Instead, a photoelectron emission plate 65•1 is placed above the wafer W in the sample chamber 61•1, and the UV lamp 61•5 is placed at a position such that emitted ultraviolet light is applied to the photoelectron emission plate 65•1. The negative pole of a power supply 71•7 is connected to the photoelectron emission plate 65•1, and the positive pole of the power supply is connected to the stage 61•2. The photoelectron emission plate 65•1 is made of metal such as Au, or may be a plate coated with such a metal.

The action of the embodiment of FIG. 65 is the same as that of the embodiment of FIG. 61. In the embodiment of FIG. 65, photoelectrons can be applied to the surface of the wafer W as appropriate, and thus an effect the same as that of the embodiment of FIG. 61 is exhibited.

FIG. 66 shows the outlined configuration of a defect inspection apparatus comprising a precharge unit according to still another embodiment of the present invention. Furthermore, components identical to those of the embodiments of FIGS. 61 and 65 are given like symbols, and detailed descriptions thereof are not presented. In the embodiment of FIG. 66, as shown in this figure, a transparent window material 66•1 is provided on the side wall of the sample chamber 61•1, and the UV lamp 61•5 is placed outside the sample chamber 61•2 so that ultraviolet light emitted from the UV lamp 61•5 is applied through the window material 66•1 to the photoelectron emission plate 65•1 placed above the wafer W in the sample chamber 61•1. In the embodiment of FIG. 66, the UV lamp 61•5 is placed outside the sample chamber 61•1 to be evacuated, and therefore necessity to consider an anti-vacuum performance of the UV lamp 61•5 is eliminated, thus making it possible to widen a choice of options of the UV lamp 61•5 compared to the embodiments of FIGS. 61 and 65.

Other actions of the embodiment of FIG. 66 are the same as those of the embodiments of FIGS. 61 and 65. In the embodiment of FIG. 66, photoelectrons can be applied to the surface of the wafer W as appropriate, and therefore an effect the same as those of the embodiments of FIGS. 61 and 65 is exhibited.

The embodiments have been described above, but the defect inspection apparatus comprising the precharge unit according to the present invention is not limited to the examples described above, but may be changed as appropriate within the sprit of the present invention. For example, the semiconductor wafer W is used as a sample to be inspected, but the sample to be inspected of the present invention is not limited thereto, and any type allowing defects to be detected with an electron beam can be selected. For example, a mask having a pattern for exposure of the wafer to light, a transparent mask (stencil mask) or the like may be dealt with as an inspection object. Furthermore, the apparatus may be used not only for the semiconductor process but also for inspection and evaluation related to micro-machines and liquid crystals as a matter of course.

Furthermore, as the electron beam apparatus for inspection of defects, the configuration of FIGS. 61 to 66 is shown, but the electro-optical system and the like may changed as appropriate. For example, the electron beam irradiating means (59•6 and 59•8) of the defect inspection apparatus shown in the figure makes the primary electron beam enter the surface of the wafer W aslant from the above, but means for deflecting the primary electron beam may be provided below the electrostatic lens 59•13 to make the primary electron beam enter the surface of the wafer W at a right angle. Such deflecting means includes, for example, a Wien filter deflecting the primary electron beam with a field E×B in which the electric field is orthogonal to the magnetic field.

Further, as means for emitting photoelectrons, any means may be employed as a matter of course other than the combination of the UV lamp 61•5 and the photoelectron emission member 61•6 or photoelectron emission plate 65•1 shown in FIGS. 61 to 66.

The flow of the flowchart of FIG. 63 is not limited thereto. For example, for a sample judged as being defective at step 63•7, inspection of defects for other areas is not carried out, but the flow of the process may be changed so that detection of defects is carried out over all the areas. Furthermore, if the area to be irradiated with the primary electron beam is enlarged so that one irradiation can cover all the inspection area of the sample, steps 63•10 and 6:11 may be omitted.

Further, in FIG. 63, if it is determined that the wafer has defects at step 63•7, the operator is immediately warned of existence of defects at step 63•8 and post-processing is carried out (step 63•9), but the flow may be changed so that defect information is recorded, and after batch processing is completed (after positive determination in step 63•12), defect information of the defective wafer is reported.

As described in detail above, according to the defect inspection apparatus and the defect inspection process according to the embodiments of FIGS. 61 and 66, electrons having energy different from that of the primary electron beam, i.e. energy lower than that of the primary electron beam is supplied to the sample, and therefore an excellent effect is obtained such that the positive charge-up on the sample surface associated with emission of secondary electrons is reduced, and hence image faults of the secondary electron beam associated with the charge-up can be eliminated, thus making it possible to inspect defects of the sample with high accuracy.

Further, if the defect inspection apparatus of FIGS. 61 and 66 is used for the device production process, an excellent effect is obtained such that the yield of products can be improved and defective products can be prevented from being dispatched, because defect inspection for the sample is carried out using the defect inspection apparatus described above.

The case has been described above where the electron beam is softly applied to the sample surface in low energy such that electron energy for precharge is mainly 100 eV or less, but an image may be acquired in the positive charge or negative charge mode or the reflection electron mode after performing precharge at 2 kV to 20 kV, preferably 3 to 10 kV, more preferably 3 to 5 kV. In the negative charge mode, precharge may be performed in energy the same as landing energy of the electron beam during inspection.

Furthermore, it is effective to coat the sample surface with a conductive thin film for control of charge. The suitable thickness in this case is 1 to 100 nm, preferably 1 to 10 nm, more preferably 1 to 3 nm. Further, if the image is acquired after the sample surface is cleaned by sputter etching or the like, a cleaner image is obtained. Coating of the conductive thin film and sputter etching may be used alone, or in combination with precharge. For example, precharge may be performed to acquire an image after sputter etching, or precharge may be performed after coating of the conductive thin film after sputter etching.

2-5) Vacuum Pumping System

A vacuum pumping system is comprised of a vacuum pump, a vacuum valve, a vacuum gage, vacuum piping and the like and an electro-optical system, a detection unit, a sample chamber and a load lock chamber are evacuated according to a predetermined sequence. In each unit, the vacuum valve is controlled so as to achieve a required degree of vacuum. The degree of vacuum is monitored all the time, and if an abnormality occurs, emergency control of an isolation valve and the like is performed with an interlock feature to ensure the degree of vacuum. For the vacuum pump, a turbo-molecular pump is used for main pumping and a roots-type dry pump is used for rough pumping. The practical pressure of the inspection site (electron beam irradiation area) is $10^{-3}$ to $10^{-5}$ Pa, preferably $10^{-4}$ to $10^{-6}$ Pa lower by one order.

2-6) Control System

A control system is mainly comprised of a main controller, a controlling controller and a stage controller. The main controller is provided with a man-machine interface, through which the operation by the operator is carried out (various kinds of instructions/command, input of recipes and the like, instruction to start inspection, switching between the automatic mode and the manual mode, input of all required commands during the manual inspection mode, and the like). In addition, communication with a host computer at a factory, control of the vacuum pumping system, transportation of a sample such as a wafer, control of alignment, transmission of commands to the other controlling controller and stage controller, reception of information and the like are carried out through the main controller. Furthermore, the controller comprises a function to acquire image signals from an optical microscope, a stage vibration correction function to make the electro-optical system feedback a stage variation signal to correct deterioration of the image, and an automatic focus correction function to detect a displacement of the sample observation position in the Z direction (axial direction of the secondary optical system), feedback the displacement to the electro-optical system, and automatically correct the focus. Exchange of feedback signals and the like with the electro-optical system, and exchange of signals from the stage are performed through the controlling controller and the stage controller, respectively.

The controlling controller is engaged in mainly control of an electron beam optical system (control of electron gun, lens, aligner, high accuracy power supply for Wien filter and the like). Specifically, control is performed so that a constant electron current is always applied to the irradiation area even when the magnification is changed, and control for automatic voltage setting for each lens system and the aligner matching each operation mode, and the like (interlock control), such as automatic voltage setting for each lens system and the aligner matching each magnification, is performed.

The stage controller mainly performs control relating to movement of the stage to allow precise movement in X and Y directions in the order of μm (with errors within about ±5 μm or smaller, preferably ±1 μm or smaller, more preferably ±0.5 μm or smaller). Furthermore, in this stage, control in the rotational direction (θ control) is performed with errors within about ±10 seconds, preferably ±1 second, more preferably ±0.3 seconds). The configuration of the control system will be specifically described below.

2-6-1) Configuration and Function

This apparatus provides a function to image a specified position in a wafer with an electron microscope or optical microscope and display the same, a function to image the specified position in the wafer with the electron microscope to detect and classify defects, and a function to image the position at which defects are detected with the electron microscope or optical microscope and display the same. Furthermore, for achievement and maintenance of the above functions, the apparatus has an electro-optical system control function, a vacuum system control function, a wafer transportation control function, a single component operation function, an imaging function, an automatic defect inspection processing function, an apparatus abnormality detection function, and an apparatus start/stop processing function.

Auxiliary functions are listed below.

(1) Electro-optical System Control Function
  (a) Lens Voltage Application Control
    (a-1) Interlock Control
    (a-2) Voltage Application with Application Function
    (a-3) Multipole Lens Interlock Voltage Application
    (a-4) Wobble Control
  (b) Electron Beam Output Adjustment
    (b-1) Preheat (Gun)
    (b-2) Heat up (Gun)
    (b-3) Emission Current Control (Bias control)

(2) Vacuum System Control Function
  (a) Individual Chamber Evacuation/$N_2$ Vent
  (b) Specified Chamber Batch Evacuation/$N_2$ Vent (3) Wafer Transportation Control Function Step operation/full automatic operation of following operations
  (a) Wafer Load
  (b) Wafer Unload (4) Single Component Operation Function (5) Imaging Function A selection is made from the following two input lines and an image is formed.
  (a) CCD Camera Optical microscope low power (pixel size: 2.75 μm/pix)

Optical microscope high power (pixel size: 0.25 μm/pix)
  (b) TDI camera
    (b-1) TDI-still
    (b-2) TDI-scan
  EB×80 (pixel size: 0.2 μm/pix)
  EB×160 (pixel size: 0.1 μm/pix)
  EB×320 (pixel size: 0.05 μm/pix)
  EB×480 (pixel size: 0.03 μm/pix).

Further, a user mode designation function is provided as a function to limit operational items according to the skill/knowledge level of the operator for prevention of an accident resulting from an erroneous operation. This user mode is designated as a user ID and a password inputted when a GUI (graphical user interface) is started.

The user mode includes a maintenance mode, a recipe creation mode, and an operator mode, the operation is carried out in the maintenance mode during setup work after installation of the apparatus and maintenance work, necessary operations and procedures are supported in the recipe creation mode during creation of a recipe, and inspection is performed using the created recipe in the operator mode during automatic defect inspection. The relation between each user mode and the apparatus operation form is shown in FIG. 67.

Maintenance mode . . . single component operation, wafer transportation, vacuum system control, electro-optical system control, observation (optical microscope imaging, TDI imaging), defect inspection, review Recipe creation mode . . . wafer transportation, observation (optical microscope imaging, TDI imaging), defect inspection, review Operator mode . . . automatic defect inspection (automatic control of necessary functions such as wafer transportation), review.

This apparatus has an apparatus constant and a recipe as variable parameters required for the operation. The apparatus constant is specified as a parameter for absorbing apparatus specific errors (such as a mounting error), and the recipe is specified as a parameter for specifying various kinds of conditions to automatically perform defect inspection. The apparatus constant is set during setup work and after maintenance work, and is essentially unchanged thereafter.

The recipe is classified into a transportation recipe, an alignment recipe, a die map recipe, a focus map recipe and an inspection recipe, defect inspection is performed according to these recipes, setting work is therefore carried out before inspection processing is performed, and a plurality of patterns of settings are stored.

For the procedure during recipe creation, the wafer is conveyed onto the stage (wafer is loaded) as a first step as shown in FIG. 68. After a wafer cassette is installed in the apparatus, wafer search is carried out to detect existence/nonexistence of the wafer in each slot in the cassette, a wafer size, a notch/ori-fla type, and a notch direction (when loaded onto the stage) are designated for the detected wafer, and the wafer is loaded according to the procedure shown in FIGS. 69 and 70. These conditions are stored in the transportation recipe. The direction of placement of the die of the wafer loaded onto the stage does not necessarily match the scan direction of the TDI camera (FIG. 71). In order that the directions match each other, an operation for rotating the wafer on a θ stage is required, and this operation is called alignment (FIG. 72). Alignment practice conditions after the wafer is loaded onto the stage are stored in the alignment recipe.

Furthermore, a die map (FIG. 73) showing the arrangement of dies during alignment is created, the die size, the position of the origin die (starting point showing the position of the die) and the like are stored in the die map recipe.

2-6-2) Alignment Procedure

For the alignment (positioning) procedure, rough positioning is performed with a low power of an optical microscope, then positioning is performed with a high power of the optical microscope, and finally fine positioning is performed with an EB image.

A. Imaging with Optical Microscope Low Power (1) <First, Second and Third Search Die Designation and Template Designation>

(1-1) First search die designation and template designation

The stage is moved by a user operation so that the lower left corner of the die positioned below the wafer is positioned near the center of a camera, the position is determined, and then a template image for pattern matching is acquired. This die is a die serving as a reference for positioning, and the coordinates of the lower left corner are coordinates of a feature point. Hereinafter, pattern matching is performed with this template image, whereby correct positional coordinates of any die on the substrate are measured. For this template image, an image forming a unique pattern in the search area must be selected.

Furthermore, in this example, the lower left corner is a template image acquirement position for pattern matching, but the position is not limited thereto, and any position in the die may be selected as a feature point. Generally, however, since coordinates can be identified more easily for the corners than for points in the die and on the edge of the die, any one of the four corners is preferably selected. Similarly, in this example, the template image for pattern matching is acquired for the die positioned below the wafer but as a matter of course, any die may be selected such that alignment can more easily be performed.

(1-2) Second search die designation

The die at the immediate right of the search die is designated as a second search die, the stage is moved by a user operation so that the lower left corner of the second search die is positioned near the center of the camera, the position is determined, and then the template image acquired in the procedure (1-1) is used to automatically perform pattern matching, whereby accurate coordinate values of the second search die matching the template image designated with the first search die is acquired.

Furthermore, in this example, the die at the immediate right of the first search die is the second search die, but the second search die of the present invention is not limited thereto, as a matter of course. It is essential that a point should be selected which makes it possible to correctly know by pattern matching a positional relation of dies in the line direction from the reference point with which the positional coordinates of the correct feature point are known. Thus, for example, the die at the immediate left of the first search die can be designated as the second search die.

(1-3) Third search die designation

The die just above the second search die is designated as a third die, the stage is moved by a user operation so that the lower left corner of the third search die is positioned near the center of the camera, the position is determined, and then the template image acquired in the procedure (1-1) is used to automatically perform pattern matching, whereby accurate coordinate values of the third search die matching the template image designated with the first search die is acquired.

Furthermore, in this example, the die just above the second search die is the third search die, but the third search die of the present invention is not limited thereto, as a matter of course. It is essential that a positional relation including distances of the coordinates of the feature point of dies in the row direction can be known using, as a reference, the die with which the correct coordinates of the feature point are known. Thus, the die just above the first search die can be suitably used as an alternate.

(2) <Optical Microscope Low Power Y Direction Pattern Matching>

(2-1) The amount of movement to the pattern of the upper neighboring die is calculated from the relation between the pattern match coordinates (X2, Y2) of the second search die and the pattern match coordinates (X3, Y3) of the third search die.

$$dX = X3 - X2$$

$$dY = Y3 - Y2$$

(2-2) Using the calculated amount of movement (dX, dY), the stage is moved to the coordinates (XN, YN) at which the pattern just above the first search die exists (is expected to exist).

$$XN = X1 + dX$$

$$YN = Y1 + dY$$

(X1, Y1): coordinates of pattern of first search die (2-3) After movement of the stage, imaging is performed with an optical microscope low magnification, the template image is used to carry out pattern matching to acquire the accurate coordinate values (XN, YN) of the pattern that is currently observed, and 1 is set as an initial value of a number of detected dies (DN).

(2-4) The amount of movement (dX, dY) from the pattern coordinates (X1, Y1) of the first search die to the coordinates (XN, YN) of the pattern that is currently imaged is calculated.

$$dX = XN - X1$$

$$dY = YN - Y1$$

(2-5) The stage is moved in an amount of movement (2*dX, 2*dY) twice as large as the calculated amount of movement (dX, dY) with the first search die as a starting point.

(2-6) After movement of the stage, imaging is performed with an optical microscope low magnification, the template image is used to carry out pattern matching to update the accurate coordinate values (XN, YN) of the pattern that is currently observed, and the number of detected dies is increased by a factor of 2. See FIG. 74 for this procedure.

(2-7) The procedures (2-4) to (2-6) are repeatedly carried out toward the upper part of the wafer until a predesignated Y coordinate value is exceeded.

Furthermore, in this example, to improve accuracy, to reduce the number of processes (number of repetitions) and to reduce processing time, movement is repeated in a twofold amount of movement. If there is no problem with accuracy, and further reduction in processing time is desired, movement may be carried out in a high integral multiple amount greater than twofold amount, such as a three-fold or four-fold amount. For further improvement in accuracy, movement may be repeated in a fixed amount of movement. Any of these cases is incorporated in the number of detected dies as a matter of course.

(3) <Optical Microscope Low Magnification θ Rotation>

(3-1) Using the amount of movement from the pattern coordinates (X1, Y1) of the first search die to the accurate coordinate values (XN, YN) of the pattern of the die searched lastly, and the number of dies (DN) detected in the meantime, an amount of rotation (θ) and a die size in the Y direction (YD) are calculated (see FIG. 75).

$dX=XN-X1$ $dY=YN-Y1$ $\theta=\tan^{-1}(dX/dY)$ $YD=\text{sqrt}((dX)^2+(dY)^2)/DN$ $*\text{sqrt}(A)=(A)^{1/2}$ (3-2) The stage is rotated to θ in the calculated amount of rotation (θ).

B. Imaging with Optical Microscope High Magnification (1) A procedure the same as the procedure (1) for the optical microscope low magnification is carried out using an optical microscope high magnification image.
(2) A procedure the same as the procedure (2) for the optical microscope low magnification is carried out using an optical microscope high magnification image.
(3) A procedure the same as the procedure for the optical microscope low magnification is carried out.
(4) <Check of allowable value after optical microscope high power θ rotation>

(4-1) "First search die, designation of template of optical microscope high magnification"

The coordinates (X'1, Y'1) of the first search die after rotation are calculated from the coordinated (X1, Y1) before rotation and the amount of rotation (θ), the stage is moved to the coordinates (X'1, Y'1), the position is determined, and then a template image for pattern matching is acquired.

$X'1=x_1*\cos\theta-y_1*\sin\theta$ $Y'1=x_1*\sin\theta+y_1*\cos\theta$ (4-2) Optical microscope high magnification Y direction pattern matching The stage is moved in the Y direction by dY from the coordinates (X'1, Y'1) of the first search die after rotation, and pattern matching is carried out to acquire the accurate coordinate values (XN, YN) of the pattern that is currently observed.

(4-3) An amount of movement (dX, dY) from the coordinates (X'1, Y'1) of the first search die after rotation to the coordinates (XN, YN) of the pattern that is currently imaged is calculated.

$dX=XN-X'1$ $dY=YN-Y'1$ (4-4) The stage is moved in an amount of movement (2*dX, 2*dY) twice as large as the calculated amount of movement (dX, dY) with the first search die as a starting point.

(4-5) After movement of the stage, imaging is performed with an optical microscope high magnification, and the template image is used to carry out pattern matching to update the accurate coordinate values (XN, YN) of the pattern that is currently observed.

(4-6) The procedures (4-3) to (4-5) are repeatedly carried out toward the upper part of the wafer until a predesignated Y coordinate value is exceeded.

(4-7) Calculation of Rotation of θ

Using the amount of movement from the coordinates (X'1, Y'1) of the first search die after rotation to the accurate coordinate values (XN, YN) of the pattern of the die searched lastly, an amount of rotation (θ) is calculated.

$dX=XN-X1$ $dY=YN-Y1$ $\theta=\tan^{-1}(dX/dY)$ (4-8) Check of optical microscope high magnification θ allowable value Whether the amount of rotation (θ) calculated in the procedure (4-7) equals a predefined value or smaller is checked. If the amount of rotation (θ) is greater than the predefined value, the calculated amount of rotation (θ) is used to rotate the stage to θ, and then the procedures (4-1) to (4-8) are carried out again. However, in case where the amount of rotation (θ) is not within an allowable range even if the procedures (4-1) to (4-8) are carried out a specified number of times, the operation is considered as an error and processing is stopped.

C. Alignment with EB Image (1) <Y Search First Die, Designation of Template of EB>

A procedure the same as the procedure (1) for the optical microscope high magnification is carried out using an EB image.

(2) <EB: Y Direction Pattern Matching>

A procedure the same as the procedure (2) for the optical microscope high magnification is carried out using an EB image.

(3) <EB: θ Rotation>

A procedure the same as the procedure (3) for the optical microscope high magnification is carried out using an EB image.

(4) <EB: Check of Allowable Value After θ Rotation>

A procedure the same as the procedure (4) for the optical microscope high magnification is carried out using an EB image.

(5) The procedures (1) to (4) are carried out using an EB image of a high magnification as required.
(6) An appropriate value of an X direction die size (XD) is calculated from the coordinates (X1, Y1) of the first search die and the coordinates (X2, Y2) of the second search die.

$dX=X2-X1$ $dY=Y2-Y1$ $XD=\text{sqrt}((dX)^2+(dY)^2)$ $*\text{sqrt}(A)=\sqrt{A}$ D. Creation of Die Map Recipe (1) <X Search First Die, Designation of Template of EB>

The stage is moved by a user operation so that the lower left corner of the die positioned at the left end of the wafer is positioned near the center of a TDI camera, the position is determined, and then a template image for pattern matching is acquired. For this template image, an image forming a unique pattern in the search area must be selected.

(2) <EB: X Direction Pattern Matching>

(2-1) The approximate value of the X direction die size (XD) is used to move the stage to coordinates (X1+XD, Y1) at which the pattern of the die at the immediate right of the X search first die exists (is expected to exist).

(2-2) After movement of the stage, an EB image is formed by the TDI camera, the template image is used to perform pattern matching to acquire the accurate coordinates (XN, YN) of the pattern that is currently observed, and 1 is set as an initial value of the number of detected dies (DN).

(2-3) An amount of movement (dX, dY) from the pattern coordinates of the X search first die to the coordinates (XN, YN) of the pattern that is currently observed.

$$dX=XN-X1$$

$$dY=YN-Y1$$

(2-4) The stage is moved in an amount of movement (2*dX, 2*dY) twice as large as the calculated amount of movement (dX, dY) with the X search first die as a starting point.

(2-5) After movement of the stage, an EB image is formed by the TDI camera, the template image is used to perform pattern matching to update the accurate coordinates (XN, YN) of the pattern that is currently observed, and the number of detected dies is increased by a factor of 2.

(2-6) The procedures (2-3) to (2-5) are repeatedly carried out in the right direction of the wafer until a predesignated X coordinate value is exceeded.

(3) <Calculation of X Direction Gradient>

A stage movement direct error ($\Phi$) and an X direction die size (XD) are calculated using the amount of movement from the pattern coordinates (X1, Y1) of the X search first die to the accurate coordinate values (XN, YN) of the pattern of the die searched lastly, and the number of dies (DN) detected in the meantime.

$$dX=XN-X1$$

$$dY=YN-Y1$$

$$\Phi=\tan^{-1}(dX/dY)$$

$$XD=\text{sqrt}((dX)^2+(dY)^2)/DN$$

$$*\text{sqrt}(A)=\sqrt{A}$$

(4) <Creation of Die Map>

In this way, the X direction die size (XD) is determined, and it is combined with the Y direction die size (YD) previously determined when the amount of rotation ($\theta$) is calculated to create a die map (information of an ideal arrangement of dies). From the die map, an ideal arrangement of dies is known. On the other hand, actual dies on the substrate are influenced by, for example, mechanical errors of the stage (errors of parts such as a guide, and assembly), errors of an interferometer (e.g. due to problems of assembly of a mirror or the like), and deformation of the image due to charge-up, and may not be necessarily observed as an ideal arrangement, but the error between the position of the actual dies and the ideal arrangement on the die map is known, and this error is considered and automatically corrected while inspection is carried out.

E. Procedure for Creation of Focus Recipe

A procedure for creation of a focus recipe will now be described. The focus recipe stores information of an optimum focus position at any position on the surface of a sample such as a substrate, or various conditions about the focus position in a predetermined format such as a table. In a focus map recipe, focus conditions are set only for designated positions on the wafer, and focus values between designated positions are linearly interpolated (see FIG. 76). The procedure for creation of a focus recipe is as follows.

(1) Focus measurement object dies are selected from the die map.

(2) Focus measurement points in the die are set.

(3) The stage is moved to each measurement point, and a focus value (CL12 voltage) is manually adjusted based on an image and a contrast value.

The die map created by alignment processing provides ideal position information calculated from die coordinates at the both ends of the wafer, and an error occurs between the die position on the die map and the actual die position due to various factors (see FIG. 77). A procedure for creating parameters for absorbing the error is called fine alignment, and information of the error between the die map (ideal die position information) and the actual die position is stored in a fine alignment recipe. The information set here is used during defect inspection. In the fine alignment recipe, errors are measured only for dies designated on the die map, and errors between designated dies are lineally interpolated.

F. Fine Alignment Procedure (1) Error measurement object dies for fine alignment are designated from the die map.

(2) A reference die is selected from the error measurement object dies, and the position of the reference die is defined as a point where the error with the die map is zero.

(3) The lower left corner of the reference die is imaged by the TDI camera to acquire a template image for pattern matching.

A unique pattern in the search area is selected as a template image.

(4) Coordinates (X0, Y0) (on the die map) at the lower left of the neighboring error measurement object die is acquired, and the stage is moved. After movement of the stage, imaging is performed by the TDI camera, and pattern matching is carried out using the template image of the procedure (3) to acquire accurate coordinate values (X, Y).

(5) Error between the coordinate values (X, Y) acquired by pattern matching and coordinate values (X0, Y0) on the die map are stored.

(6) The procedures (4) and (5) are carried out for all the error measurement object dies.

2-6-3) Defect Inspection

For defect inspection, as shown in FIG. 78, conditions of the electro-optical system are set (imaging magnification and the like are set), the stage is moved while irradiating an electron beam to perform TDI scan imaging (FIG. 79), and defect inspection is carried out in real time by an inspection dedicated processing unit (IPE) according to the set inspection conditions (array inspection conditions, random inspection conditions, inspection areas).

In an inspection recipe, conditions of the electro-optical system, inspection object dies, inspection areas, the inspection process (random/array) and the like are set (A and B of FIG. 80).

Furthermore, to acquire stable images for defect inspection, EO correction for inhibiting blurring of formed images resulting from positional deviations and speed unevenness, die position correction for absorbing errors between the ideal arrangement on the die map and the actual die position, and focus adjustment for interpolating focus values of the entire wafer area using focus values previously measured at finite measurement points are simultaneously carried out in real time.

In the scan operation of defect inspection, the entire area of the inspection object die is inspected (FIG. 81) and in addition, as shown in FIG. 82, the amount of step movement in a direction perpendicular to the scan direction is adjusted, whereby thinned-out inspection can be performed (reduction in inspection time).

After inspection, the number of defects, positions of dies including defects, defect sizes, defect positions in dies, defect types, defective images and reference images are displayed on a display as inspection results, and information thereof, recipe information and the like are stored in a file, whereby results of inspection in the past can be confirmed and reproduced.

During automatic defect inspection, various kinds of recipes are selected and designated, whereby the wafer is loaded according to the transportation recipe, alignment of the wafer is performed on the stage according to the alignment recipe, focus conditions are set according to the focus map recipe, inspection is carried out according to the inspection recipe, and the wafer is unloaded according to the transportation recipe (A and B of FIG. 83).

2-6-4) Control System Configuration

This apparatus is comprised of a plurality of controllers as shown in FIG. 84. A main controller conducts GUI unit/sequence operations of the apparatus (EBI), receives operation commands from a factory host computer or GUI, and gives necessary instructions to a VME controller and an IPE controller. The VME controller conducts operations of components of the apparatus (EBI), and gives instructions to a stage controller and a PLC controller according to the instructions from the main controller. The IPE controller acquires defect inspection information from an IPE node computer, classifies the acquired defects and displays an image according to the instructions from the main controller. The IPE node computer acquires an image outputted from the TDI camera and carries out defect inspection.

Upon reception of the instructions from the VME controller, the PLC controller drives devices such as valves, acquires sensor information, and monitors abnormalities such as a vacuum abnormality that should be monitored all the time. Upon reception of the instructions from the VME controller, the stage controller conducts movement in the XY direction and rotation of the wafer placed on the stage.

By forming such a distributed control system, interfaces between the controllers are kept the same to eliminate the necessity to change software and hardware of the upper-level controller if an apparatus component at the end is changed. Furthermore, even if a sequence operation is added/modified, a change in upper-level software and hardware is minimized, whereby a change in configuration can be flexibly coped with.

2-6-5) User Interface Configuration

FIG. 85 shows the device configuration of a user interface.

(1) Input Unit

The input unit is a device receiving inputs from the user, and is comprised of a "keyboard", a "mouse" and a "JOY pad".

(2) Display Unit

The display unit is a device displaying information to the user, and is comprised of two monitors.

Monitor 1: displaying an image acquired by the CCD camera or TDI camera.

Monitor 2: GUI display

Coordinate System

In this apparatus, the following three coordinate systems are specified.

(1) Stage Coordinate System $[X_S, Y_S]$

This is a reference coordinate system for indicating a position during control of a stage position.

The X coordinate value is incremented in the rightward direction and the Y coordinate value is incremented in the upward direction with the lower left corner of a chamber as an origin.

This apparatus has only one coordinate system as this coordinate system.

The position (coordinate values) shown in the stage coordinate system is situated at the center of the stage (center of the wafer).

That is, if the coordinate values [0,0] are designated in the stage coordinate system, the stage is moved so that the center of the stage (center of the wafer) is superimposed on the origin of the stage coordinate system.

[μm] is used as a unit, but the minimum resolution is $\lambda/1024$ ($\approx 0.618$ [nm]).

λ: wavelength of a laser for use in the laser interferometer ($\lambda \approx 632.991$ [nm]).

(2) Wafer Coordinate System $[X_W, Y_W]$

The coordinates are reference coordinates for indicating a position of observation (imaging/display) on the wafer.

The X coordinate value is incremented in the rightward direction and the Y coordinate value is incremented in the upward direction with the center of the wafer as an origin.

The position (coordinate values) shown in the wafer coordinate system is situated at the center of imaging by an imaging device (CCD camera, TDI camera) selected at this time.

This apparatus has only one coordinate system as this coordinate system.

[μm] is used as a unit, but the minimum resolution is $\lambda/1024$ ($\approx 0.618$ [nm]).

λ: wavelength of a laser for use in the laser interferometer ($\lambda \approx 632.991$ [nm]).

(3) Die Coordinate System $[X_D, Y_D]$

The coordinates are reference coordinates for specifying a position of observation (imaging/display) in each die.

The X coordinate value is incremented in the rightward direction and the Y coordinate value is incremented in the upward direction with the lower left corner of each die as an origin. This coordinate system exists in each die. [μm] is used as a unit, but the minimum resolution is $\lambda/1024$ ($\approx 0.618$ [nm]).

λ: wavelength of a laser for use in the laser interferometer ($\lambda \approx 632.991$ nm)).

Furthermore, dies on the wafer are numbered (subjected to numbering), and a die serving as a reference for numbering is called an origin die. By default, the die closest to the origin of the wafer coordinate system is the origin die, but the position of the origin die can be selected according to designation by the user.

The relation between the coordinate values in each coordinate system and the position of observation (display) is shown in FIG. 86. * The relation between coordinates indicated by a user interface and the direction of movement of the stage is as follows.

(1) Joystick & GUI Arrow Button

The direction indicated by a joystick and a GUI arrow button is considered as a direction in which the operator wants to make an observation, and the stage is moved in a direction opposite to the indicated direction.

Example)

Indicated direction: right . . . direction of movement of stage: left (image shifts to the left=field of view shifts to the right).

Indicated direction: upward . . . direction of movement of stage: downward (image shifts downward=field of view shifts upward)

(2) Direct Input of Coordinates on GUI

The coordinates directly inputted on the GUI are considered as a position in which the operator wants to make an observation on the wafer coordinate system, and the stage is moved so that the wafer coordinates are displayed at the center of the formed image.

2-7) Descriptions of Other Functions and Configurations

FIG. 87 shows the overall configuration of this embodiment. However, part of the configuration is omitted. In this figure, an inspection apparatus has a primary column 87•1, a secondary column 87•2 and a chamber 87•3. An electron gun 87•4 is provided in the primary column 87•1, and a primary optical system 87•5 is placed on the optical axis of an electron beam (primary beam) emitted from the electron gun 87•4. Furthermore, a stage 87•6 is placed in the chamber 87•3, and a sample W is placed on the stage 87•6.

An objective lens 87•7, a numerical aperture 87•8, a Wien filter 87•9, a second lens 87•10, a field aperture 87•11, a third lens 87•12, a fourth lens 87•13 and a detector 87•14 are placed on the optical axis of a secondary beam emitted from the sample W in the secondary column 87•2. Furthermore, the numerical aperture 87•12 corresponds to an aperture diaphragm, and is a thin plate made of metal (Mo) having a circular hole. The aperture is situated at the crossover position of the primary beam and the back focal position of the objective lens 87•7. Thus, the objective lens 87•7 and the numerical aperture 87•8 constitute a telecentric electro-optical system.

On the other hand, an output of the detector 87•14 is inputted to a control unit 87•15, and an output of the control unit 87•15 is inputted to a CPU 87•16. A control signal of the CPU 87•16 is inputted to a primary column control unit 87•17, a secondary column control unit 87•18 and a stage drive mechanism 87•19. The primary column control unit 87•17 controls a lens voltage of the primary optical system 87•5, the secondary column control unit 87•18 controls lens voltages of the objective lens 87•8 and the second to fourth lenses 87•10 to 87•13, and controls an electromagnetic field applied to the Wien filter 87•9.

Furthermore, the stage drive mechanism 87•19 transmits position information of the stage to the CPU 87•16. Further, the primary column 87•1, the secondary column 87•2 and the chamber 87•3 are connected to a vacuum pumping system (not shown), and are evacuated by a turbo-molecular pump of the vacuum pumping system to maintain vacuum conditions therein.

(Primary beam) The primary beam from the electron gun 87•4 enters the Wien filter 87•9 while receiving a lens action by the primary optical system 87•5. Here, as a tip of the electron gun, LaB$_6$ enabling a large current to be taken with a rectangular cathode is used. Furthermore, for the primary optical system 72, a rotation axis-asymmetric quadrupole or octpole electrostatic (or electromagnetic) lens is used. This can cause convergence and divergence on the X and Y axes, respectively, as in the case of so called a cylindrical lens. This lens is formed in two, three or four stages, and conditions of each lens are optimized, whereby the beam irradiation area on the sample surface can be formed into any rectangular or elliptic shape without causing a loss of irradiation electrons.

Specifically, if the electrostatic quadrupole lens is used, four circular column rods are placed around the optical axis. Opposite electrodes are potential-equalized, and given opposite voltage characteristics in phases shifted at a right angle to each other around the optical axis.

Furthermore, as the quadrupole lens, a lens having a shape such that a circular plate usually used as an electrostatic deflector quadrisected may be used instead of a circular column lens. In this case, the lens can be downsized. The primary beam passing through the primary optical system 72 has its orbit bent by a deflection action of the Wien filter 87•9. The Wien filter 87•9 orthogonalizes the magnetic field and the electric field, makes only charged particles satisfying the Wien condition of E=vB travel in a straight line where E is the electric field, B is the magnetic field, and v is the velocity of charged particles, and bends the orbit of other charged particles. For the primary beam, a force FB by the magnetic field and a force FE by the electric force are produced, and thus the beam orbit is bent. On the other hand, for the secondary beam, the force FB and the force FE act in opposite directions, and are thus mutually canceled, and therefore the secondary beam travels in a straight line.

The lens voltage of the primary optical system 87•5 is previously set so that the primary beam is made to form an image at the aperture of the numerical aperture 87•8. The numerical aperture 87•8 inhibits arrival at the sample surface of an excessive electron beam scattered in the apparatus, thus preventing charge-up and contamination of the sample W. Further, since the numerical aperture 87•8 and the objective lens 87•7 constitute a telecentric electro-optical system, the primary beam passing through the objective lens 87•7 is a parallel beam, and is equally and uniformly applied to the sample W. That is, Koehler illumination is achieved as in the optical microscope.

(Secondary beam) When the primary beam is irradiated to the sample, secondary electrons, reflection electrons or back-scattered electrons are generated as secondary particles from the beam irradiation surface of the sample.

The secondary particles passes through the lens while receiving a lens action by the objective lens 87•7. The objective lens 87•7 is constituted by three electrodes. The lowermost electrode is designed to form a positive electric field with a potential on the sample W side to attract electrons (particularly secondary electrons having low directivity) and guide the electrons into the lens efficiently. Furthermore, the lens action is achieved by applying a voltage to first and second electrodes of the objective lens 87•7, and keeping the third electrode at zero potential. On the other hand, the numerical aperture 87•8 is situated at the position of the focus of the objective lens 87•7, i.e. the position of the back focal position from the sample W. Thus, a light flux of the electron beam exiting from an acentric (off-axis) area of the field of view passes through the central position of the numerical aperture 87•8 as a parallel beam without causing an eclipse.

Furthermore, the numerical aperture 87•8 plays a role to reduce lens aberrations of the second to fourth lenses 87•10 to 87•13 for the secondary beam. The secondary beam passing through the numerical aperture 87•8 travels away in a straight line without receiving a deflection action of the Wien filter 87•9. Furthermore, by changing the electromagnetic field applied to the Wien filter 87•9, only electrons having specific energy (e.g. secondary electrons, or reflection electrons, or back-scattered electrons) can be guided to the detector 87•14.

If secondary particles are made to form an image by the objective lens 87•7 alone, the lens action becomes so strong that the aberration tends to occur. Thus, the secondary particles are made to form an image one time by a combination of the objective lens 87•7 and the second lens 87•10. The secondary particles are subjected to intermediate imaging on the field aperture 87•11 by the objective lens 87•7 and the second lens 87•10. In this case, usually, the magnification necessary as the secondary optical system is often insufficient, and thus as a lens for magnifying the intermediate image, the third lens 87•12 and the fourth lens 87•13 are added. The secondary particles are made to form an image under magnification by the third lens 87•12 and the fourth lens 87•13, respectively, i.e. they are made to form an image total three times here. Furthermore, they may be made to form an image one time (total twice) by the third lens 87•12 and the fourth lens 87•13 in combination.

Furthermore, the second to fourth lenses 87•10 to 87•13 are each a rotation axis-symmetric lens called a unipotential or Einzwell lens. Each lens is comprised of three electrodes, in which two outside electrodes are usually at zero potential, and the lens is caused to perform a lens action and controlled with a voltage applied to the central electrode. Furthermore, the field aperture 87•11 is situated at the intermediate imaging point. The field aperture 87•11 limits the field of view to a necessary range like a field diaphragm of an optical microscope, but in the case of the electron beam, an excessive beam is blocked with the third lens 87•12 and the fourth lens 87•13 to prevent charge-up and contamination of the detector 87•14. Furthermore, the magnification is set by changing the lens conditions (focal distance) of the third lens 87•12 and the fourth lens 87•13.

The secondary particles are projected under magnification by the secondary optical system, and form an image on the detection surface of the detector 87•14. The detector 87•14 is comprised of an MCP amplifying electrons, a fluorescent screen converting electrons into light, a lens for communicating between the vacuum system and the outside and transmitting an optical image and other optical elements, and an imaging device (CCD, etc.). The secondary particles form an image on the MCP detection surface and amplified, and electrons are converted into optical signals by the fluorescent screen, and converted into photoelectric signals by the imaging element.

The control unit 87•15 reads an image signal of the sample from the detector 87•14, and transmits the signal to the CPU 87•16. The CPU 87•16 carries out defect inspection of the pattern by template matching or the like from the image signal. Furthermore, the stage 87•6 can be moved in the XY direction by the stage drive mechanism 87•19. The CPU 87•16 reads the position of the stage 87•6, outputs a drive control signal to the stage drive mechanism 87•19, drives the stage 87•6, and performs detection and inspection of images one after another.

In this way, in the inspection apparatus of this embodiment, the numerical aperture 87•8 and the objective lens 87•7 constitute a telecentric electro-optical system, thus making it possible to uniformly irradiate the beam to the sample for the primary beam. That is, Koehler illumination can easily be achieved.

Further, for secondary particles, all main beams from the sample W enter the objective lens 87•7 at a right angle (in parallel to the lens optical axis), and pass through the numerical aperture 87•8, and therefore periphery light is not eclipsed, and the image brightness of the periphery of the sample is not reduced. Furthermore, position of image formation varies, i.e. a transverse chromatic aberration occurs due to variations in energy of electrons (particularly, secondary electrons have large variations in energy, and therefore cause a large transverse chromatic aberration), but this transverse chromatic aberration can be inhibited by placing the numerical aperture 87•8 at the focus point of the objective lens 87•7.

Furthermore, since the magnification is changed after the beam passes through the numerical aperture 87•8, a uniform image can be obtained over the entire field of view at the detection side even if the set powers of lens conditions of the third lens 87•10 and the fourth lens 87•13 are changed. Furthermore, in this embodiment, a uniform image having no unevenness can be acquired but usually, if the magnification is increased, the problem arises such that the brightness of the image is reduced. Thus, to solve this problem, the lens conditions of the primary optical system are set so that when the lens conditions of the secondary optical system are changed to change the magnification, the effective field of view on the sample surface determined accordingly and the electron beam irradiated to the sample surface have the same size.

That is, if the magnification is increased, the field of view is reduced accordingly, but by increasing the current density of the electron beam, the signal density of detection electrons is kept constant, and thus the brightness of the image is not reduced, even if the electron beam is projected under magnification by the secondary optical system.

Furthermore, in the inspection apparatus of this embodiment, the Wien filter 87•9 bending the orbit of the primary beam and making the secondary beam travel in a straight line is used, but the Wien filter is not limited to this configuration, and the apparatus may have a configuration using a Wien filter making the orbit of the primary beam travel in a straight line and bending the orbit of the secondary beam. The E×B is used here, but only a magnetic field may be used. In this case, for example, both the direction in which primary electrons enter and direction in which signal electrons are made to travel toward the detector may follow a Y-shaped configuration.

Furthermore, in this embodiment, a rectangular beam is formed from a rectangular cathode and a quadrupole lens, but the invention is not limited thereto and, for example, a rectangular or elliptic beam may be made from a circular beam, or a circular beam may be made to pass through a slit to take a rectangular beam. Furthermore, either a linear beam or a plurality of beams may be used, and they may be scanned.

2-7-1) Control Electrode

An electrode approximately axisymmetric to an irradiation optical axis of an electron beam (25•8 in FIG. 25-1) is placed between the objective lens 87•7 and the wafer W. Examples of the shape of the electrode are shown in FIGS. 88 and 89. FIGS. 88 and 89 are perspective views of electrodes 88•1 and 89•1. FIG. 88 is a perspective view showing the electrode 88•1 having an axisymmetrically cylindrical shape, and FIG. 89 is a perspective view showing the electrode 89•1 having an axisymmetrically discoid shape.

In this embodiment, the electrode 88•1 having a cylindrical shape shown in FIG. 88 is used, but, the electrode 89•1 having a discoid shape shown in FIG. 89 may be used as long as it is approximately axisymmetric to the irradiation optical axis of the electron beam. Further, a predetermined voltage (negative potential) lower than a voltage applied to the wafer W (potential is 0 V because the wafer W is grounded in this embodiment) is applied to the electrode 88•1 by the power supply 25•9 to generate an electric field for preventing a discharge between the objective lens 87•7 (25•7 in FIG. 25-1) and the wafer W. A potential distribution between the wafer W and the objective lens 97•7 at this time will be described with reference to FIG. 90.

FIG. 90 is a graph showing a voltage distribution between the wafer W and the objective lens 87•7. This figure shows a voltage distribution from the wafer W to the position of the objective lens 87•7 with the position on the irradiation optical axis of the electron beam as a horizontal axis. In the conventional electron beam apparatus having no electrode 88•1, the voltage distribution from the objective lens 87•7 to the wafer W gently changes up to the grounded wafer W with the voltage applied the objective lens 87•7 being the maximum (narrow line in FIG. 90), while in the electron beam apparatus of this embodiment, the electrode 88•1 is placed between the objective lens 87•7 and the wafer W, and a predetermined voltage (negative potential) lower than a voltage applied to the wafer is applied to the electrode 88•1, so that the electric field of the wafer W is weakened (thick line in FIG. 90). Accordingly, in the electron beam apparatus of this embodiment, the electric field is not concentrated near the via 25•13 in the wafer (FIG. 25-1), and thus the electric field is not increased. If the electron beam is applied to the via 25•13 to emit secondary electrons, the emitted secondary electrons are not accelerated to the extent that residual gas is ionized, thus making it possible to prevent a discharge occurring between the objective lens 87•7 and the wafer W.

Furthermore, since a discharge can be prevented between the objective lens 87•7 and the via 25•13 (FIG. 25-1), there is no possibility that the pattern of the wafer W and the like are damaged with discharge. Furthermore, in the embodiment described above, a discharge between the objective lens 87•7 and the wafer W having the via 25•3 can be prevented, but since a negative potential is applied to the electrode 88•1, the efficiency of detection of secondary electrons by the detector 87•14 may be reduced. Accordingly, if the detection efficiency is reduced, a series of operations of irradiating the electron beam to detect secondary electrons are carried out two or more times, and a plurality of obtained detection results are subjected to processing such as cumulative addition and equalization to obtain a predetermined signal quality (S/N ratio of signal). This embodiment is described using a signal to noise ratio (S/N ratio) as the detection efficiency as one example.

The secondary electron detection operation will now be described with reference to FIG. 91. FIG. 91 is a flowchart showing the secondary electron detection operation of the electron beam apparatus. First, secondary electrons from an inspection subject sample are detected by the detector 87•14 (step 91•1). Then, whether the signal to noise ratio (S/N ratio) is equal to or greater than a predetermined value or not is determined (step 91•2). If the signal to noise ratio is equal to or greater than the predetermined value at step 91•2, it means that secondary electrons have been detected sufficiently by the detector 87•14, and thus the secondary electron detection operation is ended.

On the other hand, if the signal to noise ratio is smaller than the predetermined value at step 91•2, a series of operations of irradiating the electron beam to detect secondary electrons are carried out 4N times, and equalization processing is carried out (step 91•3). Here, since the initial value of N is set to "1", the secondary electron detection operation is carried out 4 times at the initial round at step 91•3.

Then, "1" is added to N to count up (step 91•4), and again whether the signal to noise ratio is equal to or greater than the predetermined value is determined at step 91•2. Here, if the signal to noise ratio is smaller than the predetermined value, processing proceeds to step 91•3 again, where the secondary electron detection operation is carried out 8 times in this case. Then, N is counted up, and steps 91•2 to 91•4 are repeated until the signal to noise ratio is equal to or greater than the predetermined value.

Furthermore, in this embodiment, a predetermined voltage (negative potential) lower than a voltage applied to the wafer W is applied to the electrode 88•1 to prevent a discharge to the wafer W having the via 25•13 but in this case, the efficiency of detection of secondary electrodes may be reduced. Accordingly, if the inspection subject sample is a type of inspection subject sample hard to cause a discharge between itself and the objective lens 87•7, such as a wafer having no via, the voltage applied to the electrode 88•1 can be controlled so that the efficiency of detection of secondary electrons in the detector 87•14 is improved.

Specifically, even when the inspection subject sample is grounded, a predetermined voltage higher than the voltage applied to the inspection subject sample, for example a voltage of +10 V is applied to the electrode 88•1. Furthermore, at this time, the distance between the electrode 88•1 and the inspection subject sample is set to a distance such that no discharge occurs between the electrode 88•1 and the inspection subject sample.

In this case, secondary electrons generated by irradiation of the electron beam to the inspection subject sample are accelerated toward the detector 87•14 side by an electric field generated with the voltage applied to the electrode 88•1. The secondary electrons are further accelerated toward the detector 87•14 side with an electric field generated with a voltage applied to the objective lens 87•7 and subjected to a convergence action, and therefore a large number of secondary electrons enter the detector 87•14, thus making it possible to the detection efficiency.

Furthermore, the electrode 88•1 is axisymmetric, and thus has a lens action for convergence of the electron beam applied to the inspection subject sample. Thus, the primary electron beam can be more finely focused with the voltage applied to the electrode 88•1. Furthermore, since the primary electron beam can be finely focused with the electrode 88•1, an objective lens system having a lower aberration can be formed with a combination with the objective lens 87•7. The electrode 88•1 may be approximately axisymmetric to the extent that this lens action can be achieved.

According to the electron beam apparatus of the embodiment described above, an electrode having a shape approximately axisymmetric to the irradiation axis of the electron beam and controlling the intensity of the electric field on the surface of the inspection subject sample irradiated with the electron beam is provided between the inspection subject sample and the objective lens, thus making it possible to control the electric field between the inspection subject sample and the objective lens.

An electrode having a shape approximately axisymmetric to the irradiation axis of the electron beam and reducing the intensity of the electric field on the surface of the inspection subject sample irradiated with the electron beam, thus making it possible to eliminate a discharge between the inspection subject sample and the objective lens. Furthermore, since alterations such as reduction of the voltage applied to the objective lens are not made, secondary electrons can be made to pass through the objective lens efficiently, thus making it possible to improve the detection efficiency and obtain a signal having a good S/N ratio.

The voltage for reducing the intensity of the electric field on the surface of the inspection subject sample irradiated with the electron beam can be controlled depending on the type of inspection subject sample. For example, if the inspection subject sample is a type of inspection subject sample that tends to cause a discharge between itself and the objective lens, the discharge can be prevented by changing the voltage of the electrode to reduce the intensity of the electric field on the surface of the inspection subject sample irradiated with the electron beam.

The voltage given to the electrode can be changed, i.e. the voltage for reducing the intensity of the electric field on the surface of a semiconductor wafer irradiated with the electron beam can be changed. For example, if the inspection subject sample is a type of inspection subject sample that tends to cause a discharge between itself and the objective lens, a discharge especially in the via or around the via can be prevented by changing the electric field by the electrode to reduce the intensity of the electric field on the surface of the inspection subject sample irradiated with the electron beam. Furthermore, since a discharge between the via and the objective lens can be discharged, the pattern of the semiconductor wafer or the like is never damaged with discharge. Furthermore, since the potential given to the electrode is lower than the charge given to the inspection subject sample, the intensity of the electric field on the surface of the inspection subject sample irradiated with the electron beam can be reduced, thus making it possible to prevent a discharge to the inspection subject sample. Since the potential given to the electrode is a negative potential, and the inspection subject sample is grounded, the intensity of the electric field on the surface of the inspection subject sample irradiated with the electron beam can be reduced, thus making it possible to prevent a discharge to the inspection subject sample.

Use of the control electrode for the purpose of preventing a discharge has been mainly described, but the control electrode may be used for screening energy of secondary electrons emitted from the wafer. That is, if only secondary electrons having energy at a certain level or greater, which have highest signal detection efficiency, are detected, and so on, to obtain an image of high resolution, a predetermined negative voltage can be applied to the control electrode, and the control electrode can be used as a barrier of energy of secondary electrons. Since a negative potential is applied to the control electrode, a force repelling secondary electrons back to the sample is exerted. Secondary electrons incapable of passing over this potential barrier go back to the sample, and only secondary electrons passing over the potential barrier are detected by the detector, thus making it possible to obtain an image having a desired resolution.

2-7-2) Potential Application Method

In FIG. 92, a potential application mechanism 92•1 controls generation of secondary electrons by applying a potential of ±several volts to a mounting table of a stage on which the wafer is placed, based on the fact that information of secondary electrons emitted from the wafer depends on the potential of the wafer. Furthermore, this potential application mechanism also plays a role to attenuate energy originally possessed by irradiation electrons so that irradiation electron energy of about 100 to 500 eV is applied to the wafer.

As shown in FIG. 92, the potential application mechanism 92•1 comprises a voltage application apparatus 92•4 electrically connected to a holding surface 92•3 of a stage apparatus 92•2, and a charge-up examination and a voltage determination system (hereinafter referred to as an examination and determination system) 92•5. The inspection and determination system 92•5 comprises a monitor 92•7 electrically connected to an image formation unit 92•6 of the detection system of the electro-optical apparatus 13•8 (FIG. 13), an operator 92•8 connected to the monitor 92•7, and a CPU 92•9 connected to the operator 92•84. The CPU 92•9 supplies signals to the voltage application apparatus 92•4.

The potential application mechanism described above is designed to search for a potential at which the wafer as an inspection object is hard to be charged, and apply the potential.

A method for inspecting electric defects of the inspection sample may use the fact the interest area has a different voltage in the case where the interest area is electrically conductive with an originally electrically insulated area.

Specifically, first, a charge is previously given to the sample to cause a difference between the voltage of the originally electrically insulated area and the voltage of the area that is originally electrically insulated but becomes electrically conductive by some cause, then the beam of the present invention is applied to acquire data of the difference in voltage, and the acquired data is analyzed to detect that the area is electrically conductive.

2-7-3) Electron Beam Calibration Method

In FIG. 93, an electron beam calibration mechanism 93•1 comprises a plurality of faraday cups 93•4 and 93•5 for measurement of beam currents, placed at a plurality of locations on the side part of a holding surface 93•3 of the wafer on a rotation table 93•2. The faraday cup 93•4 is for a narrow beam (about ϕ2 μm), and the faraday cup 93•5 is for a thick beam (about ϕ2 μm). For the faraday cup 93•4 for a narrow beam, the rotation table 93•2 is moved stepwise to measure a beam profile, while for the faraday cup 93•5 for a thick beam, the total amount of current of the beam is measured. The faraday cups 93•4 and 93•5 are arranged so that the upper surfaces are at the same level of the upper surface of the wafer W placed on the holding surface 93•3. In this way, the primary electron beam emitted from the electron gun is always monitored. This is because the electron gun cannot always emit a constant electron beam, but the emission is changed with time.

2-7-4) Cleaning of Electrode

When the electron beam apparatus of the present invention is activated, a target material is floated by a proximity interaction (charge of particles near the surface) and attracted to a high-pressure area, and therefore organic materials are deposited on various electrodes for use in formation and deflection of the electron beam. Insulating materials that are gradually deposited with the charge of the surface badly affect formation of the electron beam and the deflection mechanism, and therefore the deposited insulating materials must be removed periodically. The periodic removal of insulating materials is carried out by producing plasmas of hydrogen, oxygen or fluorine and compounds containing those elements such as HF, $O_2$, $H_2O$ and $C_MF_N$ under vacuum using electrodes near the area on which insulating materials are deposited, and keeping the plasma potential in a space at a potential (several kVs, e.g. 20 V to 5 kV) at which spatters occur on the surface of the electrode to oxidize, hydrogenise and fluorinate only organic materials. Furthermore, by passing a gas having a cleaning effect, contaminants on the surfaces of the electrode and the insulator can be removed.

2-7-5) Alignment Control Method

An alignment control apparatus 94•1 of FIG. 94 is an apparatus positioning the wafer W with respect to an electro-optical apparatus 94•2 using a stage apparatus, and performs control such as rough adjustment of the wafer by a wide-field observation using an optical microscope 94•3 (measurement under a lower magnification than measurement by the electro-optical system), adjustment under a high magnification using an electro-optical system of the electro-optical apparatus 94•2, focus adjustment, setting of an inspection area, pattern alignment. The reason why the wafer is inspected under a low magnification using an optical system is that an alignment mark should be easily detected with an electron beam when the pattern of the wafer is observed to perform wafer alignment in a narrow-field using the electron beam to automatically inspect the pattern of the wafer.

The optical microscope 94•3 is provided in a housing (may be movably provided in the housing), and a light source (not shown) for operating the optical microscope is housed. Furthermore, the electro-optical system (primary optical system and secondary optical system) of the electro-optical apparatus 94•2 is also used as an electro-optical system for making an observation under a high magnification. The outlined configuration thereof is shown in FIG. 94. To observe an observation subject point on the wafer under a low magnification, an X stage on the stage apparatus is moved in the X direction to shift the observation subject point on the wafer to within the field of view of the optical microscope. The wafer is visually recognized in a wide field with the optical microscope 94•3, the position of the wafer to be observed is displayed on a monitor 94•5 via a CCD 94•4, and the observation position is roughly determined. In this case, the magnification of the optical microscope may be changed from a low magnification to a high magnification.

Then, the stage apparatus is moved by a distance equivalent to an interval δx between the optical axis of the electro-optical apparatus 94•2 and the optical axis of the optical microscope 94•3 to shift the observation subject point on the wafer predefined by the optical microscope to the position of the field of view of the electro-optical apparatus. In this case, a distance δx between the axial line $O_3$—$O_3$ of the electro-optical apparatus and the optical axis $O_4$—$O_4$ of the optical microscope 94•3 (both axes are deviated in position only along the direction of the X axis in this embodiment, but may be deviated in position along the direction of the Y axis and the direction of the Y axis) is already know, and therefore movement of the stage apparatus by the value δx can shift the observation subject point to the visually recognized position. After the shift of the observation subject point to the visually recognized position of the electro-optical apparatus is completed, the observation subject point is SEM-imaged under a high magnification by the electro-optical system, and the image is stored or displayed on a monitor 94•7 via a CCD 94•6.

After the observation point on the wafer is displayed on the monitor under a high magnification with the electro-optical system in this way, a positional deviation in the direction of rotation of the wafer with respect to the center of rotation of the rotation table of the stage apparatus, and a deviation δθ in the direction of rotation of the wafer with respect to the optical axis $O_3$—$O_3$ of the electro-optical system are detected, and a deviation in position in the X and Y axes of a predetermined pattern with respect to the electro-optical system is detected. The operation of the stage apparatus 94•8 is controlled based on the detected value and separately obtained data of an inspection mark provided on the wafer or data about the shape of the pattern of the wafer to perform alignment of the wafer. The range of alignment is within ±10 pixels in XY coordinates. It is preferably within ±5 pixels, more preferably within ±2 pixels.

2-7-6) EO Correction

A. Overview

When the beam from the wafer is imaged with a TDI, the wafer should be correctly positioned but actually, the wafer is placed on the X-Y stage and mechanically positioned, and hence the accuracy is in the range of several hundreds of nm to several tens of μm, and the response time is several seconds to several milliseconds as practical values.

On the other hand, the design rule is refined toward several tens of nm, and thus wiring with the line width of several tens of nm and vias with the diameter of several tens of nm should be inspected to detect their shape defects and electric defects, and dust with the diameter of several tens of nm. Imaging dependent solely on the mechanical positioning results in a significant difficulty in acquirement of a correct image because the order of the response time and positioning accuracy considerably differs from the order of the design rule and imaging accuracy.

A sequence of imaging is carried out by a combination of a step (x axis) and a constant speed scan (y axis), and relatively dynamic control (y axis) generally has a large control residual, and thus is required to be high level control for preventing a blur of an image.

In view of these items, an X-Y stage having high accuracy and excellent responsivity is provided as a matter of course, but further a function of EO correction is provided to achieve accuracy of control of the beam for an imaging unit and a speed, which cannot be ensured by the stage.

The fundamental method is such that the position of the wafer on the stage is correctly recognized within a time delay of several micro seconds in the order of sub nm with a laser interferometer and a bar mirror placed on the x-y axis, a mechanical actuator is driven by an automatic control loop, and the wafer is positioned at a target position with a temporal delay and a residual. The control residual as a result of positioning by this control is determined by a difference between the target position generated within a control apparatus and the current position obtained by a laser interferometer system. On the other hand, the beam passes through various electrodes, and is then guided to an imaging apparatus via a deflection electrode for correction. The deflection electrode for correction has a sensitivity capable of deflection within about several hundreds of μm, preferably within a hundred μm, more preferably within several tens of μm equivalent to the distance on the wafer, and by applying a voltage to the electrode, the beam can be deflected to any position on a two-dimensional basis. The control residual is subjected to calculation by a calculation apparatus, and then converted into a voltage by a D/A converter, and the voltage is applied to the deflection electrode for correction in a direction for offsetting the residual. The above configuration makes it possible to carry out correction close to the resolution of the laser interferometer.

As another method, the mean described above is used for the X axis (step direction), and a transfer clock of the TDI as an imaging device is transferred in synchronization with the speed of movement of the stage for the Y axis.

The concept of EO correction is shown in FIG. 95. An indication 95•1 to a target position is outputted, and given to a control feedback loop 95•2 including a mechanical actuator. This part corresponds to a stage. The result of occurrence of a positional displacement by driving is subjected to feedback by a position detector 95•3, and the positional displacement of a drive system converses into the target position from the position indication, but a gain of a control system is finite, and therefore a residual occurs. The current position is detected in the order of sub nm by a position output system 95•4 (a laser interferometer is used here), a difference with the position indication apparatus 95•1 is detected by a residual detector 95•5, a voltage is applied to a deflection electrode 95•7 using a high-pressure and high-speed amplifier 95•6, a voltage is applied in a direction for offsetting the residual, and if this function is not originally provided, a function to reduce a generated variation as denoted by reference numeral 95•8 to a variation denoted by a reference numeral 95•9 is provided.

The specific configuration of devices is shown in FIG. 96. An XY stage 96•1 drives the X axis with a servo motor 96•2 for driving the X axis and an encoder 96•3, and detects a rough position thereof and a speed to achieve smooth servo characteristics. In this example, the servo motor is used, but a similar configuration can be provided with an actuator such as a linear motor or ultrasonic motor. Reference numeral 96•6 denotes a power amplifier for driving the motor. Precise position information of the X axis achieves a position detection function having a resolution in sub nm by a combination of a mirror 96•7, an interferometer 96•8, a receiver 96•9, a laser light source 96•10 and an interferometer board 96•11.

The Y axis functions similarly to the X axis orthogonal thereto, and is comprised of a servo motor 96•12, an amplifier 96•13, a mirror 96•14, an interferometer 9•5 and a receiver 96•16.

An X-Y stage controller 96•17 collectively controls these devices, thereby enabling the stage to be moved two-dimensionally, achieves accuracy of 1000 μm to 1 nm, preferably 100 μm to 2 nm, more preferably 1 μm to 2 nm, further more preferably 0.1 μm to 2 nm, and achieves a performance such that the response time is several thousands of milliseconds or less, preferably several tens of milliseconds, more preferably several milliseconds. On the other hand, an X reference value and a Y reference value are outputted from the X-Y stage controller 96•17 to an EO corrector 96•18, position information is outputted in a 32 bit binary format from the interferometer 96•11, and the EO corrector 96•18 receives the current position via a high-speed buffer board 96•19. Calculation is internally performed, then a voltage is amplified with high-voltage and high-speed amplifiers 96•20 and 96•21, then the voltage is applied to a deflection electrode 96•22, and deflected for correction of a residual, and an image information electron beam with a positional deviation reduced to a minimum is guided to a TDI (imaging device) 96•23. Reference numeral 96•24 denotes a portion for generating a timing signal for determining a transfer speed of the TDI 96•23 as described later.

A function of generating a target position in the scan direction in this apparatus will now be described. EO correction is a function of determining a difference between the target position and the actual position, deflecting the electron beam so as to offset the difference to correct the position, but the correction range is limited to a range of about several tens of μm. This is determined by an electrode sensitivity, a dynamic range of the high-voltage and high-speed amplifier, a noise level, and the number of bits of the D/A converter. However, the actual position of the stage during scanning is considerably deviated with respect to the target position, compared with the position when the stage is stopped, due to the fact that the gain of the control loop is finite. If the stage travels at 20 mm/s, the difference between the actual position and the target position is about 400 μm, and the correction range is considerably exceeded to saturate the system if the difference is calculated and outputted directly.

To prevent such a phenomenon, this apparatus uses the following means to avoid problems. The concept thereof is shown in FIG. 97.

A position 97•1 is the target position of the stage, and is lineally incremented with time because the stage is moved at a constant speed during scanning. On the other hand, a mechanical position 97•2 of the stage as a result of actually being controlled includes mechanical vibrations of several microns and has a steady-state deviation 97•3 of about 400 μm. As a measure for removing this steady-state deviation, it can be considered that a filter is used to smooth position information when the stage travels but in this case, there is a disadvantage that a delay absolutely occurs due to a time constant of the filter, and if a time constant such that a ripple is negligible is provided, a measurement starting area is strictly limited, leading to a considerable increase in overall measurement time. Thus, in this proposal, for detecting this steady-state deviation, at least a difference between the current position at the time of previous scanning and the target position is integrated at least about $2^{16}$ times, the resulting value is divided by the number of samples to determine an average value 97•4 of the steady-state deviation between the target position and the current position, and calculation is performed as a target position 97•6 synthesized by subtracting an average value 97•4 from a target position 97•5 during present scanning to achieve a configuration enabling EO correction to be performed within the dynamic range as shown by 98•1 of FIG. 98. Furthermore, the number of integrations are not limited to this value, but may be a smaller number of integration stages as long as a target level of accuracy is obtained.

FIG. 99 is a block diagram. A current position 99•2 is subtracted from a target value 99•1, and the •integration calculation is carried out within a block of 99•3 during scanning. On the other hand, the average value of the steady-state deviation previously determined in the same manner is outputted to a position 99•3 from a position 99•4. The position 99•4 is subtracted from the target value 99•1 to obtain a synthesized target position 99•6 by a subtractor 99•5, and this value is subtracted from a current position 99•7 from an interferometer to achieve EO correction data free from a delay in response and a ripple.

FIG. 100 shows a structure of detection of an average of a difference of a block of 99•3 in FIG. 99. Integration is carried out by an ALU 100•1 and a latch 100•2, a word of a data selector 100•4 is selected by a value of a cumulative time counter 100•3, calculation equivalent to division is carried out, and an average value of the steady-state deviation is outputted.

An idea of a transfer clock of the TDI is shown in FIG. 101. The TDI is an imaging device having photoelectric elements connected in a multiple stage in the scan direction, and transmitting charges of imaging devices to subsequent devices to improve the sensitivity and reduce random noises, but as shown in FIG. 101, it is important that imaging objects on the stage correspond to pixels on the TDI on a one-to-one basis, and if this relation is broken, an image is blurred. Synchronous relations are shown in FIGS. 1-1, 1-2, 2-1 and 2-2, and asynchronous relations are shown in FIGS. 3-1, 3-2, 4-1 and 4-2. Since the TDI is transferred to a next stage in synchronization with an external pulse, this is achieved by generating a transfer pulse when the stage is moved in an amount equivalent to one pixel.

However, the output of position information in a laser interferometer that is in the mainstream takes a form of outputting a 32 bit binary output in synchronization with its own internal clock of 10 MHz, and thus this cannot be easily achieved in the original state. Furthermore, if the resolution is several tens of nm, the accuracy of the transfer pulse is also important, and thus high-speed and high-accuracy digital processing is required. A method devised in the invention is shown in FIG. 102. In this figure, position information of the interferometer and a synchronization signal of 10 MHz are introduced into a main circuit via a buffer 102•1. A 10 MHz clock 102•2 generates a clock of 100 MHz synchronized with a PLL 102•3, and supplies the same to each circuit. Calculation processing is carried out for every 10 states of this synchronization signal 102•4. Present position information is retained in a latch 102•5, and a pervious value is retained in a latch 102•6. A difference between both the values is calculated by an ALU 102•7, and a difference of positions for every 10 states is outputted from a component 102•8. This difference value is loaded to a parallel serial comparator 102•9 as a parallel value, and outputted from an OR 102•10 as a number of serial pulses in synchronization with the clock of 100 MHz. A comparator 102•11 has a similar function, but is configured to be capable of operating continuously for every 10 states in combination with components 102•12 and 102•13. As a result, a serial pulse matching a position difference is outputted from a summation circuit 102•10 to a counter 102•14 for every 10 MHz. Provided that the resolution of the laser interferometer is 0.6 nm and one pixel has a size of 48 nm, 19 pulses are outputted at the time when the counter becomes equivalent to one pixel if a comparator 102•15 is set at 80. Use of this signal as a transfer pulse from outside the TDI allows an operation synchronized with even a variation in stage speed, thus making it possible to prevent blurring.

A timing chart is shown in FIG. 103., Reference numeral 1 denotes interferometer coordinate (position) information, in which numbers show positions as examples. Reference numeral 2 denotes a synchronization signal of 100 MHZ created by a PLL. A bank A is operation timing of the parallel serial converter 102•9, and a bank B is operation timing of the comparator 102•11. After latch timing 7 for storing position information, difference calculation timing 8 is executed, a value is loaded to the parallel serial converter 102•9, time of one cycle of a next 10 M clock 3 is used to execute an output of 4. The bank B carries out a similar operation in timing delayed by one cycle of the 10 M clock 3 to achieve pulse generation of 6 without difficulties.

2-7-7) Image Comparison Method

FIG. 104 shows the outlined configuration of a defect inspection apparatus according to an alteration example of the present invention. The defect inspection apparatus is the projection type inspection apparatus described above, and comprises an electron gun 104•1 emitting a primary electron beam, an electrostatic lens 104•2 deflecting and shaping the emitted primary electron beam, an E×B deflector 104•3 deflecting the shaped primary electron beam so that the primary electron beam impinges upon the semiconductor wafer W at almost a right angle in a field where an electric field E and a magnetic filed B are orthogonal, an objective lens 104•4 making the deflected primary electron beam form an image on the wafer W, a stage 104•5 provided in a sample chamber (not shown) capable of being evacuated and movable in a horizontal plane with the wafer W placed thereon, an electrostatic lens 104•6 of a projection system magnifying and projecting a secondary electron beam and/or a reflection electron beam emitted from the wafer W with irradiation of the primary electron beam under a predetermined magnification to form an image, a detector 104•7 detecting the formed image as a secondary electron image of the wafer, and a control unit 104•8 controlling the entire apparatus, and carrying out processing for detecting defects of the wafer based on the secondary electron image detected by the detector 104•7. Furthermore, not only secondary electrons but also scattered electrons and reflection electrons contribute to the secondary electron image described above, but it is called a secondary electron image herein.

Furthermore, a deflection electrode 104•9 deflecting with the electric field or the like an angle at which the primary electron beam enters the wafer is provided between the objective lens 104•4 and the wafer W. A deflection controller 104•10 controlling the electric field of the deflection electrode is connected to the deflection electrode 104•9. The deflection controller 104•10 is connected to the control unit 104•8, and controls the deflection electrode so that an electric field matching a command from the control unit 104•8 is generated in the deflection electrode 104•9. Furthermore, the deflection controller 104•10 can be formed as a voltage control apparatus controlling a voltage given to the deflection electrode 104•9.

The detector 104•7 may have any configuration as long as the secondary electron image formed by the electrostatic lens 104•6 can be converted into a signal capable of being subjected to post-processing. For example, as shown in detail in FIG. 62, the detector 104•7 may comprise a micro-channel plate 62•1, a fluorescent screen 62•2, a relay optical system 62•3, and an imaging sensor 62•4 constituted by a large number of CCD elements. The micro-channel plate 62•1 has a large number of channels in a plate, and further generates a large number of electrons while secondary electrons made to form an image by the electrostatic lens 104•6 pass through the channels. That is, secondary electrons are amplified. The fluorescent screen 62•2 converts secondary electrons into light by emitting fluorescence with amplified secondary electrons. The relay lens 62•3 guides the fluorescence to the CCD imaging sensor 62•4, and the CCD imaging sensor 62•4 converts an intensity distribution of secondary electrons on the surface of the wafer W into an electric signal for each element, i.e. digital image data, and outputs the same to the control unit 104•8. Here, the micro-channel plate 62•1 may be omitted and in this case, blurring caused by expansion between the micro-channel plate 62•1 and the fluorescent screen can be reduced. For example, an image of 0.2 in MTF can be enhanced to 0.3–0.6.

The control unit 104•8 may be constituted by a general personal computer or the like as illustrated in FIG. 104. This computer comprises a control unit main body 104•11 for various kinds of control and calculation processing according to a predetermined program, a CRT 104•12 displaying the result of processing by the main body 104•11, and an input unit 104•13 such as a keyboard and a mouse for an operator to input instructions. Of course, the control unit 104•8 may be constituted by hardware dedicated to defect inspection apparatus, a workstation or the like.

The control main body 104•11 is comprised of a CPU, a RAM, a ROM, a hard disk, various kinds of control boards such as a video board, and the like (not shown). A secondary electron image storage area 104•14 for storing electric signals received from the detector 104•7, i.e. digital image data of the secondary electron image of the wafer W is assigned onto a memory of a RAM or hard disk. Furthermore, a reference image storage unit 104•15 for storing in advance reference image data of the wafer having no defects exists on the hard disk. Furthermore, in addition to a control program for controlling the entire defect inspection apparatus, a defect detection program 104•16 for reading secondary electron image data from the storage area 104•14 and automatically detecting defects of the wafer W according to a predetermined algorithm based on the image data is stored on the hard disk. As describe in detail later, this defect detection program 104•16 has a function that the reference image read from the reference image storage unit 104•15 and an actually detected secondary electron image are made to match each other to automatically detect defective areas, and if it is determined that defects exist, warning display is provided to the operator. At this time, a secondary electron image 104•17 may be displayed on a display unit of the CRT 104•12.

The action of the defect inspection apparatus according to the embodiment will now be described using flowcharts of FIGS. 105 to 107 as an example. First, as shown in the flow of a main routine of FIG. 105, the wafer W as an inspection object is set on the stage 104•5 (step 105•1). A large number of wafers stored in a loader may be all set on the stage 104•5 on one-by-one basis as described previously.

Then, images of a plurality of inspection subject areas mutually displaced and partially overlapping on the XY plane of the surface of the wafer W are each acquired (step 105•2). The plurality of inspection subject areas, images of which are to be acquired, are, for example, rectangular areas denoted by reference numerals 108•2a, 108•2b, . . . , 108•2k, . . . on a wafer inspection surface 108•1, and it can be understood that these areas are mutually displaced while partially overlapping around an inspection pattern 108•3 of the wafer. For example, as shown in FIG. 109, images 109•1 (inspection subject images) of 16 inspection subject areas are acquired. Here, in the image shown in FIG. 109, a rectangular cell corresponds to one pixel (or may be a block unit larger than a pixel), and black-painted cells correspond to an image area of the pattern on the wafer W. The details of the step 105•2 will be described later with the flowchart of FIG. 106.

Then, image data of the plurality of inspection subject areas acquired at step 105•2 are each compared with reference image data stored in the storage unit 104•15 (step 105•3 in FIG. 105) to determine whether or not defects exist on the wafer inspection surface covered by the plurality of inspection object areas. In this step, processing of so called matching between image data is carried out, and the details thereof will be described later with the flowchart of FIG. 107.

If it is determined that defects exist on the wafer inspection surface covered by the plurality of inspection subject areas (positive determination in step 105•4) as a result of comparison at step 105•3, the operator is warned of existence of defects (step 105•5). As a method for warning, for example, a message indicating existence of defects is displayed on the display unit of the CRT 104•12, and an enlarged image 104•17 of a pattern having defects may be displayed at the same time. The defective wafer may be immediately taken out from the sample chamber, and stored at a storage site different from that for the wafer having no defects (step 105•6).

If it is determined that the wafer W has no defects (negative determination in step 105•4) as a result of comparison at step 105•5, whether any area to be inspected still exists or not is determined for the wafer W that is currently an inspection object (step 105•7). If an area to be inspected still exists (positive determination in step 105•7), the stage 104•5 is driven to move the wafer W so that other area to be inspected next is included in the area of irradiation with the primary electron beam (step 105•8). Then, processing returns to step 105•2, where the same processing is repeated for the other inspection area.

If no area to be inspected exists (negative determination in step 105•7), or after the step of taking out the defective wafer (step 105•6), whether the wafer W that is currently an inspection object is a last wafer or not, i.e. whether or not any wafer that has not been inspected yet still exists on a loader (not shown) is determined (step 105•9). If the wafer W is not a last wafer (negative determination in step 105•9), the inspected wafer is stored at a predetermined storage site and instead, a new wafer that has not been inspected is set on the stage 104•5 (step 105•10). Then, processing returns to step 105•2, where the same processing is repeated for the wafer. If the wafer W is the last wafer (positive determination in step 105•9), the inspected wafer is stored at the predetermined storage site to complete all the steps. An identification number is assigned to each cassette or each wafer, and the wafer being inspected is recognized and monitored to prevent duplicated inspection of a wafer, for example.

The flow of processing at step 105•2 will now be described according to the flowchart of FIG. 106. In this figure, first, an image number I is set to an initial value 1 (step 106•1). The image number is an identification number assigned sequentially to each of a plurality of inspection subject area images. Then, an image position $(X_i, Y_i)$ is determined for the inspection subject area of the set image number i (step 106•2). This image position is defined as a specified position in the area for demarcating the inspection subject area, for example a central position of the area. At present, the image position is $(X_1, Y_1)$ because i equals 1, this corresponds to, for example, the central position of an inspection subject area 108•2a shown in FIG. 108. The image positions of all inspection subject image areas are defined in advance, and are stored on the hard disk of the control unit 104•8, for example, and read at step 106•2.

Then, the deflection controller 104•10 applies a potential to the deflection electrode 104•9 so that the primary electron beam passing through the deflection electrode 104•9 of FIG. 104 is applied to the inspection subject image area of the image position $(X_i, Y_i)$ determined at step 106•2 (step 106•3 of FIG. 106).

Then, the primary electron beam is emitted from the electron gun 104•1, and applied to the surface of the set wafer W through the electrostatic lens 104•2, the E×B deflector 104•3, the objective lens 104•4 and the deflection electrode 104•9 (step 106•4). At this time, the primary electron beam is deflected by an electric field produced by the deflection electrode 104•9, and applied over the entire inspection subject image area at the image position ($X_i$, $Y_i$) on the wafer inspection surface 108•1. If the image number i equals 1, the inspection subject area is an area 108•2a.

Secondary electrons and/or reflection electrons (hereinafter referred to as only "secondary electrons") are emitted from the inspection subject area of irradiation with the primary electron beam. Then, the generated secondary electron beam is made to form an image on the detector 104•7 under a predetermined magnification by the electrostatic lens 104•6 of an enlargement projection system. The detector 104•7 detects the secondary electron beam made to form an image, and converts the image into an electric signal or digital image data for each detecting element and outputs the same (step 106•5). Detected digital image data with the image number of i is transferred to the secondary electron image storage area 104•14 (step 106•6).

Then, the image number i is incremented by 1 (step 106•7), and whether the incremented image number (i+1) exceeds a fixed value $i_{MAX}$ or not is determined (step 106•8). This value $i_{MAX}$ is the number of inspection subject images to be acquired, and equals "16" in the example of FIG. 109 described above.

If the image number i does not exceed the fixed value $i_{MAX}$ (negative determination in step 106•8), processing returns to step 106•2, where the image position ($X_{i+1}$, $Y_{i+1}$) is determined again for the incremented image number (i+1). This image position is a position obtained by shifting the image from the image position ($X_i$, $Y_i$) determined in the pervious routine in the X direction and/or Y direction by a predetermined distance ($\Delta X_i$, $\Delta Y_i$). In the example of FIG. 108, the inspection subject area is at a position ($X_2$, $Y_2$) obtained by shifting the image from ($X_i$, $Y_i$) only in the Y direction, which corresponds to a rectangular area 108•2b shown by a broken line. Furthermore, the values of ($\Delta X_i$, $\Delta Y_i$) (i=1, 2, ... $i_{MAX}$) may be defined as appropriate based on data of how a pattern 108•3 of the wafer inspection surface 108•1 is actually shifted empirically from the field of view of the detector 104•7, and the number and area of inspection subject areas.

Processing at steps 106•2 to 106•7 is carried out one after another repeatedly for $i_{MAX}$ inspection subject areas. As shown in FIG. 108, these inspection subject area are mutually shifted in position while partially overlapping on the wafer inspection surface 108•1 so that an image position ($X_k$, $Y_k$) is obtained by making k shifts. In this way, 16 inspection subject image data illustrated in FIG. 109 are captured in the image storage area 104•14. It can be understood that an image (inspection subject image) 109•1 of the acquired plurality of inspection subject areas has partially or fully captured therein an image 109•2 of the pattern 108•3 on the wafer inspection surface 108•1.

If the incremented image number i exceeds $i_{MAX}$ (positive determination in step 106•8), this subroutine is returned, and processing proceeds to a comparison step.

Furthermore, image data memory-transferred at step 106•6 consists of the intensity value of secondary electrons for each pixel (so called solid data) detected by the detector 104•7, but may be stored in the storage area 104•14 with the image data subjected various calculation processing because the image data is subjected to matching calculation with a reference image at the subsequent comparison step (step 105•3). Such calculation processing includes, for example, normalization processing for making the size and/or density of image data match the size and/or density of reference image data, and processing of removing as a noise an isolated group of images having a predetermined number or smaller number of pixels. Further, instead of simple solid data, data may be compressed and converted into a feature matrix with a feature of a detection pattern extracted within the bounds of not reducing the detection accuracy of a precise pattern. Such feature matrixes include, for example, an m×n feature matrix having as each component the total of secondary electron intensity values of pixels (or, normalized value obtained by dividing the total value by the total number of pixels of the entire inspection subject area) included in each of m×n blocks (m<M, n<N) into which a two-dimensional inspection subject area consisting of M×N pixels is divided. In this case, reference image data is also stored in the same form. The image data cited in the embodiments of the present invention includes not only mere solid data but also image data feature-extracted with any algorithm as described above.

The flow of processing at step 105•3 will now be described according to the flowchart of FIG. 107. First, the CPU of the control unit 104•8 reads reference image data from the reference image storage unit 104•15 (FIG. 104) onto a working memory of a RAM or the like (step 107•1). This reference image is denoted by reference numeral 109•3 in FIG. 109. The image number i is set to 1 (step 107•2), and inspection subject image data with the image number of i is read from the storage area 104•14 onto the working memory (step 107•3).

Then, the read reference image data is made to match the data of the image i to calculate a distance value $D_i$ between both the data (step 1074). This distance value $D_i$ indicates similarity between the reference image and the inspection subject image i, which means that the larger the distance value, greater the difference between the reference image and the inspection subject image. Any quantity indicating similarity may be employed as the distance value $D_i$. For example, if image data consists of M×N pixels, the secondary electron intensity (or feature amount) of each pixel may be considered as each vector component of a M×N-dimensional space, and a Euclidean distance or a coefficient of correlation between a reference image vector and an image i vector on the M×N-dimensional space may be calculated. Of course, a distance other than the Euclidean distance, for example, so called an urban area distance or the like may be calculated. Further, if a large number of pixels exist, the calculation amount considerably increases, and therefore the distance value between image data expressed by the m×n feature vector may be calculated as described above.

Then, whether the calculated distance value $D_i$ is smaller than a threshold value Th or not is determined (step 107•5). This threshold value Th is determined empirically as a reference when whether the reference image sufficiently matches the inspection subject image is determined. If the distance value $D_i$ is smaller than the predetermined threshold value Th (positive determination in step 107•5), it is determined that "no defect exits" on the inspection surface 1034 of the wafer W (step 107•6), and this sub routine is returned. That is, if even only one of inspection subject images approximately matches the reference image, it is determined that "no defect exists". In this way, it is not necessary that the reference image should be matched with all inspection subject images, thus making it possible to make a determination quickly. In the example of FIG. 109, it can be understood that the inspection subject image of third line and third row approximately matches the reference image with no shift in position with respect to the reference image.

If the distance value $D_i$ is equal to or larger than the predetermined threshold value Th (negative determination in step 107•5), the image number i is incremented by 1 (step 107•7), and whether the incremented image number (i+1) exceeds the fixed number $i_{MAX}$ or not is determined (step 107•8).

If the image number i does not exceed the fixed value $i_{MAX}$ (negative determination in step 107•8), processing returns to step 107•3, where image data is read for the incremented image number (i+1), and the same processing is repeated.

If the image number i exceeds the fixed value $i_{MAX}$ (positive determination in step 107•8), it is determined that "defects exit" on the inspection surface 1034 of the wafer W (step 107•9), and this sub routine is returned. That is, if none of inspection subject images approximately match the reference image, it is determined that "defects exist".

Each embodiment of the stage apparatus has been described above, but the present invention is not limited to the above examples, and may be altered arbitrarily and appropriately within the substance of the present invention.

For example, the semiconductor wafer W is used as an inspection subject sample, but the inspection subject sample of the present invention is not limited thereto, and any sample allowing defects to be detected with an electron beam can be selected. For example, a mask or the like provided with a pattern for light exposure for the wafer may be used as an inspection object.

Furthermore, the present invention can be applied not only to apparatuses detecting defects using charged particle beams other than electrons, but also to any apparatus capable of acquiring images allowing defects of samples to be inspected.

Further, the deflection electrode 104•9 may be placed not only between the objective lens 104•4 and the wafer W, but also at any position as long as the area of irradiation with the primary electron beam can be changed. For example, it may be placed between the ExB deflector 104•3 and the objective lens 104•4, between the electron gun 104•1 and the ExB deflector 104•3, or the like. Further, by controlling a field generated by the ExB deflector 104•3, the direction of deflection may be controlled. That is, the ExB deflector 104•3 may also have a function as the deflection electrode 104•9.

Furthermore, in the embodiment described above, any one of matching between pixels and matching between feature vectors is performed when performing matching between image data, but both types of matching may be combined. For example, compatibility between enhancement of the speed and accuracy can be achieved by two-stage processing such that first, high-speed matching is performed with feature vectors having small calculation amounts and as a result, for high-similarity inspection subject images, matching is performed with more precise pixel data.

Furthermore, in the embodiment of the present invention, a positional shift of the inspection subject image is coped with only by shifting the position of the area of irradiation with the primary electron beam, but processing of searching for an optimum matching area on image data before or during matching processing (detecting areas of high coefficients of correlation and performing matching between the areas) may be combined with the present invention. According to this, a large positional shift of the inspection subject image can be coped with by shifting the position of the area of irradiation with the primary electron beam according to the present invention, and also a relatively small positional shift can be absorbed in subsequent digital image processing, thus making it possible to improve the accuracy of defect detection.

Further, the configuration in FIG. 104 has been shown as an electron beam apparatus for defect detection, but the electro-optical system and the like can be altered arbitrarily and appropriately. For example, electron beam irradiating means (104•1, 104•2, 104•3) of the defect inspection apparatus shown in FIG. 104 has a form such that the primary electron beam is made to enter the surface of the wafer W uprightly from above, but the ExB deflector 104•3 may be omitted, and the primary electron beam may be made to enter the surface of the wafer W slantingly.

Furthermore, the flow of the flowchart of FIG. 105 is not limited to the examples described above. For example, for a sample for which it is determined that defects exist at step 105•4, defect inspection in other areas is not carried, but the flow of processing may be changed so that defects are detected covering all areas. Furthermore, if the area of irradiation with the primary electron beam is expanded so that almost all inspection areas of the sample can be covered with one irradiation, steps 105•7 and 105•8 may be omitted.

As described in detail above, according to the defect inspection apparatus of this embodiment, images of a plurality of inspection subject areas mutually displaced while partially overlapping on the sample are each acquired, and the images of the inspection subject areas are compared with the reference image to inspect defects of the sample, thus making it possible to obtain an excellent effect such that a reduction in accuracy of defect inspection resulting from a positional shift between the inspection subject image and the reference image can be prevented.

Further, according to the device production process of the present invention, defect inspection of the sample is carried out using the defect inspection apparatus described above, thus making it possible to obtain an excellent effect such that the yield of products can be improved and defective products can be prevented from being dispatched.

2-7-8) Device Production Process

The embodiment of a process for producing a semiconductor device according to the present invention will now be described with reference to FIGS. 110 and 111. FIG. 110 is a flowchart showing one embodiment of the process for producing a semiconductor device according to the present invention. The production process of this embodiment includes the following main steps.

(1) Wafer production step of producing a wafer (or wafer preparation step of preparing a wafer) (step 110•1).

(2) Mask production step of producing a mask for use in light exposure (or mask preparation step of preparing a mask) (step 110•2).

(3) Wafer processing step of subjecting the wafer to necessary process processing (step 110•3).

(4) Chip assembly step of cutting out chips formed on the wafer on one-by-one basis and making the chips operable (step 1110•4).

(5) Chip inspection step of inspecting the assembled chips (step 110•5).

Furthermore, the main steps described above each consist of several sub-steps. It is the wafer processing step (3) among these main steps that has decisive influences on the performance of the semiconductor device. In this step, designed circuit patterns are stacked on the wafer one after another to form a large number of chips operating as memories and MPUs. This wafer processing step includes the following steps.

(A) Thin film formation step of forming a dielectric thin film and a wiring portion serving as an insulating layer or a thin metal film forming an electrode portion (using CVD, spattering or the like).
(B) Oxidization step of oxidizing the thin film layer and the wafer substrate.
(C) Lithography step of forming a resist pattern using a mask (reticle) for selectively processing the thin film layer, the wafer substrate and the like.
(D) Etching step of processing the thin film layer and the substrate according to the resist pattern (e.g. using a dry etching technique).
(E) Ion/impurity injection and diffusion step.
(F) Resist peeling step.
(G) Step of inspecting the processed wafer.

Furthermore, the wafer processing step is repeated for a necessary number of layers to produce a semiconductor device operating as designed.

FIG. 111 is a flowchart showing the lithography step lying at the heart of the wafer processing step. The lithography step includes the following steps.
(a) Resist coating step of coating a resist on the wafer having the circuit pattern formed at the previous step (step 111•1).
(b) Step of exposing the resist to light (step 111•2).
(c) Development step of developing the exposed resist to obtain a pattern of the resist (step 111•3).
(d) Annealing step for stabilizing the developed resist pattern (step 111•4).

The semiconductor device production step, the wafer processing step and the lithography step described above are well known, and thus are not required to be described further in detail.

If the defect inspection process and defect inspection apparatus according to the present invention are used in the inspection step (G), even a semiconductor device having a fine pattern can be inspected in high throughput, and therefore 100% inspection can be performed, thus making it possible to improve the yield of products and prevent defective products from being dispatched.

2-7-9) Inspection

Inspection procedures in the inspection step of (G) will be described using FIG. 112. Generally, the defect inspection apparatus using electron beams is expensive, and has low throughput compared to other process apparatuses, and is thus used, at present, after an important step considered to require most strictest inspection (e.g. etching, film formation, CMP (chemical-mechanical polishing) flatness processing, etc.), or in a more precise wiring step part, i.e. 1 to 2 steps of the wiring step and the gate wiring step as a pervious step in the case of the wiring step. Particularly, it is important that shape defects and electric defects of wiring having a design rule of 100 nm or less, i.e. a line width of 100 nm or less, a via hole having a diameter of 100 nm or less and the like are found, and fed back to the process.

The wafer to be inspected is aligned on a very precise X-Y stage through an atmosphere transportation system and a vacuum transportation system, then fixed by an electrostatic chuck mechanism or the like, and then subjected to defect inspection according to procedures (of FIG. 112). First, the position of each die is checked and the height of each site is detected as necessary by an optical microscope, and the results are stored. In addition thereto, the optical microscope acquires microscopic images of areas required to be observed such as defects, and the microscopic images are used for comparison with electron beam images. Then, the conditions of the electro-optical system are set, and the electro beam image is used to modify information set with the optical microscope to improve the accuracy.

Then, information of a recipe appropriate to the type of wafer (immediately preceding step, whether the wafer size is 200 mm or 300 mm, and the like) is inputted to the apparatus, followed by setting the inspection site, the electro-optical system, inspection conditions and the like, and then defect inspection is carried out usually in real time while acquiring an image. Comparison between cells and die comparison are carried out by a high-speed information processing system having algorithms, and the results are outputted to a CRT and the like and stored in a memory as necessary.

Defects include particle defects, shape abnormalities (pattern defects) and electric defects (breakage and poor conduction of wiring or vias, etc.), and these defects can be identified, and defects can be automatically classified in real time on the basis of the size of the defect and whether or not the defect is a killer defect (serious defect resulting in an unusable chip, etc.). Particularly, the process is effective in classifying the defects of wiring having a line width of 100 nm or less, a via having a diameter of 100 nm or less and the like. Detection of electric defects is achieved by detecting a contrast abnormality. For example, the site of poor conduction is usually charged positively and has a contrast reduced by irradiation with the electron beam (about 500 eV), and thus can be differentiated from a normal site. The electron beam irradiating means in this case refers to low-potential (energy) electron beam generating means (generation of thermal electrons, UV/photoelectrons) provided for clarifying the contrast by the difference in potential, aside from electron beam irradiating means for usual inspection. Before irradiating the electron beam for inspection to the inspection object area, this low-potential electron beam (having energy of 100 eV or less, for example) is generated/applied. In the case of the projection system in which the inspection site can be positively charged only by irradiating an electron beam for inspection, it is not necessary to provide separately low-potential electron beam generating means depending on specifications. Furthermore, defect inspection can be carried out using a difference in contrast caused by application of a positive or negative potential to a sample such as a wafer with respect to the reference potential or the like (caused by a difference in flowability depending on the forward direction or inverse direction of the element).

The contrast by a difference in potential may be converted into an image of a signal effective for displaying potential contrast data and then displayed. The potential contrast image can be analyzed to identify a structure at a voltage higher or lower than an expected value, i.e. poor insulation or poor conduction and defects. For example, potential contrast images are acquired from different dies on the wafer, respectively, and differences between the images are detected to recognize defects. Furthermore, image data equivalent to the potential contrast image of the inspection subject die is generated from design data such as CAD data, and a difference between this image data and the potential contrast image acquired from the inspection subject die on the wafer is detected to recognize defects.

The process can be used in a line width measurement apparatus and measurement of matching accuracy. Information of the wafer to be inspected, for example the number of the cassette and the number of the wafer (or lot number) is all stored and managed as to the current position and sate of the wafer. Thus, there arises no trouble of erroneously performing inspection twice or performing no inspection.

2-8) Inspection Process
   2-8-1) Overview

The basic flow of inspection is shown in FIG. 113. First, after transportation of the wafer including an alignment operation 113•1, a recipe specifying conditions and the like related inspection (113•2). At least one recipe are required for the inspection subject wafer, but a plurality of recipes may exist for one inspection subject recipe for coping with a plurality of inspection conditions. Furthermore, if there are a plurality of wafers having the same pattern, the plurality of wafers may be inspected with one recipe. A path 113•3 of FIG. 113 indicates that creation of the recipe is not required immediately before the inspection operation if inspection is carried out with a recipe created in the past in this way. Subsequently, in FIG. 113, an inspection operation 113•4 carries out inspection according to conditions and sequences described in the recipe. Defect extraction is carried out immediately each time a defect is found during the inspection operation, and the following operations are carried out almost in parallel:
a) operation of classifying defects (113•5) and adding extracted defect information and defect classification information to a result output file;
b) operation of adding an extracted defect image to an image dedicated result output file or file; and
c) operation of displaying defect information such as a position of an extracted defect on an operation screen.

When inspection is completed for each inspection subject wafer, the following operations are carried out almost in parallel:
a) operation of closing and storing the result output file;
b) operation of sending the inspection result if the inspection result is requested by external communication; and
c) operation of discharging the wafer.

If a setting for continuously inspecting wafers is made, a next inspection subject wafer is conveyed, and the series of operations described above are repeated.

The flow of FIG. 113 will be described further in detail below.

(1) Creation of Recipe

The recipe is a set file for conditions and the like relating to inspection, and can be stored. The recipe is used to make a setting of apparatus during inspection or before inspection, the conditions relating to inspection described in the recipe are as follows:
a) inspection object dies;
b) inspection areas within die;
c) inspection algorithm;
d) detection conditions (conditions necessary for defect extraction such as inspection sensitivity); and
e) observation conditions (conditions necessary for observation such as magnification, lens voltage, stage speed and inspection order). c) inspection algorithm will be described specifically later.

For the setting of inspection object die among these conditions, the operator designates dies to be inspected with respect to a die map screen displayed on the operation screen as shown in FIG. 114. In the example of FIG. 114, a die 1 on the end face of the wafer and a die 2 judged as an apparently defective die 2 in the previously step are grayed out and omitted from the inspection object, and remaining dies are defined as inspection object dies. Furthermore, a function of automatically designating inspection dies based on a distance from the end face of the wafer and pass/fail information of dies detected in the previous step is also provided.

Furthermore, to set inspection areas within the die, the operator designates inspection areas with an input device such as a mouse based on images acquired with an optical microscope or EB microscope, with respect to an in-die inspection area setting screen displayed on the operation screen, as shown in FIG. 115. In the example of FIG. 115, an area 115•1 indicated by a solid line and an area 115•2 indicated by a broken line are set.

The area 115•1 has almost an entire area of the die as a set area. An adjacent die comparison method (die-die inspection) is used as the inspection algorithm, and the details of detection conditions and observation conditions for this area are set separately. For the area 115•2, array inspection (inspection) is used as the inspection algorithm, and the details of detection conditions and observation conditions are set separately. That is, a plurality of inspection areas can be set, and a unique inspection algorithm and inspection sensitivity can be set for each inspection area. Furthermore, one inspection area can be superimposed on the other, and the same area can be processed with different inspection algorithms at a time.

(2) Inspection Operation

For inspection, the inspection subject wafer is finely divided into certain scan widths and scanned as shown in FIG. 116. The scan width approximately depends on the length of a line sensor, but the end portions of line sensors slightly overlap one another. This is for the purpose of evaluating continuity between lines when detected defects are finally subjected to integration processing, and providing allowance for alignment of images when comparison inspection is carried out. The overlap amount thereof is about 16 dots for the line sensor of 2048 dots.

The scan direction and sequence are schematically shown in FIG. 117. That is, a two-way operation A for reduction of inspection time, a one-way operation B due to mechanical limitation, or the like can be selected by the operator.

Furthermore, a function of automatically calculating an operation for reducing the scan amount based on the setting of inspection object dies in the recipe to carry out inspection is also provided. FIG. 118-1 shows an example of scanning where there is one inspection die 118•1, in which unnecessary scans are not performed.

2-8-2) Inspection Algorithm

Algorithms of inspection carried out by this apparatus are classified broadly into the following two types:
1. array inspection (cell inspection); and
2. random inspection (die inspection).

As shown in FIG. 118-2, the die is separated into a cell portion 118•2 having a cycle structure that is used mainly for a memory, and a random portion 118•3 having no cycle structure. The cell portion 118•2 having a cycle structure is capable of being inspected by comparison between cells in the same die because a plurality of comparative objects exist in the same die. On the other hand, the random portion 118•3 requires comparison between dies because there is no comparative object in the same die. Random inspection is further classified as follows according to comparative objects:
   a) adjacent die comparison method (Die-Die inspection);
   b) reference die comparison method (die-Any Die inspection); and
   c) CAD data comparison method (Cad Data-Any Die inspection).

A method generally called as a golden template method refers to the methods b) and c), and the reference die is a golden template on the reference die comparison method, while CAD data is a golden template in the CAD data comparison method.

The operation of each algorithm will be described below.

2-8-2-1) Array Inspection (Cell Inspection)

Array inspection is applied for inspection of the cycle structure. A DRAM cell or the like is one example thereof.

For inspection, a reference image as a reference is compared with an inspection subject image, and a difference thereof is extracted as a defect. The reference image and the inspection subject image may be binary images or multi-value images for improvement of detection accuracy.

The defect may be the difference itself between the reference image and the inspection subject image, but a secondary determination for prevention of erroneous detection may be made based on difference information such as the amount of detected difference and the total area of images having the difference.

In array inspection, the reference image is compared with the inspection subject image in a structure cycle unit. That is, images collectively acquired with the CCD or the like may be compared in one structure cycle unit while reading the images, or if the reference image has n structure cycle units, n structure cycle units may be compared at a time.

One example of a method for generating a reference image is shown in FIG. 119. Here, an example of comparison in one structure cycle unit is described, and thus generation of one structure cycle unit is shown. The number of cycles can be set to n in the same method.

As a premise, the inspection direction is a direction A in FIG. 119. Furthermore, a cycle 4 is an inspection subject cycle. The magnitude of the cycle is inputted by the operator watching the image, and therefore cycles 1 to 6 can easily be recognized in FIG. 119.

A reference cycle image is generated by adding cycles 1 to 3 immediately before the inspection subject cycle in each pixel. Even if defects exist in any of cycles 1 to 3, influences thereof are not significant because equalization processing is performed. This generated reference cycle image is compared with an inspection subject cycle image 4 to extract defects.

When an inspection subject cycle image 5 is then inspected, cycles 2 to 4 are added and averaged to generate a reference cycle image. Subsequently, an inspection subject cycle image is similarly generated from images obtained before acquirement of the inspection subject cycle image to continue inspection.

2-8-2-2) Random Inspection (Die Inspection)

Random inspection can be applied without being limited by the structure of the die. For inspection, a reference image as a reference is compared with an inspection subject image, and a difference thereof is extracted as a defect. The reference image and the inspection subject image may be binary images or multi-value images for improvement of detection accuracy. The defect may be the difference itself between the reference image and the inspection subject image, but a secondary determination for prevention of erroneous detection may be made based on difference information such as the amount of detected difference and the total area of images having the difference. Random inspection can be classified based on how the reference image is determined. The operation will be described below.

A. Adjacent Die Comparison Method (Die-Die Inspection)

A reference image is a die adjacent to an inspection subject die. The inspection subject image is compared with two dies adjacent thereto to make a determination on defects. That is, in FIGS. 120 and 121, the method has the following steps in a situation in which a switch 121•4 and a switch 121•5 are set so that a memory 121•1 and a memory 121•2 of an image processing apparatus are connected to a path 121•41 from a camera 121•3:

a) step of storing a die image 1 in the memory 121•1 from the path 121•41 along a scan direction S;

b) step of storing a die image 2 in the memory 121•2 from the path 121•41;

c) acquiring the die image 2 from the path 121•42 while carrying out the step b), and at the same time comparing the acquired die image 2 with image data stored in the memory 121•1, having the same relative position in the die, to determine a difference;

d) step of storing the difference determined in the step c);

e) step of storing a die image 3 in the memory 121•1 from the path 121•41;

f) acquiring the die image 3 from the path 121•42 while carrying out the step c), and at the same time comparing the acquired die image 3 with image data stored in the memory 121•1, having the same relative position in the die, to determine a difference;

g) step of storing the difference determined in the step f);

h) step of making a determination on defects of the die image 2 from the results stored in the steps d) and g); and i) step of repeating steps a) to h) in subsequent continuous dies.

By setting, before determining the difference in steps c) and f), position alignment of compared two images by setting: correction that is carried out so that a difference in position is eliminated; or density alignment: correction that is carried out so that a difference in density is eliminated; or both position alignment and density alignment may be performed.

B. Reference Die Comparison Method (Die-Any Die Inspection)

A reference die is designated by the operator. The reference die is a die existing on the wafer, or a die image stored before inspection, and the reference die is first scanned or transferred, and the image is stored in a memory as a reference image. That is, in FIGS. 121 and 122, the method has the following steps:

a) step of selecting a reference die from dies of the inspection subject wafer or die images stored before inspection by the operator;

b) step of setting the switch 121•4 and the switch 121•5 so that at least one of the memory 121•1 and the memory 121•2 of the image processing apparatus are connected to the path 121•41 from the camera 121•3, if the reference die exists on the inspection subject wafer;

c) step of setting the switch 121•4 and the switch 121•5 so that at least one of the memory 121•1 and the memory 121•2 of the image processing apparatus are connected to a path 121•7 from a memory 121•6 having a reference image as a die image stored therein, if the reference die is a die image stored before inspection;

d) step of scanning the reference die and transferring the reference image as a reference die image to the memory of the image processing apparatus, if the reference die exists on the inspection subject wafer;

e) step of transferring the reference image as a reference die image to the memory of the image processing apparatus without necessity to perform scanning, if the reference die is a die image stored before inspection;

f) step of comparing an image obtained by sequentially scanning the inspection subject image, the image in the memory to which the reference image as a reference die image is transferred, and image data having the same relative position in the die to determine a difference;

g) step of making a determination defects from the difference obtained at step f); and h) step of inspecting the same area with respect to the scan position of the reference die and the die origin of the inspection subject die for the entire wafer continuously as shown in FIG. 124, and repeating the steps d) to g) while changing the scan position of the reference die until the entire die is inspected.

By setting, before determining the difference in step f), position alignment of compared two images by setting: correction that is carried out so that a difference in position is eliminated; or density alignment: correction that is carried out so that a difference in density is eliminated; or both position alignment and density alignment may be performed.

The reference die image stored in the memory of the image processing apparatus at the step d) or e) may be the entire reference die, or may be inspected while being updated as part of the reference die.

C. CAD Data Comparison Method (CAD Data-Any Die Inspection)

In the step of production of a semiconductor shown in FIG. 123, a comparison image is created from CAD data being an output of a step of designing a semiconductor pattern with CAD and the comparison image is defined as a reference image. The reference image may be an image of the entire die or part of the die including an inspection area.

Furthermore, the CAD data is usually vector data, and cannot be used as a comparison image unless the data is converted into raster data equivalent to image data equivalent to image data obtained by a scanning operation. In this way, the following conversions are carried out for CAD data processing work.

a) Vector data being CAD data is converted into raster data.

b) The conversion a) is carried out in a unit of image scan width obtained by scanning the inspection subject die during inspection.

c) The conversion b) converts an image to be obtained by scanning the inspection subject die and image data having the same relative position in the die.

d) The conversion c) is carried out with inspection scanning and conversion work overlapping one another.

The conversions a) to d) are examples of conversion in an unit of image scan width for enhancement of the speed, but scanning can be performed even if the conversion unit is not fixed to the image scan width. Furthermore, the method has at least one of the following functions as an additional function for work of converting vector data into raster data:

a) function of processing raster data into a multiple value;

b) function of setting a gray scale weight and an offset in the processing into a multiple value in view of the sensitivity of the inspection apparatus with respect to the function a); and c) function of carrying out image processing for subjecting pixels to processing such as expansion and contraction after converting vector data into raster data.

In FIG. 121, inspection steps by the CAD data comparison method are as follows:

a) step of converting CAD data into raster data with a calculator 1, and generating a comparison image with the additional function and storing the comparison image in the memory 121•6;

b) step of setting the switch 121•4 and the switch 121•5 so that at least one of the memory 121•1 and the memory 121•2 of the image processing apparatus are connected to the path 121•7 from the memory 121•6;

c) step of transferring the comparison image of the memory 121•6 to the memory of the image processing apparatus;

d) step of comparing an image obtained by sequentially scanning the inspection subject image, the image in the memory to which the comparison image is transferred, and image data having the same relative position in the die to determine a difference;

e) step of making a determination defects from the difference obtained at step d); and f) step of inspecting the same area of the inspection subject die over the entire wafer with the scan position of the reference die as a comparison image continuously as shown in FIG. 124, and repeating steps a) to e) while changing the scan position of the reference die until the entire die is inspected.

By setting, before determining the difference in step d), position alignment of compared two images by setting: correction that is carried out so that a difference in position is eliminated; or density alignment: correction that is carried out so that a difference in density is eliminated; or both position alignment and density alignment may be performed.

The reference die image stored in the memory of the image processing apparatus at step c) may be the entire reference die, or may be inspected while being updated as part of the reference die.

2-8-2-2') Method for Carrying Out Cell Inspection and Die Inspection at the Same Time The algorithms of array inspection (cell inspection) and random inspection for inspecting the cycle structure have been described, but cell inspection and die inspection can be carried out at the same time. Specifically, the cell portion and the random portion are processed separately, and a comparison is made between cells in the die for the cell portion, while a comparison with an adjacent die, the reference die or CAD data is made for the random portion. This allows inspection time to be considerably reduced, resulting in an improvement in throughput.

Furthermore, in this case, it is preferable that inspection circuits of the cell portion are individually independently provided. Furthermore, if inspection is not carried out at the same time, it is also possible to provide one inspection circuit, wherein a setting is made so that the switch can be made between software for cell inspection and random inspection, and comparison inspection is carried out by switching of software. That is, if inspection of a pattern is carried out using algorithms for a plurality of operations, different circuits may be prepared for the algorithms to carry out inspection at a time, or algorithms matching those operations may be provided to carry out inspection with the switch made between the algorithms with one circuit. In any case, the present invention can be applied even if the type of the cell portion is complicate, and a comparison is made between cells for this type of cell portion, and a comparison is made between dies or between the die and CAD data for the random portion.

2-8-2-3) Focus Mapping

The basic flow of a focus function is shown in FIG. 125. First, after transportation of the wafer including the alignment operation, a recipe specifying conditions and the like relating to inspection is created. There is a focus map recipe as one of such recipes, and auto-focusing is performed during the inspection operation and the review operation according to focus information specified in the recipe. Procedures for creating the focus map recipe and operational procedures of auto-focusing will be described below.

Procedures for Creating Focus Map Recipe

The focus map recipe has an independent input screen in this example, and the operator carries out the following steps to create the recipe, but the recipe may be added to an input screen provided for a different purpose.

a) Step of inputting focus map coordinates such as a die position in which a focus value is inputted, and a pattern in the die. Switch 126•1 in FIG. 126.

b) Step of setting a die pattern required when the focus value is automatically measured. This step may be skipped if the focus value is not automatically measured.

c) Step of setting the best focus value of the focus map coordinates determined at step a).

At step a), the operator may designate any die, but all dies may be selected, or dies may be selected for every n dies. Furthermore, in the input screen, the operator may select either a diagram schematically showing a die arrangement or an image using a real image.

At step c), a selection/setting is made in a mode in which the operator manually sets a value with a focus switch 126•2 associated with the voltage value of an electrode for focusing (switch 126•3 in FIG. 126) or a mode in which the focus value is automatically determined (switch 126•4 in FIG. 126).

Procedures for Automatically Measuring a Focus Value

In FIG. 127, for example, the procedures for automatically determining a focus value at step c) include:

a) obtaining an image of focus position Z=1 and calculating a contrast thereof;

b) carrying out the procedure a) for Z=2, 3, 4.

c) determining a contrast function with regression from the contrast values obtained in the procedures a) and b) (FIG. 127); and d) calculating Z providing a maximum value of the contrast function and setting the maximum value to the best focus value.

For example, the die pattern required when the focus value is automatically measured shows a good result if a line & space shown in FIG. 128 is selected, but the contrast can be measured irrespective of the shape as long as a black-and-white pattern is provided.

By carrying out the procedures a) to d), the best focus value of one point is determined. The data format at this time is (X, Y, Z), wherein XY is coordinates with which the focus is determined, Z is a set of the best focus value, and the focus map coordinate number (X, Y, Z) determined with the focus map recipe exists. This is called a focus map file as part of the focus map recipe.

Operational Procedures of Auto-focusing

The method for setting the focus to the best focus during the inspection operation of acquiring images from the focus map recipe and the review operation comprises the following steps.

a) Position information is subdivided based on a focus map file 1 created during creation of the focus map recipe, the best focus at this time is calculated, and a subdivided focus map file 2 is created;

b) The calculation of step a) is performed with an interpolation function;

c) The interpolation function of step b) is linear interpolation, spline interpolation or the like, which is designated by the operator during creation of the focus map recipe.

d) The XY position of the stage is monitored to change the voltage of the electrode for focusing to a focus value suitable for the current XY position, described in the focus map file 2.

To describe the procedures more specifically, in FIG. 129, the black circle corresponds to focus values of the focus map file 1, and the white circle corresponds to focus values of the focus map file 2, wherein 1. intervals between focus values of the focus map file are interpolated with focus values of the focus map file, and 2. the focus position Z is changed according to scanning to maintain the best focus value and at this time, for the interval between focus map files (white circles), a value is retained up to a position at which the value is changed.

2-8-2-4) Litho-Margin Measurement

Embodiments relating to litho-margin measurement will be described below.

(1) Embodiment 10 (Litho-Margin Measurement 1)

Overview

1. The range of conditions for a light-exposure machine and best conditions are determined. The target is the focus.

2. This embodiment is a method of application of inspection apparatus, and is not limited to the electron beam mapping method and the scanning method. That is, the method using light, the electron beam method, and any combination of such methods with the mapping method or scanning method may be used.

3. Application of reference die comparison method (Die-Any Die inspection)

FIG. 130 shows a flow showing the operation of the embodiment 1. The embodiment will be described based on this figure.

At step 130•1, conditions are changed to two dimensionally expose the surface of the wafer to light using focus conditions and exposure time conditions as parameters as shown in FIG. 131 as an example. Furthermore, an image pattern of one shot=1 die is used.

Many stepper light-exposure machines have a function of automatically changing the parameter to perform light-exposure, generally called TEST exposure, and this function may be used directly.

At step 130•2, steps of development, resist peeling, etching, CVD, CMP, plating and the like may be carried out, and particularly in observation with the electron beam, the resist is charged and is thus hard to be observed, and therefore steps of development, resist peeling and plating are carried out. Resist observation is desirable.

Details of step 130•3 will be described with FIG. 132. In this step, using a function of measuring a contrast of an image set by the operator of the inspection apparatus carrying out step 130•4, the minimum line & space portion of the die pattern is recorded as an area where the contrast is measured, and the following work is conducted.

First, an upper limit Db and a lower limit Da of exposure time are determined. For exposure time equal to or greater than Db and exposure time equal to or less than Da, the contrast value is extremely low, and thus such exposure time is excluded from inspection (grayed-out part in FIG. 132).

Then, an upper limit Fb and a lower limit Fa of the focus value are determined. For any focus value equal to or greater than Fb and any focus value equal to or smaller than Fa, the contrast value is extremely low, and thus such focus values are excluded from inspection (grayed-out part in FIG. 133).

Then, a die at intersection of a row of dies Ds in the middle between Da and Db and a row of dies Fs in the middle between Fa and Fb is selected as a best exposure condition shot. The step of selecting the best exposure condition shot is all carried out automatically.

At step 130•4, inspection is carried out by the reference die comparison method (Die-Any Sie inspection) with the reference die as a comparison image and with white dies as inspection subject dies in FIG. 132.

At step 130•5, a determination is made on exposure conditions using the inspection result in step 130•4. That is, an effect is used such that if exposure conditions are not appropriate, for example, the line and space of the die pattern are not resolved, or the edge portion of the pattern has an obtuse angle, so a difference occurs between the reference image and the inspection subject image, resulting in detection as pattern defects. Of course, pattern defects and particles caused by erroneous exposure, not caused by exposure conditions, may be detected, but in this case, inspection is carried out again. However, the frequency of occurrence of such a case is so low in terms of probability that no problem arises.

Specific procedures of the step 1305 are as follows.
1) Because higher priority is given to determination of a focus margin, exposure time is fixed at Ds in FIG. 132, and a relation between the focus value and the number of defects is determined (FIG. 133).
2) At this time, the criterion for determination on the focus value is such that no defect occurs due to exposure conditions, and therefore focus values acceptable as exposure conditions are values in the range of F1 to F2 as a conclusion.
3) For the type of value/unit of expression in the light-exposure machine which F1 and F2 specifically have, it can be easily calculated by transferring the position of the die and its exposure conditions through a communication path connected from the light-exposure machine via RS232C or Ethernet. The apparatus has a function of converting the value into a value capable of being directly inputted to the exposure machine and displaying together with a function of pass/fail determination as exposure conditions.
4) Furthermore, if a dedicated communication path or a communication path of SEMI standard or the like is used, the result by this inspection apparatus can be fed back to the light-exposure machine. The above procedures are further carried out with exposure conditions (exposure time) changed to determine the margin of focus and exposure.

(2) Embodiment 11 (Litho-Margin Measurement 2)

Overview

The range of conditions for a light-exposure machine and best conditions are determined. The target is the focus.
1. This embodiment is a method of application of inspection apparatus, and is not limited to the electron beam mapping method and the scanning method. The optical method, the electron beam method, and combinations of such methods with the mapping method or scanning method may be used.
2. Application of CAD data comparison method (CAD Data-Any Die inspection)

FIG. 134 shows a flow showing the operation of the embodiment 2. The embodiment will be described based on this figure.

At step 134•1, conditions are changed to two dimensionally expose the surface of the wafer to light using focus conditions and exposure time conditions as parameters as shown in FIG. 135 as an example. Furthermore, an image pattern of one shot=1 die is used.

Many stepper light-exposure machines have a function of automatically changing the parameter to perform light-exposure, generally called TEST exposure, and this function may be used directly.

At step 134•2, steps of development, resist peeling, etching, CVD, CMP, plating and the like may be carried out, and particularly in observation with the electron beam, the resist is charged and is thus hard to be observed, and therefore steps of development, resist peeling and plating are carried out. Preferably, the step is ended with observation at the level of the resist.

At step 134•3, a reference image required to have best conditions where possible is generated from CAD data having an exposed shot pattern. At this time, raster data as image data is processed into a multiple value. As shown in FIG. 136, in patterns having different line widths, for example a pattern A, a pattern B and a pattern C, the pattern C is finer than the pattern B, but when a comparison is made for the level of white of the pattern empirically, the level of white of the pattern C is closer to black than that of the pattern B, and when a comparison is made for the level of black of the pattern, the level of black of the pattern C is closer to white than that of the pattern B. Thus, image data is processed into a multiple value in consideration of not just two values, one appearing black and the other appearing white as an image, but the shape and fineness of the pattern, the pattern position on the wafer and the like.

Furthermore, in consideration of setting conditions of the observation system and influences of charge-up, magnetic fields and the like at the same time, image data generated from CAD data is subjected to image processing such that a difference is not recognized as pseudo defects when an image obtained by actual observation is compared with image data generated from CAD data.

At step 134•4, the image generated at step 134•3 is defined as a comparison image, dies on the wafer are defined as inspection subject images, and die comparisons are made to carry out inspection.

At step 134•5, a determination is made on exposure conditions using the inspection result at step 134•4. That is, an effect is used such that if exposure conditions are not appropriate, for example, the line and space of the die pattern are not resolved, or the edge portion of the pattern has an obtuse angle, so a difference occurs between the reference image and the inspection subject image, resulting in detection as pattern defects. Of course, pattern defects and particles caused by erroneous exposure, not caused by exposure conditions, may be detected, but in this case, inspection is carried out again. However, the frequency of occurrence of such a case is so low in terms of probability that no problem arises.

Specific procedures of the step 134•5 are as follows.
1) Because higher priority is given to determination of a focus margin, exposure time is set to an empirically obtained fixed value, and a relation between the focus value and the number of defects in this case is determined (FIG. 137).

2) At this time, the criterion for determination on the focus value is such that no defect occurs due to exposure conditions, and therefore focus values acceptable as exposure conditions are values in the range of F1 to F2 as a conclusion.

3) For the type of value/unit of expression in the light-exposure machine which F1 and F2 specifically have, it can be easily calculated by transferring the position of the die and its exposure conditions through a communication path connected from the light-exposure machine via RS232C or Ethernet. The apparatus has a function of converting the value into a value capable of being directly inputted to the exposure machine and displaying together with a function of pass/fail determination as exposure conditions.

4) Furthermore, if a dedicated communication path or a communication path of SEMI standard or the like is used, the result by this inspection apparatus can be fed back to the light-exposure machine.

The litho-margin measurement of exposure conditions has been described above, a reticle or stencil mask as a mask for exposure may be inspected. In this case, inspection for determination of exposure conditions can be simplified.

3. Other Embodiments 3-1) Alteration Example of Stage Apparatus

FIG. 138 shows one alteration example of stage apparatus in a detection apparatus of the present invention.

A partition plate 138•4 largely protruding almost horizontally in the +Y direction and −Y direction (lateral direction in FIG. 139) is mounted on the upper face of a Y direction movable portion 138•2 of a stage 138•1, and a diaphragm portion 138•5 having a small conductance is always formed between the partition plate 138•4 and the upper face of an X direction movable portion 138•4. Furthermore, a similar partition plate 138•6 is formed on the upper face of the X direction movable portion 138•4 in such a manner as to protrude in the ±X direction (lateral direction in (A) of FIG. 138), and a diaphragm portion 1388 is always formed between the partition plate 138•6 and the upper face of a stage table 138•7. The stage table 138•7 is fixed on the bottom wall in a housing 138•9 by a well known method.

Accordingly, the diaphragm portions 138•5 and 138•8 are always formed irrespective of the position to which a sample table 138•10 moves, and therefore if gas is emitted from guide surfaces 138•11 and 138•12 when the movable portions 138•2 and 138•4 move, movement of emitted gas is prevented by the diaphragms 138•5 and 138•8, thus making it possible to considerably reduce an increase in pressure of a space 138•13 near the sample to which a charged beam is applied.

Grooves for differential exhaust shown in FIG. 140 are formed around a static pressure bearing 138•14 on the side face and lower face of the movable portion 138•2 of the stage and the lower face of the movable portion 138•4, and the apparatus is evacuated through the grooves, and therefore if the diaphragm portions 138•5 and 138•8 are formed, emitted gas from the guide surface is mainly discharged by the differential exhaust portions. Accordingly, the pressures of spaces 138•15 and 138•16 within the stage are higher than the pressure within a chamber C. Thus, by additionally providing sites to be evacuated not just evacuating the spaces 138•15 and 138•16 through differential exhaust grooves 140•1 and 140•2, the pressures of the spaces 138•15 and 138•16 can be reduced, and an increase in pressure of the space 138•13 near the sample can be reduced to a lower level. Evacuation channels 138•17 and 138•18 for this purpose are provided. The evacuation channel extends through the stage table 138•7 and the housing 138•9 to outside a housing 138•9. Furthermore, the evacuation channel 138•18 is formed in the X direction movable portion 138•4, and extends through the lower face of the X direction movable portion 138•4.

Furthermore, if the partition plates 138•3 and 138•6 are placed, the chamber should be upsized so that the chamber and the partition plate do not interfere with each other, but this can be improved by employing a flexible material or structure for the partition plate. In this embodiment, it can be considered that the partition plate is formed by a rubber or formed into a bellow shape, and the end portion in the traveling direction is fixed to the X direction movable portion 138•4 for the partition plate 138•3, and fixed to the inner wall of the housing 138•9 for the partition plate 138•6. Furthermore, reference numeral 138•19 denotes a column.

FIG. 141 shows a second alteration example of stage apparatus. In this aspect, a cylindrical partition 141•2 is formed around the end portion of a column or a charged beam irradiating portion 141•1 so that a diaphragm is provided between the partition and the upper face of a sample W. In this configuration, even if gas is emitted from the XY stage to increase the pressure within the C chamber, a space 141•3 inside the partition is partitioned by the partition 141•2 and evacuated through a vacuum tube 141•4, and therefore a difference in pressure is produced between the space within the chamber C and the space 141•3 inside the partition, so that the increase in pressure of the space 141•3 inside the partition can be reduced to a low level. The size of a gap between the partition 141•2 and the surface of the sample depends on the level at which the pressures within the chamber C and around the irradiation area 141•1 are kept, but is appropriately several tens of μm to several mm. Furthermore, the partition 141•2 is made to communicate with the vacuum tube by a well known method.

Furthermore, in a charged beam irradiation apparatus, there are cases where a high voltage of about several kilovolts is applied to the sample W, and a discharge may be caused if a conductive material is placed near the sample. In this case, if an insulating material such as ceramics is used for the material of the partition 141•2, no discharge is caused between the sample W and the partition 141•2.

Furthermore, a ring member 141•5 placed around the sample W (wafer) is a platy adjustment part fixed on a sample table 141•6, and is adjusted to have a height equal to that of the wafer so that very small gaps 141•7 are formed over the entire circumference of the leading end portion of the partition 141•2 even if a charged beam is applied to a sample such as a wafer. Consequently, irrespective of the position of the wafer W to which the charged beam is applied, constant very small gaps 952 are always formed at the leading end portion of the partition 141•2, thus making it possible to stably keep the pressure of the space 141•3 around the leading end portion of the column.

Another alteration example is shown in FIG. 142. A partition 142•1 including a differential exhaust structure is provided around the charged beam irradiating portion 141•2 of the column 138•19. The partition 142•1 has a cylindrical shape, a circular groove 142•2 is formed therein, and an evacuation channel 142•3 extends upward from the circular groove. The evacuation channel is connected to a vacuum tube 142•5 via an internal space 142•4. A very small gap of about several tens of μm to several mm is formed between the lower end of the partition 142•1 and the upper face of the sample W.

In this configuration, even if gas is emitted from with movement of the stage to increase the pressure within the chamber C, and the gas flows into the leading end portion or charged beam irradiating portion 141•2, the partition 142•1 reduces the gap between itself and the sample W to considerably diminish the conductance, so that the gas is hindered from flowing into the leading end portion and thus the amount of inflow is reduced. Further, the gas flowing into the portion is exhausted from the circular groove 142•2 to the vacuum tube 142•5, and thus little gas flows into a space 141•6 around the charged beam irradiating portion 141•2, thus making it possible to keep the pressure in the charged beam irradiating portion 141•2 at a desired vacuum.

Still another alteration example is shown in FIG. 143. a partition 143•1 is provided around the chamber C and the charged beam irradiating portion 141•1 to isolate the charged beam irradiating portion 141•1 from the chamber C. The partition 143•1 is coupled to a freezer 143•3 via a support member 143•2 made of material having a high thermal conductivity such as copper or aluminum, and is cooled to about −10° C. to −200° C. A member 143•4 is intended for hindering thermal conduction between the cooled partition 143•1 and the column 138•19, and is made of material having a low thermal conductivity such as ceramics or resin material. Furthermore, a member 143•5 is made of non-insulating material such as ceramics, and is formed at the lower end of the partition 143•1 to prevent the sample W and the partition 143•1 from causing a discharge.

Owing to this configuration, gas molecules flowing from the chamber into the charged beam irradiating portion is hindered from flowing into the charged beam irradiating portion by the partition 143•1, or frozen and collected on the surface of the partition 143•1 even if they flow into the portion, thus making it possible to keep the pressure of the charged beam irradiating portion 143•6 at low level.

Furthermore, for the freezer, various freezers such as cooling with liquid nitrogen, a He freezer and a pulse tube-type freezer may be used.

Still another alteration example is shown in FIG. 144. Partition plates 144•1 and 144•2 are provided on both the movable portions of the stage as in the case of the configuration shown in FIG. 138, and a space 144•4 and the chamber C are partitioned via diaphragms 144•5 and 144•6 by these partitions even if a sample table 144•3 moves to any position. Further, a partition 144•7 similar to that shown in FIG. 141 is formed around the charged beam irradiating portion 141•1, and the chamber C and a space including the charged beam irradiating portion 141•1 are partitioned via a diaphragm 144•8. Thus, even if gas adsorbed on the stage is emitted into the space 144•4 to increase the pressure of this area during movement of the stage, an increase in pressure of the chamber C is reduced to a low level, and an increase in pressure of a space 144•9 is reduced to a lower level. Consequently, the pressure of the charged beam irradiation space 144•9 can be kept at a low level. Furthermore, the partition 142•1 including a differential exhaust mechanism as shown in the partition 144•7 is used, or a partition cooled by a freezer as shown in FIG. 142 is used, whereby the space 144•9 can be stably kept at a lower pressure.

According to these embodiments, the following effects can be exhibited.

(1) The stage apparatus can exhibit a accurate positioning performance under vacuum, and the pressure at the charged beam irradiation position is hard to increase. That is, the sample can be accurately processed with a charged beam.

(2) Gas emitted from the static-pressure bearing support portion can hardly pass through the partition to the charged beam irradiation area side. In this way, the vacuum at the charged beam irradiation position can be further stabilized.

(3) Emitted gas is hard to pass to the charged beam irradiation area side, and thus the vacuum in the charged beam irradiation area can be easily maintained with stability.

(4) The inside of the vacuum chamber is divided into a charged beam irradiation chamber, a static-pressure bearing chamber and an intermediate chamber via a small conductance. A vacuum pumping system is formed such that the charged beam irradiation chamber, the intermediate chamber and the static-pressure bearing chamber are arranged in ascending order of pressure. Variations in pressure in the intermediate chamber are further reduced, and variations in pressure in the charged beam irradiation chamber are further reduced by one more partition, thus making it possible to reduce variations in pressure to a level causing substantially no problem.

(5) An increase in pressure when the stage is moved can be reduced to a low level.

(6) An increase in pressure when the stage is moved can be reduced to a lower level.

(7) An inspection apparatus having a high performance in positioning of the stage and having a stabilized degree of vacuum of the charged beam irradiation area can be achieved, thus making it possible to provide an inspection apparatus having a high inspection performance and not contaminating the sample.

(8) A light-exposure apparatus having a high performance in positioning of the stage and having a stabilized degree of vacuum of the charged beam irradiation area can be achieved, thus making it possible to provide a light-exposure apparatus having a high exposure accuracy and not contaminating the sample.

(9) A semiconductor is produced by an apparatus having a high performance in positioning of the stage and having a stabilized degree of vacuum of the charged beam irradiation area, whereby a fine semiconductor circuit can be formed.

Furthermore, it is apparent that the stage apparatus of FIGS. 138 to 144 can be applied to the stage 13•6 of FIG. 13.

Another embodiment of the XY stage according to the present invention will be described with reference to FIGS. 145 to 147. Furthermore, in the example of the conventional technique and embodiment of FIG. 148, like reference numerals are given to common components. Furthermore, the "vacuum" means a vacuum called in the art, and does not necessarily refer to an absolute vacuum.

Another embodiment of the XY stage is shown in FIG. 145. The leading end portion of a column 145•1 irradiating a charged beam to a sample, i.e. a charged beam irradiating portion 145•2 is attached to a housing 145•3 sectioning a vacuum chamber C. The sample W placed on a table movable in the X direction (lateral direction in FIG. 145) of an XY stage 145•4 is placed just below the column. The charged beam can be applied accurately to any position on the surface of the sample W by the high-accurate XY stage 145•4.

A seat 145•5 of the XY stage 145•4 is fixed on the bottom wall of the housing 145•3, and a Y table 145•6 moving in the Y direction (direction perpendicular to the plane in FIG.

145) is placed on the seat 145•5. Raised portions protruding into recessed grooves formed on a pair of Y direction guides 145•7 and 145•8 placed on the seat 145•5 on the side facing the Y table are formed on both side faces (left and right side faces in FIG. 145) of the Y table 145•6. The recessed groove extends in the Y direction over almost the entire length of the Y direction guide. Static-pressure bearings 145•9, 145•10, 14511 and 145•12 each having a well known structure are provided on the upper and lower faces and the side faces, respectively, of the raised portion protruding into the recessed groove, and by blowing high-pressure gas via these static-pressure bearings, the Y table 145•6 is supported on the Y direction guides 145•7 and 145•8 in a non-contact manner, and can smoothly reciprocate in the Y direction. Furthermore, a linear motor 145•13 having a well known structure is placed between the seat 145•5 and the Y table 145•6, and drive in the Y direction is performed by the linear motor. High-pressure gas is supplied to the Y table through a flexible tube 145•14 for supply of high-pressure gas, and high-pressure gas is supplied to the static-pressure bearings 145•10 and 145•9 and 145•12 and 145•11 through a gas channel (not shown) formed in the Y table. The high-pressure gas supplied to the static-pressure bearings is ejected into a gap of several microns to several tens of microns formed between opposite guide surfaces of the Y direction guide to correctly position the Y table in the X direction and Z direction (vertical direction in FIG. 145) with respect to the guide surface of the Y table.

An X table 145•14 is placed on the Y table such that it is movable in the X direction (lateral direction in FIG. 145). On the Y table 145•6, a pair of X direction guides 145•15 (145•16) (only X direction guide 145•15 is shown) having the same structure as those of the Y direction guides 145•7 and 145•8 for the Y table are provided with the X table 145•14 held therebetween. A recessed groove is formed on the X direction guide on the side facing the X table, and a raised portion protruding into the recessed groove is formed on the side part (side part facing the X direction guide) of the X table. The recessed groove extends over almost the entire length of the X direction guide. Static-pressure bearings (not shown) similar to the static-pressure bearings 145•9, 145•10, 145•17, 145•11, 145•12 and 145•18 are provided in a similar arrangement on the upper and lower faces and the side faces of the X direction table 145•14 protruding into the recessed groove. A linear motor 145•19 having a well known structure is placed between the Y table 145•6 and the X table 145•14, and the X table is driven in the X direction by the linear motor. High-pressure gas is supplied to the X table 145•14 through a flexible tube 145•20, and high-pressure gas is supplied to the static-pressure bearing. This high-pressure gas is ejected from the static-pressure bearings to the guide surface of the X direction guide, whereby the X table 145•14 is accurately supported on the Y direction guide in a non-contact manner.

The vacuum chamber C is evacuated through vacuum tubes 145•21, 145•22 and 145•23 connected to a vacuum pump or the like having a well known structure. The tubes 145•22 and 145•23 on the inlet side (inner side of vacuum chamber) extend through the seat 145•5, and form on the upper face thereof openings near the position at which the high-pressure gas is discharged from the XY stage 145•4, and prevent an increase in pressure within the vacuum chamber due to the high-pressure gas ejected from the static-pressure bearings where possible.

A differential exhaust mechanism 145•24 is provided around the leading end portion of the column, 145•1, i.e. a charged beam irradiating portion 145•2, so that the pressure of a charged beam irradiation space 145•25 is kept at a sufficiently low level even if the pressure within the vacuum chamber C is high. That is, A cyclic member 145•26 of the differential exhaust mechanism 145•24 provided around the charged beam irradiating portion 145•2 is positioned with respect to the housing 145•3 so that a very small gap (several microns to several hundreds of microns) 145•27 is formed between the lower face (face on the sample W side) of the cyclic member 145•26, and a cyclic groove 145•28 is formed on the lower face thereof. The cyclic groove 145•28 is connected to a vacuum pump or the like (not shown) by an exhaust tube 145•29. Thus, the very small gap 145•27 is evacuated through the cyclic groove 145•28 and the exhaust port 145•29, and gas molecules about to enter the space 145•25 surrounded by the cyclic member 145•26 from the vacuum chamber C is discharged. In this way, the pressure within the charged beam irradiation space 145•25 can be kept at a low level, and the charged beam can be applied without any problems. This cyclic groove may have a double or triple structure depending on the pressure within the charged beam irradiation space 145•25.

For the high-pressure gas supplied to the static-pressure bearing, dry nitrogen is generally used. However, if possible, inert gas of higher purity is preferably used. This is because if impurities such as water and oil are contained in the gas, the impurity molecules are deposited on the inner surface of the housing sectioning the vacuum chamber and the surfaces of stage components to reduce the degree of vacuum, and deposited on the sample surface to reduce the degree of vacuum in the charged beam irradiation space. Furthermore, in the above description, the sample W is not usually placed directly on the X table, but placed on a sample table having functions of detachably holding the sample, slightly changing the position with respect to the XY stage 145•4, and so on, but existence/nonexistence of the sample table and its structure are not related to the spirit of this embodiment, and are therefore omitted for the sake of simplification.

In the charged beam apparatus described above, the stage mechanism of the static-pressure bearing that is used in the atmosphere can be almost directly used, thus making it possible to achieve a high-accuracy XY stage equivalent to the atmosphere high-accuracy stage for use in the light-exposure apparatus or the like for the XY stage for charged beam apparatus at almost the same cost and in almost the same size. Furthermore, the structure and layout of the static-pressure guide and the actuator (linear motor) described above are only one example, and any static-pressure guide and actuator capable of being used in the atmosphere may be employed.

Next, examples of values of sizes of the cyclic member 145•26 of the differential exhaust mechanism and the cyclic groove formed thereon are shown in FIG. 146. Furthermore, in this example, the cyclic groove has a double structure of structures 146•1 and 146•2, and these structures are isolated from each other in the radial direction.

The flow rate of high-pressure gas supplied to the static-pressure bearing is usually about 20 L/min (atmospheric pressure equivalent). Provided that the vacuum chamber C is evacuated through a vacuum tube having an inner diameter of 50 mm and a length of 2 m by a dry pump having a pumping speed of 2000 L/min, the pressure within the vacuum chamber is about 160 Pa (about 1.2 Torr). At this time, if the sizes of the cyclic member 146•3 of the differential exhaust mechanism, the cyclic groove and the like are set to those shown in FIG. 146, the pressure within the charged beam irradiation space 141•1 can be kept at $10^{-4}$ Pa ($10^{-6}$ Torr).

Another embodiment of the XY stage is shown in FIG. 147. A dry pump 1474 is connected through vacuum tubes 147•2 and 147•3 to the vacuum chamber C sectioned by a housing 147•1. Furthermore, a turbo-molecular pump 147•9 being an ultrahigh vacuum pump is connected to a cyclic groove 147•6 of a differential exhaust mechanism 147•6 through a vacuum tube 147•8 connected to an exhaust port 147•7. Further, a turbo-molecular pump 147•13 is connected to the inside of a column 147•10 through a vacuum tube 147•12 connected to an exhaust port 147•11. These turbo-molecular pumps 147•9 and 147•13 are connected to the dry vacuum pump 147•4 by vacuum tubes 147•14 and 147•15. In the figure, one dry vacuum pump is used for the roughing vacuum pump of the turbo-molecular pump and the pump for evacuation of the vacuum chamber, but they may be evacuated with dry vacuum pumps of different systems depending on the flow rate of high-pressure gas supplied to the static-pressure bearing of the XY stage, the volume and the area of the inner surface of the vacuum chamber, and the inner diameter and the length of the vacuum tube.

High-purity inert gas ($N_2$ gas, Ar gas, etc.) is supplied to the static-pressure bearing of the XY stage through flexible tubes 147•16 and 147•16. The gas molecules ejected from the static-pressure bearing diffuse into the vacuum chamber, and are discharged by the dry vacuum pump 147•4 through exhaust ports 147•18, 147•19 and 147•20. Furthermore, these gas molecules entering the differential exhaust mechanism and the charged beam irradiation space are suctioned through the cyclic groove 147•6 or the leading end portion of the column 147•10, discharged by the turbo-molecular pumps 147•9 and 147•13 through the exhaust ports 147•7 and 147•11, discharged from the turbo-molecular pumps, and then discharged by the dry vacuum pump 147•4. In this way, the high-purity inert gas supplied to the static-pressure bearing is collected in the dry vacuum pump and discharged.

On the other hand, the exhaust port of the dry vacuum pump 147•4 is connected to a compressor 147•22 through a tube 147•21, and the exhaust port of the compressor 147•22 is connected to the flexible tubes 147•16 and 147•17 through tubes 147•23, 147•24 and 147•25 and regulators 147•26 and 147•27. Accordingly, the high-purity inert gas discharged from the dry vacuum pump 147•4 is pressured again by the compressor 147•22, adjusted to have an appropriate pressure by the regulators 147•26 and 147•27, and then supplied again to the static-pressure bearing of the XY stage.

Furthermore, since the gas supplied to the static-pressure bearing should be purified as highly as possible, as described above, so that no water and oil is contained in the gas, the turbo-molecular pump, the dry pump and the compressor are required to have a structure such that no water and oil enters the gas channel. Furthermore, it is also effective to a cold trap, filter or the like (147•28) is provided at some midpoint in the tube 147•23 on the discharge side of the compressor to trap impurities such as water and oil entering the circulating gas, so that they are not supplied to the static-pressure bearing.

Consequently, the high-purity inert gas can be circulated and reused, thus making it possible to save the high-purity inert gas, and the inert gas is not discharged into a room where this apparatus is installed, thus making it possible to eliminate the possibility that accidents such as suffocation by inert gas occur.

A high-purity inert gas supply system 147•29 is connected to a circulation piping system, and plays a role to fill high-pressure inert gas in the entire circulation system including the vacuum chamber C, the vacuum tubes 147•8, 147•12, 147•14, 147•15, 147•2 and 147•3 and the pressure tubes 147•21, 147•23, 147•24, 147•25 and 147•30 when circulation of the gas is started, and a role to supply an amount of gas equivalent to a shortfall in case where the flow rate of gas drops for some cause. Furthermore, by imparting to the dry vacuum pump 147•4 a function of compression to an atmospheric pressure or higher, one pump can be made to serve as both the dry vacuum pump 147•4 and compressor 147•22.

Further, for the ultrahigh vacuum pump for use in evacuation of the column, a pump such as an ion pump or getter pump may be used instead of the turbo-molecular pump. However, if such an entrapment vacuum pump is used, the circulation piping system cannot be built in the area of the pump. Furthermore, instead of the dry vacuum pump, a dry pump of a different system such as diaphragm-type dry pump may be used as a matter of course.

An optical system and a detector of the charged beam apparatus according to this embodiment are schematically shown in FIG. 149. The optical system is provided in a column, but the optical system and detector are illustrative, and any optical system and detector may be used as required. An optical system 149•1 of the charged beam apparatus comprises a primary optical system 149•3 irradiating a charged beam to a sample W placed on a stage 149•2, and a secondary optical system 149•4 into which secondary electrons emitted from the sample are introduced. The primary optical system 149•3 comprises an electron gun 149•5 emitting a charged beam, a lens system 149•6 constituted by two-stage electrostatic lens converging the charged beam emitted from the electron gun 149•5, a deflector 149•7, a Wien filter or E×B separator 149•8 deflecting the charged beam so that its optical axis is perpendicular to the surface of the object, and a lens system 149•9 constituted by a two-stage lens, and these components are placed in order slantingly with respect to the line of the optical axis of the charged beam perpendicular to the surface of the sample (sample surface) with the electron gun 149•5 situated at the uppermost position as shown in FIG. 149. The E×B deflector 149•8 comprises an electrode 149•10 and a magnet 149•11.

The secondary optical system 149•4 is an optical system into which secondary electrons emitted from the sample W are introduced, and comprises a lens system 149•12 constituted by a two-stage electrostatic lens placed on the upper side of the E×B deflector 149•8 of the primary optical system. A detector 149•13 detects secondary electrons sent through the secondary optical system 149•4. The structures and functions of the components of the optical system 149•1 and the detector 149•13 are the same as those of the conventional system, and therefore detailed descriptions thereof are not presented.

The charged beam emitted from the electron gun 149•5 is shaped by a square aperture of the electron gun, downscaled by the two-stage lens system 149•6, and has the optical axis adjusted by the deflector 149•7 to form an image of a square of 1.925 mm×1.925 mm on the deflection central plane of the E×B deflector. The E×B deflector 149•8 has a structure such that an electric field is orthogonal to a magnetic field in the plane perpendicular to the normal line of the sample, in which when a relation in energy between the electric field and the magnetic field and the electron meets a certain requirement, the electron is made to travel in a straight line, and otherwise deflected in a predetermined direction according to the mutual relation between the electric field and the magnetic field and the electric field. In FIG. 149, the charged beam from the electron gun is made to enter the sample W at a right angle, and secondary electrons emitted from the sample are made to travel toward the detector 149•13 in a straight line. The shaped beam deflected by the ExB deflector is downscaled to ⅕ of the original scale by the lens system 149•9 and projected on the sample W. Secondary electrons having information of a pattern image, emitted from the sample W, are enlarged by the lens systems 149•9 and 149•4 and form a secondary electron image in the detector 149•13. This four-stage enlargement lens is a deformation-free lens because the lens system 149•9 forms a symmetric tablet lens and the lens system 149•12 also forms a symmetric tablet lens.

According to this embodiment, the following effects can be exhibited.

(1) Using a stage having a structure similar to that of a static-pressure bearing-type stage that is generally used in the atmosphere (static-pressure bearing support-type stage having no differential exhaust mechanism), a sample on the stage can be stably processed with a charged beam.

(2) Influences on the degree of vacuum of a charged beam irradiation area can be reduced to a minimum, and processing of the sample with the charged beam can be stabilized.

(3) An inspection apparatus having a high performance in positioning of the stage and having a stabilized degree of vacuum of the charged beam irradiation area can be provided at a low cost.

(4) A light-exposure apparatus having a high performance in positioning of the stage and having a stabilized degree of vacuum of the charged beam irradiation area can be provided at a low cost.

(5) A semiconductor is produced by an apparatus having a high performance in positioning of the stage and having a stabilized degree of vacuum of the charged beam irradiation area, whereby a fine semiconductor circuit can be formed.

3-2) Other Embodiments of Electron Beam Apparatus

Further, another system with consideration of solving the problems of this projection electron microscope type system is a system in which using a plurality of primary electron beams, the plurality of electron beams are scanned two-dimensionally (in X-Y direction) (raster-scanned) to irradiate observation areas of the sample surface, and the secondary electro-optical system employs a projection system.

This system has the advantage of the projection type system described previously, and can solve the problems of this mapping system such that (1) charge-up easily occurs on the sample surface because the electron beam is collectively applied, and (2) the current of the electron beam obtained with this system is limited (to about 1.6 μA), which hinders an improvement in inspection speed, by scanning a plurality of electron beams. That is, because the electron beam irradiation spot is shifted, the charge easily escapes, resulting in a reduction in charge-up. Furthermore, by increasing the number of the electron beams, the current value can easily be increased. In the embodiment, if four electron beams are used, total 2 μA of current is obtained with 500 nA of current for one electron beam (diameter of electron beam: 10 μm). The number of electron beams can easily be increased to about 16 and in this case, it is possible to obtain 8 μA in principle. The scan of a plurality of electron beams is not limited to the raster scan described above, but may be any other from of scan such as a Lissajou's figure as long as the amount of irradiation with a plurality of electron beams is uniformly distributed over the irradiation area. Thus, the direction in which the stage is scanned is not necessarily be perpendicular to the direction of scan of the electron beam.

3-2-1) Electron Gun (Electron Beam Source)

A thermal electron beam source is used as an electron beam source for use in this embodiment. The electron emission (emitter) material is LaB6. Any other material can be used as long as it is a material having a high melting point (low vapor pressure at high temperature) and having a small work function. To obtain a plurality of electron beams, two methods are used. One is a method in which one electron beam is drawn from one emitter (one protrusion) and made to pass through a thin plate having a plurality oh holes (aperture plate) to obtain a plurality of electron beams, and the other is a method in which a plurality of protrusions are formed on one emitter and a plurality of electron beams are draw directly therefrom. Both the methods utilize the nature such that the electron beam is easily emitted from the leading end of the protrusion. Other types of electron beam sources, for example, a thermal electron beam emission-type electron beam and a Shottky type can be used. Further, the electron beam gun may emit a rectangular or linear beam, an aperture shape may be used to create such a shape, the electron generation portion (chip, filament or the like) of the electron gun may be formed into a rectangular or linear shape.

Furthermore, the thermal electron beam source is a type of electron beam source in which the electron emission material is heated to emit electrons, and the thermal electric field emission electron beam source is a type of electron beam source in which a high electric field is applied to the electron emission material to emit electrons, and the electron beam emission portion is heated to stabilize the emission of electrons.

FIG. 150A is a schematic diagram of electron beam apparatus of another embodiment. On the other hand, FIG. 150B is a schematic diagram showing an aspect in which a sample is scanned with a plurality of primary electron beams. An electron gun 150•1 capable of being activated under space-charge limitation conditions forms a multi-beam denoted by reference numeral 150•2 in FIG. 150B. The multi-beam 150•2 is constituted by primary electron beams 150•3 that are 8 circular beams situated along a circumference.

A plurality of primary electron beams 150•3 generated at the electron gun 150•1 are converged using lenses 150•5 and 150•6, and is adapted to enter a sample W at a right angle by an ExB separator 150•9 comprised of an electrode 150•7 and a magnet 150•8. The multi-beam 150•2 constituted by a plurality of primary electron beams 150•3 converged on the sample W by a primary optical system including the components 150•4, 150•5, 150•6, 150•9, a lens 150•10 and an objective lens 150•11 is used for scanning on the sample W by a two-stage deflector (not shown, included in the primary optical system) provided on the downstream side of the lens 150•6.

The sample W is scanned in the direction of the x axis with the main face of the objective lens 150•11 as the center of reflection. As shown in FIG. 150B, the primary electron beams 150•3 of the multi-beam 150•2 are situated at a distance from each other along a circumference, and are designed so that the distances between the mutually adjacent primary electron beams 150•3 (measured at the center of each primary electron beam) are the same when the primary electron beams 150•3 are projected on the y axis orthogonal to the x direction being a scan direction. At this time, the mutually adjacent primary electron beams 150•3 may be separated from each other, contact each other or partially overlap each other.

The overlapping pitch may be set to any value equal to or smaller than 100 μm, preferably equal to or smaller than 50 μm, more preferably equal to or smaller than 10 μm. By setting the overlapping pitch to a value equal to or smaller than the pitch of the beam shape, beams can be made to contact one another to form a linear shape. Furthermore, beams originally formed into a rectangular or linear shape may be used.

As shown in FIG. 150B, the primary electron beams 150•3 constituting the multi-beam 150•2 are situated at a distance from one another, whereby the limit value of the current density of the individual primary electron beam, i.e. the marginal current density value causing no charge on the sample W can be maintained at a level equivalent to that when a single circular beam is used, thereby making it possible to prevent a drop in S/N ratio. Furthermore, the primary electron beams 150•3 are situated at a distance from one another, and thus the space charge effect is insignificant.

On the other hand, the multi-beam 150•2 can scan the sample W over an entire filed of view 150•12 in a uniform density with one scan. Consequently, image formation can be performed in high throughput, thus making it possible to achieve a reduction in inspection time. In FIG. 150B, provided that reference numeral 150•2 denotes a multi beam at the starting point of scanning, reference numeral 150•13 denotes a multi-beam at the endpoint of scanning.

The sample W is placed on a sample table (not shown). This table is continuously moved along the y direction orthogonal to the scan direction x at the time when the sample W is scanned in the x direction (e.g. scanned in a width of 20 μm). In this way, raster scanning is performed. A drive apparatus (not shown) for moving the table having the sample placed thereon.

Secondary electrons generated from the sample W during scanning and emitted in various directions are accelerated in the direction of the optical axis by the objective lens 150•11 and as a result, the secondary electrons emitted in various directions from various points are each narrowly converged, and intervals of images are enlarged with lenses 150•10, 150•11, 150•14 and 150•15. A secondary electron beam 150•16 formed via a secondary electron optical system including the lenses 150•10, 150•11, 150•14 and 150•15 is projected on the light-receiving surface of a detector 150•17 to form an enlarged image of a field of view.

The detector 150•17 included in the optical system amplifies the secondary electron beam with an MCP (microchannel plate), converts the amplified secondary electron beam into an optical signal with a scintillator, and converts the optical signal into an electric signal with a CCD detector. By the electric signal from the CCD, a two-dimensional image of the sample W can be formed. Each primary electron beam 150•3 should have a dimension of at least two pixels of CCD pixels.

By operating the electron gun 150•1 under space-charge limitation conditions, the shot noise of the primary electron beam 150•3 can be reduced in a order of one digit compared to operating the electron gun under temperature limitation conditions. Thus, the shot noise of the secondary electron signal can be reduced in a order of one digit, thus making it possible to obtain a signal of a high S/N ratio.

According to the electron beam apparatus of this embodiment, the limit value of the current density of the primary electron beam causing no charge on the sample is maintained at a level equivalent to that when a single circular beam is used, whereby a drop in S/N ratio is prevented, and images are formed in high throughput, whereby inspection time can be reduced.

In the device production process according to this embodiment, such an electron beam apparatus is used to evaluate the wafer after each wafer process is completed, whereby an improvement in yield can be achieved.

FIG. 151 shows the details of the electron beam apparatus according to the embodiment of FIG. 150A. Four electron beams 151•2 (151•3 to 151•6) emitted from an electron gun 151•1 are shaped by an aperture diaphragm 151•7, made to form an elliptic image of 10 μm×12 μm at the central face of deflection of a Wien filter 151•10 by two-stage lenses 151•8 and 151•9, raster-scanned by a deflector 151•11, and made to form an image so as to uniformly cover a rectangular area of 1 mm×0.25 mm as entire four electron beams. A plurality of electron beams deflected by the E×B 151•10 form a crossover with an NA diaphragm, and are downscaled to ⅕ of the original scale by the lens 151•11 to cover the sample with an area of 200μ×50 μm, and applied and projected on the sample surface at a right angle (called Koehler illumination). Four secondary electron beams 151•12 having information of an pattern image (sample image F), emitted from the sample, are enlarged by lenses 15•11, 151•13, 151•14, and form an image on an MCP 15115 as a rectangular image (enlarged projection image F') synthesized with the four secondary electron beams as a whole. The enlarged projection image F' with the four secondary electron beams 151•12 are intensified by a factor of ten thousands by the MCP 151•15, converted into light by a fluorescent screen, changed to an electric signal synchronized with the speed of continuous movement of the sample at a TDI-CCD 151•16, acquired as a continuous image at an image display unit 151•17, and outputted to a CRT or the like.

The electron beam irradiating portion should irradiate the sample surface with an electron beam in an elliptic or rectangular form as uniformly as possible and with reduced irradiation unevenness, and should irradiate the irradiation area with the electron beam with a larger current to improve the throughput. In the conventional system, the electron beam irradiation unevenness is about ±10%, the image has large contrast unevenness, and the electron beam irradiation current is only about 500 nA in the irradiation area, resulting in a problem such that high throughput cannot be obtained. Furthermore, this system has a problem such that image formation tends to be hindered due to charge-up because a wide image observation area is correctively irradiated with the electron beam, compared with the scanning electron beam microscope (SEM) system.

A method for irradiating a primary electron beam in this embodiment is shown in FIG. 152. A primary electron beam 152•1 is constituted by four electron beams 152•2 to 152•5, each beam has an elliptic shape of 2 μm×2.4 μm, a rectangular area of 200 μm×12.5 μm is raster-scanned with one beam, and the beams are added together in such a manner that they do not overlap one another to irradiate a rectangular area of 200μ×50 μm as a whole. The beam 151•2 reaches a spot 151•2' in finite time, then returns to just below the spot 151•2 shifted by the diameter of the beam spot (10 μm) with almost no time loss, moves again to just below the spot 1512' (toward a spot 1513') in parallel to the line 151•2 to 151•2' in finite time in the same manner as described previously, repeats this scan to scan ¼ of a rectangular irradiation area (200 μm×12.5 μm) shown by the dotted line in the figure, then returns to the original spot 152•1, and repeats this scan at a high speed.

The other electron beams 152•3 to 152•5 repeat scans at the same speed as in the case of the electron beam 152•2 to scan the rectangular irradiation area (200μx50 μm) as a whole uniformly and at a high speed.

The scan is not limited to the raster scan as long as the sample can be uniformly irradiated. For example, the sample may be scanned in such a manner as to draw a Lissajou's figure. Thus, the direction of movement of the stage is not limited to the direction A shown in the figure. In other words, the direction is not necessarily perpendicular to the scan direction (lateral high-speed scan direction in the figure).

In this embodiment, the sample can be irradiated with electron beam irradiation unevenness of about ±3%. The irradiation current is 250 nA for one electron beam, and 1.0 μA of irradiation current can be obtained with four electron beams as a whole on the sample surface (twice as large as the irradiation current in the conventional system). By increasing the number of electron beams, the current can be increased, and thus high throughput can be obtained. Furthermore, the irradiation spot is small compared to the conventional system (about 1/80 in area), and the charge-up can be reduced to 1/20 of that of the conventional system because the sample is moved.

Although not shown in the figure, this apparatus comprises units required for irradiation with the electron beam and image formation such as a limitation field diaphragm, a deflector (aligner) having 4 or more poles for adjustment of the axis of the electron beam, an astigmatism corrector (stigmater), and a plurality of quadrupolar lenses (quadrupole lenses) for shaping a beam, in addition to lenses.

3-2-2) Structure of Electrode

FIG. 153 shows an electron beam apparatus having an electrode structure for preventing insulation breakdown in an electro-optical system using an electrostatic lens for irradiating the sample with an electron beam.

Considerations have been made for using an electron beam apparatus of high sensitivity and high resolution using an electron beam to inspect the surface state of a fine sample such that a sufficient sensitivity and resolution cannot be obtained by optical inspection.

In this electron beam apparatus, an electron beam is emitted by an electron beam source, the emitted electron beam is accelerated and converged with an electrostatic system such as an electrostatic lens, and made to enter a sample as an inspection object. Then, a secondary electron beam emitted from the sample with entrance of the electron beam is detected, whereby a signal matching the detected secondary electron beam is generated, and for example, data of the sample is formed with this signal. The formed data is used to inspect the surface state of the sample.

In the electro-optical system using an electrostatic lens such as an electrostatic lens for use in the electron beam apparatus, electrodes generating electric fields for accelerating and converging the electron beam are provided in multiple stages along the optical axis of the electron beam. A predetermined voltage is applied to each of these electrodes and in this way, the electron beam is accelerated and converged to a predetermined spot on the optical axis by the electric field produced due to a difference in potential between electrodes.

In the conventional electron beam apparatus, part of the electron beam emitted from the electron beam source may impinge upon the electrode irrespective of the electric field in the electro-optical system using the electrostatic lens. In this case, as the electron beam impinges upon the electrode, a secondary electron beam is emitted from the electrode itself. The amount of the secondary electron beam emitted from the electrode varies depending on the material of the electrode, or the material coated on the electrode. If the amount of the secondary electron beam emitted from the electrode increases, the secondary electron beam is accelerated by the electric field of the electrode and ionizes residual gas in the apparatus, and the ions impinge upon the electrode, whereby a secondary electron beam is further emitted from the electrode. Therefore, if a large amount of secondary electron beam is emitted, a discharge tends to occur between electrodes, thus raising the probability of occurrence of insulation breakdown between electrodes.

For example, comparison of the probability of insulation breakdown between the electrode coated with aluminum and the electrode coated with gold showed that the probability of insulation breakdown between electrodes was slightly higher in the case of the electrode coated with aluminum. The work function of aluminum is 4.2 [eV] and the work function of gold is 4.9 [eV]. Here, the work function means minimum energy required for taking one electron beam in a metal into a vacuum (unit: eV).

Furthermore, if the electrode is coated with gold, and the sample in the electron beam apparatus is a semiconductor wafer, the gold may be sputtered and deposited on the surface of the semiconductor wafer as the electron beam impinges upon the gold coating. If the gold is deposited on the surface of the semiconductor, the gold is scattered in silicon crystals in a subsequent heating step, resulting in degradation in performance of a transistor. Thus, in this case, the electron beam apparatus is not suitable for inspection of semiconductor wafers.

On the other hand, for example, in the electrostatic lens of the electro-optical system using an electrostatic lens, an electrostatic lens having a small focal distance is obtained by reducing the distance between electrodes. If the focal distance is small, the electrostatic lens has a reduced aberration coefficient and hence a low aberration, and therefore the resolution of the electrostatic lens increases, resulting in an improvement in resolution of an evaluation apparatus.

Also, by increasing a difference in potential to given to between electrodes of the electrostatic lens, the focal distance of the electrostatic lens can be reduced. Accordingly, as in the case of reducing the distance between electrodes, the electrostatic lens has a low aberration and a high resolution, and thus the resolution of the electron beam apparatus is improved. Thus, if the distance between electrodes is reduced and the difference in potential between electrodes is increased, a reduction in aberration and an increase in resolution of the electrostatic lens can be achieved in a synergistic manner. However, if the distance between electrodes is reduced and the difference in potential between electrodes is increased, a discharge tends to occur between electrodes, thus increasing the probability of occurrence of insulation breakdown between electrodes.

Hitherto, the insulation between electrodes has been retained by inserting an insulating material between electrodes, and supporting the electrodes with this insulating material. Furthermore, the insulation performance of the insulating material has been improved by increasing the shortest creepage distance (insulation surface length) of the insulating material between electrodes. For example, by forming the surface of the insulating material into a corrugation along the distance between electrodes, the shortest creepage distance between electrodes can has been increased.

Generally, however, the processing of the surface of the insulating material is difficult compared to the processing of a metal, and thus requires a high process cost. Furthermore, if the surface of the insulating material is formed into a corrugation, the surface area of the insulating material is increased, and therefore the amount of gas emitted from the insulating material may increase in the case where a vacuum is maintained in the electron beam apparatus. Accordingly, there have been many cases where the degree of vacuum decreases, resulting in a drop in withstand pressure between electrodes.

The embodiment of FIG. 153 has been proposed for solving these problems, and the configuration and operation of a projection electron microscope type evaluation apparatus and a device production process using the apparatus where an electron beam apparatus capable of preventing insulation breakdown between electrodes of an electrostatic optical system is applied to the projection electron microscope type evaluation apparatus having the electrostatic optical system, according to this embodiment, will be described below.

In FIG. 153, for a projection electron microscope type evaluation apparatus 153•1, an electron beam applied to a sample has predetermined emitting surface, and a secondary electron beam emitted from the sample with irradiation of the electron beam also has a predetermined emitting surface. An electron beam having a two-dimensional area, for example rectangular emitting surface is emitted from an electron beam source 153•2, and enlarged by a predetermined magnification by an electrostatic lens system 153•3. The enlarged electron beam is made to enter an E×B deflector 153•4 slantingly from above, and deflected toward a semiconductor wafer 153•5 as a sample (solid line in FIG. 153) by a field in which an electric field and a magnetic field of the E×B deflector 153•4 are orthogonal to each other.

The electron beam deflected toward the semiconductor wafer 153•5 by the E×B deflector 153•4 is retarded by an electric field produced by a voltage applied to electrodes in an electrostatic objective lens system 153•6, and made to form an image on the semiconductor wafer 153•5 by the electrostatic objective lens system 153•6.

Then, the secondary electron beam produced with irradiation of the electron beam to the semiconductor wafer 153•5 is accelerated toward a detector 153•7 (dotted line in FIG. 153) by the electric field of the electrostatic objective lens system 153•6, and made to enter the E×B deflector 153•4. The E×B deflector 153•4 forces the accelerated secondary electron beam toward an electrostatic intermediate lens system 153•8, then causes the electrostatic intermediate lens system 153•8 to make the secondary electron beam enter the detector 153•7, whereby the secondary electron beam is detected. The secondary electron beam detected by the detector 153•7 is converted into data and sent to a display apparatus 153•9, an image of the electron beam is displayed on the display apparatus 153•9, and a pattern of the semiconductor wafer 153•5 is inspected.

The configurations of the electrostatic lens system 153•3, the electrostatic objective lens system 153•6, the electrostatic intermediate lens system 153•8 and the E×B deflector 153•4 in the projection type evaluation apparatus 153•1 will now be described in detail. The electrostatic lens system 153•3 and the electrostatic objective lens system 153•6 through which the electron beam passes, and the electrostatic intermediate lens system 153•8 through which the secondary electron beam passes include a plurality of electrodes for producing a predetermined electric field. Furthermore, the surfaces of all the electrodes are coated with platinum. Further, the surface of an electrode 153•10 of the E×B deflector 153•4 is also coated with platinum.

Now, the probability of occurrence of insulation breakdown for each metal coated on the electrode will be described with reference to FIG. 154. Furthermore, in the projection type evaluation apparatus, other inspection conditions excluding the type of metal coated on the electrode are the same.

First, comparison in probability of occurrence of insulation breakdown between the case where aluminum is used as a metal coated on the electrode and the case where gold is used as such a metal showed that the probability of occurrence of insulation breakdown was slightly lower in the electrode coated with gold. Thus, it was shown that gold had more effective in prevention of insulation breakdown. Furthermore, comparison in probability of occurrence of insulation breakdown between the case where gold is used as a metal coated on the electrode and the case where platinum is used as such a metal showed that the probability of occurrence of insulation breakdown was lower in the electrode coated with platinum.

Here, the work functions of the metals are 4.2 [eV] for aluminum, 4.9 [eV] for gold, and 5.3 [eV] for platinum. The work function of the metal means minimum energy (unit: eV) required for taking one electron in the metal into a vacuum. That is, as the value of the work function increases, the electron beam becomes harder to be taken.

Accordingly, in the projection type evaluation apparatus 153•1, when the electron beam emitted from the electron beam source 153•2 impinges upon the electrode, the amount of secondary electron beam emitted from the electrode decreases and thus the probability of occurrence of insulation breakdown of the electrode is reduced as long as the electrode is coated with a metal having a large work function value (including an alloy having as a main material a metal having a large work function value). Therefore, any material having a large work function is somewhat acceptable. Specifically, if the work function of the metal coated on the electrode is 5 [eV], the probability of occurrence of insulation breakdown of the electrode can be kept at a low level.

Furthermore, if, as in this embodiment, the sample to be inspected is the semiconductor wafer 153•5, and the metal coated on the electrode is gold, gold may be deposited on the pattern of the semiconductor wafer 153•5 as the electron beam impinges upon the gold. Accordingly, in this embodiment, if the metal coated on the electrode is platinum, platinum is never deposited on the pattern of the semiconductor wafer 153•5, and the device performance is never compromised even if the platinum is deposited on the pattern. Further, the probability of occurrence of insulation breakdown of the electrode can be reduced, and thus platinum is more preferable.

One example of the shape and configuration of the electrode will now be described with reference to FIGS. 155 and 156. In FIG. 155, an electrode 155•1 is an electrode of an electrostatic lens included in the electrostatic lens system 153•3, the electrostatic objective lens system 153•6 and the electrostatic intermediate lens system 153•8.

The electrode 155•1 has a disk-like shape having at almost the center a through-hole allowing the electron beam and secondary electron beam to pass therethrough, and in the projection type evaluation apparatus 153•1 of this embodiment, a predetermined voltage is applied to the electrode 155•1 by a power supply apparatus (not shown).

FIG. 156 is a partial sectional view of a surface portion of the electrode 155•1. Furthermore, the surface of the electrode 153•10 of the E×B deflector 153•4 may have the same configuration as that of the surface of the electrode 155•1. The electrode 155•1 is made of silicon copper (silicon bronze) 156•1, and titanium 156•2 is sputter-coated in the thickness of 50 nm on the silicon copper 156•1 processed into a necessary size and shape, and platinum 156•3 is sputter-coated in the thickness of 200 nm on the titanium 156•2 to form the electrode 155•1.

Now, the electron configuration for preventing insulation breakdown between electrodes when the difference in potential between electrodes is large in this embodiment will now be described in detail with reference of FIGS. 157 and 158. Electrodes 157•1 and 157•2 of FIG. 157 are, for example, electrodes included in the electrostatic objective lens system 153•6, and the electrodes are coated with platinum as described above. Furthermore, predetermined voltages are applied to the electrodes 157•1 and 157•2 by a power supply apparatus (not shown). In this embodiment, a high voltage, for example a voltage of 15 kV is applied to the electrode 157•2 on the semiconductor wafer 153•5 side, and a voltage of 5 kV is applied to the electrode 157•1.

A through-hole 157•3 through which the electron beam and the secondary electron beam pass is situated in the middle between the electrodes 157•1 and 157•2, an electric field is formed in the through-hole 157•3 by a difference in potential between the electrodes 157•1 and 157•2. By this electric filed, the electron beam is retarded and retarded, and is applied to the semiconductor wafer 153•5. At this time the difference in potential between the electrodes is large, and therefore the electrostatic objective lens system 153•6 can have an electrostatic objective lens having a small focal distance. Accordingly, the electrostatic objective lens system 153•6 has a low aberration and a high resolution.

An insulating spacer 157•4 is inserted between the electrodes 157•1 and 157•2, and the insulating spacer 157•4 approximately perpendicularly supports the electrodes 157•1 and 157•2. The shortest creepage distance between electrodes in the insulating spacer 157•4 is proximately the same as the distance between electrodes in the area of the supported electrode. That is, the surface of the insulating spacer 157•4 between electrodes are not corrugated or the like, but is almost a straight line.

The electrode 157•2 has a first electrode surface 157•5 with the shortest distance between electrodes, a second electrode surface 157•6 having a distance between electrodes longer than the first electrode surface 157•5, and a step 157•7 in the direction of the distance between these two electrodes between the first electrode surface 157•5 and the second electrode surface 157•6 (FIG. 158). The insulating spacer 157•4 supports the electrode 157•2 with the second electrode surface 157•6.

Owing to this configuration of the electrode 157•2, the shortest creepage distance of the insulating spacer 157•4 can be made to be longer than the shortest distance between electrodes with the shortest distance between electrodes being kept at a predetermined distance and without processing the surface of the insulating spacer 157•4 into a corrugated shape in the direction of the distance between electrodes. Furthermore, since a large electric field is not applied to the surface of the insulating spacer 157•4, a structure can be provided such that a creepage discharge is hard to occur.

Thus, the electrostatic objective lens system 135•6 can be made to have an electrostatic objective lens having a small focal distance, and have a low aberration and a high resolution, and the performance of the insulating spacer 157•4 to provide insulation between electrodes is not degraded, thus making it possible to prevent insulation breakdown between electrodes. Furthermore, since the electrode 157•2 made of metal is processed so as to provide the step 157•7 thereon, the process cost is reduced compared with the case where the insulating spacer 157•4 is processed. In addition, the surface of the insulating spacer 157•4 in the direction of the distance between electrodes has almost no irregularities, and the amount of emitted gas from the insulating spacer 157•4 never increases. Further, corner portions of an open end portion 157•8 of the through-hole 157•3 of the electrode 157•1 and an open end portion 157•9 of the through-hole 157•3 of the electrode 157•2 have curvatures, and therefore the electric field is never concentrated on both the corner portions, thus making it possible to more reliably prevent insulation breakdown between electrodes. Furthermore, a corner portion of the step 157•7 of the electrode 157•2 on the side between electrodes has a curvature, and therefore the electric field is never concentrated on the corner portion, thus making it possible to more reliably prevent insulation breakdown between electrodes.

Furthermore, in this embodiment, the step 157•7 is provided on the electrode 157•2, but the electrode 157•1 may also be processed so as to provide a step in the direction of the electrode 157•2, or only the electrode 157•1 may be processed so as to provide a step in the direction of the electrode 157•2 with the electrode 157•2 having no step. Furthermore, the electrodes with the insulating spacer 157•4 inserted therebetween has been described in the electrostatic objective lens system 153•6, but if there are electrodes having a large difference in potential in other electrostatic lens system, the spacer 157•4 may be applied to the electrostatic lens system to prevent insulation breakdown between electrodes.

By using the embodiment described with FIGS. 153 to 158 in inspection steps in the device production process already described, the semiconductor wafer can be evaluated without causing insulation breakdown to occur between electrodes of the electrostatic lens system.

3-3) Embodiment for Anti-vibration Apparatus

This embodiment relates to an electron beam apparatus performing at least any one of processing, production, observation and inspection of a material by irradiating an electron beam to the target position of the material, more particularly to an electron beam apparatus having reduced undesired mechanical vibrations occurring in a mechanical structure positioning the electron beam, an anti-vibration method thereof, and a semiconductor production process comprising a step of performing at least any one of processing, production, observation and inspection of a semiconductor device using the electron beam apparatus.

Generally, means for observing a fine structure of a material using an electron beam includes an inspection apparatus for inspecting defects of a pattern formed on a wafer or the like, a scanning electron beam microscope (SEM) and the like but in this case, the observation resolution is μm to several tens of nm, and it is therefore required to sufficiently remove external vibrations to make an observation. Furthermore, in an apparatus for performing exposure system using an electron beam, a vibration removal apparatus for sufficiently removing external vibrations should be used to deflect an electron beam to correctly irradiate the beam to the target position, and the rigidity should be improved to reduce a drift caused by a mechanical resonance resulting from the structure of a column portion to a minimum possible level. To improve the rigidity of the structure, an improvement in rigidity by reduction in size can hardly achieved because of the physical limitation in size due to the electro-optical system, and thus an improvement in rigidity is often achieved by thickening the wall of the column portion, increasing the size and so on. However, the improvement in rigidity by this method has many disadvantages including design restrictions on the degree of freedom including an increase in weight of apparatus, limitations on the shape and increase in size of a vibration removal table, as well as economic aspects.

In view of the facts described above, this embodiment provides an electron beam apparatus in which alleviation of design restrictions, reduction in size and weight of apparatus, and improvement in economy are achieved by appropriately attenuating undesired vibrations by a resonance of a mechanical structure for positioning a beam so that the positioning of the beam can be maintained with high accuracy without necessarily improving the rigidity of the mechanical structure, and a semiconductor production process capable of performing production, inspection, processing, observation and the like using the apparatus in steps of producing a semiconductor device.

FIG. 159 shows the configuration where this embodiment is applied to an electron beam inspection apparatus inspecting defects of a semiconductor wafer using en electron beam. An electron beam inspection apparatus 159•1 shown in this figure is so called a projection type apparatus, and has a mechanical structure of an A block and a B block protruding upward slantingly from the A block. Primary electron beam irradiating means for irradiating a primary electron beam is placed in the B block, and a projection type optical system for mapping and projecting a secondary electron beam, and imaging means for detecting the intensity of the secondary electron beam are included in the A block. The A block is coupled to a lowermost fixation base 159•2.

The primary electron beam irradiating means placed in the B block comprises an electron beam source 159•3 constituted by a cathode and an anode to emit and accelerate a primary electron beam, an oblong opening 159•4 shaping the primary electron beam into an oblong, and a quadrupole lens 159•5 reducing the primary electron beam and making the primary electron beam form an image in a reduced size. An E×B deflector 159•7 deflecting the reduced primary electron beam so as to impinge upon a semiconductor wafer 159•6 at approximately a right angle in a field in which an electric field E and a magnetic filed B are orthogonal to each other, an aperture (NA) 159•8, and an objective lens 159•9 making the primary electron beam passing through the aperture form an image on the wafer 159•6 are placed in the lower part of the A block.

Here, the primary electron beam reduced by the quadrupole lens 159•5 forms an image of, for example, 500 μm×250 μm on the deflection main surface of the E×B deflector 159•7, and also forms a crossover image of the electron beam source 159•3 on the aperture 159•8, so that Keller illumination conditions are satisfied. An image of, for example, 100 μm×50 μm is formed on the wafer 159•6 by the objective lens 159•6.

The wafer 159•6 is placed in a sample chamber (not shown) capable of being evacuated, and also placed on a stage 159•10 movable in the X-Y horizontal plane. Here, a relation between the A and B blocks and an XYZ orthogonal coordinate system is shown in FIG. 160(a). The wafer surface is situated in the X-Y horizontal plane, and the Z axis is appropriately parallel to the optical axis of a projection optical system. As the stage 159•10 moves in the X-Y horizontal plane with the wafer 159•6 placed thereon, the inspection surface of the wafer 159•6 is sequentially scanned with the primary electron beam. Furthermore, the stage 159•10 is placed on the fixation base 159•2.

The projection type optical system placed in the upper part of the A block comprises an intermediate electrostatic lens 159•11, a projection electrostatic lens 159•12, and a diaphragm 159•13 placed in the middle between these lenses. A secondary electron beam, a reflection electron beam and a scattered electron beam emitted from the wafer 159•6 with irradiation of the primary electron beam are projected under a predetermined magnification (e.g. by factor of 200 to 300), and made to form an image on the lower face of a micro-channel plate 159•14.

Imaging means placed at the top of the A block comprises the micro-channel plate 159•14, a fluorescent screen 159•15, a relay lens 159•16 and an imaging unit 159•17. The micro-channel plate 159•14 has a large number of channels, and further generates a large number of electron beams while the secondary electron beam made to form an image by the electrostatic lenses 159•11 and 159•12 passes through the channels. That is, the secondary electron beam is amplified. The fluorescent screen 159•15 emits fluorescence having an intensity appropriate to the intensity of the secondary electron beam as the amplified secondary electron beam is applied. That is, the intensity of the secondary electron beam is converted into the intensity of light. The relay lens 159•16 is so situated as to guide the fluorescence to the imaging unit 159•17. The imaging unit 159•17 is constituted by a large number of imaging devices for converting light guided by the relay lens 159•16 into an electric signal. So called a TDI detector is preferably used to improve the S/N ratio of a detection signal. Furthermore, not only the secondary electron beam but also the back-scattered electron beam and the reflection electron beam are generated with irradiation of the primary electron beam, but these beams are collectively referred to as the secondary electron beam here.

A column 160•1 comprised of the mechanical structure of the A block and the B block coupled thereto usually has one or more characteristic vibration modes. The resonance frequency and the resonance direction of each characteristic vibration mode are determined according to the shape, the weight distribution, the size, the layout of internal machines and the like. For example, as shown in FIG. 160(b), the column 160•1 has at least a mode 1 of characteristic vibrations 160•2. In this mode 1, the column 160•1 drifts at a frequency of 150 Hz approximately along the Y direction, for example. One example of a transfer function of the column in this case is shown in FIG. 161. In FIG. 161, the horizontal axis represents the frequency, and the vertical axis represents the logarithm of vibration amplitude A. The transfer function has a gain of a resonance magnification of 30 dB (about a factor of 30) at a resonance frequency of 150 Hz. Thus, even if very small vibrations are externally applied, frequency components at near 150 Hz are amplified by a factor of about 30 to vibrate the column if such frequency components are included in the vibrations. As a result, a detrimental event such as blurring of mapping is caused to occur.

To prevent such an event, the conventional technique takes large-scale measures such as placing the entire column on a vibration removal table to remove external vibrations, and/or reconsidering the wall-thickness and structure of the column to reduce the resonance magnification.

In this embodiment, to prevent the detrimental event, an actuator 160•4 applying pressure vibrations 160•3 to the column so as to cancel out the vibrations 160•2 is placed in the base part of the block A as shown in FIG. 160(c). This actuator 160•4 is electrically connected to a vibration attenuating circuit 159•18.

The outlined configurations of the actuator 160•4 and the vibration attenuating circuit 159•18 are shown in FIG. 162. As shown in this figure, the actuator 160•4 has a piezoelectric element 162•4 having a dielectric material 162•1 with a piezoelectric effect held between electrodes 162•2 and 162•3, and a support base 162•5 fixed on the fixation base 159•2 for supporting the piezoelectric element from the electrode 162•3 side. The piezoelectric element 162•4 is held between the A block of the column 160•1 and the support base 162•5, the electrode 162•2 is fixed to the outer wall of the A block, and the electrode 162•3 is fixed to the support base 162•5. In this way, by the reciprocating vibrations 160•2, the piezoelectric element 162•4 receives a positive pressure when the column 160•1 moves close to the element, and receives a negative pressure when the column moves away from the element. The piezoelectric element 162•4 is situated at an effective position for inhibiting the vibrations 160•2 of the column 160•1. For example, it is preferably situated so that the direction of the vibrations 160•2 is orthogonal to the electrodes 162•2 and 162•3.

The vibration attenuating circuit 159•18 is comprised of a variable inductance 162•6 and a resistance 162•7 connected in series between both the electrodes 162•2 and 162•3 of the piezoelectric element 162•4. Since the variable inductance 162•6 has an inductance L, the resistance 162•7 has a resistance value of $R_D$, and the piezoelectric element 162•4 has an electric capacitance of C, the piezoelectric element 162•4 and the vibration attenuating circuit 159•18 connected in series are equivalent to a series resonance circuit denoted by reference numeral 162•8. The resonance frequency $f_0'$ of this series resonance circuit is expressed by the following equation:

$$f_0' = 1/\{2\pi(LC)^{1/2}\}.$$

In this embodiment, each parameter is set so that the resonance frequency $f_0'$ of the series resonance circuit approximately equals the resonance frequency $f_0$ of the column 160•1. That is, the inductance L of the variable inductance 162•6 is adjusted so that the following equation holds for the electric capacitance C of the piezoelectric element 162•4:

$$f_0 = 1/2\{2\pi(LC)^{1/2}\}.$$

Actually, the capacitance C of the piezoelectric element 162•4 is small in forming the resonance circuit according to the mechanical resonance frequency, and hence a very large inductance L is often required but in this case, a calculation amplifier or the like is used to form equivalently large inductance, whereby the resonance circuit can be achieved.

Furthermore, the value $R_D$ of the resistance 162•7 is selected so that the Q value of a resonance frequency component of the series resonance circuit approximately equals to the Q value of a resonance component having a peak in the transfer function shown in FIG. 161. A series resonance circuit 162•8 created in this way has an electric frequency characteristic denoted by reference numeral 161•1 of FIG. 161.

The electron beam inspection apparatus 159•1 shown in FIG. 159 is controlled/managed by a control unit 159•19. The control unit 159•19 can be constituted by a general personal computer or the like as shown in FIG. 159. This computer a control unit main body 159•20 carrying out various kinds of control and calculation operations according to a predetermined program, a CRT 159•21 displaying results of operations by the main body, and input unit 159•22 such as a keyboard, a mouse and the like for the operator to input instructions. Of course, the control unit 159•19 may be constituted by hardware dedicated to the electron beam inspection apparatus, a workstation or the like.

The control unit main body 159•20 is constituted by a CPU, an RAM, an ROM, a hard disk, various kinds of boards such as a video board and the like (not shown). A secondary electron beam image storage area 159•23 for storing electric signals received from the imaging unit 159•17, i.e. digital image data of secondary electron beam images of the wafer 159•6 is assigned on a memory of the RAM or hard disk. Furthermore, a reference image storage unit 159•24 for storing reference image data of the wafer having no defects in advance exists on the hard disk. Further, in addition to a control program for controlling the entire electron beam inspection apparatus, a defect detection program 159•25 is stored on the hard disk. This defect detection program 159•25 has a function of controlling the movement of the stage 159•10 in the XY plane, while carrying out various kinds of calculation operations such as addition for digital image data received from the imaging unit 159•17, and reconstituting a secondary electron beam image on the storage area from data obtained as a result of the operations. Further, this defect detection program 159•25 reads secondary electron beam image data constituted on the storage area 159•23, and automatically detects defects of the wafer 159•6 according to a predetermined algorithm based on the image data.

The action of this embodiment will now be described. The primary electron beam is emitted from the electron beam source 159•3, and applied to the surface of the set wafer 159•6 through the oblong opening 159•4, quadrupole lens 159•5, the E×B deflector 159•7 and the objective lens 159•9. As described above, an inspection subject area of, for example, 100 μm×50 μm is illuminated on the wafer 159•6, and the secondary electron beam is emitted. This secondary electron beam is magnified and projected in the lower face of the multi-channel plate 159•14 by the intermediate electrostatic lens 159•11 and the projection electrostatic lens 159•12, and imaged by the imaging unit 159•17 to obtain a secondary electron beam image of a projected area on the wafer 159•6. By driving the stage 159•10 to move the wafer 159•6 successively by each predetermined width in the X-Y horizontal surface to carry out the above procedures, whereby an image of the entire inspection surface can be obtained.

If an external force including a vibration component of the resonance frequency f0 (150 Hz) is exerted on the column 160•1 while the enlarged secondary electron beam image is formed, the column 160•1 amplifies this vibration component with a resonance magnification (30 dB) determined by the transfer function thereof and characteristically vibrates. The vibrations 160•2 applies positive and negative pressures to the piezoelectric element 162•4. The piezoelectric element 162•4 temporarily converts vibration energy of the column 160•1 into electric energy and outputs the same. Since the inductance 162•6 (L) and the resistance 162•7 ($R_D$) are connected in series to both the electrodes 162•2 and 162•3 to a resonance circuit, the capacitive impedance of the piezoelectric element 162•4 and the dielectric impedance L of the inductance 162•6 offset each other in the resonance frequency f0, and the impedance of the resonance circuit is only the resistance $R_D$ in effect. Thus, during resonance, electric energy outputted from the piezoelectric element 162•4 is almost fully consumed by the resistance 162•7 ($R_D$).

In this way, the piezoelectric element 162•4 produces a force so as to offset an external force applied from the column 160•1 to the piezoelectric element 162•4, and vibrations 160•2 produced by mechanical resonance can be offset to increase the resonance magnification. The secondary electron beam is enlarged and mapped, and therefore a drift in mapping by vibrations is further increased but in this embodiment, blurring caused by this drift can be prevented before it occurs.

As shown in FIG. 163, the resonance component of the transfer function 161•1 of the column 160•1 (corresponding to FIG. 161) as a mechanical structure is offset by the resonance component of the series resonance circuit 162•8 having electric frequency characteristics 163•1, and thus the column 160•1 has a total transfer function 163•2 having a low resonance magnification as a whole.

As described above, when a satisfactory secondary electron beam image free from blurring in mapping is obtained, then the electron beam inspection apparatus 159•1 of this embodiment carries out processing for inspecting defects of the wafer 159•6 from the image. As defect inspection processing, so called a pattern matching method or the like may be used. In this method, the reference image read from the reference image storage unit 159•24 is matched with the actually detected secondary electron beam image to calculate a distance value representing similarity between both the images. If the distance value is smaller than threshold value, it is determined that the similarity is high to determine "no defects exit". On the other hand, if the distance value is equal to or greater than the predetermined threshold value, it is determined that the similarity is low to determine that "defects exist". If it is determined that "defects exist", it may be displayed for warning the operator. At this time, the secondary electron beam image 159•26 may be displayed on the display unit of the CRT 159•21. Furthermore, the pattern matching method may be used for each partial area of the secondary electron beam image.

There is a defect inspection method shown in FIGS. 164(*a*) to (*c*) other than the pattern matching method. In FIG. 164(*a*), an image 164•1 of a die detected first and an image 164•2 of another die detected second are shown. If it is determined that still an image of still another die detected third is identical or similar to the first image 164•1, it is determined that an area 164•3 of the second die image 164•2 has defects, and thus the defect area can be detected.

In FIG. 164(*b*), an example of measurement of a line width of a pattern formed on the wafer is shown. Reference numeral 164•6 denotes an intensity signal of an actual secondary electron beam when an actual pattern 164•4 on a wafer is scanned in a direction 164•5, and a width 164•8 of an area in which this signal continuously exceeds a threshold level 164•7 corrected and defined in advance can be measured as the line width of the pattern 164•4. If the line width measured in this way does not fall within a predetermined range, it can be determined that the pattern has defects.

In FIG. 164(*c*), an example of measurement of a potential contrast of a pattern formed on a wafer is shown. In the configuration shown in FIG. 159, an axisymmetric electrode 164•9 is provided above the wafer 159•6 and, for example, a potential of −10 V is given to the electrode with respect to the potential of the wafer of 0 V. The equipotential surface of −2 V at this time has a shape denoted by reference numeral 14•10. Here, patterns 164•11 and 164•12 formed on the wafer have potentials of −4 V and 0 V, respectively. In this case, a secondary electron beam emitted from the pattern 164•11 has a upward speed equivalent to kinetic energy of 2 eV on the −2 V equipotential surface 164•10, and therefore passes over the potential barrier 164•10, and escapes from the electrode 164•9 as shown in an orbit 164•13, and is detected by a detector. On the other hand, a secondary electron beam emitted from the pattern 164•12 cannot pass over the potential barrier of −2 V, and is forced back to the wafer surface as shown in an orbit 164•14, and therefore is not detected. Thus, the detection image of the pattern 164•11 is bright, and the detection image of the pattern 164•12 is dark. In this way, a potential contrast is obtained. If the brightness and the potential of the detection image are corrected in advance, the potential of the pattern can be measured from the detection image. A defective area of the pattern can be evaluated from the potential distribution.

As described above, by making measurements described above for the satisfactory secondary electron beam image free from blurring in mapping obtained from this embodiment, more accurate defect inspection can be achieved.

If the electron beam inspection apparatus described as this embodiment is used in wafer inspection steps in the device production process, degradation in the detection image due to vibrations of the mechanical structure can be prevented before it occurs, and therefore accurate inspection can be carried out effectively, thus making it possible to prevent defective products from being dispatched.

Furthermore, this embodiment is not limited to what has been described above, but may be altered arbitrarily and suitably in the spirit of the present invention. For example, not necessarily just one mechanical resonance frequency and mode, but two or more mechanical resonance frequencies and modes generally occur and in this case, they can be coped with by placing a necessary number of actuators 160•4 at appropriate positions in the column. For example, if the mechanical structure block A shown in FIG. 160(*b*) has not only vibrations 160•2 in the Y direction but also vibrations in the X direction, a different actuator may be placed so as to offset the vibrations in the X direction. Further, if the B block and the D block have independent characteristic vibrations, actuators may be placed for these blocks.

The vibration actuating circuit 159•18 is not necessarily equivalent to the series resonance circuit 162•8, but may be matched with a circuit having a plurality of resonance frequencies as electric frequency characteristics of the circuit if mechanical characteristic vibrations have a plurality of resonance frequencies in the same vibration direction.

The location in which the actuator is placed is not limited to the column, but the actuator can also be applied to parts required to correctly position the beam, for example the X-Y stage 159•10, or optical parts of various kinds of optical instruments.

The semiconductor wafer 159•6 is used as an example of the inspection subject sample of the electron beam inspection apparatus of this embodiment, but the inspection subject sample is not limited thereto, and any sample allowing defects to be detected with an electron beam can be selected. For example, a mask or the like provided with a pattern for light exposure for a wafer may be used as an inspection object.

Further, this embodiment may be generally applied to the electron beam irradiation apparatus irradiating a beam to a target position in a material. In this case, this embodiment may be applied not only to the apparatus carrying out inspection of the material but also extensively applied to the apparatus carrying out any of processing, production and observation thereof. Of course, the concept of the material refers not only the wafer and the mask described above, but also any object capable of being subjected to at least any one of inspection, processing, production and observation with a beam. Similarly, the device manufacturing method may be applied not only to inspection during the step of producing a semiconductor device, but also to a process itself for producing the semiconductor device with the beam.

Furthermore, the configuration shown in FIG. 159 is shown as that of the electron beam inspection apparatus of this embodiment, but the electro-optical system and the like may be altered arbitrarily and suitably. For example, the electron beam irradiating means of the electron beam inspection apparatus 159•1 has a form of making a primary electron beam enter the surface of the wafer 159•6 at a right angle from above, but the E×B deflector 159•7 may be omitted to cause the primary electron beam enter the surface of the wafer 159•6 slantingly.

3-4) Embodiment for Wafer Holding

This embodiment relates to an electrostatic chuck adsorbing and holding a wafer in an electrostatic manner in the electron beam apparatus, a combination of a wafer and an electrostatic chuck, particularly a combination of an electrostatic chuck and a wafer capable of being used in an electron beam apparatus using a retarding-field objective lens, and a device production process using an electron beam apparatus comprising an electrostatic chuck and a wafer.

A well known electrostatic chuck adsorbing and fixing a wafer in an electrostatic manner, an electrode layer to be placed on a substrate is formed with a plurality of mutually insulated electrodes, and a power supply apparatus applying voltages one after another from one electrode to another electrode is provided. Furthermore, an electron beam apparatus using a retarding-field objective lens is well known.

If the wafer under process is evaluated by the electron beam apparatus using the retarding-field objective lens, it is necessary to apply a negative high voltage to the wafer. In this case, if the negative high voltage is rapidly applied, the device under process may be broken, and therefore the voltage should be gradually applied.

On the other hand, for most wafers, insulation films such as $SiO_2$ or nitride films are deposited on the side and back faces of the wafer, and therefore a problem arises such that when a zero potential or low potential is to be given to the wafer, the voltage is not applied. Further, there is a problem such that a wafer raised at the center toward the electrostatic chuck side can be relatively easily adsorbed and fixed, but a wafer recessed at the center toward the chuck side is held with its edge portion chucked and its central portion not chucked with a unipolar electrostatic chuck.

To solve the above problems, this embodiment provides an electrostatic chuck capable of being used with the retarding-field objective lens, having the side and back faces covered with insulation films and capable of chucking the wafer recessed at the center toward the chuck side, and a combination of a wafer and an electrostatic chuck, and provides a device production process for evaluating a wafer under process using this electrostatic chuck or combination of an electrostatic chuck and wafer.

FIG. 165 is a plan view of an electrostatic chuck 1410 in this embodiment, showing an electrode plate 165•1 after removal of a wafer. FIG. 166 is a schematic sectional view in a vertical direction along the M—M line of the electrostatic chuck of FIG. 165, showing a state in which the wafer is placed and no voltage is applied. An electrostatic chuck 165•2 has a laminated structure comprised of a substrate 166•1, an electrode plate 166•2 and an insulation layer 166•3 as shown in FIG. 166. The electrode plate 166•2 includes a first electrode 165•2 and a second electrode 165•3. The first electrode 165•2 and the second electrode 165•3 are separated from each other so that voltages can be separately applied thereto, and they are made of thin film so that a movement can be made at a high speed without producing an eddy current in a magnetic field.

The first electrode 165•2 is comprised of the central part and part of the periphery of the circular electrode plate 166•2 in the plan view, and the second electrode 165•3 is comprised of the rest horseshoe peripheral part of the electrode plate. The insulation layer 166•3 is placed above the electrode plate 166•2. The insulation layer 1663 is made of a sapphire substrate having a thickness of 1 mm. Sapphire is made of single crystals of alumina and has no pores unlike alumina ceramics, and therefore its insulation breakdown voltage is high. For example, the sapphire substrate having a thickness of 1 mm can sufficiently endure a difference in potential of $10^4$ V or greater.

A voltage is applied to a wafer 166•4 via a contact 166•5 having a knife-edged metal portion. As shown in FIG. 166, two contacts 166•5 are made to contact the side face of the wafer 166•4. The reason why two contacts 166•5 are used is that conduction may not be established if only one contact is used, and occurrence of a force of pushing the wafer 166•4 toward one side should be avoided. An insulation layer (not shown) is broken to establish conduction, but because particles may be scattered when electrons are discharged, the contact 166•5 is connected through a power supply 166•7 through a resistance 166•6 to prevent occurrence of a large discharge. If this resistance 166•6 is too large, no conduction hole is formed, and if the resistance 166•6 is too small, a large discharge occurs to cause particles to be scattered, and therefore the allowable value of the resistance is determined for each insulation layer (not shown). This is because the thickness of the insulation layer varies depending on the history of the wafer, and hence the allowable value of the resistance should be determined for each wafer.

FIG. 167(a) shows a time chart of voltage application. A voltage of 4 kV is applied to the first electrode at a time of $t=0$ as shown by the line A. A voltage of 4 kV is applied to the second electrode as shown by the line B at a time of $t=t_0$ when the central part and peripheral part of the wafer are both chucked. Control is performed so that a voltage C of the wafer is gradually deepened (reduced) at a time of $t=t_1$, and reaches −4 kV at a time $t=t_2$. The first and second electrodes have voltages gradually reduced from a time of $t=t_1$ to a time of $t=t_2$, and it reaches 0 V at a time $t=t_2$.

At a time $t=t_3$ when evaluation of the wafer adsorbed and held by the chuck is completed, the voltage C of the wafer reaches 0 V, and the wafer is taken to the outside.

If the electrostatic chuck adsorbs and holds the wafer with a difference in potential of only 2 kV instead of 4 kV, voltages A' and B' of 2 kV are applied to the first and second electrodes, respectively, as shown by the dash-dot in FIG. 167. When a voltage of −4 kV is applied to the wafer, voltages of −2 kV are applied to the first and second electrodes, respectively. In this way, through voltage application, application of a voltage to an insulation layer 2104 more than necessary can be prevented, thus making it possible to prevent breakage of the insulation layer.

FIG. 168 is a block diagram showing an electron beam apparatus comprising the electrostatic chuck described above. An electron beam emitted from an electron beam source 168•1 has an unnecessary beam removed with an aperture of an anode 168•2 determining an aperture (NA), reduced by a condenser lens 168•7 and an objective lens 168•13, made to form an image on the wafer 166•4 having a voltage of −4 kV applied thereto, and made to scan the wafer 166•4 by deflectors 168•8 and 168•12. A secondary electron beam emitted from the wafer 166•4 is collected by the objective lens 168•13, bent to the right at an angle of about 35° by an ExB separator 168•12, and detected with a secondary electron beam detector 168•10, and a SEM image on the wafer is obtained. In the electron beam apparatus of FIG. 168, reference numerals 168•3 and 168•5 denote axis alignment devices, reference numeral 168•4 denotes an astigmatic correction device, reference numeral 168•6 denotes an aperture plate, reference numeral 168•11 denotes a shield, and reference numeral 168•14 denotes an electrode. The electrostatic chuck described with FIGS. 166 and 167 is placed below the wafer 166•4.

By using this embodiment in inspection steps in the device production process, a semiconductor device having a fine pattern can be inspected in high throughput, and 100% inspection can be performed, thus making it possible to improve the yield of products and prevent defective products being from dispatched.

Furthermore, how the voltage applied to the electrostatic chuck increases and decreases is not limited to the way shown in FIG. 167(a). For example, the voltage may exponentially vary as shown in FIG. 167(b). It is only essential that the voltage should reach a predetermined voltage within certain time.

The first to twelfth embodiments of the present invention have been described in detail above but in any of the embodiments, the term "predetermined voltage" means a voltage with which measurements such as inspection are carried out.

Furthermore, the embodiments described previously use electron beams as charged particle beams, but the charged particle beam is not limited thereto, and a charged particle beam other than an electron beam, or a non-charged particle beam such as a neutron beam having no charge, laser light or an electromagnetic wave may be used.

Furthermore, when the charged particle beam apparatus according to the present invention is activated, a target material is caused to float and attracted to a high-pressure area by an adjacent interaction (charge of particles near the surface), and therefore organic materials are deposited on various electrodes for use in formation and deflection of the charged particle beam. Organic-materials gradually deposited as the surface is charged badly affect mechanisms for forming and deflecting the charged particle beam, and therefore these deposited organic materials must be removed periodically. Thus, to periodically remove the deposited organic materials, it is preferable that using an electrode near the area having the organic materials deposited thereon, plasmas of hydrogen, oxygen or fluorine and HF, $H_2O$, $C_MF_N$ and the like containing these elements are produced under vacuum, and a plasma potential in a space is kept at a potential (several kilovolts, e.g. 20 V to 5 kV) allowing sputter to occur on the electrode surface to remove only organic materials by oxidization, hydrogenation and fluorination.

3-5) Embodiment of ExB Separator

FIG. 169 shows an ExB separator 169•1 of this embodiment. The ExB separator 169•1 is comprised of an electrostatic deflector and an electromagnetic deflector, and is shown as a sectional view on the x-y plane orthogonal to the optical axis (axis perpendicular to the sheet face: z axis) in FIG. 169. The x axis direction and the Y axis direction are also orthogonal to each other.

The electrostatic deflector comprises a pair of electrodes (electrostatic deflection electrodes) 169•2 provided in a vacuum chamber, and generates an electric field E in the X axis direction. The electrostatic deflection electrodes 169•2 are attached to a vacuum wall 169•4 of the vacuum chamber via an insulation spacer 169•3, and a distance D between these electrodes is set to a value smaller than a length 2L in the y axis direction of the electrostatic deflection electrode 169•2. By this setting, a range of uniform electric field intensity formed around the Z axis can be made to be relatively large but ideally, as long as the requirement of D<L is met, the range of uniform electric field intensity can be increased.

That is, since the range extending from the edge of the electrode to the position of D/2 does not have a uniform electric field intensity, an area of almost uniform electric field intensity is an area of 2L−D at the central part excluding the end area that does not have a uniform electric field. Accordingly, in order that there exist an area of uniform electric field intensity, the requirement of 2L>D should be met, and by setting the requirement of L>D, the area of uniform electric field intensity is further increased.

An electromagnetic deflector for generating a magnetic field M in the Y axis direction is provided outside the vacuum wall 169•4. The electromagnetic deflector comprises an electromagnetic coil 169•5 and an electromagnetic coil 169•6, and these coils generate magnetic fields in x axis and Y axis directions, respectively. Furthermore, a magnetic field M in the y axis direction can be generated with the coil 169•6 alone, but a coil generating a magnetic field in the x axis direction is provided for improving the orthogonality between the electric field and the magnetic field M. That is, by canceling out a magnetic component in the +x axis direction generated with the coil 169•6 by a magnetic component in the −x axis direction generated with the coil 169•6, the orthogonality between the electric field and the magnetic field can be improved.

Since the coils 169•5 and 168•6 for generating magnetic fields are provided outside the vacuum chamber, these coils are each divided into two parts, and they are attached from both sides of the vacuum wall 169•4, and fastened by screwing or the like in parts 169•7 to bond the parts together as one united body.

An outermost layer 169•8 of the ExB separator is constituted as a yoke made of permalloy or ferrite. The outermost layer 169•8 may be divided into two parts, and the divided parts may be attached to the outer face of the coil 169•6 from both sides, and bonded together in the part 169•7 by screwing or the like as in the case of the coils 169•5 and 169•6.

FIG. 170 shows a cross section orthogonal to the optical axis (z axis) of an ExB separator 170•1 of this embodiment. The ExB separator 170•1 of FIG. 170 is different from the ExB separator of the embodiment shown in FIG. 169 in that six electrostatic deflection electrodes 170•1 are provided. The electrostatic deflection electrodes 170•1 are each supplied with a voltage k·cos $θ_i$ (k is constant) proportional to cos $θ_i$ where an angle between a line extending from the center of each electrode to the optical axis (z axis) and the direction of the electric field (x axis direction) is $θ_i$ (i=0, 1, 2, 3, 4, 5). The $θ_i$ is an arbitrary angle.

In the embodiment shown in FIG. 170, only the electric field in the x axis direction can be produced, and thus the coils 169•5 and 169•6 for generating the magnetic field in the y axis direction are provided to correct the orthogonality. According to this embodiment, the area of uniform electric field intensity can be further increased compared with the embodiment shown in FIG. 169.

In the E×B separators of the embodiments shown in FIGS. 169 and 170, the coil for generating a magnetic field is formed as a saddle type, but a toroidal-type coil may be used.

In the E×B separator 169·1 of FIG. 169, since parallel flat plate-type electrodes in which the size along the direction perpendicular to the optical axis is larger than the distance between electrodes are used as a pair of electrodes of the electrostatic deflector to generate an electric field, the area in which a uniform-intensity and parallel electric field is generated around the optical axis is increased.

Further, in the E×B separators of FIGS. 169 and 170, since saddle-type coils are used for the electromagnetic deflector, and the angle between the optical axis and the coil is set to $2\pi/3$ on one side, no $3\theta$ is generated and accordingly, the area in which a uniform-intensity and parallel electric field is generated around the optical axis is increased. Furthermore, since the magnetic field is generated with the electromagnetic coil, a deflection current can be superimposed on the coil and accordingly, a scanning function can be provided.

The E×B separators of FIGS. 169 and 170 are each constituted as a combination of an electrostatic deflector and an electromagnetic deflector, and therefore by calculating the aberration of the electrostatic deflector and the lens system, calculating the aberration of the electromagnetic deflector and the lens system aside therefrom, and summing the aberrations, the aberration of the optical system can be obtained.

3-6) Embodiment of Production Line

FIG. 171 shows an example of a production line using the apparatus of the present invention. Information such as the lot number of a wafer to be inspected by an inspection apparatus 171·1 and the history of production apparatus involved in production can be read from a memory provided in an SMIF or FOUP 171·2, or the lot number can be recognized by reading ID number of the SMIF, FOUP or wafer cassette. During transportation of the wafer, the amount of water is controlled to prevent oxidization and the like of metal wiring.

The defect inspection apparatus 171·1 can be connected a network system of the production line, and information such as the lot number of the wafer as an inspection subject and the results of inspection can be sent to a production line control computer 171·4 controlling the production line, each production apparatus 171·5 and other inspection apparatus via the network system 171·3. The production apparatuses include lithography-related apparatuses, for example, a light-exposure apparatus, a coater, a cure apparatus and a developer, or film formation apparatuses such as an etching apparatus, a spattering apparatus and a CVD apparatus, a CMP apparatus, various kinds of measurement apparatuses, other inspection apparatuses and a review apparatus.

3-7) Embodiment Using Other Electrons

The essential object of the present invention is to irradiate an electron beam to a sample such as a substrate provided with a wiring pattern having a line width of 100 nm or smaller, and detect electrons obtaining information of the surface of the substrate, acquiring an image of the surface of the substrate from the detected electrons to inspect the sample surface. Particularly, the present invention proposes an inspection process and apparatus in which when the electron beam is applied to the sample, an electron beam having an area including a certain imaging area is applied, electrons emitted from the imaging area on the substrate are made to form an image using a CCD, CCD-TDI or the like to acquire an image of the imaging area, and the obtained image is inspected with cell inspection and die comparison inspection combined as appropriate depending on the pattern of dies, whereby throughput much higher compared to the SEM process is achieved. That is, the inspection process and inspection apparatus using an electron beam in the present invention solves both problems such that in an optical inspection apparatus, defects of a pattern having a line width of 100 nm or smaller cannot be sufficiently inspected due to a low resolution, and that in a SEM inspection apparatus, inspection requires too much time to meet the requirement of high throughput, thus making it possible to inspect a wiring pattern having a line width of 100 nm or smaller in a sufficient resolution and high throughput.

In inspection of the sample, it is desirable in terms of the resolution that the electron beam is made to impinge upon the substrate, and electrons emitted from the substrate are detected to obtain an image of the surface of the substrate. Thus, the examples of the present invention have been described mainly focusing on secondary electrons, reflection electrons and back-scattered electrons emitted from the substrate. However, electrons to be detected may be any electrons obtaining information of the surface of the substrate, and may be, for example, mirror electrons (reflection electrons in a brad sense) reflected near the substrate instead of directly impinging upon the substrate by forming an inverse electric field near the substrate, transmission electrons passing through the substrate, or the like. In particular, use of mirror electrons has an advantage that the effect of charge-up is very small because electrons do not directly impinge upon the sample.

In the case where mirror electrons are used, a negative potential lower than an accelerating voltage is applied to the sample to form an inverse electric field near the sample. This negative potential is preferably set to a value such that most electron beams are forced back near the surface of the substrate. Specifically, it may be set at a potential that is 0.5 to 1.0 V or more lower than the acceleration voltage. For example, in the present invention, the voltage to be applied to the sample is preferably set to −4.000 kV to −4.050 kV if the accelerating voltage is −4 kV. It is more preferably set to −4.0005 kV to −4.020 kV, further more preferably −4.0005 kV to −4.010 kV.

Furthermore, in the case where transmission electrons are used, the voltage to be applied to the sample is set to 0 to −4 kV, preferably 0 to −3.9 kV, more preferably 0 to −3.5 kV if the accelerating voltage is set to −4 kV.

In addition, an X ray may be used instead of the electron beam. The secondary system and die comparison can be sufficiently applied.

Irrespective of which of mirror electrons or transmission electrons are used, the electron gun, the primary optical system, the deflector for separating the primary electron beam from the detection electron beam, the detector using the CCD or CCD-TDI, the image processing apparatus, the calculation device for die comparison, and the like already described are used. An electron beam having a certain area such as an ellipse is used, but a finely focused electron beam for use in a SEM type may be used as a matter of course. One electron beam or two or more electron beams may be used as a matter of course. For the deflector for separating the primary electron beam from the detection electron beam, a Wien filter forming both electric and magnetic fields may be used, or a deflector forming only the magnetic field may be used. For the detector, a CCD or CCD-TDI capable of forming an imaging area on the detector to carry out speedy inspection is used, but if a SEM-type electron gun is used, a semiconductor detector or the like corresponding to such a type of electron gun is used as a matter of course. If an image of the surface of the substrate is acquired, and comparison inspection of dies is carried out, cell inspection to be applied to a cyclic pattern and comparison inspection of dies to be applied a random pattern are used as appropriated depending on the pattern of dies. Of course, only comparison inspection of dies may be carried out and in the case of comparison inspection of dies, a dies on the same substrate may be compared, or dies on different substrates may be compared, or the die may be compared with CAD data. Suitable of them may be arbitrarily used. Further, the substrate is aligned before inspection. A positional deviation of the substrate is measured, and a deviation in rotation angle is corrected. At this time, a focus map may be created to carry out inspection while correcting the position of the substrate on the plane and a deviation in focus in consideration of the map during inspection.

Furthermore, when the apparatus of the present invention is used in production steps, it is desirable that information of the wafer as an inspection object is acquired from a computer connected to the network system for controlling the production system, and inspection results are sent to incorporate the results in production conditions of apparatuses in the production line.

3-8) Embodiment Using Secondary Electrons and Reflection Electrons

This embodiment relates to a projection type electron beam apparatus of high resolution and high throughput capable of irradiating an inspection object with a plane beam and switching between secondary electrons and reflection electrons depending on the inspection object. In this way, the type of irradiating an electron beam not to one spot on a sample but to a field of view extending at least two-dimensionally to form an image of the field of view is called a "projection electron microscope type". This projection-type electron beam apparatus is a high-resolution and high-throughput apparatus capable of avoiding a space charge effect, having a high signal-to-noise ratio and having an enhanced image processing by parallel processing.

The implementation of the projection-type electron beam apparatus of this embodiment as a defect inspection apparatus will be described in detail below with reference to FIGS. 172 to 181. Furthermore, in these figures, like reference numerals or reference symbols denote identical or corresponding components.

In FIGS. 172(A) and (B), an electron gun EG of a defect inspection apparatus EBI has a thermal electron beam emitting $LaB_6$ cathode 1 capable of operating at a large current, and primary electrons emitted in a first direction from the electron gun EG pass through a primary optical system including several stages of quadrupole lenses 2 to have the beam shape adjusted, and then pass through a Wien filter 172•1. By the Wien filter 172•1, the traveling direction of the primary electrons is changed to a second direction so that they enter a wafer W as an inspection object. The primary electrons exiting from the Wien filter 172•1 and traveling in the second direction has the beam diameter limited by an NA aperture plate 172•2, pass through an objective lens 172•3, and are applied to the wafer W. The objective lens 172•3 is a high-accuracy electrostatic lens.

In this way, in the primary optical system, an electron gun of high luminance made of $LaB_6$ is used as the electron gun EG, thus making it possible to obtain a primary beam having low energy, a large current and a large area compared to the conventional scanning defect inspection apparatus.

Since the wafer W is irradiated with a plane beam with the cross-section formed into a rectangular shape of, for example, 200 μm×50 μm by the primary optical system, a small area on the wafer W having a predetermined area can be irradiated. To irradiate the wafer W with this plane beam, the wafer W is placed on a high-accuracy XY stage (not shown) coping with a 300 mm wafer, for example, and the XY stage is two-dimensionally moved with the plane beam fixed. Furthermore, because it is not necessary to focus the primary electrons on a beam spot, the plane beam has a low current density, and thus the damage of the wafer W is reduced. For example, the current density of the beam spot is $10^3$ A/cm$^2$ in the conventional beam scanning defect inspection apparatus, while the current density of the plane beam is only 0.1 A/cm$^2$ to 0.01 A/cm$^2$ in the defect inspection apparatus EBI shown in the figure. On the other hand, the dose is $1\times10^{-5}$ C/cm$^2$ in the conventional beam scanning type, while the dose is $1\times10^{-4}$ C/cm$^2$ to $3\times10^{-5}$ C/cm$^2$ in this type, and this type of apparatus has a higher sensitivity.

Secondary electrons and reflection electrons are emitted from an area of the wafer irradiated with the plane beam-shaped primary electrons. Reflection electrodes will be described later and for explanation of detection of secondary electrons, first, the secondary electrons emitted from the wafer W, destined to travel in a direction opposite to the second direction, are enlarged by the objective lens 172•3, pass through the NA aperture plate 172•2 and the Wien filter 172•1, are enlarged again by an intermediate lens 172•4, further enlarged by a projection lens 172•5, and enters a secondary electron detection system D. In a secondary optical system guiding secondary electrons, the objective lens 172•3, the intermediate lens 172•4 and the projection lens 172•5 are all high-accuracy lenses, and the secondary optical system is configured to have a variable magnification. Because the primary electrons are made to enter the wafer W at almost a right angle, and the secondary electrons are taken out at almost a right angle, shading caused by irregularities on the surface of the wafer does not occur.

The secondary electron detection system D receiving secondary electrons from the projection lens 172•5 comprises a micro-channel plate 172•6 multiplying entering secondary electrons, a fluorescent screen 192•7 converting the electrons exiting the micro-channel plate 172•6 into light, and a sensor unit 172•8 converting the light emitting from the fluorescent screen 172•6 into an electric signal. The sensor unit 172•8 has a high-sensitivity line sensor 172•9 constituted by a large number of two-dimensionally arranged solid imaging devices, and fluorescence emitted from the fluorescent screen 172•7 is converted into an electric signal by the line sensor 172•9, sent to an image processing unit 172•10, and processed in parallel, in multiple stages and at a high speed.

While the wafer W is moved to irradiate and scan individual areas on the wafer W with a plane beam one after another, the image processing unit 172•10 accumulates data about XY coordinates and images of areas including defects, and creates an inspection result file including coordinates and images of all areas of an inspection object including defects for one wafer. In this way, inspection results can be collectively managed. When this inspection result file is read out, a defect distribution and a defect detail list of the wafer is displayed on a display of the image processing unit 172•10.

In fact, of various components of the defect inspection apparatus EBI, the sensor unit 172•8 is placed in the atmosphere, but other components are placed in a column kept under vacuum and therefore, in this embodiment, a light guide is provided on an appropriate wall surface of the column, so that light exiting from the fluorescent screen 172•7 is taken out into the atmosphere through the light guide, and passed to the line sensor 172•9.

FIG. 173 shows a specific example of the configuration of the secondary electron detection system D in the defect inspection apparatus EBI of FIG. 172. A secondary electron image or reflection electron image 173•1 is formed on the entrance surface of the micro-channel plate 172•6 by the projection lens 172•5. The micro-channel plate 172•6 has, for example, a resolution of 16 μm, a gain of $10^3$ to $10^4$ and 2100×520, and multiplies electrons according to the formed electron image 173•1 to irradiate the fluorescent screen 172•7. Consequently, fluorescence is emitted from an area of the fluorescent screen 172•7 irradiated with electrons, and the emitted fluorescence is discharged into the atmosphere through the light guide 173•2 of low deformation (e.g. 0.4%). The emitted fluorescence is made to enter the line sensor 172•9 through an optical relay lens 173•3. For example, the optical relay lens 173•3 has a magnification of ½, a transmittance of 2.3% and a deformation of 0.4%, and the line sensor 172•9 has a pixel number of 2048×512. The optical relay lens 173•3 forms an optical image 173•4 matching the electron image 173•1 on the entrance surface of the line sensor 172•9. An FOP (fiber optic plate) may be used instead of the light guide 173•2 and the relay lens 173•3 and in this case, the magnification is 1×.

The defect inspection apparatus EBI shown in FIG. 172 can be operated in one of a positive charge mode and a negative charge mode, in the case of secondary electrons, by adjusting an accelerating voltage of the electron gun EG and a wafer electrode applied to the wafer W and using the electron detection system D. Further, by adjusting the accelerating voltage of the electron gun EG, the wafer voltage applied to the wafer W and objective lens conditions, the defect inspection apparatus EBI can be operated in a reflection electron imaging mode to detect reflection electrodes of high energy emitted from the wafer W with irradiation of primary electrons. Since reflection electrodes have energy equal to energy of the primary electrons entering a sample such as the wafer W, and thus have energy higher than that of secondary electrons, the reflection electrodes are hard to be influenced by a potential such as charge of the surface of the sample. For the electron detection system, an electron impact detector such as an electron impact CCD or electron impact TDI outputting an electric signal matching the intensity of secondary electrons or reflection electrons may be used. In this case, the micro-channel plate 172•6, the fluorescent screen 172•7 and the relay lens 173•3 (or FOP) are not used, but the electron impact detector is placed at an image formation position and used. This configuration enables the defect inspection apparatus EBI to operate in a mode suitable for an inspection object. For example, the negative charge mode or reflection electron imaging mode may be used for detecting defects of metal wiring, defects of gate contact (GC) wiring or defects of a resist pattern, and the reflection electron imaging mode may be used to detect poor conduction of a via, or residues on the bottom of the via after etching.

FIG. 174(A) illustrates requirements for operating the defect inspection apparatus EBI of FIG. 1 in the three modes described above. The accelerating voltage of the electron gun EG is $V_A$, the wafer voltage applied to the wafer W is $V_W$, the irradiation energy of primary electrons when the wafer W is irradiated is $E_{IN}$, and the signal energy of secondary electrons entering the electron detection system D is $E_{OUT}$. The electron gun EG is configured so that the accelerating voltage $V_A$ is variable, and the variable wafer voltage $V_W$ is applied to the wafer W from an appropriate power supply (not shown). Then, if the accelerating voltage $V_A$ and the wafer voltage $V_W$ are adjusted, and the electron detection system D is used, the defect inspection apparatus EBI can operate in the positive charge mode in the range of the secondary electron yield greater than 1, and can operate in the negative mode in the range of the secondary electron yield smaller than 1 as shown in FIG. 174(B). Furthermore, by adjusting the accelerating voltage $V_A$, the wafer voltage $V_W$ and the objective lens conditions, the defect inspection apparatus EBI can operate in the reflection electron imaging mode using a difference in energy between secondary electrons and reflection electrons. Furthermore, in FIG. 174(B), in fact, the value of electron irradiation energy $E_{IN}$ at the boundary between the positive charge area and the negative charge area varies depending on the sample.

One example of values of $V_A$, $V_W$, $E_{IN}$ and $E_{OUT}$ for operating the defect inspection apparatus EBI in the reflection electron imaging mode, the negative charge mode and the positive charge mode is described below.

Values in reflection electron imaging mode:

$V_A$=−4.0 kV;

$V_W$=−2.5 kV;

$E_{IN}$=1.5 keV; and $E_{OUT}$=4 keV.

Values in negative charge mode:

$V_A$=−7.0 kV;

$V_W$=−4.0 kV;

$E_{IN}$=3.0 keV; and $E_{OUT}$=4 keV+α(α=energy width of secondary electrons).

Values in positive charge mode:

$V_A$=−4.5 kV;

$V_W$=−4.0 kV;

$E_{IN}$=0.5 keV; and $E_{OUT}$=4 keV+α(α=energy width of secondary electrons).

In fact, the detection amounts of secondary electrons and reflection electrons vary depending on the surface composition of the inspection subject area on the wafer W, the pattern shape and the surface potential. That is, the yield of secondary electrons and the amount of reflection electrons vary depending on the surface composition of the inspection subject on the wafer W, and the yield of secondary electrons and the amount of reflection electrons are larger at pointed sites and corners than in plane areas. Furthermore, if the surface potential of the inspection subject on the wafer W is high, the amount of emitted secondary electrons decreases. In this way, the intensities of electric signals obtained from secondary electrons and reflection electrons detected by the detection system D vary depending on the material, the pattern shape and the surface potential.

FIG. 175 shows the shape of the cross-section of each electrode of the electrostatic lens for use in the electro-optical system of the defect inspection apparatus EBI shown in FIG. 172. As shown in FIG. 175, the distance between the wafer W and the micro-channel plate 172•6 is, for example, 800 mm, and the objective lens 172•3, the intermediate lens 172•4 and the projection lens 172•5 are electrostatic lenses each having a plurality of electrodes having specific shapes. Now, if a voltage of −4 kV is applied to the wafer W, a voltage of +20 kV is applied to an electrode of the objective lens 172•3, which is closest to the wafer W, and a voltage of −1476 V is applied to other electrodes. At the same time, a voltage of −2450 V is applied to the intermediate lens 172•4, and a voltage of −4120 V is applied to the projection lens 172•5. As a result, the magnification obtained with the secondary optical system is 2.4 with the objective lens 172•5, 2.8 with the intermediate lens 172•4, and 37 with the projection lens 172•5, resulting in total 260. Furthermore, in FIG. 175, reference numerals 175•1 and 175•2 denote field apertures for limiting the beam diameter, and reference numeral 175•3 denotes a deflector.

FIG. 176(A) schematically shows the configuration of a multi-beam/multi-pixel-type defect inspection apparatus EBI that is another embodiment of a projection type electron beam apparatus. An electron gun EGm in this defect inspection apparatus is a multi-beam-type electron gun having a $LaB_6$ cathode and capable of emitting a plurality of primary electron beams 176•1. The primary electron beams 176•1 have beam diameters adjusted by an aperture plate 176•2 provided with pores at positions corresponding to the primary electron beams, then have beam positions adjusted by two-stage axisymmetric lenses 176•3 and 176•4, travel in a first direction, pass through the Wien filter 172•1, change the traveling direction from the first direction to a second direction, and travel so as to enter the wafer W. Thereafter, the primary electron beams 176•1 pass through the NA aperture plate 172•2 and the objective lens 172•3, and are applied to predetermined areas of the wafer W.

Secondary electrodes and reflection electrodes 176•5 emitted from the wafer W with irradiation of the primary electron beams 176•1 travel in a direction opposite to the second direction to pass through the objective lens 172•3, the NA aperture plate 172•2, the Wien filter 172•1, the intermediate lens 172•4 and the projection lens 172•5, enters the detection system D, and is converted into an electric signal by the sensor unit 172•8 in the same manner as described with FIG. 172(A).

A deflector 176•6 for deflecting the primary electron beams 176•1 is placed between the axisymmetric lens 176•4 situated on the downstream side when seen from the electron gun EGm and the Wien filter 172•1. To scan a certain area R on the wafer W with the primary electron beams 176•1, the primary electron beams 176•1 are deflected in the x axis direction perpendicular to the Y axis at a time by the deflector 176•6 while the wafer W is moved in the Y axis as shown in FIG. 176(B). In this way, the area R is raster-scanned with the primary electron beams 176•1.

FIG. 177(A) shows the outlined configuration of a multi-beam/mono-pixel-type defect inspection apparatus EBI that is still another embodiment of a projection type electron beam apparatus. In this figure, the electron gun EGm can emit a plurality of primary electron beams 176•1, and the emitted primary electron beams 176•1 are guided by the aperture plate 176•2, the axisymmetric lenses 176•3 and 176•4, the deflector 176•6, the Wien filter 172•1 and the objective lens 172•3 so as to travel in the first direction, and are applied to the wafer W in the same manner as described with FIG. 176(A).

Secondary electrons or reflection electrons 176•5 emitted from the wafer W with irradiation of the primary electron beams 176•1 pass through the objective lens 172•3, then have the traveling direction changed by a predetermined angle by the Wien filter 172•1, then pass through the intermediate lens 172•4 and the projection lens 172•5, and enter a multi-detection system D'. The multi-detection system D' in this figure is a secondary electron detection system, and comprises a multi-aperture plate 177•1 provided with pores identical in number to n pores formed in the aperture electrode 176•2, n detectors 177•2 provided in correspondence with the pores of the multi-aperture plate 177•1 so that secondary electrons passing through the n pores of the aperture plate 177•1 are captured and converted into electric signals indicating the intensity of the secondary electrons, n amplifiers 177•3 amplifying the electric signals outputted from the detectors 177•2, and an image processing unit 172•10' converting into digital signals the electric signals amplified by the amplifiers 177•3, and performing storage, display, comparison and the like of image signals of an scan subject area R on the wafer W.

In the defect inspection apparatus EBI shown in FIG. 177(A), the area is scanned with the primary electron beams 176•1 in a manner as shown in FIG. 177(B). That is, as shown in FIG. 177(B), the area R is divided in the Y axis direction by the number of primary electron beams 176•1 into sub-areas, for example, r1, r2, r3 and r4, and each of the primary electron beams 176•1 is assigned to each of the sub-areas r1 to r4. Then, the primary electron beams 176•1 are deflected in the X axis direction at a time by the deflector 176•6 while the wafer W is moved in the Y axis direction to scan the sub-areas r1 to r4 with the primary electron beams 176•1. In this way, the area R is scanned with the primary electron beams 176•1.

Furthermore, the primary optical system of the multi-beam is not limited to that of FIG. 176, but it is only essential that the beam should be a multi-beam at the time when it is applied to the sample and, for example, a single electron gun may be used.

In the defect inspection apparatus EBI described above, a mechanism capable of placing the wafer W on a stage and positioning the stage accurately in a vacuum chamber is preferably used. To accurately position the stage, for example, a structure in which the stage is supported by a static-pressure bearing in a non-contact manner is employed. In this case, in order that high-pressure gas supplied from the static-pressure bearing is not discharged into the vacuum chamber, it is desirable that a differential exhaust mechanism discharging high-pressure gas is formed in the area of the static-pressure bearing to maintain the degree of vacuum of the vacuum chamber.

FIG. 178 shows one example of the configuration of a mechanism for accurately positioning a stage holding the wafer W in a vacuum chamber, and a circulation piping system of inert gas. In FIG. 178, the leading end portion of a column 178•1 irradiating primary electrons to the wafer W, i.e. a primary electron irradiating portion 178•2 is attached to a housing 178•3 sectioning a vacuum chamber C. The wafer W placed on a movable table in the X direction (lateral direction in FIG. 178) of a high-accuracy XY stage 178•4 is placed just below the column 178•1. By moving the XY stage 178•4 in X and Y directions (direction perpendicular to sheet face in FIG. 178), primary electrons can be correctly irradiated with respect to any position on the surface of the wafer W.

A seat 178•5 of the XY stage 178•4 is fixed on the bottom wall of the housing 178•3, and a Y table 178•6 moving in the Y direction is placed on the seat 178•5. Raised portions are formed on both side faces of the Y table 178•6 (left and right side faces in FIG. 178), and the raised portions fit into a pair of recessed grooves formed on a pair of Y direction guides 178•7a and 178•7b provided on the seat 178•5. The recessed grooves extend in the Y direction over almost the full lengths of the Y direction guides 178•7a and 178•7b. Static-pressure bearings (not shown) each having a well known structure are provided on the upper and lower faces and the side faces of the raised portions protruding into the recessed grooves. By blowing high-pressure and high-purity inert gas (N2 gas, Ar gas, etc.) via the static-pressure bearings, the Y table 178•6 is supported on the Y direction guides 178•7a and 178•7b in a non-contact manner, and can make a reciprocating motion. Furthermore, a linear motor 178•8 having a well known structure is placed between the seat 178•5 and the Y table 178•6 for driving the Y table 178•6 in the Y direction.

On the upper side of the Y table 178•6, an X table 178•9 is placed in such a manner that it can move in the X direction. A pair of X direction guides 3178•10a and 178•10b (only X direction guide 178•10a is shown in FIG. 178) identical in structure to the Y direction guides 178•7a and 178•7b for the Y table 178•6 are provided in such a manner as to surround the X table 178•9. Recessed grooves are formed on the sides of the X direction guides facing the X table 178•9, and raised portions protruding into the grooves are formed on the side parts of the X table 178•9 facing the X direction guides. These recessed grooves extend over the full lengths of the X direction guides. Static-pressure bearings (not shown) similar to the static-pressure bearings for supporting the Y table 178•6 in a non-contact manner are provided on the upper and lower faces and side faces of the raised portions of the X direction table 178•9 protruding into the recessed grooves. By supplying high-pressure and high-purity inert gas to the static-pressure bearings to blow the inert gas from the static-pressure bearings to the guide surfaces of the X direction guides 178•10a and 178•10b, the X table 178•9 is accurately supported on the X direction guides 178•10a and 178•10b in a non-contact manner. A linear motor 178•11 having a well known structure is placed on the Y table 178•6 for driving the X table 178•9 in the X direction.

Since a stage mechanism with static-pressure bearings that is used in the atmosphere can be directly used as the XY stage 178•4, an XY stage equivalent in accuracy in to an high-accuracy stage for the atmosphere for use in a light-exposure apparatus or the like can be achieved as an XY stage for defect inspection apparatus at almost the same cost and in almost the same size. Furthermore, the wafer W is not placed directly on the X table 178•9, but is usually placed on a sample table having a function of detachably holding the wafer W and changing the position by a small amount with respect to the XY stage 178•4.

The inert gas is supplied to the static-pressure bearings through flexible tubes 178•12 and 178•13 and a gas channel (not shown) formed in the XY stage 178•4. The high-pressure inert gas supplied to the static-pressure bearings are blown into gaps of several microns and several tens of microns formed between the static-pressure bearings and the opposite guide surfaces of the Y direction guides 178•7a and 1878•7b and the X direction guides 178•10a and 178•10b to correctly position the Y table 178•6 and the X table 178•9 in the X direction, Y direction and Z direction (vertical direction in FIG. 178) with respect to the guide surfaces. Gas molecules of the inert gas blown from the static-pressure bearings diffuse into the vacuum chamber C, and are discharged through exhaust ports 178•14, 178•15a and 178•15b and vacuum tubes 178•16 and 178•17 by a dry vacuum pump 178•18. The seat 178•5 is cut through so that the suction ports of the exhaust ports 178•15a and 178•15b are provided on the upper face of the seat 178•5. In this way, the suction ports are situated near the position at which the high-pressure is discharged from the XY stage 178•4, thus preventing the pressure within the vacuum chamber C from being increased by the high-pressure gas blown from the static-pressure bearings.

The exhaust port of the dry vacuum pump 178•18 is connected to a compressor 178•20 through a tube 178•19, and the exhaust port of the compressor 178•20 is connected to the flexible tubes 178•12 and 178•13 through tubes 178•21, 178•22, 178•23 and regulators 178•24 and 178•25. Accordingly, inert gas discharged from the dry vacuum pump 178•18 is compressed again by the compressor 178•20, adjusted to have an appropriate pressure by the regulators 178•24 and 178•25, then supplied again to the static-pressure bearings of the XY table. In this way, high-purity inert gas is circulated and reused, thus making it possible to save inert gas, and no inert gas is emitted from the defect inspection apparatus EBI, thus making it possible to prevent an accident such as suffocation with inert gas. Furthermore, removal means 178•26 such as a cold trap or filter is preferably provided at some midpoint in the tube 178•21 on the discharge side of the compressor 178•20, so that impurities such as water and oil entering the circulating gas are trapped and prevented from being supplied to the static-pressure bearings.

A differential exhaust mechanism 178•27 is provided around the leading end portion of the column 178•1, i.e. the primary electron irradiating portion 178•2. This is intended to keep the pressure of a primary electron beam irradiation space 178•28 at a sufficiently low level even if the pressure within the vacuum pump is high. A ring member 178•29 of the differential exhaust mechanism 178•27 provided around the primary electron irradiating portion 178•2 is positioned with respect to the housing 178•3 so that a very small gap of several microns to several tens of microns is formed between the lower face of the ring member (face opposite to the wafer W) and the wafer W.

A ring groove 178•30 is formed in the lower face of the ring member 178•29, and the ring groove 178•30 is connected to an exhaust port 178•31. The exhaust port 178•31 is connected to a turbo-molecular pump 178•33 being an ultra-high vacuum pump through a vacuum tube 178•32. Furthermore, an exhaust port 178•34 is provided at an appropriate location in the column 178•1, and the air exhaust port 178•34 is connected to a turbo-molecular pump 178•36 through a vacuum tube 178•35. The turbo-molecular pumps 178•33 and 178•36 are connected to the dry vacuum pump 178•18 by vacuum tubes 178•37 and 178•38. Thus, gas molecules of inert gas entering the differential exhaust mechanism 178•27 and the charged electron beam irradiation space 178•26 are discharged through the ring groove 178•30, the exhaust port 178•31 and the vacuum tube 178•32 by the turbo-molecular pump 178•33, and therefore gas molecules entering the space 178•28 surrounded by the ring member 178•29 from the vacuum chamber C. In this way, the pressure within the primary electron irradiation space 178•28 can be kept at a low level, thus making it possible to apply primary electrons without any problems. Furthermore, gas molecules suctioned from the leading end portion of the column 178•1 are discharged through the air exhaust port 178•34 and the vacuum tube 178•35 by the turbo-molecular pump 178•36. The gas molecules discharged from the turbo-molecular pumps 178•33 and 178•36 are collected by the dry vacuum pump 178•18 and supplied to the compressor 178•20.

Furthermore, the ring groove 178•30 may have a double or triple structure depending on the pressure within the vacuum chamber C or the pressure within the primary electron irradiation space 178•28. Furthermore, in the inspection apparatus shown in FIG. 178, one dry vacuum pump is used for the roughing vacuum pump of the turbo-molecular pump and the pump for evacuating the vacuum chamber, but the chamber may be evacuated with dry vacuum pumps of different lines depending on the flow rate of high-pressure gas supplied to the static-pressure bearing of the XY stage, the volume and inner surface area of the vacuum chamber, the inner diameter and length of the vacuum tube and the like.

Dry nitrogen is generally used as high-pressure gas supplied to the static-pressure bearing of the XY stage 178•4. If possible, however, inert gas of higher purity is preferably used. This is because if impurities such as water and oil are contained in the gas, molecules of theses impurities are deposited on the inner surface of the housing 178•3 sectioning the vacuum chamber C and the surfaces of the stage components to reduce the degree of vacuum, or deposited on the surface of the wafer W to reduce the degree of vacuum of the primary electron irradiation space 178•28. Furthermore, since it is necessary to prevent the situation in which the gas contains water and oil where possible, the turbo-molecular pumps 178•33 and 178•36, the dry vacuum pump 178•18 and the compressor 178•20 are each required to have a structure such that no water and oil enters the gas channel.

Furthermore, as shown in FIG. 178, a high-purity inert gas supply system is connected to the circulation piping system of inert gas, and plays a role to fill high-purity inert gas in the vacuum chamber C and all circulation systems including the vacuum tubes 178•16, 178•15, 178•32, 178•35 and 178•37 and the pressure tubes 178•19, 178•21, 17822, 178•23 and 178•39 when circulation of gas is started, and a role to supply an amount of gas equivalent to a shortfall in case where a flow rate of circulating gas drops for some cause. Furthermore, by imparting to the dry vacuum pump 178•18 a function of compression to an atmospheric pressure or higher, the dry vacuum pump 178•18 can be made to serve also as the compressor 178•20. Further, instead of the turbo-molecular pump 178•36, a pump such as an ion pump or getter pump can be used as an ultra-high vacuum pump for use in evacuation of the column 178•1. However, if such an entrapment pump is used, a circulation piping system cannot be built. Instead of the dry vacuum pump 178•18, a different type of dry pump such as diaphragm-type dry pump may be used.

FIG. 179 shows examples of values of the sizes of the ring member 178•29 of the differential exhaust mechanism 178•27 and the ring groove 178•30 formed thereon. Here, double ring grooves isolated from each other in a radial direction are provided. The flow rate supplied to the static-pressure bearing is usually about 20 L/min (equivalent in atmospheric pressure). Provided that the vacuum chamber C is evacuated with a dry pump having a pumping speed of 20000 L/min through a vacuum tube having an inner diameter of 50 mm and a length of 2 m, the pressure within the vacuum chamber is about 160 Pa (about 1.2 Torr). At this time, if the sizes of the differential exhaust mechanism 178•27, the ring member 178•29, the ring groove 178•30 and the like are set as shown in FIG. 179, the pressure within a primary electron irradiation space 56 can be kept at $10^{-4}$ Pa ($10^{-6}$ Torr).

FIG. 180 schematically shows the overall configuration of an inspection system having the defect inspection apparatus EBI described with FIGS. 172 to 179. As shown in the figure, components on the route ranging from the primary optical system of the defect inspection apparatus EBI through the wafer W and the secondary optical system to the detection system D are housed in the column 178•1 exhibiting a magnetic shield function, and the column 178•1 is placed on the upper face of a vibration removal table 180•1 supported by an active vibration removal unit so as to prevent transfer of vibrations from outside. The inside of the column 178•1 is kept under vacuum by a vacuum pumping system 180•2. A necessary voltage is supplied from a control power supply 180•3 through a high-pressure cable 180•4 to components of the primary optical system and the secondary optical system in the column 178•1.

An alignment mechanism 180•5 comprising an optical microscope and auto-focusing means is provided at an appropriate location in the column 178•1 to place components constituting the primary optical system and the secondary optical system on predetermined optical axes and make an adjustment so that primary electrons emitted from the electron gun automatically come into a focus on the wafer W.

The XY stage 178•4 comprising a chuck (not shown) for placing and fixing the wafer W is provided on the upper face of the vibration table 180•1, and the position of the XY stage 178•4 during a scan period is detected at predetermined intervals by a laser interferometer. Further, a loader 180•6 for accumulating a plurality of wafers W as inspected objects, and a transportation robot 180•7 for holding the wafer in the loader 180•6 and placing the wafer W on the XY stage 178•4 in the column 178•1, and taking the wafer W from the column 178•1 after inspection are placed on the upper face of the vibration removal table 180•1.

The operation of the overall system is controlled by a main-controller 180•8 in which necessary programs are installed. The main controller 180•8 comprises a display 180•9, and is connected to the detection system D through a cable 180•10. Consequently, the main controller 180•8 can receive a digital image signal from the detection system D through the cable 180•10 to process the signal with the image processing unit 172•10, and display the contents of an inspection result file obtained by the scanning of the wafer W, a defect distribution of the wafer W and the like on the display 180•9. Furthermore, the main controller 180•8 displays an operation state of the system on the display 180•9 to control the operation of the overall system.

Furthermore, in the above description, the stage holding the wafer W is movable in the XY plane, but in addition thereto, the stage may be rotatable about any axis perpendicular to the XY plane or extending passing the XY plane. Furthermore, the inspection object is not limited to a wafer, but any sample capable of being inspected with an electron beam, such as a mask, is included as an inspected object. Further, by mutually connecting the projection-type electron beam apparatus in this embodiment, a beam scanning defect review apparatus, a server and the main controller through a LAN, a distributed defect inspection network can be built.

As apparent from the above description, this embodiment exhibits the following remarkable effects.

(1) Because the sample is irradiated with a plane beam, throughput can be improved to the extent that for example, defect inspection time per wafer can be reduced by a factor of 7 compared to the conventional beam scanning inspection apparatus.

(2) A space charge effect can be avoided because it is not necessary to focus primary electrons on a beam spot, and the sample is not significantly damaged because the sample is irradiated in a low current density.

(3) Because the sample is irradiated with a plane beam, inspection can be performed for a size smaller than one pixel.
(4) By selecting an accelerating voltage of the electron gun and a voltage applied to the sample, and adjusting an objective lens, the apparatus can be operated in any one of a positive charge mode, a negative charge mode and a reflection electron imaging mode, thus making it possible to perform appropriate inspection according to the inspection site in the sample.
(5) By using an electrostatic lens, the primary optical system and/or the secondary optical system can be downsized and improved in accuracy.

What is claimed is:

1. An electron beam apparatus comprising:
   an electron gun for irradiating a sample with an electron beam;
   an integration-type line image (TDI) sensor for detecting and imaging electrons having image information of a surface of the sample generated by the beam irradiation of the sample and integrating the image of the surface of the sample to increase the contrast of the image;
   an image processing system for synthesizing as an image said electrons made to form the magnified image on said TDI sensor; and
   means for sequentially scanning a belt-like area on said sample, in which after said belt-like area scanned, said sample is moved stepwise to scan next said belt-like area, so that an overlapping width of said belt-like areas adjacent to each other can be adjusted.

2. The electron beam apparatus according to claim 1, wherein said electrons are at least one of secondary electrons, reflection electrons and back-scattered electrons, generated from said sample.

3. The electron beam apparatus according to claim 1, wherein said electrons are mirror electrons reflected near the surface of said sample.

4. The electron beam apparatus according to claim 1, wherein after scanning in one direction, said scanning means can scan in a direction opposite to the direction.

5. The electron beam apparatus according to claim 1, wherein the scanning speed of said scanning means is an integral multiple of a pixel size.

6. The electron beam apparatus according to claim 1, wherein the scanning speed of said scanning means is a product of the pixel size and the line frequency of a TDI.

7. The electron beam apparatus according to claim 6, wherein scanning speed of said scanning means can be changed according to the pixel size.

8. An electron beam apparatus comprising:
   an electron gun for irradiating a sample with an electron beam;
   a stage for holding and moving the sample in a direction;
   an electro-optical system for magnifying and projecting electrons having information of the surface of said sample with irradiation of said electron beam to said sample to form a magnified image on a detector;
   wherein said detector is a time delay integration sensor;
   an image processing system for synthesizing as an image said electrons made to form the magnified image on said detector; and
   a deflector for separating said electron beam from said electrons using at least of an electric field and a magnetic field,
   wherein a direction in which said deflector deflects a bundle of said electrons is matched with a direction of signal integration of said time delay integration sensor corresponding to the direction of said stage movement.

9. The electron beam apparatus according to claim 8, wherein said electrons are at least one of secondary electrons, reflection electrons and back-scattered electrons, generated from said sample.

10. The electron beam apparatus according to claim 8, wherein said electrons are mirror electrons reflected near the surface of said sample.

11. The electron beam apparatus according to claim 8, further comprising a stage capable of holding said sample and continuously moving along at least one axis on the surface of the sample, a direction of movement of said stage being matched with a direction of signal integration of said semiconductor imaging element.

12. A substrate inspection apparatus for inspecting the surface of a substrate using an electron beam, comprising:
    a cassette for holding a substrate;
    a transportation robot having a robot hand capable of transporting substrates of a plurality of sizes;
    a stage apparatus comprising an electrostatic chuck capable of adsorbing and fixing the substrates of a plurality of sizes by using a correction ring;
    an electron gun for irradiating an electron beam to the surface of said substrate;
    a detector for detecting electrons having information of the surface of said substrate;
    an image processing apparatus for obtaining an image of the surface of said substrate from said detected electrons; and
    a calculation device for comparing and inspecting the surfaces of said substrates.

13. The substrate inspection apparatus according to claim 12, wherein said electrostatic chuck has a plurality of correction rings appropriate to the size of said substrate.

14. The substrate inspection apparatus according to claim 13, wherein said correction ring has a dropping mechanism appropriate to the size of said substrate.

15. The substrate inspection apparatus according to claim 12, wherein said robot hand has a substrate dropping portion appropriate to the size of said substrate.

16. The substrate inspection apparatus according to claim 12, further comprising load lock chamber for said transportation robot to place said substrate in the correction ring, and a pre-aligner provided in a range of activation of said transportation robot for correcting alignment of said substrate wit respect to the correction ring.

17. The substrate inspection apparatus according to claim 16, wherein said load lock chamber comprises a multiple-stage elevator mechanism for carrying said wafer as an inspection object in said stage apparatus, and carrying inspected said substrate out of said stage apparatus.

18. The substrate inspection apparatus according to claim 16, wherein a site for replacement of said correction ring is provided within the range of activation of said transportation robot.

19. A detector positioning method in a substrate inspection apparatus, said method comprising the steps of:
    rotating a detector by a very small angle with respect to a stage apparatus, and performing scan imaging by said detector for each rotation to quantitatively evaluate a quality of an image;
    calculating a function indicating a relation between a position of rotation of said detector and said image quality; and determining an optimum value of the position of rotation of said detector from said function, and aligning said detector in a position corresponding to said optimum value.

20. The positioning method according to claim 19, wherein said stage apparatus, said detector is housed in a lens column, said lens column being separated into an upper lens column and a lower lens column, and said detector being mounted on said upper lens column.

21. The positioning method according to claim 20, further comprising a seal provided between said upper lens column and said lower lens column for keeping the inside of said lens column under vacuum.

22. The positioning method according to claim 21, wherein a space containing said seal portion is connected to an exhaust channel.

* * * * *